US012642464B2

(12) United States Patent　　(10) Patent No.: US 12,642,464 B2
Taub et al.　　(45) Date of Patent: Jun. 2, 2026

(54) DEVICES, SYSTEMS, AND METHODS ASSOCIATED WITH ANALYTE MONITORING DEVICES AND DEVICES INCORPORATING THE SAME

(71) Applicant: ABBOTT DIABETES CARE INC., Alameda, CA (US)

(72) Inventors: Marc B. Taub, Mountain View, CA (US); Jai Karan, Hyderabad (IN); Annie C. Tan, Redwood City, CA (US); Timothy C. Dunn, San Francisco, CA (US); Joel M. Goldsmith, Oakland, CA (US); Christine M. Neuhaus, San Jose, CA (US); Stephen A. Rossi, Clayton, CA (US); Sujit R. Jangam, Castro Valley, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 19/259,668

(22) Filed: Jul. 3, 2025

(65) Prior Publication Data

US 2025/0331748 A1　Oct. 30, 2025

Related U.S. Application Data

(63) Continuation of application No. 17/902,703, filed on Sep. 2, 2022, now abandoned, which is a continuation (Continued)

(51) Int. Cl.
*A61B 5/1473* (2006.01)
*A61B 5/00* (2006.01)

(Continued)

(52) U.S. Cl.
CPC ........ *A61B 5/1473* (2013.01); *A61B 5/14532* (2013.01); *G01N 33/48792* (2013.01);

(Continued)

(58) Field of Classification Search
CPC . A61B 5/1473; A61B 5/14532; A61B 5/0004; A61B 5/6833; A61B 5/6847;

(Continued)

(56) References Cited

U.S. PATENT DOCUMENTS 3,581,062 A　5/1971　Aston
3,926,760 A　12/1975　Allen et al.

(Continued)

FOREIGN PATENT DOCUMENTS

CN　100354871 C　* 12/2007　.............. A61B 5/743
CN　101610714 A　12/2009

(Continued)

OTHER PUBLICATIONS

"Abbott's App for Freestyler Libre System Now Available in Europe for Both Iphone™ and Android™", 2018, retrieved from https://abbott.mediaroom.com/2018-02-07-Abbotts-App-for-FreeStyle-R-Libre-System-Now-Available-in-Europe-for-Both-iPhone-TM-and-Android-TM#:~:text=Abbott's%20FreeStyle%20LibreLink%20app%20is, Switzerland%20and%20the%20United%20Kingdom., 3 pages.

(Continued)

*Primary Examiner* — Navin Natnithithadha
(74) *Attorney, Agent, or Firm* — ONE LLP

(57) ABSTRACT

Analyte monitoring systems, devices, and methods associated with analyte monitoring devices, and devices incorporating the same are provided. Various graphical user interfaces (GUI) and navigation flows are provided for performing various features, activities, functions, etc., associated with the analyte monitoring device or system. Intui- (Continued)

tive navigation is provided to enhance the interpretation of analyte measurements.

27 Claims, 187 Drawing Sheets

Related U.S. Application Data of application No. 17/557,534, filed on Dec. 21, 2021, now Pat. No. 11,534,089, which is a continuation of application No. 16/175,157, filed on Oct. 30, 2018, now Pat. No. 11,627,898, which is a continuation of application No. 14/214,430, filed on Mar. 14, 2014, now Pat. No. 10,136,845, which is a continuation-in-part of application No. 13/407,617, filed on Feb. 28, 2012, now Pat. No. 9,532,737.

(60) Provisional application No. 61/801,518, filed on Mar. 15, 2013, provisional application No. 61/492,266, filed on Jun. 1, 2011, provisional application No. 61/489,098, filed on May 23, 2011, provisional application No. 61/447,645, filed on Feb. 28, 2011.

(51) Int. Cl.
A61B 5/145 (2006.01)
G01N 33/487 (2006.01)

(52) U.S. Cl.
CPC ........... *A61B 5/0004* (2013.01); *A61B 5/6833* (2013.01); *A61B 5/6847* (2013.01); *A61B 5/7435* (2013.01); *A61B 5/744* (2013.01); *A61B 2560/0209* (2013.01); *A61B 2560/0252* (2013.01)

(58) Field of Classification Search
CPC .................. A61B 5/7435; A61B 5/744; A61B 2560/0209; A61B 2560/0252; G01N 33/48792
See application file for complete search history.

(56) References Cited

U.S. PATENT DOCUMENTS

| | | | |
|---|---|---|---|
| 3,949,388 A | 4/1976 | Fuller | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,425,920 A | 1/1984 | Bourland et al. | |
| 4,431,004 A | 2/1984 | Bessman et al. | |
| 4,441,968 A | 4/1984 | Emmer et al. | |
| 4,464,170 A | 8/1984 | Clemens et al. | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,545,382 A | 10/1985 | Higgins et al. | |
| 4,619,793 A | 10/1986 | Lee | |
| 4,671,288 A | 6/1987 | Gough | |
| 4,703,756 A | 11/1987 | Gough et al. | |
| 4,711,245 A | 12/1987 | Higgins et al. | |
| 4,731,726 A | 3/1988 | Allen, III | |
| 4,749,985 A | 6/1988 | Corsberg | |
| 4,757,022 A | 7/1988 | Shults et al. | |
| 4,777,953 A | 10/1988 | Ash et al. | |
| 4,779,618 A | 10/1988 | Mund et al. | |
| 4,847,785 A | 7/1989 | Stephens | |
| 4,854,322 A | 8/1989 | Ash et al. | |
| 4,890,620 A | 1/1990 | Gough | |
| 4,925,268 A | 5/1990 | Iyer et al. | |
| 4,953,552 A | 9/1990 | DeMarzo | |
| 4,986,271 A | 1/1991 | Wilkins | |
| 4,995,402 A | 2/1991 | Smith et al. | |
| 5,000,180 A | 3/1991 | Kuypers et al. | |
| 5,002,054 A | 3/1991 | Ash et al. | |
| 5,019,974 A | 5/1991 | Beckers | |
| 5,050,612 A | 9/1991 | Matsumura | |
| 5,051,688 A | 9/1991 | Murase et al. | |
| 5,055,171 A | 10/1991 | Peck | |
| 5,082,550 A | 1/1992 | Rishpon et al. | |
| 5,106,365 A | 4/1992 | Hernandez | |
| 5,122,925 A | 6/1992 | Inpyn | |
| 5,135,004 A | 8/1992 | Adams et al. | |
| 5,165,407 A | 11/1992 | Wilson et al. | |
| 5,202,261 A | 4/1993 | Musho et al. | |
| 5,210,778 A | 5/1993 | Massart | |
| 5,228,449 A | 7/1993 | Christ et al. | |
| 5,231,988 A | 8/1993 | Wernicke et al. | |
| 5,246,867 A | 9/1993 | Lakowicz et al. | |
| 5,251,126 A | 10/1993 | Kahn et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,320,715 A | 6/1994 | Berg | |
| 5,320,725 A | 6/1994 | Gregg et al. | |
| 5,322,063 A | 6/1994 | Allen et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,372,427 A | 12/1994 | Padovani et al. | |
| 5,379,238 A | 1/1995 | Stark | |
| 5,384,547 A | 1/1995 | Lynk et al. | |
| 5,390,671 A | 2/1995 | Lord et al. | |
| 5,391,250 A | 2/1995 | Cheney, II et al. | |
| 5,394,877 A | 3/1995 | Orr et al. | |
| 5,402,780 A | 4/1995 | Faasse, Jr. | |
| 5,408,999 A | 4/1995 | Singh et al. | |
| 5,410,326 A | 4/1995 | Goldstein | |
| 5,411,647 A | 5/1995 | Johnson et al. | |
| 5,431,160 A | 7/1995 | Wilkins | |
| 5,431,921 A | 7/1995 | Thombre | |
| 5,462,645 A | 10/1995 | Albery et al. | |
| 5,472,317 A | 12/1995 | Field et al. | |
| 5,489,414 A | 2/1996 | Schreiber et al. | |
| 5,497,772 A | 3/1996 | Schulman et al. | |
| 5,507,288 A | 4/1996 | Bocker et al. | |
| 5,509,410 A | 4/1996 | Hill et al. | |
| 5,514,718 A | 5/1996 | Lewis et al. | |
| 5,531,878 A | 7/1996 | Vadgama et al. | |
| 5,532,686 A | 7/1996 | Urbas et al. | |
| 5,543,326 A | 8/1996 | Heller et al. | |
| 5,552,997 A | 9/1996 | Massart | |
| 5,568,806 A | 10/1996 | Cheney, II et al. | |
| 5,569,186 A | 10/1996 | Lord et al. | |
| 5,582,184 A | 12/1996 | Erickson et al. | |
| 5,586,553 A | 12/1996 | Halili et al. | |
| 5,593,852 A | 1/1997 | Heller et al. | |
| 5,601,435 A | 2/1997 | Quy | |
| 5,609,575 A | 3/1997 | Larson et al. | |
| 5,628,310 A | 5/1997 | Rao et al. | |
| 5,628,890 A | 5/1997 | Carter et al. | |
| 5,634,468 A | 6/1997 | Platt et al. | |
| 5,640,954 A | 6/1997 | Pfeiffer et al. | |
| 5,653,239 A | 8/1997 | Pompei et al. | |
| 5,665,222 A | 9/1997 | Heller et al. | |
| 5,707,502 A | 1/1998 | McCaffrey et al. | |
| 5,711,001 A | 1/1998 | Bussan et al. | |
| 5,711,861 A | 1/1998 | Ward et al. | |
| 5,724,030 A | 3/1998 | Urbas et al. | |
| 5,726,646 A | 3/1998 | Bane et al. | |
| 5,735,285 A | 4/1998 | Albert et al. | |

(56)                References Cited

U.S. PATENT DOCUMENTS

| | | | |
|---|---|---|---|
| 5,748,103 A | 5/1998 | Flach et al. |
| 5,749,907 A | 5/1998 | Mann |
| 5,772,586 A | 6/1998 | Heinonen et al. |
| 5,791,344 A | 8/1998 | Schulman et al. |
| 5,794,219 A | 8/1998 | Brown |
| 5,804,047 A | 9/1998 | Karube et al. |
| 5,807,375 A | 9/1998 | Gross et al. |
| 5,820,551 A | 10/1998 | Hill et al. |
| 5,822,715 A | 10/1998 | Worthington et al. |
| 5,875,186 A | 2/1999 | Belanger et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,942,979 A | 8/1999 | Luppino |
| 5,951,485 A | 9/1999 | Cyrus et al. |
| 5,951,521 A | 9/1999 | Mastrototaro et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,973,613 A | 10/1999 | Reis et al. |
| 5,987,353 A | 11/1999 | Khatchatrian et al. |
| 5,995,860 A | 11/1999 | Sun et al. |
| 6,001,067 A | 12/1999 | Shults et al. |
| 6,022,315 A | 2/2000 | Lliff |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,071,391 A | 6/2000 | Gotoh et al. |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,823 A | 10/2000 | Hughes et al. |
| 6,130,623 A | 10/2000 | MacLellan et al. |
| 6,134,461 A | 10/2000 | Say et al. |
| 6,141,573 A | 10/2000 | Kurnik et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,167,362 A | 12/2000 | Brown et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,065 B1 | 6/2001 | Brown |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,368,273 B1 | 4/2002 | Brown |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,400,974 B1 | 6/2002 | Lesho |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,045 B1 | 11/2002 | Holker et al. |
| 6,484,046 B1 | 11/2002 | Say et al. |
| 6,493,069 B1 | 12/2002 | Nagashimada et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,503,381 B1 | 1/2003 | Gotoh et al. |
| 6,510,344 B1 | 1/2003 | Halpern |
| 6,514,460 B1 | 2/2003 | Fendrock |
| 6,514,718 B2 | 2/2003 | Heller et al. |
| 6,540,891 B1 | 4/2003 | Stewart et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,676,816 B2 | 1/2004 | Mao et al. |
| 6,687,546 B2 | 2/2004 | Lebel et al. |

(56)　　　　　　References Cited

U.S. PATENT DOCUMENTS

| | | | |
|---|---|---|---|
| 6,689,056 | B1 | 2/2004 | Kilcoyne et al. |
| 6,694,191 | B2 | 2/2004 | Starkweather et al. |
| 6,695,860 | B1 | 2/2004 | Ward et al. |
| 6,702,857 | B2 | 3/2004 | Brauker et al. |
| 6,730,200 | B1 | 5/2004 | Stewart et al. |
| 6,731,976 | B2 | 5/2004 | Penn et al. |
| 6,733,446 | B2 | 5/2004 | Lebel et al. |
| 6,735,183 | B2 | 5/2004 | O'Toole et al. |
| 6,736,957 | B1 | 5/2004 | Forrow et al. |
| 6,740,075 | B2 | 5/2004 | Lebel et al. |
| 6,741,877 | B1 | 5/2004 | Shults et al. |
| 6,743,635 | B2 | 6/2004 | Neel et al. |
| 6,746,582 | B2 | 6/2004 | Heller et al. |
| 6,749,740 | B2 | 6/2004 | Liamos et al. |
| 6,758,810 | B2 | 7/2004 | Lebel et al. |
| 6,764,581 | B1 | 7/2004 | Forrow et al. |
| 6,770,030 | B1 | 8/2004 | Schaupp et al. |
| 6,773,671 | B1 | 8/2004 | Lewis et al. |
| 6,789,195 | B1 | 9/2004 | Prihoda et al. |
| 6,790,178 | B1 | 9/2004 | Mault et al. |
| 6,804,558 | B2 | 10/2004 | Haller et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,837,858 | B2 | 1/2005 | Cunningham et al. |
| 6,862,465 | B2 | 3/2005 | Shults et al. |
| 6,873,268 | B2 | 3/2005 | Lebel et al. |
| 6,878,112 | B2 | 4/2005 | Linberg et al. |
| 6,881,551 | B2 | 4/2005 | Heller et al. |
| 6,892,085 | B2 | 5/2005 | McIvor et al. |
| 6,893,545 | B2 | 5/2005 | Gotoh et al. |
| 6,895,265 | B2 | 5/2005 | Silver |
| 6,923,763 | B1 | 8/2005 | Kovatchev et al. |
| 6,923,764 | B2 | 8/2005 | Aceti et al. |
| 6,931,327 | B2 | 8/2005 | Goode, Jr. et al. |
| 6,932,892 | B2 | 8/2005 | Chen et al. |
| 6,932,894 | B2 | 8/2005 | Mao et al. |
| 6,936,006 | B2 | 8/2005 | Sabra |
| 6,940,403 | B2 | 9/2005 | Kail, IV |
| 6,941,163 | B2 | 9/2005 | Ford et al. |
| 6,942,518 | B2 | 9/2005 | Liamos et al. |
| 6,950,708 | B2 | 9/2005 | Bowman IV et al. |
| 6,958,705 | B2 | 10/2005 | Lebel et al. |
| 6,968,294 | B2 | 11/2005 | Gutta et al. |
| 6,968,375 | B1 | 11/2005 | Brown |
| 6,971,274 | B2 | 12/2005 | Olin |
| 6,974,437 | B2 | 12/2005 | Lebel et al. |
| 6,990,366 | B2 | 1/2006 | Say et al. |
| 6,997,907 | B2 | 2/2006 | Safabash et al. |
| 6,998,247 | B2 | 2/2006 | Monfre et al. |
| 6,999,854 | B2 | 2/2006 | Roth |
| 7,003,336 | B2 | 2/2006 | Holker et al. |
| 7,003,340 | B2 | 2/2006 | Say et al. |
| 7,003,341 | B2 | 2/2006 | Say et al. |
| 7,009,511 | B2 | 3/2006 | Mazar et al. |
| 7,015,817 | B2 | 3/2006 | Copley et al. |
| 7,016,713 | B2 | 3/2006 | Gardner et al. |
| 7,020,508 | B2 | 3/2006 | Stivoric et al. |
| 7,024,236 | B2 | 4/2006 | Ford et al. |
| 7,024,245 | B2 | 4/2006 | Lebel et al. |
| 7,025,774 | B2 | 4/2006 | Freeman et al. |
| 7,027,848 | B2 | 4/2006 | Robinson et al. |
| 7,027,931 | B1 | 4/2006 | Jones et al. |
| 7,041,068 | B2 | 5/2006 | Freeman et al. |
| 7,041,468 | B2 | 5/2006 | Drucker et al. |
| 7,043,305 | B2 | 5/2006 | KenKnight et al. |
| 7,046,153 | B2 | 5/2006 | Oja et al. |
| 7,052,483 | B2 | 5/2006 | Wojcik |
| 7,056,302 | B2 | 6/2006 | Douglas |
| 7,058,453 | B2 | 6/2006 | Nelson et al. |
| 7,060,031 | B2 | 6/2006 | Webb et al. |
| 7,074,307 | B2 | 7/2006 | Simpson et al. |
| 7,081,195 | B2 | 7/2006 | Simpson et al. |
| 7,082,334 | B2 | 7/2006 | Boute et al. |
| 7,092,891 | B2 | 8/2006 | Maus et al. |
| 7,098,803 | B2 | 8/2006 | Mann et al. |
| 7,108,778 | B2 | 9/2006 | Simpson et al. |
| 7,110,803 | B2 | 9/2006 | Shults et al. |
| 7,113,821 | B1 | 9/2006 | Sun et al. |
| 7,123,950 | B2 | 10/2006 | Mannheimer |
| 7,125,382 | B2 | 10/2006 | Zhou et al. |
| 7,134,999 | B2 | 11/2006 | Brauker et al. |
| 7,136,689 | B2 | 11/2006 | Shults et al. |
| 7,153,265 | B2 | 12/2006 | Vachon |
| 7,155,290 | B2 | 12/2006 | Von Arx et al. |
| 7,155,729 | B1 | 12/2006 | Andrew et al. |
| 7,167,818 | B2 | 1/2007 | Brown |
| 7,171,274 | B2 | 1/2007 | Starkweather et al. |
| 7,179,226 | B2 | 2/2007 | Crothall et al. |
| 7,190,988 | B2 | 3/2007 | Say et al. |
| 7,192,450 | B2 | 3/2007 | Brauker et al. |
| 7,198,606 | B2 | 4/2007 | Boecker et al. |
| 7,203,549 | B2 | 4/2007 | Schommer et al. |
| 7,207,974 | B2 | 4/2007 | Safabash et al. |
| 7,223,236 | B2 | 5/2007 | Brown |
| 7,226,442 | B2 | 6/2007 | Sheppard et al. |
| 7,226,978 | B2 | 6/2007 | Tapsak et al. |
| 7,228,182 | B2 | 6/2007 | Healy et al. |
| 7,237,712 | B2 | 7/2007 | DeRocco et al. |
| 7,258,666 | B2 | 8/2007 | Brown |
| 7,276,029 | B2 | 10/2007 | Goode, Jr. et al. |
| 7,278,983 | B2 | 10/2007 | Ireland et al. |
| 7,286,894 | B1 | 10/2007 | Grant et al. |
| 7,299,082 | B2 | 11/2007 | Feldman et al. |
| 7,301,463 | B1 | 11/2007 | Paterno |
| 7,310,544 | B2 | 12/2007 | Brister et al. |
| 7,318,816 | B2 | 1/2008 | Bobroff et al. |
| 7,324,012 | B2 | 1/2008 | Mann et al. |
| 7,324,850 | B2 | 1/2008 | Persen et al. |
| 7,329,239 | B2 | 2/2008 | Safabash et al. |
| 7,335,294 | B2 | 2/2008 | Heller et al. |
| 7,347,819 | B2 | 3/2008 | Lebel et al. |
| 7,354,420 | B2 | 4/2008 | Steil et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,381,184 | B2 | 6/2008 | Funderburk et al. |
| 7,384,397 | B2 | 6/2008 | Zhang et al. |
| 7,387,010 | B2 | 6/2008 | Sunshine et al. |
| 7,392,167 | B2 | 6/2008 | Brown |
| 7,399,277 | B2 | 7/2008 | Saidara et al. |
| 7,402,153 | B2 | 7/2008 | Steil et al. |
| 7,419,573 | B2 | 9/2008 | Gundel |
| 7,424,318 | B2 | 9/2008 | Brister et al. |
| 7,429,258 | B2 | 9/2008 | Angel et al. |
| 7,455,663 | B2 | 11/2008 | Bikovsky |
| 7,460,898 | B2 | 12/2008 | Brister et al. |
| 7,462,264 | B2 | 12/2008 | Heller et al. |
| 7,467,003 | B2 | 12/2008 | Brister et al. |
| 7,471,972 | B2 | 12/2008 | Rhodes et al. |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,499,002 | B2 | 3/2009 | Blasko et al. |
| 7,501,053 | B2 | 3/2009 | Karinka et al. |
| 7,519,408 | B2 | 4/2009 | Rasdal et al. |
| 7,565,197 | B2 | 7/2009 | Haubrich et al. |
| 7,574,266 | B2 | 8/2009 | Dudding et al. |
| 7,583,990 | B2 | 9/2009 | Goode, Jr. et al. |
| 7,591,801 | B2 | 9/2009 | Brauker et al. |
| 7,599,726 | B2 | 10/2009 | Goode, Jr. et al. |
| 7,602,310 | B2 | 10/2009 | Mann et al. |
| 7,604,178 | B2 | 10/2009 | Stewart |
| 7,613,491 | B2 | 11/2009 | Boock et al. |
| 7,615,007 | B2 | 11/2009 | Shults et al. |
| 7,618,369 | B2 | 11/2009 | Hayter et al. |
| 7,624,028 | B1 | 11/2009 | Brown |
| 7,630,748 | B2 | 12/2009 | Budiman |
| 7,632,228 | B2 | 12/2009 | Brauker et al. |
| 7,635,594 | B2 | 12/2009 | Holmes et al. |
| 7,637,868 | B2 | 12/2009 | Saint et al. |
| 7,640,048 | B2 | 12/2009 | Dobbles et al. |

(56)                References Cited

U.S. PATENT DOCUMENTS

| | | | |
|---|---|---|---|
| 7,643,971 | B2 | 1/2010 | Brown |
| 7,647,237 | B2 | 1/2010 | Malave et al. |
| 7,651,596 | B2 | 1/2010 | Petisce et al. |
| 7,651,845 | B2 | 1/2010 | Doyle, III et al. |
| 7,654,956 | B2 | 2/2010 | Brister et al. |
| 7,657,297 | B2 | 2/2010 | Simpson et al. |
| 7,659,823 | B1 | 2/2010 | Killian et al. |
| 7,668,596 | B2 | 2/2010 | Von Arx et al. |
| 7,684,999 | B2 | 3/2010 | Brown |
| 7,689,440 | B2 | 3/2010 | Brown |
| 7,697,967 | B2 | 4/2010 | Stafford |
| 7,699,775 | B2 | 4/2010 | Desai et al. |
| 7,711,402 | B2 | 5/2010 | Shults et al. |
| 7,713,574 | B2 | 5/2010 | Brister et al. |
| 7,715,893 | B2 | 5/2010 | Kamath et al. |
| 7,727,147 | B1 | 6/2010 | Osorio et al. |
| 7,731,657 | B2 | 6/2010 | Stafford |
| 7,736,310 | B2 | 6/2010 | Taub |
| 7,736,344 | B2 | 6/2010 | Moberg et al. |
| 7,741,734 | B2 | 6/2010 | Joannopoulos et al. |
| 7,754,093 | B2 | 7/2010 | Forrow et al. |
| 7,763,042 | B2 | 7/2010 | Iio et al. |
| 7,766,829 | B2 | 8/2010 | Sloan et al. |
| 7,768,387 | B2 | 8/2010 | Fennell et al. |
| 7,779,332 | B2 | 8/2010 | Karr et al. |
| 7,782,192 | B2 | 8/2010 | Jeckelmann et al. |
| 7,783,333 | B2 | 8/2010 | Brister et al. |
| 7,791,467 | B2 | 9/2010 | Mazar et al. |
| 7,792,562 | B2 | 9/2010 | Shults et al. |
| 7,811,231 | B2 | 10/2010 | Jin et al. |
| 7,813,809 | B2 | 10/2010 | Strother et al. |
| 7,822,454 | B1 | 10/2010 | Alden et al. |
| 7,826,382 | B2 | 11/2010 | Sicurello et al. |
| 7,831,310 | B2 | 11/2010 | Lebel et al. |
| 7,860,574 | B2 | 12/2010 | Von Arx et al. |
| 7,866,026 | B1 | 1/2011 | Wang et al. |
| 7,877,274 | B2 | 1/2011 | Brown |
| 7,877,276 | B2 | 1/2011 | Brown |
| 7,882,611 | B2 | 2/2011 | Shah et al. |
| 7,889,069 | B2 | 2/2011 | Fifolt et al. |
| 7,899,545 | B2 | 3/2011 | John |
| 7,912,674 | B2 | 3/2011 | Killoren Clark et al. |
| 7,914,460 | B2 | 3/2011 | Melker et al. |
| 7,916,013 | B2 | 3/2011 | Stevenson |
| 7,921,186 | B2 | 4/2011 | Brown |
| 7,937,255 | B2 | 5/2011 | Brown |
| 7,938,797 | B2 | 5/2011 | Estes |
| 7,941,200 | B2 | 5/2011 | Weinert et al. |
| 7,941,308 | B2 | 5/2011 | Brown |
| 7,941,323 | B2 | 5/2011 | Brown |
| 7,941,326 | B2 | 5/2011 | Brown |
| 7,941,327 | B2 | 5/2011 | Brown |
| 7,946,985 | B2 | 5/2011 | Mastrototaro et al. |
| 7,949,507 | B2 | 5/2011 | Brown |
| 7,955,258 | B2 | 6/2011 | Goscha et al. |
| 7,966,230 | B2 | 6/2011 | Brown |
| 7,970,448 | B2 | 6/2011 | Shults et al. |
| 7,970,620 | B2 | 6/2011 | Brown |
| 7,972,267 | B2 | 7/2011 | Brown |
| 7,972,296 | B2 | 7/2011 | Braig et al. |
| 7,976,466 | B2 | 7/2011 | Ward et al. |
| 7,976,467 | B2 | 7/2011 | Young et al. |
| 7,978,063 | B2 | 7/2011 | Baldus et al. |
| 7,979,259 | B2 | 7/2011 | Brown |
| 7,979,284 | B2 | 7/2011 | Brown |
| 7,999,674 | B2 | 8/2011 | Kamer |
| 8,010,174 | B2 | 8/2011 | Goode et al. |
| 8,010,256 | B2 | 8/2011 | Oowada |
| 8,015,025 | B2 | 9/2011 | Brown |
| 8,015,030 | B2 | 9/2011 | Brown |
| 8,015,033 | B2 | 9/2011 | Brown |
| 8,019,618 | B2 | 9/2011 | Brown |
| 8,024,201 | B2 | 9/2011 | Brown |
| 8,032,399 | B2 | 10/2011 | Brown |
| 8,072,310 | B1 | 12/2011 | Everhart |
| 8,090,445 | B2 | 1/2012 | Ginggen |
| 8,093,991 | B2 | 1/2012 | Stevenson et al. |
| 8,094,009 | B2 | 1/2012 | Allen et al. |
| 8,098,159 | B2 | 1/2012 | Batra et al. |
| 8,098,160 | B2 | 1/2012 | Howarth et al. |
| 8,098,161 | B2 | 1/2012 | Lavedas |
| 8,098,201 | B2 | 1/2012 | Choi et al. |
| 8,098,208 | B2 | 1/2012 | Ficker et al. |
| 8,102,021 | B2 | 1/2012 | Degani |
| 8,102,154 | B2 | 1/2012 | Bishop et al. |
| 8,102,263 | B2 | 1/2012 | Yeo et al. |
| 8,102,789 | B2 | 1/2012 | Rosar et al. |
| 8,103,241 | B2 | 1/2012 | Young et al. |
| 8,103,325 | B2 | 1/2012 | Swedlow et al. |
| 8,111,042 | B2 | 2/2012 | Bennett |
| 8,115,488 | B2 | 2/2012 | McDowell |
| 8,116,681 | B2 | 2/2012 | Baarman |
| 8,116,683 | B2 | 2/2012 | Baarman |
| 8,117,481 | B2 | 2/2012 | Anselmi et al. |
| 8,120,493 | B2 | 2/2012 | Burr |
| 8,124,452 | B2 | 2/2012 | Sheats |
| 8,130,093 | B2 | 3/2012 | Mazar et al. |
| 8,131,351 | B2 | 3/2012 | Kalgren et al. |
| 8,131,365 | B2 | 3/2012 | Zhang et al. |
| 8,131,565 | B2 | 3/2012 | Dicks et al. |
| 8,132,037 | B2 | 3/2012 | Fehr et al. |
| 8,135,352 | B2 | 3/2012 | Langsweirdt et al. |
| 8,136,735 | B2 | 3/2012 | Arai et al. |
| 8,138,925 | B2 | 3/2012 | Downie et al. |
| 8,140,160 | B2 | 3/2012 | Pless et al. |
| 8,140,168 | B2 | 3/2012 | Olson et al. |
| 8,140,299 | B2 | 3/2012 | Siess |
| 8,150,321 | B2 | 4/2012 | Winter et al. |
| 8,150,516 | B2 | 4/2012 | Levine et al. |
| 8,160,669 | B2 | 4/2012 | Brauker et al. |
| 8,160,900 | B2 | 4/2012 | Taub et al. |
| 8,179,266 | B2 | 5/2012 | Hermle |
| 8,192,394 | B2 | 6/2012 | Estes et al. |
| 8,216,138 | B1 | 7/2012 | McGarraugh et al. |
| 8,282,549 | B2 | 10/2012 | Brauker et al. |
| 8,328,719 | B2 | 12/2012 | Young et al. |
| 8,348,843 | B2 | 1/2013 | Young et al. |
| 8,461,985 | B2 | 6/2013 | Fennell et al. |
| 8,514,086 | B2 | 8/2013 | Harper et al. |
| 8,521,558 | B2 | 8/2013 | Malave et al. |
| 8,597,570 | B2 | 12/2013 | Terashima et al. |
| 8,652,037 | B2 | 2/2014 | Bakarania et al. |
| 8,816,862 | B2 | 8/2014 | Taub et al. |
| 8,905,965 | B2 | 12/2014 | Mandro et al. |
| 9,000,914 | B2 | 4/2015 | Baker et al. |
| 9,041,730 | B2 | 5/2015 | Johnson et al. |
| 9,119,528 | B2 | 9/2015 | Cobelli et al. |
| 9,136,939 | B2 | 9/2015 | Galley et al. |
| 9,186,113 | B2 | 11/2015 | Harper et al. |
| 9,226,714 | B2 | 1/2016 | Harper et al. |
| 9,341,614 | B2 | 5/2016 | Bielawa et al. |
| 9,419,704 | B2 | 8/2016 | Galley et al. |
| 9,445,757 | B2 | 9/2016 | Desborough et al. |
| 9,498,164 | B2 | 11/2016 | Johnson et al. |
| 9,498,165 | B2 | 11/2016 | Johnson et al. |
| 9,504,430 | B2 | 11/2016 | Johnson et al. |
| 9,532,737 | B2 | 1/2017 | Karan et al. |
| 9,801,541 | B2 | 10/2017 | Mensinger et al. |
| 9,833,199 | B2 | 12/2017 | Johnson et al. |
| 9,980,140 | B1 | 5/2018 | Spencer et al. |
| 10,010,273 | B2 | 7/2018 | Sloan et al. |
| 10,165,986 | B2 | 1/2019 | Johnson et al. |
| 10,265,030 | B2 | 4/2019 | Johnson et al. |
| 10,278,650 | B2 | 5/2019 | Johnson et al. |
| 10,375,222 | B2 | 8/2019 | Mandapaka et al. |
| 10,391,242 | B2 | 8/2019 | Agrawal et al. |
| 10,595,756 | B2 | 3/2020 | Sloan et al. |
| 10,702,215 | B2 | 7/2020 | Hampapuram et al. |
| 10,779,754 | B2 | 9/2020 | Desborough et al. |
| 10,855,788 | B2 | 12/2020 | Arabo et al. |
| 10,963,417 | B2 | 3/2021 | Anderson et al. |
| 11,213,204 | B2 | 1/2022 | Mensinger et al. |
| 11,272,890 | B2 | 3/2022 | McGarraugh |
| 11,991,175 | B2 | 5/2024 | Rolfe et al. |

(56)          References Cited

U.S. PATENT DOCUMENTS

| | | |
|---|---|---|
| 2001/0011224 A1 | 8/2001 | Brown |
| 2001/0020124 A1 | 9/2001 | Tamada |
| 2001/0037060 A1 | 11/2001 | Thompson et al. |
| 2001/0037366 A1 | 11/2001 | Webb et al. |
| 2001/0047604 A1 | 12/2001 | Valiulis |
| 2002/0019022 A1 | 2/2002 | Dunn et al. |
| 2002/0042090 A1 | 4/2002 | Heller et al. |
| 2002/0054320 A1 | 5/2002 | Ogino |
| 2002/0072784 A1 | 6/2002 | Sheppard et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0111832 A1 | 8/2002 | Judge |
| 2002/0128594 A1 | 9/2002 | Das et al. |
| 2002/0133107 A1 | 9/2002 | Darcey |
| 2002/0147135 A1 | 10/2002 | Schnell |
| 2002/0161288 A1 | 10/2002 | Shin et al. |
| 2002/0188748 A1 | 12/2002 | Blackwell et al. |
| 2003/0005464 A1 | 1/2003 | Gropper et al. |
| 2003/0021729 A1 | 1/2003 | Moller et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0114897 A1 | 6/2003 | Von Arx et al. |
| 2003/0134347 A1 | 7/2003 | Heller et al. |
| 2003/0147515 A1 | 8/2003 | Kai et al. |
| 2003/0163351 A1 | 8/2003 | Brown et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0208113 A1 | 11/2003 | Mault et al. |
| 2003/0211617 A1 | 11/2003 | Jones |
| 2003/0212379 A1 | 11/2003 | Bylund et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0015102 A1 | 1/2004 | Cummings et al. |
| 2004/0040840 A1 | 3/2004 | Mao et al. |
| 2004/0041749 A1 | 3/2004 | Dixon |
| 2004/0044272 A1* | 3/2004 | Moerman ................ A61P 7/04 |
| | | 600/300 |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0063435 A1 | 4/2004 | Sakamoto et al. |
| 2004/0064068 A1 | 4/2004 | DeNuzzio et al. |
| 2004/0073266 A1 | 4/2004 | Haefner et al. |
| 2004/0078215 A1 | 4/2004 | Dahlin et al. |
| 2004/0099529 A1 | 5/2004 | Mao et al. |
| 2004/0106858 A1 | 6/2004 | Say et al. |
| 2004/0117210 A1 | 6/2004 | Brown |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0147872 A1 | 7/2004 | Thompson |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0223985 A1 | 11/2004 | Dunfield et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0031689 A1 | 2/2005 | Shults et al. |
| 2005/0038332 A1 | 2/2005 | Saodara et al. |
| 2005/0038680 A1 | 2/2005 | McMahon |
| 2005/0043598 A1 | 2/2005 | Goode, Jr. et al. |
| 2005/0049179 A1 | 3/2005 | Davidson et al. |
| 2005/0060194 A1 | 3/2005 | Brown |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096516 A1 | 5/2005 | Soykan et al. |
| 2005/0112169 A1 | 5/2005 | Brauker et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0148890 A1 | 7/2005 | Hastings |
| 2005/0154271 A1 | 7/2005 | Rasdal et al. |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0184153 A1 | 8/2005 | Auchinleck |
| 2005/0187442 A1 | 8/2005 | Cho et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0209515 A1 | 9/2005 | Hockersmith et al. |
| 2005/0214892 A1 | 9/2005 | Kovatchev et al. |
| 2005/0228883 A1 | 10/2005 | Brown |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0251033 A1 | 11/2005 | Scarantino et al. |
| 2005/0277164 A1 | 12/2005 | Drucker et al. |
| 2005/0277912 A1 | 12/2005 | John |
| 2005/0280521 A1 | 12/2005 | Mizumaki |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0010014 A1 | 1/2006 | Brown |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0031094 A1 | 2/2006 | Cohen et al. |
| 2006/0036139 A1 | 2/2006 | Brister et al. |
| 2006/0036140 A1 | 2/2006 | Brister et al. |

(56) References Cited

U.S. PATENT DOCUMENTS

| | | |
|---|---|---|
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0166629 A1 | 7/2006 | Reggiardo |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0189863 A1 | 8/2006 | Peyser et al. |
| 2006/0193375 A1 | 8/2006 | Lee et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0234202 A1 | 10/2006 | Brown |
| 2006/0235722 A1 | 10/2006 | Brown |
| 2006/0241975 A1 | 10/2006 | Brown |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0258929 A1 | 11/2006 | Goode et al. |
| 2006/0272652 A1 | 12/2006 | Stocker et al. |
| 2006/0276771 A1 | 12/2006 | Galley et al. |
| 2006/0285660 A1 | 12/2006 | Brown |
| 2006/0285736 A1 | 12/2006 | Brown |
| 2006/0287691 A1 | 12/2006 | Drew |
| 2006/0287889 A1 | 12/2006 | Brown |
| 2006/0287931 A1 | 12/2006 | Brown |
| 2006/0290496 A1 | 12/2006 | Peeters et al. |
| 2006/0293607 A1 | 12/2006 | Alt et al. |
| 2007/0010950 A1 | 1/2007 | Abensour et al. |
| 2007/0011320 A1 | 1/2007 | Brown |
| 2007/0016381 A1 | 1/2007 | Kamath et al. |
| 2007/0016445 A1 | 1/2007 | Brown |
| 2007/0017983 A1 | 1/2007 | Frank et al. |
| 2007/0021984 A1 | 1/2007 | Brown |
| 2007/0027381 A1 | 2/2007 | Stafford |
| 2007/0032717 A1 | 2/2007 | Brister et al. |
| 2007/0033074 A1 | 2/2007 | Nitzan et al. |
| 2007/0055799 A1 | 3/2007 | Koehler et al. |
| 2007/0056858 A1 | 3/2007 | Chen et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0061167 A1 | 3/2007 | Brown |
| 2007/0066956 A1 | 3/2007 | Finkel |
| 2007/0068807 A1 | 3/2007 | Feldman et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078818 A1 | 4/2007 | Zvitz et al. |
| 2007/0093786 A1 | 4/2007 | Goldsmith et al. |
| 2007/0095661 A1 | 5/2007 | Wang et al. |
| 2007/0106135 A1 | 5/2007 | Sloan et al. |
| 2007/0107973 A1 | 5/2007 | Jiang et al. |
| 2007/0108048 A1 | 5/2007 | Wang et al. |
| 2007/0118588 A1 | 5/2007 | Brown |
| 2007/0149875 A1 | 6/2007 | Ouyang et al. |
| 2007/0156033 A1 | 7/2007 | Causey, III et al. |
| 2007/0156457 A1 | 7/2007 | Brown |
| 2007/0163880 A1 | 7/2007 | Woo et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0191701 A1 | 8/2007 | Feldman et al. |
| 2007/0191702 A1 | 8/2007 | Yodfat et al. |
| 2007/0199818 A1 | 8/2007 | Petyt et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213605 A1 | 9/2007 | Brown |
| 2007/0227911 A1 | 10/2007 | Wang et al. |
| 2007/0228071 A1 | 10/2007 | Kamen et al. |
| 2007/0231846 A1 | 10/2007 | Cosentino et al. |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0285238 A1 | 12/2007 | Batra |
| 2007/0294360 A1 | 12/2007 | Ebling et al. |
| 2008/0004515 A1 | 1/2008 | Jennewine et al. |
| 2008/0004601 A1 | 1/2008 | Jennewine et al. |
| 2008/0004904 A1 | 1/2008 | Tran |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058773 A1 | 3/2008 | John |
| 2008/0060955 A1 | 3/2008 | Goodnow |
| 2008/0061961 A1 | 3/2008 | John |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071328 A1 | 3/2008 | Haubrich et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0102441 A1 | 5/2008 | Chen et al. |
| 2008/0103447 A1 | 5/2008 | Reggiardo et al. |
| 2008/0108942 A1 | 5/2008 | Brister et al. |
| 2008/0114228 A1 | 5/2008 | McCluskey et al. |
| 2008/0114229 A1 | 5/2008 | Brown |
| 2008/0119705 A1 | 5/2008 | Patel et al. |
| 2008/0119710 A1 | 5/2008 | Reggiardo et al. |
| 2008/0125636 A1 | 5/2008 | Ward et al. |
| 2008/0127052 A1 | 5/2008 | Rostoker |
| 2008/0148873 A1 | 6/2008 | Wang |
| 2008/0154099 A1 | 6/2008 | Aspel et al. |
| 2008/0167572 A1 | 7/2008 | Stivoric et al. |
| 2008/0177149 A1 | 7/2008 | Weinert et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |

(56)        References Cited

U.S. PATENT DOCUMENTS

| | | |
|---|---|---|
| 2008/0228055 A1 | 9/2008 | Sher |
| 2008/0234943 A1 | 9/2008 | Ray et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0249470 A1 | 10/2008 | Malave et al. |
| 2008/0254544 A1 | 10/2008 | Modzelewski et al. |
| 2008/0255438 A1 | 10/2008 | Saidara et al. |
| 2008/0262469 A1 | 10/2008 | Brister et al. |
| 2008/0267823 A1 | 10/2008 | Wang et al. |
| 2008/0269571 A1 | 10/2008 | Brown |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0278333 A1 | 11/2008 | Fennell et al. |
| 2008/0287761 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0319085 A1 | 12/2008 | Wright et al. |
| 2008/0319294 A1 | 12/2008 | Taub et al. |
| 2008/0319295 A1 | 12/2008 | Bernstein et al. |
| 2008/0319296 A1 | 12/2008 | Bernstein et al. |
| 2009/0006034 A1 | 1/2009 | Hayter et al. |
| 2009/0006061 A1 | 1/2009 | Thukral et al. |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0030641 A1 | 1/2009 | Fjield et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub |
| 2009/0093687 A1 | 4/2009 | Telfort et al. |
| 2009/0099436 A1 | 4/2009 | Brister et al. |
| 2009/0105554 A1 | 4/2009 | Stahmann et al. |
| 2009/0105570 A1 | 4/2009 | Sloan et al. |
| 2009/0105571 A1 | 4/2009 | Fennell et al. |
| 2009/0112478 A1 | 4/2009 | Mueller, Jr. et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143661 A1 | 6/2009 | Taub et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0221890 A1 | 9/2009 | Saffer et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0248380 A1 | 10/2009 | Brown |
| 2009/0267765 A1 | 10/2009 | Greene et al. |
| 2009/0275815 A1 | 11/2009 | Bickoff et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0294277 A1 | 12/2009 | Thomas et al. |
| 2009/0296742 A1 | 12/2009 | Sicurello et al. |
| 2009/0298182 A1 | 12/2009 | Schulat et al. |
| 2009/0299151 A1 | 12/2009 | Taub et al. |
| 2009/0299152 A1 | 12/2009 | Taub et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010330 A1 | 1/2010 | Rankers et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045425 A1 | 2/2010 | Chivallier |
| 2010/0045465 A1 | 2/2010 | Brauker et al. |
| 2010/0049024 A1 | 2/2010 | Saint et al. |
| 2010/0057042 A1 | 3/2010 | Hayter |
| 2010/0063373 A1 | 3/2010 | Kamath et al. |
| 2010/0076283 A1 | 3/2010 | Simpson et al. |
| 2010/0081905 A1 | 4/2010 | Bommakanti et al. |
| 2010/0081908 A1 | 4/2010 | Dobbles et al. |
| 2010/0081910 A1 | 4/2010 | Brister et al. |
| 2010/0082364 A1 | 4/2010 | Taub et al. |
| 2010/0087724 A1 | 4/2010 | Brauker et al. |
| 2010/0093786 A1 | 4/2010 | Watanabe et al. |

(56)　　　　　References Cited

U.S. PATENT DOCUMENTS

| 2010/0096259 | A1 | 4/2010 | Zhang et al. |
| 2010/0099970 | A1 | 4/2010 | Shults et al. |
| 2010/0099971 | A1 | 4/2010 | Shults et al. |
| 2010/0105999 | A1 | 4/2010 | Dixon et al. |
| 2010/0119693 | A1 | 5/2010 | Tapsak et al. |
| 2010/0121167 | A1 | 5/2010 | McGarraugh et al. |
| 2010/0121169 | A1 | 5/2010 | Petisce et al. |
| 2010/0141656 | A1 | 6/2010 | Krieftewirth |
| 2010/0145172 | A1 | 6/2010 | Petisce et al. |
| 2010/0146300 | A1 | 6/2010 | Brown |
| 2010/0152554 | A1 | 6/2010 | Steine et al. |
| 2010/0160759 | A1 | 6/2010 | Celentano et al. |
| 2010/0160760 | A1 | 6/2010 | Shults et al. |
| 2010/0161269 | A1 | 6/2010 | Kamath et al. |
| 2010/0168538 | A1 | 7/2010 | Keenan et al. |
| 2010/0168540 | A1 | 7/2010 | Kamath et al. |
| 2010/0168541 | A1 | 7/2010 | Kamath et al. |
| 2010/0168542 | A1 | 7/2010 | Kamath et al. |
| 2010/0168543 | A1 | 7/2010 | Kamath et al. |
| 2010/0168544 | A1 | 7/2010 | Kamath et al. |
| 2010/0168545 | A1 | 7/2010 | Kamath et al. |
| 2010/0168546 | A1 | 7/2010 | Kamath et al. |
| 2010/0168657 | A1 | 7/2010 | Kamath et al. |
| 2010/0174157 | A1 | 7/2010 | Brister et al. |
| 2010/0174158 | A1 | 7/2010 | Kamath et al. |
| 2010/0174163 | A1 | 7/2010 | Brister et al. |
| 2010/0174164 | A1 | 7/2010 | Brister et al. |
| 2010/0174165 | A1 | 7/2010 | Brister et al. |
| 2010/0174166 | A1 | 7/2010 | Brister et al. |
| 2010/0174167 | A1 | 7/2010 | Kamath et al. |
| 2010/0174168 | A1 | 7/2010 | Goode et al. |
| 2010/0174266 | A1 | 7/2010 | Estes |
| 2010/0174553 | A1 | 7/2010 | Kaufman et al. |
| 2010/0179399 | A1 | 7/2010 | Goode et al. |
| 2010/0179400 | A1 | 7/2010 | Brauker et al. |
| 2010/0179401 | A1 | 7/2010 | Rasdal et al. |
| 2010/0179402 | A1 | 7/2010 | Goode et al. |
| 2010/0179404 | A1 | 7/2010 | Kamath et al. |
| 2010/0179405 | A1 | 7/2010 | Goode et al. |
| 2010/0179407 | A1 | 7/2010 | Goode et al. |
| 2010/0179408 | A1 | 7/2010 | Kamath et al. |
| 2010/0179409 | A1 | 7/2010 | Kamath et al. |
| 2010/0185065 | A1 | 7/2010 | Goode et al. |
| 2010/0185069 | A1 | 7/2010 | Brister et al. |
| 2010/0185070 | A1 | 7/2010 | Brister et al. |
| 2010/0185071 | A1 | 7/2010 | Simpson et al. |
| 2010/0185072 | A1 | 7/2010 | Goode et al. |
| 2010/0185073 | A1 | 7/2010 | Goode et al. |
| 2010/0185074 | A1 | 7/2010 | Goode et al. |
| 2010/0185075 | A1 | 7/2010 | Brister et al. |
| 2010/0185175 | A1 | 7/2010 | Kamen et al. |
| 2010/0190435 | A1 | 7/2010 | Cook et al. |
| 2010/0191082 | A1 | 7/2010 | Brister et al. |
| 2010/0191472 | A1 | 7/2010 | Doniger et al. |
| 2010/0198034 | A1 | 8/2010 | Thomas et al. |
| 2010/0198035 | A1 | 8/2010 | Kamath et al. |
| 2010/0198036 | A1 | 8/2010 | Kamath et al. |
| 2010/0198142 | A1 | 8/2010 | Sloan et al. |
| 2010/0198314 | A1 | 8/2010 | Wei |
| 2010/0204557 | A1 | 8/2010 | Kiaie et al. |
| 2010/0213080 | A1 | 8/2010 | Celentano et al. |
| 2010/0230285 | A1 | 9/2010 | Hoss et al. |
| 2010/0268157 | A1 | 10/2010 | Wehba et al. |
| 2010/0274111 | A1 | 10/2010 | Say et al. |
| 2010/0274515 | A1 | 10/2010 | Hoss et al. |
| 2010/0275108 | A1 | 10/2010 | Sloan et al. |
| 2010/0313105 | A1 | 12/2010 | Nekoomaram et al. |
| 2010/0326842 | A1 | 12/2010 | Mazza et al. |
| 2011/0004276 | A1 | 1/2011 | Blair et al. |
| 2011/0021889 | A1 | 1/2011 | Hoss et al. |
| 2011/0024043 | A1 | 2/2011 | Boock et al. |
| 2011/0024307 | A1 | 2/2011 | Simpson et al. |
| 2011/0027127 | A1 | 2/2011 | Simpson et al. |
| 2011/0027453 | A1 | 2/2011 | Boock et al. |
| 2011/0027458 | A1 | 2/2011 | Boock et al. |

| 2011/0028815 | A1 | 2/2011 | Simpson et al. |
| 2011/0028816 | A1 | 2/2011 | Simpson et al. |
| 2011/0031986 | A1 | 2/2011 | Bhat et al. |
| 2011/0054282 | A1 | 3/2011 | Nekoomaram et al. |
| 2011/0060530 | A1 | 3/2011 | Fennell |
| 2011/0077490 | A1 | 3/2011 | Simpson et al. |
| 2011/0077494 | A1 | 3/2011 | Doniger et al. |
| 2011/0081726 | A1 | 4/2011 | Berman et al. |
| 2011/0106011 | A1 | 5/2011 | Cinar et al. |
| 2011/0131307 | A1 | 6/2011 | El Bazzal et al. |
| 2011/0148905 | A1 | 6/2011 | Simmons et al. |
| 2011/0152637 | A1 | 6/2011 | Kateraas et al. |
| 2011/0173308 | A1 | 7/2011 | Gutekunst |
| 2011/0178717 | A1 | 7/2011 | Goodnow et al. |
| 2011/0184267 | A1 | 7/2011 | Duke et al. |
| 2011/0184268 | A1 | 7/2011 | Taub |
| 2011/0193704 | A1 | 8/2011 | Harper et al. |
| 2011/0202495 | A1 | 8/2011 | Gawlick |
| 2011/0208027 | A1 | 8/2011 | Wagner et al. |
| 2011/0213225 | A1 | 9/2011 | Bernstein et al. |
| 2011/0257895 | A1 | 10/2011 | Brauker et al. |
| 2011/0287528 | A1 | 11/2011 | Fern et al. |
| 2011/0289497 | A1 | 11/2011 | Kiaie et al. |
| 2011/0313349 | A1 | 12/2011 | Krulevitch et al. |
| 2011/0319729 | A1 | 12/2011 | Donnay et al. |
| 2011/0320130 | A1 | 12/2011 | Valdes et al. |
| 2012/0010642 | A1 | 1/2012 | Lee et al. |
| 2012/0078071 | A1 | 3/2012 | Bohm et al. |
| 2012/0088995 | A1 | 4/2012 | Fennell et al. |
| 2012/0108934 | A1 | 5/2012 | Valdes et al. |
| 2012/0165626 | A1 | 6/2012 | Irina et al. |
| 2012/0165640 | A1 | 6/2012 | Galley et al. |
| 2012/0173200 | A1 | 7/2012 | Breton et al. |
| 2012/0185416 | A1 | 7/2012 | Baras et al. |
| 2012/0232520 | A1 | 9/2012 | Sloan et al. |
| 2012/0245447 | A1 | 9/2012 | Karan et al. |
| 2012/0313785 | A1 | 12/2012 | Hanson et al. |
| 2013/0035575 | A1 | 2/2013 | Mayou et al. |
| 2013/0109944 | A1 | 5/2013 | Sparacino et al. |
| 2013/0184547 | A1 | 7/2013 | Taub et al. |
| 2013/0235166 | A1 | 9/2013 | Jones et al. |
| 2013/0338629 | A1 | 12/2013 | Agrawal et al. |
| 2013/0338630 | A1 | 12/2013 | Agrawal et al. |
| 2014/0012511 | A1 | 1/2014 | Mensinger et al. |
| 2014/0066735 | A1 | 3/2014 | Engelhardt et al. |
| 2014/0088393 | A1 | 3/2014 | Bernstein et al. |
| 2014/0121480 | A1 | 5/2014 | Budiman et al. |
| 2014/0266785 | A1 | 9/2014 | Miller et al. |
| 2014/0313052 | A1 | 10/2014 | Yarger et al. |
| 2014/0379273 | A1 | 12/2014 | Petisce et al. |
| 2015/0123810 | A1 | 5/2015 | Hernandez-Rosas et al. |
| 2015/0205947 | A1 | 7/2015 | Berman et al. |
| 2015/0207796 | A1 | 7/2015 | Love et al. |
| 2019/0192087 | A1 | 6/2019 | Johnson et al. |
| 2020/0037965 | A1 | 2/2020 | Johnson et al. |
| 2020/0221983 | A1 | 7/2020 | Taub et al. |
| 2020/0246543 | A1 | 8/2020 | Sadehhzadeh et al. |
| 2020/0268325 | A1 | 8/2020 | Johnson et al. |
| 2021/0074424 | A1 | 3/2021 | Johnson et al. |
| 2022/0101995 | A1 | 3/2022 | Johnson et al. |

FOREIGN PATENT DOCUMENTS

| CN | 102163206 | A | 8/2011 |
| DE | 4401400 | | 7/1995 |
| EP | 0098592 | | 1/1984 |
| EP | 0127958 | | 12/1984 |
| EP | 0320109 | | 6/1989 |
| EP | 0353328 | | 2/1990 |
| EP | 0390390 | | 10/1990 |
| EP | 0396788 | | 11/1990 |
| EP | 0286118 | | 1/1995 |
| EP | 1048264 | | 11/2000 |
| EP | 2 109 394 | B1 | 5/2018 |
| EP | 2 914 159 | B1 | 4/2021 |
| EP | 2 939 158 | B1 | 3/2022 |
| WO | WO-1996/025089 | | 8/1996 |
| WO | WO-1996/035370 | | 11/1996 |
| WO | WO 99/04043 | A1 | 1/1999 |

(56) References Cited

FOREIGN PATENT DOCUMENTS

| WO | WO-2000/049940 | | 8/2000 | | |
| WO | WO-2000/059370 | | 10/2000 | | |
| WO | WO-2000/074753 | | 12/2000 | | |
| WO | WO-2001/052935 | | 7/2001 | | |
| WO | WO-2001/054753 | | 8/2001 | | |
| WO | WO-2002/016905 | | 2/2002 | | |
| WO | WO-02062212 | A2 * | 8/2002 | ........... | A61B 5/7475 |
| WO | WO-2003/076893 | | 9/2003 | | |
| WO | WO-2003/082091 | | 10/2003 | | |
| WO | WO 2004/006982 | A2 | 1/2004 | | |
| WO | WO 2004/093648 | A2 | 11/2004 | | |
| WO | WO 2005/065538 | A2 | 7/2005 | | |
| WO | WO 2005/121785 | A2 | 12/2005 | | |
| WO | WO-2006/024671 | | 3/2006 | | |
| WO | WO 2006/079867 | A1 | 8/2006 | | |
| WO | WO-2008/001366 | | 1/2008 | | |
| WO | WO-2008/086541 | | 7/2008 | | |
| WO | WO 2008/153693 | A1 | 12/2008 | | |
| WO | WO 2009/136372 | A1 | 11/2009 | | |
| WO | WO-2010/077329 | | 7/2010 | | |
| WO | WO 2010/127169 | A2 | 11/2010 | | |
| WO | WO 2011/032177 | A2 | 3/2011 | | |
| WO | WO 2012/154286 | A1 | 11/2012 | | |
| WO | WO 2014/070456 | A1 | 5/2014 | | |
| WO | WO 2015/069797 | A1 | 5/2015 | | |
| WO | WO 2016/092448 | A1 | 6/2016 | | |

OTHER PUBLICATIONS

About Dexcom—Continuous Glucose Monitoring Company, 2021, 12 pages.

About the Congressional Record, Congress.gov, Library of Congress, retrieved from https://www.congress.gov/help/congressional-record on Feb. 22, 2022, 3 pages.

Aleppo, G., et al., "Replace-BG: A Randomized Trial Comparing Continuous Glucose Monitoring With and Without Routine Blood Glucose Monitoring in Adults With Well-Controlled Type 1 Diabetes", Diabetes Care, 2017, vol. 40, pp. 538-545.

Alva, S., et al., "Accuracy of a 14-Day Factory-Calibrated Continuous Glucose Monitoring System With Advanced Algorithm in Pediatric and Adult Population With Diabetes", Journal of Diabetes Science and Technology, 2022, vol. 16, No. 1, pp. 70-77.

Amended Specification, 30 pages.

Amended Specification, 170 pages.

American Diabetes Association, "Standards of Medical Care in Diabetes—2009", Diabetes Care, 2009, vol. 32, Supplement 1, pp. S13-S61.

American Diabetes Association Workgroup on Hypoglycemia, "Defining and Reporting Hypoglycemia in Diabetes", Diabetes Care, 2005, vol. 28, No. 5, pp. 1245-1249.

Amiel, S. A., et al., "Hypoglycaemia in Type 2 diabetes", Diabetic Medicine, 2008, vol. 25, pp. 245-254.

Ananthi, S., A Text Book of Medical Instruments, 2005, pp. 283-284, 289, and 404.

"Animas® Vibe™, the First Integrated Offering from Animas Corporation and Dexcom, Inc., Receives European CE Mark Approval", 2011, retrieved from https://www.jnj.com/media-center/press-releases/animas-vibe-the-first-integrated-offering-from-animas-corporation-and-dexcom-inc-receives-european-ce-mark-approval, 3 pages.

"Authentication", Newton's Telecom Dictionary, 30th Updated, Expanded, Anniversary Edition, 2016, pp. 175-176.

"Authentication", A Dictionary of Computer Science, Seventh Edition, 2016, p. 32.

Bailey, T. S., et al., "Reduction in Hemoglobin A1c with Real-Time Continuous Glucose Monitoring: Results from a 12-Week Observational Study", Diabetes Technology & Therapeutics, 2007, vol. 9, No. 3, pp. 203-210.

Ballard, B., User Interface Design Guidelines for J2ME MIDP 2.0, 2005, pp. 5 and 17-22.

Bequette, B. W., "Continuous Glucose Monitoring: Real-Time Algorithms for Calibration, Filtering, and Alarms", Journal of Diabetes Science and Technology, 2010, vol. 4, Issue 2, pp. 404-418.

Bindra, D.S., et al., "Design and in Vitro Studies of a Needle-Type Glucose Sensor for Subcutaneous Monitoring," Anal. Chem., 1991, vol. 63, No. 17, pp. 1692-1696.

Biomedical Engineering Desk Reference, 2009, pp. 473 and 475.

Bluetooth® Secure Simple Pairing Using NFC, NFC Forum™, 2014, 39 pages.

Bode, B., et al., "Alarms Based on Real-Time Sensor Glucose Values Alert Patients to Hypo- and Hyperglycemia: The Guardian Continuous Glucose Monitoring System", Diabetes Technology & Therapeutics, 2004, vol. 6, No. 2, pp. 105-113.

Breen, C., The iPhone Pocket Guide, Sixth Edition, 2012, 96 pages.

Brown, A., et al., "test drive—Dexcom's G4 Platinum CGM", diaTribe Learn Making Sense of Diabetes, 2012, 4 pages.

Buckingham, B., et al., "Prevention of Nocturnal Hypoglycemia Using Predictive Alarm Algorithms and Insulin Pump Suspension", Diabetes Care, 2010, vol. 33, No. 5, pp. 1013-1017.

Burr, W. E., et al., Electronic Authentication Guideline, NIST Special Publication 800-63-2, 2013, 123 pages.

Burton, D., Urging FDA to Act Promptly to Approve Artificial Pancreas Technologies, Congressional Record (Bound Edition), 2011, vol. 157, Part 13, 3 pages.

Campbell, F. M., et al., "Outcomes of using flash glucose monitoring technology by children and young people with type 1 diabetes in a single arm study", Pediatric Diabetes, 2018, vol. 19, pp. 1294-1301.

CGMS® iPro™ Continuous Glucose Recorder User Guide, 2007, pp. 1-36.

"CGMS® System Gold™ Continuous Glucose Monitoring Overview", 2004, retrieved from http://www.minimed.com/doctors/md_products_cgms_ov_completepic.shtml, 20 pages.

Choudhary, P., et al., "Insulin Pump Therapy with Automated Insulin Suspension in Response to Hypoglycemia", Diabetes Care, 2011, vol. 34, pp. 2023-2025.

Choudhary, P., et al., "Hypoglycemia in the treatment of diabetes mellitus", Chapter 13.4.8, Oxford Textbook of Endocrinology and Diabetes, Wass et al., Eds., 2011, pp. 1849-1860.

Claims, Specification and Drawings for System and Methods for Providing Sensitive and Specific Alarms, 103 pages.

Clarke, W. L., et al., "Continuous Glucose Sensors: Continuing Questions about Clinical Accuracy", Journal of Diabetes Science and Technology, 2007, vol. 1, No. 5, pp. 669-675.

Clarke, W., et al., "Statistical Tools to Analyze Continuous Glucose Monitor Data", Diabetes Technology & Therapeutics, 2009, vol. 11, Suppl. 1, pp. S-45-S-54.

Close, K., "Test Driving Dexcom's Short-Term Sensor (STS): A Look at Continuous Glucose Monitoring", 2006, retrieved from https://diatribe.org/test-driving-dexcoms-short-term-sensor-sts-look-continuous-glucose-monitoring, 2 pages.

Committee for Proprietary Medicinal Products (CPMP), The European Agency for the Evaluation of Medicinal Products, 2002, pp. 1-12.

Continuous Glucose Monitoring (CGM)/Real-Time Flash Glucose Scanning (FGS) Training for Healthcare Professionals and Patients, Association of Children's Diabetes Clinicians, 2017, 50 pages.

Cryer, P. E., "Preventing hypoglycaemia: what is the appropriate glucose alert value?", Diabetologia, 2009, vol. 52, pp. 35-37.

In Vivo Glucose Sensing, Cunningham et al., Eds., 2010, Chemical Analysis, vol. 174, pp. 1-466.

Custodio, V., et al., "A Review on Architectures and Communications Technologies for Wearable Health-Monitoring Systems", Sensors, 2012, vol. 12, pp. 13907-13946.

DAFNE Study Group, "Training in flexible, intensive insulin management to enable dietary freedom in people with type 1 diabetes: dose adjustment for normal eating (DAFNE) randomized controlled trial", British Medical Journal, 2002, vol. 325, pp. 1-6.

Dassau, E., et al., "Real-Time Hypoglycemia Prediction Suite Using Continuous Glucose Monitoring, A safety net for the artificial pancreas", Diabetes Care, 2010, vol. 33, No. 3, pp. 1249-1254.

(56)　　　References Cited

OTHER PUBLICATIONS

Declaration of Duncan Hall (2021) including DexCom™ STS™ Continuous Glucose Monitoring System User's Guide (2006), 64 pages.
Declaration of Thomas Edward Foster, Jan. 30, 2024, 160 pages.
Desalvo, D. J., et al., "Remote Glucose Monitoring in Camp Setting Reduces the Risk of Prolonged Nocturnal Hypoglycemia", Diabetes Technology & Therapeutics, 2014, vol. 16, No. 1, pp. 1-10.
Deshmukh, H., et al., "Effect of Flash Glucose Monitoring on Glycemic Control, Hypoglycemia, Diabetes-Related Distress, and Resource Utilization in the Association of British Clinical Diabetologists (ABCD) Nationwide Audit", Diabetes Care, 2020, vol. 43, No. 9, pp. 2153-2160.
Devries, J. H., "Glucose Sensing Issues for the Artificial Pancreas", Journal of Diabetes Science and Technology, 2008, vol. 2, No. 4, pp. 732-734.
Dexcom 2022 Annual Report, retrieved from https://s201.q4cdn.com/758408164/files/doc_financials/2022/ar/d439095dars.pdf, 148 pages.
Dexcom 2023 Investor Day Presentation, retrieved from https://s201.q4cdn.com/758408164/files/doc_presentation/2023/06/Investor-Day-Presentation_June-2023.pdf, 74 pages.
Dexcom Distributor Code of Conduct, 2022, retrieved from https://dexcompdf.s3.us-west-2.amazonaws.com/Global+Trust+Center/LBL-1000720+Rev002+Distributor+Code+of+Conduct.pdf, 21 pages.
Dexcom EC Declarations of Conformity for G6 and G7 Systems in Belgium, Denmark, Finland, France, Germany, Italy, Luxembourg, Malta, Netherland, Portugal, Slovenia, and Sweden, 2024, retrieved from https://www.dexcom.com/doc, 408 pages.
Dexcom Form 10-K, 2022, 368 pages.
Dexcom Form 10-K, 2023, 303 pages.
Dexcom G4 Continuous Glucose Monitoring System User's Guide, 2013, pp. 1-156.
"Dexcom G6® CGM System Receives CE Mark", 2018, retrieved from https://investors.dexcom.com/news/news-details/2018/Dexcom-G6-CGM-System-Receives-CE-Mark/default.aspx#:~:text=The%20CE%20Marking%20confirms%20that,About%20Dexcom%20G6, 3 pages.
Dexcom G6 Sensor 3 Pack, 2003-2022, retrieved from https://www.protherapysupplies.com/Shop-By-Category/Blood-Glucose-Monitors-Supplies-Insurance/Dexcom-G6-Sensor-3-Pack_2, 2 pages.
Dexcom G6 User Guide, 2023, 124 pages.
Dexcom_G7_Presentation, 2024, retrieved from https://apkpure.com/dexcom-g7/com.dexcom.g7, 6 pages.
Dexcom G7 Start Here Guide, 2023, 7 pages.
Dexcom G7 User Guide, 2023, 154 pages.
"Dexcom, Inc. Announces Acquisition of its Distributor in Germany, Switzerland and Austria", 2016, retrieved from https://investors.dexcom.com/news/news-details/2016/Dexcom-Inc.-Announces-Acquisition-of-its-Distributor-in-Germany-Switzerland-and-Austria/default.aspx, 1 page.
Dexcom International Limited Filing History, 2018, 83 pages.
Dexcom International Limited Overview, 2018, 1 page.
Dexcom Privacy Policy, 2021, 59 pages.
Dexcom Seven Plus Continuous Glucose Monitoring System FDA Premarket Approval (PMA), 2024, pp. 1-3.
DexCom™ STS™ Sensor Instructions for Use, 2006, pp. 1-6.
DexCom™ STS™ Summary of Safety and Effectiveness Data, 2006, pp. 1-20.
DexCom™ STS™ Continuous Glucose Monitoring System User's Guide, 2006, pp. 1-57.
Dexcom STS-7 Continuous Glucose Monitoring System FDA Premarket Approval (PMA), 2007, pp. 1-7.
Dexcom STS®-7 Continuous Glucose Monitoring System User's Guide, 2007, pp. 1-74.
Dexcom STS®-7 Summary of Safety and Effectiveness Data, 2007, pp. 1-14.
Dexcom Terms of Use, 2023, 33 pages.
"Dexcom Unlocks Access to Real-Time CGM for a Further Half a Million People With Diabetes in France", 2023, retrieved from https://investors.dexcom.com/news/news-details/2023/Dexcom-Unlocks-Access-to-Real-Time-CGM-for-a-Further-Half-a-Million-People-With-Diabetes-in-France/default.aspx#:~:text=%E2%80%9CWe%20believe%20this%20is%20truly,time%20in%20range3%2D5., 2 pages.
The Diabetes Control and Complications Trial Research Group, "The Effect of Intensive Treatment of Diabetes on the Development and Progression of Long-Term Complications in Insulin-Dependent Diabetes Mellitus", The New England Journal of Medicine, 1993, vol. 329, No. 14, pp. 977-986.
The Diabetes Research in Children Network (DirecNet) Study Group, "GlucoWatch® G2™ Biographer (GW2B) Alarm Reliability During Hypoglycemia in Children", Diabetes Technology & Therapeutics, 2004, vol. 6, No. 5, pp. 559-566.
Diabetes (Type 1) Top 10, James Lind Alliance, 2022, retrieved from https://www.jla.nihr.ac.uk/priority-setting-partnerships/diabetes-type-1/top-10-priorities/, 3 pages.
"Empowering people to take control of health", 2024, https://www.dexcom.com/about-dexcom, 5 pages.
Eriksen, K., et al., Orthospinology Procedures: An Evidence-Based Approach to Spinal Care, 2007, Chapter 10: Outcome Assessments and Documentation, pp. 128-129.
Evidence of Dexcom G7 launch in Belgium, 2023, retrieved from https://www.instagram.com/p/CxphQmtsG9R/, 1 page.
"Extracellular fluid", 2023, Wikipedia, 3 pages.
Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.
"FDA Premarket Approval (PMA)" retrieved from https://www.accessdata.fda.gov/scripts/cdrh/cfdocs/cfpma/pma.cfm?ID=P050020, 6 pages.
Feature Analysis, 1 page.
Federal Register, 2011, vol. 76, No. 120, pp. 36542-36543.
File History of U.S. Pat. No. 9,119,528.
File History of U.S. Pat. No. 9,801,541.
File History of U.S. Pat. No. 10,375,222.
File History of U.S. Pat. No. 11,213,204.
U.S. Appl. No. 61/551,773.
Fogt, E. J., et al., "< Development and Evaluation of a Glucose Analyzer for a Glucose-Controlled Insulin Infusion System (Biostater®), Clinical Chemistry, 1978, vol. 24, No. 8, pp. 1366-1372.
FreeStyle Libre 2 User's Manual, 2019-2021, pp. 1-141.
FreeStyle Libre 3 User's Manual, 2022, pp. 1-59.
FreeStyle Navigator Continuous Glucose Monitoring System FDA Premarket Approval (PMA), 2008, pp. 1-7.
FreeStyle Navigator Continuous Glucose Monitoring System User's Guide, 2008, 38 pages.
Freestyle Navigator User's Guide, 2008, pp. 1-195.
Freestyle Navigator User's Guide, 2010, pp. 1-135.
Freestyle Navigator Summary of Safety and Effectiveness Data, 2008, pp. 1-27.
FreeStyle Navigator II User's Manual, 2011, pp. 1-36.
Frier, B. M., "Defining hypoglycaemia: what level has clinical relevance?", Diabetologia, 2009, vol. 52, pp. 31-34.
"Function", A Dictionary of Computing, Sixth Edition, 2008, p. 213.
Garg, S.K., et al., "Improved Glucose Excursions Using an Implantable Real-Time Continuous Glucose Sensor in Adults with Type 1 Diabetes", Diabetes Care, 2004, vol. 27, No. 3, pp. 734-738.
Garg, S., et al., "Relationship of Fasting and Hourly Blood Glucose Levels to HbA$_{1c}$ Values", Diabetes Care, 2006, vol. 29, No. 12, pp. 2644-2649.
GlucoWatch® G2™ Automatic Glucose Biographer User's Guide, 2002, pp. 1-70.
Guerra, S., et al., "A Dynamic Risk Measure from Continuous Glucose Monitoring Data", Diabetes Technology & Therapeutics, 2011, vol. 13, No. 8, pp. 843-852.
"Guideline on clinical investigation of medicinal products in the treatment or prevention of diabetes mellitus", European Medicines Agency, 2012, pp. 1-28.

(56) References Cited

OTHER PUBLICATIONS

Haak, T., et al., "Use of a Flash Glucose-Sensing Technology for 12 months as a Replacement for Blood Glucose Monitoring in Insulin-treated Type 2 Diabetes", Diabetes Ther., 2017, vol. 8, No. 3, pp. 573-586.

Hanlon, M., "DexCom's 7-Day STS Continuous Glucose Monitoring System", 2007, retrieved from https://newatlas.com/dexcoms-7-day-sts-continuous-glucose-monitoring-system/7376/, 1 page.

Harvey, R. A., et al., "Clinically Relevant Hypoglycemia Prediction Metrics for Event Migration", Diabetes Technology & Therapeutics, 2012, vol. 14, No. 8, pp. 720-727.

Hashimoto, N., et al., "Efficacy of color indicator function on One Touch Ultra Vue™", Medicine and Pharmacy, 2010, vol. 63, No. 4, pp. 637-642.

Hayter, P. G. et al., "Performance Standards for Continuous Glucose Monitors", Diabetes Technology & Therapeutics, 2005, vol. 7, No. 5, pp. 721-726.

Heinemann, L., et al., "Glucose Clamps with the Biostator: A Critical Reappraisal", Hormone and Metabolic Research, 1994, vol. 26, No. 12, pp. 579-583.

Heller, A., et al., "Electrochemical Glucose Sensors and Their Applications in Diabetes Management", Chemical Reviews, 2008, vol. 108, No. 7, pp. 2482-2505.

Hermanns, N., et al., "The Impact of Continuous Glucose Monitoring on Low Interstitial Glucose Values and Low Blood Glucose Values Assessed by Point-of-care Blood Glucose Meters: Results of a Crossover Trial", Journal of Diabetes Science and Technology, 2014, vol. 8, No. 3, pp. 516-522.

"Home screen", Merrian-Webster.com Dictionary, 2024, retrieved from https://www.merriam-webster.com/dictionary/home%20screen, 4 pages.

Hovorka, R., "Closing the loop", Chapter 13.4.9.2, Oxford Textbook of Endocrinology and Diabetes, Wass et al., Eds., 2011, p. 1869.

Hoyng, W., "The Unified Patent Court (UPC) opens its doors!", 2023, retrieved from https://www.hoyngrokhmonegier.com/assets/media/2023/05/TiU_230100_TLS_Redeboekje_Willem-Hoyng_BW.pdf, 41 pages.

Hughes, C. S., et al., "Hypoglycemia Prevention via Pump Attenuation and Red-Yellow-Green "Traffic" Lights Using Continuous Glucose Monitoring and Insulin Pump Data", Journal of Diabetes Science and Technology, 2010, vol. 4, No. 5, pp. 1146-1155.

Huizinga, D., et al., Automated Defect Prevention, Best Practices in Software Management, 2007, pp. 191-192.

"Icon", Merrian-Webster.com Dictionary, 2024, retrieved from https://www.merriam-webster.com/dictionary/icon, 6 pages.

Innovation Milestones et al., 2021, retrieved from https://www.medtronicdiabetes.com/about-medtronic-innovation/milestone-timeline, 37 pages.

Instructions for Use DexCom™ STS™ Sensor, 1 page.

International Hypoglycaemia Study Group, "Glucose Concentrations of Less Than 3.0 mmol/L (54 mg/dL) Should Be Reported in Clinical Trials: A Joint Position Statement of the American Diabetes Association and the European Association for the Study of Diabetes", Diabetes Care, 2017, vol. 40, pp. 155-157.

International Standard, IEC 60601-1-8, Medical Electrical Equipment, 2006, 166 pages.

"Introducing the new Dexcom G6 CGM System." 2024, retrieved from https://www.dexcom.com/en-LB/dexcom-g6-cgm-system, 12 pages.

IPhone (1st generation), 2024, Wikipedia, 7 pages.

Javanmardi, C. A., et al., "G4 Platinum Continuous Glucose Monitor", 2013, retrieved from https://www.uspharmacist.com/article/g4-platinum-continuous-glucose-monitor-43117, 8 pages.

Kamath, A., et al., "Methods of Evaluating the Utility of Continuous Glucose Monitor Alerts", Journal of Diabetes Science and Technology, 2010, vol. 4, No. 1, pp. 57-66.

Keith-Hynes, P., et al., "The Diabetes Assistant: A Smartphone-Based System for Real-Time Control of Blood Glucose", Electronics, 2014, vol. 3, pp. 609-623.

Klonoff, D. C., et al., "Innovations in Technology for the Treatment of Diabetes: Clinical Development of the Artificial Pancreas (an Autonomous System)", Journal of Diabetes Science and Technology, 2011, vol. 5, Issue 3, pp. 804-826.

Kovatchev, B. P., et al., "Symmetrization of the Blood Glucose Measurement Scale and Its Applications", Diabetes Care, 1997, vol. 20, No. 11, pp. 1655-1658.

Kowalski, A. J., "Can We Really Close the Loop and How Soon? Accelerating the Availability of an Artificial Pancreas: A Roadmap to Better Diabetes Outcomes", Diabetes Technology & Therapeutics, 2009, vol. 11, Suppl. 1, pp. S-113-S-119.

Letter from Department of Health & Human Services re. FreeStyle Navigator Continuous Glucose Monitoring System, 2008, 7 pages.

Letter to EPO re. Divisional Application of EP Application No. 13784079.9 in the name of Dexcom, Inc., 2020, 2 pages.

Ley, T., "Continuous Glucose Monitoring: A Movie is Worth a Thousand Pictures A Review of the Medtronic Guardian REAL-time system", 2021, retrieved from https://nfb.org/images/nfb/publications/vod/vod_22_4/vodfal0702.htm, 3 pages.

McDaniel, D., et al., "Remote Management of Cardiac Patients, The Forefront of a New Standard", Modern Healthcare, 2011, 6 pages.

McMurry, J. F., "The Artificial Pancreas Today", Henry Ford Hospital Medical Journal, 1983, vol. 31, No. 2, Article 4, pp. 77-83.

Medtronic Guardian® REAL-Time Continuous Glucose Monitoring System User Guide, 2006, pp. 1-181.

"Medtronic Launches First-of-Its-Kind mySentry™ Remote Glucose Monitor", 2012, retrieved from https://news.medtronic.com/2012-01-04-Medtronic-Launches-First-of-Its-Kind-mySentry-TM-Remote-Glucose-Monitor, 8 pages.

Medtronic MiniMed Paradigm® REAL-Time Revel™ Insulin Pump User Guide, 2009, Chapters 1-5, pp. ix-179.

Microsoft Applications for Windows Mobile 6 User Guide, Revision A, 2008, Motorola, Inc., 182 pages.

Mosa, ASM, et al., "A Systematic Review of Healthcare Applications for Smartphones", BMC Medical Informatics and Decision Making, 2012, vol. 12, No. 67, pp. 1-31.

Murphy, H. R., et al., "Closed-Loop Insulin Delivery During Pregnancy complicated by Type 1 Diabetes", Diabetes Care, 2011, vol. 34, pp. 406-411.

MySentry™ User Guide, Medtronic Minimed, 2010, 80 pages.

National Service Framework for Diabetes: Standards, 2001, pp. 1-45.

Oliver, N. S., et al., "Glucose sensors: a review of current and emerging technology", Diabetic Medicine, 2009, vol. 26, pp. 197-2110.

Omre, A. H., "Bluetooth Low Energy: Wireless Connectivity for Medical Monitoring", Journal of Diabetes Science and Technology, 2010, vol. 4, No. 2, pp. 458-463.

One Touch Ultra Vue™ Handling Instructions, 2018, p. 34.

Select pages from OneTouch UltraVue User Manual published on Oct. 1, 2009 (with English Translation), 4 pages.

Padgette, J., et al., "Guide to Bluetooth Security", Revision 1, 2012, 48 pages.

Palerm, C. C., et al., "Hypoglycemia Prediction and Detection Using Optimal Estimation", Diabetes Technology & Therapeutics, 2005, vol. 7, No. 1, pp. 3-14.

Palerm, C. C., et al., "Hypoglycemia Detection and Prediction Using Continuous Glucose Monitoring—A Study on Hypoglycemic Clamp Data", Journal of Diabetes Science and Technology, 2007, vol. 1, No. 5, pp. 624-629.

Pickup, J. C., et al., "Glycaemic control in type 1 diabetes during real time continuous glucose monitoring compared with self monitoring of blood glucose: meta-analysis of randomised controlled trials using individual patient data", British Medical Journal, 2011, pp. 1-14.

Pickup, J. C., "Glucose monitoring", Chapter 13.4.9.1, Oxford Textbook of Endocrinology and Diabetes, Wass et al., Eds., 2011, pp. 1861-1868.

Pickup, J. C., et al., "Semi-Closed-Loop Insulin Delivery Systems: Early Experience with Low-Glucose Insulin Suspend Pumps", Diabetes Technology & Therapeutics, 2011, vol. 13, No. 7, pp. 695-698.

(56)                  References Cited

OTHER PUBLICATIONS

Place, J., et al., "DiAs Web Monitoring: A Real-Time Remote Monitoring System Designed for Artificial Pancreas Outpatient Trials", Journal of Diabetes Science and Technology, 2013, vol. 7, No. 6, pp. 1427-1435.

"PMA Approvals" retrieved from https://www.fda.gov/medical-devices/device-approvals-denials-and-clearances/pma-approvals#monthly, 3 pages.

"PMA Final Decisions Rendered for May 2007", retrieved on Jan. 30, 2024 from https://web.archive.org/web/20070630150626/http:/www.fda.gov.cdrh/pma/pmamay07.html, 21 pages.

Puhr, S., et al., "Real-World Hypoglycemia Avoidance With a Predictive Low Glucose Alert Does Not Depend on Frequent Screen Views", Journal of Diabetes Science and Technology, 2020, vol. 14, No. 1, pp. 83-86.

"Reaching More of the World", Johnson & Johnson Annual Report 2010, 2 pages.

Rilstone, S., et al., "The impact of CGM with a predictive hypoglycaemia alert function on hypoglycaemia in physical activity for people with type 1 diabetes: PACE study", 58th Annual Meeting of the European Association for the Study of Diabetes, Stockholm, 2022, 2 pages.

Roussel, R., et al., "Important Drop in Rate of Acute Diabetes Complications in People With Type 1 or Type 2 Diabetes After Initiation of Flash Glucose Monitoring in France: The RELIEF Study", Diabetes Care, 2021, vol. 44, No. 6, pp. 1368-1376.

Sandham, W., et al., "Blood Glucose Prediction for Diabetes Therapy Using a Recurrent Artificial Neural Network", 9th European Signal Processing Conference, 1998, Rhodes, Greece, pp. 1-4.

Schiavon, M., "An online method for prevention of the risk of glycemic shock in diabetic patients from continuous glucose monitoring data", Apr. 20, 2010, pp. 1-117 (Machine Translation of Summary).

Sommervile, I., Software Engineering, Eighth Edition, 2007, p. 374.

Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.

Specification of the Bluetooth System, Version 1.2, 2003, Specification vol. 0, pp. 2-40, 224-236 and 746-783.

Specification of the Bluetooth System, Version 4, 2010, Specification vol. 0, pp. 2-38, 85-92, 1056-1110, 295-313, and 362-374.

Steil, G. M., et al., "Feasibility of Automating Insulin Delivery for the Treatment of Type 1 Diabetes", Diabetes, 2006, vol. 55, pp. 3344-3350.

Stone, D., et al., User Interface Design and Evaluation, 2005, Chapter 5, Part 2, pp. 89-101, Chapter 9, Part 3, pp. 165-186, Chapter 13, Part 3, pp. 247-269, Chapter 17, Part 3, pp. 331-369, and Glossary, Part 5, pp. 605-629.

Strömmer, E., et al., "Application of Near Field Communication for Health Monitoring in Daily Life", Proceedings of the 28th IEEE EMBS Annual International Conference, New York City, USA, Aug. 30-Sep. 3, 2006, pp. 3246-3249.

STS-7 Continuous Glucose Monitoring System—P050012/S001, 2007, retrieved from https://web.archive.org/web/20070705190828/http:/www.fda.gov:80/cdrh/pdf5/p050012s001.html, 1 page.

Swinnen, S. G. H. A., et al., "Changing the glucose cut-off values that define hypoglycaemia has a major effect on reported frequencies of hypoglycaemia", Diabetologia, 2009, vol. 52, pp. 38-41.

"text", Merrian-Webster.com Dictionary, 2024, retrieved from https://www.merriam-webster.com/dictionary/text, 7 pages.

Townsend, K., et al., "Getting Started with Bluetooth Low Energy", 2014, 180 pages.

"Type 1 diabetes: diagnosis and management of type 1 diabetes in children, young people and adults", National Collaborating Centre for Women's and Children's Health and the National Collaborating Centre for Chronic Conditions, Clinical Guideline 15, 2004, pp. 1-112.

"Type 1 Diabetes Research Roadmap", JDRF, 2013, pp. 1-38.

Wang, J., et al., "A Feasible IMD Communication Protocol: Security without Obscurity", NYIT School of Engineering and Computing Sciences, 2015, 1 page.

Weinstein, M., et al., "Diabetes Care, ADA 2006: Spotlight on Continuous Glucose Monitoring", JP Morgan, North America Equity Research, 2006, pp. 1-15.

Weinzimer, S. A., et al., "Fully Automated Closed-Loop Insulin Delivery Versus Semiautomated Hybrid Control in Pediatric Patients with Type 1 Diabetes Using an Artificial Pancreas", Diabetes Care, 2008, vol. 31, No. 5, pp. 934-939.

Wettlaufer, G. J., "merlin.net Automation of External Reports Verification Process", A Thesis Presented to The Faculty of California Polytechnic State University, San Luis Obispo, 2010, 53 pages.

Wiklund, M. E., Medical Device Equipment: Usability Engineering and Ergonomics, 1995, pp. 149-150 and 264.

Williams, S., et al., "The Guardian REAL-Time Continuous Glucose Monitoring System", 2007, retrieved from https://www.uspharmacist.com/article/the-guardian-real-time-continuous-glucose-momitoring-system, 16 pages.

Wilson, G. S., et al., In Vivo Glucose Sensing, Chapter 1, Introduction to the Glucose Sensing Problem, 2010, pp. 1-27.

Zhang, T., et al., "Bluetooth Low Energy for Wearable Sensor-based Healthcare Systems", IEEE Health Innovations and Point-of-Care Technologies Conference, Seattle, Washington, Oct. 8-10, 2014, pp. 251-254.

CN, 201480016099.2 Office Action, Sep. 15, 2017.

CN, 201480016099.2 Third Office Action, Feb. 27, 2019.

EP, 05851833.3 Decision of the Enlarged Board of Appea, Mar. 24, 2015.

EP, 14762779.8 Supplementary Search Report, Jul. 6, 2016.

EP, 19161571.5 Search Report, Jan. 15, 2020.

GB, Approved Judgment, Claim Nos. HP-2021-000025 & HP-2021-000026, Jan. 15, 2024.

GB, Approved Judgment, Claim No. HP-2021-000025, Oct. 18, 2023.

JP, 2016-503198 Notice of Grounds for Rejection, Mar. 6, 2018.

UP, Application to Communicate Information Pursuant to Rule 191, Case No. ACT_587074/2023 and CC_20188/2024, Jun. 17, 2024.

UP, Application to Amend the Patent Pursuant to Rule 30, Case No. ACT_587074/2023 and CC_20188/2024, Jun. 17, 2024.

UP. Order, Action Number UPC_CoA_335/2023 and APP_576355/2023, Feb. 26, 2024.

US, Declaration of Lane Desborough in Support of Petition for Inter Partes Review of U.S. Pat. No. 11,213,204 Under 35 U.S.C. §§ 311-319 and 37 C.F.R. § 42.100 et seq., IPR No. 2024-00853, May 3, 2024.

US, Declaration of Sylvia D. Hall-Ellis, Ph.D., IPR N0. 2024-00840, Apr. 24, 2024.

US, Declaration of David Rodbard, M.D. in Support of Petition for Inter Partes Review of U.S. Pat. No. 9,119,528, IPR No. 2024-00840, May 1, 2024.

US, Declaration of Dr. Sayfe Kiael, Ph.D., IPR No. 2024-00797, Apr. 9, 2024.

Armour, J. C., et al., "Application of Chronic Intravascular Blood Glucose Sensor in Dogs", Diabetes, vol. 39, 1990, pp. 1519-1526.

Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1070.

Bennion, N., et al., "Alternate Site Glucose Testing: A Crossover Design", Diabetes Technology & Therapeutics, vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Brooks, S. L., et al., "Development of an On-Line Glucose Sensor for Fermentation Monitoring", Biosensors, vol. 3, 1987/88, pp. 45-56.

Cass, A. E., et al., "Ferrocene-Medicated Enzyme Electrode for Amperometric Determination of Glucose", Analytical Chemistry, vol. 56, No. 4, 1984, 667-671.

(56) References Cited

OTHER PUBLICATIONS

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.

Csoregi, E., et al., "Design and Optimization of a Selective Sub-cutaneously Implantable Glucose Electrode Based on 'Wired' Glucose Oxidase", Analytical Chemistry, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Garg, S., et al., "Improvement in Glycemic Excursions with a Transcutaneous, Real-Time Continuous Glucose Sensor", Diabetes Care, vol. 29, No. 1, 2006, pp. 44-50.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, pp. 198.

Jovanovic, L., "The Role of Continuous Glucose Monitoring in Gestational Diabetes Mellitus", Diabetes Technology & Therapeutics, vol. 2, Sup. 1, 2000, pp. S67-S71.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Li, Y., et al., "In Vivo Release From a Drug Delivery MEMS Device", Journal of Controlled Release, vol. 100, 2004, 99. 211-219.

Lodwig, V., et al., "Continuous Glucose Monitoring with Glucose Sensors: Calibration and Assessment Criteria", Diabetes Technology & Therapeutics, vol. 5, No. 4, 2003, pp. 573-587.

Lortz, J., et al., "What is Bluetooth? We Explain The Newest Short-Range Connectivity Technology", Smart Computing Learning Series, Wireless Computing, vol. 8, Issue 5, 2002, pp. 72-74.

Malin, S. F., et al., "Noninvasive Prediction of Glucose by Near-Infrared Diffuse Reflectance Spectoscopy", Clinical Chemistry, vol. 45, No. 9, 1999, pp. 1651-1658.

McGarraugh, G., et al., "Glucose Measurements Using Blood Extracted from the Forearm and the Finger", TheraSense, Inc., 2001, 16 Pages.

McGarraugh, G., et al., "Physiological Influences on Off-Finger Glucose Testing", Diabetes Technology & Therapeutics, vol. 3, No. 3, 2001, pp. 367-376.

McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.

Mougiakakou, et al., "A Real Time Simulation Model of Glucose-Insulin Metabolism for Type 1 Diabetes Patients", Proceedings of the 2005 IEEE, 2005, pp. 298-301.

Panteleon, A. E., et al., "The Role of the Independent Variable to Glucose Sensor Calibration", Diabetes Technology & Therapeutics, vol. 5, No. 3, 2003, pp. 401-410.

Parker, R., et al., "Robust H∞ Glucose Control in Diabetes Using a Physiological Model", AlChE Journal, vol. 46, No. 12, 2000, pp. 2537-2549.

Pickup, J., et al., "Implantable Glucose Sensors: Choosing the Appropriate Sensing Strategy", Biosensors, vol. 3, 1987/88, pp. 335-346.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", The American Physiological Society, 1995, E155-E161.

Roe, J. N., et al., "Bloodless Glucose Measurements", Critical Review in Therapeutic Drug Carrier Systems, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salehi, C., et al., "A Telemetry-Instrumentation System for Long-Term Implantable Glucose and Oxygen Sensors", Analytical Letters, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M., et al., "Glycaemic Control in Pancreatectomized Dogs with a Wearable Artificial Endocrine Pancreas", Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.

Shichiri, M., et al., "Membrane Design for Extending the Long-Life of an Implantable Glucose Sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.

Shichiri, M., et al., "Wearable Artificial Endocrine Pancreas With Needle-Type Glucose Sensor", The Lancet, 1982, pp. 1129-1131.

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Sternberg, R., et al., "Study and Development of Multilayer Needle-Type Enzyme-Based Glucose Microsensors", Biosensors, vol. 4, 1988, pp. 27-40.

Thompson, M., et al., "In Vivo Probes: Problems and Perspectives", Clinical Biochemistry, vol. 19, 1986, pp. 255-261.

Turner, A., et al., "Diabetes Mellitus: Biosensors for Research and Management", Biosensors, vol. 1, 1985, pp. 85-115.

Updike, S. J., et al., "Principles of Long-Term Fully Implanted Sensors with Emphasis on Radiotelemetric Monitoring of Blood

(56) References Cited

OTHER PUBLICATIONS

Glucose from Inside a Subcutaneous Foreign Body Capsule (FBC)",
Biosensors in the Body: Continuous in vivo Monitoring, Chapter 4,
1997, pp. 117-137.
Velho, G., et al., "Strategies for Calibrating a Subcutaneous Glucose
Sensor", Biomedica Biochimica Acta, vol. 48, 1989, pp. 957-964.
Wilson, G. S., et al., "Progress Toward the Development of an
Implantable Sensor for Glucose", Clinical Chemistry, vol. 38, No.
9, 1992, pp. 1613-1617.

* cited by examiner

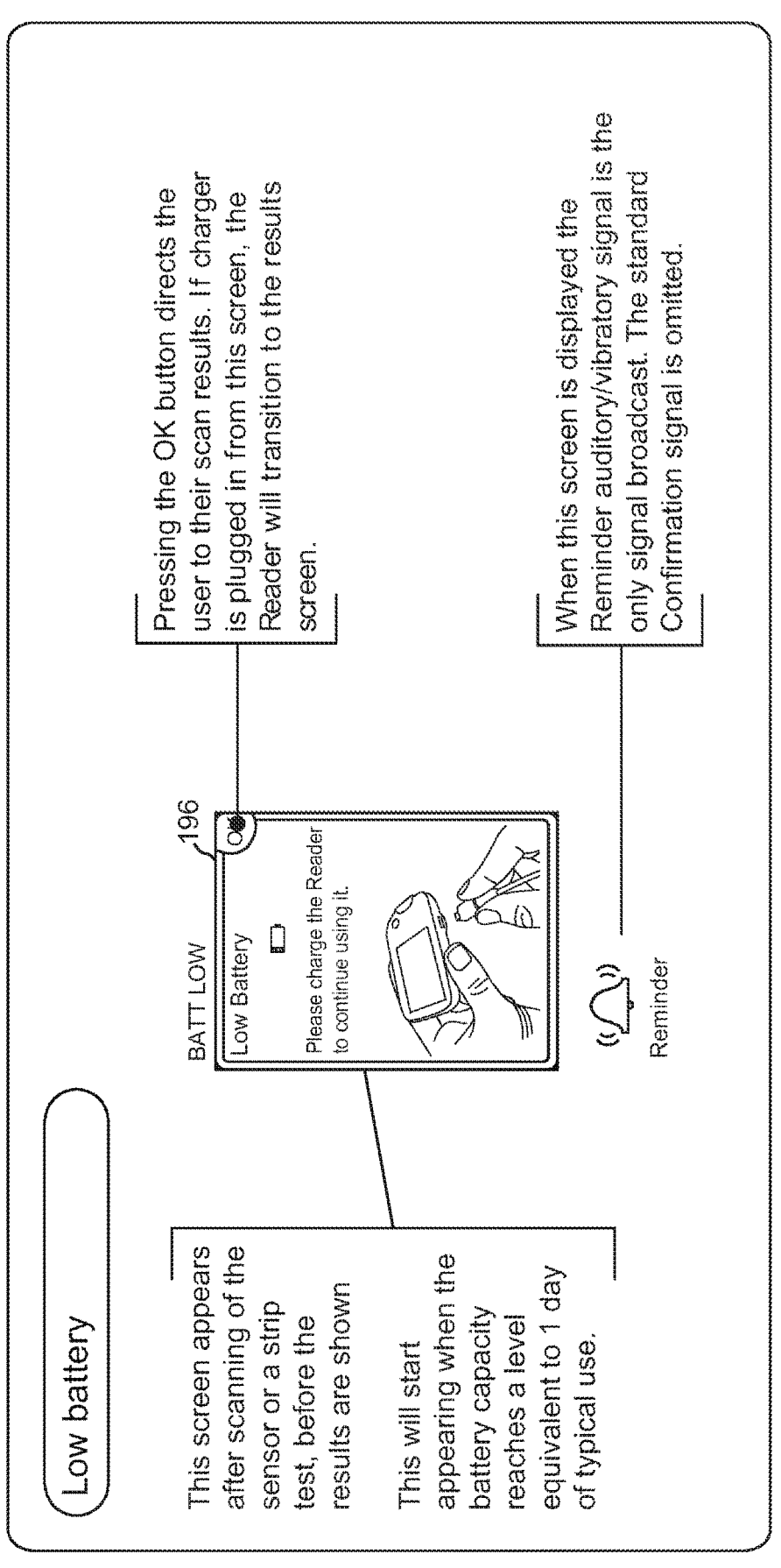

Low battery

This screen appears after scanning of the sensor or a strip test, before the results are shown This will start appearing when the battery capacity reaches a level equivalent to 1 day of typical use.

196

BATT LOW

Low Battery

Please charge the Reader to continue using it.

Reminder

Pressing the OK button directs the user to their scan results. If charger is plugged in from this screen, the Reader will transition to the results screen.

When this screen is displayed the Reminder auditory/vibratory signal is the only signal broadcast. The standard Confirmation signal is omitted.

FIG. 5E

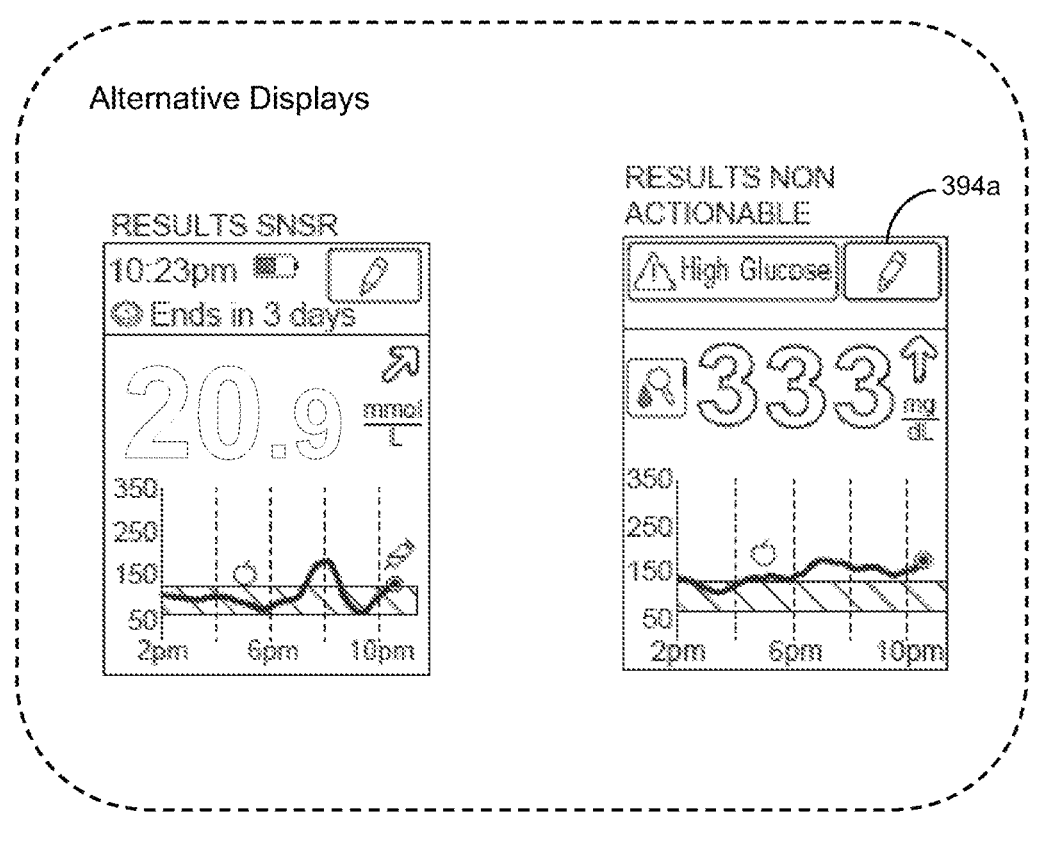
FIG. 10L                    FIG. 10M

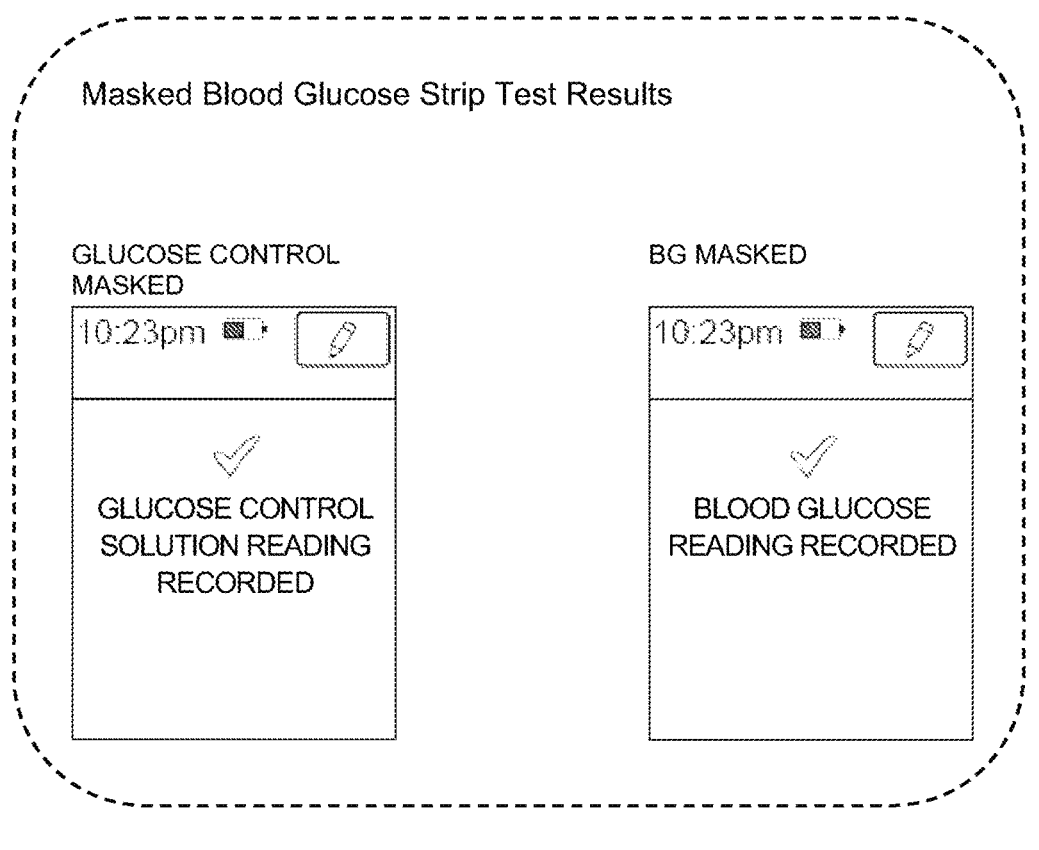
FIG. 12H                    FIG. 12I

Ketone Results     FIG. 14A     578

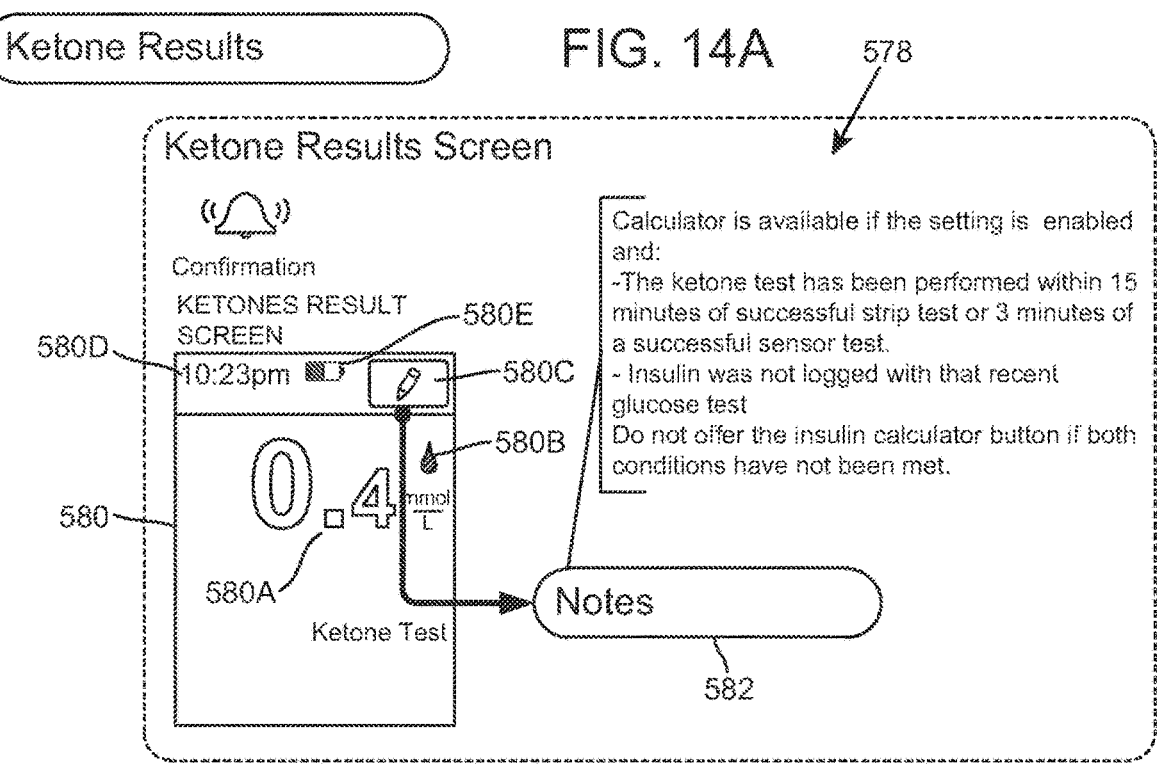

Ketone Results Screen

Confirmation
KETONES RESULT SCREEN — 580E
580D
10:23pm — 580C
0.4 mmol/L — 580B
580
580A
Ketone Test Calculator is available if the setting is enabled and:
-The ketone test has been performed within 15 minutes of successful strip test or 3 minutes of a successful sensor test.
- Insulin was not logged with that recent glucose test
Do not offer the insulin calculator button if both conditions have not been met.

Notes

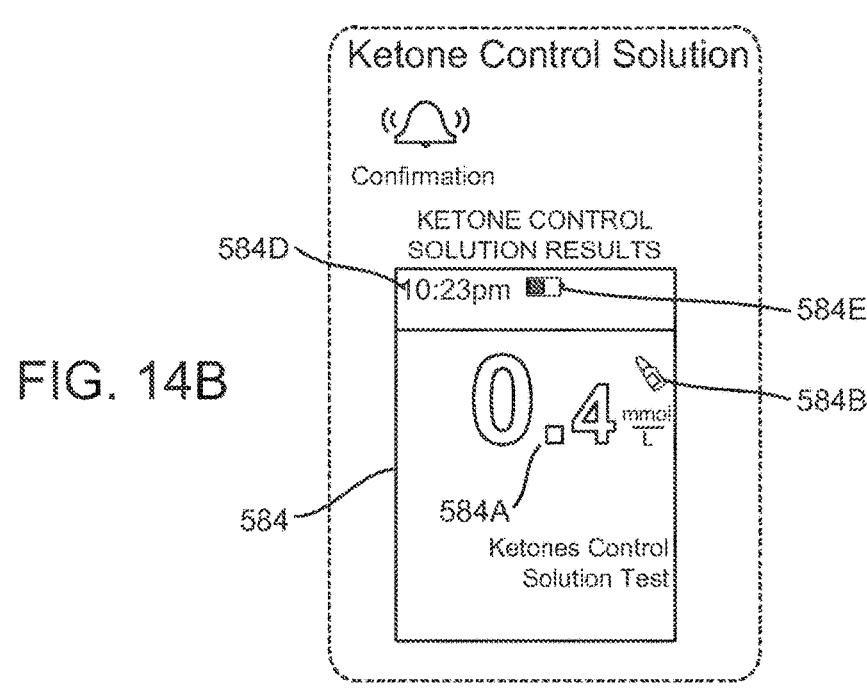

Ketone Control Solution

Confirmation

KETONE CONTROL SOLUTION RESULTS 584D
10:23pm — 584E
0.4 mmol/L — 584B
584
584A
Ketones Control Solution Test

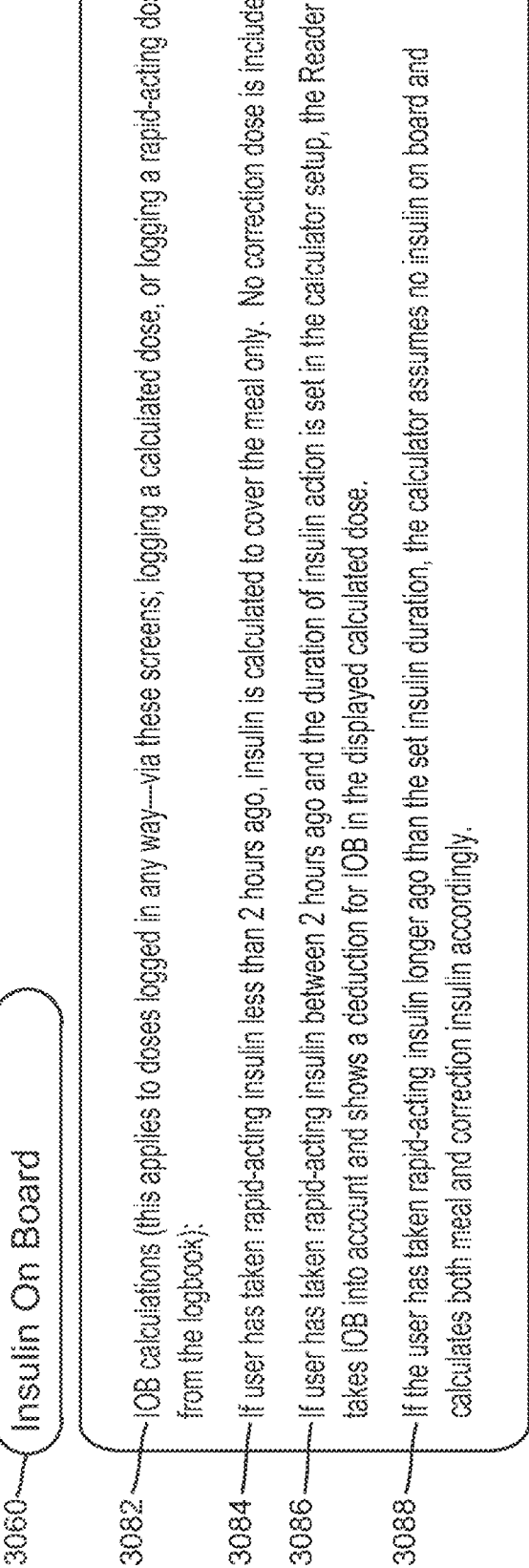

Insulin On Board

3060

IOB calculations (this applies to doses logged in any way—via these screens; logging a calculated dose, or logging a rapid-acting dose from the logbook):

3082

If user has taken rapid-acting insulin less than 2 hours ago, insulin is calculated to cover the meal only. No correction dose is included.

3084

If user has taken rapid-acting insulin between 2 hours ago and the duration of insulin action is set in the calculator setup, the Reader takes IOB into account and shows a deduction for IOB in the displayed calculated dose.

3086

If the user has taken rapid-acting insulin longer ago than the set insulin duration, the calculator assumes no insulin on board and calculates both meal and correction insulin accordingly.

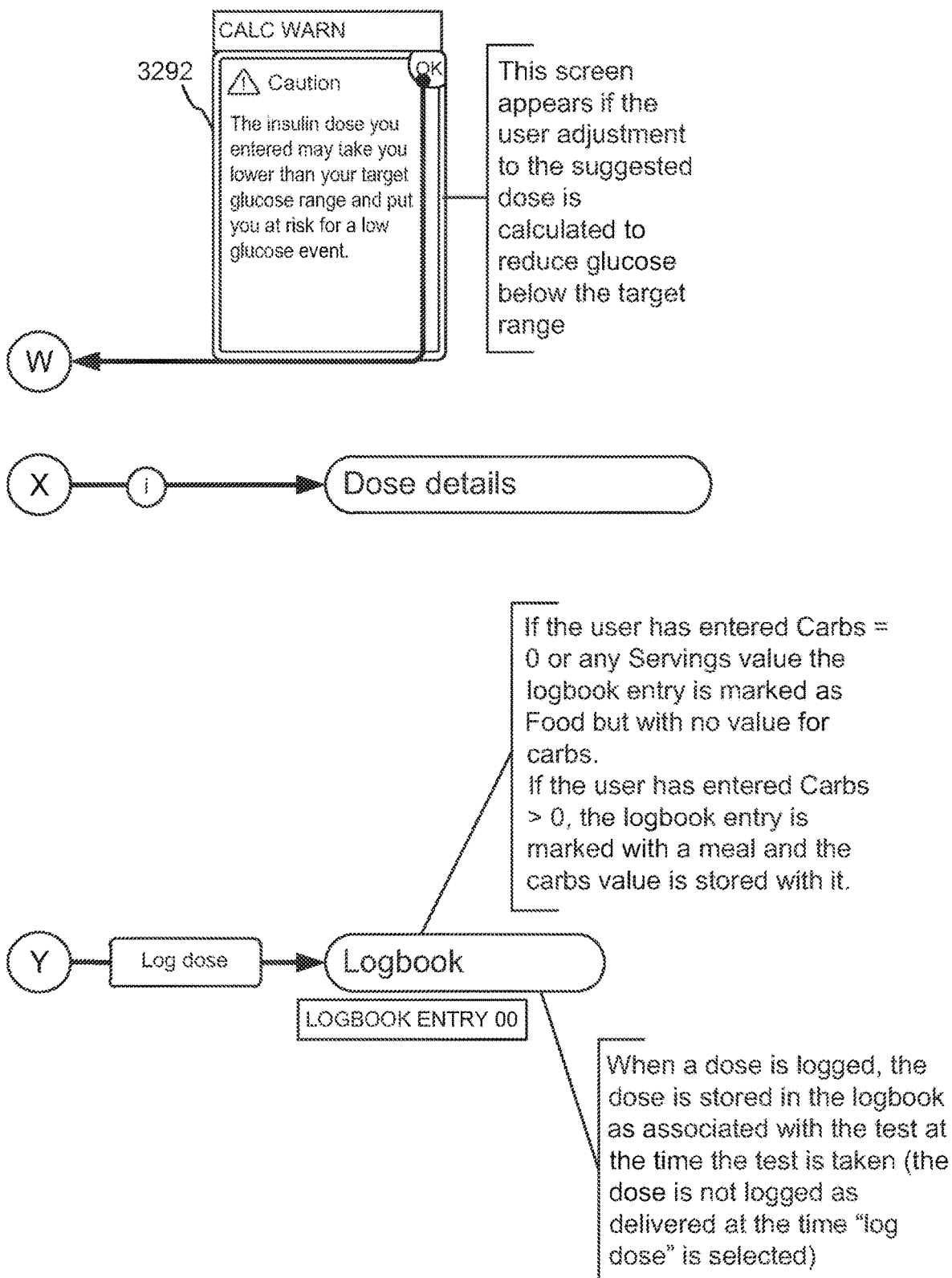

3292

CALC WARN

⚠ Caution

The insulin dose you entered may take you lower than your target glucose range and put you at risk for a low glucose event.

OK

This screen appears if the user adjustment to the suggested dose is calculated to reduce glucose below the target range

W

X —— i ——▶ Dose details

If the user has entered Carbs = 0 or any Servings value the logbook entry is marked as Food but with no value for carbs.
If the user has entered Carbs > 0, the logbook entry is marked with a meal and the carbs value is stored with it.

Y —— Log dose ——▶ Logbook

LOGBOOK ENTRY 00

When a dose is logged, the dose is stored in the logbook as associated with the test at the time the test is taken (the dose is not logged as delivered at the time "log dose" is selected)

FIG. 17D

Dose details —3296

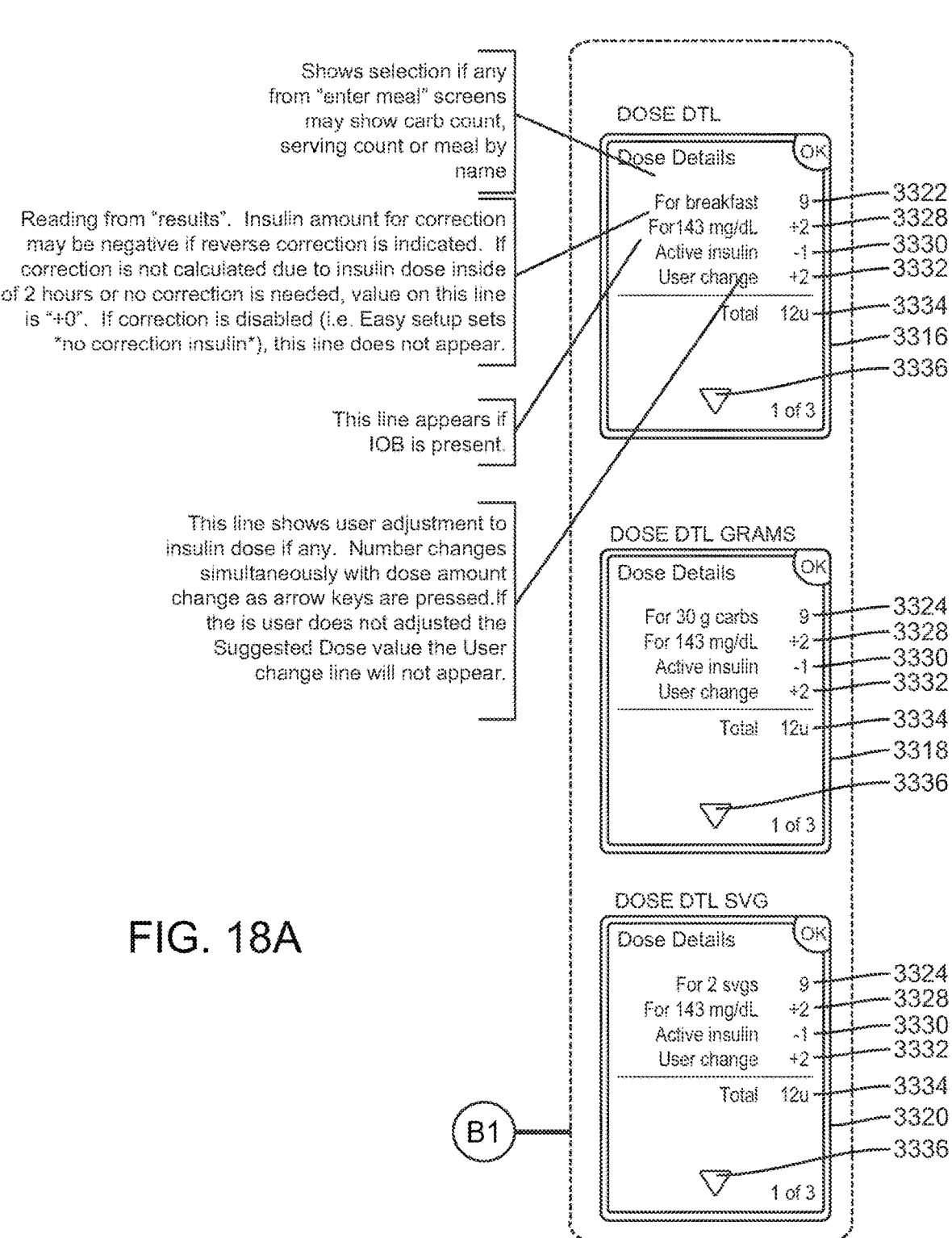

Shows selection if any from "enter meal" screens may show carb count, serving count or meal by name Reading from "results". Insulin amount for correction may be negative if reverse correction is indicated. If correction is not calculated due to insulin dose inside of 2 hours or no correction is needed, value on this line is "+0". If correction is disabled (i.e. Easy setup sets "no correction insulin"), this line does not appear.

This line appears if IOB is present.

This line shows user adjustment to insulin dose if any. Number changes simultaneously with dose amount change as arrow keys are pressed.If the is user does not adjusted the Suggested Dose value the User change line will not appear.

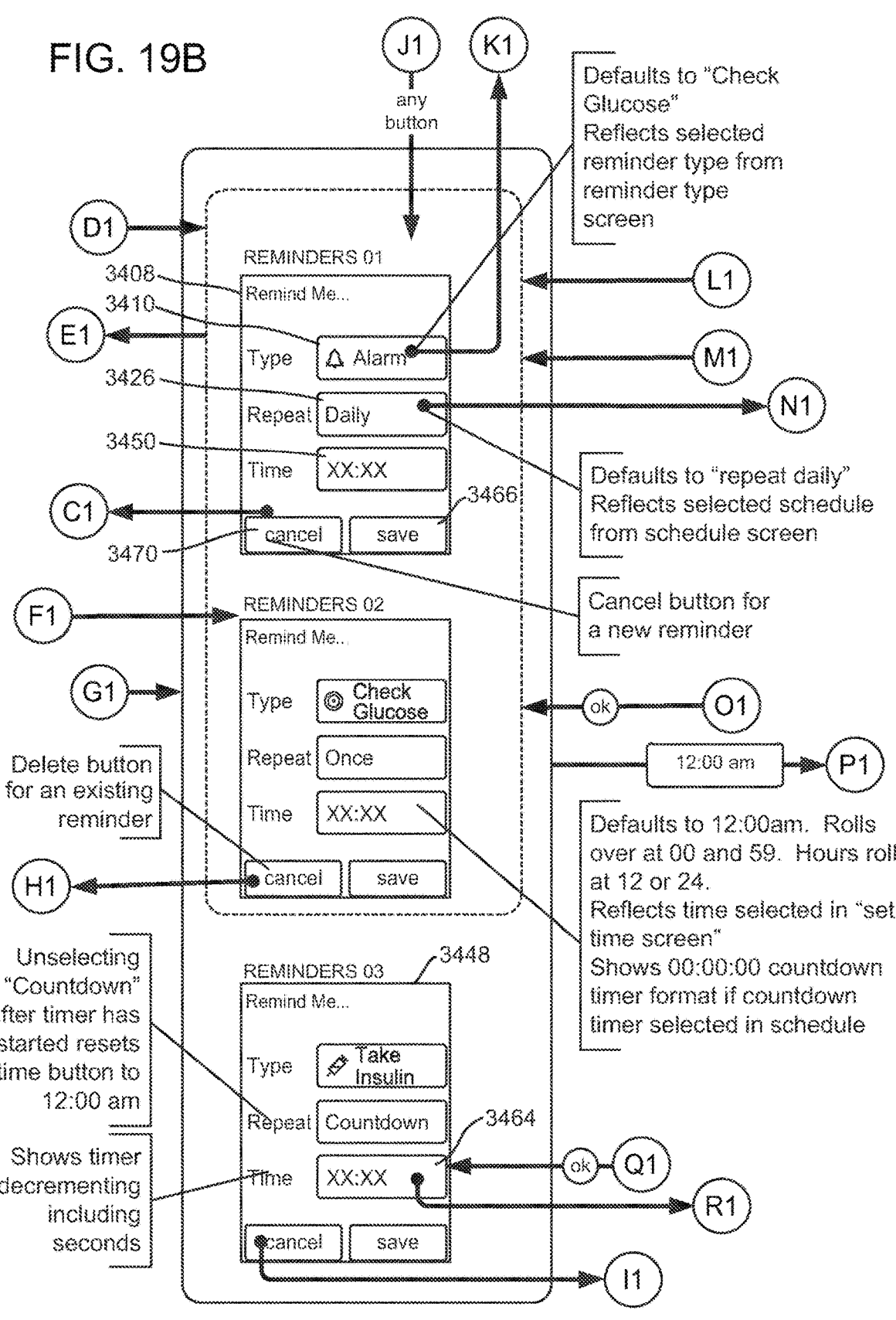

Defaults to "Check Glucose"
Reflects selected reminder type from reminder type screen Defaults to "repeat daily"
Reflects selected schedule from schedule screen Cancel button for a new reminder Delete button for an existing reminder Unselecting "Countdown" after timer has started resets time button to 12:00 am Shows timer decrementing including seconds Defaults to 12:00am. Rolls over at 00 and 59. Hours roll at 12 or 24.
Reflects time selected in "set time screen"
Shows 00:00:00 countdown timer format if countdown timer selected in schedule

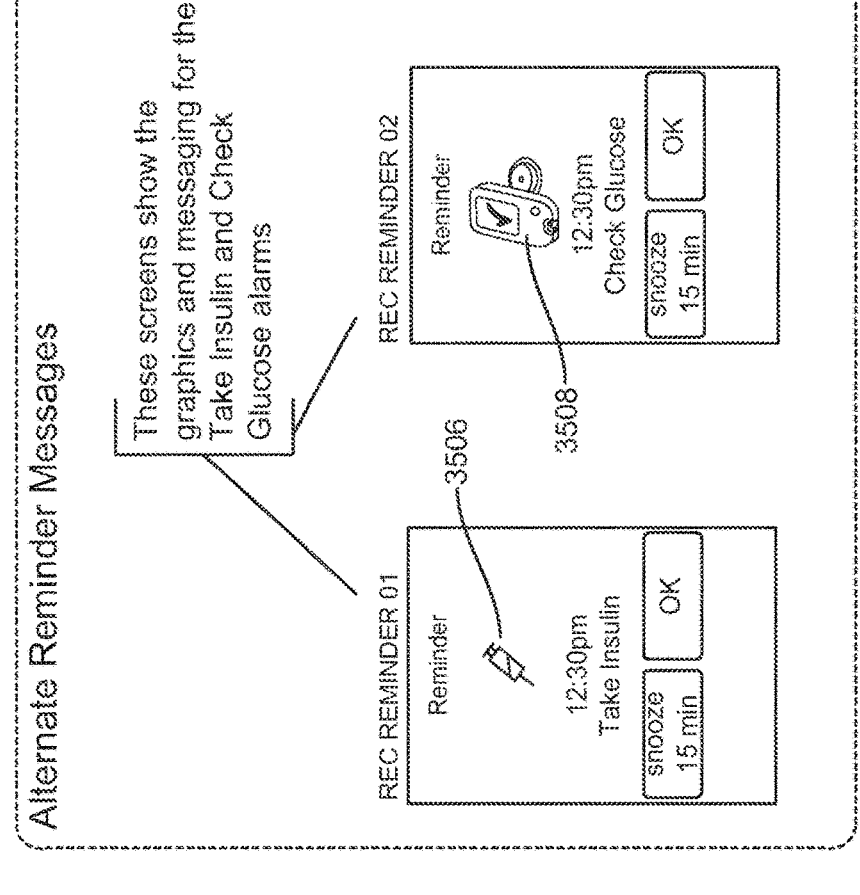

Alternate Reminder Messages

These screens show the graphics and messaging for the Take Insulin and Check Glucose alarms Receive reminder — 3500

If Reminder sound is set to on, beep sounds with appearance of any reminders screen.

See "symbols and notes" for specifications of duration of reminder sounds.

If a reminder is ignored, the reminder will appear on screen with the next power on (whether by hardware button or strip insertion).

If multiple reminders are active, "Receive reminder" screens will stack up with the most recent reminder showing first. They will require dismissal one by one.

If daily repeated reminders have been missed, once a new day's reminder is current the previous day's reminder for that time is no longer active and is not part of that stack-up.

Figure 20B:
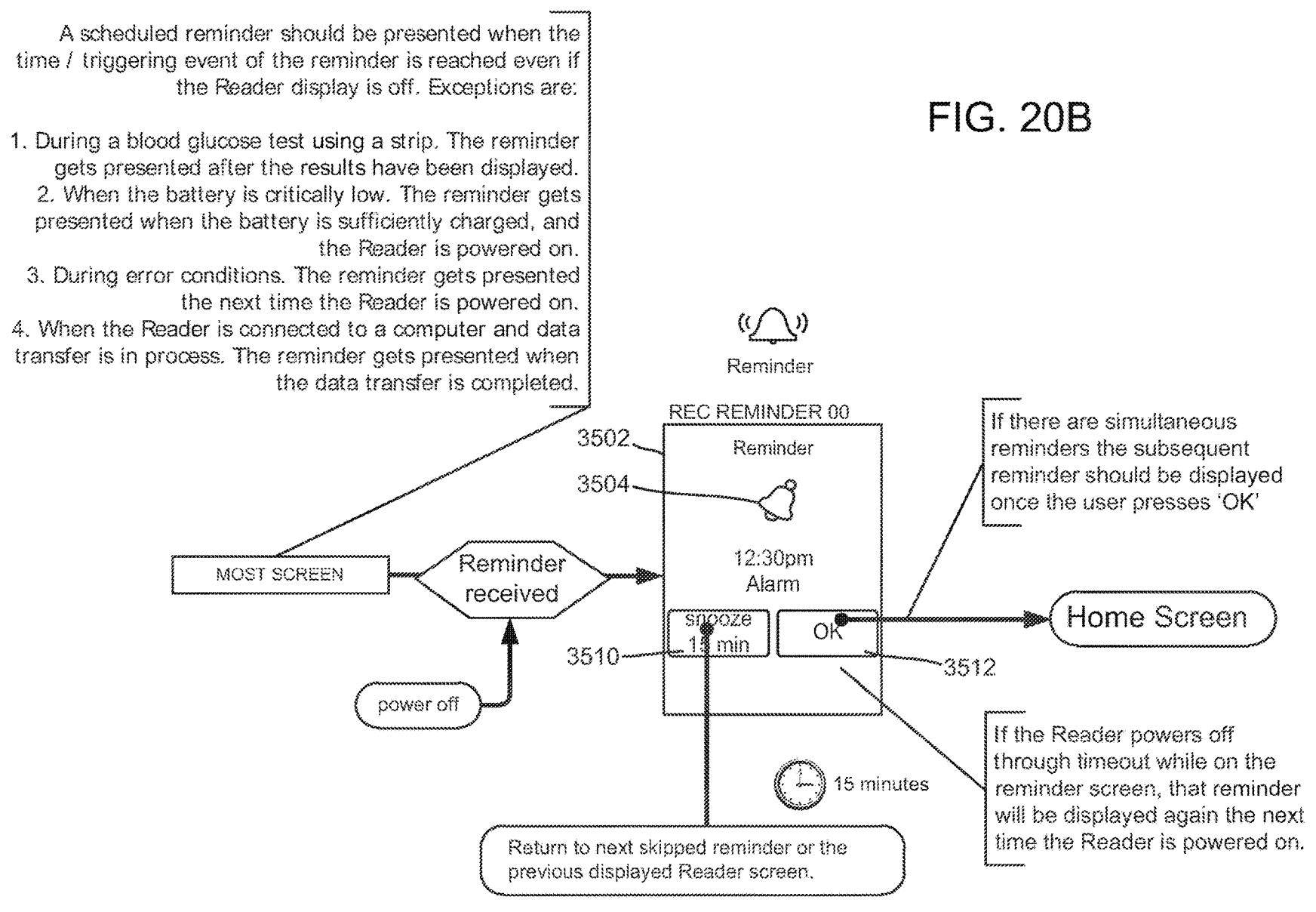

A scheduled reminder should be presented when the time / triggering event of the reminder is reached even if the Reader display is off. Exceptions are:

1. During a blood glucose test using a strip. The reminder gets presented after the results have been displayed.
2. When the battery is critically low. The reminder gets presented when the battery is sufficiently charged, and the Reader is powered on.
3. During error conditions. The reminder gets presented the next time the Reader is powered on.
4. When the Reader is connected to a computer and data transfer is in process. The reminder gets presented when the data transfer is completed.

REC REMINDER 00

Reminder

Reminder 12.30pm
Alarm

Snooze
1 min

OK

3502

3504

3510

3512.

Reminder received

MOST SCREEN power off 15 minutes

Home Screen

If there are simultaneous reminders the subsequent reminder should be displayed once the user presses 'OK'

If the Reader powers off through timeout while on the reminder screen, that reminder will be displayed again the next time the Reader is powered on.

Return to next skipped reminder or the previous displayed Reader screen.

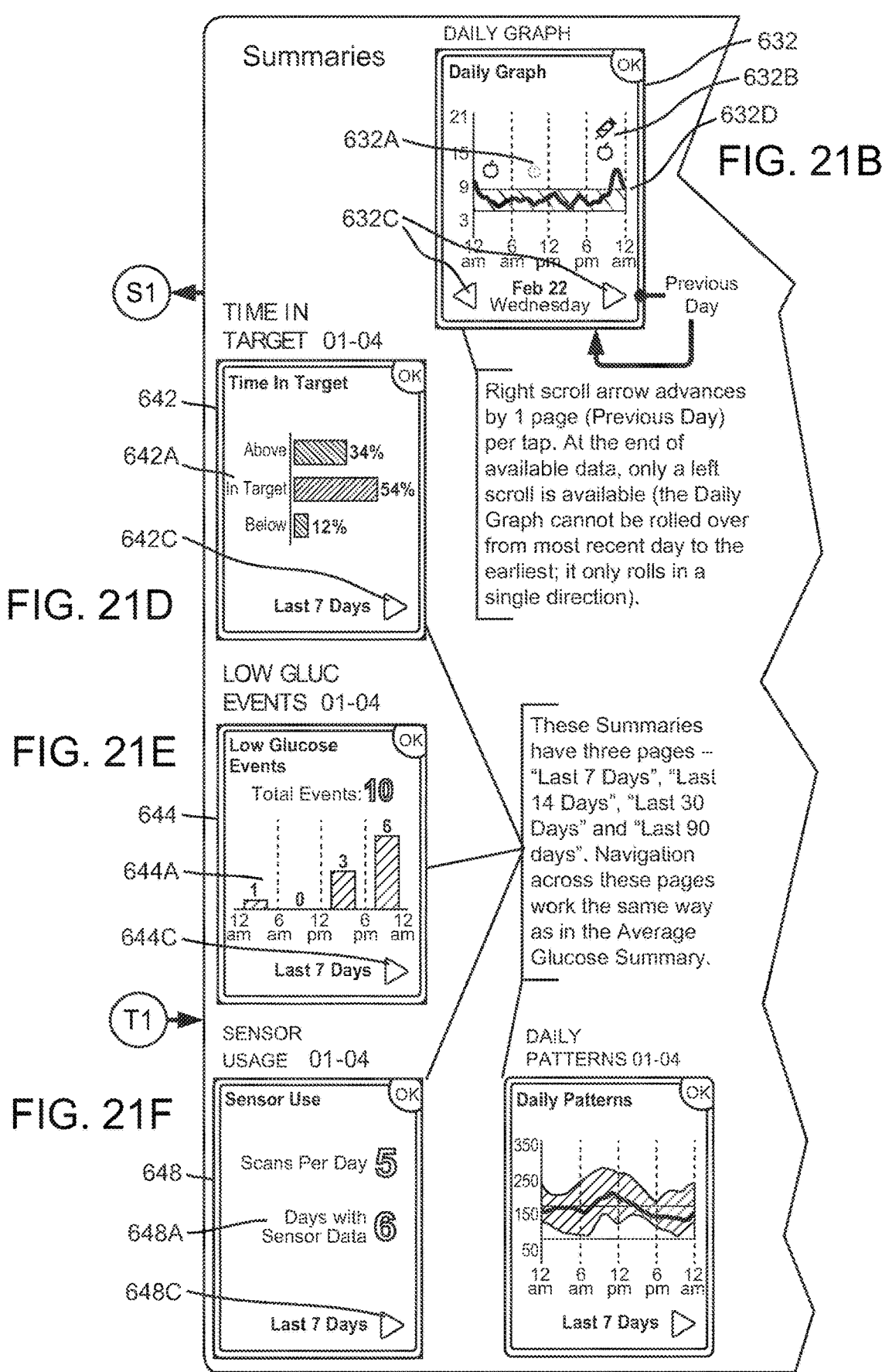

Summaries

DAILY GRAPH 632
632B
632D

Daily Graph    OK

632A 21
15
9
3
12   6   12   6   12
am  am  pm  pm  am

632C

Feb 22
Wednesday

Previous Day

TIME IN
TARGET  01-04

Right scroll arrow advances by 1 page (Previous Day) per tap. At the end of available data, only a left scroll is available (the Daily Graph cannot be rolled over from most recent day to the earliest; it only rolls in a single direction).

642      Time In Target    OK

642A     Above [//] 34%
         In Target [////] 54%
642C     Below [/] 12%

FIG. 21D

Last 7 Days

LOW GLUC
EVENTS  01-04

FIG. 21E

644      Low Glucose
         Events    OK
         Total Events: 10

644A                    6
                  3
         1    0
         12   6   12   6   12
         am  am  pm  pm  am

644C     Last 7 Days

These Summaries have three pages -- "Last 7 Days", "Last 14 Days", "Last 30 Days" and "Last 90 days". Navigation across these pages work the same way as in the Average Glucose Summary.

T1

SENSOR
USAGE  01-04

FIG. 21F

648      Sensor Use    OK

Scans Per Day  5

648A     Days with
         Sensor Data  6

648C     Last 7 Days

DAILY
PATTERNS 01-04

Daily Patterns    OK 350
250
150
50
12   6   12   6   12
am  am  pm  pm  am

Last 7 Days

LOGBOOK ENTRY
UNLOGGED DOSE

Rapid-Acting Insulin OK

Dose amount 9u

Time of dose 9:00am

Time logged 10:23am

LOGBOOK ENTRY
TIME CHANGE

Time Change OK

From: 22 Feb / 11:23am

To: 22 Feb / 10L23am

Other history options may be affected.

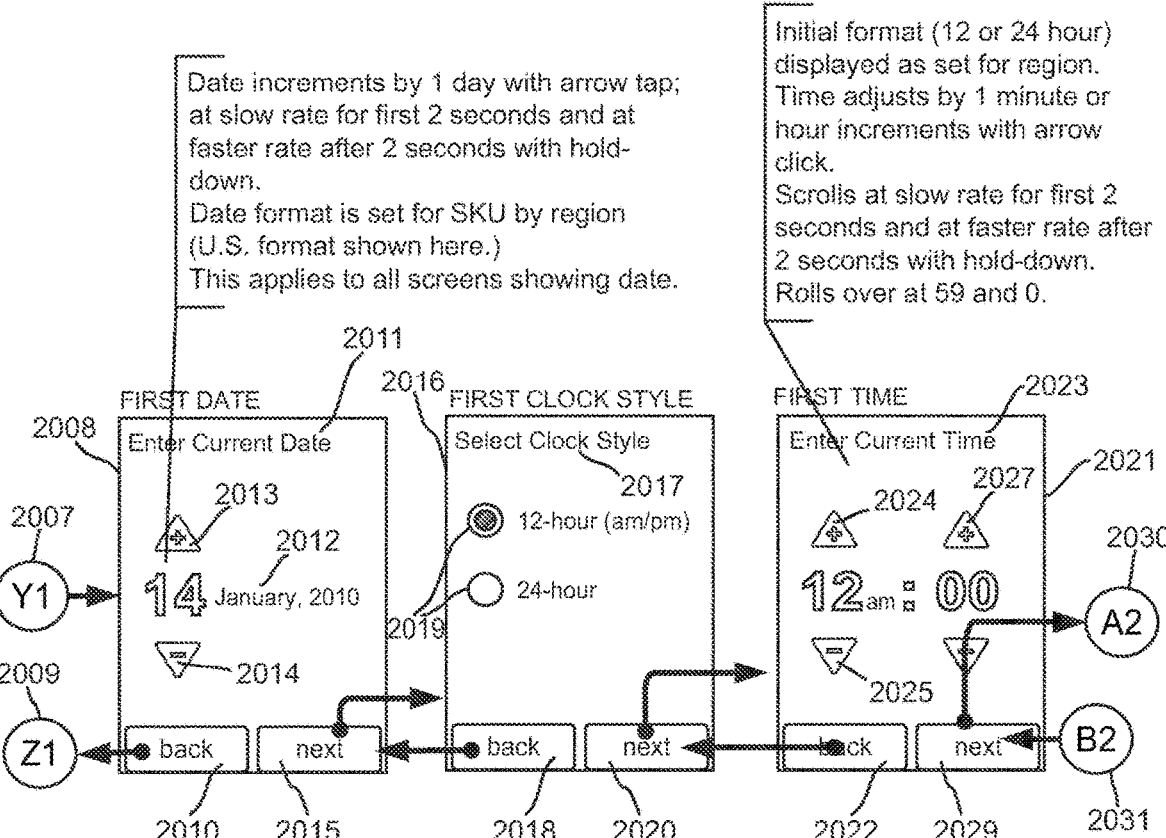

Date increments by 1 day with arrow tap; at slow rate for first 2 seconds and at faster rate after 2 seconds with hold-down.
Date format is set for SKU by region (U.S. format shown here.)
This applies to all screens showing date.

Initial format (12 or 24 hour) displayed as set for region.
Time adjusts by 1 minute or hour increments with arrow click.
Scrolls at slow rate for first 2 seconds and at faster rate after 2 seconds with hold-down.
Rolls over at 59 and 0.

FIRST DATE
Enter Current Date
14 January, 2010
back   next

FIRST CLOCK STYLE
Select Clock Style
○ 12-hour (am/pm)
○ 24-hour
back   next

FIRST TIME
Enter Current Time
12 am : 00
back   next

Note: Reader can be turned off by a single Home button press during LANG, FIRST DATE, or FIRST TIME. These settings will not be saved.

Note: If a strip is inserted before language, date, and time are set up, strip insertion launches the First Start sequence which aborts after FIRST TIME is completed (FIRST HOME BTTN and FIRST DONE are not displayed) and goes to the Test sequence (APPLY BLOOD). FIRST HOME BTTN and FIRST DONE will not ever be seen by this user.

If a USB-to-PC is inserted before the First Start sequence, the Reader displays DATA TRANSFER in English. First Start sequence will be displayed on the PC Application.

If a USB-to-AC Power is inserted, the First Start sequence will initiate as if the Reader was powered on using the Power button.

If the First Start sequence is not completed, settings are NOT retained. Successive Reader activation (via strip insertion, power button or USB insertion (from AC-only)) will bring up the first step in the sequence until it is complete.

FIG. 24 (Cont)

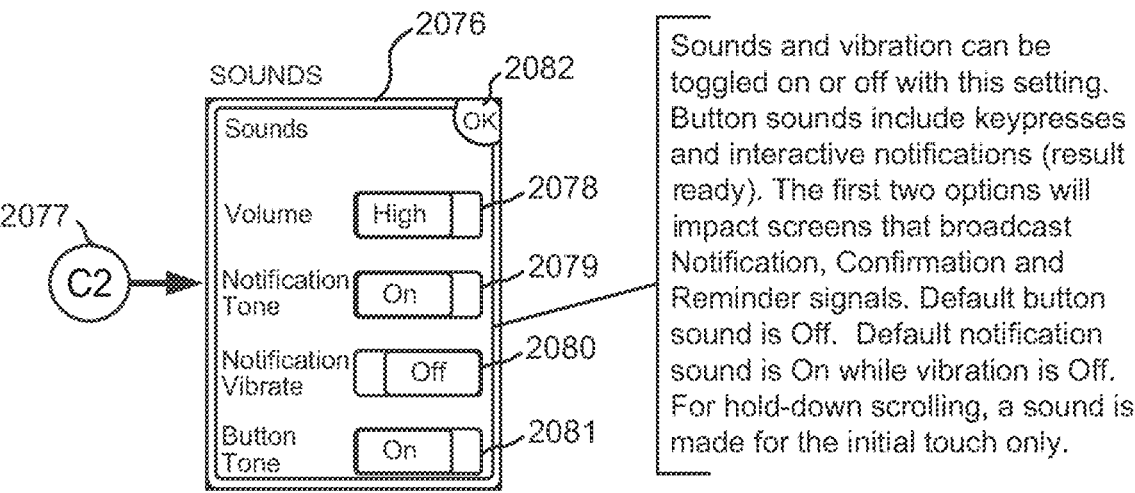

SOUNDS — 2076

2077 — C2

Sounds — 2082 OK

Volume — High — 2078

Notification Tone — On — 2079

Notification Vibrate — Off — 2080

Button Tone — On — 2081

Sounds and vibration can be toggled on or off with this setting. Button sounds include keypresses and interactive notifications (result ready). The first two options will impact screens that broadcast Notification, Confirmation and Reminder signals. Default button sound is Off. Default notification sound is On while vibration is Off. For hold-down scrolling, a sound is made for the initial touch only.

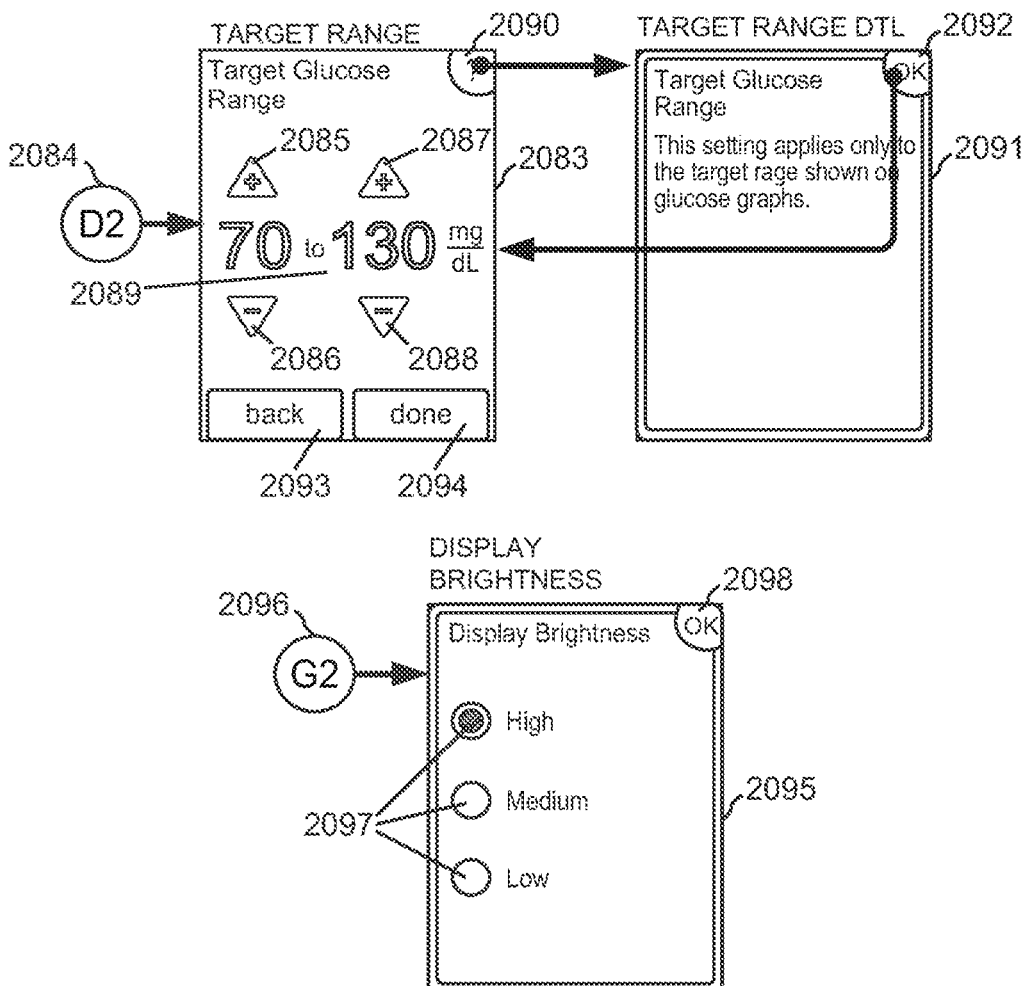

TARGET RANGE — 2090

2084 — D2

Target Glucose Range

2085 — 2087

70 to 130 mg/dL — 2089

2086 — 2088 back — 2093     done — 2094

TARGET RANGE DTL — 2092

Target Glucose Range

This setting applies only to the target rage shown on glucose graphs. — 2091

DISPLAY BRIGHTNESS

2096 — G2

Display Brightness — 2098 OK

High

2097 — Medium — 2095

Low

FIG. 25 (Cont)

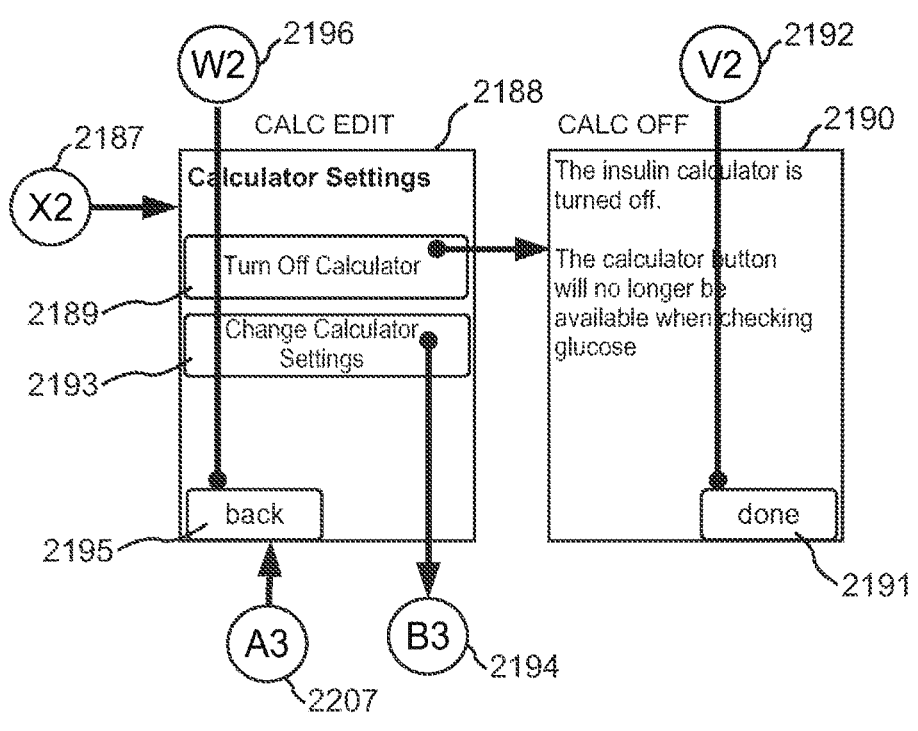
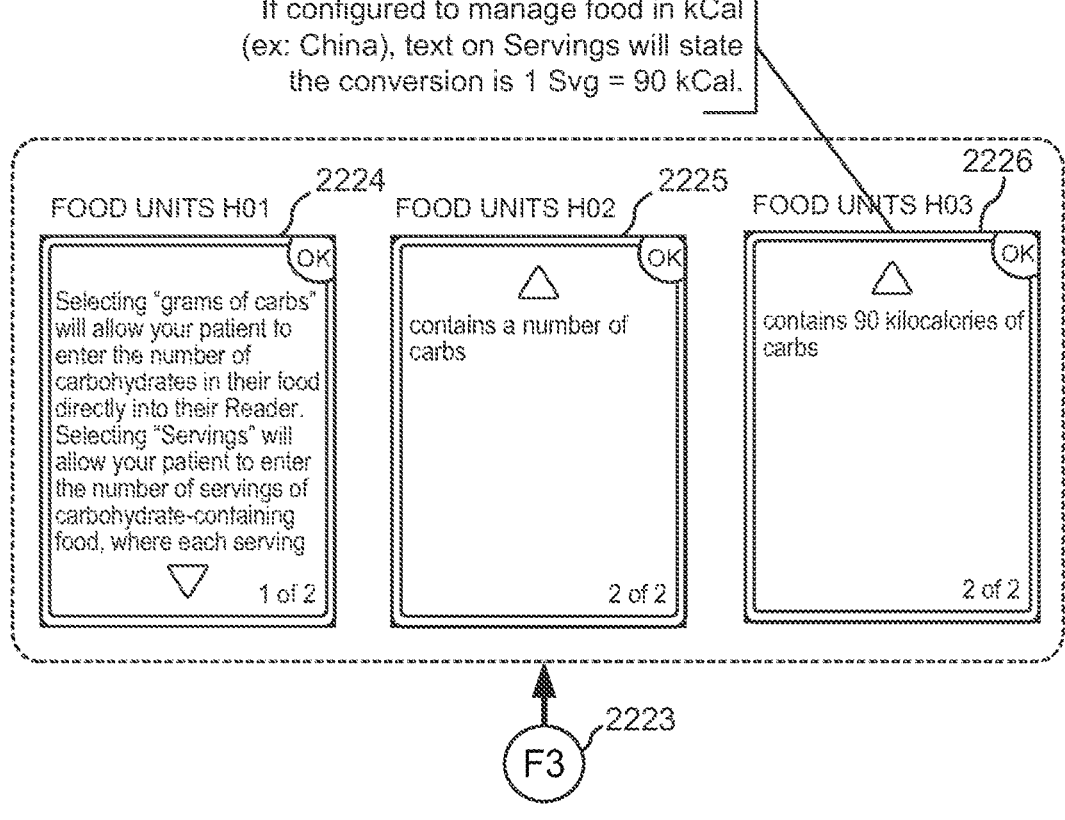
FIG. 29 (Cont)

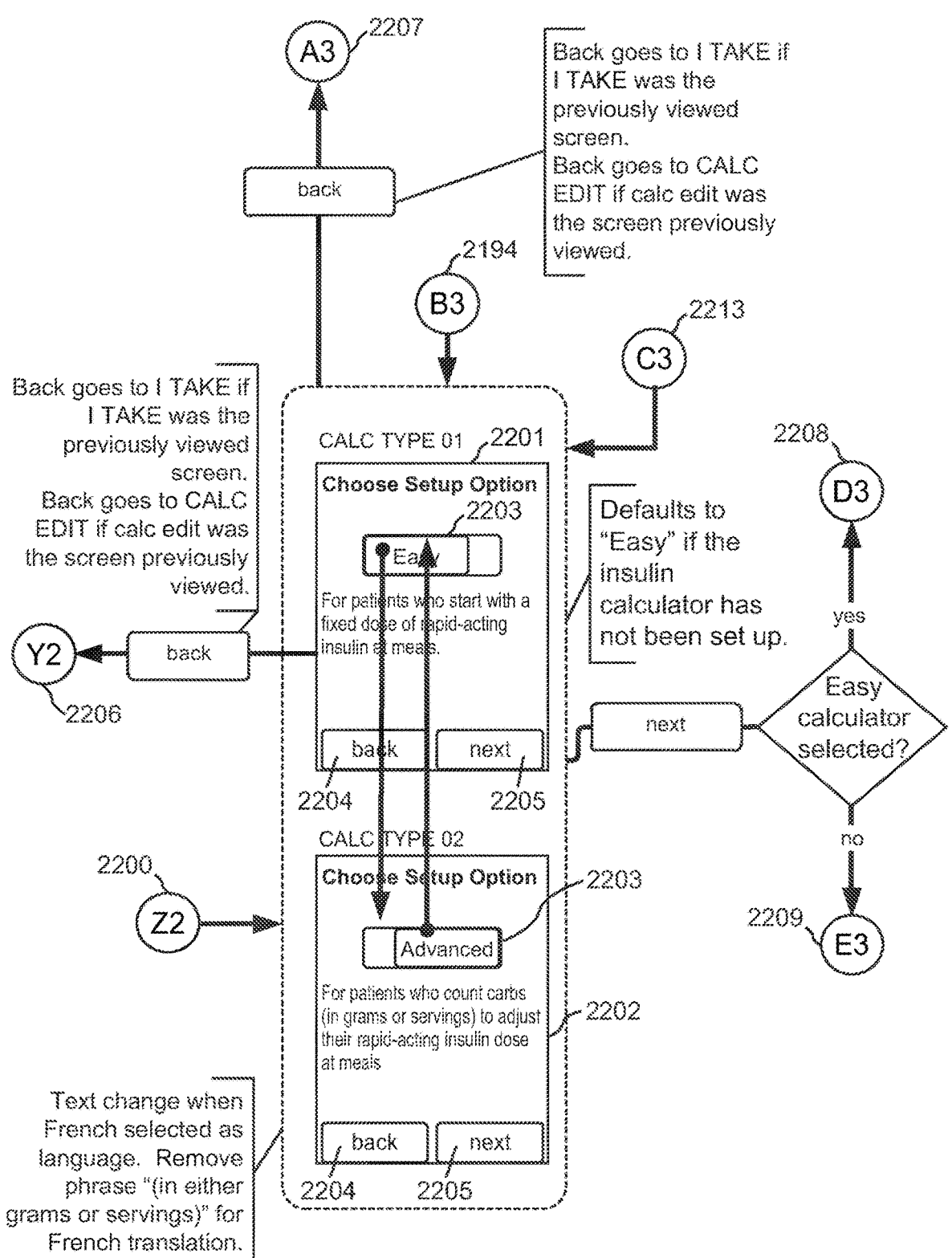

Back goes to I TAKE if I TAKE was the previously viewed screen.
Back goes to CALC EDIT if calc edit was the screen previously viewed.

Back goes to I TAKE if I TAKE was the previously viewed screen.
Back goes to CALC EDIT if calc edit was the screen previously viewed.

Defaults to "Easy" if the insulin calculator has not been set up.

Text change when French selected as language. Remove phrase "(in either grams or servings)" for French translation.

FIG. 29 (Cont)

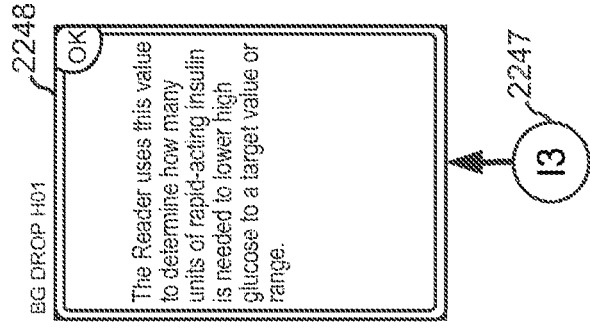
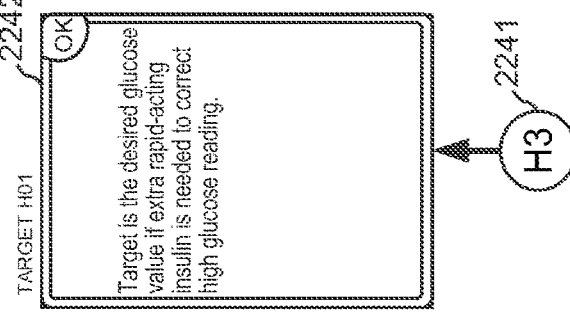
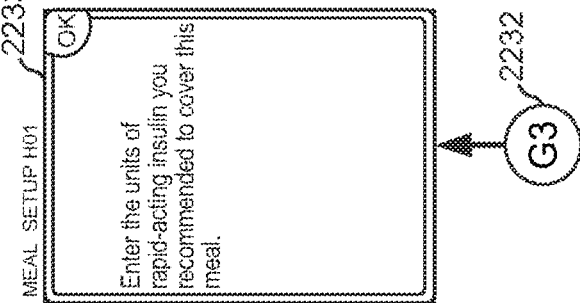
FIG. 30 (Cont)

FIG. 35

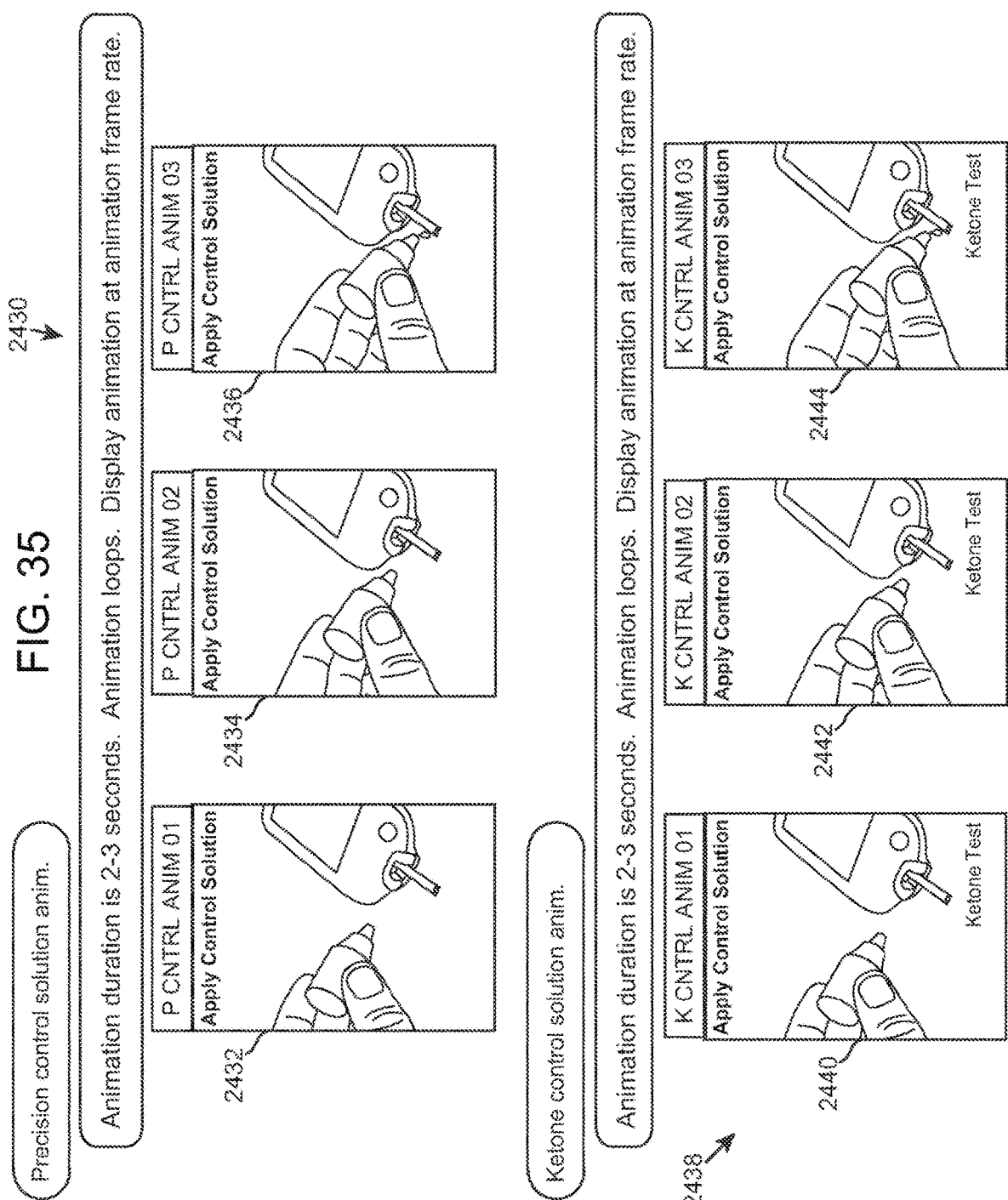

2430

Precision control solution anim.

Animation duration is 2-3 seconds.  Animation loops.  Display animation at animation frame rate.

P CNTRL ANIM 01
Apply Control Solution
2432

P CNTRL ANIM 02
Apply Control Solution
2434

P CNTRL ANIM 03
Apply Control Solution
2436

Ketone control solution anim.

Animation duration is 2-3 seconds.  Animation loops.  Display animation at animation frame rate.

K CNTRL ANIM 01
Apply Control Solution
Ketone Test
2440

K CNTRL ANIM 02
Apply Control Solution
Ketone Test
2442

K CNTRL ANIM 03
Apply Control Solution
Ketone Test
2444

2438

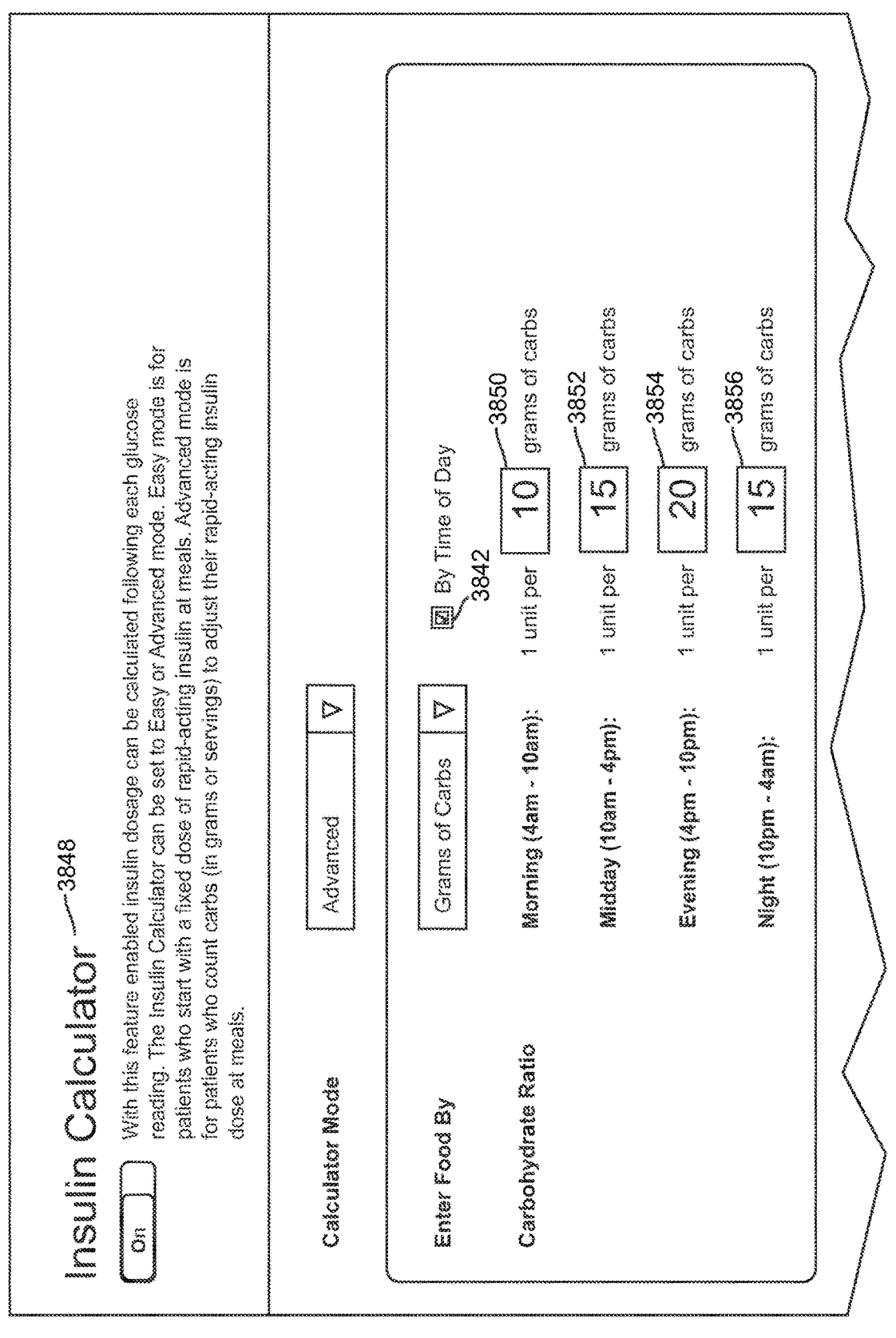

Insulin Calculator — 3848

[On]

With this feature enabled insulin dosage can be calculated following each glucose reading. The Insulin Calculator can be set to Easy or Advanced mode. Easy mode is for patients who start with a fixed dose of rapid-acting insulin at meals. Advanced mode is for patients who count carbs (in grams or servings) to adjust their rapid-acting insulin dose at meals.

Calculator Mode        [Advanced ▽]

Enter Food By          [Grams of Carbs ▽]

Carbohydrate Ratio     ☑ By Time of Day
                           3842

Morning (4am - 10am):    1 unit per  [10]  grams of carbs — 3850

Midday (10am - 4pm):     1 unit per  [15]  grams of carbs — 3852

Evening (4pm - 10pm):    1 unit per  [20]  grams of carbs — 3854

Night (10pm - 4am):      1 unit per  [15]  grams of carbs — 3856

FIG. 45A

| | DAILY AVG. | 12am | 2am | 4am | 6am | 8am | 10am | 12pm | 2pm | 4pm | 6pm | 8pm | 10pm |
|---|---|---|---|---|---|---|---|---|---|---|---|---|---|
| GLUCOSE mg/dL (5374) | 178 | 172 | 180 | 165 | 155 | 180 | 200 | 180 | 170 | 160 | 160 | 150 | 175 |

AVERAGE

| | DAILY AVG. | 12am | 2am | 4am | 6am | 8am | 10am | 12pm | 2pm | 4pm | 6pm | 8pm | 10pm |
|---|---|---|---|---|---|---|---|---|---|---|---|---|---|
| CARBS grams (5376) | 255 | 10 (1) | -- | -- | 45 (8) | 20 (3) | 30 (1) | 55 (5) | -- | 15 (2) | 65 (7) | -- | 15 (2) |

AVERAGE (NUMBER OF NOTES)

| INSULIN units | DAILY AVG. | 12am | 2am | 4am | 6am | 8am | 10am | 12pm | 2pm | 4pm | 6pm | 8pm | 10pm |
|---|---|---|---|---|---|---|---|---|---|---|---|---|---|
| Rapid-Acting | 20 | -- | -- | -- | 4.5 (2) | -- | -- | 9.5 (4) | -- | -- | 6.0 (5) | -- | -- |
| Long-Acting | 25 | -- | -- | -- | -- | -- | -- | -- | -- | -- | -- | -- | 25 (1) |

AVERAGE (NUMBER OF NOTES)

LEGEND:
— Target Range   ▬▬ Median   ▨ 10th to 90th Percentile   ▧ 25th to 75th Percentile   ▨ Carbs   ▨ Rapid-Acting Insulin
⎯⎯ Target Range   ▬▬ Insulin

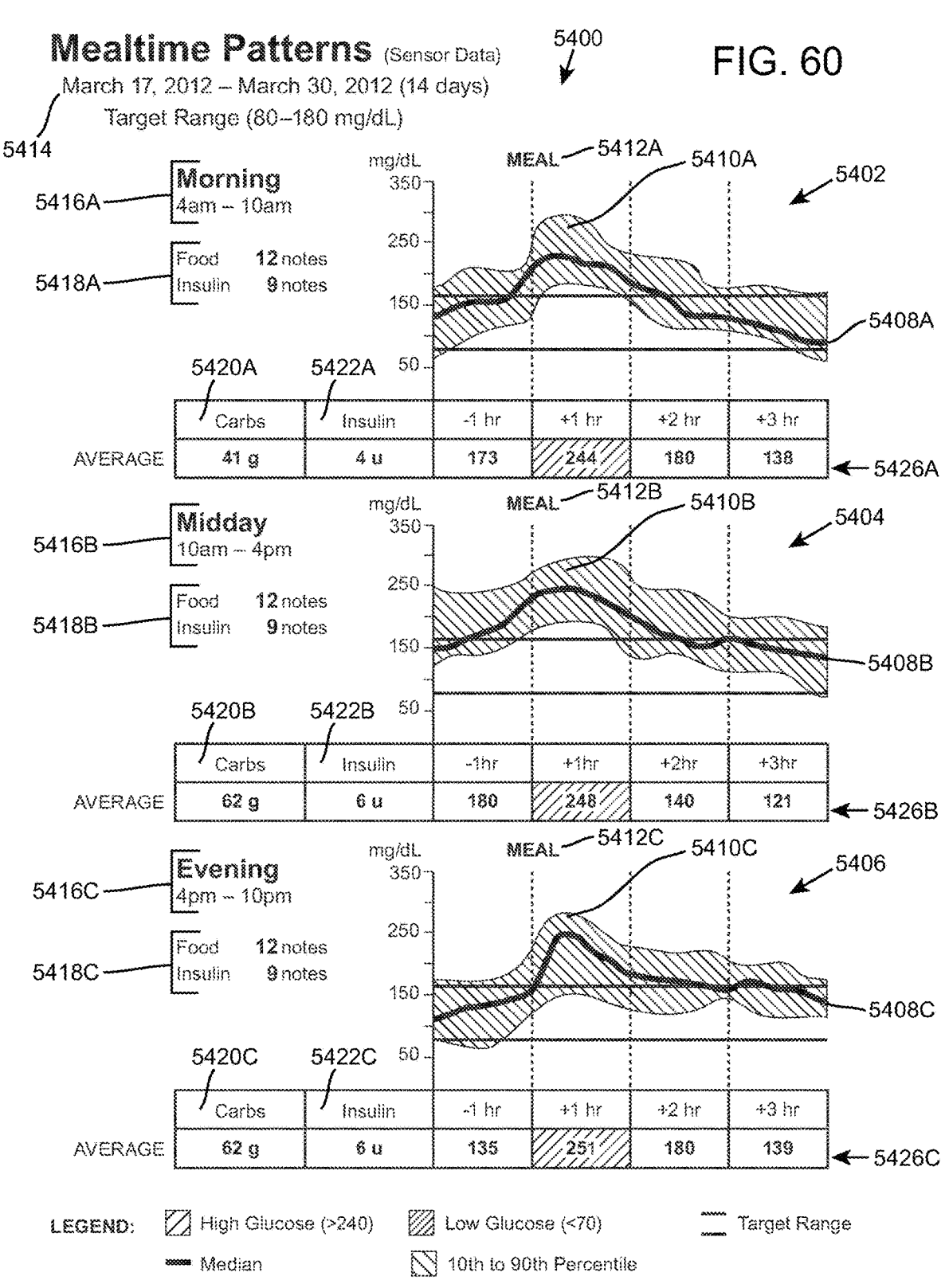

Mealtime Patterns (Sensor Data)

FIG. 60

March 17, 2012 – March 30, 2012 (14 days)

Target Range (80–180 mg/dL)

5414

Morning

5416A — 4am – 10am

5418A — Food 12 notes / Insulin 9 notes

MEAL — 5412A   5410A   5402

5408A

| | Carbs | Insulin | -1 hr | +1 hr | +2 hr | +3 hr |
|---|---|---|---|---|---|---|
| AVERAGE | 41 g | 4 u | 173 | 244 | 180 | 138 |

5420A  5422A  5426A

Midday

5416B — 10am – 4pm

5418B — Food 12 notes / Insulin 9 notes

MEAL — 5412B   5410B   5404

5408B

| | Carbs | Insulin | -1hr | +1hr | +2hr | +3hr |
|---|---|---|---|---|---|---|
| AVERAGE | 62 g | 6 u | 180 | 248 | 140 | 121 |

5420B  5422B  5426B

Evening

5416C — 4pm – 10pm

5418C — Food 12 notes / Insulin 9 notes

MEAL — 5412C   5410C   5406

5408C

| | Carbs | Insulin | -1 hr | +1 hr | +2 hr | +3 hr |
|---|---|---|---|---|---|---|
| AVERAGE | 62 g | 6 u | 135 | 251 | 180 | 139 |

5420C  5422C  5426C

LEGEND: ▨ High Glucose (>240)  ▨ Low Glucose (<70)  ⎯ Target Range  ▬ Median  ◺ 10th to 90th Percentile

5600

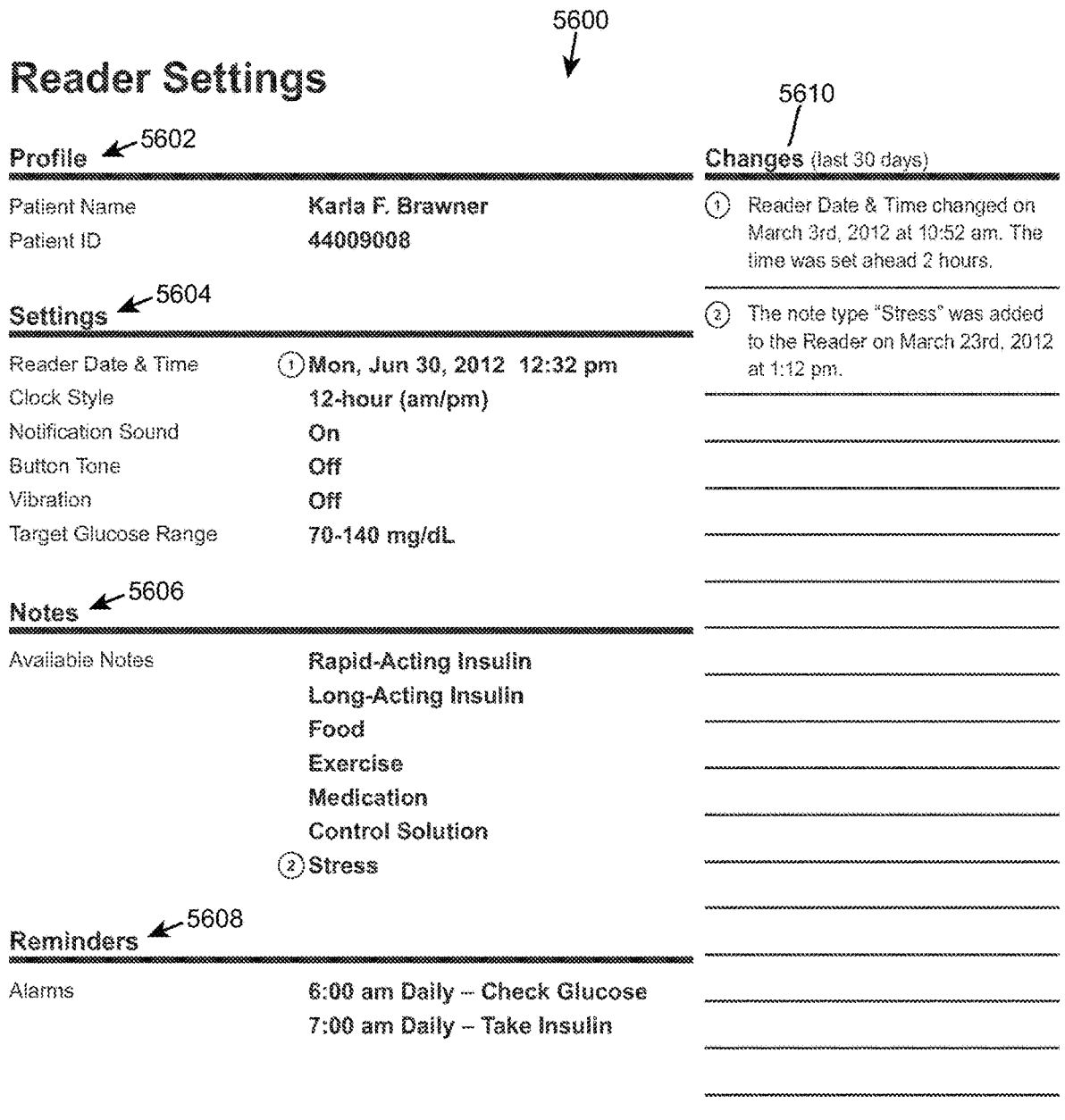

Reader Settings

Profile 5602

| | |
|---|---|
| Patient Name | Karla F. Brawner |
| Patient ID | 44009008 |

Settings 5604

| | |
|---|---|
| Reader Date & Time | ① Mon, Jun 30, 2012  12:32 pm |
| Clock Style | 12-hour (am/pm) |
| Notification Sound | On |
| Button Tone | Off |
| Vibration | Off |
| Target Glucose Range | 70-140 mg/dL |

Notes 5606

| | |
|---|---|
| Available Notes | Rapid-Acting Insulin |
| | Long-Acting Insulin |
| | Food |
| | Exercise |
| | Medication |
| | Control Solution |
| | ② Stress |

Reminders 5608

| | |
|---|---|
| Alarms | 6:00 am Daily – Check Glucose |
| | 7:00 am Daily – Take Insulin |

5610

Changes (last 30 days)

① Reader Date & Time changed on March 3rd, 2012 at 10:52 am. The time was set ahead 2 hours.

② The note type "Stress" was added to the Reader on March 23rd, 2012 at 1:12 pm.

Reader Settings

Insulin Calculator ◄─5622

| | |
|---|---|
| Rapid-Acting Insulin Calculator | On |
| Calculator Mode | Advanced |
| Carbohydrate Ratio | 1 unit per 10 grams of carbs |
| Correction Target | 70-130 mg/dL |
| Correction Factor | |
| Morning (4am-10am) | 1 unit per 30 mg/dL |
| Midday (10am-4pm) | 1 unit per 20 mg/dL |
| Evening (4pm-10pm) | 1 unit per 20 mg/dL |
| Night (10am-4pm) | 1 unit per 50 mg/dL |

Masked Mode ◄─5624                                          ③

| | |
|---|---|
| Masked Sensor Reading | On |
| Check Glucose Reminder | On |
| Remind Every | 8:00 (hr:min) |

Changes (last 30 days)

 ③  Masked Mode was enabled March 30th, 2012 at 3:14 pm.

FIG. 65

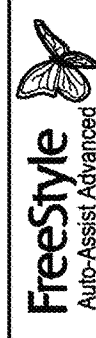

FreeStyle
Auto-Assist Advanced

Welcome to FreeStyle Auto-Assist Advanced

Reader Connected

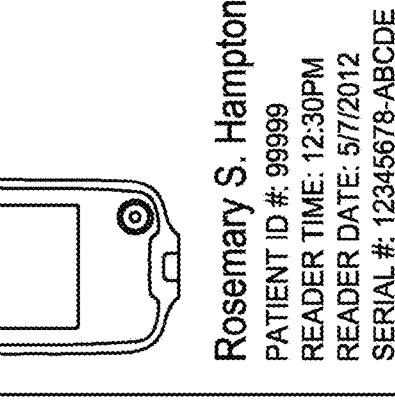

Rosemary S. Hampton
PATIENT ID #: 99999
READER TIME: 12:30PM
READER DATE: 5/7/2012
SERIAL #: 12345678-ABCDE

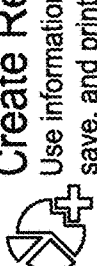

Create Reports
Use information on your Reader to create, view, save, and print a variety of reports.

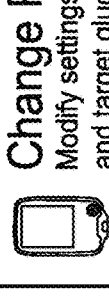

Change Reader Settings
Modify settings on your Reader, including date, time, and target glucose range.

Update Pending
An update for FreeStyle Auto-Assist Advanced Software has been downloaded. The update will be installed when the application is shut down.

Figure 75:
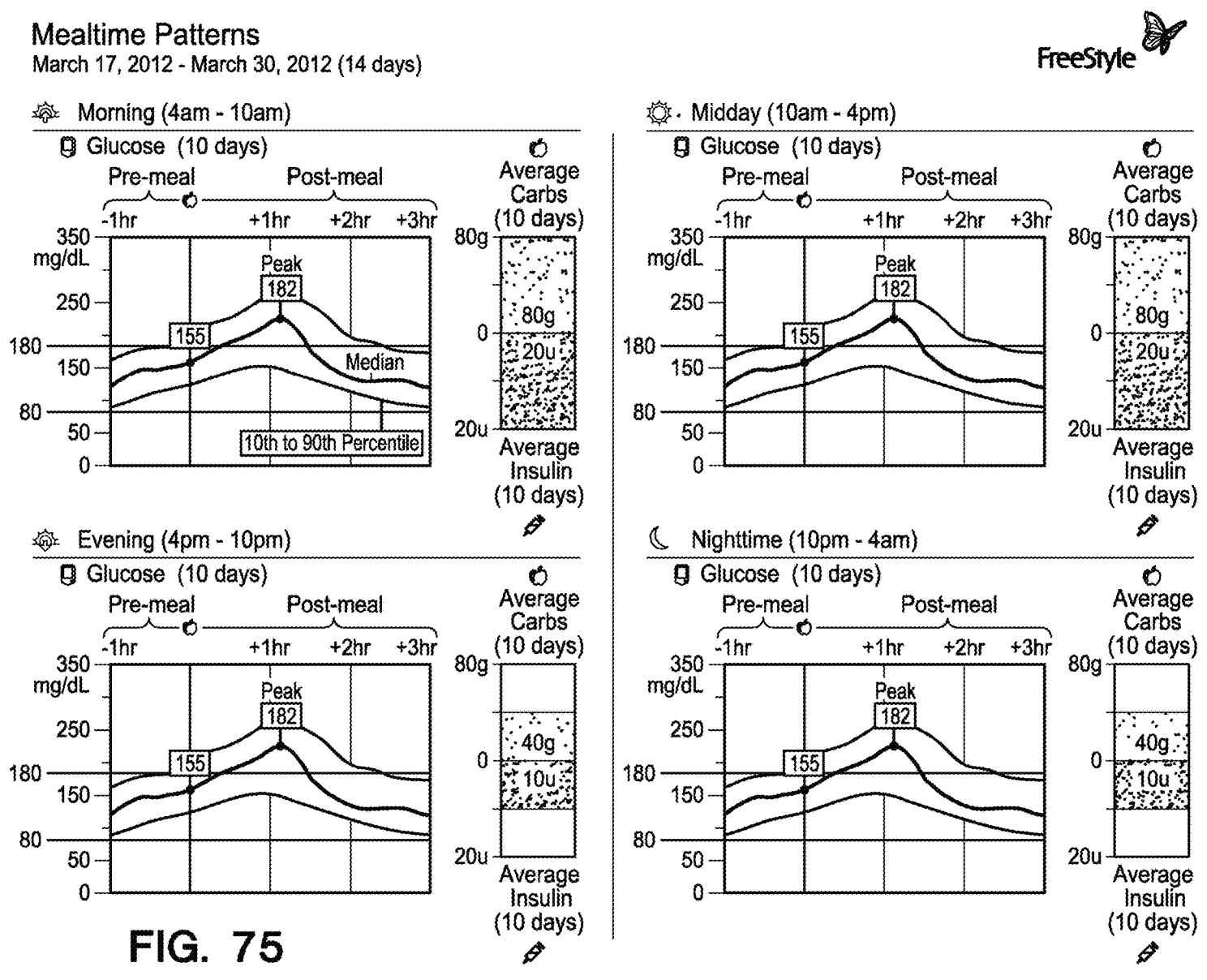

FreeStyle

Mealtime Patterns
March 17, 2012 - March 30, 2012 (14 days)

Midday (10am - 4pm)

Average Carbs (10 days)

80g | 20u

Average Insulin (10 days)

Glucose (10 days)

Pre-meal | Post-meal

-1hr | +1hr | +2hr | +3hr

Peak 182

155

350 mg/dL 250 180 150 80 50 0

Nighttime (10pm - 4am)

Average Carbs (10 days)

40g | 10u

Average Insulin (10 days)

Glucose (10 days)

Pre-meal | Post-meal

-1hr | +1hr | +2hr | +3hr

Peak 182

155

350 mg/dL 250 180 150 80 50 0

Morning (4am - 10am)

Average Carbs (10 days)

80g | 20u

Average Insulin (10 days)

Glucose (10 days)

Pre-meal | Post-meal

-1hr | +1hr | +2hr | +3hr

Peak 182

Median

10th to 90th Percentile

155

350 mg/dL 250 180 150 80 50 0

Evening (4pm - 10pm)

Average Carbs (10 days)

40g | 10u

Average Insulin (10 days)

Glucose (10 days)

Pre-meal | Post-meal

-1hr | +1hr | +2hr | +3hr

Peak 182

Monthly Summary

March 2012

🅖 Average Glucose

📶 Scans/Day

🅛 Low Glucose Events

*FreeStyle* 🦋

| Monday | Tuesday | Wednesday | Thursday | Friday | Saturday | Sunday |
|---|---|---|---|---|---|---|
|  |  |  |  |  | 1<br>175 mg/dL<br>3 📶 | 2<br>175 mg/dL<br>3 📶 |
| 3<br>175 mg/dL<br>3 📶 | 4<br>175 mg/dL<br>3 📶 | 5<br>Low<br>64 mg/dL<br>3 📶<br>🅛🅛🅛🅛🅛+ | 6<br>175 mg/dL<br>3 📶 | 7<br>High<br>243 mg/dL<br>3 📶 | 8<br>175 mg/dL<br>3 📶 | 9<br>175 mg/dL<br>3 📶 |
| 10<br>175 mg/dL<br>3 📶 | 11<br>175 mg/dL<br>3 📶 | 12<br>175 mg/dL<br>3 📶 | 13<br>175 mg/dL<br>3 📶 | 14<br>175 mg/dL<br>3 📶 | 15<br>175 mg/dL<br>3 📶 | 16<br>175 mg/dL<br>3 📶 |
| 17<br>175 mg/dL<br>3 📶 | 18<br>175 mg/dL<br>3 📶 | 19<br>175 mg/dL<br>3 📶 | 20<br>175 mg/dL<br>3 📶 | 21<br>175 mg/dL<br>3 📶 | 22<br>175 mg/dL<br>3 📶 | 23<br>175 mg/dL<br>3 📶 |
| 24<br>175 mg/dL<br>3 📶 | 25<br>175 mg/dL<br>3 📶 | 26<br>175 mg/dL<br>3 📶 | 27<br>175 mg/dL<br>3 📶 | 28<br>175 mg/dL<br>3 📶 | 29<br>175 mg/dL<br>3 📶 | 30<br>175 mg/dL<br>3 📶 |
| 31<br>175 mg/dL.<br>3 📶 |  |  |  |  |  |  |

FIG. 76

Reader Details

FreeStyle

Profile

| Patient Name | Karla F. Brawner |
|---|---|
| Patient ID | 44009900 |

Settings

| Reader Date & Time | ① Mon, Jun 30, 2012  12:32 pm |
|---|---|
| Clock Style | 12-hour (am/pm) |
| Notification Sound | On |
| Button Tone | Off |
| Vibration | Off |
| Target Glucose Range | 70-140 mg/dL |

Notes

| Available Notes | Rapid-Acting Insulin |
|---|---|
| | Long-Acting Insulin |
| | Food |
| | Exercise |
| | Medication |
| | Control Solution |
| | ② Stress |

Reminders

| Alarms | 6:00 am Daily |
|---|---|
| | Check Glucose |
| | 7:00 am Daily |
| | Take Insulin |

Changes (last 30 days)

① Reader Date & Time changed on March 3rd, 2012 at 10:52am. The time was set ahead 2 hours.

② The note type "Stress" was added to the Reader on March 23rd, 2012 at 1:12pm.

FIG. 79A

Reader Details

FreeStyle

| Insulin Calculator | |
| --- | --- |
| Rapid-Acting Insulin Calculator | On |
| Calculator Mode | Advanced |
| Carbohydrate Ratio | 1 unit per 10 grams of carbs |
| Carbohydrate Target | 70-130 mg/dL |
| Correction Factor | |
| Morning (4am-10am) | 1 unit per 30 mg/dL |
| Midday (10am-4pm) | 1 unit per 20 mg/dL |
| Evening (4pm-10pm) | 1 unit per 20 mg/dL |
| Night (10pm-4am) | 1 unit per 50 mg/dL |

Changes (last 30 days)

③Masked Mode was enabled March 30th, 2012 at 3:14 pm.

③Masked Mode

| | |
| --- | --- |
| Masked Sensor Reading | On |
| Check Glucose Reminder | On |
| Remind Every | 8 hr 00 min |

FIG. 79B

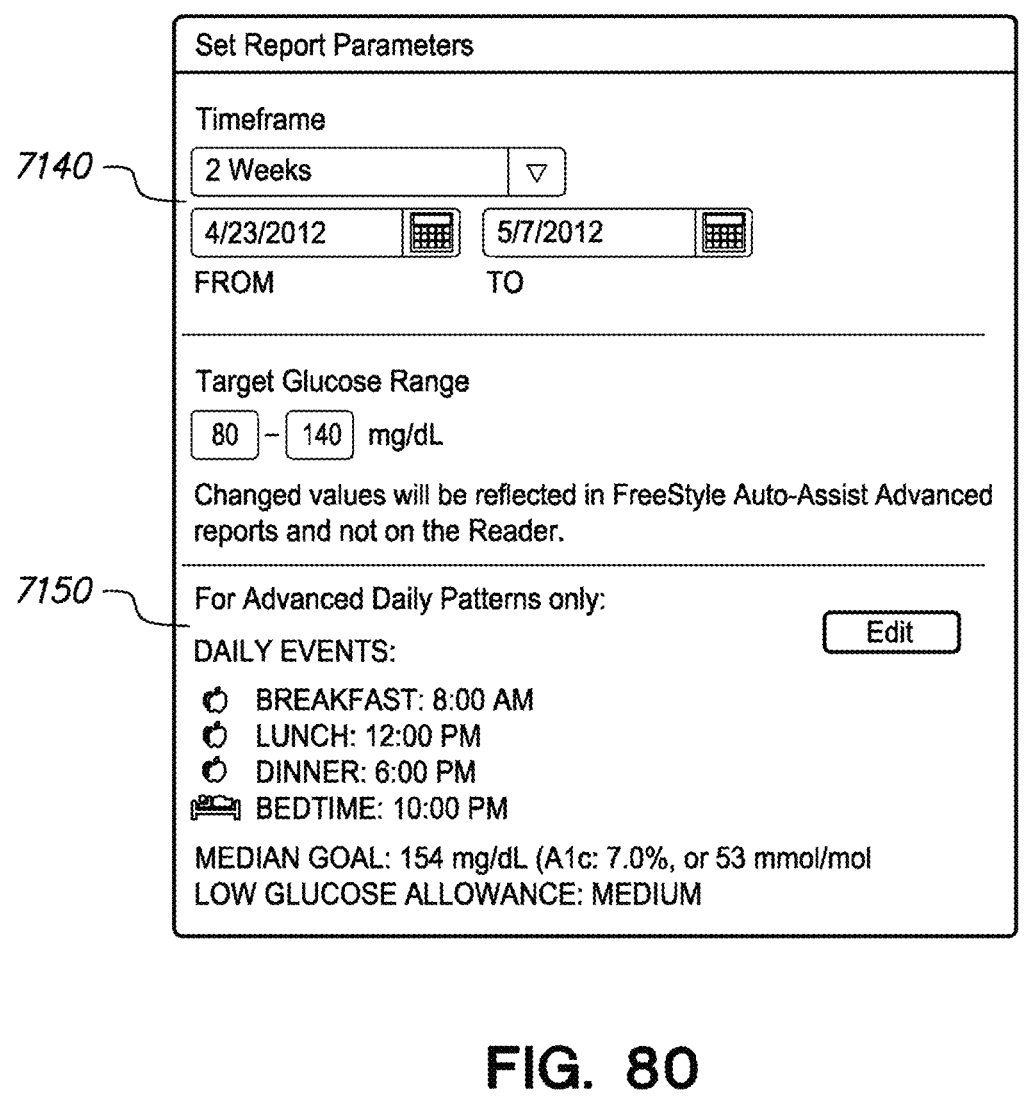

Set Report Parameters

Timeframe

7140 —

2 Weeks                    ▽

4/23/2012    ⊞        5/7/2012    ⊞
FROM                 TO

Target Glucose Range

80  –  140  mg/dL

Changed values will be reflected in FreeStyle Auto-Assist Advanced reports and not on the Reader.

7150 —

For Advanced Daily Patterns only:

DAILY EVENTS:                                    Edit

🍎  BREAKFAST: 8:00 AM
🍎  LUNCH: 12:00 PM
🍎  DINNER: 6:00 PM
🛏  BEDTIME: 10:00 PM

MEDIAN GOAL: 154 mg/dL (A1c: 7.0%, or 53 mmol/mol
LOW GLUCOSE ALLOWANCE: MEDIUM

FIG. 80

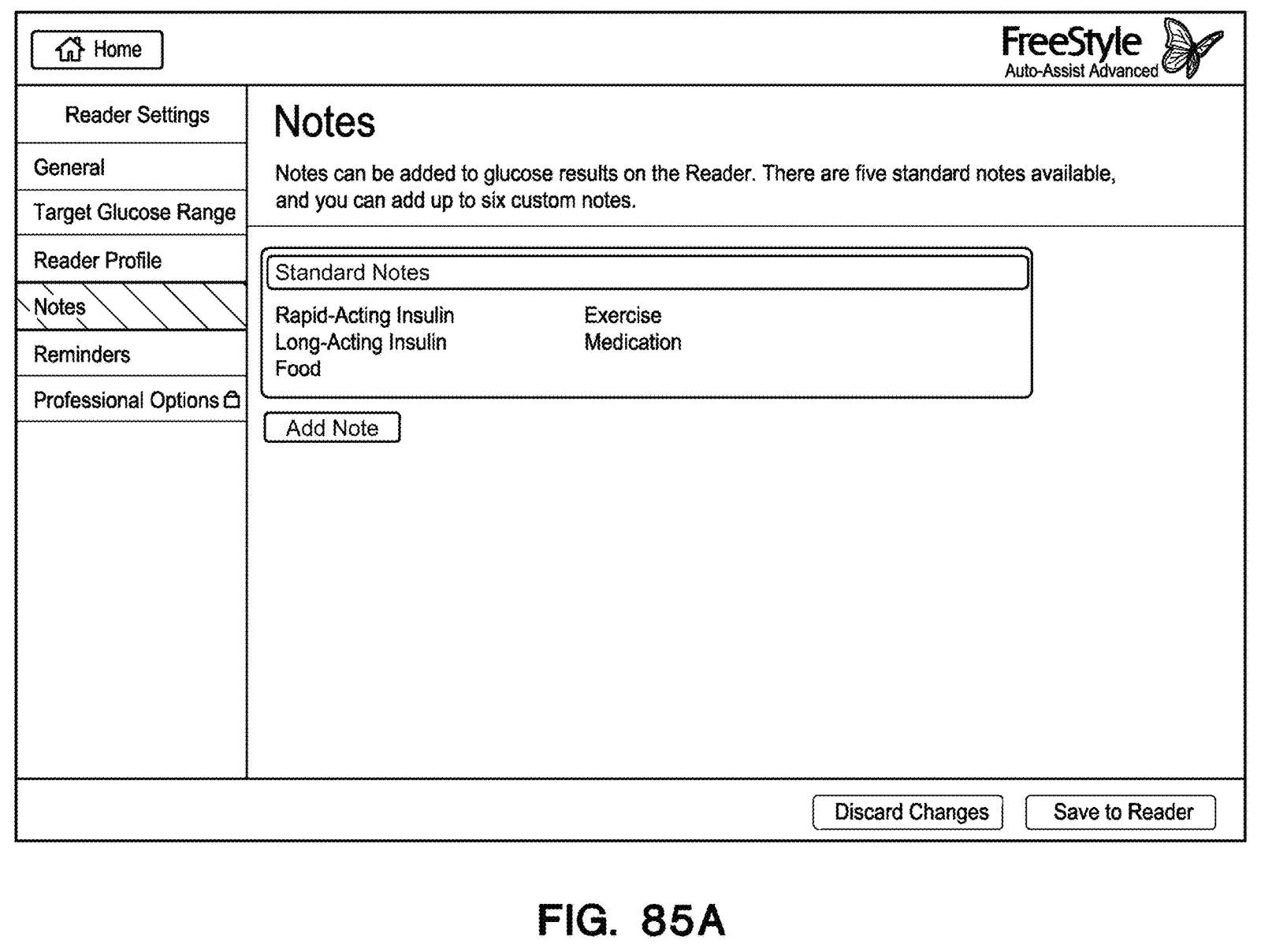

FreeStyle
Auto-Assist Advanced

Home

Reader Settings

General

Target Glucose Range

Reader Profile

Notes

Reminders

Professional Options

Notes

Notes can be added to glucose results on the Reader. There are five standard notes available, and you can add up to six custom notes.

Standard Notes

Rapid-Acting Insulin          Exercise
Long-Acting Insulin           Medication
Food Add Note Discard Changes          Save to Reader

FIG. 85A

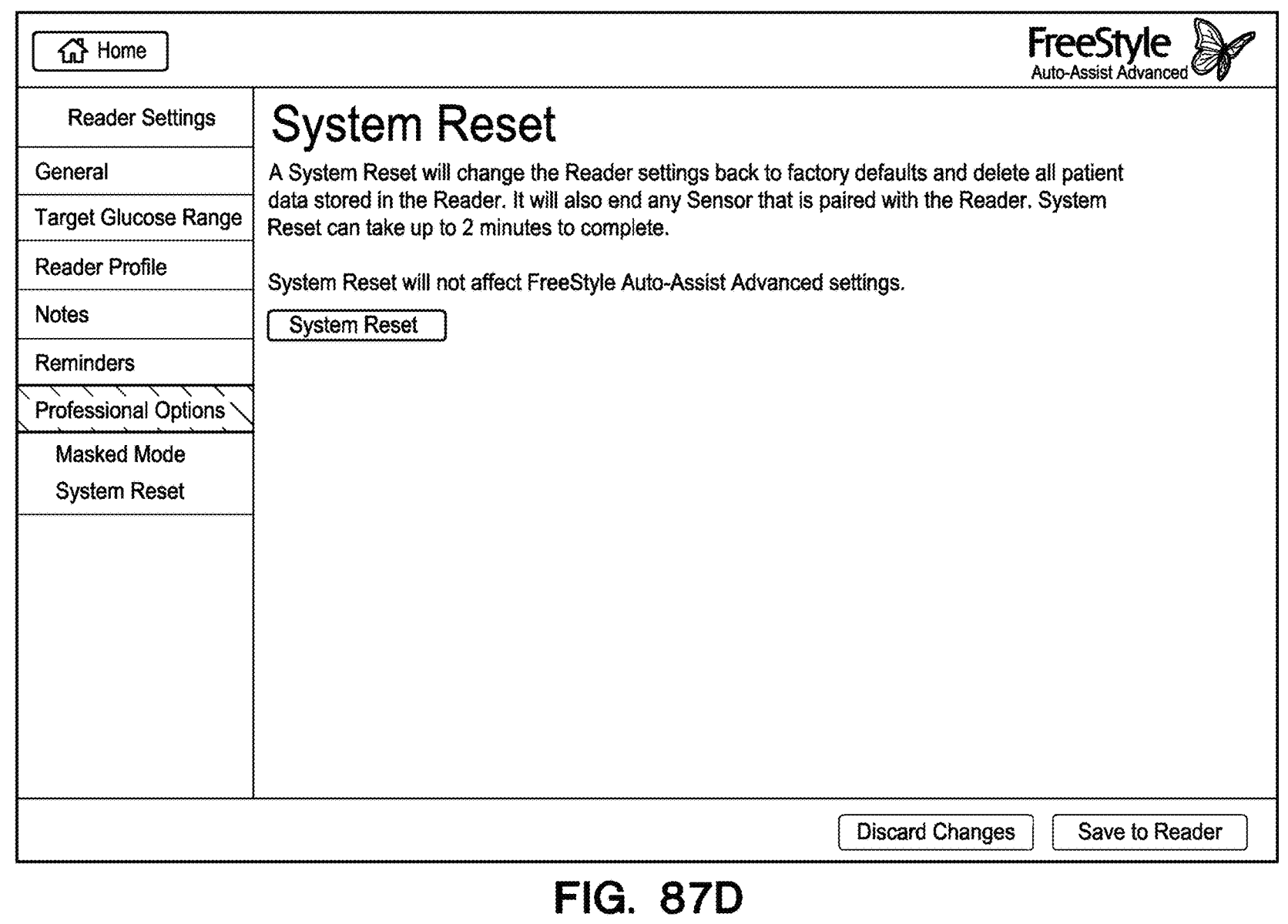

FreeStyle
Auto-Assist Advanced

Home

Reader Settings

General

Target Glucose Range

Reader Profile

Notes

Reminders

Professional Options

Masked Mode

System Reset

System Reset

A System Reset will change the Reader settings back to factory defaults and delete all patient data stored in the Reader. It will also end any Sensor that is paired with the Reader. System Reset can take up to 2 minutes to complete.

System Reset will not affect FreeStyle Auto-Assist Advanced settings.

System Reset

Discard Changes

Save to Reader

FIG. 87D

FreeStyle Auto-Assist Advanced                                    ☒

Auto-Save
Enable this feature to automatically save a PDF version of the reports
whenever you print or view them.

☑ Enable Auto-Save

File name format                          Save location

Name_Date.pdf              ▽          C: \Users\Private\Secure\Clinic\

Hampton_Rosemary_S_03022014.pdf
                                          Choose Cancel          Done

DEVICES, SYSTEMS, AND METHODS ASSOCIATED WITH ANALYTE MONITORING DEVICES AND DEVICES INCORPORATING THE SAME

RELATED APPLICATIONS

The present application is a continuation of U.S. patent application Ser. No. 17/902,703, filed Sep. 2, 2022, which is a continuation of U.S. patent application Ser. No. 17/557,534, filed Dec. 21, 2021, now U.S. Pat. No. 11,534,089, which is a continuation of U.S. patent application Ser. No. 16/175,157, filed Oct. 30, 2018, now U.S. Pat. No. 11,627,898, which is a continuation of U.S. patent application Ser. No. 14/214,430, filed Mar. 14, 2014, now U.S. Pat. No. 10,136,845, which is a continuation-in-part of and claims priority under 35 U.S.C. § 120 to U.S. patent application Ser. No. 13/407,617 filed Feb. 28, 2012, now U.S. Pat. No. 9,532,737, which claims priority under 35 U.S.C. § 119(e) to U.S. Provisional Application No. 61/492,266 filed Jun. 1, 2011, entitled "Devices, Systems, and Methods Associated with Analyte Monitoring Devices and Devices Incorporating the Same," to U.S. Provisional Application No. 61/489,098 filed May 23, 2011, entitled "Devices, Systems, and Methods Associated with Analyte Monitoring Devices and Devices Incorporating the Same," and to U.S. Provisional Application No. 61/447,645 filed Feb. 28, 2011, entitled "Devices, Systems, and Methods Associated with Analyte Monitoring Devices and Devices Incorporating the Same," the disclosures of each of which are incorporated herein by reference for all purposes. U.S. patent application Ser. No. 14/214,430 also claims priority under 35 U.S.C. § 119(e) to U.S. Provisional Application No. 61/801,518 filed Mar. 15, 2013, entitled "Devices, Systems, and Methods Associated with Analyte Monitoring Devices and Devices Incorporating the Same," the disclosure of which is incorporated herein by reference for all purposes.

BACKGROUND

Analyte monitoring devices have been used as medical diagnostic devices to determine a level of analyte from a sample. One common application is glucose measurements. For example, an analyte monitoring device is used with a remote sensor to perform an analyte reading. The sensor may be configured for implantation (e.g., subcutaneous, venous, or arterial implantation) into a patient. The analyte monitoring device processes signals from the remote sensor to determine the concentration or level of analyte in the subcutaneous tissue and may display the current level of the analyte.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included are the following:

FIG. 5E illustrates a battery low screen for an analyte monitoring device that indicates that the battery of the device is low, according to one embodiment.

FIGS. 10A and 10L illustrate example Sensor Results screens, according to certain embodiments.

FIGS. 10B and 10M illustrate example Results Non-Actionable screens, according to certain embodiments.

FIG. 10C illustrates an example Results-Masked screen, according to one embodiment.

FIGS. 12H and 12I illustrate display screens for masked results of a blood glucose control solution test and blood glucose test strip results, respectively, according to one embodiment.

FIG. 14A illustrates an example Ketone Results screen, according to one embodiment.

FIG. 14B illustrates an example interface for indicating the results of a ketone control solution test, according to one embodiment.

FIGS. 16A-16C illustrate an Insulin on Board Interface for entering insulin on board information on a Reader, according to embodiments of the present disclosure.

FIGS. 17A-17E illustrate an Insulin Calculator Interface for using an insulin calculator on a Reader, according to embodiments of the present disclosure.

FIGS. 18A and 18B illustrate a Dose Detail Interface for displaying insulin dose details on a Reader, according to embodiments of the present disclosure.

FIGS. 19A-19D illustrate a Reminders Interface for setting reminders on a Reader, according to embodiments of the present disclosure.

FIGS. 20A and 20B illustrate a Receive Reminder Interface for receiving reminders on a Reader, according to embodiments of the present disclosure.

FIG. 21B illustrates a Daily Graph screen for showing a daily graph of sensor readings obtained over a single day or 24 hour time period, according to one embodiment.

FIG. 21D illustrates an exemplary screen for showing the percentage of time the sensor readings were within a target zone, according to one embodiment.

FIG. 21E illustrates an exemplary screen for showing a graph of the number of events associated with sensor readings obtained over a time period, wherein the events are summarized with respect to a predetermined time period, according to one embodiment.

FIG. 21F illustrates an exemplary screen for indicating information associated with the use of the sensor over a time period, according to one embodiment.

FIG. 35 illustrates example animation interfaces, according to certain embodiments.

FIGS. 45A and 45B illustrate an Insulin Calculator Setup Interface for health management software configured for an advanced insulin calculator set to count carbs by grams of carbs and by time of day, according to embodiments of the present disclosure.

FIG. 60 illustrates a Meal Patterns report, according to one embodiment.

FIG. 64 illustrates an example Reader Settings Report, according to one embodiment.

FIG. 65 illustrates a Reader Settings Report, according to one embodiment.

FIGS. 70A-70D illustrate a home screen for the data management software when an update to the software is available, in accordance with some embodiments of the present disclosure.

FIG. 72 illustrates an exemplary snapshot report in accordance with some embodiments of the present disclosure.

FIG. 75 illustrates an exemplary mealtime pattern report in accordance with some embodiments of the present disclosure.

FIG. 76 illustrates an exemplary monthly summery report in accordance with some embodiments of the present disclosure.

FIGS. 79A and 79B illustrate an exemplary reader details report in accordance with some embodiments of the present disclosure.

FIG. 80 illustrates an exemplary frame of the generate reports menu for setting report parameters in accordance with some embodiments of the present disclosure.

FIGS. 81A and 81B illustrate an advanced daily pattern report settings screen in accordance with some embodiments of the present disclosure.

FIGS. 82-86 illustrate exemplary screens for adjusting settings of the Reader device in certain embodiments.

FIGS. 87A-87E illustrate screens associated with professional options of the Reader device in accordance with some embodiments of the present disclosure.

FIG. 88 illustrates options available in main systems menus of the data management software.

FIG. 89 illustrates an auto-save option screen in one embodiment.

DETAILED DESCRIPTION

Figure 1:
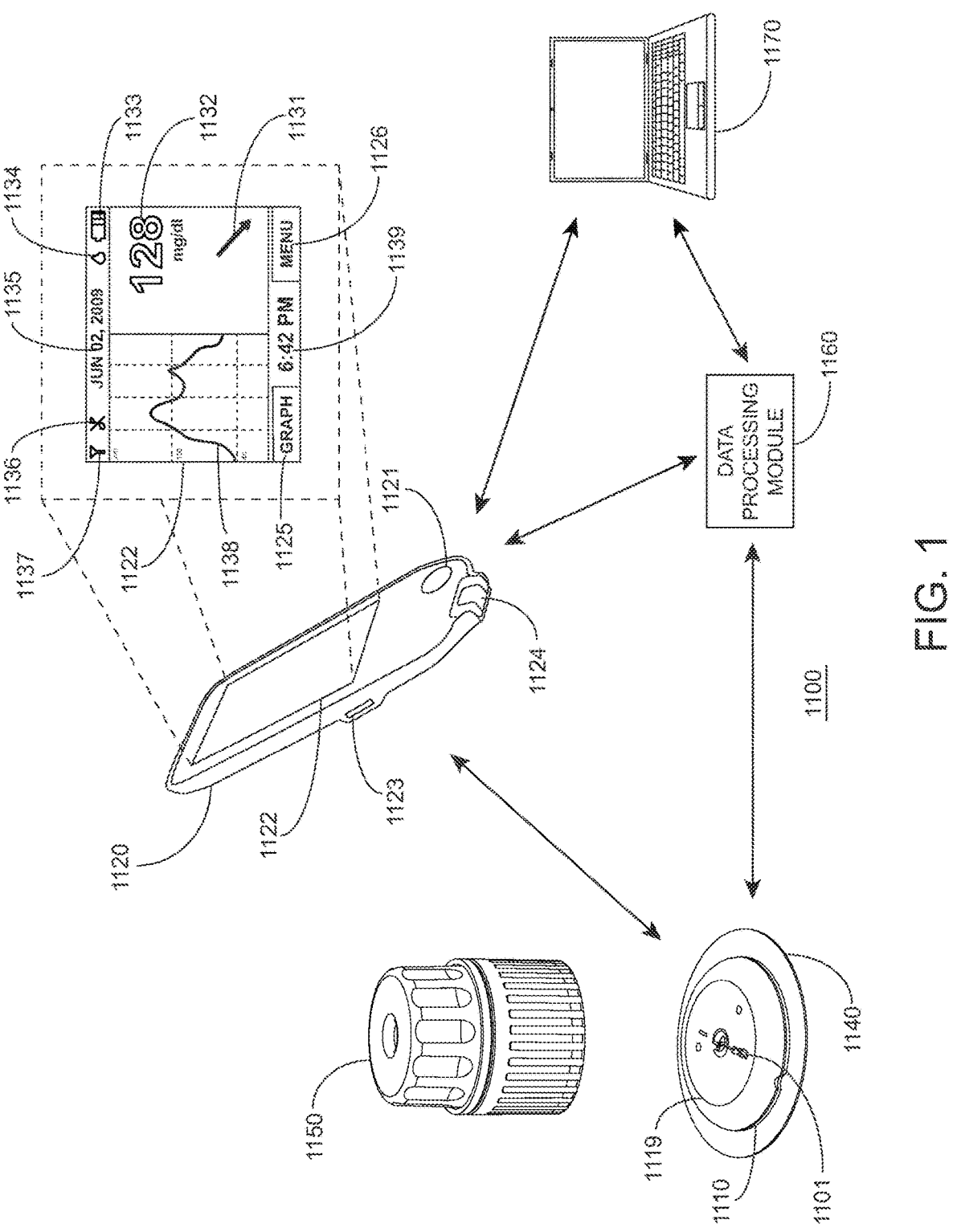
FIG. 1 illustrates an In-Vivo Analyte Monitoring System, according to one embodiment.

Before the present inventions are described, it is to be understood that this invention is not limited to particular aspects described, as such may, of course, vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a program update" includes a plurality of such program updates and reference to "the program update" includes reference to one or more program updates and equivalents thereof known to those skilled in the art, and so forth.

Generally, embodiments of the present disclosure relate to in vivo methods and devices for detecting at least one analyte such as glucose in body fluid. Accordingly, embodiments include in vivo analyte sensors configured so that at least a portion of the sensor is positioned in the body of a user (e.g., within the ISF), to obtain information about at least one analyte of the body, e.g., transcutaneously positioned in user's body. In certain embodiments, an in vivo analyte sensor is coupled to an electronics unit that is maintained on the body of the user such as on a skin surface, where such coupling provides on body, in vivo analyte sensor electronics assemblies.

In certain embodiments, analyte information is communicated from a first device such as an on body electronics unit to a second analyte monitoring device which may include user interface features, including a display, and/or the like.

In many embodiments of the system, analyte information derived by the sensor/on body electronics (for example, on body electronics assembly) is made available in a user-usable or viewable form only when queried by the user such that the timing of data communication is selected by the user. The on-body electronics may take periodic measurement and record such data until an on-demand reading is taken by the user (e.g., the display device brought in close vicinity of the on-body electronics and sensor). Upon communication, the on-body electronics may communicate the recorded data for a set time period. For example, the on-body electronics may have 8 hours of memory in which it stores periodic measurements taken every 15 minutes. When an on-demand reading is taken, the entire 8 hours is transferred to the device. It should be appreciated that if the user does not take an on-demand reading for longer than 8 hours, some of the data may be lost.

Accordingly, in certain embodiments once a sensor electronics assembly is placed on the body so that at least a portion of the in vivo sensor is in contact with bodily fluid such as ISF and the sensor is electrically coupled to the electronics unit, sensor derived analyte information may be communicated from the on body electronics to a display device on-demand by powering on the display device, and executing a software algorithm stored in and accessed from a memory of the display device, to generate one or more request commands, control signal or data packet to send to the on body electronics. The software algorithm executed under, for example, the control of the microprocessor or application specific integrated circuit (ASIC) of the display device may include routines to detect the position of the on body electronics relative to the display device to initiate the transmission of the generated request command, control signal and/or data packet.

Display devices may also include programming stored in memory for execution by one or more microprocessors and/or ASICs to generate and transmit the one or more request command, control signal or data packet to send to the on body electronics in response to a user activation of an input mechanism on the display device such as depressing a button on the display device, triggering a soft button associated with the data communication function, and so on. The input mechanism may be alternatively or additionally provided on or in the on body electronics which may be configured for user activation. In certain embodiments, voice commands or audible signals may be used to prompt or instruct the microprocessor or ASIC to execute the software routine(s) stored in the memory to generate and transmit the one or more request command, control signal or data packet to the on body device. In the embodiments that are voice activated or responsive to voice commands or audible signals, on body electronics and/or display device includes a microphone, a speaker, and processing routines stored in the respective memories of the on body electronics and/or the display device to process the voice commands and/or audible signals. In certain embodiments, positioning the on body device and the display device within a predetermined distance (e.g., close proximity) relative to each other initiates one or more software routines stored in the memory of the display device to generate and transmit a request command, control signal or data packet.

Different types and/or forms and/or amounts of information may be sent for each on demand reading, including but not limited to one or more of current analyte level information (i.e., real time or the most recently obtained analyte level information temporally corresponding to the time the reading is initiated), rate of change of an analyte over a predetermined time period, rate of the rate of change of an analyte (acceleration in the rate of change), historical analyte information corresponding to analyte information obtained prior to a given reading and stored in memory of the assembly. Some or all of real time, historical, rate of change, rate of rate of change (such as acceleration or deceleration) information may be sent to a display device for a given reading. In certain embodiments, the type and/or form and/or amount of information sent to a display device may be preprogrammed and/or unchangeable (e.g., preset at manufacturing), or may not be preprogrammed and/or unchangeable so that it may be selectable and/or changeable in the field one or more times (e.g., by activating a switch of the system, etc). Accordingly, in certain embodiments, for each on demand reading, a display device will output a current (real time) sensor-derived analyte value (e.g., in numerical format), a current rate of analyte change (e.g., in the form of an analyte rate indicator such as a arrow pointing in a direction to indicate the current rate), and analyte trend history data based on sensor readings acquired by and stored in memory of on body electronics (e.g., in the form of a graphical trace). Additionally, the on skin or sensor temperature reading or measurement associated with each on demand reading may be communicated from the on body electronics to the display device. The temperature reading or measurement, however, may not be output or displayed on the display device, but rather, used in conjunction with a software routine executed by the display device to correct or compensate the analyte measurement output to the user on the display device.

As described, embodiments include in vivo analyte sensors and on body electronics that together provide body wearable sensor electronics assemblies (also referred to herein as a "patch"). In certain embodiments, in vivo analyte sensors are fully integrated with on body electronics (fixedly connected during manufacture), while in other embodiments they are separate but connectable post manufacture (e.g., before, during or after sensor insertion into a body). On body electronics may include an in vivo glucose sensor, electronics, battery, and antenna encased (except for the sensor portion that is for in vivo positioning) in a waterproof housing that includes or is attachable to an adhesive pad.

Embodiments include sensor insertion devices, which also may be referred to herein as sensor delivery units, or the like. Insertion devices may retain on body electronics assemblies completely in an interior compartment, i.e., an insertion device may be "pre-loaded" with on body electronics assemblies during the manufacturing process (e.g., on body electronics may be packaged in a sterile interior compartment of an insertion device). In such embodiments, insertion devices may form sensor assembly packages (including sterile packages) for pre-use or new on body electronics assemblies, and insertion devices configured to apply on body electronics assemblies to recipient bodies.

Embodiments include portable handheld display devices, as separate devices and spaced apart from an on body electronics assembly, that collects information from the assemblies and provide sensor derived analyte readings to users. Such devices may also be referred to as meters, readers, monitors, receivers, human interface devices, companions, or the like. Certain embodiments may include an integrated in vitro analyte meter. In certain embodiments, display devices include one or more wired or wireless communications ports such as USB, serial, parallel, or the like, configured to establish communication between a display device and another unit (e.g., on body electronics, power unit to recharge a battery, a PC, etc.).

Compatible informatics software in certain embodiments include, for example, but not limited to stand alone or network connection enabled data management software program, resident or running on a display device, personal computer, a server terminal, for example, to perform data analysis, charting, data storage, data archiving and data communication as well as data synchronization. Informatics software in certain embodiments may also include software for executing field upgradable functions to upgrade firmware of a display device and/or on body electronics unit to upgrade the resident software on the display device and/or the on body electronics unit, e.g., with versions of firmware that include additional features and/or include software bugs or errors fixed, etc.

Embodiments may include a haptic feedback feature such as a vibration motor or the like, configured so that corresponding notifications (e.g., a successful on-demand reading received at a display device), may be delivered in the form of haptic feedback.

Embodiments include programming embedded on a computer readable medium, i.e., computer-based application software (may also be referred to herein as informatics software or programming or the like) that processes analyte information obtained from the system and/or user self-reported data. Application software may be installed on a host computer such as a mobile telephone, PC, an Internet-enabled human interface device such as an Internet-enabled phone, personal digital assistant, or the like, by a display device or an on body electronics unit. Informatics programming may transform data acquired and stored on a display device or on body unit for use by a user.

Embodiments of the subject disclosure are described primarily with respect to glucose monitoring devices and systems, and methods of glucose monitoring, for convenience only and such description is in no way intended to limit the scope of the disclosure. It is to be understood that the analyte monitoring system may be configured to monitor a variety of analytes at the same time or at different times.

For example, analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times, with a single sensor or with a plurality of sensors which may use the same on body electronics (e.g., simultaneously) or with different on body electronics.

As described in detail below, embodiments include devices, systems, kits and/or methods to monitor one or more physiological parameters such as, for example, but not limited to, analyte levels, temperature levels, heart rate, user activity level, over a predetermined monitoring time period. Also provided are methods of manufacturing. Predetermined monitoring time periods may be less than about 1 hour, or may include about 1 hour or more, e.g., about a few hours or more, e.g., about a few days of more, e.g., about 3 or more days, e.g., about 5 days or more, e.g., about 7 days or more, e.g., about 10 days or more, e.g., about 14 days or more, e.g., about several weeks, e.g., about 1 month or more. In certain embodiments, after the expiration of the predetermined monitoring time period, one or more features of the system may be automatically deactivated or disabled at the on body electronics assembly and/or display device.

For example, a predetermined monitoring time period may begin with positioning the sensor in vivo and in contact with a body fluid such as ISF, and/or with the initiation (or powering on to full operational mode) of the on body electronics. Initialization of on body electronics may be implemented with a command generated and transmitted by a display device in response to the activation of a switch and/or by placing the display device within a predetermined distance (e.g., close proximity) to the on body electronics, or by user manual activation of a switch on the on body electronics unit, e.g., depressing a button, or such activation may be caused by the insertion device, e.g., as described in U.S. patent application Ser. No. 12/698,129, filed on Feb. 1, 2010, and U.S. Provisional Application Nos. 61/238,646, 61/246,825, 61/247,516, 61/249,535, 61/317,243, 61/345, 562, and 61/361,374, the disclosures of each of which are incorporated herein by reference for all purposes.

When initialized in response to a received command from a display device, the on body electronics retrieves and executes from its memory software routine to fully power on the components of the on body electronics, effectively placing the on body electronics in full operational mode in response to receiving the activation command from the display device. For example, prior to the receipt of the command from the display device, a portion of the components in the on body electronics may be powered by its internal power supply such as a battery while another portion of the components in the on body electronics may be in powered down or low power including no power, inactive mode, or all components may be in an inactive mode, powered down mode. Upon receipt of the command, the remaining portion (or all) of the components of the on body electronics is switched to active, fully operational mode.

Embodiments include transcutaneous sensors and also wholly implantable sensors and wholly implantable assemblies in which a single assembly including the analyte sensor and electronics are provided in a sealed housing (e.g., hermetically sealed biocompatible housing) for implantation in a user's body for monitoring one or more physiological parameters.

Exemplary analyte monitoring systems that relate to the present disclosure and that may be utilized in connection with the disclosed analyte measurement system include those described in U.S. Pat. Nos. 7,041,468; 5,356,786; 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; 5,264,014; 5,262,305; 5,320,715; 5,593,852; 6,746,582; 6,284,478; 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. US2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; US patent Application Publication No. 2010/ 0198034; and U.S. provisional application No. 61/149,639 titled "Compact On-Body Physiological Monitoring Device and Methods Thereof", the disclosures of each of which are incorporated herein by reference in their entirety.

Additional relevant subject matter is provided in the following disclosures: U.S. Provisional Application No. 61/498,142, filed Jun. 17, 2011; U.S. application Ser. Nos. 13/071,461, 13/071,487, and 13/071,497, which were both filed on Mar. 24, 2011, and Ser. No. 13/091,557 which was filed on Apr. 21, 2011; U.S. Patent Application Publication No. 2010/0081905, 2011/0021889, 2010/0230285, and 2011/0021889; and U.S. Pat. Nos. 6,736,957, 7,501,053 and 7,754,093; the disclosures of which are each incorporated by reference herein in their entirety and for all purposes.

FIG. 1 illustrates an example embodiment of In-Vivo Analyte Monitoring System and is described below. FIG. 1 shows an exemplary in vivo-based analyte monitoring system 1100 in accordance with embodiments of the present disclosure. As shown, in certain embodiments, analyte monitoring system 1100 includes on body electronics 1110 electrically coupled to in vivo analyte sensor 1101 (a proximal portion of which is shown in FIG. 1) and attached to adhesive layer 1140 for attachment on a skin surface on the body of a user. On body electronics 1110 includes on body housing 1119 that defines an interior compartment. Also shown in FIG. 1 is insertion device 1150 that, when operated, transcutaneously positions a portion of analyte sensor 1101 through a skin surface and in fluid contact with ISF, and positions on body electronics 1110 and adhesive layer 1140 on a skin surface In certain embodiments, on body electronics 1110, analyte sensor 1101 and adhesive layer 1140 are sealed within the housing of insertion device 150 before use, and in certain embodiments, adhesive layer 1140 is also sealed within the housing or itself provides a terminal seal of the insertion device 1150. Devices, systems and methods that maybe used with embodiments herein are described, e.g., in U.S. patent application Ser. No. 12/698, 129 and U.S. Provisional Application Nos. 61/238,646, 61/246,825, 61/247,516, 61/249,535, 61/317,243, 61/345, 562, and 61/361,374, the disclosures of each of which are incorporated herein by reference for all purposes.

Referring back to the FIG. 1, analyte monitoring system 100 includes display device 1120 which includes a display 1122 to output information to the user, an input component 1121 such as a button, actuator, a touch sensitive switch, a capacitive switch, pressure sensitive switch, jog wheel or the like, to input data or command to display device 1120 or otherwise control the operation of display device 1120. It is noted that some embodiments may include display-less devices or devices without any user interface components. These devices may be functionalized to store data as a data logger and/or provide a conduit to transfer data from on body electronics and/or a display-less device to another device and/or location. Embodiments will be described herein as display devices for exemplary purposes which are in no way intended to limit the embodiments of the present disclosure. It will be apparent that display-less devices may also be used in certain embodiments.

In certain embodiments, display 1122 and input component 1121 may be integrated into a single component, for example a display that can detect the presence and location of a physical contact touch upon the display such as a touch screen user interface. In such embodiments, the user may control the operation of display device 1120 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Display device 1120 may be a dynamic color LCD display. In certain embodiments, display device 1120 may have preset and customizable options, including display resolution, quality and backlight options. Display device, in one embodiment, may have a dynamic color palette of up to 65,000 colors and include graphical displays from 256 color subsets of the 65,000 color dynamic display. In other embodiments, the LCD display may include a backlight, which may be an LED backlight. The LCD backlight may be preprogrammed to dim or shut off after certain periods of time of non-activity elapse. For example, in certain embodiments, the default time before the display shuts off may be 1 minute for most screens, including a dimming feature of the backlight after 15 seconds. In some embodiments, the time until display shut off or display dim may vary based on the current screen or mode of the device, e.g., an apply blood to test strip screen, as described herein below in more detail, may have a longer time out than the default 1 minute, e.g., 2 minutes. In other embodiments, the display does not dim or turn off unless a user manually commands the device to turn off the display.

Display device 1120 also includes data communication port 1123 for wired data communication with external devices such as remote terminal (personal computer) 1170, for example. Example embodiments of the data communication port 1123 include USB port, mini USB port, RS-232 port, Ethernet port, Firewire port, or other similar data communication ports configured to connect to the compatible data cables. Display device 1120 may also include an integrated in vitro glucose meter, including in vitro test strip port 1124 to receive an in vitro glucose test strip for performing in vitro blood glucose measurements.

Referring still to FIG. 1, display 1122 in certain embodiments is configured to display a variety of information— some or all of which may be displayed at the same or different time on display 1122. Display 1122 may include but is not limited to graphical display 1138, for example, providing a graphical output of glucose values over a monitored time period (which may show important markers such as meals, exercise, sleep, heart rate, blood pressure, etc, numerical display 1132, for example, providing monitored glucose values (acquired or received in response to the request for the information), and trend or directional arrow display 1131 that indicates a rate of analyte change and/or a rate of the rate of analyte change, e.g., by moving locations on display 1122.

As further shown in FIG. 1, display 1122 may also include date display 1135 providing for example, date information for the user, time of day information display 1139 providing time of day information to the user, battery level indicator display 1133 which graphically shows the condition of the battery (rechargeable or disposable) of the display device 1120, sensor calibration status icon display 1134 for example, in monitoring systems that require periodic, routine or a predetermined number of user calibration events, notifying the user that the analyte sensor calibration is necessary, audio/vibratory settings icon display 1136 for displaying the status of the audio/vibratory output or alarm state, and wireless connectivity status icon display 1137 that provides indication of wireless communication connection with other devices such as on body electronics, data processing module1160, and/or remote terminal 1170. As additionally shown in FIG. 1, display 1122 may further include simulated touch screen buttons 1125,1126 for accessing menus, changing display graph output configurations or otherwise for controlling the operation of display device 1120.

Referring back to FIG. 1, in certain embodiments, display 1122 of display device 1120 may be additionally, or instead of visual display, configured to output alarms notifications such as alarm and/or alert notifications, glucose values etc, which may be audible, tactile, or any combination thereof. In one aspect, the display device 1120 may include other output components such as a speaker, vibratory output component and the like to provide audible and/or vibratory output indication to the user in addition to the visual output indication provided on display 1122. Further details and other display embodiments can be found in, e.g., U.S. patent application Ser. No. 12/871,901 and U.S. Provisional Application Nos. 61/238,672, 61/247,541, 61/297,625, the disclosures of each of which are incorporated herein by reference for all purposes.

After the positioning of on body electronics 1110 on the skin surface and analyte sensor 1101 in vivo to establish fluid contact with ISF (or other appropriate body fluid), on body electronics 1110 in certain embodiments is configured to wirelessly communicate analyte related data (such as, for example, data corresponding to monitored analyte level and/or monitored temperature data, and/or stored historical analyte related data) when on body electronics 1110 receives a command or request signal from display device 120. In certain embodiments, on body electronics 1110 may be configured to at least periodically broadcast real time data associated with monitored analyte level which is received by display device 1120 when display device 1120 is within communication range of the data broadcast from on body electronics 1110, i.e., it does not need a command or request from a display device to send information.

For example, display device 1120 may be configured to transmit one or more commands to on body electronics 1110 to initiate data transfer, and in response, on body electronics 1110 may be configured to wirelessly transmit stored analyte related data collected during the monitoring time period to display device 1120. Display device 1120 may in turn be connected to a remote terminal 1170 such as a personal computer and functions as a data conduit to transfer the stored analyte level information from the on body electronics 1110 to remote terminal 1170. In certain embodiments, the received data from the on body electronics 1110 may be stored (permanently or temporarily) in one or more memory of the display device 1120. In certain other embodiments, display device 1120 is configured as a data conduit to pass the data received from on body electronics 1110 to remote terminal 1170 that is connected to display device 1120.

Referring still to FIG. 1, also shown in analyte monitoring system 1100 are data processing module 1160 and remote terminal 1170. Remote terminal 1170 may include a personal computer, a server terminal a laptop computer or other suitable data processing devices including software for data management and analysis and communication with the components in the analyte monitoring system 1100. For example, remote terminal 1170 may be connected to a local area network (LAN), a wide area network (WAN), or other data network for uni-directional or bi-directional data communication between remote terminal 1170 and display device 1120 and/or data processing module 1160.

Remote terminal 1170 in certain embodiments may include one or more computer terminals located at a physician's office or a hospital. For example, remote terminal 1170 may be located at a location other than the location of display device 1120. Remote terminal 1170 and display device 1120 could be in different rooms or different buildings. Remote terminal 1170 and display device 1120 could be at least about one mile apart, e.g., at least about 110 miles apart, e.g., at least about 1100 miles apart. For example, remote terminal 1170 could be in the same city as display device 1120, remote terminal 1170 could be in a different city than display device 1120, remote terminal 1170 could be in the same state as display device 1120, remote terminal 1170 could be in a different state than display device 1120, remote terminal 1170 could be in the same country as display device 1120, or remote terminal 1170 could be in a different country than display device 1120, for example. In certain embodiments, a separate, optional data communication/processing device such as data processing module 1160 may be provided in analyte monitoring system 1100. Data processing module 160 may include components to communicate using one or more wireless communication protocols such as, for example, but not limited to, infrared (IR) protocol, Bluetooth® protocol, Zigbee® protocol, and 802.11 wireless LAN protocol. Additional description of communication protocols including those based on Bluetooth® protocol and/or Zigbee® protocol can be found in U.S. Patent Publication No. 2006/0193375 incorporated herein by reference for all purposes. Data processing module 1160 may further include communication ports, drivers or connectors to establish wired communication with one or more of display device 1120, on body electronics 1110, or remote terminal 1170 including, for example, but not limited to USB connector and/or USB port, Ethernet connector and/or port, Fire Wire connector and/or port, or RS-232 port and/or connector.

In certain embodiments, control logic or microprocessors of on body electronics 1110 include software programs to determine future or anticipated analyte levels based on information obtained from analyte sensor 1101, e.g., the current analyte level, the rate of change of the analyte level, the acceleration of the analyte level change, and/or analyte trend information determined based on stored monitored analyte data providing a historical trend or direction of analyte level fluctuation as function time during monitored time period. Predictive alarm parameters may be programmed or programmable in display device 1120, or the on body electronics 1110, or both, and output to the user in advance of anticipating the user's analyte level reaching the future level. This provides the user an opportunity to take timely corrective action.

Information, such as variation or fluctuation of the monitored analyte level as a function of time over the monitored time period providing analyte trend information, for example, may be determined by one or more control logic or microprocessors of display device 1120, data processing module 160, and/or remote terminal 1170, and/or on body electronics 1110. Such information may be displayed as, for example, a graph (such as a line graph) to indicate to the user the current and/or historical and/or and predicted future analyte levels as measured and predicted by the analyte monitoring system 1100. Such information may also be displayed as directional arrows (for example, see trend or directional arrow display 1131) or other icon(s), e.g., the position of which on the screen relative to a reference point indicated whether the analyte level is increasing or decreasing as well as the acceleration or deceleration of the increase or decrease in analyte level. This information may be utilized by the user to determine any necessary corrective actions to ensure the analyte level remains within an acceptable and/or clinically safe range. Other visual indicators, including colors, flashing, fading, etc., as well as audio indicators including a change in pitch, volume, or tone of an audio output and/or vibratory or other tactile indicators may also be incorporated into the display of trend data as means of notifying the user of the current level and/or direction and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, the system 1100 may include an algorithm stored on computer readable medium to determine the time it will take to reach a clinically significant level and will output notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring again back to FIG. 1, in certain embodiments, software algorithm(s) for execution by data processing module 1160 may be stored in an external memory device such as an SD card, microSD card, compact flash card, XD card, Memory Stick card, Memory Stick Duo card, or USB memory stick/device including executable programs stored in such devices for execution upon connection to the respective one or more of the on body electronics 1110, remote terminal 1170 or display device 1120. In a further aspect, software algorithms for execution by data processing module 160 may be provided to a communication device such as a mobile telephone including, for example, WiFi or Internet enabled smart phones or personal digital assistants (PDAs) as a downloadable application for execution by the downloading communication device.

Examples of smart phones include Windows®, Android™, iPhone® operating system, Palm® WebOS™, Blackberry® operating system, or Symbian® operating system based mobile telephones with data network connectivity functionality for data communication over an internet connection and/or a local area network (LAN). PDAs as described above include, for example, portable electronic devices including one or more microprocessors and data communication capability with a user interface (e.g., display/output unit and/or input unit, and configured for performing data processing, data upload/download over the internet, for example. In such embodiments, remote terminal 170 may be configured to provide the executable application software to the one or more of the communication devices described above when communication between the remote terminal 1170 and the devices are established.

In still further embodiments, executable software applications may be provided over-the-air (OTA) as an OTA download such that wired connection to remote terminal 1170 is not necessary. For example, executable applications may be automatically downloaded as software download to the communication device, and depending upon the configuration of the communication device, installed on the device for use automatically, or based on user confirmation or acknowledgement on the communication device to execute the installation of the application. The OTA download and installation of software may include software applications and/or routines that are updates or upgrades to the existing functions or features of data processing module 1160 and/or display device 1120.

Referring back to remote terminal 1170 of FIG. 1, in certain embodiments, new software and/or software updates such as software patches or fixes, firmware updates or software driver upgrades, among others, for display device 1120 and/or on body electronics 1110 and/or data processing module 1160 may be provided by remote terminal 1170 when communication between the remote terminal 1170 and display device 1120 and/or data processing module 1160 is established. For example, software upgrades, executable programming changes or modification for on body electronics 1110 may be received from remote terminal 1170 by one or more of display device 1120 or data processing module 1160, and thereafter, provided to on body electronics 1110 to update its software or programmable functions. For example, in certain embodiments, software received and installed in on body electronics 1110 may include software bug fixes, modification to the previously stalled software parameters (modification to analyte related data storage time interval, resetting or adjusting time base or information of on body electronics 1110, modification to the transmitted data type, data transmission sequence, or data storage time period, among others). Additional details describing field upgradability of software of portable electronic devices, and data processing are provided in U.S. application Ser. Nos. 12/698,124, 12/794,721, 12/699,653, and 12/699,844, and U.S. Provisional Application Nos. 61/359,265 and 61/325,155, the disclosures of all of which are incorporated by reference herein for all purposes.

In some aspects, the display device (also referred to herein as "analyte monitoring device" or simply "device") is configured to receive a signal from a remote sensor using radio-frequency identification (RFID) technology.

This configuration may be used to provide glucose on demand capabilities, for example, in which case when a measurement reading is desired, the analyte monitoring device is brought within close vicinity of the implantable sensor. It should be appreciated that in other embodiments the wireless communication unit may communicate with the sensor using a different wireless communication technology than RFID. When within range, the device may be configured to verify that the sensor is the appropriate sensor that it has been configured to operate with. If not, the device ignores the sensor and does not initiate operation with the sensor. If so, the device initiates operation with the sensor.

The analyte monitoring device may perform a variety of functions, including for example: modifying the signals from the sensor using calibration data and/or measurements from a temperature probe (not shown); determining a level of an analyte in the interstitial fluid; determining a level of an analyte in the bloodstream based on the sensor measurements in the interstitial fluid; determining if the level, rate of change, and/or acceleration in the rate of change of the analyte exceeds or meets one or more threshold values; activating an alarm system if a threshold value is met or exceeded; evaluating trends in the level of an analyte based on a series of sensor signals; therapy management (e.g., determine a dose of a medication, etc.); and reduce noise or error contributions (e.g., through signal averaging or comparing readings from multiple electrodes); etc. The analyte monitoring device may be simple and perform only one or a small number of these functions or the analyte monitoring device may perform all or most of these functions.

Software for the Remote Device

In some aspects, the analyte monitoring device may be communicatively coupled to a remote data processing device for management purposes. Remote device may include, for example, a personal computer, laptop, PDA, cellular phone, smartphone, set-top box, etc. The remote device may include, for example, a control unit including any variety of processor, microprocessor, microcontroller, etc. The remote device may also include a memory unit comprising non-volatile memory and volatile memory.

The term "remote device" is used herein to represent any device that is external to the analyte monitoring device. The remote device may require software to fully communicate with the analyte monitoring device, manage data from the analyte monitoring device, modify settings on the analyte monitoring device, or otherwise operate with analyte monitoring device. This auto-assisting user interface software is referred to herein as "remote device software" or "RD software" or "data management software" to distinguish it from the user interface software running on the analyte monitoring device. The RD software may be obtained from one or more methods such as downloading from the web, CD-ROM, memory stick, etc. The RD software is generally discussed here and additional details regarding various flows and screens are provided later.

In some embodiments, the analyte monitoring device includes the RD software programs and/or applications to be run on the remote device. In some instances, the RD software may be configured to automatically launch when the analyte monitoring device is coupled to the computer. For example, the analyte monitoring device may include an installer program that is stored in non-volatile memory and executed when the analyte monitoring device is coupled to the remote device. The installer program may be executed when the user couples the analyte monitoring device to the remote device. The installer program may then initiate the launch of the RD software on the remote device.

In some embodiments, the RD software is not stored in non-volatile memory on the remote device. The RD software is stored on the analyte monitoring device and used to launch the RD software on the remote device is coupled to the analyte monitoring device.

In some embodiments, the RD software may be downloaded and stored in non-volatile memory on the remote device. For example, the RD software may be downloaded via a network connection (e.g., via an internet connection), by storage device (e.g., CD-ROM, memory stick, etc.), and/or downloaded from the analyte monitoring device. In some instances, the RD software is capable of being run even when the device is not coupled to the computer.

It should be understood that the RD software may be compatible with various hardware systems (e.g., PC, MAC) and various operating systems (e.g., Windows, MAC OS, Linux).

The analyte monitoring device may be communicatively coupled to the remote device via wired technologies. Example wired technologies may include, but are not limited to, the following technologies, or family of technologies: USB, FireWire, SPI, SDIO, RS-232 port, etc.

The analyte monitoring device may include, for example, a communication connector unit to permit wired communication and coupling to the remote device. The communication connector unit provides the capability to communicate with a remote device having an appropriate interface to operatively couple with the communication connector. In some embodiments, the communication connector is configured to communicate with a smartphone such as an iPhone or Blackberry.

The communication connector unit may be any variety of connection interfaces—e.g., male or female connection interfaces. Using USB as an example, the communication connector may be any of the variety of USB plugs or USB receptacles/ports. As USB receptacles are typically located on computer and other devices, a corresponding USB plug used as a communication connector unit will enable the analyte monitoring device to be plugged directly into the USB receptacle, avoiding the use of cables. In other instances, the appropriate USB receptacle may be used on the analyte monitoring device to enable communication using a USB cable (similar to many other devices such as digital cameras, cellular phones, smartphones, etc.).

It should be appreciated that the in some embodiments the analyte monitoring device may be communicably coupled to the remote device via wireless technology. In such instances, the analyte monitoring device may include corresponding transmitters, receivers, and/or transceivers. The analyte monitoring device may be configured to wirelessly communicate using a technology including, but not limited to, radio frequency (RF) communication, Zigbee® communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM), etc.

The functionality of the RD software launched on the remote device may include a variety of functions relating to, for example, data acquisition; data management; management of features, settings, configurations, etc., of the analyte monitoring device; generation, saving, transmitting, and/or printing of reports, management of updates (e.g., field updates to device firmware and RD software); access to training content, web-based content, web-based marketing; etc.

The RD software may be launched on a remote device and used by the user (e.g., the patient) and/or a health care provider (HCP) (e.g., physician, hospital staff, etc.). For example, the HCP and/or patient may use the RD software on a remote device to analyze the patient data, view and print reports, view and change device settings, update device firmware and application software, etc.

In some instances, the RD software may initiate a comparison between the time date on the analyte monitoring device and that on the remote device and/or remote time server accessed via an internet connection from the remote device. The RD software may account for discrepancies and take action accordingly. For example, thresholds may be set (e.g., 5 minute difference) and if the threshold is reached, the analyte monitoring device prompts the user with a warning, question, indicator, etc., to acknowledge the discrepancy and/or remedy the discrepancy (e.g., adjust the time on one of the devices). In some instances, a similar comparison may be performed by the RD software to account for other discrepancies between the analyte monitoring device and remote device—e.g., discrepancies between data logs, data values, stored files, device and/or user interface configurations and settings, etc. The appropriate action can then be taken or requested.

Various defaults and customized configurations and settings may be established for generating, printing, saving, exporting, etc., reports. For example, the various formats for the report may be established (e.g., layout, style, themes, color, etc.); various file types to save the report as (e.g., PDF, Word document, Excel spreadsheet, etc. In some instances, for example, the RD software may provide the user with the ability to export tab-delimited text files or XML exports of the meter data (e.g., including blood glucose, ketones, carbs, insulin, and event tags, etc.). In some instances, the RD software may enable the user to save, print, and/or export preferences, including favorite reports, target blood glucose ranges, auto save, auto print, color/black and white printing, device/software update settings for multiple devices, etc.

In some aspects, the RD software is used to control the configuration of the device and data from the device. This control may be utilized by the user and/or HCP. In some instances, the RD software shall provide access to one or more informative documents, trainings, tutorials, etc. For example, the RD software application may provide links or to manufacturer sponsored websites intended for any variety of purposes such as marketing and training content.

In some aspects, the RD software may include an update management function to help facilitate the detection, download, and installation of updates (e.g., firmware, informatics application updates, etc.) for the analyte meter device and/or the RD software. The updates may be detected and downloaded automatically in some instances (e.g., when an internet connection is active) and/or detected and downloaded upon user confirmation or request. In some instances, updates to the software shall also update its installation files stored on the device. Moreover, in some instances, when the device firmware is updated, required labeling/user documentation is also updated on the device. In some instances, when device firmware is updated, the existing device settings and testing history (e.g., blood glucose, insulin, carb data, etc.) is preserved.

In some aspects of the present disclosure, data management software may be loaded and launched on a remote data processing device to operate with a coupled analyte monitoring device. The data management software may include one or more GUI's for communicating with the analyte monitoring device. It should be appreciated a GUI may be used to represent one or more of graphical elements displayed on the display of the remote device for interfacing with the user. Thus, "graphical user interface" or "GUI" may encompass the entire display, an application window, pop-up windows, menus, progress and status bars, buttons, etc.

In some aspects of the present disclosure, the data management software provides a meter mode to provide access to settings and functions that are used to setup and control the analyte monitoring device. The data management software may also provide a meter setup mode to guide the user through the initial setup of the analyte monitoring device. The data management software may provide a reports mode to provide access to settings and function for creating, viewing, saving, and/or printing various reports. In addition, the data management software may provide a reports setup mode to guide a user through the initial reports setup and creation process. The data management software may also provide the function for users to export data from the analyte monitoring device—e.g., as a tab-delimited file or other spreadsheet-compatible format. In some instances, the data management software may provide functions for providing help documents, tutorials, etc. to the user. The data management software may provide functions for checking for software update and for acquiring updates. For example, checks may be automatically initiated and/or initiated by the user. In some instances, the software updates may be checked for and acquired via a network connection on the remote device.

Example Devices & Systems

Figure 2:
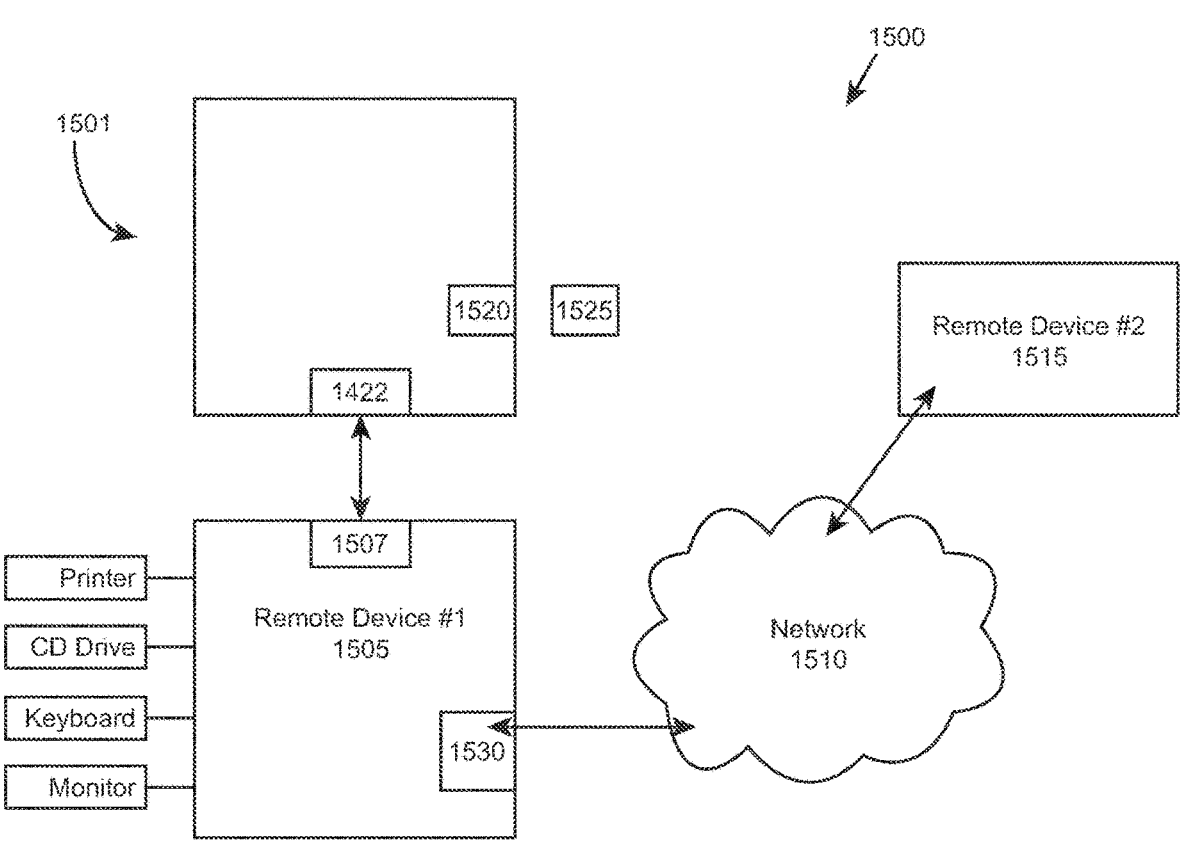
FIG. 2 illustrates a block diagram of a system including an analyte monitoring device and remote data processing device, according to one embodiment.

FIG. 2 illustrates a block diagram of a system including an analyte monitoring device and remote data processing device, according to some embodiments. System 1500 is shown to comprising analyte monitoring device 1501 communicably coupled to remote device 1505. In some instances, as shown, remote device 1505 may have network access to a network 1510 in which a second remote device 1515 is shown coupled to. It should be understood that network 1510 may include one or more networks, including LANs, WANs, and/or the internet.

Analyte monitoring device 1501 is shown removably coupled to remote device 1505 via communication connector unit 1422. Communication connector unit, for example, includes a USB plug which couples with a USB receptacle 1507 in remote device 1505. Remote device 1505 may include peripheral devices, such as printer, keyboard, monitor, CD drive, etc. Remote device 1505 may also include, as shown, a network interface 1530 which connects it to network 510. Remote device 1515 is also connected to network 1510 and may communicate with remote device1 505 via network 1510.

The following paragraphs describe system 1500 during operation, according to some embodiments. In some instances, the analyte monitoring device described is a glucose monitoring device which measures the glucose concentration level of a blood sample. It should be understood that the description applies equally to other analytes and to other forms of samples.

In use, analyte monitoring device 1501 receives a test strip 1525 for measuring an analyte level of a sample applied to test strip 1525. Test strip 1525 is received at strip port unit 1520. Analyte monitoring device 1501 performs a measurement computation on the sample and the user can view the measurement reading on, for example, a touchscreen display (not shown). The user may also be presented with a menu on the touchscreen display to view and select—e.g., menus for storing data, downloading data, performing bolus calculations based on the measurement, etc.

The user may couple the analyte monitoring device 1501 to remote device 505 (e.g., a personal computer) via a communication connector unit. For example, the user may decide to store the measurement data and then choose to download stored test data (including stored measurement readings) to a remote device 1505.

Analyte monitoring device1 501 may then be coupled to remote device 1505 via communication connector unit 1422. Communication connector unit 1422 may, for example, include a USB plug which couples to a USB receptacle 1507 on remote device 1505.

In some instances, the analyte monitoring device 1501 may be powered by the remote device 1505 when coupled via the communication connector unit 1422. In such case, the user would couple the analyte monitoring device 1501 to the remote device 1505 and then insert test strip 1525 into the strip port 1520 to take a measurement reading. In some instances, the analyte monitoring device includes its own power source, such as button or AAA-size batteries, for example, and is not powered by the remote device 1505.

In some instances, the analyte monitoring device may be "locked" or prevented from performing a test while coupled to the remote device 1505. For example, medical device regulations such as high voltage isolation testing may be required if the analyte monitoring device is configured to perform tests while coupled to a remote device. Thus, "locking" or preventing the analyte monitoring device from performing a test while coupled to the remote device allows the analyte monitoring device to not be subjected to the additional testing, if so desired.

In some aspects, the analyte monitoring device 1501 may initiate a user interface application (e.g., RD software) to execute on the analyte monitoring device, and/or the remote device 1505 when coupled to the remote device 1505. The user interface application may be stored in a memory unit on the analyte monitoring device 1501, for example. In some aspects, the user is not required to have previously loaded software on the remote device 1505 to operate with the analyte monitoring device 1501. In some aspects, the analyte monitoring device may be configured to initiate the user interface application automatically upon coupling to the remote device. It should be understood that the user interface application may be configured to be compatible with various hardware systems (e.g., PC, MAC) and various operating systems (e.g., Windows, MAC OS, Linux).

The user interface application may include, for example, diabetes management related applications. The user interface application may provide a variety of menus, selections, charts, alarms, reminders, visual indicators, etc. For example, the user may be presented with menus and options, such as whether to take a measurement reading, to view stored measurement readings, to store data, to download data, to perform bolus calculation based on the measurement, etc.

The user interface program may, for example, allow the user to perform the following steps: (1) generate a replica of the test data stored on the analyte monitoring device 1501, on the remote device 1505; and (2) synchronize test data from the analyte monitoring device 1501 to the database on the remote device 1505. Meter settings and/or user settings/preferences from the analyte monitoring device may also be included in the test data and synchronized with the remote device. Date and time for the remote device 1505 and analyte monitoring device 1501 may also be synched.

To read test data from the analyte monitoring device 1501 and write it to the remote device 1505, it is recognized herein that data in the remote device may be organized into tables, which may be organized into records, which may be broken down into predefined fields. Similarly, at some level data will be organized into records with a consistent field structure on the analyte monitoring device 1501. The user interface application may read test data from the analyte monitoring device and write it out to tables on the remote device 1505. The user interface application may also read data from table in the remote device 1505 and write them out to the analyte monitoring device 1501. Various types of data conversion may be used. For example, data residing in fields in the analyte monitoring device may be converted from the format it exists in the analyte monitoring device to a format compatible with the remote device, and vice versa. The logical structure of the records in the two systems may be different.

Remote device 1505 may include peripheral devices, such as printer, keyboard, monitor, CD drive, etc. Remote device 1505 includes a network interface which connects it to network 1510 (e.g., the internet). The user interface application may provide the user with the option to view test data on the monitor, to store test data on storage media (e.g., CD-ROM, memory card, etc.), further analyze and/or manipulate test data, transmit data to another device), and/or print out test data such as charts, reports, etc., on the printer.

As shown, remote device 1505 may also include a network interface 1530 (e.g., network interface card (NIC), modem, router, RF front end, etc.) used to connect the remote device 1505 to network 1510. For example, in some aspects, analyte monitoring device 1501 may couple via a USB connection to the remote device which may be a personal computer or laptop connected to the internet using a wireless modem and/or router. In some aspects, analyte monitoring device 1501 may couple via a micro USB connection to a remote device 1505 which is a smartphone having an RF front end to access a mobile network. The user interface application may provide a user interface for using the network connection of the remote device 1505—e.g., to forward test data to a physician, hospital, health provider, and/or other third party located at a second remote device

1515 on network 1510. Appropriate action may then be taken by the receiving party at the second remote device 1515.

Referring back to FIG. 2, the analyte monitoring device may include a wireless communication unit, for example, which may include, for example, a receiver and/or transmitter for communicating with another device, e.g., remote device 1505, a medication delivery device, and/or a patient monitoring device (e.g., a continuous glucose monitoring device or a health management system, such as the CoPi-lot™ system available from Abbott Diabetes Care Inc., Alameda, CA), etc. The wireless communication unit may be configured to wirelessly communicate using a technology including, but not limited to, radio frequency (RF) communication, Zigbee® communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM), etc. In some aspects, the wireless communication unit is configured for bi-directional radio frequency (RF) communication with another device to transmit and/or receive data to and from the analyte monitoring device 1501.

In some aspects, the wireless communication unit may be used to communicate with a remote device as described above for the communication connector unit. In some aspects where the analyte monitoring device includes a communication connector unit, the wireless communication unit may replace or provide an optional channel of communication for the functions provided by the communication connector unit discussed above. Referring back to FIG. 2, analyte monitoring device 1501 may be coupled to remote device 1505 via a wireless communication unit and provide an optional alternative communication channel with remote device 1505. In some aspects, analyte monitoring device 1501 may not include a communication connector unit 1422, and instead only communicate with the remote device 1505 via a wireless communication unit present on analyte monitoring device 1501. In some aspects, the analyte monitoring device is configured to receive a program update from a remote device via the wireless communication unit.

In some aspects, the wireless communication module may be configured to communicate with a smartphone (e.g., iphone, Blackberry, etc). It is typical for smartphones to include various wireless technologies such as Wi-Fi, infrared, Bluetooth®, etc.

In some aspects, the analyte monitoring device may be configured to wirelessly communicate via the wireless communication unit with a server device, e.g., using a common standard such as 802.11 or Bluetooth® RF protocol, or an IrDA infrared protocol. The server device could be another portable device, such as a Personal Digital Assistant (PDA) or notebook computer, or a larger device such as a desktop computer, appliance, etc. In some aspects, the server device has a display, such as a liquid crystal display (LCD), as well as an input device, such as buttons, a keyboard, mouse or touchscreen. With such an arrangement, the user can control the meter indirectly by interacting with the user interface(s) of the server device, which in turn interacts with the meter across a wireless link.

In some aspects, the wireless communication module is used to communicate with a remote sensor—e.g., a sensor configured for implantation into a patient or user. Examples of sensors for use in the analyte monitoring systems of the present disclosure are described in U.S. Pat. No. 6,175,752; and U.S. patent application Ser. No. 09/034,372, incorporated herein by reference. Additional information regarding sensors and continuous analyte monitoring systems and devices are described in U.S. Pat. Nos. 5,356,786; 6,175, 752; 6,560,471; 5,262,035; 6,881,551; 6,121,009; 7,167, 818; 6,270,455; 6,161,095; 5,918,603; 6,144,837; 5,601, 435; 5,822,715; 5,899,855; 6,071,391; 6,120,676; 6,143, 164; 6,299,757; 6,338,790; 6,377,894; 6,600,997; 6,773, 671; 6,514,460; 6,592,745; 5,628,890; 5,820,551; 6,736, 957; 4,545,382; 4,711,245; 5,509,410; 6,540,891; 6,730, 100; 6,764,581; 6,299,757; 6,461,496; 6,503,381; 6,591, 125; 6,616,819; 6,618,934; 6,676,816; 6,749,740; 6,893, 545; 6,942,518; 6,514,718; 5,264,014; 5,262,305; 5,320, 715; 5,593,852; 6,746,582; 6,284,478; 7,299,082; U.S. patent application Ser. No. 10/745,878, filed Dec. 26, 1003, entitled "Continuous Glucose Monitoring System and Methods of Use"; and U.S. Patent Application No. 61/149,639 entitled "Compact On-Body Physiological Monitoring Device and Methods Thereof", the disclosures of each which are incorporated by reference herein.

Figure 3:
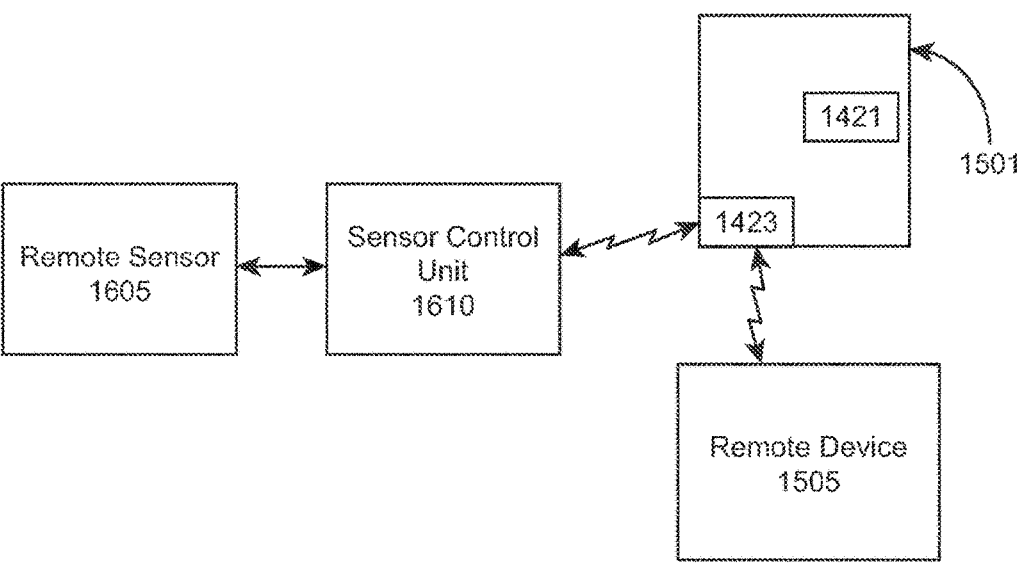
FIG. 3 illustrates an analyte monitoring device used with a remote sensor, according to one embodiment.

FIG. 3 illustrates an analyte monitoring device used with a remote sensor, according to some embodiments. Sensor 1605 may be configured for implantation (e.g., subcutaneous, venous, or arterial implantation) into a patient. The sensor 1605 is coupled to sensor control unit 1610 which is typically attached to the skin of a patient. The sensor control unit 1610 operates the sensor 1605, including, for example, providing a voltage across the electrodes of the sensor 1605 and collecting signals from the sensor 1605. The sensor control unit 1610 may evaluate the signals from the sensor 605 and/or transmit the signals to wireless communication unit 1423 on analyte monitoring device 1501 for evaluation.

In some aspects, the wireless communication unit 1423 is configured to receive a signal from a remote sensor using radio-frequency identification (RFID) technology. This configuration may be used to provide glucose on demand capabilities, in which case when a measurement reading is desired, the analyte monitoring device is brought within close vicinity of the implantable sensor. In some instances, RFID technology may be used in continuous glucose monitoring (CGM) applications.

The analyte monitoring device 1501 processes the signals from the on-skin sensor control unit 1610 to determine the concentration or level of analyte in the subcutaneous tissue and may display the current level of the analyte via display unit 1421. Furthermore, the sensor control unit 1610 and/or the analyte monitoring device 1501 may indicate to the patient, via, for example, an audible, visual, or other sensory-stimulating alarm, when the level of the analyte is at or near a threshold level. For example, if glucose is monitored then an alarm may be used to alert the patient to a hypoglycemic or hyperglycemic glucose level and/or to impending hypoglycemia or hyperglycemia.

The analyte monitoring device 1501 may perform a variety of functions, including for example: modifying the signals from the sensor 605 using calibration data and/or measurements from a temperature probe (not shown); determining a level of an analyte in the interstitial fluid; determining a level of an analyte in the bloodstream based on the sensor measurements in the interstitial fluid; determining if the level, rate of change, and/or acceleration in the rate of change of the analyte exceeds or meets one or more threshold values; activating an alarm system if a threshold value is met or exceeded; evaluating trends in the level of an analyte based on a series of sensor signals; therapy management (e.g., determine a dose of a medication, etc.); and reduce noise or error contributions (e.g., through signal averaging or comparing readings from multiple electrodes); etc. The analyte monitoring device may be simple and perform only one or a small number of these functions or the analyte monitoring device may perform all or most of these functions.

Analyte monitoring device 1501 may communicate with a remote device 505 via communication connector unit 1422, and/or wireless communication unit 1423, and/or a second wireless communication unit (not shown), as described earlier. It should also be understood that the analyte monitoring device may be configured with one or more wireless communication units.

User Interface for the Analyte Monitoring Device

In some aspects, the analyte monitoring device includes software used to perform various operation and functions with the device, such as, but not limited to, the functions described above. The device may include, for example, software instructions that are stored within a machine-readable storage medium (e.g., flash memory or other non-volatile memory) and executed by one or more general-purpose or special-purpose programmable microprocessors and/or microcontrollers, or other type of processing device. It should be appreciated that machine-readable storage medium may include any variety of non-volatile memory (e.g., Flash memory) or volatile memory (e.g., random access memory (RAM)), and may include one or more memory components.

In some aspects, the analyte monitoring device may include software that is used to provide the overall user interface for operation of the device and general user-experience with the device. The user interface may encompass graphical user interfaces (GUIs) that are displayed for a variety of features that may be provided by the device—e.g., Home screen, Glucose Reading screen, Logbook screen, Reader Summary screens, Reader Usage screens, etc. The user interface also encompasses screen navigation/flows for various operations that may be performed by the device—e.g., on-demand readings; activating a patch; replacing a patch; providing the status of a patch; notification of patch expiration; activating various information screens such as logbooks, summary screens, usage reports, etc.; creation of reports for display, communication, printing, etc.; etc.

It should be noted that the term "sensor" and "patch" are used herein to refer generally to the implanted sensor and on-body electronics together.

In some aspects of the present disclosure, the analyte monitoring device provides various graphical user interfaces (GUIs) or screens that are displayed on a display of the analyte monitoring device to assist the user with operation of the device or provide information to the user. It should be understood that the terms "graphical user interface", "GUI", "interface" and "screen" are used broadly herein to represent any graphical interface element displayed on the display, and are used interchangeably. For example, the graphical user interface may comprise a graphical icon, element, picture, video, text box, pop-up window, application window, home screen, etc.

Furthermore, it must be noted that the terms "graphical user interface", "GUI", "interface", and "screen" are used broadly herein and may include plural referents unless the context clearly dictates otherwise. Therefore, for example, reference to a "Setup screen" may include one or more screens in the setup process, and reference to "the Setup screen" may include reference to one or more program updates and equivalents thereof known to those skilled in the art, and so forth.

Furthermore, it should be understood that one or more GUIs may be implemented for various features, functions and/or settings. Further, different GUIs may be combined in some instances without compromising the underlying principles of the disclosure. Still further, the term The user may navigate through branches of various screens via trigger elements on the device. The trigger elements may be any variety of trigger elements—e.g., buttons, keys, toggle switches, wheels, arrows, etc. The trigger elements may be physical and tangible trigger elements located on the device (e.g., hardware buttons or keys on the housing or keyboard, etc.) and/or may be nontangible trigger elements (e.g., graphical user interface elements) displayed on the device. It should also be understood that the branches of navigation may be displayed on the home screen (e.g., as icons on the display) and triggered by corresponding physical and tangible trigger elements on the housing of keyboard.

In some embodiments, a touchscreen display is implemented, and the trigger elements are icons displayed on the touchscreen. The trigger element is activated by the user touching the corresponding trigger element (e.g., icon). It should be understood that icons are used broadly herein to represent any text, image, video, graphic, etc. For example, the trigger element may be suggestive of its function or feature—e.g., an image of a gear representing a trigger element for accessing the setup menu, an arrow keys, check boxes, toggle switches, buttons (e.g., with identifying text or image inside), etc.

Home Screen:

In some aspects of the present disclosure a Home screen is provided. The home screen or landing screen is displayed on the display of the analyte monitoring device and functions as a reference point or relative reference point to perform various functions or features on the device. From the home screen the user can navigate to any of the various GUI's to perform or access various functions and features of the device. For instance, the user can navigate to a screen enabling the user to access a logbook, setup menu, reminders, etc. From that point, the user may access additional features and functions related to the selected item.

Active Screens:

In some aspects of the present disclosure an Active screen is provided. The Active Screen (e.g., Scan Prompt screen) awaits the user to perform an on-demand reading or otherwise "ping", "scan", or "swipe" the sensor. It should be appreciated that the term "ping", "scan", and "swipe" are used interchangeably herein and refer broadly to bringing the analyte monitoring device in sufficiently close distance of the sensor to perform a communication (e.g., on-demand reading, sensor activation, etc.).

On-Demand Reader Screens:

In some aspects of the present disclosure, On-Demand Reader screens are provided to convey information pertaining to analyte readings (e.g., glucose levels). While embodiments are described in relation to on-demand glucose readings, it should be appreciated that other analytes may be implemented in other embodiments.

In some instances, the On-Demand Reader screens may include one or more of the following: a reading, trend symbol, trigger element for calculating insulin, trigger element for food intake, trigger element for adding notes, trigger element for switching between screens, patch status information, trail information, the current time, battery status, etc. The reading provides glucose levels for a current reading. The trend symbol provides trending information related to increasing or decreasing patterns of glucose levels. When activated, the trigger element for calculating insulin displays a screen for providing an insulin calculation for the user—e.g., based on the current glucose reading. When activated, the trigger element for food intake displays a screen for entering food intake and/or displaying food intake. When activated, the trigger element for notes displays a screen for entering notes and/or displaying previously entered notes. The trail information displays readings leading up to the current reading.

Some of the embodiments have a single screen layout in which all the information for the on-demand glucose reading is displayed on a single screen. Other embodiments include a dual screen layout which provides the information for the on-demand glucose reading over two screens. The user may switch between the two-screens with a trigger element such as an icon or box on the screen. In some instances, the user may be able to switch between screens by sliding a finger across the display of the device.

Reader Summary/Reports Screens:

In some aspects of the present disclosure, the analyte monitoring device displays summary screens that convey a collection of information associated with readings that have been performed.

Event Summary Views:

The Event Summary screen displays summarized information regarding the history of the user's readings.

Event Detail View:

The Event Detail screen displays a detailed view of the user's readings associated with an event—e.g., a hypoglycemic event.

Logbook Screen:

The Logbook screen displays recorded readings and associated data regarding the user's readings.

Usage Report:

The Usage Report screen displays the meter utilization to indicate user engagement. Any gaps in time (e.g., extended durations where the user did not take any readings) are recorded and shown in the Usage Report.

Personalization Picture:

In some embodiments, the analyte monitoring device includes a personalization screen that displays a personalized image—e.g., selected or uploaded by the user. The personalized screen may be displayed at specific times. For example, the personalized screen may be displayed after the device is powered on. Once the power up process is complete, the analyte monitoring device displays another screen, such as an active screen. In another embodiment, the home screen is displayed after the power up process.

Screen Qualities:

It should be appreciated that the analyte monitoring device may be implemented with different screen qualities—e.g., gray-scale and higher-resolution. In some embodiments, the analyte monitoring device may be capable of being operated in different screen qualities. For example, the analyte monitoring device may include a color touchscreen and be capable of being run in color mode or gray-scale mode.

The following paragraphs describe various navigation flows between user screens for performing various functions and features of the device.

Navigation Flows

The following paragraphs describe various navigation flows between user screens for performing various functions and features of the analyte monitoring device. For example, software or firmware implementing flows introduced herein may be stored on a machine-readable storage medium and may be executed by one or more general-purpose or special-purpose programmable microprocessors.

Hardware

An exemplary embodiment of a graphical user interface which may be utilized in connection with an analyte monitoring device (e.g., analyte reader device) as described herein and which functions to perform various hardware-related actions is provided.

Hardware—Power on Interface

Figure 4:
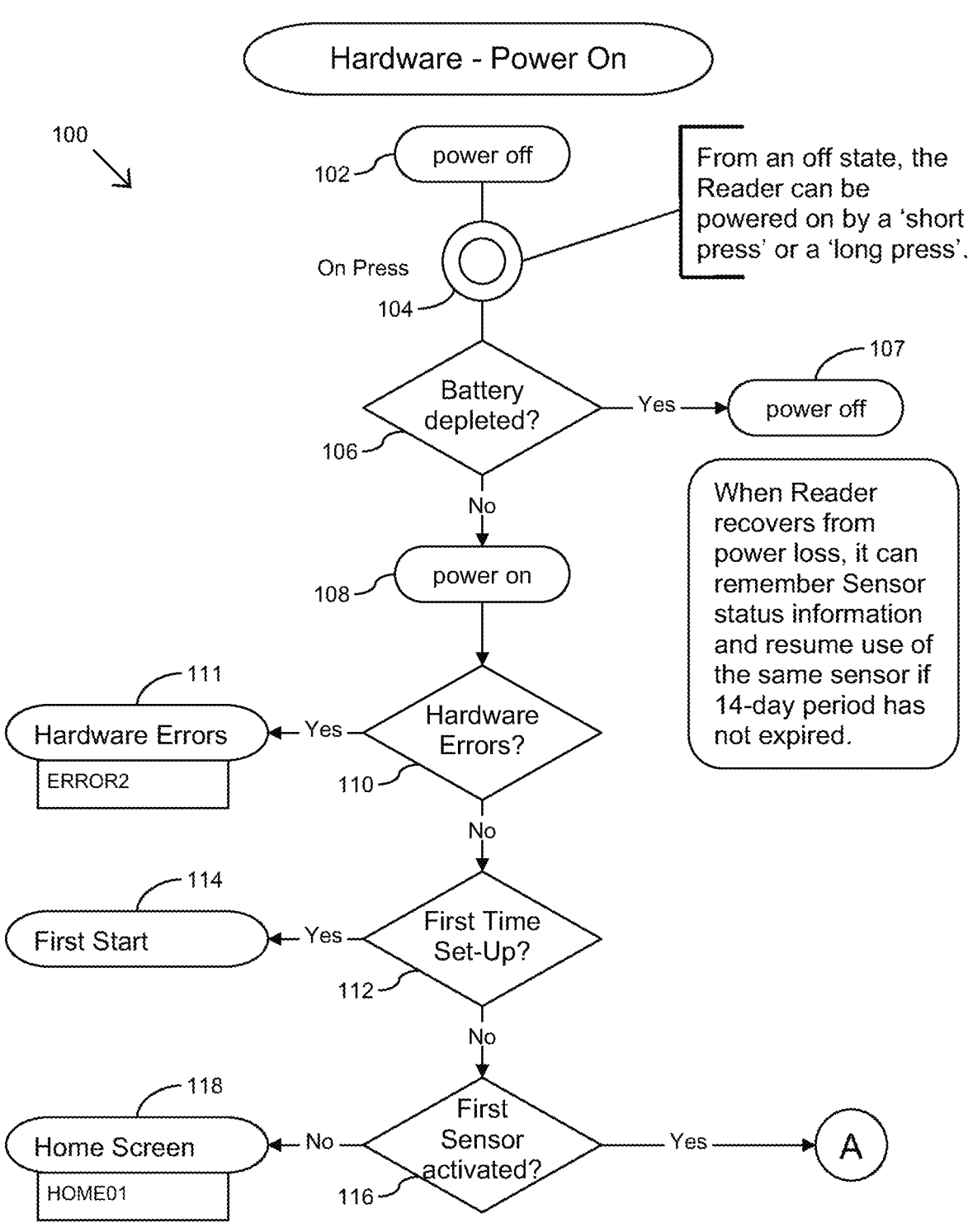
FIG. 4 illustrates a method of powering on an analyte monitoring device, such as a glucose monitoring device, according to one embodiment.
Figure 4:
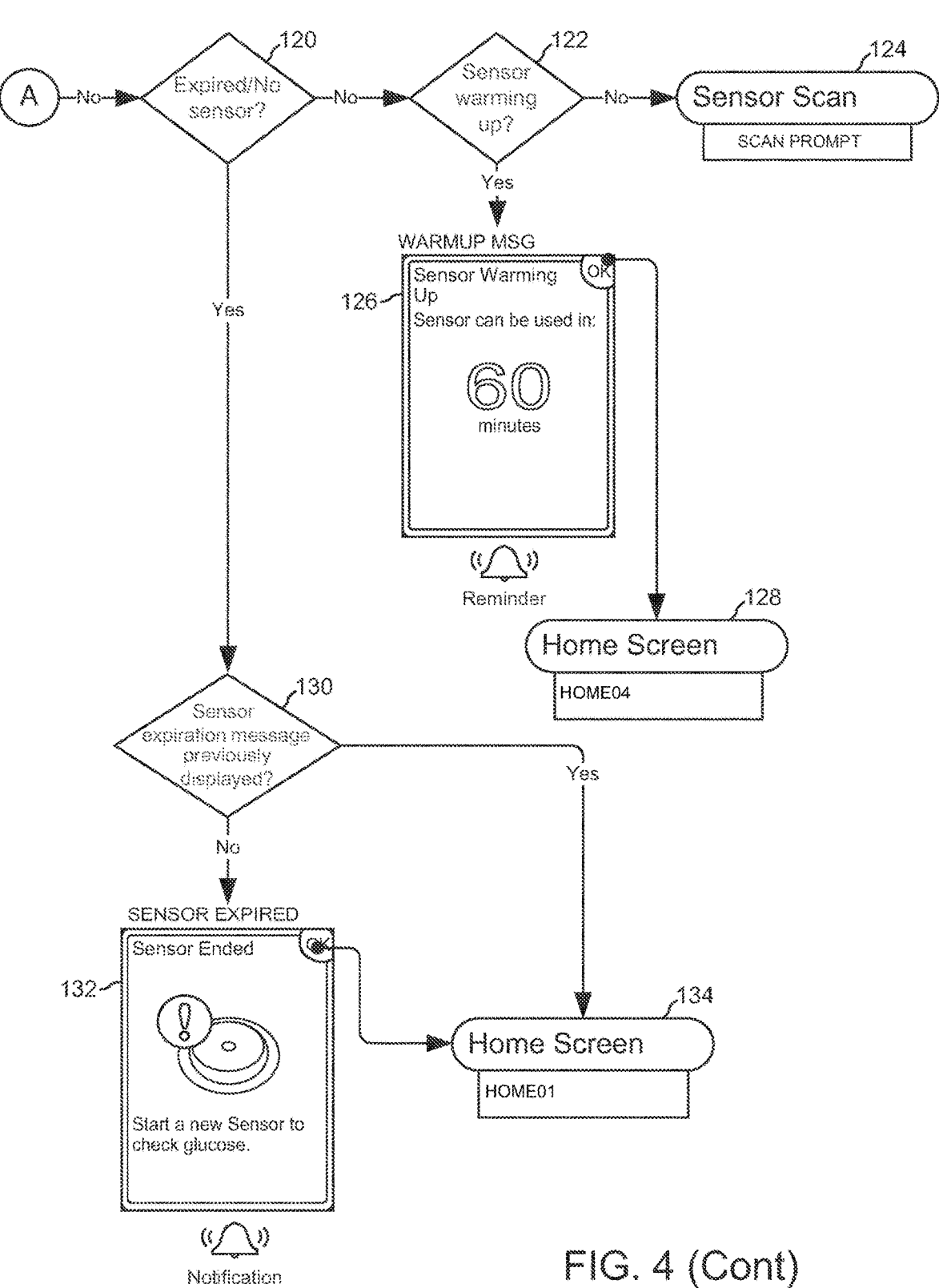

FIG. 4 illustrates a method 100 of powering on an analyte monitoring device, such as a glucose monitoring device, according to one embodiment. The analyte monitoring device may also be referred to herein as a "reader" which takes measurement readings from the analyte sensor. From the off state, as represented by block 102, the device can be powered on by depressing a power button—e.g., by a "short press" or a "long press", as represented by block 104. At block 106, a test is performed to determine if the battery is depleted. If so, the device is powered off, as shown by block 107. In some instances, when the device recovers from a power loss, it can remember "sensor" status information and resume use of the same sensor if the sensor has not expired—e.g., a 14-day period, or other predetermined period, has not elapsed. If the battery is determined to not be depleted, then the device is powered on, as shown at block 108.

At block 110, the device processor determines the presence of any errors in the hardware functionality of the device. Upon being powered on, if the device processor determines a hardware failure, such as the device is not working properly, the device will display a hardware error message as shown at block 111, such as those described herein below in the present application. If no hardware errors are detected, at block 112, it is determined if this is the first time the device is to be set up. If it is the first time, then a First Start procedure is initiated to begin the setup of the device, as shown at block 114. If it is determined that this is not a first time setup, then it is determined if the sensor has already been activated. If not activated, then the home screen is displayed, as shown at block 118. If already activated, then it is determined whether the sensor is expired, as shown at block 120. If the sensor is expired, it is determined if the sensor expiration message has been previously displayed, as shown at block 130. If so, then the home screen is displayed, as shown at block 134. If not, then a sensor expiration screen is displayed, as shown at block 132. In some instances, an audible notification may also be provided. The sensor expiration screen may also inform the use that a new sensor must be started to take a glucose reading. Once confirmed by the user, for example by pressing "ok", the home screen is displayed on the device.

Referring back to block 120, if the sensor is not expired, then it is determined if the sensor is warming up, as shown by block 122. If not, then a prompt is displayed for a sensor scan. If the sensor is warming up, then a warm-up message screen is displayed that informs the user that the sensor is warming up, as shown at block 126. In some instances, such as shown, the warm-up message screen indicates the time remaining before the sensor can be used. An audible reminder may also be present, as shown. Once confirmed by the user, for example by pressing "ok", the home screen is displayed on the device.

Go Home/Off Interface

Figure 5A:
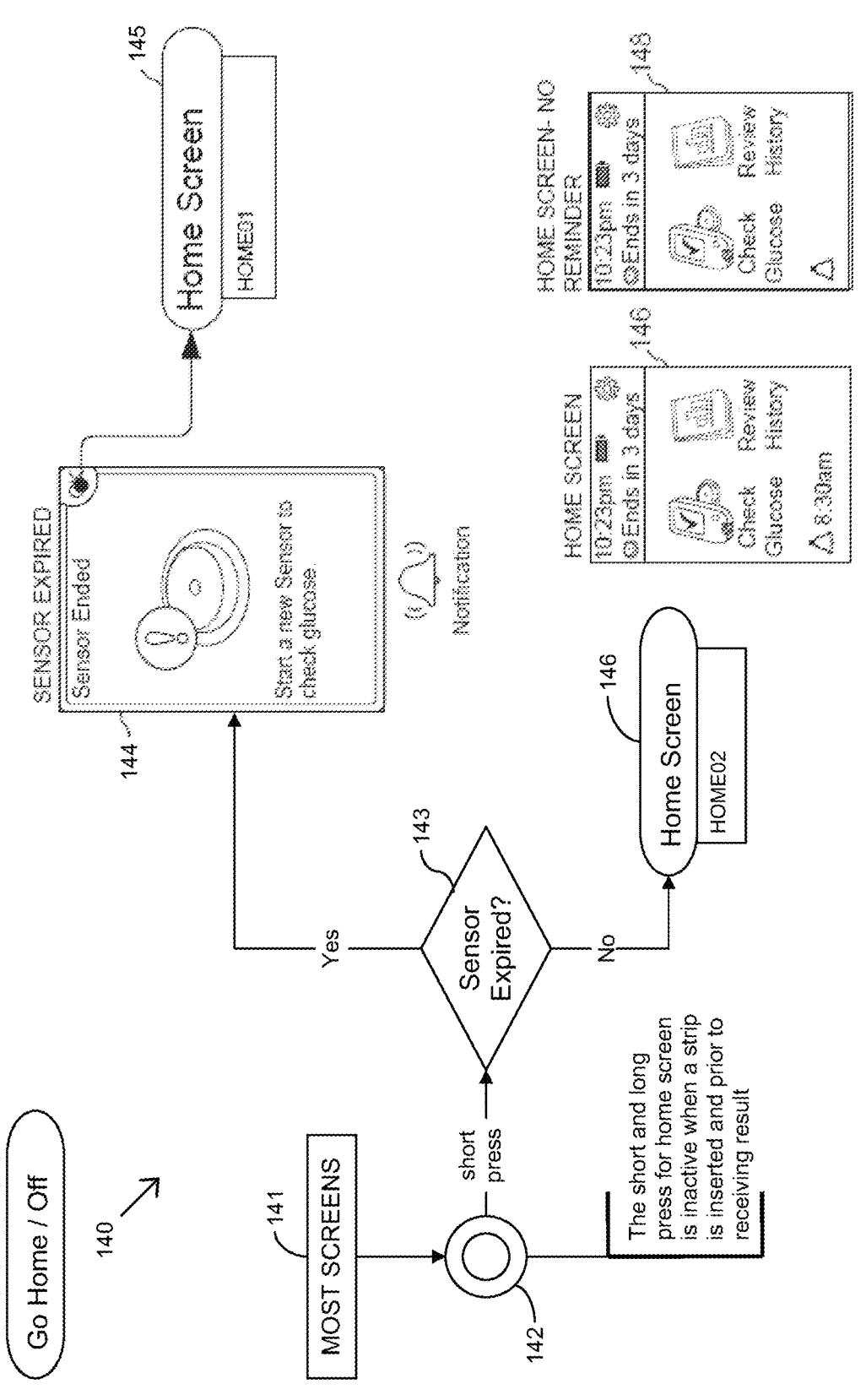
FIG. 5A illustrates a method of navigating to a home screen from other screens on an analyte monitoring device, according to one embodiment.

FIG. 5A illustrates a method 140 of navigating to a home screen from other screens for an analyte monitoring device, according to one embodiment. At block 141, the device is displaying a screen other than the home screen. At block 142 the home trigger button is pressed (e.g., by a short press). When the home trigger button is pressed, the device processor checks whether the sensor is expired, e.g., after 14 days, as shown at block 143. If the sensor is expired, then a sensor expiration screen is displayed, as shown at block 144. In some instances, an audible notification may also be provided. The sensor expiration screen may also inform the user that a new sensor must be started to take a glucose reading. Once confirmed by the user, for example by pressing "ok", the home screen is displayed on the device, as shown at block 145. If the sensor is not expired, then the home screen is displayed, as shown at block 146. An alternative home screen 148 is shown that does not include a reminder. In some instances, a short press of the trigger button for the home screen is not activated when a test strip is inserted within the device a prior to receiving a result. It should be appreciated that there may be some screens in which the home trigger button does not lead to a display of the home screen. In some embodiments, from some screens, pressing the home trigger button does not navigate to the home screen. Such exceptions are described herein below.

Figures 5B, 5C, 5D:
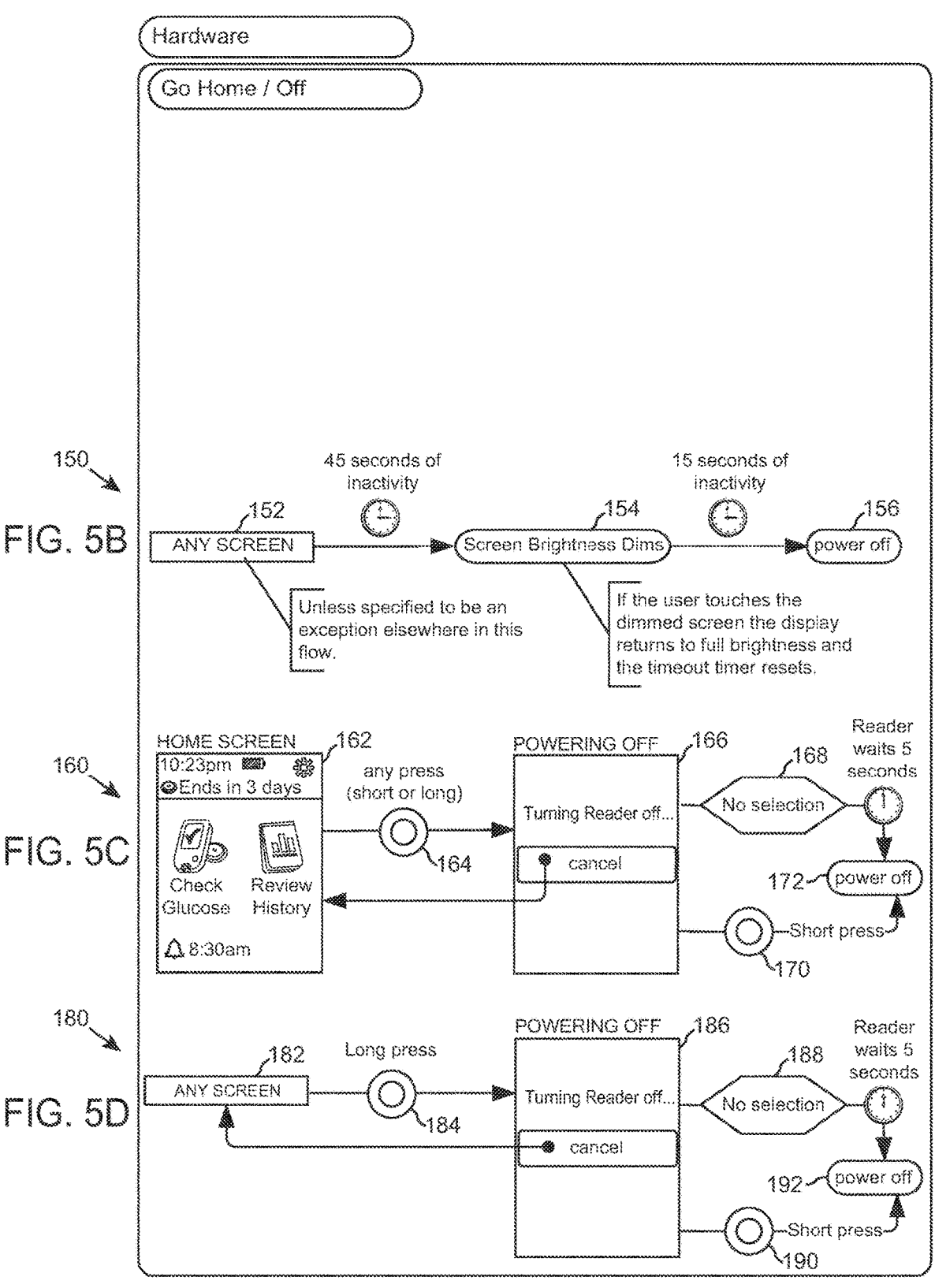
FIG. 5B illustrates a method of powering an analyte monitoring device off, according to one embodiment.
FIG. 5C illustrates a method of powering an analyte monitoring device off, according to one embodiment.
FIG. 5D illustrates a method of powering off an analyte monitoring device, according to one embodiment.

FIG. 5B illustrates a method 150 of powering an analyte monitoring device off, according to one embodiment. At block 152, a current screen is displayed on the device. When a screen has been displayed for a predetermined period of time—e.g., 45 seconds or some other period of time, the screen brightness may dim to say power, as shown at block 154. If the user touches the dimmed screen the display returns to full brightness and the timeout timer resets. After the screen is dimmed, if another predetermined period of time has passed without any activity—e.g., 15 seconds or other time period-then the device will power off. It should be appreciated that there may be certain screens in which such method does not apply.

FIG. 5C illustrates a method 160 of powering an analyte monitoring device off, according to one embodiment. From the home screen, shown at block 162, the pressing (e.g., short or long) of the home trigger button, as shown at block 164, will trigger the display of a screen indicating the device is powering off. The user may be provided with an option to cancel the power down process. If no selection is detected, as shown at block 168, then the device may power down after a predetermined period of time—e.g., 5 seconds or some other time period, as represented by block 172. If at block 166 the trigger button is pressed, as shown at block 170, then the device is powered off, as represented by block 172.

FIG. 5D illustrates a method 180 of powering off an analyte monitoring device, according to one embodiment. From a current screen, shown at block 182, the depression of the trigger button (e.g., a long depression) triggers the display of a power down screen shown at block 186. The user may be provided with an option to cancel the power down process. If no selection is detected, as shown at block 188, then the device may power down after a predetermined period of time—e.g., 5 seconds or some other time period, as represented by block 192. If at block 186 the trigger button is pressed, as shown at block 190, then the device is powered off, as represented by block 192.

Low Battery Interface

FIG. 5E illustrates a battery low screen 196 for an analyte monitoring device that indicates that the battery of the device is low, according to one embodiment. In one embodiment, for example, this screen may appear after scanning of the sensor or a strip test, but before the results are shown. In some instance, this screen will start appearing when the battery capacity reaches a level equivalent to 1 day of typical use. This may be a predetermined value or based on a user history. In some instances, when the screen is display, a reminder auditory/vibratory signal is the only signal broadcast. The standard confirmation signal is omitted. A user confirmation element may be displayed that directs the user to scan results when the user confirms. In some instances, if the charger is plugged in from the battery low screen, the device will transition to the results screen.

PC Link/Data Transfer Interface

Figures 5F, 5G:
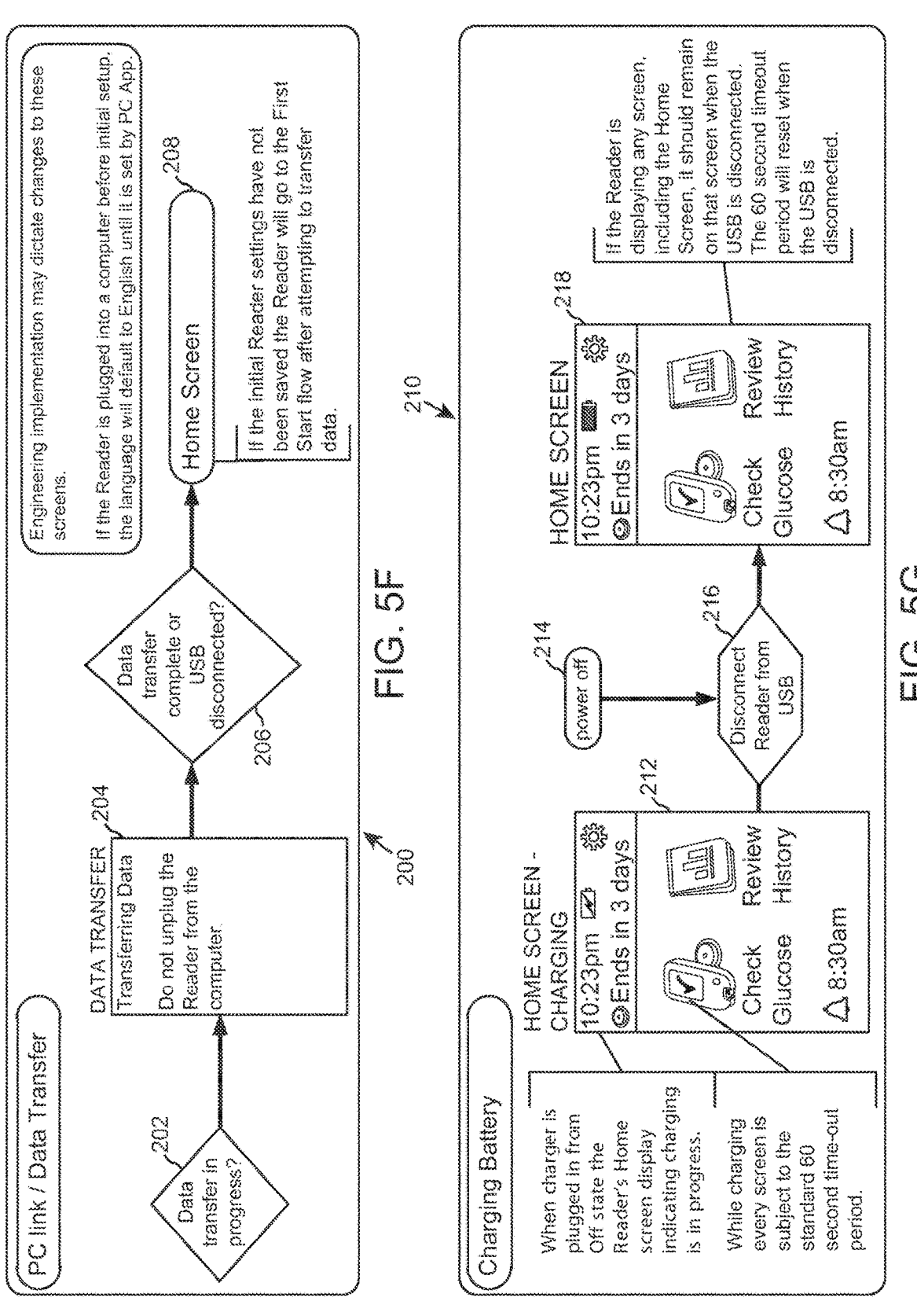
FIG. 5F illustrates a method for linking an analyte monitoring device to a PC and transferring data between the two, according to one embodiment.
FIG. 5G illustrates a method for charging a battery for an analyte monitoring device, according to one embodiment.

FIG. 5F illustrates a method 200 for linking an analyte monitoring device to a PC and transferring data between the two, according to one embodiment. At block 202, the device is connected to the PC via a wired or wireless connection, and data is transferred between the device and the PC. When data is being transferred, a data transfer screen is displayed and indicates that the data transfer is in process. The example shown also instructs the user not to unplug the device from the computer. If the data transfer completes or the connection between the device and PC (e.g., USB connection) is disconnected, then the home screen is displayed. In one embodiment, if the initial Reader settings have not been saved the Reader will go to the First Start procedure after attempting to transfer data. It should be appreciated that engineering implementation may dictate changes to these screens in other embodiments. In some instances, if the device is plugged into a computer before initial setup, the language will default to English until it is set by PC App.

Charging Battery Interface

FIG. 5G illustrates a method 210 for charging a battery for an analyte monitoring device, according to one embodiment. The device may be charged by connecting the device to a PC or other device (e.g., via a USB connection, etc.) or by connecting the device to an AC adapter that is plugged into an AC outlet, for example. When the charger is plugged in from the off state, the home screen is displayed and indicates the device is charging—e.g., via a charging icon or symbol, such as a battery symbol—such as shown at block 212. In one embodiment, while charging every screen is subject to a standard time-out period, such as a 60 second time-out period for instance.

If the device is disconnected from the charger (e.g., from the USB connection port), shown at 216, then the home screen continues to be displayed without the charging symbol or icon. This may be replaced by an icon or symbol indicating the current state of the battery life. In one embodiment, if the device is displaying any screen, including the home screen, it will remain on that screen when the charger is disconnected, and the predetermined timeout period will reset when the charger is disconnected.

Home Screen

An exemplary embodiment of a graphical user interface which may be utilized in connection with a reader as described herein and which functions to navigate the device in relation to the Home screen is provided.

Sensor Scan or System Check Interface

Figure 6A:
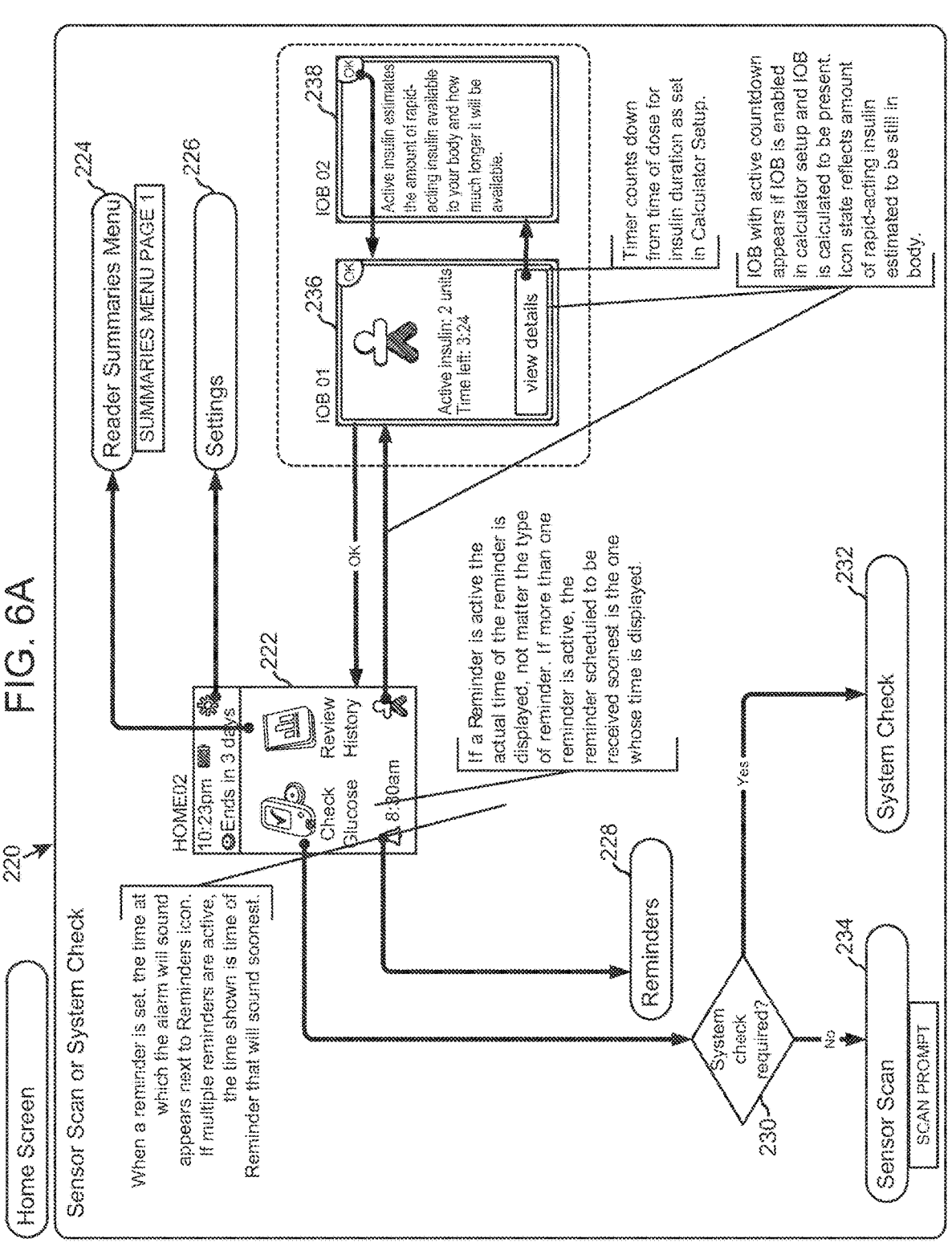
FIG. 6A illustrates a method for performing a sensor scan or system check, according to one embodiment.

FIG. 6A illustrates a method 220 for performing a sensor scan or system check, according to one embodiment. From the home screen at block 222, if a glucose check is initiated, it is determined if a system check is required, as shown at block 230. If so, then a system check is performed, as shown at block 232. If a system check is not required, then a sensor scan prompt is displayed, as shown at block 234. The home screen may enable other features to be initiated as well. For example, a reader's summaries menu screen may be displayed when the corresponding icon is triggered at the home screen, as shown by block 224. Also, a settings screen may be displayed when the corresponding icon is triggered at the home screen, as shown by block 226.

In addition, an insulin on board screen may be displayed when the corresponding icon is triggered at the home screen, as shown by block 236. The insulin on board screen provides information related to the estimated active insulin remaining in a user's body according to insulin data previously entered. Additional details may be provided when a corresponding icon is initiated from the insulin on board screen. In one embodiment, a timer counts down from time of dose for insulin duration as set in a calculator setup. In one embodiment, the insulin on board screen with active countdown appears if the insulin on board is enabled in the calculator setup and the insulin on board is calculated to be present. The icon shown provides a visual indication that reflects the amount of rapid-acting insulin estimated to be still in body—e.g., a percentage of the body-shaped icon filled corresponding to a percentage of the active insulin remaining in the body.

Also, a reminder screen may be displayed when the corresponding icon is triggered at the home screen, as shown by block 228. In one embodiment, when a reminder is set, the time at which the alarm will sound appears next to a reminders icon. If, for example, multiple reminders are active, the time shown is the time of the reminder that will sound soonest.

Expired/No Sensor Interface

Figures 6B, 6C, 6D:
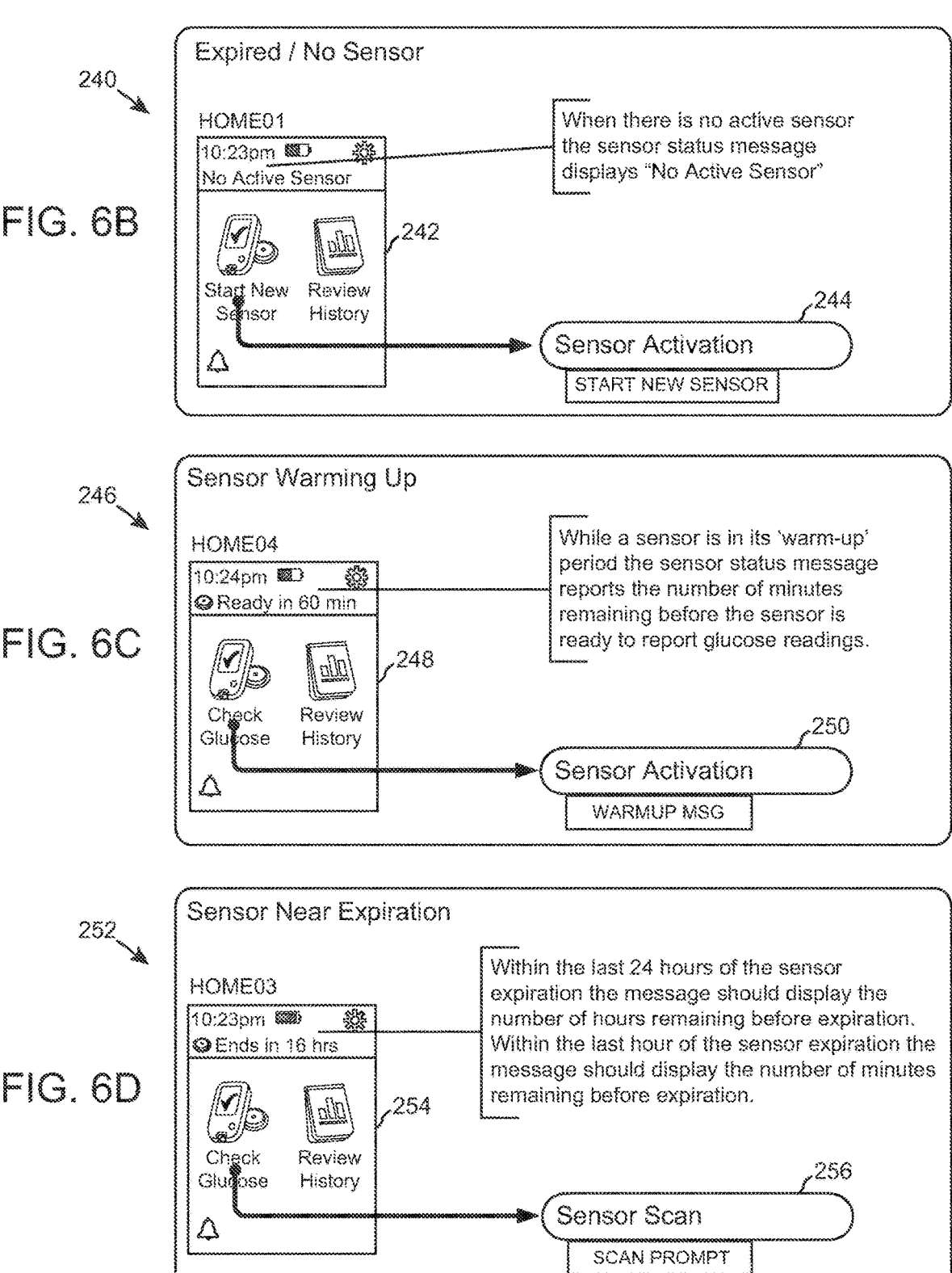
FIG. 6B illustrates a method for activating a sensor, according to one embodiment.
FIG. 6C illustrates a method for activating a sensor, according to one embodiment.
FIG. 6D illustrates a method 252 for scanning a sensor if the sensor is nearing expiration, according to one embodiment.

FIG. 6B illustrates a method for activating a sensor, according to one embodiment. In the embodiment shown, the home screen 242 indicates that no sensor is currently paired to the analyte monitoring device is displayed on the device. For example, a sensor may have never been paired to the device, or a previously paired sensor may have expired. From home screen 242, the user may trigger the activation of a sensor by pressing or otherwise selecting a corresponding icon or other trigger element displayed on the display of the device.

Sensor Warming Up Interface

FIG. 6C illustrates a method 246 for activating a sensor, according to one embodiment. After a user initiates the activation of a sensor, e.g., as represented by block 250, the device may indicate if the sensor is warming up. As illustrated, during the warm up period, the home screen 248 indicates that the sensor is warming up. For example, home screen 248 indicates the time remaining before the sensor is ready, as shown in screen 248—e.g., "Ready in 60 min".

Sensor Near Expiration Interface

FIG. 6D illustrates a method 252 for scanning a sensor if the sensor is nearing expiration, according to one embodiment. In the embodiment shown, a screen 254 indicates the time remaining before the currently paired sensor is expired—e.g., in 16 hours. From home screen 254, the user may still trigger the activation of a sensor by pressing or otherwise selecting a corresponding icon or other trigger element displayed on the display of the device, since the sensor is not yet expired.

Sensor Life Display in Title Bar

Figure 6E:
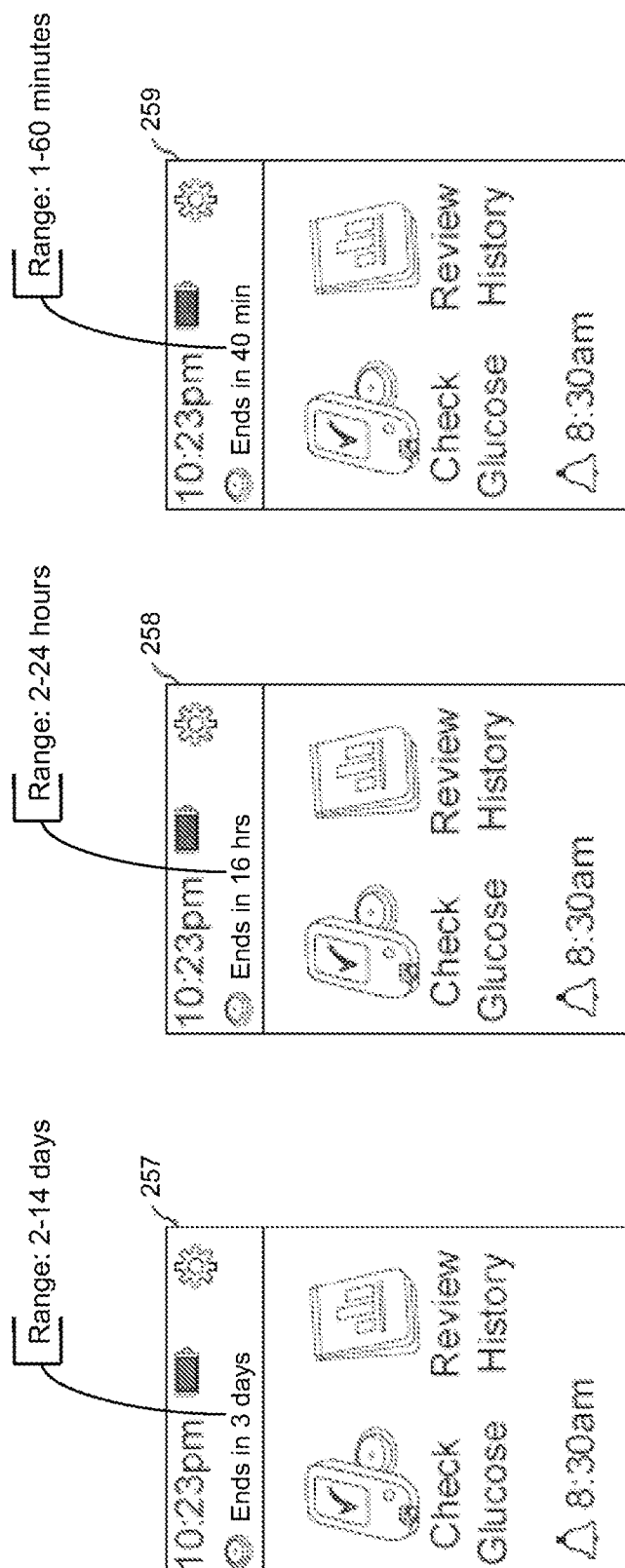
FIG. 6E illustrates exemplary embodiments of a graphical user interface displaying sensor life in varying increments.

FIG. 6E illustrates exemplary embodiments of a graphical user interface displaying sensor life in varying increments. In the embodiment shown, sensor life is displayed in three ranges: days, hours, and minutes as shown in screens 257, 258 and 259, respectively. In certain embodiments, the sensor life is rounded up—e.g., 2 days 1 hour is displayed as 3 days, 1 day 20 hours is displayed as 2 days, 1 hour 10 minutes is displayed as 2 hours. In embodiments, the sensor life display is independent of a user adjustable date and time.

Sensor Activation

An exemplary embodiment of a graphical user interface which may be utilized in connection with a reader as described herein and which functions activate the sensor is provided.

Figure 7:
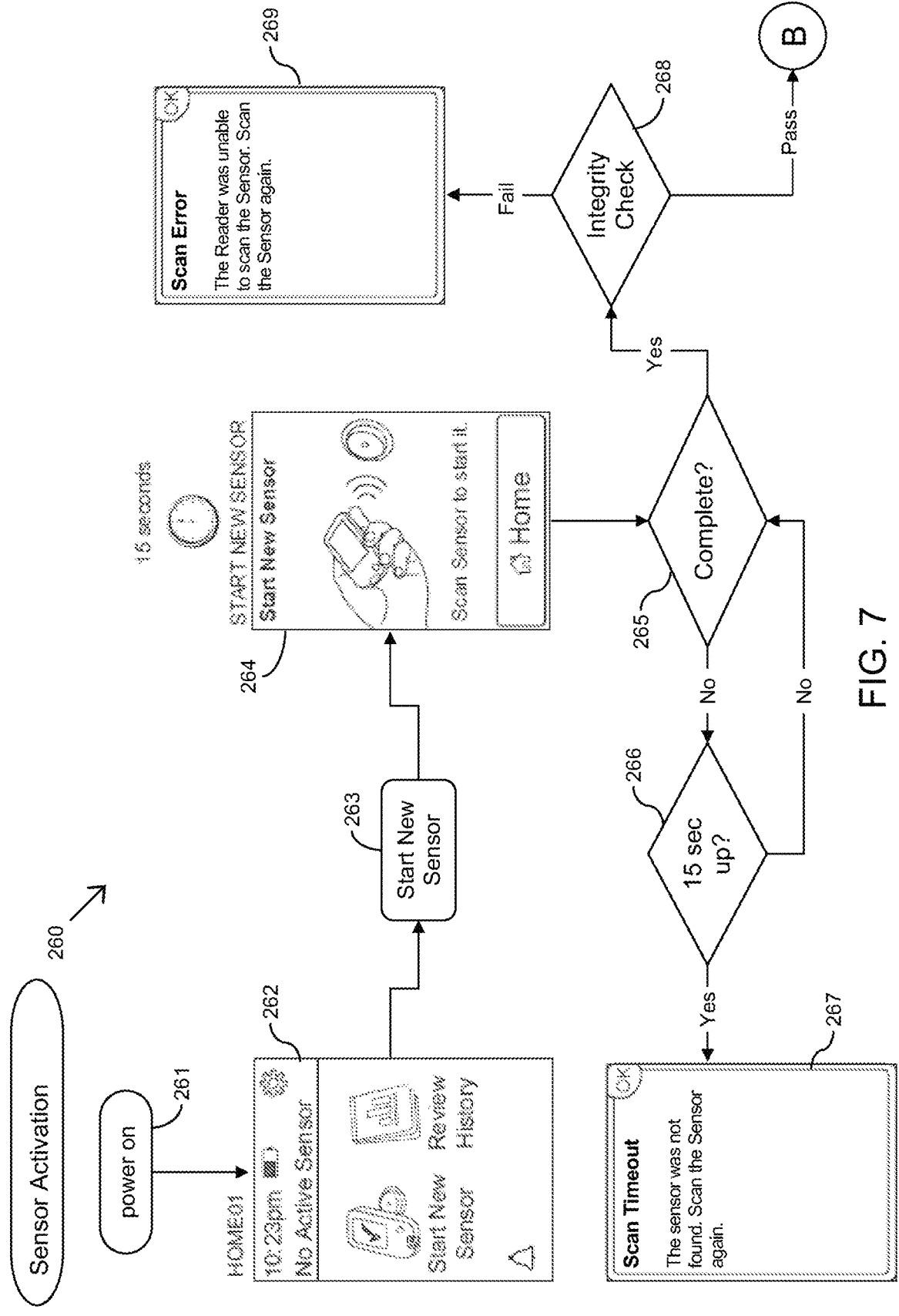
FIG. 7 illustrates a method for activating a sensor after the device is powered on, according to one embodiment.
Figure 7:
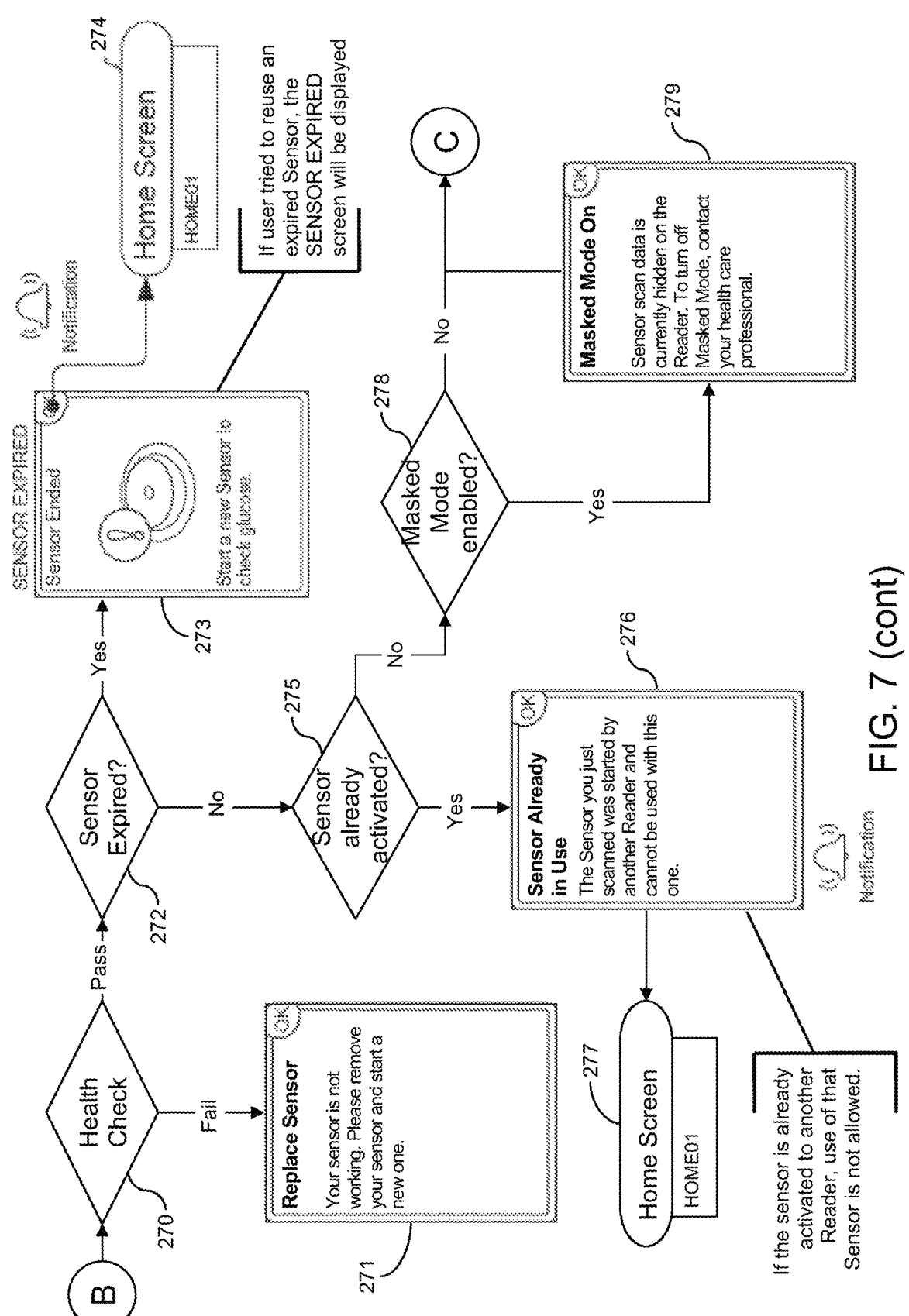
Figure 7:
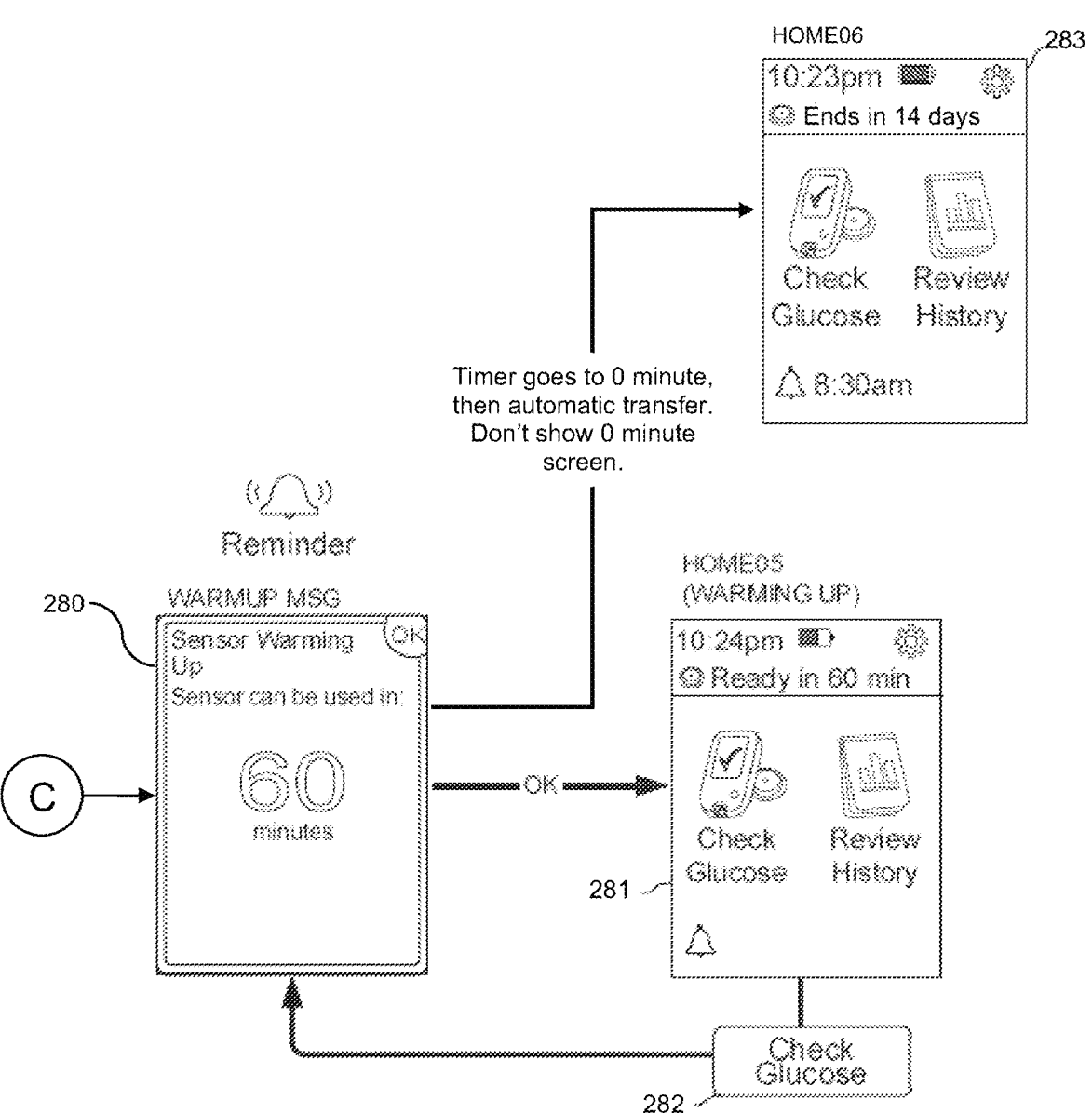

FIG. 7 illustrates a method 260 for activating a sensor after the device is powered on, according to one embodiment. At block 261, the device is powered on. Once powered, a home screen 262 is displayed. The home screen 262 indicates that there is no active sensor, and further includes an icon or other trigger element that enables the start of a new sensor. Once icon is selected by the user, as represented by block 263, a "Start New Sensor" screen 264 for starting the sensor is displayed. The start new sensor screen 264 enables the user to start a new sensor—e.g., by informing the user to scan the sensor to start it. Upon the start of the scan, the device waits (e.g., 15 seconds) for the scan to complete, as shown by blocks 265 and 266. If the wait period elapses and the scan is not yet complete, the device may display a screen informing the user that the scan has timed out 267.

Upon completion of the scan, to start a pairing of the device and sensor, the device may check the sensor for errors, including an integrity check of the scan 268, a health check of the sensor 270 and an expiration of the sensor check 272. If the device determines that the scan failed, the device may display a screen indicating that a scan error occurred, as shown at block 269. If the device determines that the sensor in not functioning properly, the device may display a screen indicating to replace the sensor with a new sensor 271. If the scan succeeds and the sensor is found to be functioning, the device may check the expiration information of the sensor, and if expired, e.g., a user tried to continue use of an expired sensor, the device may display a sensor expired screen 273. From any of the scan error, replace sensor, and sensor expired screens, selecting "ok" may navigate the device back to the home screen 262 to start a new sensor again.

Referring to block 275, if the sensor has already been activated by another device, then a screen 276 indicating that the sensor is already paired with another device is displayed. Upon user confirmation, the home screen is displayed, as shown at block 277. In certain embodiments, when a sensor is already paired with another reader device, use of that sensor with the new reader device is not allowed.

In some instances, the device may include a masked mode that enables the user to take readings of a paired sensor, but does not display the resulting readings to the user, or otherwise limits the resulting data to the user. After a non-expired sensor has been successfully scanned, the device may display a masked mode screen to indicate a masked mode is currently enabled. For example, masked mode screen 279 indicates that the device will operate in the masked mode, unless otherwise changed. In some instances, the initial configuration may be set up by the doctor or other health care profession for the patient. In certain configurations, the masked mode may only be deactivated by a health care professional. If the device is not operating in a masked mode, or after the user confirms the masked mode, then a warm up message screen 280 is displayed that indicates that the sensor is warming up. The remaining time for warm up may also be displayed. If the user confirms the message, for example by selecting the "ok" icon, then the device may navigate back to the home screen 281 and the home screen is displayed and indicates the sensor is warming up—e.g., by showing the remaining time until the sensor is ready. If the user attempts to perform a sensor scan as shown by block 282—e.g., by selecting the check glucose icon, then the warm up message screen 281 is displayed again. In some instances, the home screen may be displayed after a predetermined time showing the warm up message or the device will automatically navigate to the home screen 283 after the sensor is ready. In certain embodiments, the device will not display a message screen showing "0 minutes" remaining.

Sensor Scan and Results

Exemplary embodiment of a graphical user interfaces which may be utilized in connection with a reader as described herein and which function to scan and to provide results are provided.

Sensor Scan Interface

Figure 8:
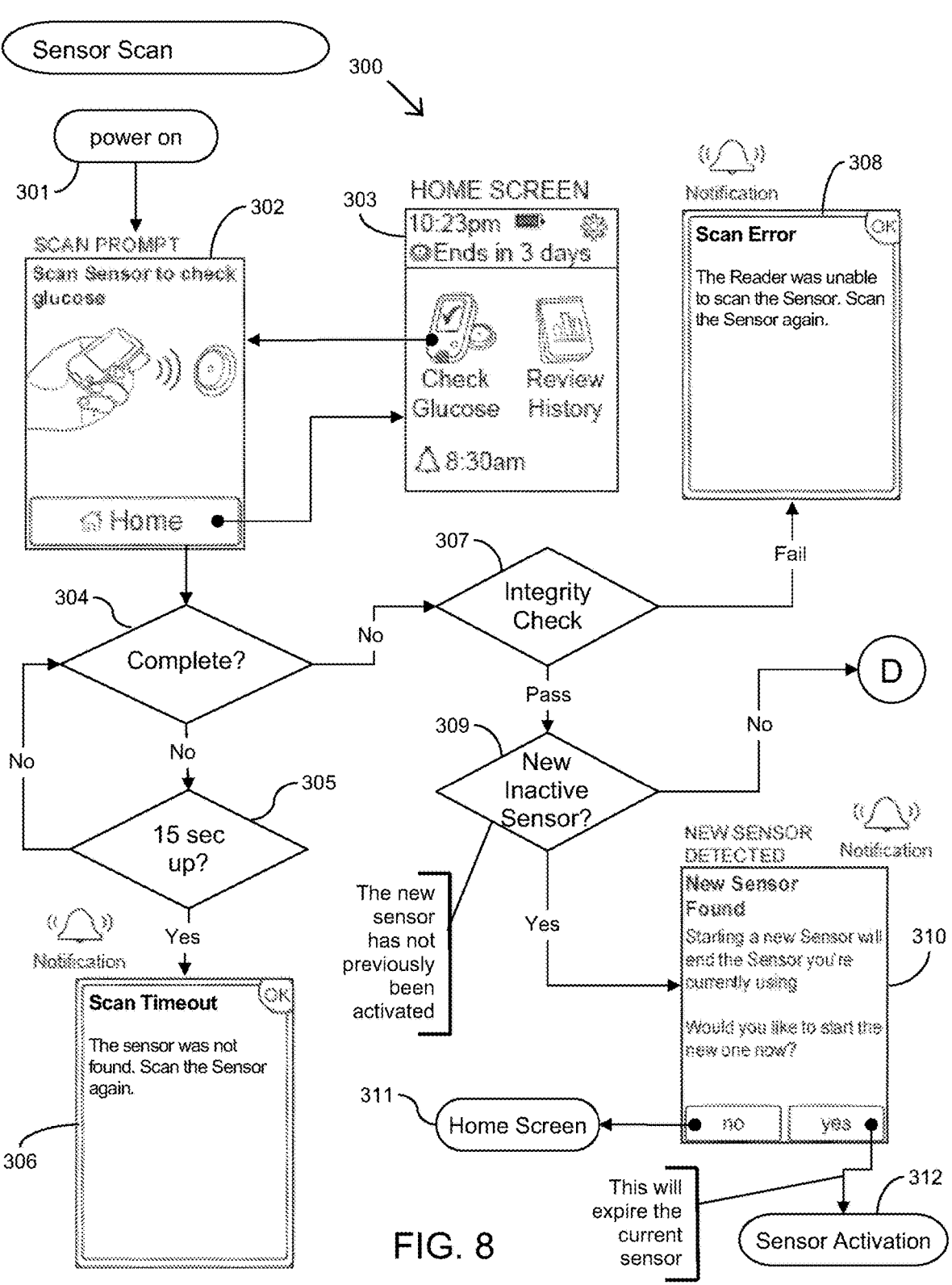
FIG. 8 illustrates a method for scanning a sensor with an analyte monitoring device, according to one embodiment.
Figure 8:
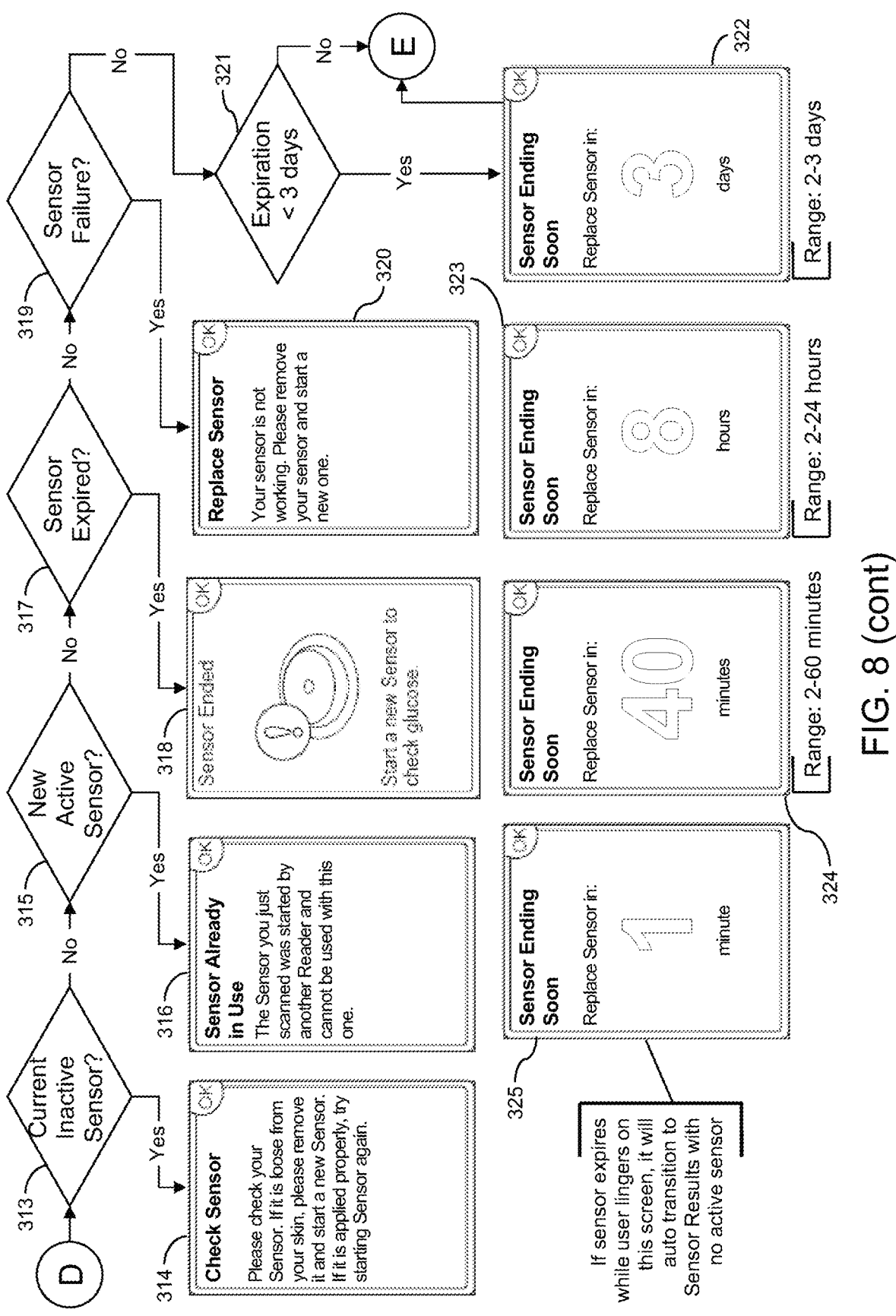
Figure 8:
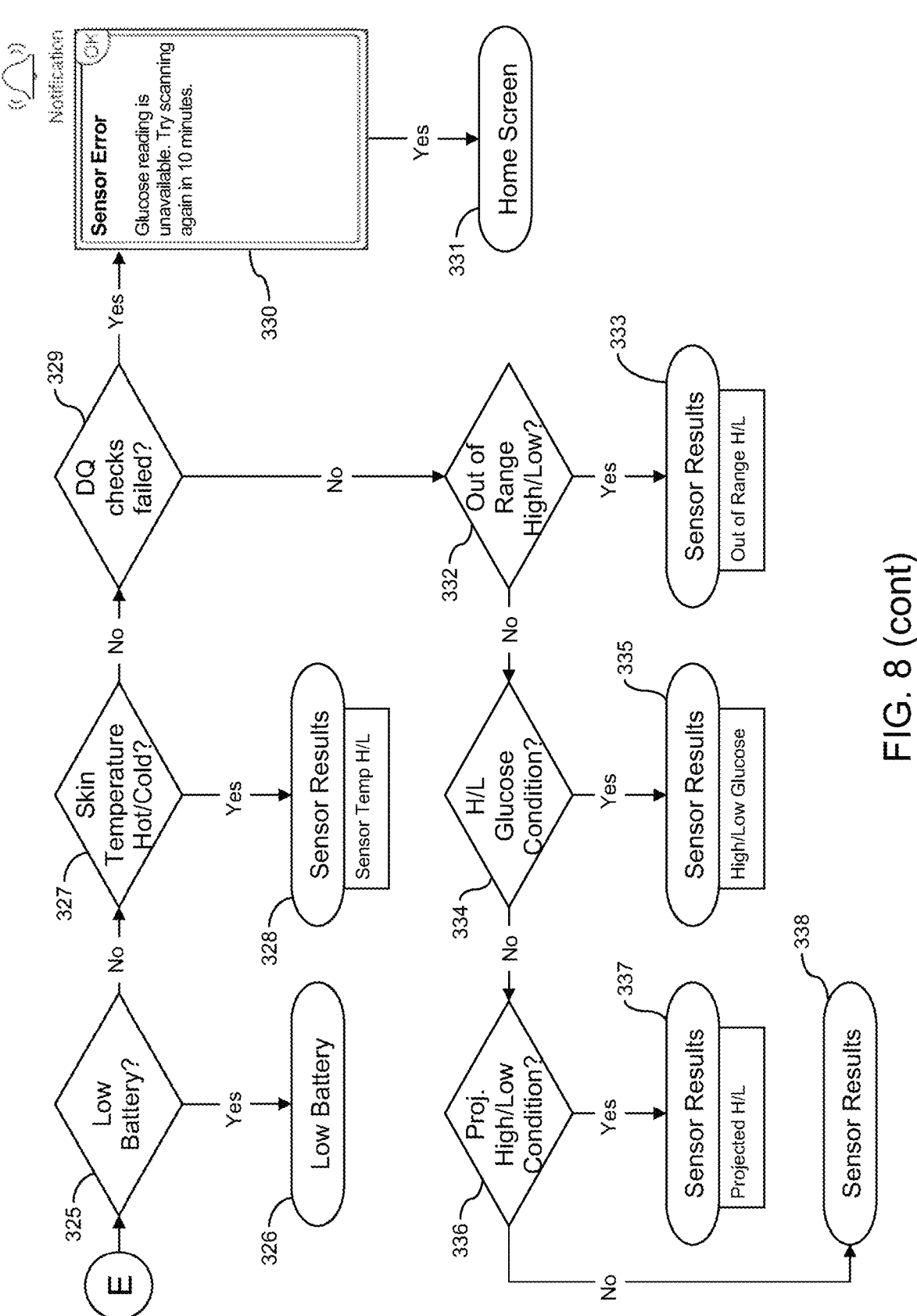

FIG. 8 illustrates a method 300 for scanning a sensor with an analyte monitoring device, according to one embodiment. At block 301, the device is powered on. A scan prompt screen 302 is displayed and indicates to the user to scan the sensor to check an analyte level (e.g., glucose level).

In the embodiment shown, an icon or trigger element is provided on screen 302 for going to the home screen 303. If selected by the user, the home screen 303 is displayed. From the home screen 303, the user may initiate a sensor scan thereafter and return to the scan prompt screen 302.

Upon the start of the scan, the device waits (e.g., 15 seconds) for the scan to complete, as shown by blocks 304 and 305. If the wait period elapses and the scan is not yet complete, the device may display a screen informing the user that the scan has timed out 306. Upon completion of the scan, the device may perform an integrity check of the scan 307. If the device determines that the scan failed, the device may display a screen indicating that a scan error occurred, as shown at block 308 and instruct the user to scan the sensor again.

If the sensor is a new inactive sensor, as shown at block 309, then a new sensor detected screen 310 is shown and indicates that the sensor is a new sensor. Screen 310 provides the user with an option to start the new sensor or not. If the user elects to start the new sensor, then the device initiates the sensor activation process, as shown by block 312. If the user elects to not start the new sensor, then the device displays the home screen, as shown by block 311.

If the device determines that the current sensor is inactive, as shown at block 313, then a check sensor screen 314 is displayed and indicates that there may be a problem with the sensor. The check sensor screen 314, in some embodiments, may suggest to the user to check if the sensor is loose or has fallen out. If the sensor is loose, the loose sensor should be removed and a new sensor shall be paired. If the sensor is correctly applied, then the sensor is scanned again.

Referring to block 315, if the sensor has already been activated by another device, then a screen 316 indicating that the sensor is already paired with another device is displayed. Upon user confirmation, the home screen is displayed. In certain embodiments, when a sensor is already paired with another reader device, use of that sensor with the new reader device is not allowed.

The device may check the expiration information of the sensor as shown at block 317, and if expired, e.g., a user tried to reuse an expired sensor, the device may display a sensor expired screen 318. From any of the scan error, replace sensor, and sensor expired screens, selecting "ok" may navigate the device back to the home screen to start a new sensor again.

If the device determines that the sensor in not functioning properly, the device may display a screen indicating to replace the sensor with a new sensor 271. If the scan succeeds and the sensor is found to be functioning, the device determines whether the sensor is to expire within a predetermined amount of time, such as within the next 3 days, as shown at block 321. It should be appreciated that the amount of time may vary in other embodiments, and in one embodiment check to see if the sensor is expired. It should also be appreciated that the predetermined amount of time may be preprogrammed in manufacturing, and/or set within the settings, etc. If at block 321, it is determined that the sensor is expiring within the predetermined amount of time, then a sensor near expiration screen 322 is displayed to indicate the sensor is close to expiring. The remaining time until the sensor expires may be displayed, for example. In certain embodiments, the remaining time message is displayed after the first scan of the day for the last three days of the sensor life and the screen is shown after every scan for the last 8 hours before sensor expiration. The screen showing the remaining time until sensor expiration may be displayed as days remaining, when the length of time is 2 days or more, hours remaining, when the length of time is between 2 hours and 1 day, and minutes remaining, when the length of time is less than an hour, wherein the time remaining is rounded up as described above in conjunction with FIG. 6E. If the time remaining screen is still active when the time remaining reaches zero, the device may automatically navigate to the Sensor Results with no active sensor screen, as described herein below.

If at block 321, it is determined that the sensor is not expiring within the predetermined amount of time, then it is determined whether the sensor battery is low, as represented at block 325. If the battery is low, then at block 326, the device indicates that the battery is low—e.g., via a low battery screen, or a low battery icon, etc. In some instances, a reading is not taken, and no results are shown for the scan.

If the battery is not low, then at block 327, it is determined if the skin temperature is too hot or cold—e.g., using a "safe" range of temperatures. The sensor may provide the temperature data to the device. If the temperature is determined to be too hot or cold, then the device displays the resulting reading and indicates that the sensor temperature was too hot or too cold, respectively, as shown at block 328. If the skin temperature is not too hot or cold, then it is determined whether the quality of the data is acceptable, as shown at block 329. If the data quality checks fail, the device may display a sensor error screen 330, informing the user that the glucose reading is unavailable. In certain embodiments, the device may suggest to the user to rescan after a predetermined waiting period, such as 10 minutes. Upon selection by the user of the "ok" confirmation element, the device may navigate back to the home screen 331.

As shown at block 332, it is determined whether the resulting reading is out of range. If the sensor is out of range, then it is determined if a high or low glucose condition has occurred. For example, a target range or acceptable range may be preset by the manufacturer or customizable by the user. If a high or low condition is present, then the user is taken to the Sensor Results screen, as shown at block 333, and the high or low condition may be indicated on the Sensor Results screen (e.g., via a message, icon, etc.) along with the sensor results.

Referring back to block 332, if it is determined that the sensor is not out of range, then it is determined if the glucose level was a high or low glucose level 334. For example, a high or low glucose level may be preset by the manufacturer or customizable by the user. If a high or low glucose level is present, then the user is taken to the Sensor Results screen, as shown at block 335, and the sensor results may be displayed. If a high or low condition is not present, then it is determined whether a high or low condition is projected, as shown at block 336. A high or low condition may be projected, for example, by trends in the measurement readings. If a high or low condition is projected, then the user is taken to the Sensor Results screen and the projected high or low condition is indicated on the Sensor Results screen along with the sensor results, as shown at block 337.

In some instances, the device is programmed such that the skin temperature test takes priority over other test conditions (e.g., out-of-range test, high/low glucose test, projected high/low glucose test, etc.) that may occur simultaneously.

Consecutive Scans Interface

An exemplary embodiment of a graphical user interface which may be utilized in connection with a reader as described herein and which functions to provide navigation when consecutive scans are present is provided.

Two Scans within Predetermined Period of Time

In some aspects, the analyte reader device is programmed to perform specific navigations when the device is scanned multiple times within a predetermined period of time.

Figure 9A:
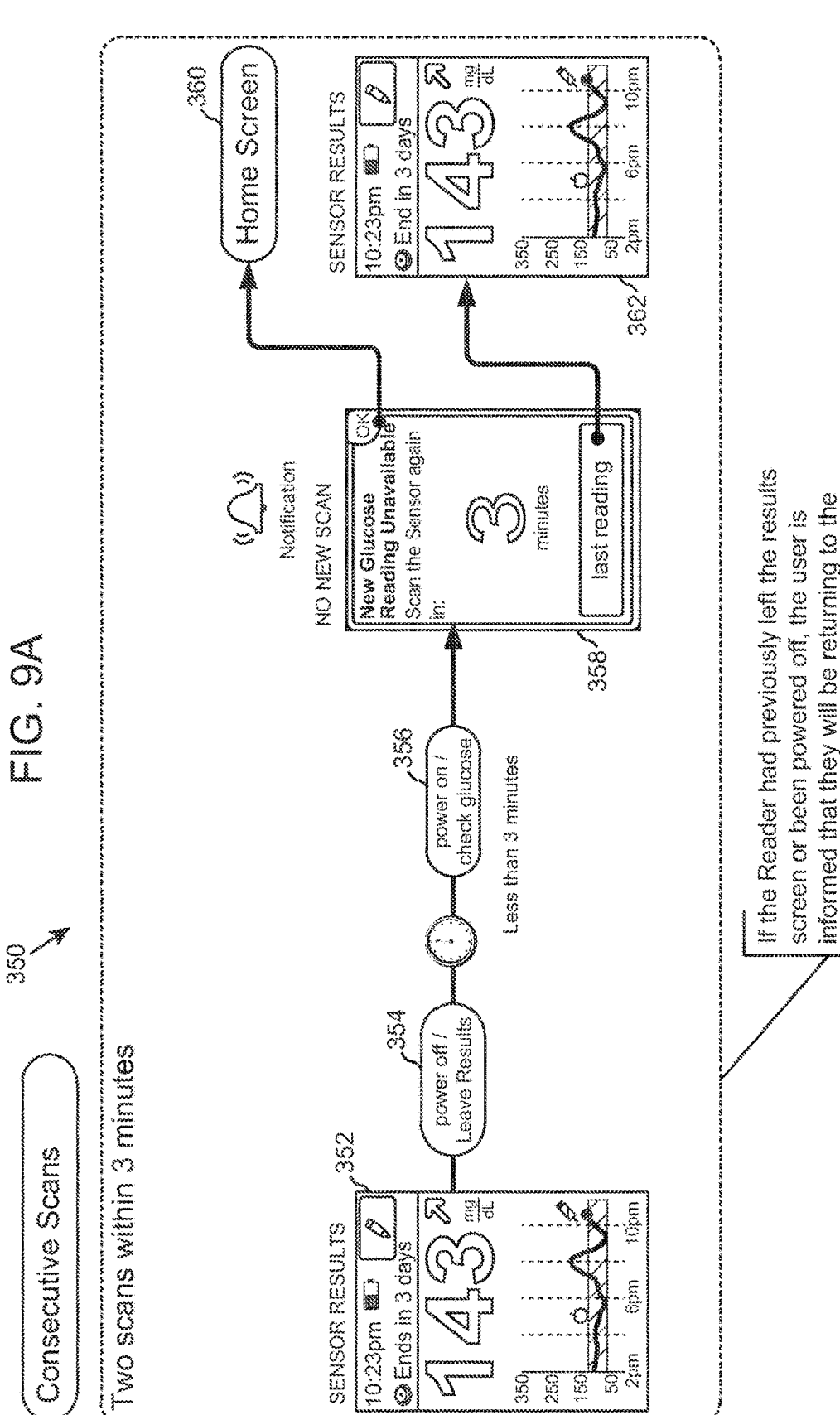
FIG. 9A illustrates a method for performing two scans within a predetermined period of time with the analyte reader, according to one embodiment.

FIG. 9A illustrates a method 350 for performing two scans within a predetermined period of time with the analyte reader, according to one embodiment. After the first scan is performed, a Sensor Results screen is displayed, as shown at block 352. If the power is turned off or the Sensor Results screen is left before a predetermined period of time (e.g., 3 minutes in the example embodiment shown), the results from the first scan are saved, as represented by block 354. If the device is powered back on, or another scan is attempted, within the predetermined period of time, the device will prevent the user from performing a new scan and display a No New Scan screen indicating that a new sensor reading is not available at this time, as shown by blocks 356 and 358. The No New Scan screen may also indicate the time remaining until another scan, as well as, enable the user to view the last Sensor Results screen if desired, as represented by Sensor Results screen 362.

Device Timeout at the Suggest Dose Screen from BG Result

In some aspects, the analyte reader device is programmed to return to a saved suggested dose screen if the reader is powered off or leaves a "Calculator/Suggested Dose" screen when a dose has been calculated but not logged, and the device is powered back on or another scan is attempted within a predetermined period of time.

Figure 9B:
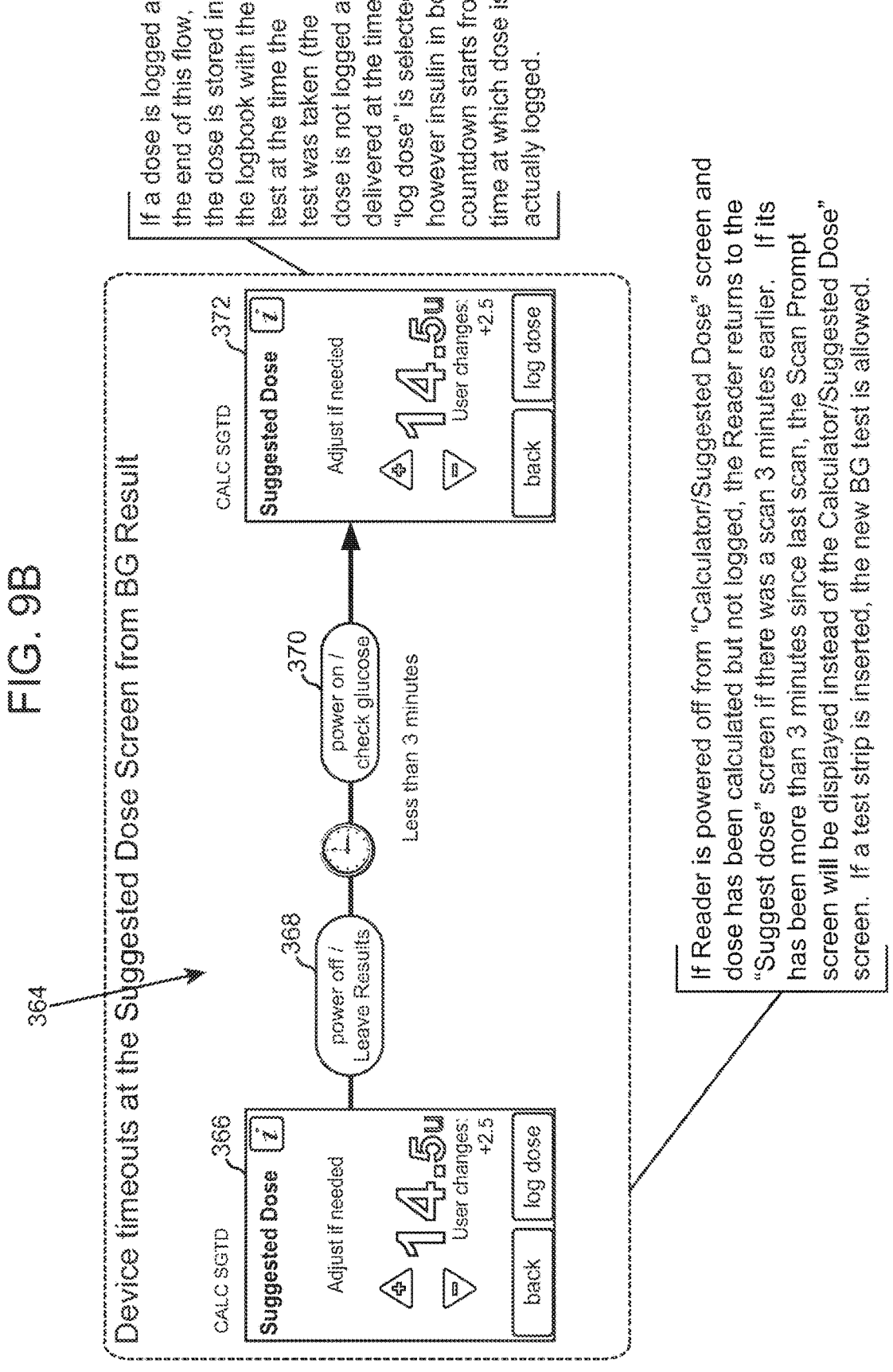
FIG. 9B illustrates a method of logging a dose calculation, according to one embodiment.

FIG. 9B illustrates a method 364 of logging a dose calculation, according to one embodiment. After a glucose reading is taken, a "Calculator/Suggested Dose" (CALC SGTD) screen 366 may be displayed to calculate and log a suggested dose of insulin. From screen 366, the user can adjust the suggested does if desired and log the dose. However, if within a predetermined period of time (e.g., 3 minutes in the embodiment shown), the device is powered off, or screen 366 is left, after a suggested dose has been calculated but not logged, then the suggested dose data is saved, as shown at block 368. If the device is powered back on, or another glucose scan is attempted, within the predetermined period of time, as shown by block 370, then the user is returned to the CALC SGTD screen 372 having the saved suggested dose data. From here, the user may continue with the dose calculation and log the calculated dose. If a dose is logged at this point, the dose is stored within the Logbook along with the test results. In one embodiment, the dose is logged as having been taken at the time the test was taken rather than at the time the dose was actually logged. The insulin in body countdown, however, starts from the time at which the does is actually logged.

Suggested Dose from BG Result Logged

In some aspects of the present disclosure, after a first scan and calculated insulin dose logged, the device is programmed to prevent a second scan within a predetermined period of time from a first scan. The user will not be able to perform the second scan, but will be able to view the Logbook.

Figure 9C:
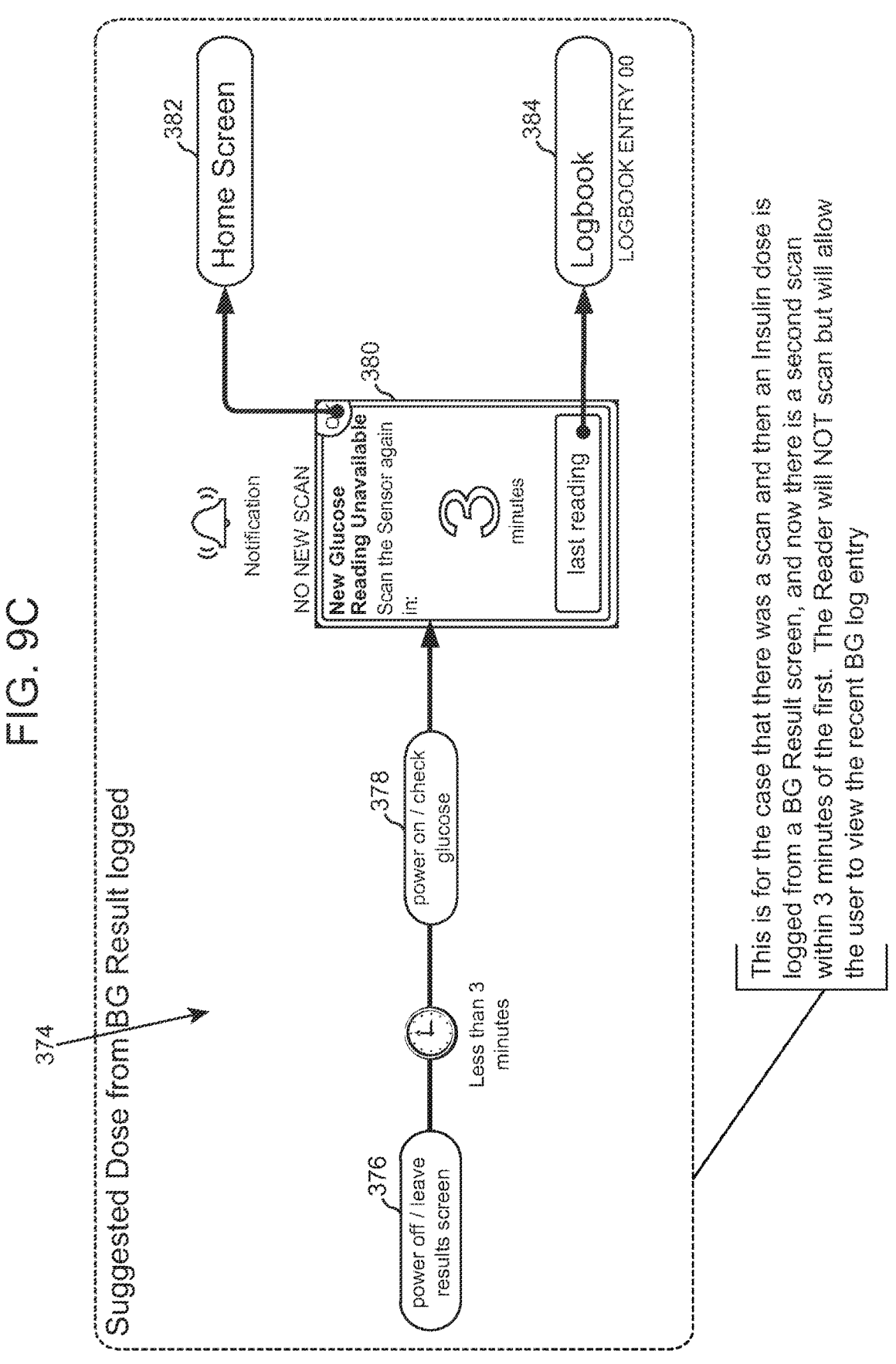
FIG. 9C illustrates a method for enabling two consecutive scans, according to one embodiment.

FIG. 9C illustrates a method 374 for enabling two consecutive scans, according to one embodiment. At block 376, the reader is powered off, or the Sensor Results screen is left, within a predetermined period of time after a first scan was taken (e.g., 3 minutes in the embodiment shown). If the device is powered back on, or another scan is attempted, within the predetermined period of time from the first scan, as shown at block 378, then the second scan is prevented from occurring until the predetermined period of time has lapsed. A No New Scan screen 380 is displayed indicating that another scan is not currently permitted. In some instances, as shown, screen 380 provides the time remaining until another scan can be taken. In the embodiment shown, user confirmation form screen 380 takes the user to the Home screen as shown at block 382. Screen 380 may also provide a selection to allow the user to view the last reading in the Logbook, as shown at block 384.

Sensor Results Interface

In some aspects of the present disclosure, a graphical user interface is provided that may be utilized in connection with a reader as described herein and which functions generally to provide sensor results.

Results

Figures 10A, 10B, 10C:
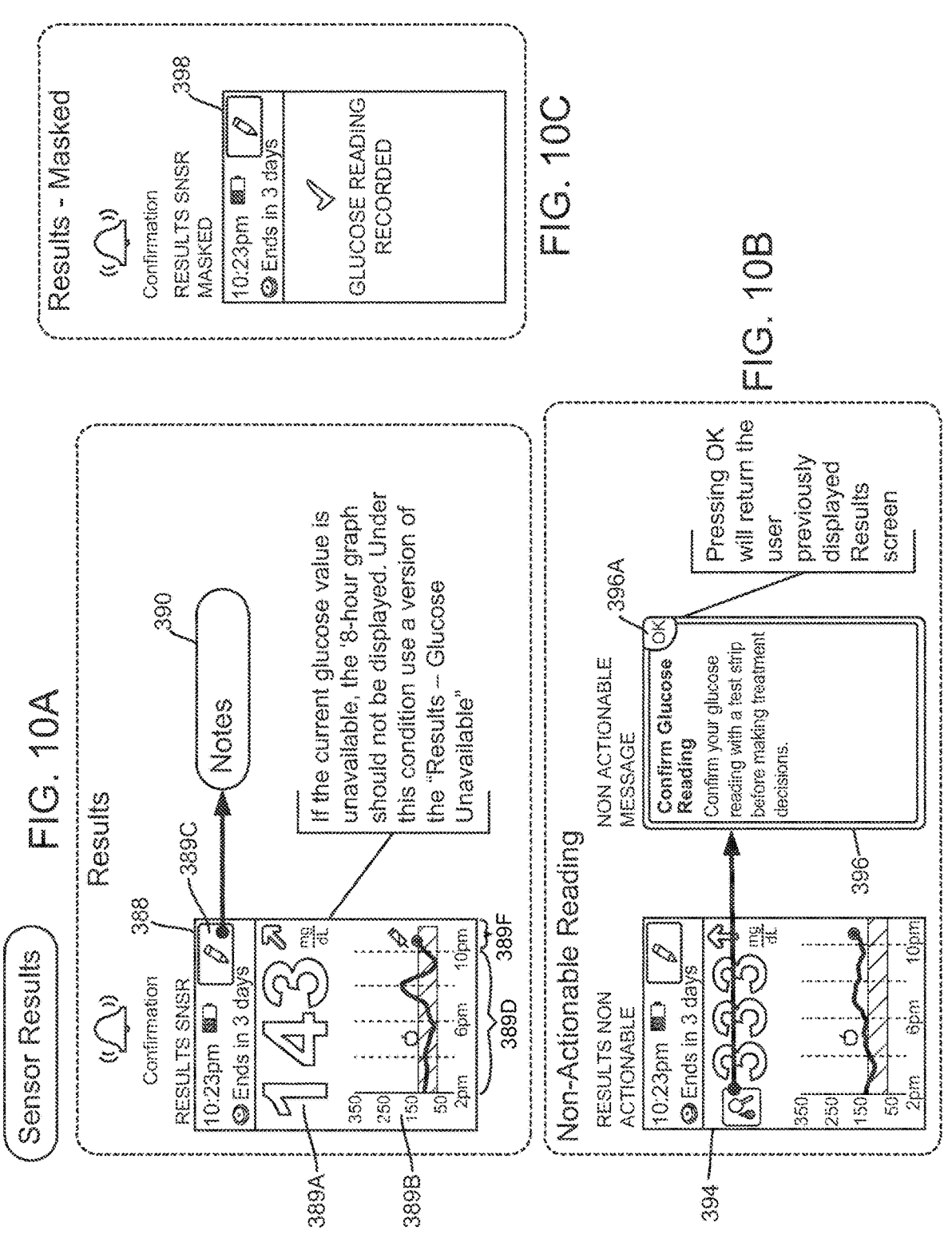

FIG. 10A illustrates an example Sensor Results screen 388, according to one embodiment. Screen 388 may be provided, for example, after a scan has been successfully performed. The example sensor results screen 388 is shown to include a sensor reading 389*a*, a graph 389*b* of glucose readings taken, and various reader/sensor related information, such as a trending arrow, current time, battery life, sensor expiration, etc. In certain embodiments, time may be displayed in 24-hours format or 12-hour (am/pm) format. In certain embodiments, numerical glucose results may be displayed in selectable units, e.g. mg/dL as shown in FIG. 10A, or mmol/L as shown in FIG. 10L, or others. A trigger element 389*c* for navigating to the Notes interface is also provided to take the user to the Notes screen as shown by block 390. It should be appreciated that other combinations of these, and other, features and trigger elements may be included in other embodiments.

In one embodiment, graph 389*b* does not display if the current glucose value is unavailable. Instead, a screen indicating that the glucose results are unavailable is displayed.

In one embodiment, graph 389*b* displays the past resulting readings for a given time period. The total time period may be sectionalized into a first predetermined period of time 389*d*, and a second predetermined period of time 389*f*. The second predetermined period 389*f* is subsequent to the first predetermined period of time 389*d* and includes more recent readings than the first predetermined period of time389*d*. For example, in the embodiment shown, at time 10:23 pm, graph 389*b* displays readings in a first predetermined time period 389*d* of 8 hours (e.g., 2 pm to 10 pm), and also displays more recent readings within the second predetermined time period 389*f* of 1 hour (e.g., 10 pm to 11 pm). As graph 389*b* is displayed at 10:23 pm, readings for the last 23 minutes (e.g., 10 pm to 10:23 pm) are shown in the second predetermined time period 389*f*. As subsequent readings are taken, graph 389*b* will track the readings within the second predetermined time period 389*f*. Once subsequent readings are taken for the entire second predetermined period of time 389*f*, the entire plot of readings is shifted in time by the second predetermined period of time 389*f* (e.g., 1 hour). In other words, once subsequent readings are obtained up to 11 pm, the plot of readings from 3 pm to 11 pm will shift to the first predetermined period of time 389*d*, and the second predetermined time period 389*f* will begin without any readings and start to track subsequent readings between 11 pm and 12 pm. Once subsequent readings are obtained up to 12 pm, then entire plot of readings is again shifted by the second predetermined period of time 389*f* (e.g., 1 hour), and the process repeats.

In one embodiment, when scanning is first started and no data has been obtained for the graph 389*b*, the graph 389*b* is not displayed until the device has obtained sensor readings for at least the first predetermined period of time 389*d* (e.g., 8 hours).

Thus, graph 389*b* begins with readings for at least the entire first predetermined period of time 389*d*. For example, in one embodiment, this threshold time period is equal to the first predetermined period of time 389*d*. In another embodiment, the threshold time period is longer than the first predetermined period of time such that sensor readings have been obtained for part or all of the second predetermined period of time.

It is appreciated that in other embodiments, a template of the graph may be displayed at first, but no sensor readings are shown on the graph until the device has obtained sensor readings for at least the first predetermined period of time 389*d*.

Non-Actionable Reading

FIG. 10B illustrates an example Results Non-Actionable screen 394, according to one embodiment. When a scan is performed and the resulting reading is non-actionable, a Results Non-Actionable screen 394 indicates to the user that the result is non-actionable and that the result should be confirmed. For example, a non-actionable result is a reading that is determined to be too high or too low for a therapy treatment, decision, or recommendation to be made—e.g., an insulin calculation. Screen 394 includes a trigger element for providing more information to the user regarding the non-actionable reading. When selected by the user, a Non-Actionable Message screen 396 is provided with additional details, recommendations, etc., such as recommending that the user take a test strip measurement before making any treatment decisions. User confirmation (e.g., by touching the "OK" button 396*a*) will return the user to the previously displayed Results screen. In certain embodiments, a Results Non-Actionable screen may also include additional icons as described below, such as a high glucose icon as illustrated in FIG. 10M. FIG. 10M illustrates a display screen 394*a* including both a Results Non-Actionable icon and a High Glucose icon.

Results—Masked Mode

FIG. 10C illustrates an example Results-Masked screen 398, according to one embodiment. When a scan is performed while the device is set for the Masked Mode, a Results-Masked screen 398 is displayed and indicates to the user that the reading was successful. Screen 398 does not provide the resulting reading to the user. The resulting reading is stored along with resulting readings from other scans in the device. These stored readings can later be accessed by a physician or other health care professional at a later time. For example, the physician or HCP may download the data during the next patient visit (e.g., via a wired or wireless connection between the reader and the physician's or HCP's computer,); or the data may be transferred via the internet from the reader (or patient's PC) to the physician's or HCP's computer or server; etc.

Sensor Temperature (Too Hot/Too Cold)

Figures 10D, 10E:
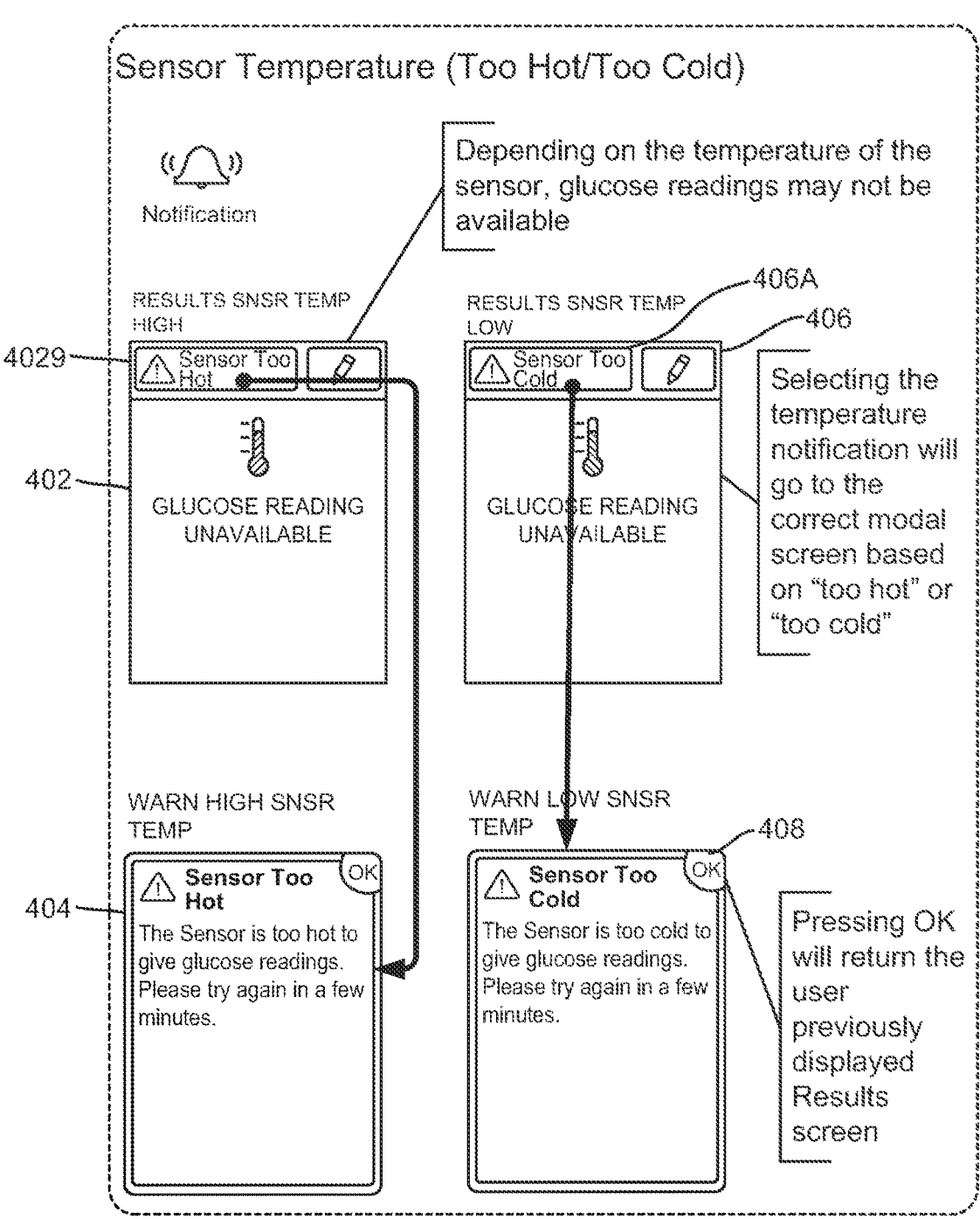
FIG. 10D illustrates an interface for indicating that the sensor temperature is too high, according to one embodiment.
FIG. 10E illustrates an interface for indicating that the sensor temperature is too low, according to one embodiment.

FIG. 10D illustrates an interface for indicating that the sensor temperature is too high, according to one embodiment. The Results Sensor Temp High screen 402 is displayed to indicate to the user that the sensor temperature is too high, such as with respect to a predetermined "safe" range of temperatures. For example, screen 402 may have a warning message and/or icon indicating a high sensor temperature and may further indicate that a glucose reading is not available, as shown. Screen 402 provides a trigger element 402*a* for providing additional information regarding the high sensor temperature. For example, when the user touches the touch-sensitive button 402*a*, another screen 404 is displayed to provide additional details or information, such as that the sensor temperature is too high and that the user should try again later.

FIG. 10E illustrates an interface for indicating that the sensor temperature is too low, according to one embodiment. The Results Sensor Temp Low screen 406 is displayed to indicate to the user that the sensor temperature is too low, such as with respect to a predetermined "safe" range of temperatures. For example, screen 406 may have a warning message and/or icon indicating a low sensor temperature and may further indicate that a glucose reading is not available, as shown. Screen 406 provides a trigger element 406*a* for providing additional information regarding the high sensor temperature. For example, when the user touches the touch-sensitive button 406*a*, another screen 408 is displayed to provide additional details or information, such as that the sensor temperature is too high and that the user should try again later.

Out of Range High/Low Readings

Figures 10F, 10G:
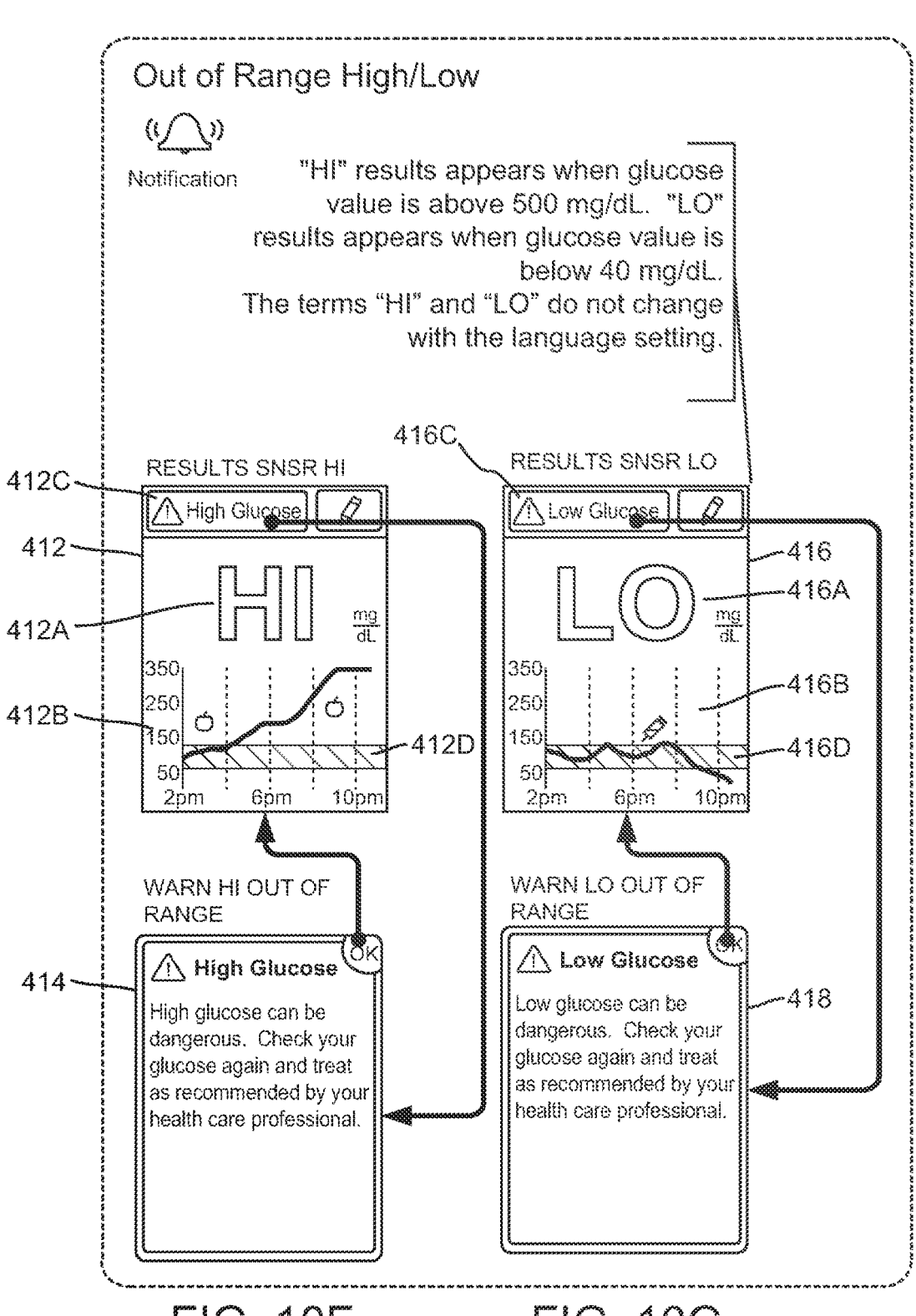
FIG. 10F illustrates an interface for indicating that the sensor reading is out of range, according to one embodiment.
FIG. 10G illustrates an interface for indicating that the sensor reading is out of range, according to one embodiment.

FIG. 10F illustrates an interface for indicating that the sensor reading is out of range, according to one embodiment. The Results Sensor HI screen 412 is displayed to indicate to the user that the sensor reading is too high and out of range of readings. Instead of a sensor reading being displayed, screen 412 displays an indicator element 412*a*, such as a message, icon, symbol, etc. For example, in the embodiment shown, the term "HI" 412*a* is shown in place of a sensor reading to indicate that the reading is out of range and too high.

The predetermined upper threshold reading value may be determined based on a predetermined number (e.g., 500 mg/dL), or may be determined relative to a predetermined "acceptable" range of readings to display (e.g., 40 mg/dL to 500 mg/dL), or with respect to a target range (e.g., 350 mg/dL over the target range), etc.

Screen 412 may also include a graph 412*b* of sensor readings that also indicates a target range 412D. Screen 412 provides a trigger element 412*c* for providing additional information, warning, instructions, etc., regarding the out of range and high sensor reading. For example, when the user touches the touch-sensitive button 412*c*, another screen 414 is displayed to provide additional details or information, such as that the glucose level is out of range high, that a high glucose level may be dangerous, and that the user should check again later and treat as recommended by their health care professional. Upon user confirmation (e.g., via selection of the "OK" button) the user is taken back to screen 412.

FIG. 10G illustrates an interface for indicating that the sensor reading is out of range, according to one embodiment. The Results Sensor LO screen 416 is displayed to indicate to the user that the sensor reading is out of range and too low. Instead of a sensor reading being displayed, screen 416 displays an indicator element 416*a*, such as a message, icon, symbol, etc. For example, in the embodiment shown, the term "LO" 416*a* is shown in place of a sensor reading to indicate that the reading is out of range and too low.

The predetermined lower threshold reading value may be determined based on a predetermined number (e.g., 40 mg/dL), or may be determined relative to a determined "acceptable" range of readings to display (e.g., 40 mg/dL to 500 mg/dL), or with respect to a target range (e.g., 20 mg/dL below the target range), etc.

Screen 416 may also include a graph 416*b* of sensor readings that also indicates a target range 416D. Screen 416 provides a trigger element 416*c* for providing additional information, warning, instructions, etc., regarding the out of range and low sensor reading. For example, when the user touches the touch-sensitive button 416*c*, another screen 418 is displayed to provide additional details or information, such as that the glucose level is out of range low, that a low glucose level may be dangerous, and that the user should check again later and treat as recommended by their health care professional. Upon user confirmation (e.g., via selection of the "OK" button) the user is taken back to screen 416.

High/Low Sensor Readings

Figures 10H, 10I:
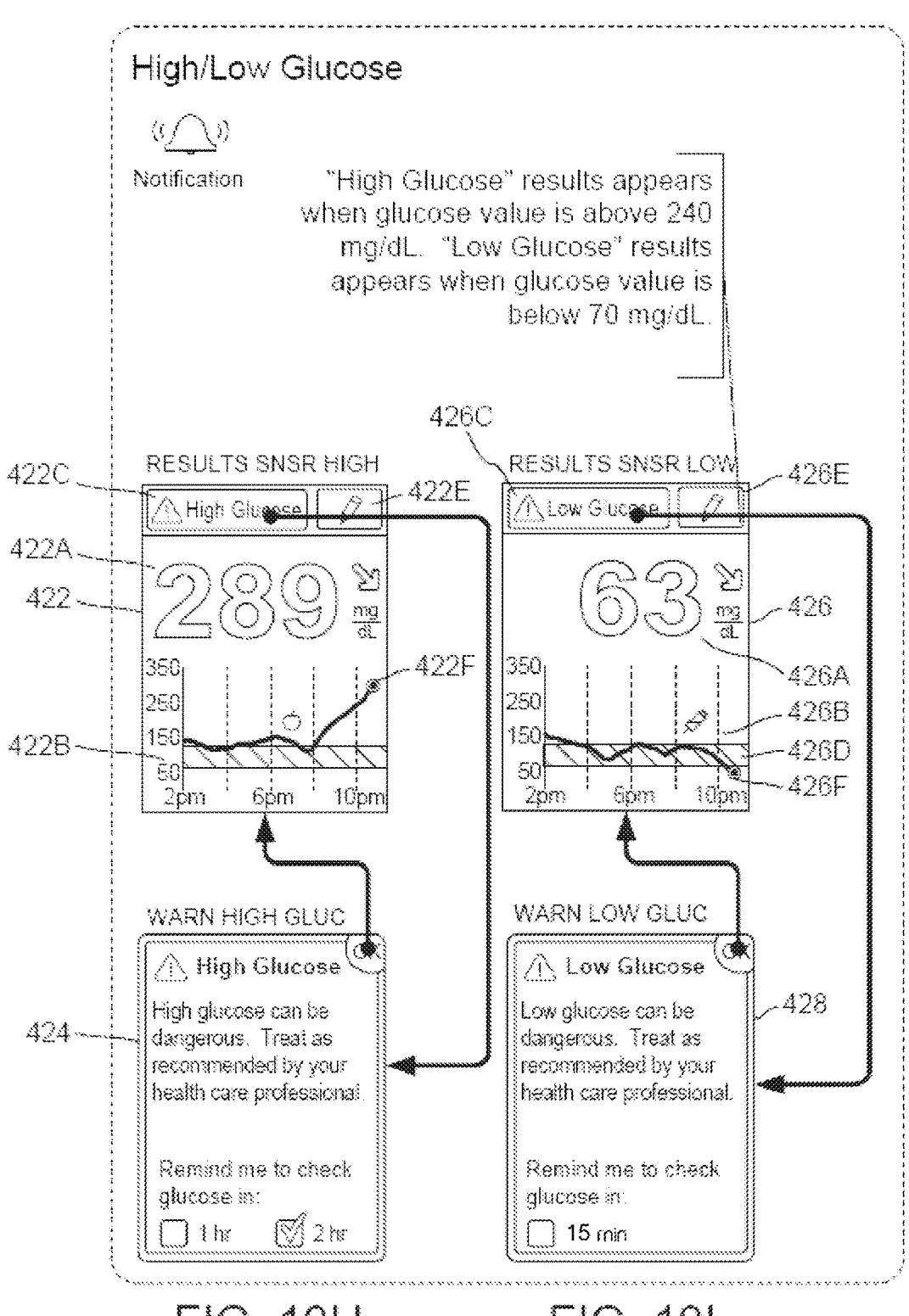
FIG. 10H illustrates an interface for indicating that the sensor reading is high, according to one embodiment.
FIG. 10I illustrates an interface for indicating that the sensor reading is low, according to one embodiment.

FIG. 10H illustrates an interface for indicating that the sensor reading is high, according to one embodiment. The Results Sensor High screen 422 is displayed to indicate to the user that the sensor reading is a high reading, such as via a message, icon, symbol, etc., 422*c*. For example, in the embodiment shown, after a high reading is obtained, screen 422 is displayed and the sensor reading 422*a* is shown. In addition to showing the sensor reading 422*a*, screen 422 includes a trigger element 422*c* for indicating the high reading and for accessing additional information, warning, instructions, etc., regarding the high sensor reading. For example, when the user touches the touch-sensitive button 422*c*, another screen 424 is displayed to provide additional details or information about the high reading, such as that the glucose level is high, that a high glucose level may be dangerous, and that the user should check again later and treat as recommended by their health care professional. In certain embodiments, the high reading screen may include reminder options. When a reminder on the high reading screen is selected, the reminder will appear on the reminder list as described below. The device will check if the reminder list is full prior to adding the new reminder. As described below, the reminders are only saved upon navigation back to the home screen from the results screen or when the device times out on the results screen. Upon user confirmation (e.g., via selection of the "OK" button) the user is taken back to screen 422.

The predetermined upper threshold reading value may be determined based on a predetermined number (e.g., 240 mg/dL), or may be determined relative to a predetermined range of readings (e.g., 70 mg/dL to 240 mg/dL), or with respect to a target range (e.g., 120 mg/dL over the target range), etc.

Screen 422 may also include a graph 422*b* of sensor readings that also indicates a target range 422*d*. In addition, screen 422 may include a distinguishing element 422*f* for identifying the high reading on the graph 422*b*—e.g., in the embodiment shown, an encircled dot 422*f*. Screen 422 may also include other trigger elements, such as a trigger element 422*e* for initiating the Notes interface.

FIG. 10I illustrates an interface for indicating that the sensor reading is low, according to one embodiment. The Results Sensor Low screen 426 is displayed to indicate to the user that the sensor reading is a low reading (e.g., with respect to a predetermined "acceptable" reading range), such as via a message, icon, symbol, etc., 426*c*. For example, in the embodiment shown, after a low reading is obtained, screen 426 is displayed and the sensor reading 426*a* is shown. In addition to showing the sensor reading 426*a*, screen 426 includes a trigger element 426*c* for indicating the low reading and for accessing additional information, warning, instructions, etc., regarding the low sensor reading. For example, when the user touches the touch-sensitive button 426*c*, another screen 428 is displayed to provide additional details or information about the low reading, such as that the glucose level is low, that a low glucose level may be dangerous, and that the user should check again later and treat as recommended by their health care professional. In certain embodiments, the low reading screen may include reminder options. When a reminder on the low reading screen is selected, the reminder will appear on the reminder list as described below. The device will check if the reminder list is full prior to adding the new reminder. As described below, the reminders are only saved upon navigation back to the home screen from the results screen or when the device times out on the results screen. Upon user confirmation (e.g., via selection of the "OK" button) the user is taken back to screen 426. In certain embodiments, the reminder times may be different for low and high glucose levels, for example, 20 minutes for low glucose and 2 hours for high glucose. Certainly, within the scope of the present disclosure, the low glucose reminder time may include other suitable times such as 15 minutes, 10 minutes, or 30 minutes, while the high glucose reminder time may include other suitable times such as one hour, 1.5 hours, 30 minutes and the like.

The predetermined lower threshold reading value may be determined based on a predetermined number (e.g., 70 mg/dL), or may be determined relative to a predetermined range of readings (e.g., 70 mg/dL to 240 mg/dL), or with respect to a target range (e.g., 10 mg/dL below the target range), etc.

Screen 426 may also include a graph 426*b* of sensor readings that also indicates a target range 426*d*. In addition, screen 426 may include a distinguishing element 426*f* for identifying the low reading on the graph 426*b*—e.g., in the embodiment shown, an encircled dot 426*f*. Screen 426 may also include other trigger elements, such as a trigger element 426*e* for initiating the Notes interface.

Projected High/Low Sensor Readings

Figures 10J, 10K:
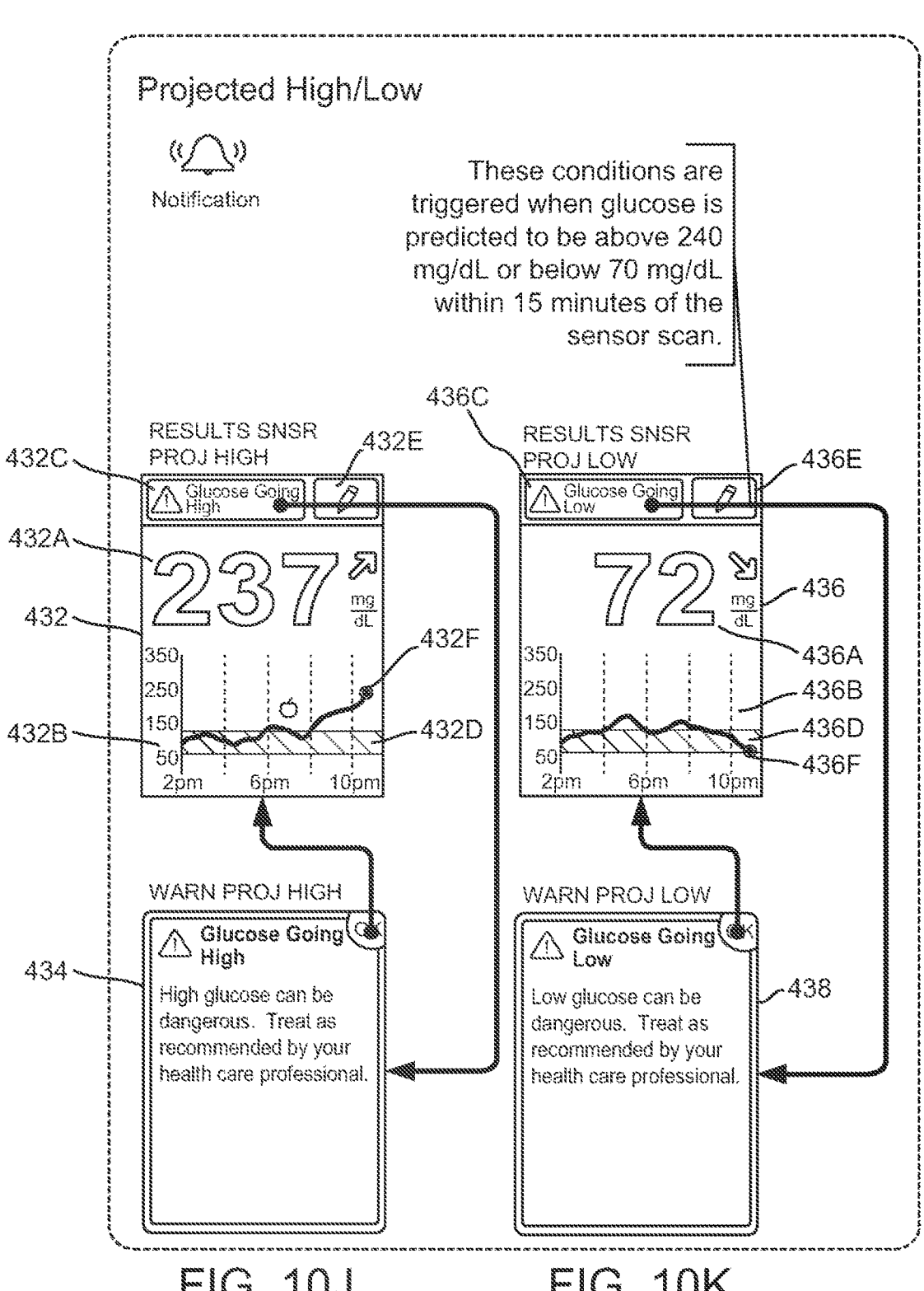
FIG. 10J illustrates an interface for indicating that a high analyte level is projected, according to one embodiment.
FIG. 10K illustrates an interface for indicating that a low analyte level is projected, according to one embodiment.

FIG. 10J illustrates an interface for indicating that a high analyte level is projected, according to one embodiment. The Results Sensor Projected High screen 432 is displayed to indicate to the user that a high analyte level is projected based on the current sensor reading and trend, such as via a message, icon, symbol, etc., 432*c*. For example, in the embodiment shown, after a sensor reading is obtained, screen 432 is displayed and the sensor reading 432*a* is shown. In addition to showing the sensor reading 432*a*, screen 432 includes a trigger element 432*c* for indicating a projected high analyte level and for accessing additional information, warning, instructions, etc., regarding the projected high analyte level. For example, when the user touches the touch-sensitive button 432*c*, another screen 434 is displayed to provide additional details or information about the projected high analyte level, such as that the glucose level is high, that a high glucose level may be dangerous, and that the user should check again later and treat as recommended by their health care professional. In certain embodiments, the projected high reading screen may include reminder options. When a reminder on the projected high reading screen is selected, the reminder will appear on the reminder list as described below. The device will check if the reminder list is full prior to adding the new reminder.

As described below, the reminders are only saved upon navigation back to the home screen from the results screen or when the device times out on the results screen. Upon user confirmation (e.g., via selection of the "OK" button) the user is taken back to screen 432.

Projected high glucose readings may be based on the projected glucose level of the user within a predetermined upcoming period of time—e.g., within the next 15 minutes. The predetermined upper threshold reading value may be determined based on a predetermined number (e.g., 240 mg/dL), or may be determined relative to a predetermined range of readings (e.g., 70 mg/dL to 240 mg/dL), or with respect to a target range (e.g., 120 mg/dL over the target range), etc.

Screen 432 may also include a graph 432*b* of sensor readings that also indicates a target range 432*d*. In addition, screen 432 may include a distinguishing element 432*f* for identifying the projected high reading on the graph 432*b*— e.g., in the embodiment shown, an encircled dot 432*f*. Screen 432 may also include other trigger elements, such as a trigger element 432*e* for initiating the Notes interface.

FIG. 10K illustrates an interface for indicating that a low analyte level is projected, according to one embodiment. The Results Sensor Projected Low screen 436 is displayed to indicate to the user that a low analyte level is projected based on the current sensor reading and trend, such as via a message, icon, symbol, etc., 436*c*. For example, in the embodiment shown, after a sensor reading is obtained, screen 426 is displayed and the sensor reading 436*a* is shown. In addition to showing the sensor reading 436*a*, screen 436 includes a trigger element 436*c* for indicating the projected low analyte level and for accessing additional information, warning, instructions, etc., regarding the projected low analyte level. For example, when the user touches the touch-sensitive button 436*c*, another screen 438 is displayed to provide additional details or information about the projected low analyte level, such as that the glucose level is low, that a low glucose level may be dangerous, and that the user should check again later and treat as recommended by their health care professional. In certain embodiments, the projected low reading screen may include reminder options. When a reminder on the projected low reading screen is selected, the reminder will appear on the reminder list as described below. The device will check if the reminder list is full prior to adding the new reminder. As described below, the reminders are only saved upon navigation back to the home screen from the results screen or when the device times out on the results screen. Upon user confirmation (e.g., via selection of the "OK" button) the user is taken back to screen 436.

Projected low glucose readings may be based on the projected glucose level of the user within a predetermined upcoming period of time—e.g., within the next 15 minutes. The predetermined lower threshold reading value may be determined based on a predetermined number (e.g., 70 mg/dL), or may be determined relative to a predetermined range of readings (e.g., 70 mg/dL to 240 mg/dL), or with respect to a target range (e.g., 10 mg/dL below the target range), etc.

Screen 436 may also include a graph 436*b* of sensor readings that also indicates a target range 436*d*. In addition, screen 436 may include a distinguishing element 436*f* for identifying the projected low reading on the graph 436*b*— e.g., in the embodiment shown, an encircled dot 436*f*. Screen 436 may also include other trigger elements, such as a trigger element 436*e* for initiating the Notes interface.

Blood Glucose Test & Results

In some aspects of the present disclosure, a graphical user interface is provided that may be utilized in connection with a reader as described herein and which functions generally to provide perform an analyte test and provide test results.

Blood Glucose Strip Test Interface

Figure 11:
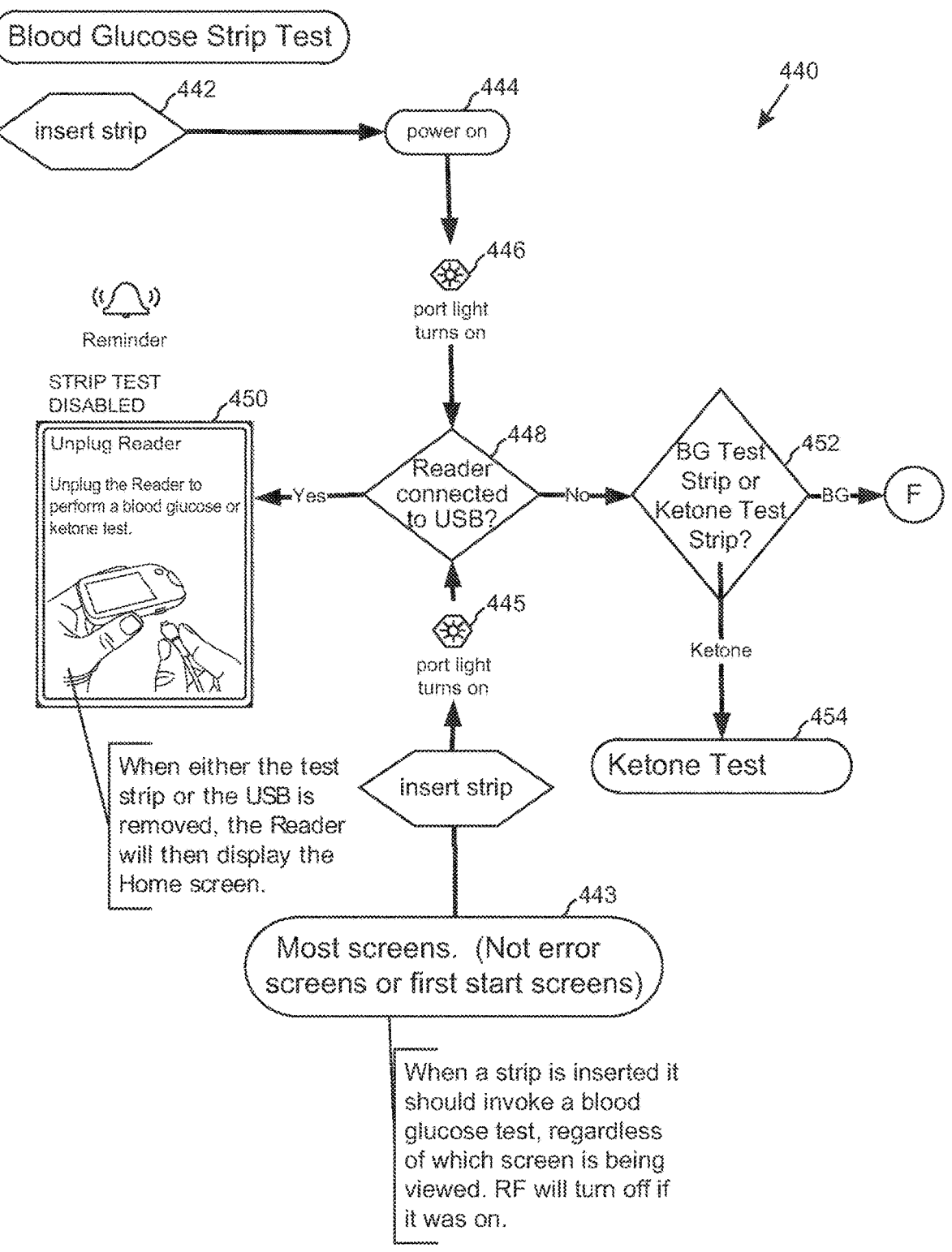
FIG. 11 illustrates an example method for performing a blood glucose test with a test strip, according to one embodiment.
Figure 11:
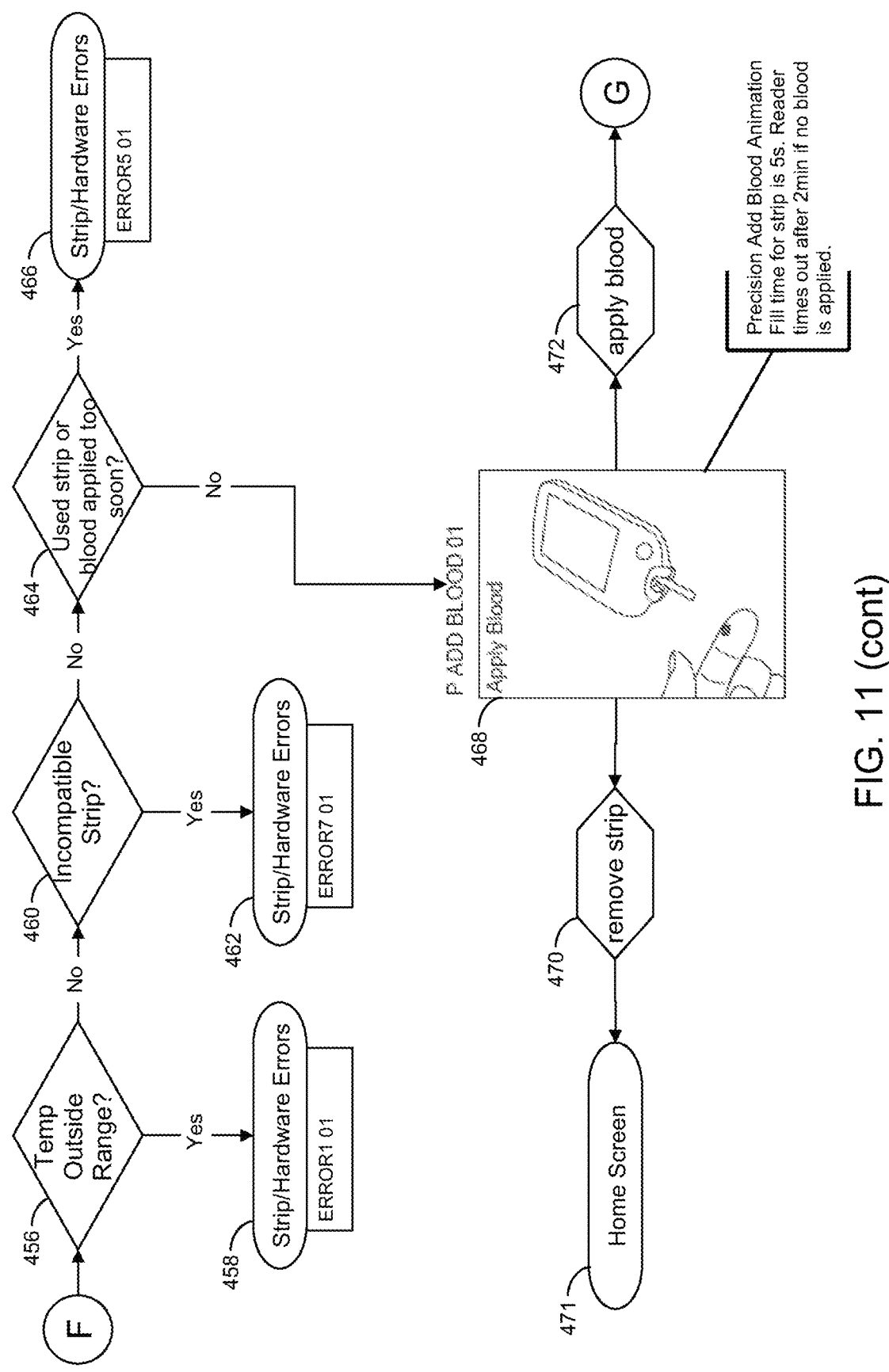
Figure 11:
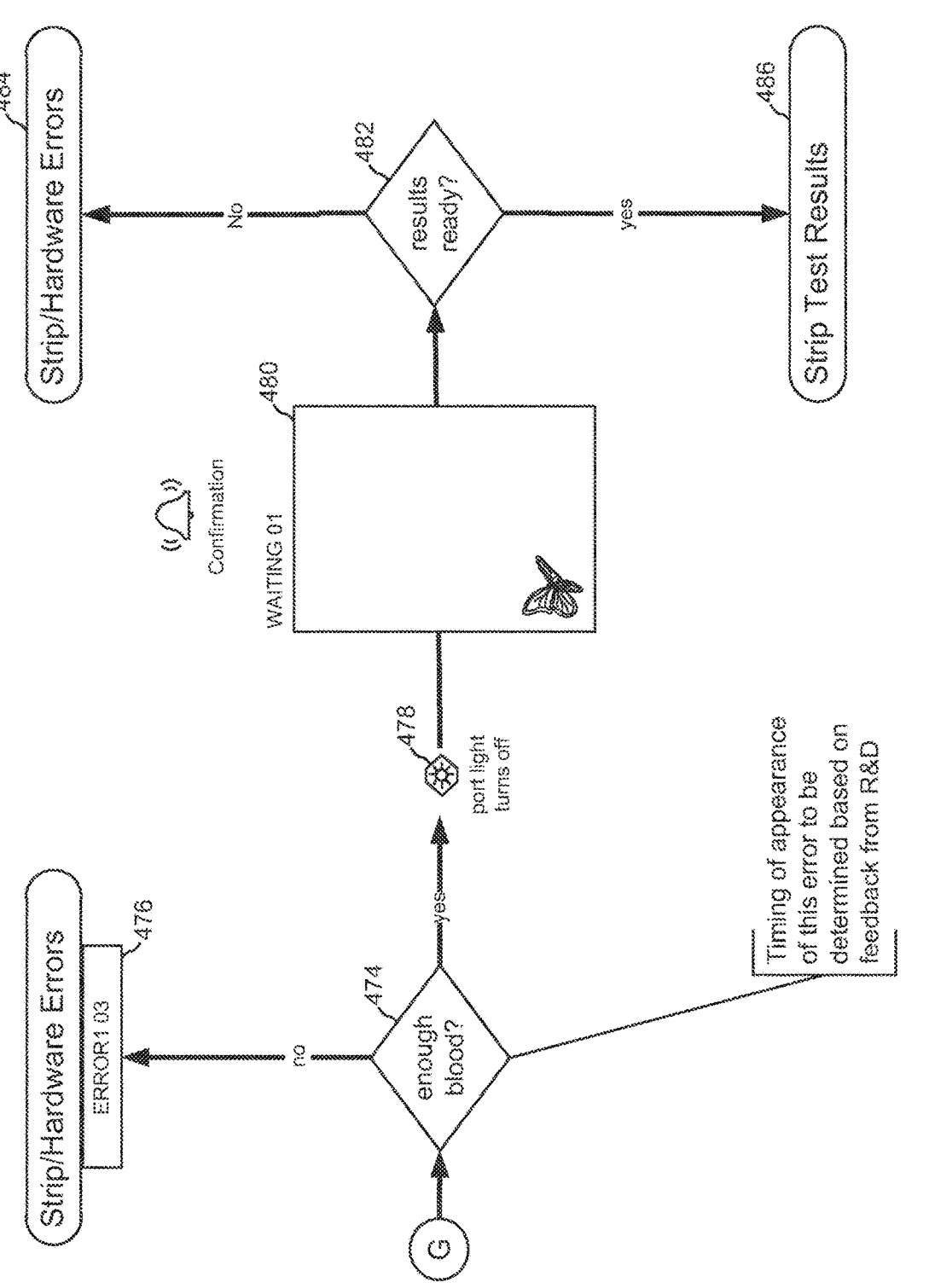

FIG. 11 illustrates an example method 440 for performing a blood glucose test with a test strip, according to one embodiment. At block 442, a test strip is inserted within an analyte monitoring device that is powered off. Once inserted into the device, the device powers on, as shown at block 444. The strip port light, such as a light emitting diode for example, turns on and provides light to the strip port, as shown at block 446. At block 448, it is determined whether a universal serial bus (USB) connection is established with the device. It should be appreciated that other communication technologies may be implemented in other embodiments—e.g., micro-USB, mini USB, RS-232, Ethernet, Firewire, or other data communication connections. If a USB connection is established, then the strip test is prevented and a Strip Test Disabled screen 450 is displayed to indicate that the strip test is not permitted, and that the user should unplug the device to perform a glucose test. If the test strip or the USB connection is removed, then the Reader will display the Home screen.

If at block 448, it is determined that a USB connection is not established, then it is determined if the inserted test strip is a blood glucose test strip or a ketone test strip, as shown at block 452. The test strip may include an identifying element, such as a specific contact configuration, to enable the device to identify what type of test strip it is. If it is determined that the test strip is a ketone test strip, then the device initiates the Ketone Test interface to perform a ketone test measurement, as shown by block 454. If, on the other hand, the test strip is determined to be a blood glucose test strip, then it is determined if the device temperature is outside of the device's operating range, as represented by block 456 and reference path F.

If it is determined that the temperature is above or below the device's operating range, then the in certain embodiments, the port light is turned off and a Strip/Hardware Error screen 458 indicating that the operating temperature is too hot or too cold is displayed.

If at block 456, it is determined that the temperature is within the device's operating range, then the strip is checked for errors, including checking the strip for damage or incompatibility, as shown at block 460, or a check to see if blood was applied to the strip too soon or the strip was used, as shown at block 464. If the device determines the strip is damaged, incompatible or already used, the display may navigate to a Strip/Hardware Error screen 462, 466.

If there are no determined strip errors, an Add Blood interface 468 is displayed to indicate that blood may be applied to the test strip. If the test strip is removed at this point, as shown by block 470, then the port light turns off and the Home screen is displayed, as represented by block 471. If at screen 468, blood is applied to the test strip, as shown by block 472, then it is determined if there was sufficient blood applied to accurately perform a test measurement, as shown by block 474. It should be appreciated that the timing of this determination may vary. If not enough blood is present, then the Strip/Hardware Errors interface is displayed to indicate that not enough blood was applied or that there was an error, as shown by block 476.

If it is determined that sufficient blood has been applied to the test strip, then the port light turns off, as shown by block 478, and a test measurement is performed. A Waiting interface 480 may be displayed while the test measurement is being performed. At block 482, it is determined if the results are ready. If ready, then the Strips Test Results screen 486 is displayed to indicate the resulting reading. If not ready (e.g., after a predetermined timeout period), then the Strip/Hardware Errors screen 484 is displayed to indicate that there was an error in the measurement. In certain embodiments, the device may also perform a low batter test prior to displaying the results as described above in conjunction with FIG. 8.

Figure 34:
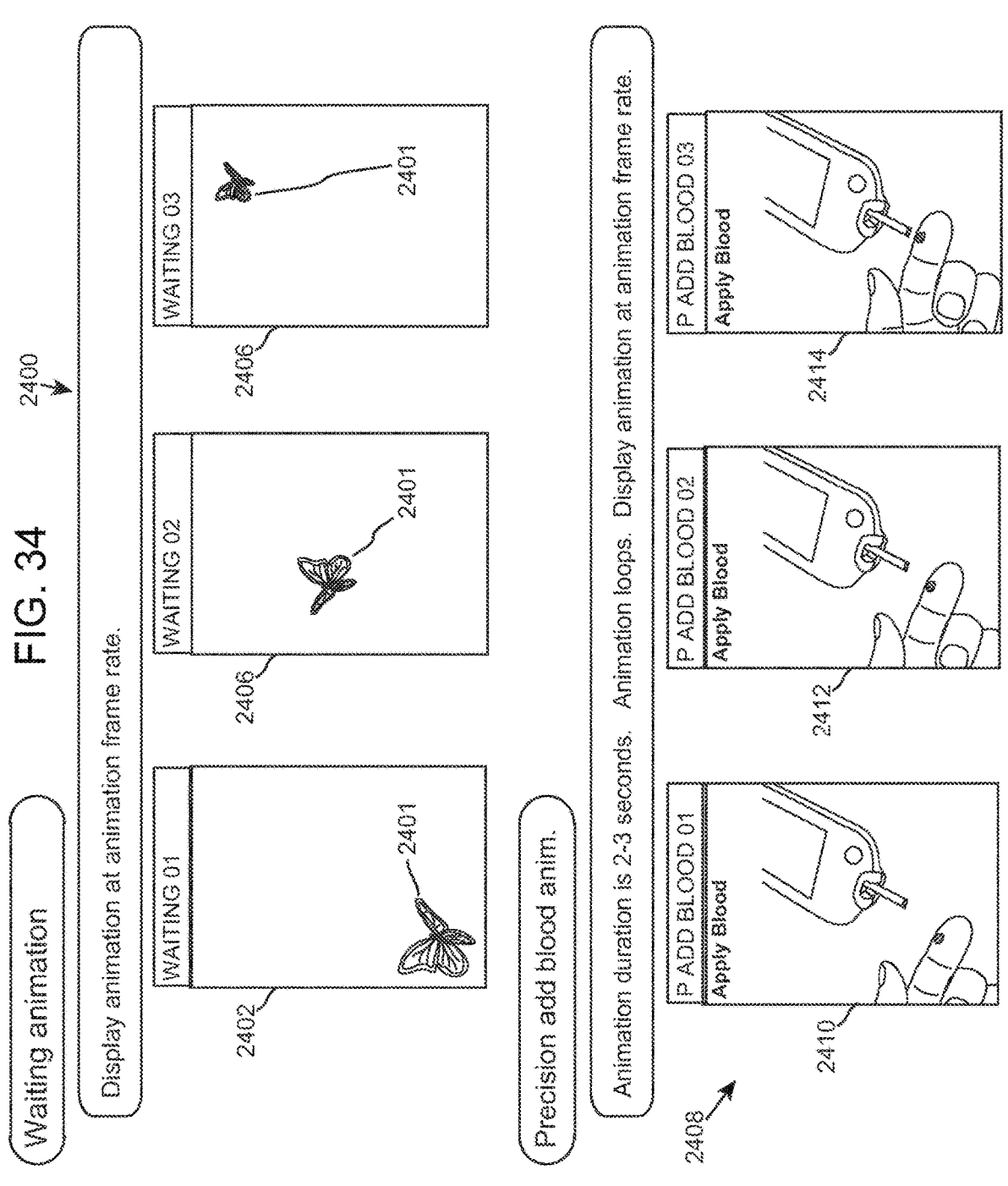
FIG. 34 illustrates example animation interfaces, according to certain embodiments.
Figure 34:
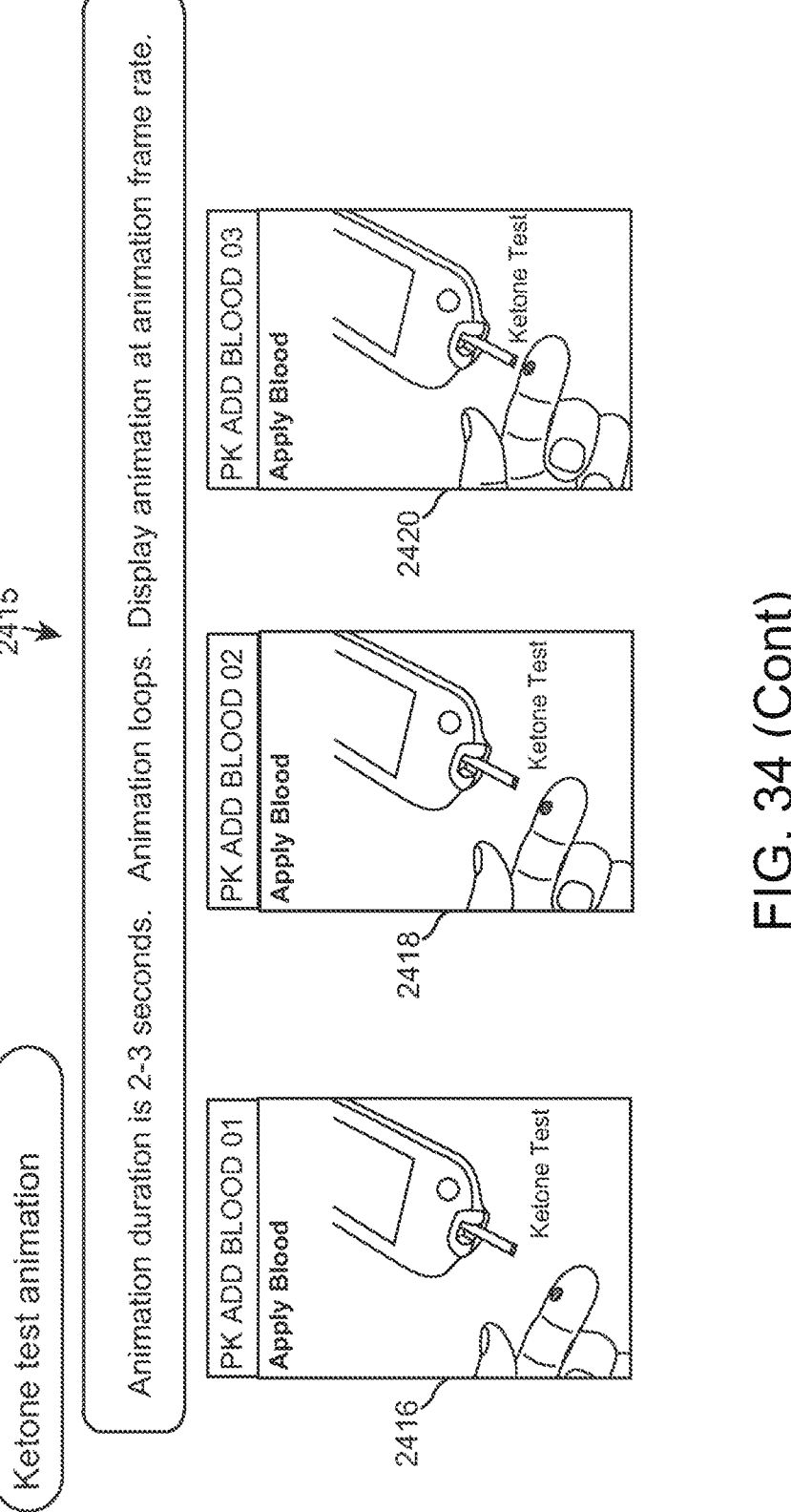

Looking ahead to FIG. 34, an example Waiting interface according to one embodiment is illustrated. Waiting interface 2400 is animated. For example, the a first screen 2402 includes a butterfly 2401 at the bottom left corner. As the next screen 2404 is displayed, the butterfly 2401 is located in a different position. Similarly, at the next screen 2406, the butterfly 2401 is again moved to a different position. When displayed consecutively, an animated sequence results.

FIG. 34 also illustrates an example animation interface 2408 to instruct the user to add blood, according to one embodiment. Screens 2410, 2412, and 2414 display an image of a finger with blood on it and an analyte monitoring device with test strip inserted into the strip port. The finger and test strip move closer as the sequence of screens 2410, 2412, and 2414 progress to animate the application of blood process. Animation interface 2408 may be displayed, for example, when the analyte monitoring device is ready to receive blood FIG. 34 also illustrates an example animation interface 2415 to instruct the user to add blood during a ketone test, according to one embodiment. Similarly to animation interface 2408, screens 2416, 2418, and 2420 display an image of a finger with blood on it and an analyte monitoring device with test strip inserted into the strip port. The finger and test strip move closer as the sequence of screens 2416, 2418, and 2420 progress to animate the application of blood process. Animation interface 2408, however includes an indication that a Ketone test is being performed—e.g., displaying the words, "Ketone Test".

Blood Glucose Strip Test Results Interface

In some aspects of the present disclosure, a graphical user interface is provided that may be utilized in connection with a reader as described herein and which functions generally to provide blood glucose strip test results.

Results Screen

Figure 12A:
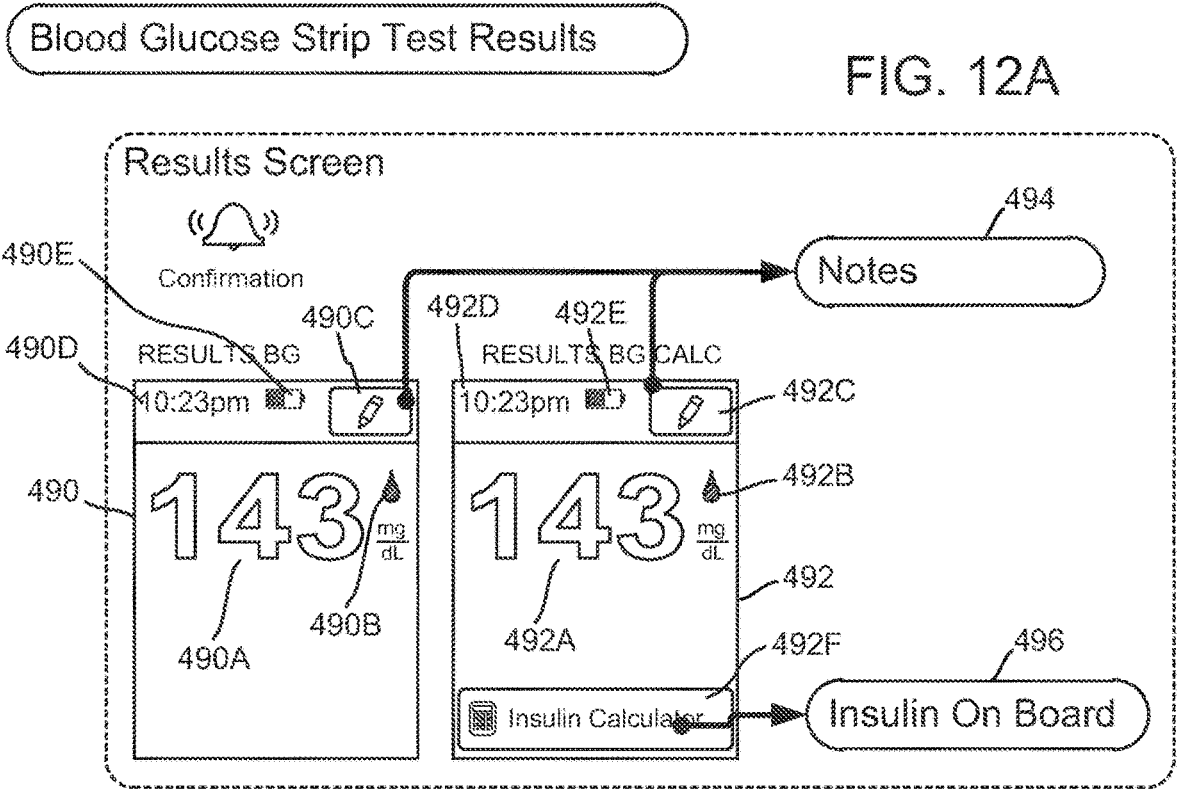
FIG. 12A illustrates an example Blood Glucose Results screen, according to one embodiment.

FIG. 12A illustrates an example blood glucose results (Results BG) screen 490, according to one embodiment. Screen 490 may be provided, for example, after a test strip measurement has been successfully performed. The example Results BG screen 490 is shown to include a test strip measurement 490a and various analyte and device related information, such as indicator elements for a blood glucose strip test 490b, current time 490d, battery life 490e, etc. A trigger element 490c for navigating to the Notes interface is also provided to take the user to the Notes screen as shown by block 494. It should be appreciated that other combinations of these, and other, features and trigger elements may be included in other embodiments.

For analyte monitoring devices with an active insulin calculator, Screen 492 may be provided, for example, after a test strip measurement has been successfully performed. The example Results BG screen 492 is shown to include a test strip measurement 492a and various analyte and device related information, such as indicator elements for a blood glucose strip test 492b, current time 492d, battery life 492e, etc. A trigger element 492c for navigating to the Notes interface is also provided to take the user to the Notes screen as shown by block 494. A trigger element 492f for navigating to an Insulin Calculation interface is also provided as shown by block 496 to provide a calculated insulin dose based on the test measurement 492a. In certain embodiments, the Insulin Calculation interface may be an Advanced Calculator interface or an Easy Calculator interface, based upon the current settings of the device, as described in further detail below. It should be appreciated that other combinations of these, and other, features and trigger elements may be included in other embodiments.

Control Solution Screen

Figure 12B:
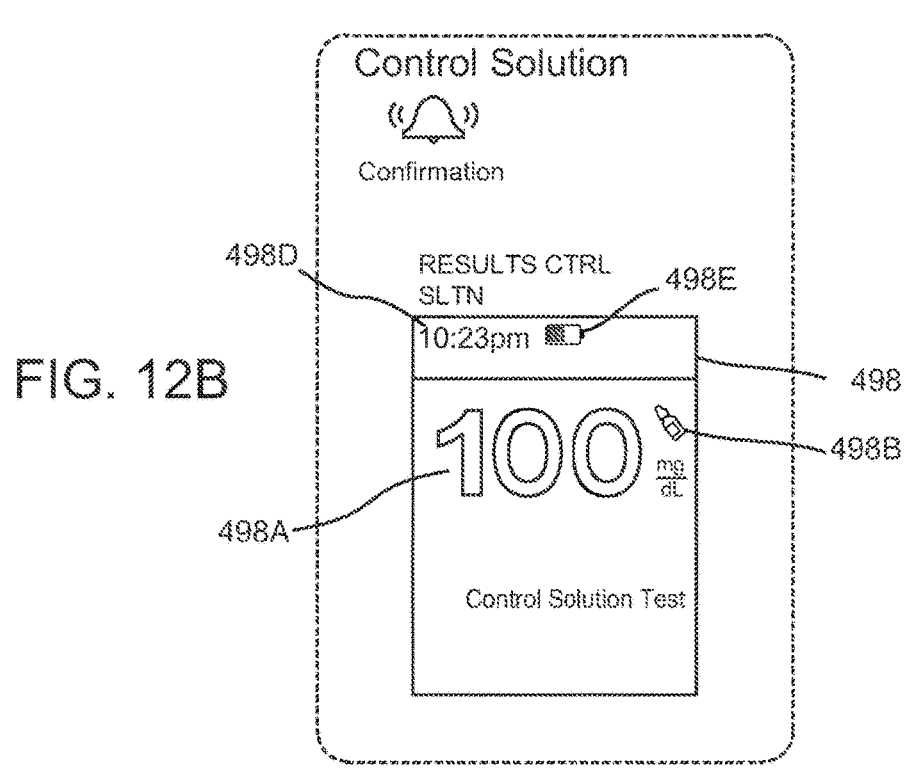
FIG. 12B illustrates an example interface for indicating the results of a blood glucose control solution test, according to one embodiment.

FIG. 12B illustrates an example interface for indicating the results of a blood glucose control solution test, according to one embodiment. The Results Control Solution (CTRL SLTN) screen 498 includes the results 498a of a blood glucose control solution test and various analyte and device related information, such as indicator elements for indicating the blood glucose control solution test 498b, indicating the current time 498d, indicating the battery life 498e, etc.

Reader Temperature Warning (Too Hot/Too Cold) Screen

Figure 12C:
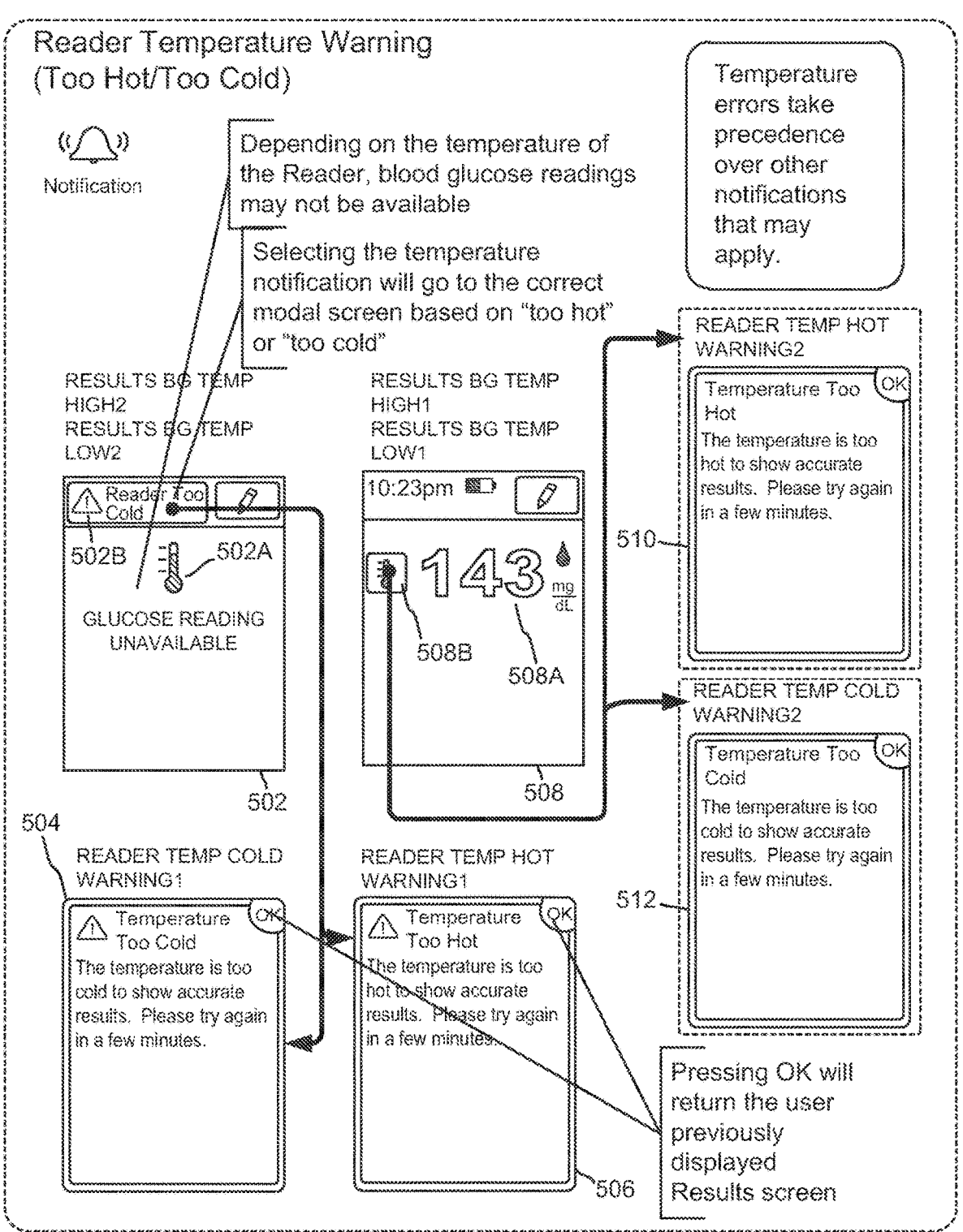
FIG. 12C illustrates example interfaces for indicating that the analyte monitoring device's temperature is too high or too low, according to one embodiment.

FIG. 12C illustrates example interfaces for indicating that the analyte monitoring device's temperature is too high or too low, according to one embodiment. Results BG Temp High2/Low2 screen 502 is displayed to indicate to the user that the device temperature is either too high or too low to provide a reading, such as with respect to a predetermined "safe" range of temperatures to perform an accurate test measurement. For example, screen 502 may have a warning message and/or icon 502a indicating too high or too low of a temperature and may further indicate that a glucose reading is not available, as shown. Screen 502 provides a trigger element 502b for providing additional information regarding the too high or too low device temperature. For example, when the user touches the touch-sensitive button 502b, another screen 504 or 506 is displayed to provide additional details or information, such as that the device temperature is too low or too high, respectively, and that the user should try again later. The user can confirm by pressing the "OK" button and return to the previously displayed Results screen, for instance.

Results BG Temp High1/Low1 screen 508 is an example interface that is displayed when a test measurement is available, but also indicates to the user that the device temperature is either high or low, such as with respect to a predetermined "safe" range of temperatures. For example, screen 508 displays the resulting test measurement 508a and also displays a warning message and/or icon 502b indicating a high or low device temperature. Icon 502b also serves as a trigger element for providing additional information regarding the high or low device temperature. For example, when the user touches the touch-sensitive button 502b, another screen 512 or 510 is displayed to provide additional details or information, such as that the device temperature is too low or too high, respectively, and that the user should try again later. In one embodiment, the device is programmed such that the temperature error takes precedence over other notifications that may be implemented.

Out of Range High/Low Screen

Figures 12D, 12E:
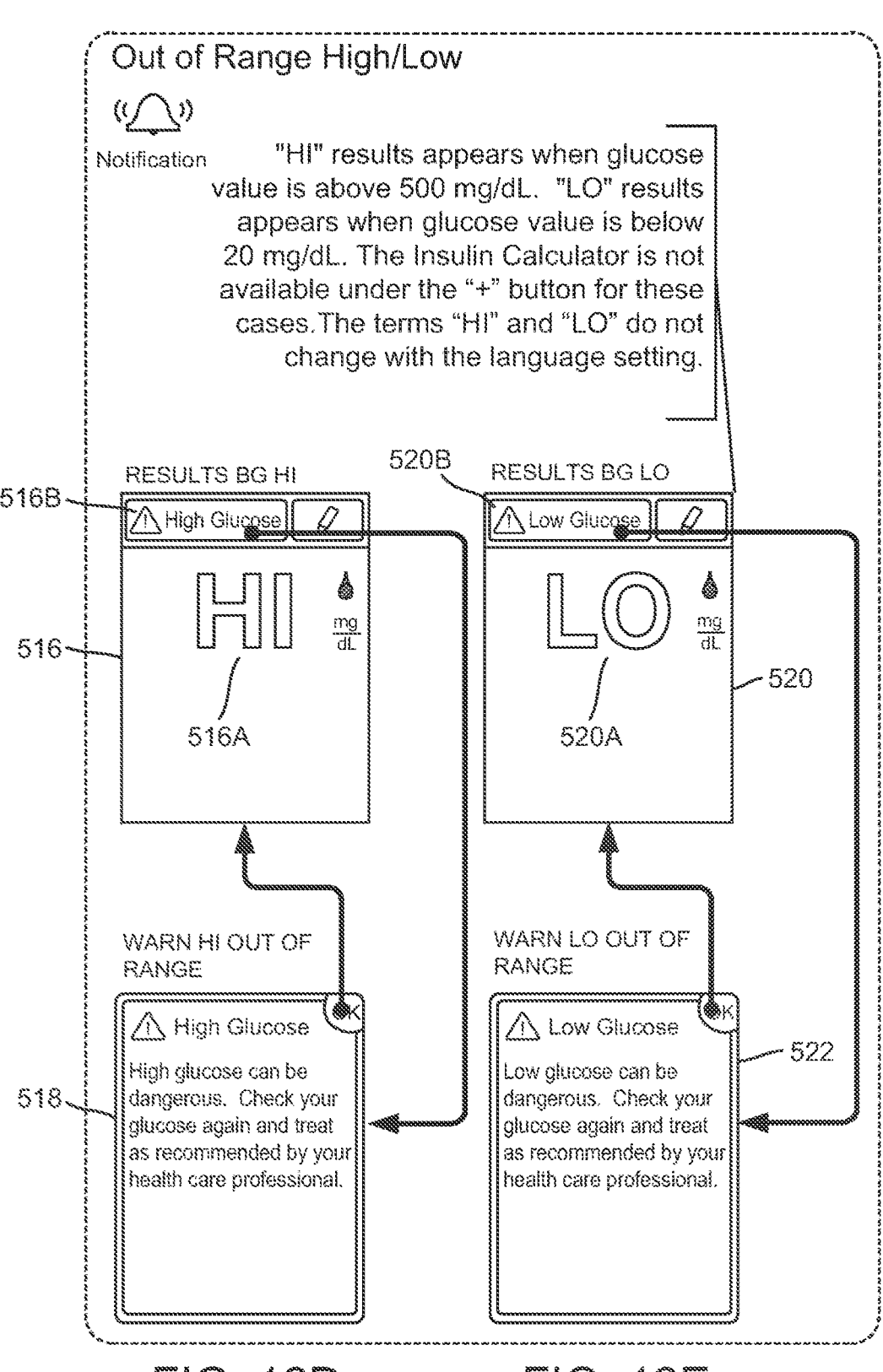
FIG. 12D illustrates an interface for indicating that the measurement reading is out of range, according to one embodiment.
FIG. 12E illustrates an interface for indicating that the measurement reading is out of range, according to one embodiment.

FIG. 12D illustrates an interface for indicating that the measurement reading is out of range, according to one embodiment. The Results BG HI screen 516 is displayed to indicate to the user that the sensor reading is too high and out of range of readings. Instead of a measurement reading being displayed, screen 516 displays an indicator element 516a, such as a message, icon, symbol, etc. For example, in the embodiment shown, the term "HI" 516a is shown in place of a measurement reading to indicate that the reading is out of range and too high.

The predetermined upper threshold reading value may be determined based on a predetermined number (e.g., 500 mg/dL), or may be determined relative to a predetermined "acceptable" range of readings to display (e.g., 20 mg/dL to 500 mg/dL), or with respect to a target range (e.g., 350 mg/dL over the target range), etc.

Screen 516 provides a trigger element 516 for providing additional information, warning, instructions, etc., regarding the out of range and high measurement reading. For example, when the user touches the touch-sensitive button 516*b*, another screen 518 is displayed to provide additional details or information, such as that the glucose level is out of range high, that a high glucose level may be dangerous, and that the user should check again later and treat as recommended by their health care professional. Upon user confirmation (e.g., via selection of the "OK" button) the user is taken back to screen 516.

FIG. 12E illustrates an interface for indicating that the measurement reading is out of range, according to one embodiment. The Results BG LO screen 520 is displayed to indicate to the user that the measurement reading is out of range and too low. Instead of a sensor reading being displayed, screen 520 displays an indicator element 520*q*, such as a message, icon, symbol, etc. For example, in the embodiment shown, the term "LO" 520*a* is shown in place of a measurement reading to indicate that the reading is out of range and too low.

The predetermined lower threshold reading value may be determined based on a predetermined number (e.g., 20 mg/dL), or may be determined relative to a determined "acceptable" range of readings to display (e.g., 20 mg/dL to 500 mg/dL), or with respect to a target range (e.g., 40 mg/dL below the target range), etc.

Screen 520 provides a trigger element 520*a* for providing additional information, warning, instructions, etc., regarding the out of range and low measurement reading. For example, when the user touches the touch-sensitive button 520*b*, another screen 522 is displayed to provide additional details or information, such as that the glucose level is out of range low, that a low glucose level may be dangerous, and that the user should check again later and treat as recommended by their health care professional. Upon user confirmation (e.g., via selection of the "OK" button) the user is taken back to screen 520.

High/Low Glucose Screen

Figures 12F, 12G:
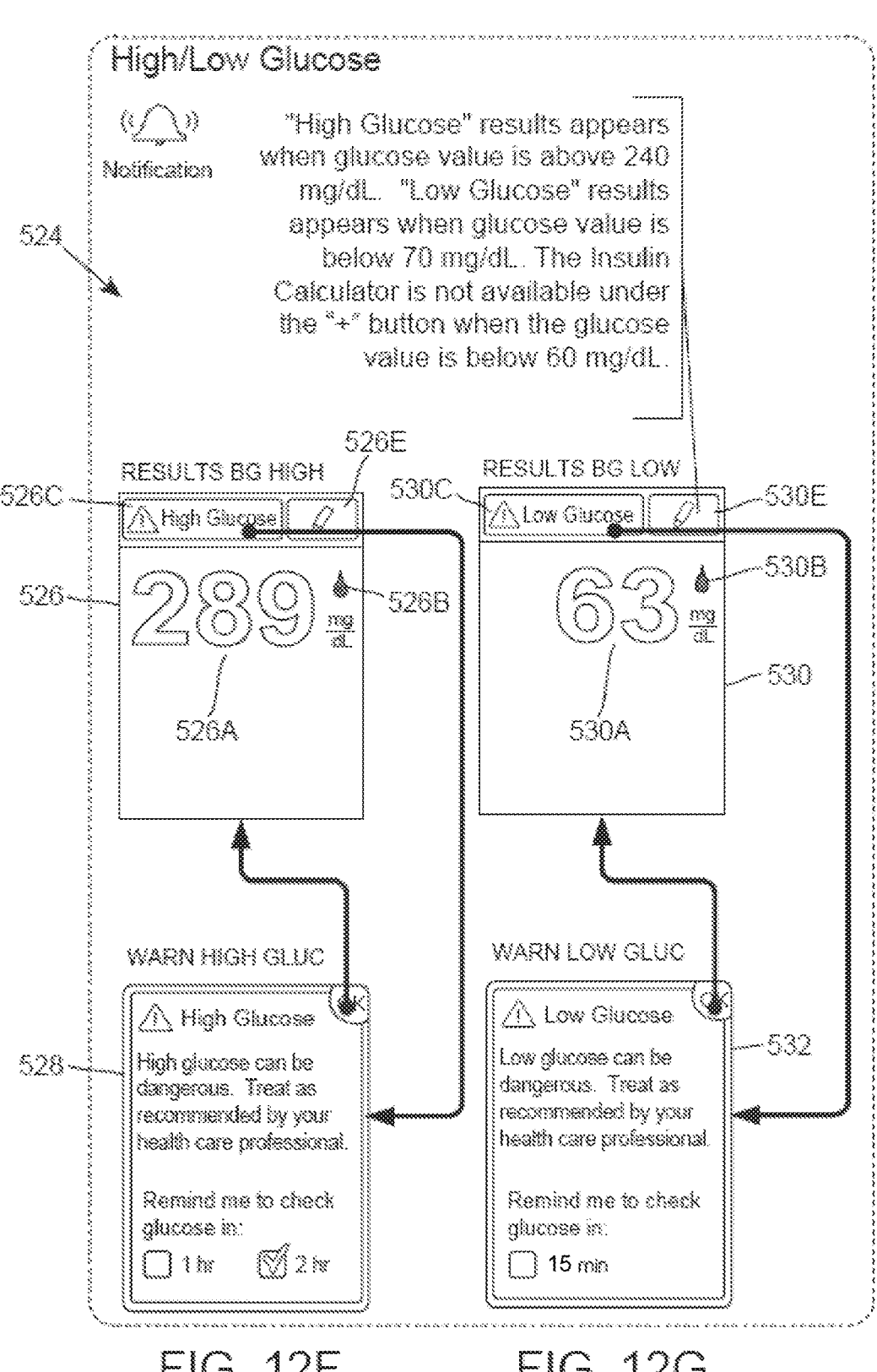
FIG. 12F illustrates an interface for indicating that the measurement reading is high, according to one embodiment.
FIG. 12G illustrates an interface for indicating that the measurement reading is low, according to one embodiment.

FIG. 12F illustrates an interface for indicating that the measurement reading is high, according to one embodiment. The Results BG High screen 526 is displayed to indicate to the user that the measurement reading is a high reading, such as via a message, icon, symbol, trigger element, etc., 526*c*. For example, in the embodiment shown, after a high reading is obtained, screen 526 is displayed and the measurement reading 526*a* is shown. In addition to showing the sensor reading 526*a*, screen 526 includes a trigger element 526*c* for indicating the high reading and for accessing additional information, warning, instructions, recommendations such as recommendation to consider checking ketones, etc., regarding the high measurement reading. For example, when the user touches the touch-sensitive button 422*c*, another screen 528 is displayed to provide additional details or information about the high reading, such as that the glucose level is high, that a high glucose level may be dangerous, and that the user should check again later and treat as recommended by their health care professional. In certain embodiments, the high glucose level screen may include reminder options. When a reminder on the high glucose level screen is selected, the reminder will appear on the reminder list as described below. The device will check if the reminder list is full prior to adding the new reminder. As described below, the reminders are only saved upon navigation back to the home screen from the results screen or when the device times out on the results screen. Upon user confirmation (e.g., via selection of the "OK" button) the user is taken back to screen 526.

The predetermined upper threshold reading value may be determined based on a predetermined number (e.g., 240 mg/dL), or may be determined relative to a predetermined range of readings (e.g., 70 mg/dL to 240 mg/dL), or with respect to a target range (e.g., 120 mg/dL over the target range), etc.

Screen 526 may also include an indicator element (e.g., icon, symbol, etc.) 526*b* that indicates that the measurement reading pertains to a blood glucose strip test. In the embodiment shown, a symbol of a blood drop 526*b* is used. Screen 526 may also include other trigger elements, such as a trigger element 526*e* for initiating the Notes interface.

FIG. 12G illustrates an interface for indicating that the measurement reading is low, according to one embodiment. The Results BG Low screen 530 is displayed to indicate to the user that the measurement reading is a low reading (e.g., with respect to a predetermined "acceptable" reading range), such as via a message, icon, symbol, trigger element, etc., 530*c*. For example, in the embodiment shown, after a low reading is obtained, screen 530 is displayed and the measurement reading 530*a* is shown. In addition to showing the measurement reading 530*a*, screen 530 includes a trigger element 530*c* for indicating the low reading and for accessing additional information, warning, instructions, etc., regarding the low sensor reading. For example, when the user touches the touch-sensitive button 530*c*, another screen 532 is displayed to provide additional details or information about the low reading, such as that the glucose level is low, that a low glucose level may be dangerous, and that the user should check again later and treat as recommended by their health care professional. In certain embodiments, the low glucose level screen may include reminder options. When a reminder on low high glucose level screen is selected, the reminder will appear on the reminder list as described below. As discussed above, in certain embodiments, the reminder times may be configured to be different for high and low glucose results—for example, 15 minutes for low glucose and 1 or 2 hours for high glucose. The device will check if the reminder list is full prior to adding the new reminder. As described below, the reminders are only saved upon navigation back to the home screen from the results screen or when the device times out on the results screen. Upon user confirmation (e.g., via selection of the "OK" button) the user is taken back to screen 530.

The predetermined lower threshold reading value may be determined based on a predetermined number (e.g., 70 mg/dL), or may be determined relative to a predetermined range of readings (e.g., 70 mg/dL to 240 mg/dL), or with respect to a target range (e.g., 10 mg/dL below the target range), etc.

Screen 530 may also include an indicator element (e.g., icon, symbol, etc.) 530*b* that indicates that the measurement reading pertains to a blood glucose strip test. In the embodiment shown, a symbol of a blood drop 530*b* is used. Screen 530 may also include other trigger elements, such as a trigger element 530*e* for initiating the Notes interface.

Masked Mode

When the device is in masked mode, the results of a blood glucose control solution test or blood glucose test strip results may be masked on the display. FIGS. 12H and 12I illustrate display screens for masked results of a blood glucose control solution test and blood glucose test strip results, respectively.

Ketone Test & Results

In some aspects of the present disclosure, a graphical user interface is provided that may be utilized in connection with a reader as described herein and which functions generally to provide perform a ketone strip test measurement and provide test results.

Ketone Strip Test Interface

Figure 13:
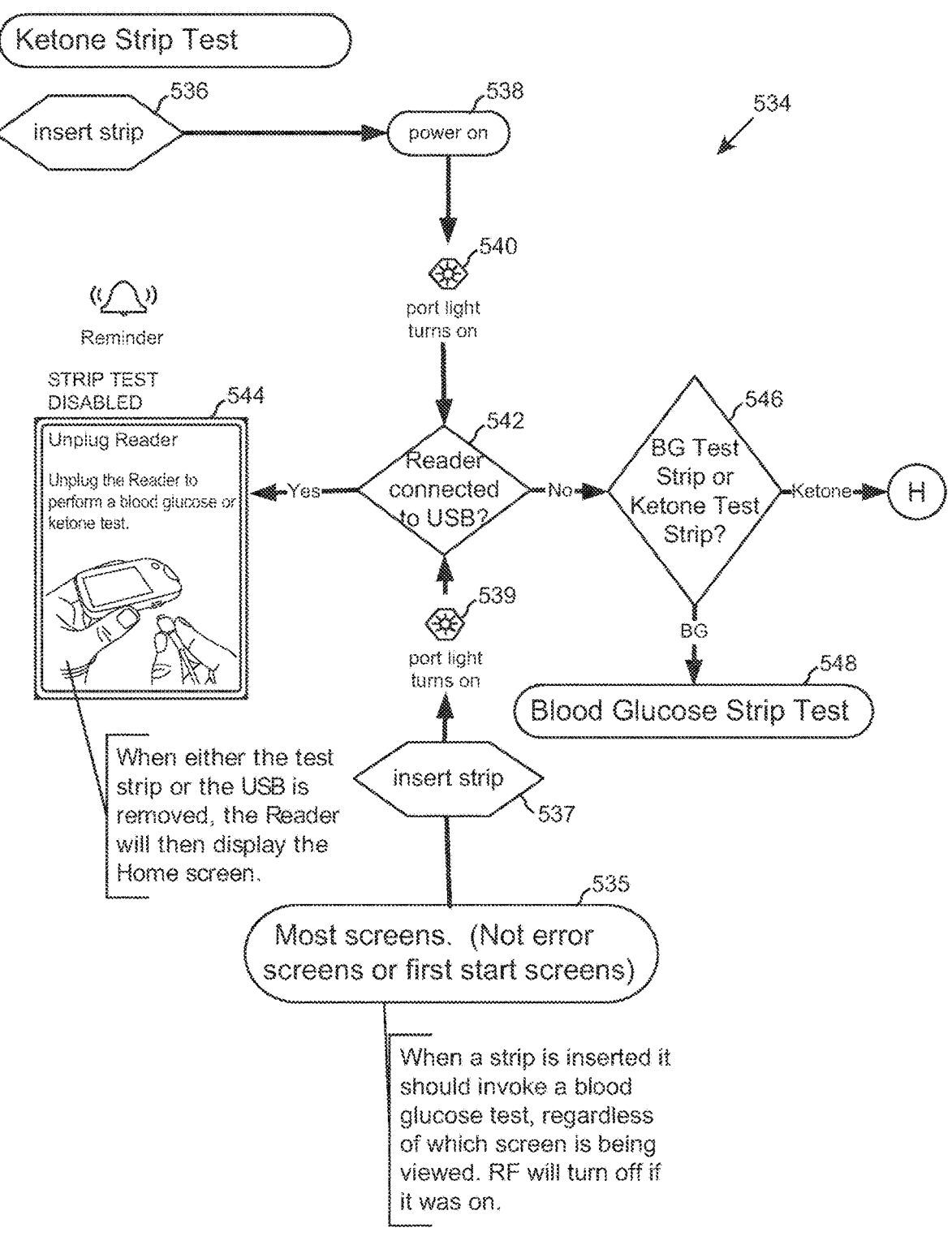
FIG. 13 illustrates an example method for performing a ketone test with a ketone test strip, according to one embodiment.
Figure 13:
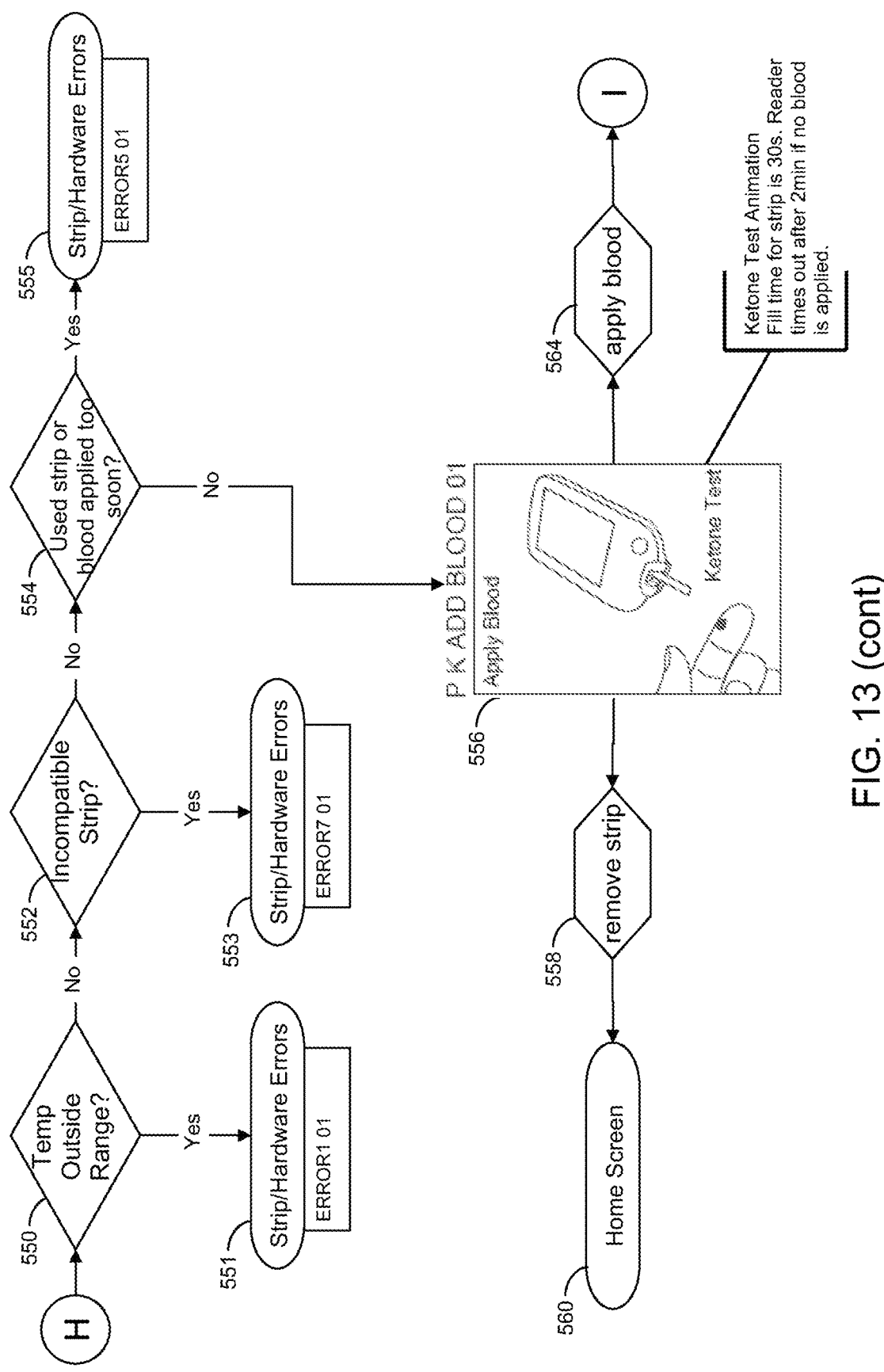
Figure 13:
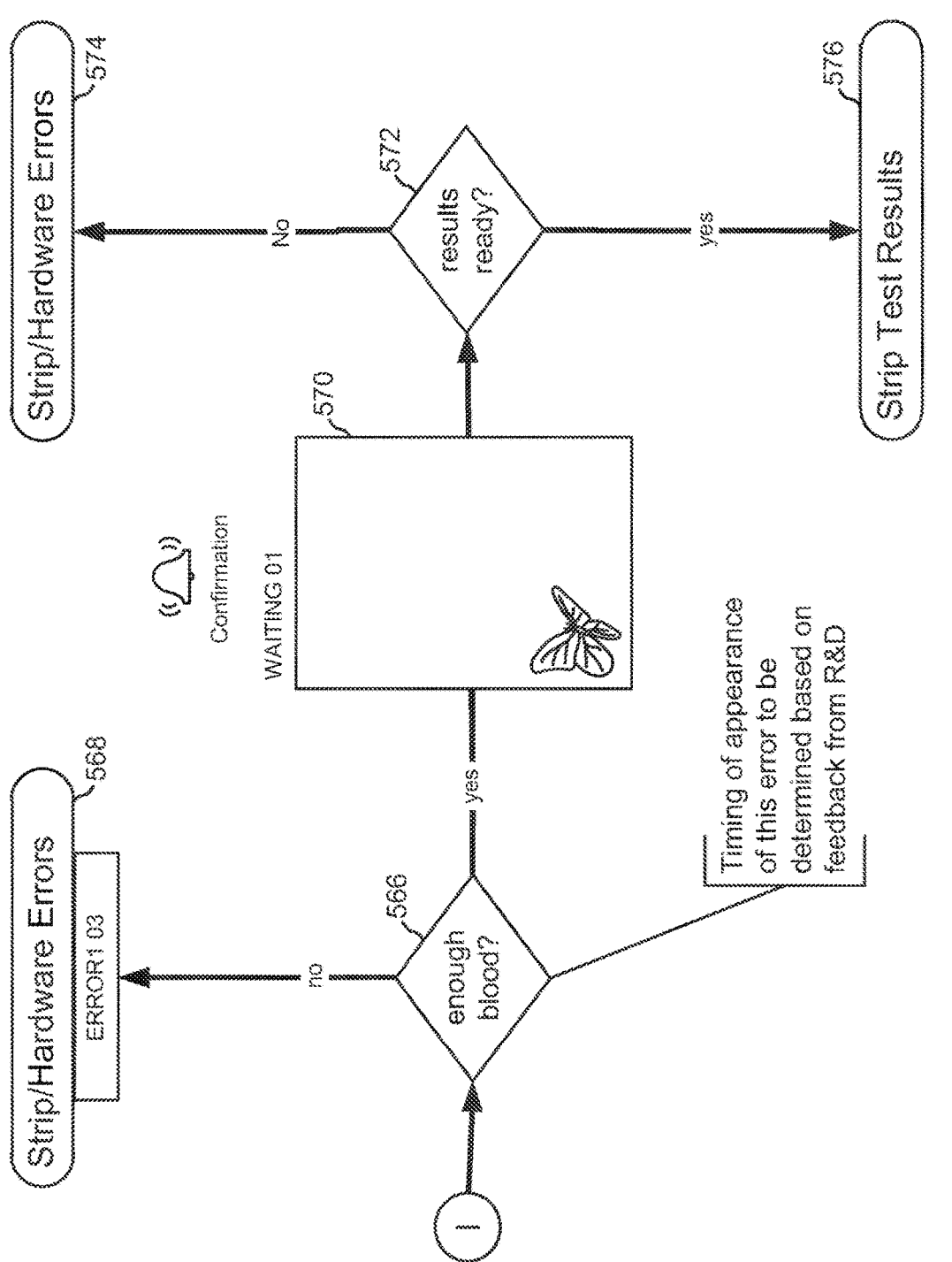

FIG. 13 illustrates an example method 534 for performing a ketone test with a ketone test strip, according to one embodiment. At block 536, a ketone test strip is inserted within an analyte monitoring device that is powered off. Once inserted into the device, the device powers on, as shown at block 538. The strip port light, such as a light emitting diode for example, turns on and provides light to the strip port, as shown at block 540. At block 542, it is determined whether a universal serial bus (USB) connection is established with the device. Again, it should be appreciated that other communication technologies may be implemented in other embodiments—e.g., micro-USB, mini USB, RS-232, Ethernet, Firewire, or other data communication connections. If a USB connection is established, then the strip test is prevented and a Strip Test Disabled screen 544 is displayed to indicate that the strip test is not permitted and that the user should unplug the device to perform a ketone or blood glucose test. If the test strip or the USB connection is removed, then the Reader will display the Home screen.

If at block 542, it is determined that a USB connection is not established, then it is determined if the inserted test strip is a blood glucose test strip or a ketone test strip, as shown at block 546. The test strip may include an identifying element, such as a specific contact configuration, to enable the device to identify what type of test strip it is. If it is determined that the test strip is a blood glucose test strip, then the device initiates the Blood Glucose Strip Test interface to perform a blood glucose test measurement, as shown by block 548. If, on the other hand, the test strip is determined to be a ketone test strip, then it is determined if the device temperature is outside of the device's operating range, as represented by block 550 and reference path H. If it is determined that the temperature is above or below the device's operating range, then the port light is turned off, and a Strip/Hardware Error screen 551 indicating that the operating temperature is too hot or too cold is displayed.

If at block 550, it is determined that the temperature is within the device's operating range, then the strip is checked for errors, including checking the strip for damage or incompatibility, as shown at block 552, or a check to see if blood was applied to the strip too soon or the strip was used, as shown at block 554. If the device determines the strip is damaged, incompatible or already used, the display may navigate to a Strip/Hardware Error screen 553, 555.

If there are no determined strip errors, a P K Add Blood interface 556 is displayed to indicate that blood may be applied to the test strip. If the test strip is removed at this point, as shown by block 558, then the port light turns off and the Home screen is displayed, as represented by block 560. If at screen 556, blood is applied to the test strip, as shown by block 564, then it is determined if there was sufficient blood applied to accurately perform a test measurement, as shown by block 566 and reference path I. It should be appreciated that the timing of this determination may vary. If not enough blood is present, then the Strip/

Hardware Errors interface is displayed to indicate that not enough blood was applied or that there was an error, as shown by block 568.

If it is determined that sufficient blood has been applied to the test strip, then a Waiting interface 570 is displayed while a test measurement is being performed. At block 572, it is determined if the results are ready. If ready, then the Strips Test Results screen 576 is displayed to indicate the resulting reading. If not ready (e.g., after a predetermined timeout period), then the Strip/Hardware Errors screen 574 is displayed to indicate that there was an error in calculating a measurement. In certain embodiments, the device may also perform a low battery test prior to displaying the results as described above in conjunction with FIG. 8.

Ketone Strip Test Results Interface

In some aspects of the present disclosure, a graphical user interface is provided that may be utilized in connection with a reader as described herein and which functions generally to provide ketone strip test results.

Results Screen

FIG. 14A illustrates an example Ketone Results screen 580, according to one embodiment. Screen 580 may be provided, for example, after a ketone test strip measurement has been successfully performed. The example Ketone Results screen 580 is shown to include a ketone test strip measurement 580a and various analyte and device related information, such as indicator elements for indicating the ketone strip test 580b, indicating the current time 580d, indicating the battery life 580e, etc. In one embodiment, the indicator element 580b for identifying the ketone test strip measurement is the same symbol as the indicator element for a blood glucose test strip measurement. In such case, the indicator element 580b is generally indicating a test strip measurement result versus a sensor reading result. It should be appreciated that in other embodiments, different indicator elements may be used for the ketone strip test and the blood glucose strip test to distinguish between the two tests.

A trigger element 580c for navigating to the Notes interface is also provided to take the user to the Notes screen as shown by block 582. It should be appreciated that other combinations of these, and other, features and trigger elements may be included in other embodiments.

In one embodiment, the insulin calculator is enabled if the setting is enabled and if both of the following are met: 1) the ketone test has been performed within a predetermined period of time (e.g., 15 minutes) of successful strip test or another predetermined period of time (e.g., 3 minutes) of a successful sensor test; and 2) insulin was not logged with that recent glucose test. Unless both conditions are met, the insulin calculator button is not provided.

Control Solution Screen

FIG. 14B illustrates an example interface for indicating the results of a ketone control solution test, according to one embodiment. The Ketone Control Solution Results screen 584 includes the results 584a of a ketone control solution test and various analyte and device related information, such as indicator elements for indicating a control solution test 584b, indicating the current time 584d, indicating the battery life 584e, etc. In one embodiment, the indicator element 584b for identifying the ketone control solution test is the same symbol as the indicator element for a blood glucose control solution test. In such case, the indicator element 584b is generally indicating a control solution test. It should be appreciated that in other embodiments, different indicator elements may be used for the ketone control solution test and the blood glucose control solution test to distinguish between the two tests.

Reader Temperature Warning (Too Hot/Too Cold) Screen

Figure 14C:
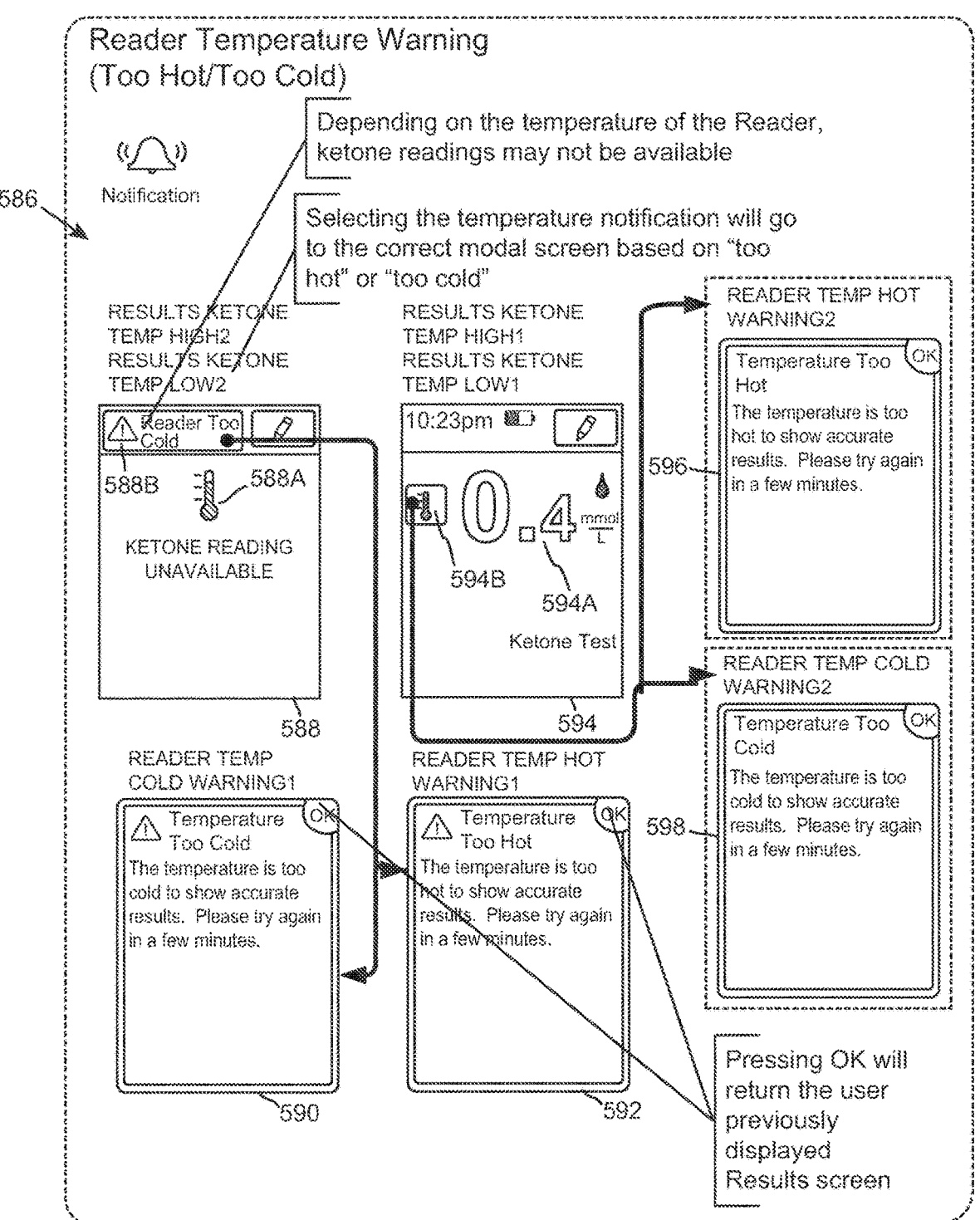
FIG. 14C illustrates example interfaces for indicating that the analyte monitoring device's temperature is too high or too low, according to one embodiment.

FIG. 14C illustrates example interfaces for indicating that the analyte monitoring device's temperature is too high or too low, according to one embodiment. Results Ketone Temp High2/Low2 screen 588 is displayed to indicate to the user that the device temperature is either too high or too low to provide a ketone reading, such as with respect to a predetermined "safe" range of temperatures to perform an accurate ketone test measurement. For example, screen 588 may have a warning message and/or icon 588a indicating too high or too low of a temperature and may further indicate that a ketone reading is not available, as shown. Screen 588 provides a trigger element 588b for providing additional information regarding the too high or too low device temperature. For example, when the user touches the touch-sensitive button 588b, another screen 590 or 592 is displayed to provide additional details or information, such as that the device temperature is too low or too high, respectively, and that the user should try again later.

Results Ketone Temp High1/Low1 screen 594 is an example interface that is displayed when a ketone test measurement is available, but also indicates to the user that the device temperature is either high or low, such as with respect to a predetermined "safe" range of temperatures. For example, screen 594 displays the resulting test measurement 594a and also displays a warning message and/or icon 594b indicating a high or low device temperature. Icon 502b also serves as a trigger element for providing additional information regarding the high or low device temperature. For example, when the user touches the touch-sensitive button 502b, another screen 598 or 596 is displayed to provide additional details or information, such as that the device temperature is too low or too high, respectively, and that the user should try again later.

Out of Range High Screen

Figure 14D:
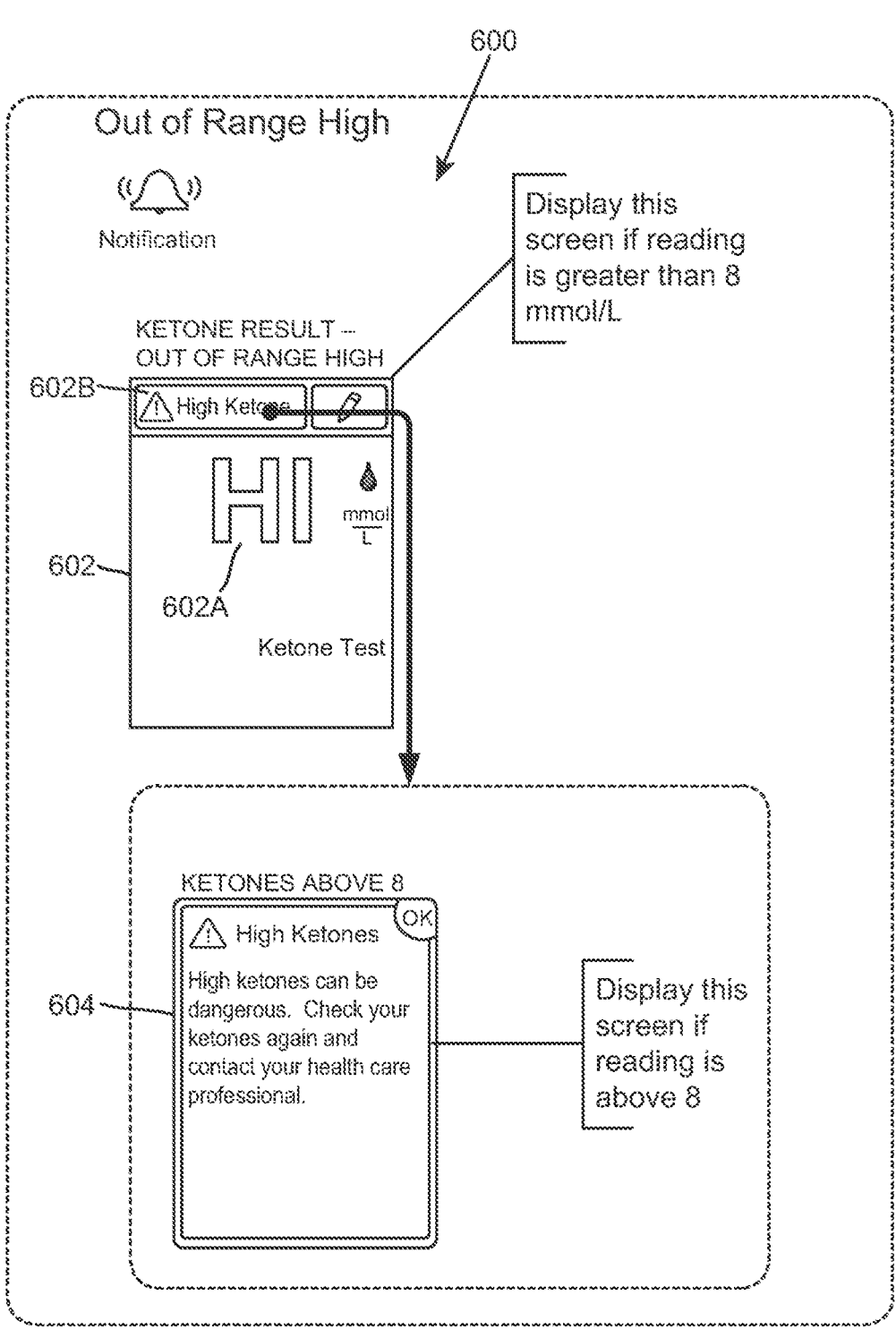
FIG. 14D illustrates an interface for indicating that the measurement reading is out of range, according to one embodiment.

FIG. 14D illustrates an interface for indicating that the measurement reading is out of range, according to one embodiment. The Ketone Results Out of Range High screen 602 is displayed to indicate to the user that the ketone measurement reading is too high and out of range of readings. Instead of a ketone measurement reading being displayed, screen 602 displays an indicator element 602a, such as a message, icon, symbol, etc. For example, in the embodiment shown, the term "HI" 602a is shown in place of a measurement reading to indicate that the reading is out of range and too high.

The predetermined upper threshold reading value may be determined based on a predetermined number, or may be determined relative to a predetermined "acceptable" range of readings to display, or with respect to a target range, etc.

Screen 602 provides a trigger element 602b for providing additional information, warning, instructions, etc., regarding the out of range and high ketone measurement reading. For example, when the user touches the touch-sensitive button 602b, another screen 604 is displayed to provide additional details or information, such as that the ketone level is out of range high, that a high ketone level may be dangerous, and that the user should check again later and treat as recommended by their health care professional. Upon user confirmation (e.g., via selection of the "OK" button) the user is taken back to screen 602.

High Ketones Screen

Figure 14E:
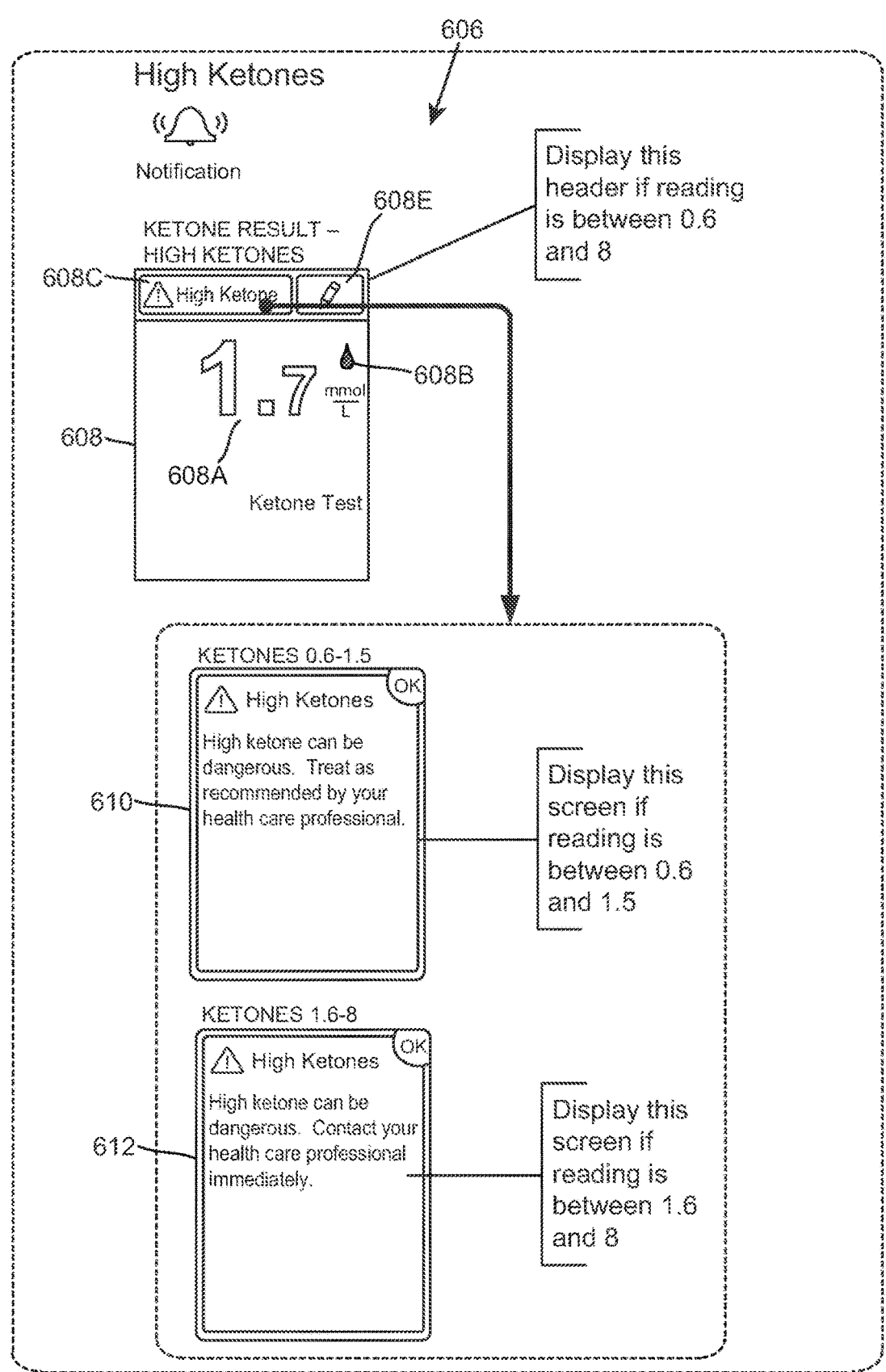
FIG. 14E illustrates an interface for indicating that the ketone measurement reading is high, according to one embodiment.

FIG. 14E illustrates an interface for indicating that the ketone measurement reading is high, according to one embodiment. The Ketone Result—High Ketones screen 608 is displayed to indicate to the user that the ketone measurement reading is a high reading, such as via a message, icon, symbol, trigger element, etc., 608c.

The predetermined upper threshold reading value may be determined based on a predetermined number, or may be determined relative to a predetermined range of readings, or with respect to a target range, etc.

In the embodiment shown, after a high ketone reading is obtained, screen 608 is displayed and the measurement reading 608a is shown. In addition to showing the sensor reading 608a, screen 608 includes a trigger element 608c for indicating the high ketone reading and for accessing additional information, warning, instructions, etc., regarding the high measurement reading. For example, when the user touches the touch-sensitive button 608c, another screen 610 or 612 is displayed to provide additional details or information about the high reading, such as that the ketone level is high, that a high ketone level may be dangerous, and that the user should check again later and treat as recommended by their health care professional. In the embodiment shown, screen 610 is displayed if the ketone reading is between a predetermined range (e.g., 0.6 to 1.5) and the second screen 612 is displayed if the ketone reading is between a high predetermined range (e.g., 1.6 to 8).

Screen 608 may also include an indicator element (e.g., icon, symbol, etc.) 608b that indicates that the measurement reading pertains to a strip test measurement (e.g., ketone test strip measurement). In the embodiment shown, a symbol of a blood drop 608b is used. Screen 608 may also include other trigger elements, such as a trigger element 608e for initiating the Notes interface.

Masked Mode

Figures 14F, 14G:
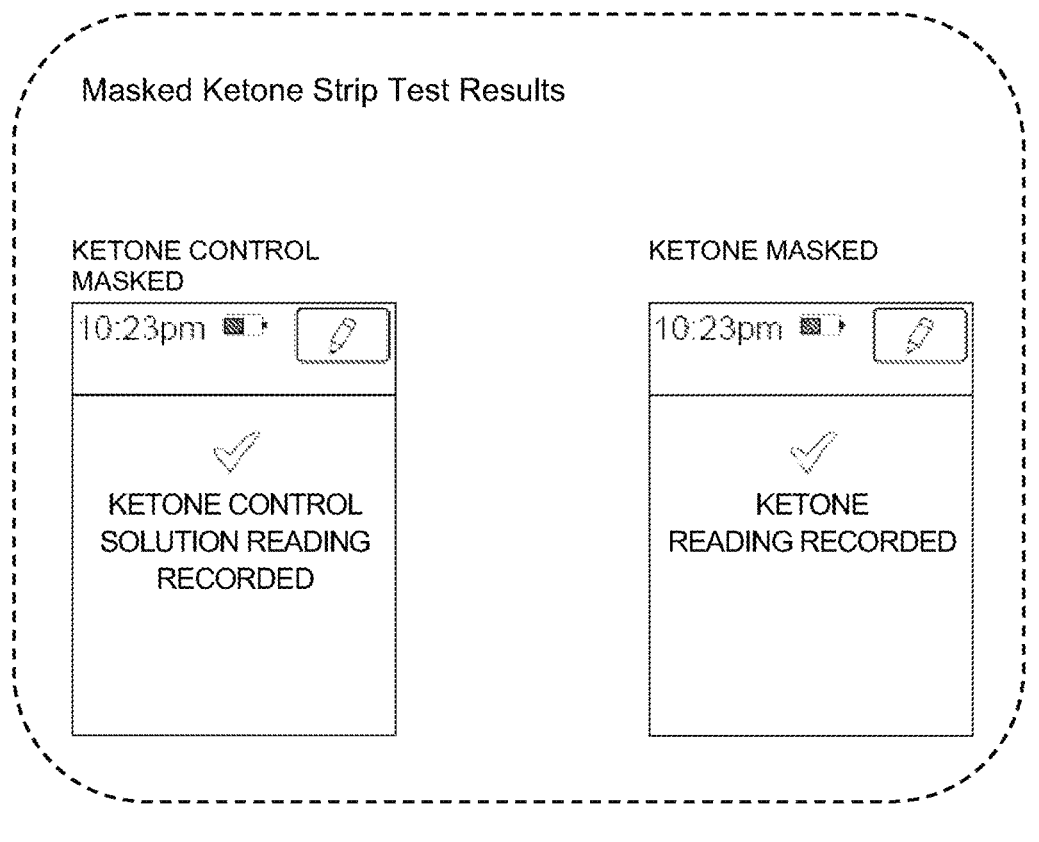
FIGS. 14F and 14G illustrate display screens for masked results of a Ketone control solution test and Ketone test strip results, respectively, according to one embodiment.

When the device is in masked mode, the results of a Ketone control solution test or Ketone test strip results may be masked on the display. FIGS. 14F and 14G illustrate display screens for masked results of a Ketone control solution test and Ketone test strip results, respectively.

Notes Interface

An exemplary embodiment of a graphical user interface which may be utilized in connection with a Reader as described herein and which facilitates a Notes procedure 3000 for entering notes into the logbook is provided. This graphical user interface is now described in greater detail with reference to FIG. 15.

A graphical user interface which facilitates the Notes procedure 3000 of the reader may include two different notes interfaces; a first notes interface for embodiments where the insulin calculator is disabled 3002, and a second notes interface for embodiments where the insulin calculator is enabled 3004. The Note (Insulin Calculator Disabled) Interface 3002, shown in FIG. 15A, begins with the display of an "Add to Logbook" screen 3006. This "Add to Logbook" screen 3006 includes a list of several different notes that may be entered into the Logbook. The list of user selectable notes may include default (e.g., preset notes) and, in some instances, custom (e.g., user-defined) notes. For example, the default notes may include one or more of the following: rapid-acting insulin 3008, long-acting insulin 3010, food 3012, exercise 3014, and medication 3016. The custom notes may include any notes generated by the user through the associated informatics software. In some cases, 12 notes may be included in the list of user-selectable notes. For example, 5 default notes and 7 custom notes may be included. In certain embodiments, 4 user-selectable notes are displayed on the touchscreen at once. If there are more than 4 user-selectable notes, the list of notes may be scrolled as necessary to view the list using scroll touchscreen buttons, such as down arrow (e.g., down triangle) touchscreen button 3018 and up arrow (e.g., up triangle) touchscreen button 3020. One or more user-selectable notes may be selected by touching the touchscreen checkbox adjacent the note desired to be selected. Touching a touchscreen checkbox will toggle the checkbox from a checked to unchecked state indicating whether the associated not is selected or not selected, respectively. For instance, the rapid-acting insulin note may be selected by touching the touchscreen checkbox 3022, which then displays a check mark in the touchscreen checkbox to indicate that the rapid-acting insulin note has been selected. The other user-selectable notes may be selected or unselected (e.g., checked or unchecked) as desired in an analogous manner.

The selection of notes may be saved by touching the "OK" touchscreen button 3024, which saves the selection of user-selectable notes and returns the graphical user interface to the previous screen. If the "OK" touchscreen button 3024 is pressed without changing the selection of user-selectable notes, then the previous selection of user-selectable notes is retained and saved.

In some embodiments, the amount of rapid-acting insulin, long-acting insulin, food, exercise, and medication may be entered by touching the numerical input touchscreen button (e.g., the "1 2 3" touchscreen button) associated with the desired selection. In some cases, the numerical input touchscreen button may not be displayed if the corresponding touchscreen checkbox is not checked, and may only be displayed if the corresponding touchscreen checkbox is checked. For example, when rapid-acting insulin checkbox 3008 is unchecked, the numerical input touchscreen button 3026 for rapid-acting insulin is not displayed. When the rapid-acting insulin checkbox is checked 3022, the numerical input touchscreen button 3026 for rapid-acting insulin is displayed and may be selected.

The amount of rapid-acting insulin may be entered by pressing the numerical input touchscreen button 3026 associated with the rapid-acting insulin note selection. Pressing the numerical input touchscreen button 3026 for rapid-acting insulin will cause a numerical input screen 3028 for rapid acting insulin (e.g., the "Enter Rapid-Acting Insulin" screen) to be displayed, as shown by reference path (J) (see FIG. 15B). In the numerical input screen 3028 for rapid-acting insulin, the amount (e.g., units) of rapid-acting insulin may be entered. The numerical input screen initially displays no value (e.g., "--" is displayed in place of any numbers), however, the amount of rapid-acting insulin may be adjusted by pressing the up arrow 3030 (e.g., "+") touchscreen button or the down arrow 3032 (e.g., "−") touchscreen button to increase or decrease, respectively, the amount of rapid-acting insulin as desired. For example, the amount of rapid-acting insulin 3034 may be adjusted by 1 unit increments by tapping the up arrow 3030 or the down arrow 3032. In some embodiments, the amount increases or decreases as appropriate at a slow-rate for the first 2 seconds and at a faster rate after 2 seconds when the up or down arrow is pressed and held. Once the desired amount of rapid-acting insulin is entered, the amount may be saved by pressing the "OK" touchscreen button 3036, which saves the entered amount of rapid-acting insulin and then returns the graphical user interface to the "Add to Logbook" screen 3006, as shown by reference path (J). Numerical values for long-acting insulin may be entered in an analogous manner by pressing the numerical input touchscreen button 3038 (e.g., the "1 2 3" touchscreen button) associated with the long-acting insulin selection on the "Add to Logbook" screen 3006.

Numerical values for food may be entered by pressing the numerical input touchscreen button 3040 (e.g., the "1 2 3" touchscreen button) associated with the food selection on the "Add to Logbook" screen 3006. Pressing the numerical input touchscreen button 3040 for food will cause a numerical input screen 3042 for carbohydrates to be displayed (e.g., the "Enter Carbs" screen), as shown by reference path (J) (see FIG. 15C). In the numerical input screen 3042 for food, the amount (e.g., grams) of carbs may be entered. The numerical input screen initially displays no value (e.g., "--" is displayed in place of any numbers), however, the amount of carbs may be adjusted by pressing the up arrow 3044 (e.g., "+") touchscreen button or the down arrow 3046 (e.g., "−") touchscreen button to increase or decrease, respectively, the amount of carbs as desired. For example, the amount of carbs 3048 may be adjusted by 1 gram increments by tapping the up arrow 3044 or the down arrow 3046. In some embodiments, the amount increases or decreases as appropriate at a slow-rate for the first 2 seconds and at a faster rate after 2 seconds when the up or down arrow is pressed and held. Once the desired amount of carbs is entered, the amount may be saved by pressing the "OK" touchscreen button 3050, which saves the entered amount of carbs and then returns the graphical user interface to the "Add to Logbook" screen 3006, as shown by reference path (J).

Figure 15A:
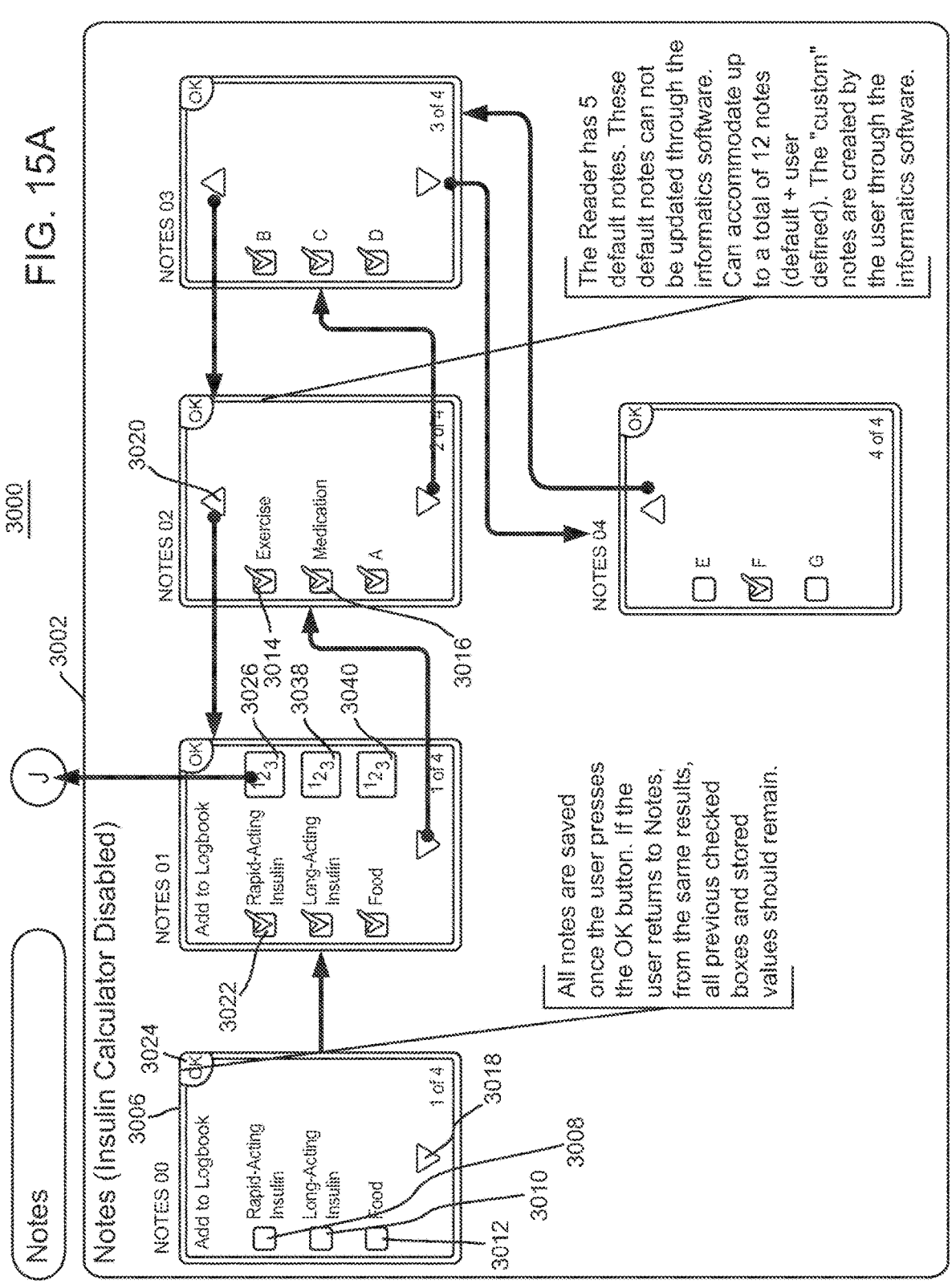
FIGS. 15A-15E illustrate a Notes Interface for entering notes on a Reader, according to embodiments of the present disclosure.
Figures 15B, 15C:
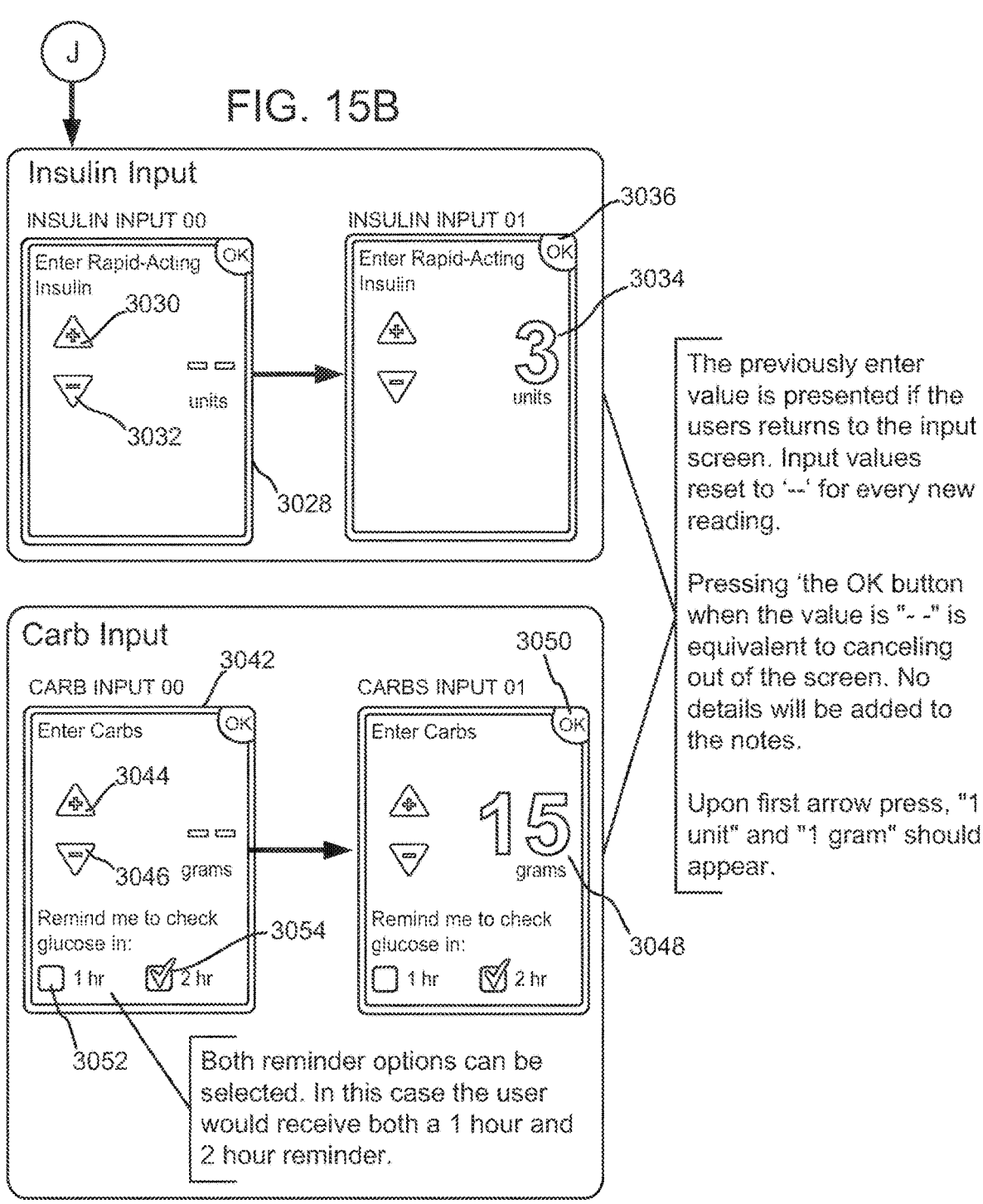
Figure 15D:
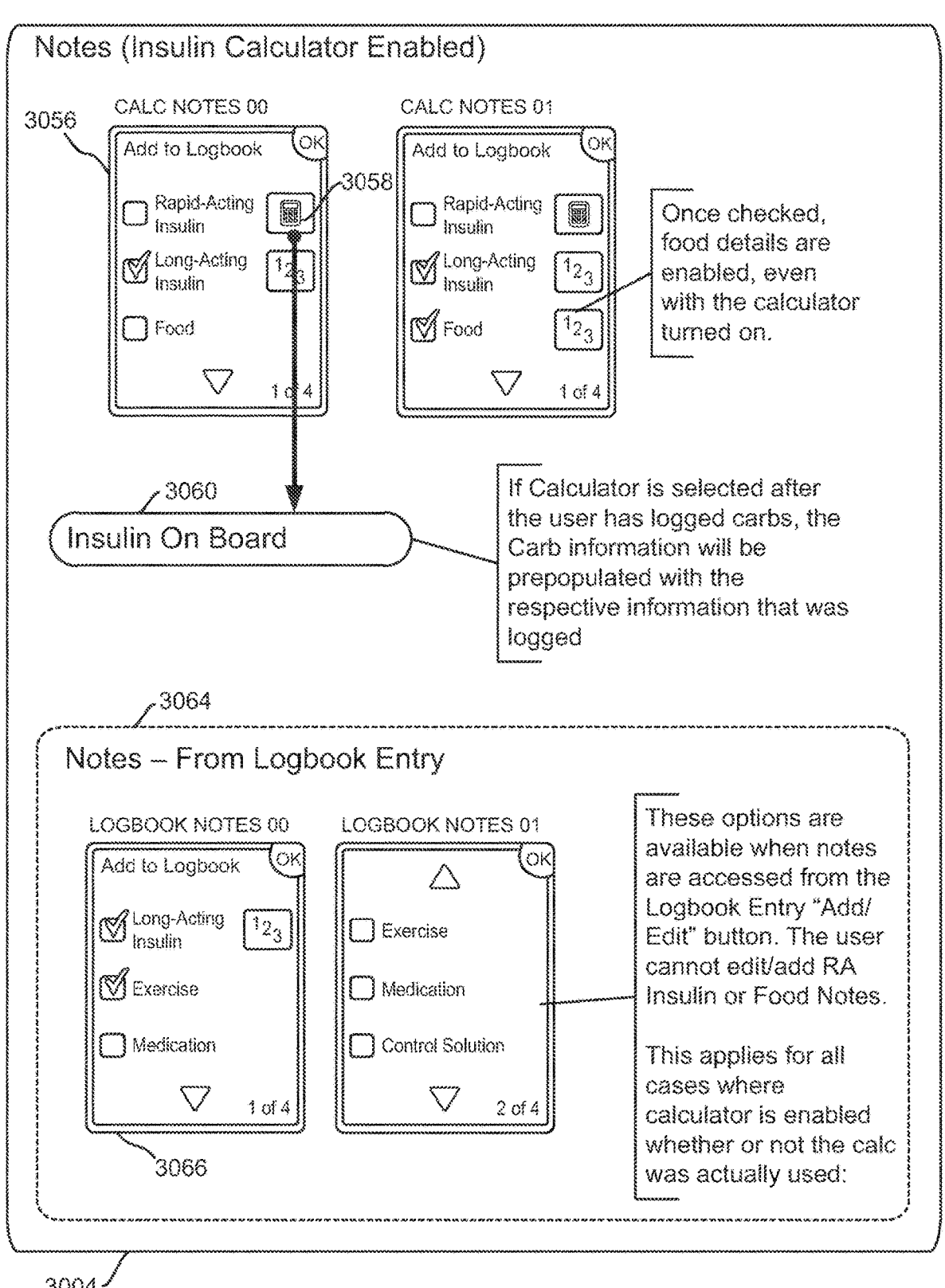
Figure 15E:
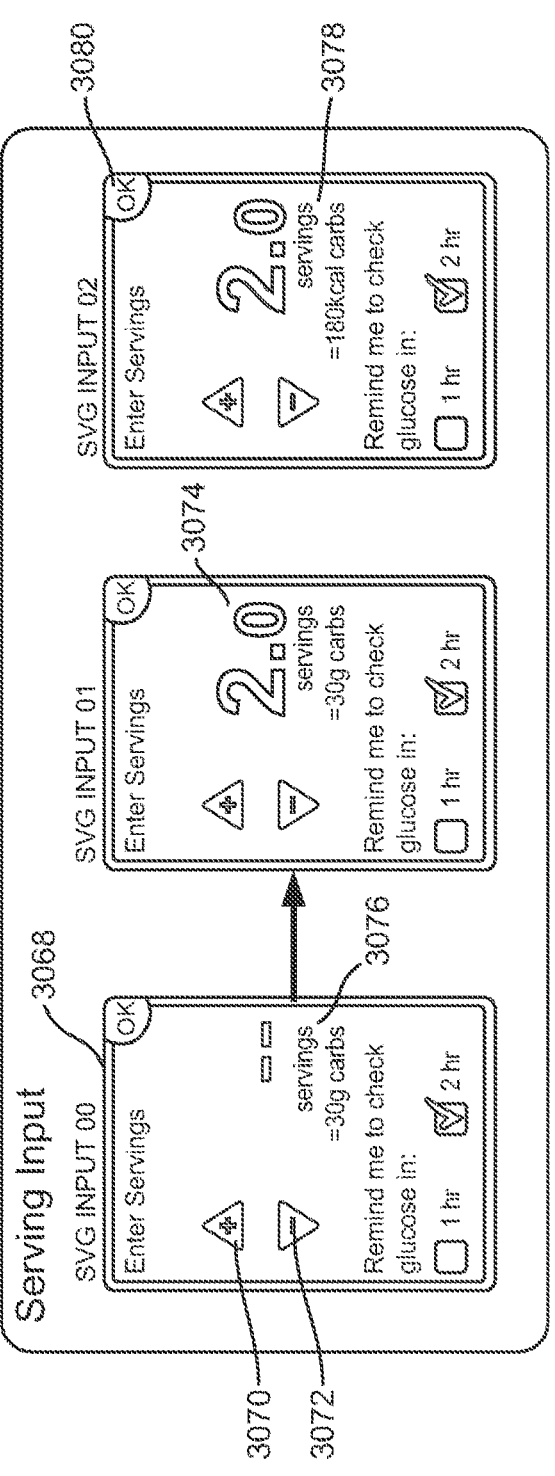

In certain embodiments, instead of entering the amount of food as grams of carbs, the amount of food may be entered as servings of carbs, as shown in FIG. 15E. In the numerical input screen 3068 for servings of carbs, the screen initially displays no value (e.g., "--" is displayed in place of any numbers), however, the servings of carbs may be adjusted by pressing the up arrow 3070 (e.g., "+") touchscreen button or the down arrow 3072 (e.g., "−") touchscreen button to increase or decrease, respectively, the servings of carbs as desired. For example, the servings of carbs 3074 may be adjusted by 0.5 serving increments by tapping the up arrow 3070 or the down arrow 3072. In some embodiments, the amount increases or decreases as appropriate at a slow-rate for the first 2 seconds and at a faster rate after 2 seconds when the up or down arrow is pressed and held. In some cases, the numerical input screen 3068 for servings of carbs may include a display of the grams of carbs 3076 that corresponds to the number of servings entered. In some cases, the numerical input screen 3068 for servings of carbs may include a display of the energy (e.g., kcal) of carbs 3078 that corresponds to the number of servings entered. Once the desired servings of carbs is entered, the value may be saved by pressing the "OK" touchscreen button 3080, which saves the entered servings of carbs and then returns the graphical user interface to the "Add to Logbook" screen 3006.

Referring back to the numerical input screen 3042 for the amount (e.g., grams) of carbs (see FIG. 15C), the numerical input screen 3042 also includes two touchscreen checkboxes configured to allow the selection of reminders to check a user's glucose. For example, the numerical input screen 3042 includes a "1 hr" touchscreen checkbox 3052 and a "2 hr" touchscreen checkbox 3054. None, one or both of the touchscreen checkboxes may be selected as desired. Pressing the "1 hr" touchscreen checkbox 3052 will display a check mark in the "1 hr" touchscreen checkbox 3052 indicating that the "1 hr" touchscreen checkbox 3052 has been selected and will set the Reader to alert the user to check the user's glucose level after 1 hour. Pressing the "2 hr" touchscreen checkbox 3054 will display a check mark in the "2 hr" touchscreen checkbox 3054 indicating that the "2 hr" touchscreen checkbox 3054 has been selected and will set the Reader to alert the user to check the user's glucose level after 2 hours. The check glucose reminder checkboxes may also be displayed on the numerical input screen 3068 for entering the servings of carbs as described above (see FIG. 15E).

As indicated above, a second notes interface may be provided for embodiments where the insulin calculator is enabled 3004. The Note (Insulin Calculator Enabled) Interface 3004, shown in FIG. 15D, begins with the display of an "Add to Logbook" screen 3056. This "Add to Logbook" screen 3056 includes a list of several different notes that may be entered into the Logbook, similar to the "Add to Logbook" screen 3006 in the Note (Insulin Calculator Disabled) Interface 3002 described above. In the "Add to Logbook" screen 3056 of the Note (Insulin Calculator Enabled) Interface 3004, the user-selectable notes (e.g., default and custom notes) may be selected (e.g., checked) or unselected (e.g., unchecked) as desired in an analogous manner as described above in relation to the Note (Insulin Calculator Disabled) Interface 3002. In addition, the numerical input touchscreen buttons (e.g., the "1 2 3" touchscreen buttons) of the Note (Insulin Calculator Enabled) Interface 3004 function in an analogous manner as described above in relation to the Note (Insulin Calculator Disabled) Interface 3002.

In the Note (Insulin Calculator Enabled) Interface 3004, the insulin on board and rapid-acting insulin calculator features of the graphical user interface are enabled. For instance, in the Note (Insulin Calculator Enabled) Interface 3004, rather than displaying a numerical input touchscreen button for rapid-acting insulin, a calculator touchscreen button 3058 is displayed with the rapid-acting insulin selection. Pressing the calculator touchscreen button 3058 will cause the graphical user interface to display the Insulin on Board Interface 3060 (see FIG. 16) and the Insulin Calculator Interface 3062 (see FIG. 17). In some embodiments, if food information (e.g., amount of carbs) is entered as described above, then when the calculator touchscreen button 3058 is pressed, the amount of carbs that was previously entered will automatically be displayed in the corresponding insulin on board and calculator interface screens.

In certain embodiments, the Notes—From Logbook Entry Interface 3064 may be displayed from the Logbook Entry screen if the "add or edit notes" touchscreen button is pressed. The Notes—From Logbook Entry Interface 3064 begins with the display of an "Add to Logbook" screen 3066. This "Add to Logbook" screen 3066 includes a list of several different user-selectable notes that may be entered into the Logbook, similar to user-selectable notes described above. In certain embodiments, the "Add to Logbook" screen 3066 of the Notes—From Logbook Entry Interface 3064 does not include a user-selectable note for rapid-acting insulin or food. The other default notes (e.g., long-acting insulin, exercise, medication) and custom notes may still be available for selection by the user as desired.

Insulin on Board Interface

As described above, pressing the calculator touchscreen button 3058 from the "Add to Logbook" screen 3056 of the Notes (Insulin Calculator Enabled) Interface 3004, will cause the graphical user interface to display the Insulin on Board Interface 3060 (see FIG. 16). Regarding FIG. 16A, in certain embodiments, a user's insulin on board (IOB) information is used in the calculation of a recommended rapid-acting insulin dosage amount. For example, if an insulin dosage has been logged (e.g., logged as a calculated dose, or entered into the logbook as a rapid-acting dose), then the insulin dosage information may be used in the calculation of a recommended rapid-acting insulin dosage amount 3082.

In certain embodiments, a user's insulin on board information is used in the calculation of a recommended rapid-acting insulin dosage amount if the user's most recent insulin dose was administered within a certain time period. In some instances, the insulin calculator may be partially locked out if the difference between the current time and the time the most recent rapid-acting insulin was administered is less than a lock out time period (e.g., the most recent insulin dose was administered within a preceding lockout time period, such as within the past 2 hours). During the lockout time period, the insulin calculator may be programmed to only calculate a meal bolus and may not calculate an additional correction bolus 3084. During the lockout time period, the insulin calculator may not include insulin on board into the calculation of a meal bolus.

If the difference between the current time and the time the most recent insulin bolus was administered is greater than a threshold time period (e.g., the lockout time period) and less than the duration of insulin action, then the insulin calculator may be programmed to include the user's IOB into the calculation of the recommended rapid-acting insulin dosage amount 3086. In the time period between the end of the lockout time period and the end of the user's duration of insulin action, the insulin calculator may be programmed to determine the recommended rapid-acting insulin dosage amount based on the determined analyte concentration and the insulin on board information. For instance, in the time period between the end of the lockout time period and the end of the user's duration of insulin action, the insulin calculator may be programmed to subtract the user's IOB from the rapid-acting insulin dosage based upon the current glucose concentration level to determine the recommended rapid-acting insulin dosage amount.

In certain instances, if the difference between the current time and the time the most recent insulin bolus was administered is greater than the user's duration of insulin action, then the insulin calculator will not include insulin on board into the calculation of a recommended rapid-acting insulin dosage amount 3088. In the time period after the user's duration of insulin action has expired (and before the next dose of insulin is administered), the insulin calculator may assume the user's insulin on board is zero. In the time period after the user's duration of insulin action has expired (and before the next dose of insulin is administered), the insulin calculator may be programmed to determine the rapid-acting insulin dosage amount based on the determined glucose concentration (without including the insulin on board information).

Figure 16B:
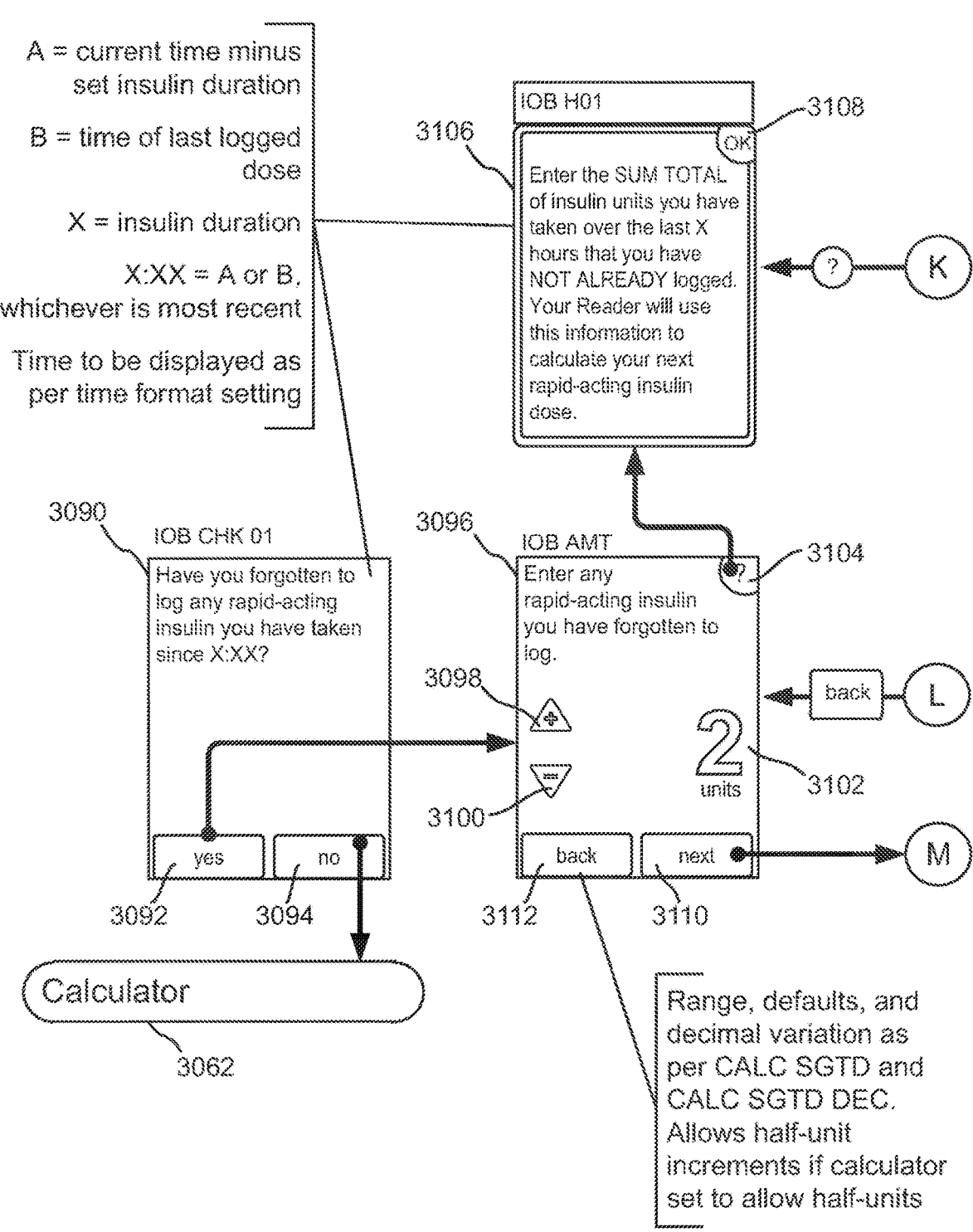

Regarding FIG. 16B, the Insulin on Board Interface is shown, and begins with a prompt screen 3090 prompting the user with a question asking if the user has forgotten to log any rapid-acting insulin the user has taken since a prior predetermined time point. The prior predetermined time point corresponds to the most recent of either: (a) the current time minus the set insulin duration of action, or (b) the time of the last logged dose of rapid-acting insulin. The prompt screen 3090 has a "Yes" touchscreen button 3092 and a "No" touchscreen button 3094 to select a yes or no answer to the prompted question. If the "No" touchscreen button 3094 is pressed, then the graphical user interface displays the Insulin Calculator Interface 3062 (see FIG. 17). If the "Yes" touchscreen button is pressed, then the graphical user interface displays a numerical input screen 3096 in the Insulin on Board Interface. On the numerical input screen 3096, the amount of rapid-acting insulin that the user has forgotten to log since the prior predetermined time point may be entered. The amount (e.g., units) of rapid-acting insulin may be adjusted by pressing the up arrow 3098 (e.g., "+") touch-screen button or the down arrow 3100 (e.g., "−") touchscreen button to increase or decrease, respectively, the amount of rapid acting insulin as desired. For example, the amount of rapid acting insulin 3102 may be adjusted by 1 unit increments by tapping the up arrow 3098 or the down arrow 3100. In some embodiments, the amount of rapid-acting insulin may be adjusted by 0.5 unit increments (not shown) if the calculator is set to allow half-unit increments. In some embodiments, the amount increases or decreases as appropriate at a slow-rate for the first 2 seconds and at a faster rate after 2 seconds when the up or down arrow is pressed and held. Numerical input screen may also include a "?" touchscreen button 3104, which, when pressed, provides a help screen 3106 that includes additional instructions to the user. For example, the help screen 3106 may instruct the user to enter the sum total of insulin units that the user has taken over the last X hours that the user has not already logged, where X is the insulin duration of action time. The help screen 3106 may also inform the user that the Reader will use the entered amount of rapid-acting insulin to calculate the user's next rapid-acting insulin dose. The help screen 3106 includes an "OK" touchscreen button 3108, which, when pressed, returns the display to the numerical input screen 3096.

Figure 16C:
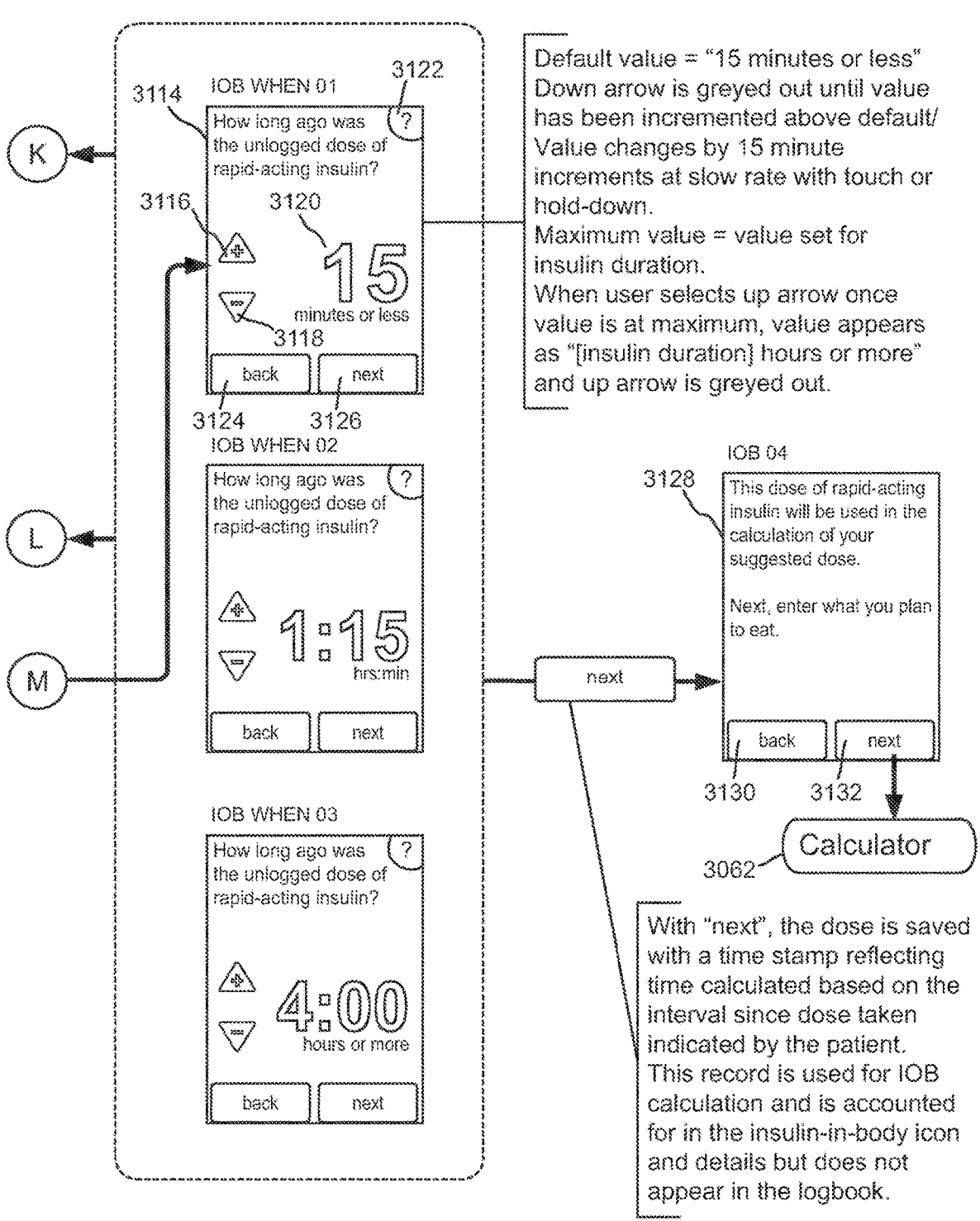

On the numerical input screen 3096, once the desired amount of rapid-acting insulin has been entered, the "Next" touchscreen button 3110 may be pressed to advance the graphical user interface to a time input screen 3114, as shown by reference path (M) (see FIG. 16C). Alternatively, on the numerical input screen 3096, the "Back" touchscreen button 3112 may be pressed, which returns the graphical user interface to the prompt screen 3090.

Regarding FIG. 16C, on the time input screen 3114, the display presents a question asking the user how long ago was the unlogged dose of rapid-acting insulin. On the time input screen 3114, the time since the last unlogged rapid-acting insulin dose may be adjusted by pressing the up arrow 3116 (e.g., "+") touchscreen button or the down arrow 3118 (e.g., "−") touchscreen button to increase or decrease, respectively, the time as desired. For example, the time 3120 may be adjusted by 15 minute increments by tapping the up arrow 3116 or the down arrow 3118. In some embodiments, the amount increases or decreases as appropriate at a slow-rate for the first 2 seconds and at a faster rate after 2 seconds when the up or down arrow is pressed and held. In some instances, the default time is 15 minutes (e.g., displayed as "15 minutes or less"). In some cases, the maximum time is the time value set for the insulin duration of action. If the user presses the up arrow 3116 once while the time is at the maximum value, then the time displayed may be shown as "[insulin duration] hours or more", and the up arrow 3116 may be displayed as greyed out and may be un-selectable by the user.

The time input screen 3114 also includes a "?" touchscreen button 3122, which, when pressed, provides a help screen 3106 that includes additional instructions to the user as described above and as indicated by reference path (K). The time input screen includes a "Back" touchscreen button 3124, which, when pressed, returns the display to the numerical input screen 3096 as shown by reference path (L). Once the desired time since the last unlogged rapid-acting insulin dose has been entered on the time input screen 3114, the "Next" touchscreen button 3126 may be pressed to advance the graphical user interface to the next screen in the Insulin on Board Interface, such as screen 3128. Pressing the "Next" touchscreen button will save the entered rapid-acting insulin dose with a time stamp reflecting the time calculated based on the interval since the dose was taken as indicated by the user in the previous time input screen 3114. Screen 3128 informs the user that the entered dose of rapid-acting insulin will be used in the calculation of the user's suggested insulin dose, and that the next screen will allow the user to enter what the user plans to eat. Screen 3128 includes a "Back" touchscreen button 3130, which, when pressed, returns the display to the time input screen 3114. Screen 3128 includes a "Next" touchscreen button 3132, which, when pressed, causes the graphical user interface to display the Insulin Calculator Interface 3062 (see FIG. 17).

Insulin Calculator Interface

Figure 17A:
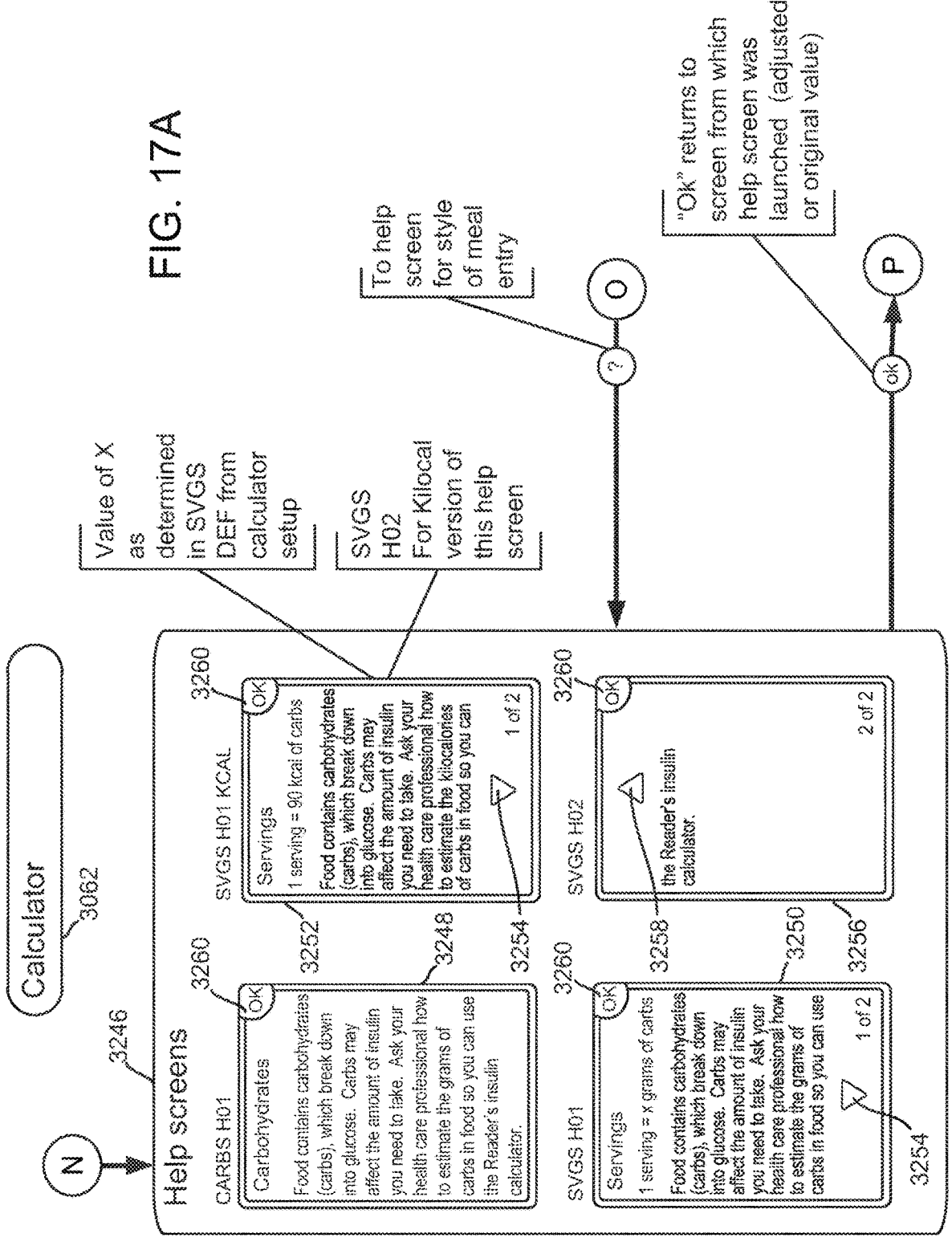
Figure 17B:
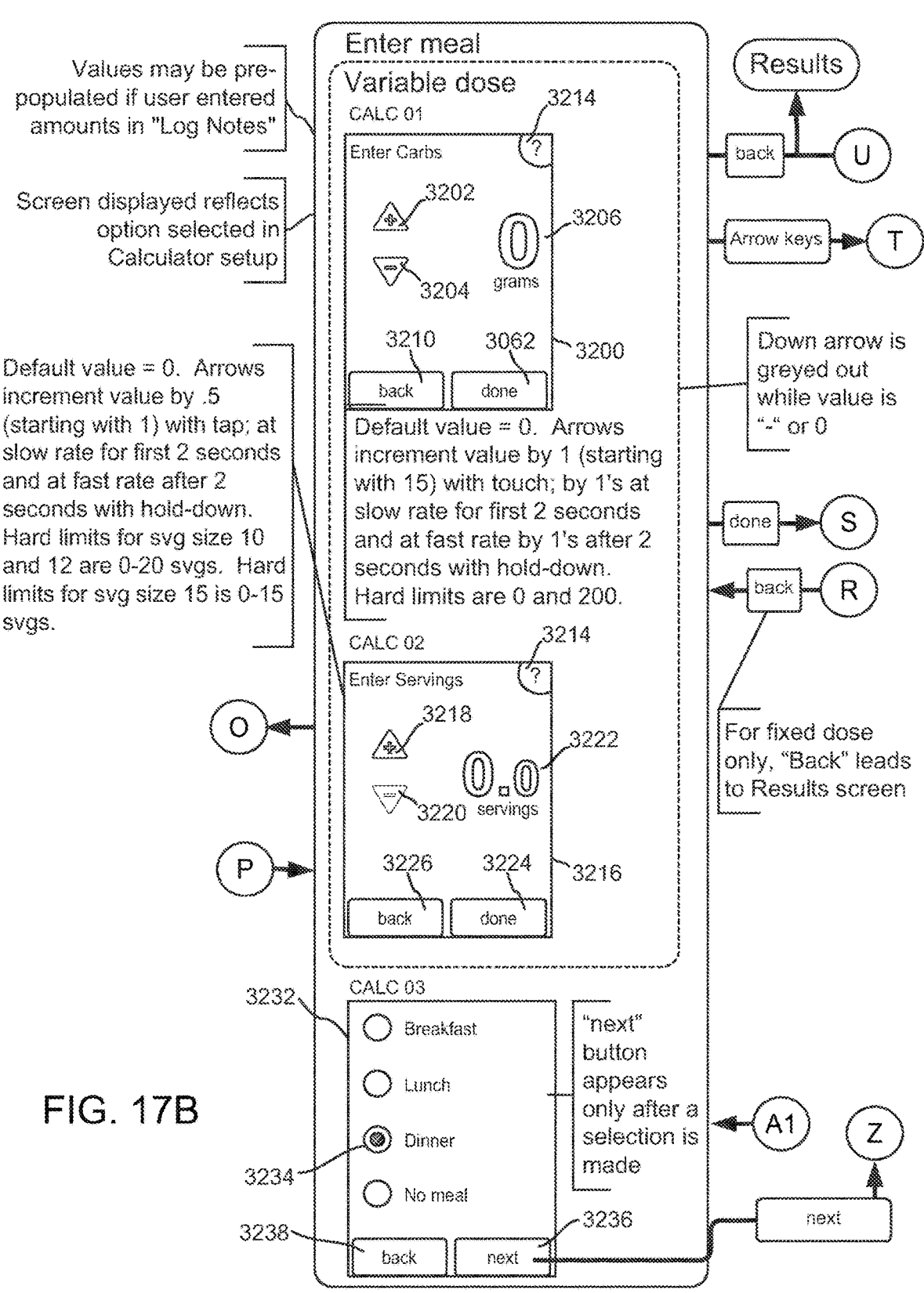

An Insulin Calculator Interface 3062 begins with the display of an "Enter Carbs" screen (see FIG. 17B). On the "Enter Carbs" screen, the amount of carbs may be entered. The amount of carbs may be entered as grams, servings, or by meal, depending on the settings of the Reader.

For example, the amount of carbs may be entered as grams of carbs on the "Enter Carbs" (grams) screen 3200. The "Enter Carbs" (grams) screen 3200 initially displays no value (e.g., "--" or "0" is displayed), however, the grams of carbs may be adjusted by pressing the up arrow 3202 (e.g., "+") touchscreen button or the down arrow 3204 (e.g., "−") touchscreen button to increase or decrease, respectively, the grams of carbs as desired, as shown by reference path (T) (see FIG. 17C). For example, the grams of carbs 3206 may be adjusted by 1 gram increments by tapping the up arrow 3202 or the down arrow 3204. In some cases, the minimum grams of carbs that may be entered is zero carbs, and the maximum grams of carbs that may be entered is 200 grams of carbs. In some embodiments, the amount increases or decreases as appropriate at a slow-rate for the first 2 seconds and at a faster rate after 2 seconds when the up or down arrow is pressed and held. Once the desired amount is entered, the amount may be saved by pressing the "Done" touchscreen button 3208, which saves the entered grams of carbs and then advances the graphical user interface to the Insulin Calculation Interface 3212, as shown by reference paths (S and V) (see FIGS. 17B, 17C and 17E). The "Enter Carbs" (grams) screen 3200 includes a "Back" touchscreen button 3210, which, when pressed, returns the display to the Results screen.

In certain embodiments, the amount of carbs may be entered as servings of carbs on the "Enter Carbs" (servings) screen 3216. The "Enter Carbs" (servings) screen 3216 initially displays no value (e.g., "--" or "0" or "0.0" is displayed), however, the servings of carbs may be adjusted by pressing the up arrow 3218 (e.g., "+") touchscreen button or the down arrow 3220 (e.g., "−") touchscreen button to increase or decrease, respectively, the servings of carbs as desired, as shown by reference path (T) (see FIG. 17C). For example, the servings of carbs 3222 may be adjusted by 0.5 serving increments by tapping the up arrow 3218 or the down arrow 3220. In some cases, the minimum servings of carbs that may be entered is zero servings. In some instances, the serving size may be set to 10 or 12 grams of carbs per serving and the maximum servings of carbs that may be entered is 20 servings. In some instances, the serving size may be set to 15 grams of carbs per serving and the maximum servings of carbs that may be entered is 15 servings. In some embodiments, the amount increases or decreases as appropriate at a slow-rate for the first 2 seconds and at a faster rate after 2 seconds when the up or down arrow is pressed and held. In some cases, the "Enter Carbs" (servings) screen 3216 may include a display of the grams of carbs 3228 that corresponds to the number of servings entered (see FIG. 17C). In some cases, the "Enter Carbs" (servings) screen 3216 may include a display of the energy (e.g., kcal) of carbs 3230 that corresponds to the number of servings entered (see FIG. 17C). Once the desired amount is entered, the amount may be saved by pressing the "Done" touchscreen button 3224, which saves the entered servings of carbs and then advances the graphical user interface to the Insulin Calculation Interface 3212, as shown by reference paths (S and V) (see FIGS. 17B, 17C and 17E). The "Enter Carbs" (servings) screen 3216 includes a "Back" touchscreen button 3226, which, when pressed, returns the display to the Results screen.

In certain embodiments, the amount of carbs may be entered by meal on the "Enter Carbs" (meal) screen 3232. The "Enter Carbs" (meal) screen 3232 displays a list of meals, such as breakfast, lunch, dinner, or no meal. Each selection includes a corresponding touchscreen radio button. For example, to select the "Dinner" meal, the touchscreen radio button 3234 associated with the "Dinner" selection may be pressed. The "Enter Carbs" (meal) screen 3232 includes a "Back" touchscreen button 3238, which, when pressed, returns the display to the Results screen. The "Enter Carbs" (meal) screen 3232 includes a "Next" touchscreen button 3236, which, when pressed, may advance the graphical user interface to the "Double Check" screen 3240 via reference path (Z), as shown in FIG. 17C.

The "Double Check" screen 3240 (see FIG. 17C) is displayed if the user has marked the same meal since midnight (12:00 AM) of the current day. The "Double Check" screen 3240 displays a warning to the user indicating that the user has already logged insulin for the selected meal that day, and asks the user if the user wants to log more insulin for the same meal that day. The "Double Check" screen 3240 includes a "No" touchscreen button, which, when pressed, returns the graphical user interface to the "Enter Carbs" (meal) screen 3232 via reference path (A1). The "Double Check" screen 3240 includes a "Yes" touchscreen button, which, when pressed, advances the graphical user interface to the Insulin Calculation Interface 3212 via reference path (Q) (see FIG. 17E).

Figure 17C:
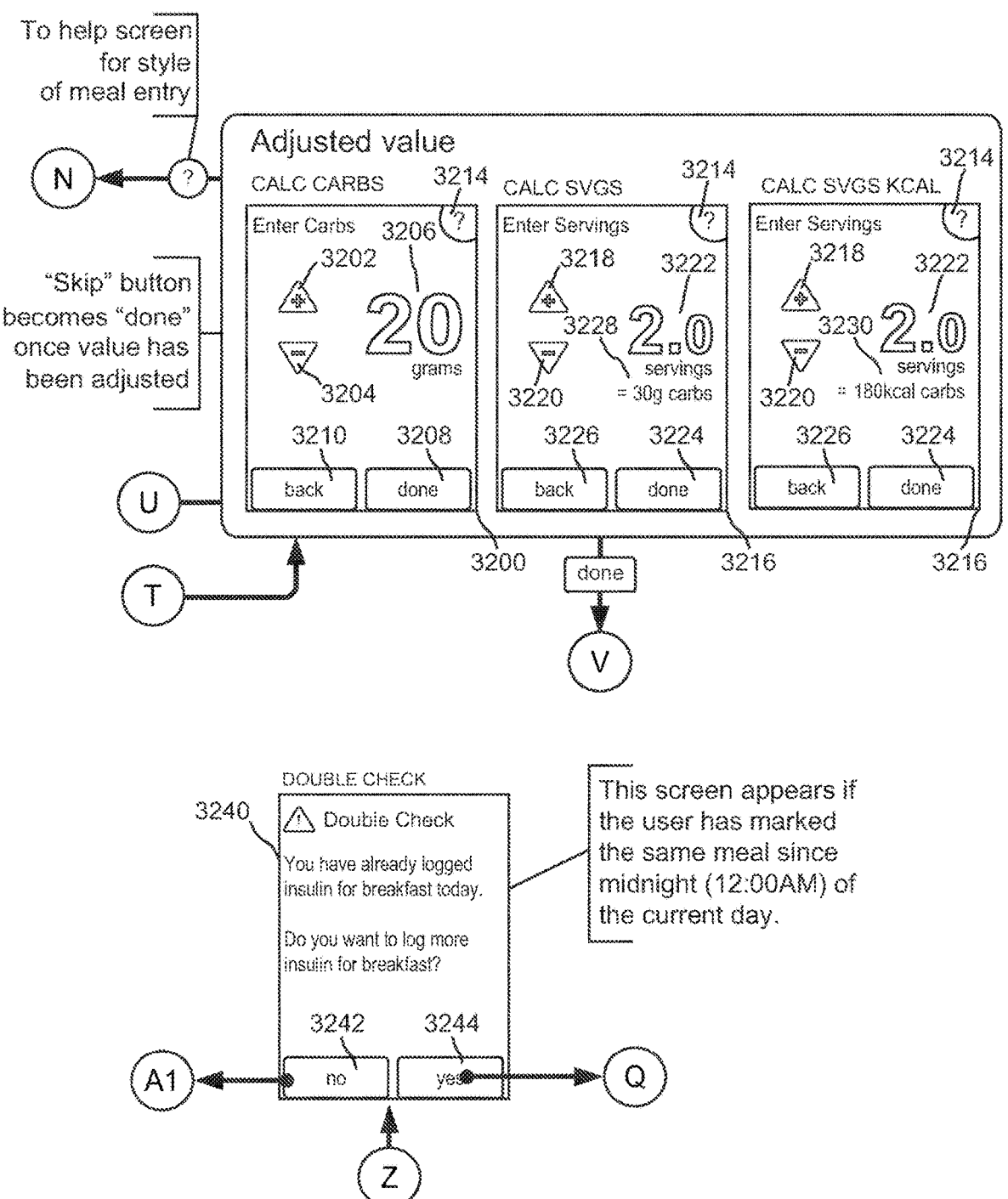

Referring again to FIG. 17B, the "Enter "Carbs" screens (e.g., the "Enter Carbs" (grams) screen 3200, and the "Enter Carbs" (servings) screen 3216) both include a "?" touchscreen button 3214, which, when pressed, causes the graphical user interface to display help screens 3246, as shown by reference path (O) in FIG. 17B, or by reference path (N) in FIG. 17C. Help screens 3246 (see FIG. 17A) may display information to the user depending on whether the Reader is set to display carbs as grams, servings by grams of carbs, or servings by kcal of carbs. For example, a help screen 3248 may be shown that displays a set of help information to the user regarding carbohydrates when the Reader is set to display carbs as grams. In other instances, the help screen 3250 may be shown that displays a different set of help information to the user regarding carbohydrates as servings by grams of carbs when the Reader is set to display servings by grams of carbs. In other instances, the help screen 3252 may be shown that displays yet a different set of help information to the user regarding carbohydrates as servings by kcal of carbs when the Reader is set to display servings by kcal of carbs. In certain instances, if the help information includes more text than is able to be displayed on a single help screen, the help screen may include a down arrow 3254, which, when pressed, causes the graphical user interface to display the remaining text on a second help screen 3256. The second help screen 3256 includes an up arrow 3258, which, when pressed, returns the graphical user interface to the first help screen 3248, 3250 or 3252 depending on the settings of the Reader as described above. The help screens 3248, 3250, 3252 and 3256 include an "OK" touchscreen button 3260, which, when pressed, returns the graphical user interface to the "Enter "Carbs" screen (e.g., the "Enter Carbs" (grams) screen 3200, or the "Enter Carbs" (servings) screen 3216) from which the help screen was launched, via reference path (P).

Figure 17E:
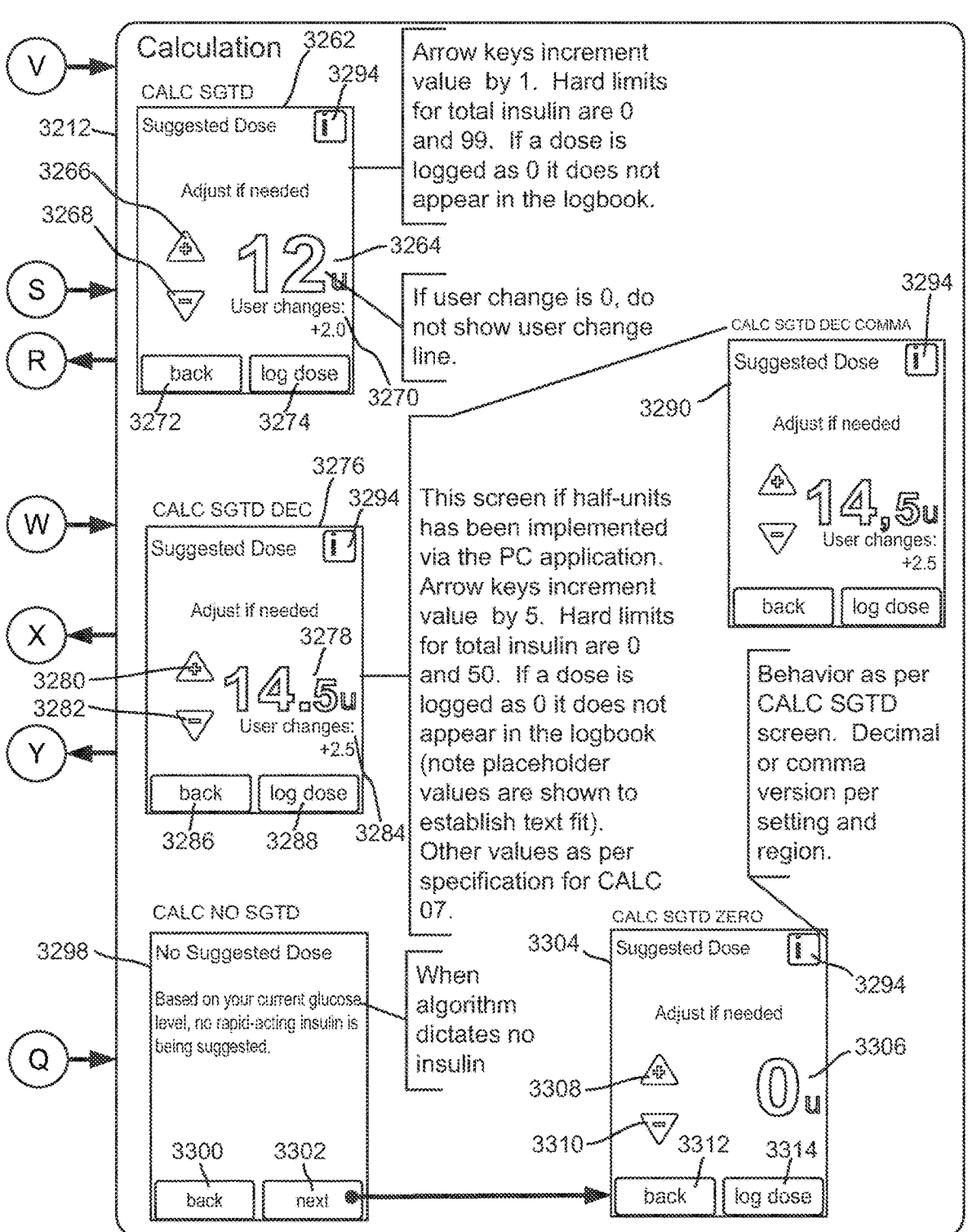

Referring to FIG. 17B, once the desired amount of carbs is entered, the amount may be saved by pressing the "Done" touchscreen button 3208 or 3224, which saves the entered amount of carbs (e.g., grams of carbs or servings of carbs) and then advances the graphical user interface to the appropriate Insulin Calculation Interface 3212, as shown by reference path(S) (see FIG. 17E). The Insulin Calculation Interface 3212 displays the suggested dose of insulin based on the amount of carbs entered by the user on the previous screens as described above and/or the user's insulin on board, if any, as described above. The Insulin Calculation Interface 3212 may vary in appearance depending on whether the Reader is set to display whole units of insulin, half units of insulin, or a decimal point or a comma between the whole and half units of insulin.

Referring to FIG. 17E, in embodiments of the Insulin Calculation Interface 3212 where the Reader is set to display whole units of insulin, the Insulin Calculation Interface 3212 will appear as Suggested Dose screen 3262. Suggested Dose screen 3262 displays the suggested dose of insulin 3264 as units of insulin. The suggested dose of insulin may be adjusted in 1 insulin unit increments by pressing the up arrow 3266 (e.g., "+") touchscreen button or the down arrow 3268 (e.g., "−") touchscreen button to increase or decrease, respectively, the suggested dose of insulin as desired. The minimum and maximum values for the suggested dose of insulin are 0 and 99, respectively. If the suggested dose of insulin is adjusted by the user from its initial value, the amount of units increased or decreased by the user 3270 will be shown below the suggested insulin dose 3264. If the user adjustment of the suggested dose of insulin is calculated to reduce the user's blood glucose below the target range, then the graphical user interface will display a warning screen 3292 that displays a caution to the user that the insulin dose entered may take the user's blood glucose lower than the user's target range and put the user at risk for a low glucose event (see FIG. 17D). The warning screen 3292 includes an "OK" touchscreen button, which, when pressed, returns the graphical user interface to the Suggested Dose screen 3262 via reference path (W). The Suggested Dose screen 3262 includes a "Back" touchscreen button 3272, which, when pressed, returns the user to the prior "Enter "Carbs" screen (e.g., the "Enter Carbs" (grams) screen 3200, or the "Enter Carbs" (servings) screen 3216) via reference path (R). The Suggested Dose screen 3262 also includes a "Log dose" touchscreen button 3274, which, when pressed, saves the suggested insulin dose in the logbook along with an associated glucose test result and the time the test was taken (e.g., the insulin dose is not saved as delivered at the time the "Log dose" touchscreen button is pressed) and advances the graphical user interface to the Logbook via reference path (Y) (see FIG. 17D).

Referring to FIG. 17E, in embodiments of the Insulin Calculation Interface 3212 where the Reader is set to display half unit increments of insulin and a decimal point between the whole and half units, the Insulin Calculation Interface 3212 will appear as Suggested Dose screen 3276. Suggested Dose screen 3276 displays the suggested dose of insulin 3278 as units of insulin in 0.5 unit increments. The suggested dose of insulin may be adjusted in 0.5 insulin unit increments by pressing the up arrow 3280 (e.g., "+") touchscreen button or the down arrow 3282 (e.g., "–") touchscreen button to increase or decrease, respectively, the suggested dose of insulin as desired. The minimum and maximum values for the suggested dose of insulin are 0 and 50, respectively. If the suggested dose of insulin is adjusted by the user from its initial value, the amount of units increased or decreased by the user 3284 will be shown below the suggested insulin dose 3278. If the user adjustment of the suggested dose of insulin is calculated to reduce the user's blood glucose below the target range, then the graphical user interface will display a warning screen 3292 that displays a caution to the user that the insulin dose entered may take the user's blood glucose lower than the user's target range and put the user at risk for a low glucose event (see FIG. 17D). The warning screen 3292 includes an "OK" touchscreen button, which, when pressed, returns the graphical user interface to the Suggested Dose screen 3276 via reference path (W). The Suggested Dose screen 3276 includes a "Back" touchscreen button 3286, which, when pressed, returns the user to the prior "Enter "Carbs" screen (e.g., the "Enter Carbs" (grams) screen 3200, or the "Enter Carbs" (servings) screen 3216) via reference path (R). The Suggested Dose screen 3276 also includes a "Log dose" touchscreen button 3288, which, when pressed, saves the suggested insulin dose in the logbook along with an associated glucose test result and the time the test was taken (e.g., the insulin dose is not saved as delivered at the time the "Log dose" touchscreen button is pressed) and advances the graphical user interface to the Logbook via reference path (Y) (see FIG. 17D).

Referring to FIG. 17E, in embodiments of the Insulin Calculation Interface 3212 where the Reader is set to display half unit increments of insulin and a comma between the whole and half units, the Insulin Calculation Interface 3212 will appear as Suggested Dose screen 3290. The functions of Suggested Dose screen 3290 are analogous to those described for Suggested Dose screen 3276 above.

If the insulin calculator of the Reader determines that no insulin dose is suggested, the Insulin Calculation Interface 3212 will be displayed as No Suggested Dose screen 3298, which displays information indicating that based on the user's current glucose level, no rapid-acting insulin is being suggested. The No Suggested Dose screen includes a "Back" touchscreen button 3300, which, when pressed, returns the user to the prior "Enter "Carbs" screen (e.g., the "Enter Carbs" (grams) screen 3200, or the "Enter Carbs" (servings) screen 3216) via reference path (R). The No Suggested Dose screen 3298 includes a "Next" touchscreen button 3302, which, when pressed, advances the graphical user interface to Suggested Dose screen 3304. Suggested Dose screen 3304 begins by displaying a suggested does of insulin 3306 as 0 units of insulin. The suggested dose of insulin may be adjusted in 1 unit or 0.5 insulin unit increments, depending on the Reader settings, by pressing the up arrow 3308 (e.g., "+") touchscreen button or the down arrow 3310 (e.g., "–") touchscreen button to increase or decrease, respectively, the suggested dose of insulin as desired. If the suggested dose of insulin is adjusted by the user from its initial value, the amount of units increased or decreased by the user will be shown below the suggested insulin dose 3306. If the user adjustment of the suggested dose of insulin is calculated to reduce the user's blood glucose below the target range, then the graphical user interface will display a warning screen 3292 that displays a caution to the user that the insulin dose entered may take the user's blood glucose lower than the user's target range and put the user at risk for a low glucose event (see FIG. 17D). The warning screen 3292 includes an "OK" touchscreen button, which, when pressed, returns the graphical user interface to the Suggested Dose screen 3304 via reference path (W). The Suggested Dose screen 3304 includes a "Back" touchscreen button 3312, which, when pressed, returns the user to the prior No Suggested Dose screen 3298. The Suggested Dose screen 3304 also includes a "Log dose" touchscreen button 3314, which, when pressed, saves the suggested insulin dose in the logbook along with an associated glucose test result and the time the test was taken (e.g., the insulin dose is not saved as delivered at the time the "Log dose" touchscreen button is pressed) and advances the graphical user interface to the Logbook via reference path (Y) (see FIG. 17D).

Suggested Dose screens 3262, 3276, 3290 and 3304 include a "Dose details" touchscreen button 3294 (e.g., an "i" touchscreen button), which, when pressed, causes graphical user interface to display Dose Details Interface via reference path (X) (see FIG. 17D).

Figure 18B:
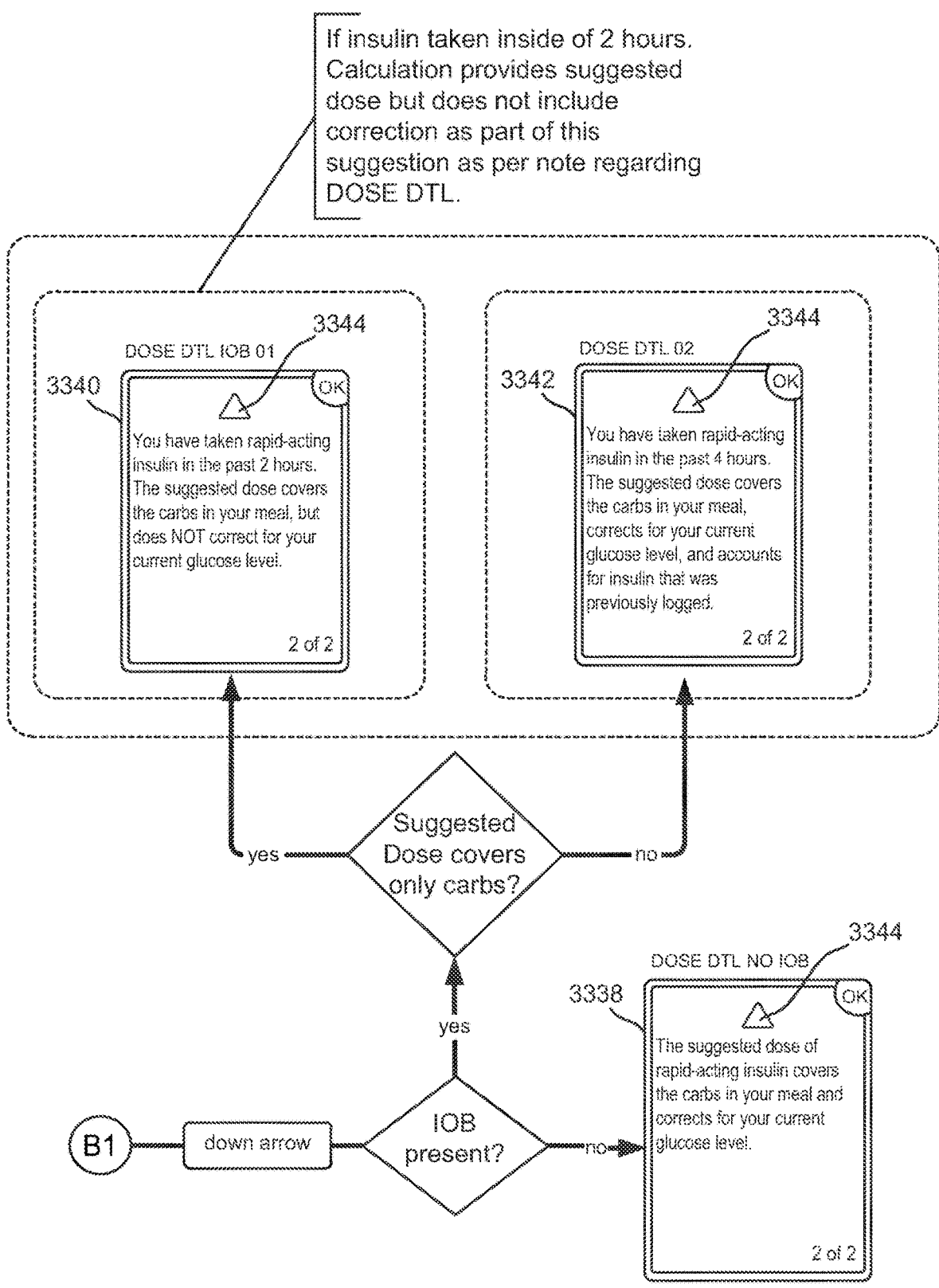

Dose Details Interface 3296 is shown in FIGS. 18A and 18B. Dose Details Interface begins a Dose Details screen (e.g., 3316, 3318 and 3320) that displays a summary of the calculated insulin dose. The Dose Details screen (e.g., 3316, 3318 and 3320) may have various appearances depending on the settings of the Reader (e.g., whether the Reader is set to display carbs as grams of carbs, servings of carbs, or by meal) and the data input by the user or calculated by the Reader (e.g., amount of carbs, insulin on board, user adjustment to the suggested dose of insulin, etc.). The Dose Details screen displays the amount of carbs by meal 3322, as grams of carbs 3324, or as servings of carbs 3326. If insulin correction is enabled on the Reader, the Dose Details screen will display the suggested insulin dose 3328. If insulin correction is disabled on the Reader (e.g., the Easy setup sets "no correction insulin") then the suggested insulin dose is not displayed. If the Reader determines that insulin on board is present, then the Dose Details screen displays the amount of insulin on board 3330. In the Reader determines that no insulin on board is present, then the amount of insulin on board is not displayed. If the user adjusted the suggested insulin dose, the Dose Details screen will display the amount the user adjusted the suggested insulin dose 3332. Based on the above data, the Dose Details screen displays the calculated insulin dose 3334.

The Dose Details screen includes a down arrow touchscreen button 3336, which, when pressed, advances the Dose Details screen to the second page of the Dose Details screen via reference path (B1) (see FIG. 18B). The information displayed on the second page of the Dose Details screen may vary depending on whether insulin on board is present and whether the suggested dose of insulin only accounts for carbs in the user's meal. If insulin on board is not present, then the second page of the Dose Details screen 3338 displays information indicating that the suggested dose of rapid-acting insulin covers the carbs in the user's meal and corrects for the user's current glucose level. If insulin on board is present and the user has taken insulin within the past 2 hours, then the second Dose Details screen 3340 displays information indicating that the user has taken rapid-acting insulin in the past 2 hours, and the suggested dose of insulin covers the carbs in the user's meal but does not correct for the user's current glucose level. If insulin on board is present and the time when the user has last taken insulin is more than 2 hours from the current time but less than the duration of insulin action, then the second Dose Details screen 3342 displays information indicating that the user has taken rapid-acting insulin in the past 4 hours, and the suggested dose of insulin covers the carbs in the user's meal, corrects for the user's current glucose level, and accounts for insulin that was previously logged. The second Dose Details screen (e.g., 3338, 3340 and 3342) include an up arrow touchscreen button 3344, which, when pressed, returns the graphical user interface to the previous Dose Details screen.

Reminders Interface

An exemplary embodiment of a graphical user interface which may be utilized in connection with a Reader as described herein and which facilitates a Reminders procedure 3400 for setting reminders is provided. This graphical user interface is now described in greater detail with reference to FIG. 19.

Figure 19A:
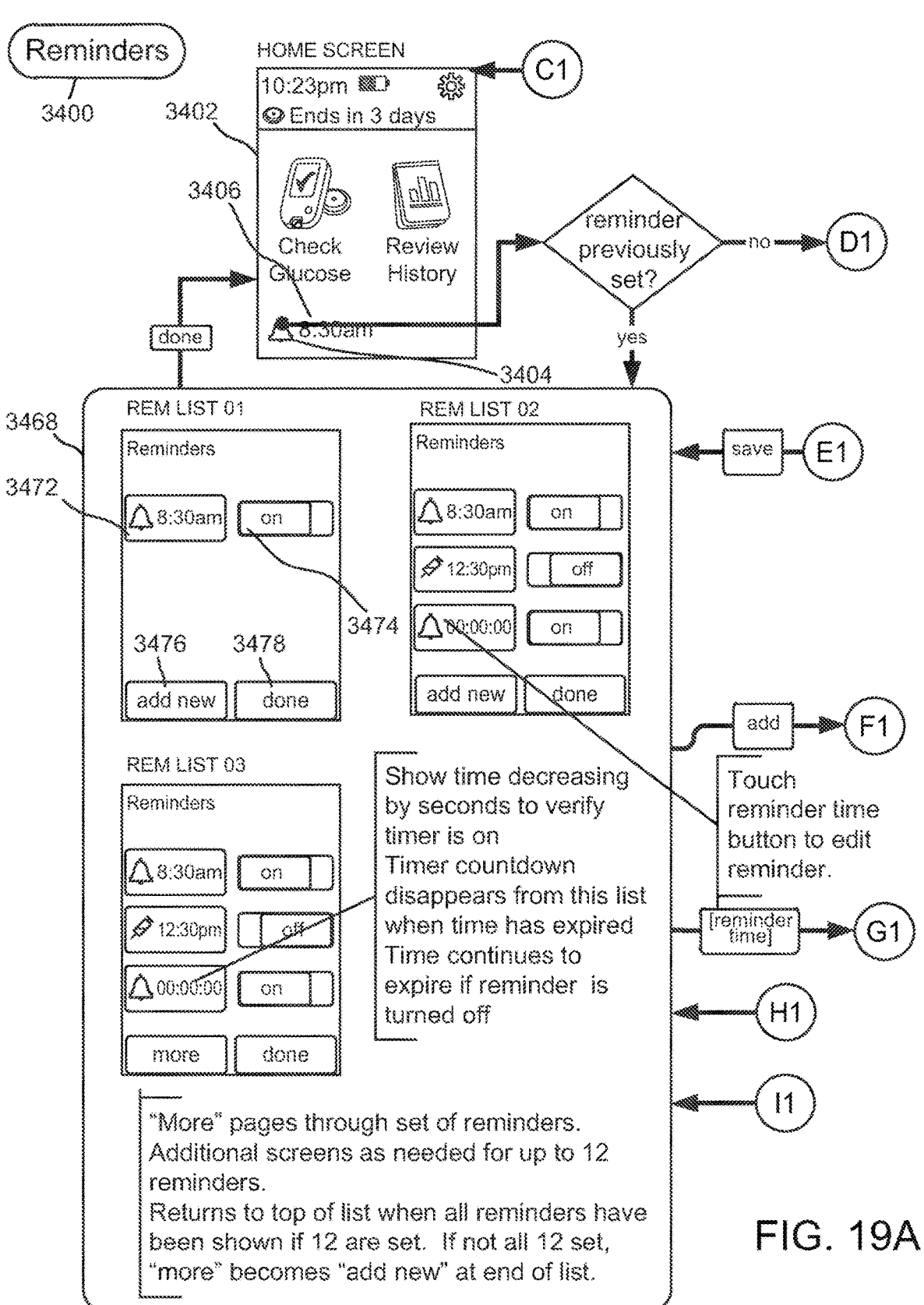
Figure 19C:
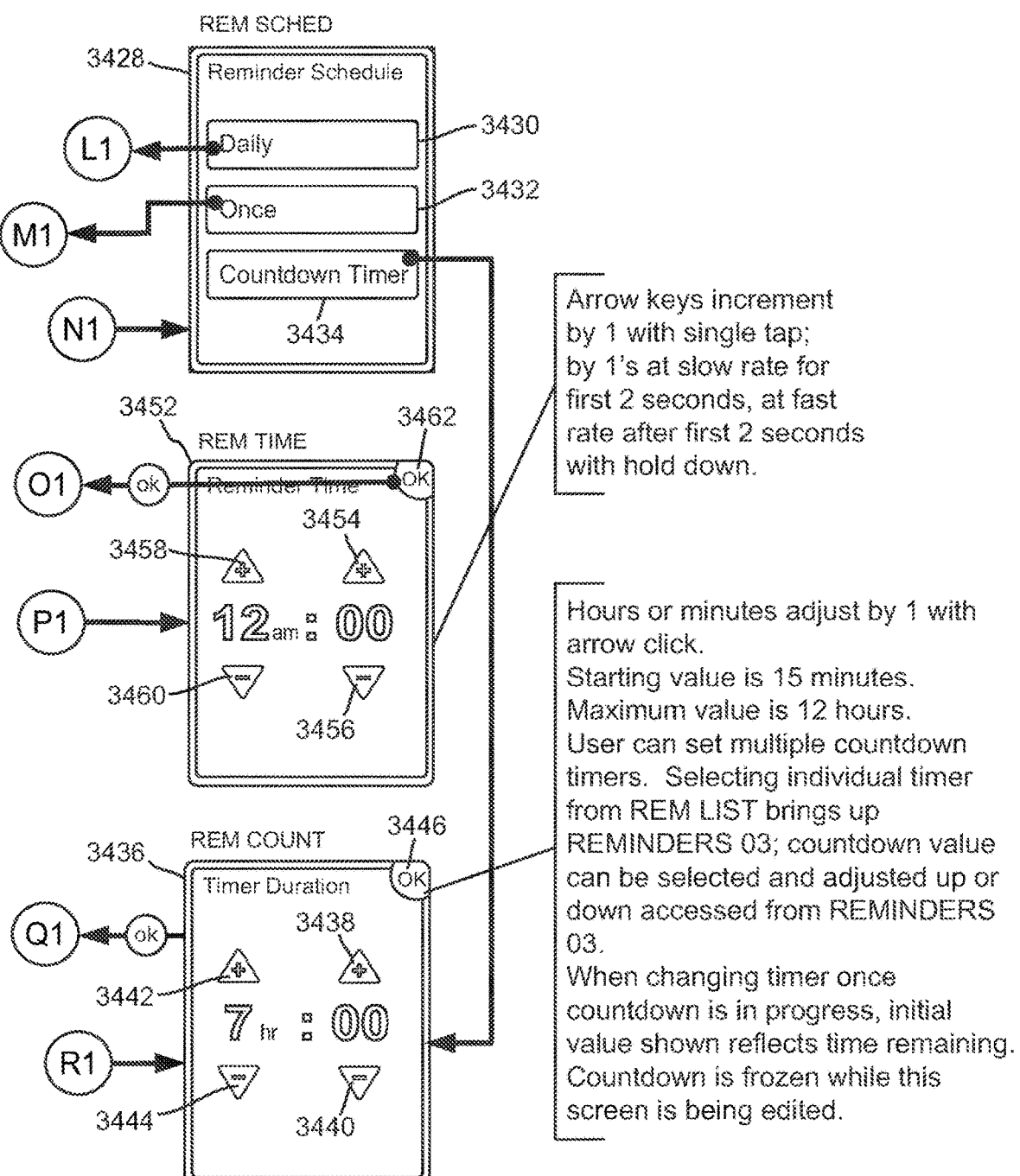
Figure 19D:
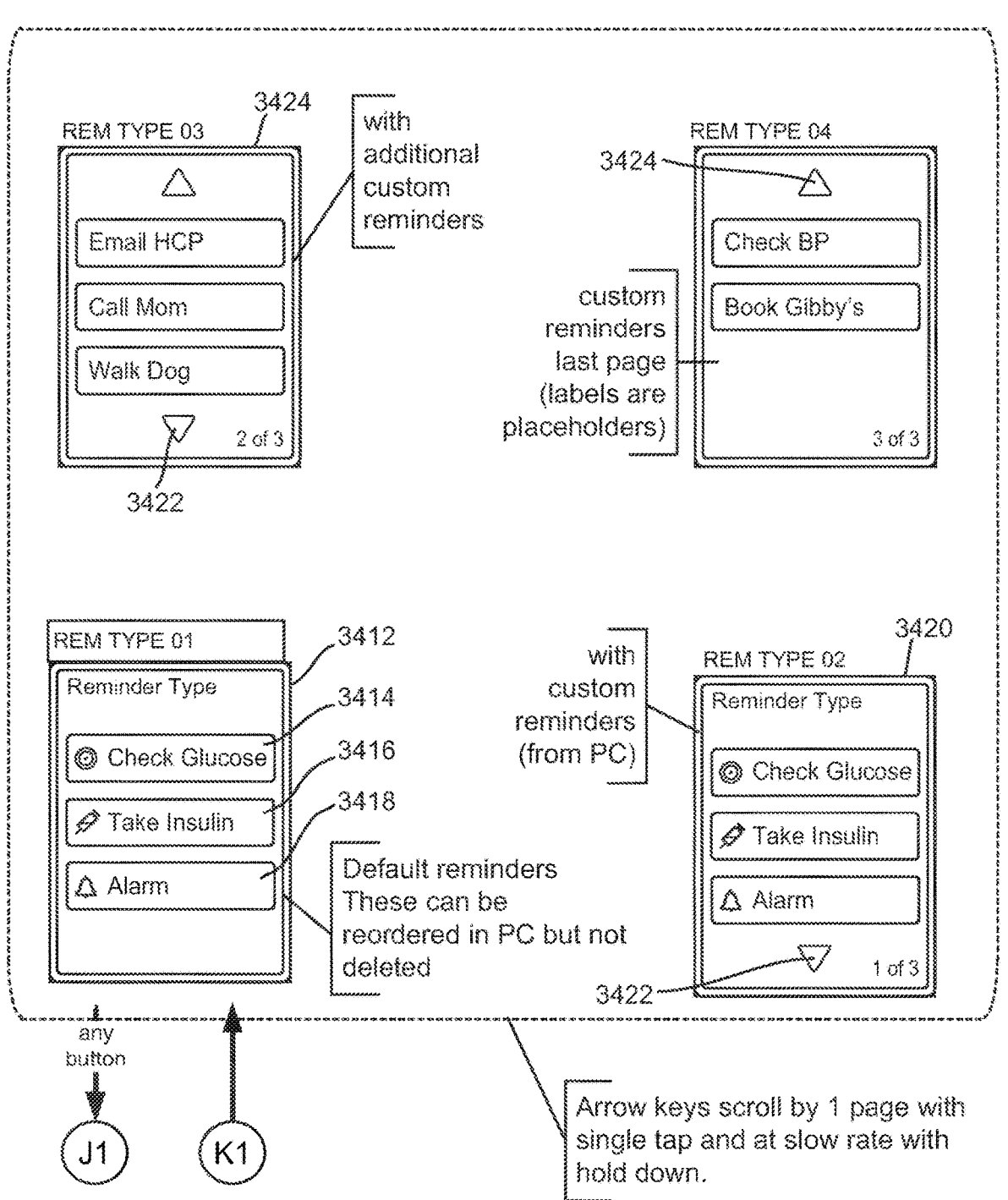

The Reminder Interface 3400, shown in FIG. 19A, begins with the display of a Home Screen 3402 of the Reader. The Home Screen includes a reminders touchscreen button 3404 (e.g., a bell shaped icon, an alarm clock icon, a clock icon, etc.), which, when pressed, begins the procedure to set and/or adjust reminders. If a reminder has been previously set, then next reminder time 3406 is displayed next to the reminders touchscreen button 3404.

Referring to FIG. 19A, if no reminder has been previously set, then pressing the reminders touchscreen button 3404 advances the graphical user interface to the Remind Me screen 3408 via reference path (D1) (see FIG. 19B). Remind Me screen 3408 includes selections for the type of reminder, the schedule for the reminder, and the time of the reminder.

For example, on the Remind Me screen 3408, the type of reminder may be selected by pressing the Reminder Type touchscreen button 3410. The reminder selection touchscreen button 3410 displays the currently selected reminder type, which has a default value of "Check Glucose". The Reminder Type touchscreen button 3410, when pressed, advances the graphical user interface to the Reminder Type screen 3412 via reference path (K1) (see FIG. 19D). The Reminder Type screen 3412 lists the available types of reminders that may be set. The Reminder Type screen 3412 displays the 3 default reminders as the "Check Glucose" touchscreen button 3414, the "Take Insulin" touchscreen button 3416, the and "Alarm" touchscreen button 3418. The default types of reminders can be reordered using the PC interface, but not deleted from the Reader. Each default reminder touchscreen button includes text describing the type of reminder, as described above, and an icon associated with each different type of default reminder. Additional custom reminders can be setup using the PC interface. If additional custom reminders have been previously setup, then they will be displayed on the Reminder Type screen 3420. The custom reminders can by any type of reminder desired by the user. The additional custom reminders can be displayed by pressing the down arrow touchscreen button 3422 on reminder Type screen 3420. For example, the list of types of reminders may be scrolled through by tapping the down arrow 3422 or the up arrow 3424. In some embodiments, the pages scroll page by page by a single press of the up or down arrow and at a slow rate after 2 seconds when the up or down arrow is pressed and held. Once a type of reminder is selected by pressing the desired type of reminder, the graphical user interface returns to the Remind Me screen 3408 via reference path (J1) (see FIG. 19B).

On the Remind Me screen 3408, the schedule of the reminder may be selected by pressing the Repeat touchscreen button 3426. The Repeat touchscreen button 3426 displays the currently selected schedule for the reminder, which has a default value of "Daily", indicating that the reminder will be repeated daily at the selected time. The Repeat touchscreen button 3426, when pressed, advances the graphical user interface to the Reminder Schedule screen 3428 via reference path (N1) (see FIG. 19C). The Reminder Schedule screen 3428 lists the available types of schedules that may be set for the reminder. The Reminder Schedule screen 3428 displays 3 types of reminder schedules as the "Daily" touchscreen button 3430, the "Once" touchscreen button 3432, the and "Countdown Timer" touchscreen button 3434. Pressing the "Daily" touchscreen button 3430 sets the reminder schedule to daily and returns the graphical user interface to the Remind Me screen 3408 via reference path (L1). Pressing the "Once" touchscreen button 3432 sets the reminder schedule to once (e.g., the reminder will not repeat) and returns the graphical user interface to the Remind Me screen 3408 via reference path (M1). Pressing the "Countdown Timer" touchscreen button 3434 sets the reminder schedule to a countdown timer and advances the graphical user interface to the Timer Duration screen 3436 (see FIG. 19C). The countdown timer may be set using the Timer Duration screen 3436. For example, the Timer Duration screen 3436 displays the current amount of time left on the countdown timer in hours and minutes. The default value for the countdown timer is 15 minutes. The amount of minutes may be adjusted by pressing the up arrow 3438 (e.g., "+") touchscreen button or the down arrow 3440 (e.g., "–") touchscreen button to increase or decrease, respectively, the amount of minutes as desired. For example, the amount of minutes may be adjusted by 1 minute increments by tapping the up arrow 3438 or the down arrow 3440. In some embodiments, the amount increases or decreases as appropriate at a slow-rate for the first 2 seconds and at a faster rate after 2 seconds when the up or down arrow is pressed and held. The amount of hours may be adjusted by pressing the up arrow 3442 (e.g., "+") touchscreen button or the down arrow 3444 (e.g., "–") touchscreen button to increase or decrease, respectively, the amount of minutes as desired. For example, the amount of hours may be adjusted by 1 hour increments by tapping the up arrow 3442 or the down arrow 3444. In some embodiments, the amount increases or decreases as appropriate at a slow-rate for the first 2 seconds and at a faster rate after 2 seconds when the up or down arrow is pressed and held. Once the desired amount of time for the countdown timer is entered, the amount may be saved by pressing the "OK" touchscreen button 3446, which saves the entered amount of time and then returns the graphical user interface to the Remind Me screen 3448, as shown by reference path (Q1) (see FIG. 19B). From the Remind Me screen 3448 (see FIG. 19B), the amount of time for the countdown timer may be adjusted by pressing the Time touchscreen button 3464, which, when pressed, advances the graphical user interface to the Timer Duration screen 3436 via reference path (R1) (see FIG. 19C). On the Timer Duration screen 3436, the time for the countdown timer may be adjusted as described above.

On the Remind Me screen 3408, the time of the reminder may be selected by pressing the Time touchscreen button 3450. The Time touchscreen button 3450 displays the currently set time for the reminder, which has a default value of 12:00 am, indicating that the reminder will be activated at the selected time. The Time touchscreen button 3450, when pressed, advances the graphical user interface to the Reminder Time screen 3452 via reference path (P1) (see FIG. 19C). The Reminder Time screen 3452 allows the user to set the time when the reminder will be activated. For example, the Reminder Time screen 3452 displays the currently set time for the reminder in hours and minutes. The reminder time may be adjusted by pressing the minutes up arrow 3454 (e.g., "+") touchscreen button or the minutes down arrow 3456 (e.g., "−") touchscreen button to increase or decrease, respectively, the minutes as desired, and the hours up arrow 3458 (e.g., "+") touchscreen button or the hours down arrow 3460 (e.g., "−") touchscreen button to increase or decrease, respectively, the hours as desired. In some embodiments, the hours and minutes increases or decreases as appropriate at a slow-rate for the first 2 seconds and at a faster rate after 2 seconds when the up or down arrow is pressed and held. Once the desired time for the reminder is entered, the time may be saved by pressing the "OK" touchscreen button 3462, which saves the entered time and then returns the graphical user interface to the Remind Me screen 3408, as shown by reference path (O1) (see FIG. 19B).

Referring to FIG. 19B, after the desired reminder type, reminder schedule and reminder time has been selected as desired, the reminder settings may be saved by pressing the "Save" touchscreen button 3466, which, when pressed, advances the graphical user interface to the Reminder List screen 3468 via reference path (E1) (see FIG. 19A). Referring back to FIG. 19B, the reminder settings may be discarded by pressing "Cancel" touchscreen button 3470. If no previous reminder has been set, then pressing "Cancel" touchscreen button 3470 returns the graphical user interface to the Home Screen 3402 via reference path (C1) (see FIG. 19A). If one or more reminders has been previously set, then pressing "Cancel" touchscreen button advances the graphical user interface to the Reminders List screen 3468 via reference path (H1) or (I1) (see FIG. 19A). In certain embodiments, if the settings for a previously set reminder are being adjusted from the Remind Me screen 3408, then "Cancel" touchscreen button 3470 may be displayed as a "Delete" touchscreen button.

Referring to FIG. 19A, from the Home Screen 3402, if one or more reminders has been previously set, then pressing the reminders touchscreen button 3404 or, in some instances, the next reminder time 3406 advances the graphical user interface to the Reminders List screen 3468. The Reminders List screen 3468 displays a list of the previously set reminders. The list of previously set reminders displays the reminder time 3472 for each previously set reminder and a corresponding "On"/"Off" toggle touchscreen button 3474 for each previously set reminder. Pressing the reminder time 3472 advances the graphical user interface to the Remind Me screen 3408 via reference path (G1), from which the reminder settings may be adjusted as described above. Pressing the "On"/"Off" toggle touchscreen button 3474 turns the corresponding reminder on or off.

The Reminders List screen includes an "Add New" touchscreen button 3476, which, when pressed, advances the graphical user interface to the Remind Me screen 3408 via reference path (F1), from which a new reminder may be setup as desired, as described above. The Reminders List screen includes a "Done" touchscreen button 3478, which, when pressed, returns the graphical user interface to the Home Screen 3402.

Receive Reminders Interface

An exemplary embodiment of a graphical user interface which may be utilized in connection with a Reader as described herein and which facilitates a Receive Reminder procedure 3500 for receiving reminders is provided. This graphical user interface is now described in greater detail with reference to FIG. 20.

The Receive Reminder Interface 3500, shown in FIG. 20B, begins when a reminder (e.g., a reminder that has been set using the Reminders Interface 3400 described above) is activated, such as when the time or triggering event of a scheduled reminder is reached. A scheduled reminder should be displayed when the time/triggering event of the reminder is reached even if the Reader display is off. In certain embodiments, a scheduled reminder is not displayed on the Reader if the time/triggering event of the reminder is reached: (1) During a blood glucose test using a strip—instead the reminder is presented after the results have been displayed; (2) When the battery is critically low—instead the reminder is presented when the battery is sufficiently charged, and the Reader is powered on; (3) During error conditions—instead the reminder is presented the next time the Reader is powered on; or (4) When the Reader is connected to a computer and data transfer is in process-instead the reminder is presented when the data transfer is completed.

When the time/triggering event of the reminder is reached, a Reminder screen is 3502 displayed (FIG. 20B). The Reminder screen 3502 includes display of the reminder with a reminder icon 3504 representing the type of reminder. For example, the reminder icon may be an "Alarm" reminder icon 3504 (e.g., a picture of a bell or alarm clock, etc.), indicating that the type of reminder is an alarm. In some instances, the reminder icon is a "Take Insulin" reminder icon 3506 (e.g., a picture of a syringe) (see FIG. 20A), indicating that the type of reminder is a reminder to the user to take insulin. In some instances, the reminder icon is a "Check Glucose" reminder icon 3508 (e.g., a picture of a glucose Reader) (see FIG. 20A), indicating that the type of reminder is a reminder to the user to check their glucose level. Other types of icons and reminders are possible.

If the Reminder sound is set to on, a beep sounds with appearance of any reminders screen. If a reminder is ignored, the reminder will appear on the screen with the next power on (whether by hardware button or strip insertion). If multiple reminders are active, the reminder screens will stack up with the most recent reminder showing first. The reminder screens will require dismissal one by one. If daily repeated reminders have been missed, once a new day's reminder is current, the previous day's reminder for that time is no longer active and is not part of the stack-up of reminder screens.

The Reminder screen 3502 includes a "Snooze 15 min" touchscreen button 3510, which, when pressed, sets the active reminder to re-active in 15 minutes, and returns the graphical user interface to the next active reminder or, if there are no other active reminders, to the previously displayed screen before the reminder was activated. The Reminder screen 3502 also includes an "OK" touchscreen button 3512, which, when pressed cancels the active reminder and returns the graphical user interface to the next active reminder or, if there are no other active reminders, returns the graphical user interface to the Home Screen. In the Reader powers off automatically due to a timeout while displaying the Reminder screen, the reminder that was active when the Reader timed-out will be displayed again the next time the Reader is powered on.

Reader Summaries

In some aspects of the present disclosure, the analyte monitoring device may be programmed with software to provide summaries of information and data related to obtain readings. The software provides an interface to view and manage features related to generated reports. Different types of summaries may be generated. For example, FIGS. 21A-D illustrate various types of interfaces for displaying summaries on the analyte monitoring device, according to certain embodiments. It should be appreciated that the summary screens illustrated are exemplary and should not be interpreted as limiting.

An exemplary embodiment of a graphical user interface which may be utilized in connection with a reader as described herein and which functions to provide the user with summaries of information and data related to obtained readings.

Summaries Menu Interface

Figures 21A, 21G:
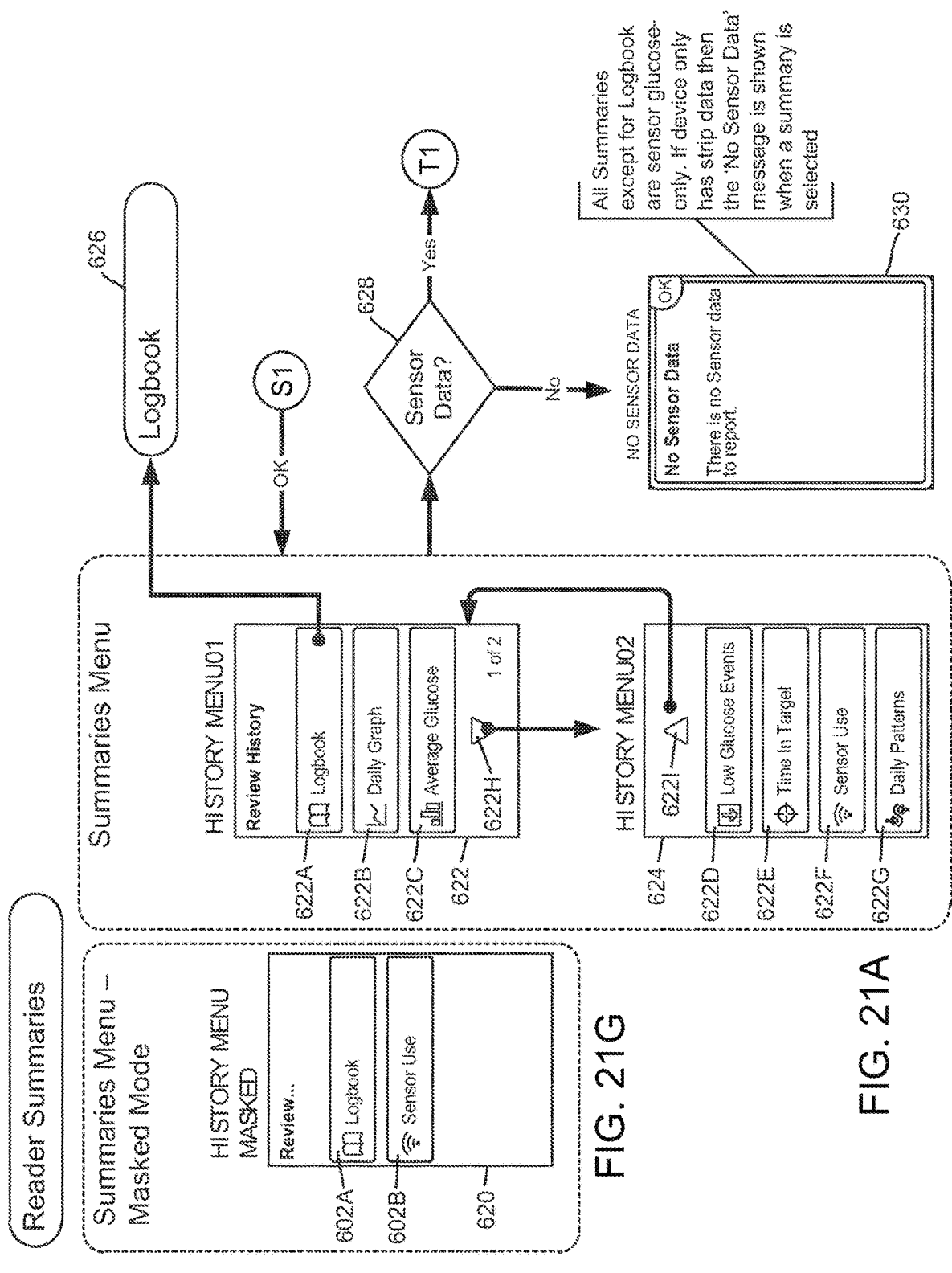
FIG. 21A illustrates an exemplary interface for providing a summaries menu on the analyte monitoring device, according to one embodiment.
FIG. 21G illustrates an example interface for providing a summaries menu on the analyte monitoring device, when the device is in masked mode, according to one embodiment.

FIG. 21A illustrates an exemplary interface for providing a summaries menu on the analyte monitoring device. History Menu01 screen 622 is shown in FIG. 21A and provides a menu of summary options that the user can select. Option 622a takes the user to a Logbook screen for viewing logged data, as shown by block 626. Option 622b takes the user to a Daily Graph screen which provides a summary of data in a daily graph format. Option 622c provides a screen for averages for glucose readings obtained for a period of time. If more options are available that can fit on a single screen shot, then a trigger element 622h (e.g., an arrow symbol) for scrolling or otherwise viewing the remaining options may be selected. When arrow 622h is selected, the user is taken to screen 624 wherein the remaining options are displayed. For example, option 624 provides a summary screen of low glucose events for a period of time. Option 622d provides a screen showing a summary of time that obtained readings were in the target zone. Option 622f provides a screen showing summarizing information related to the user of the reader device. Option 622g provides a summary screen of daily patterns that have been determined or identified based on reading acquired for a period of time. Trigger element 622i takes the user back to screen 622.

When one of the options are selected, it is determined if sensor data is present, as shown at block 628. If no data is present, a No Sensor Data screen 630 is displayed to indicate to the user that no sensor data is available for the summary. In one embodiment, the all summaries except for logbook include sensor data only (e.g., glucose data obtained from the sensor). If the device includes only strip data and insufficient sensor data, then the No Sensor Data screen is still provided when a summary option is selected.

If sensor data is provided, then the corresponding screen for the selected summary option is displayed, as represented by reference path T1. From the selected summary screen, the user can navigate back to the menu options screens 622,624 to select another menu option if desired, as shown by reference path S1.

FIG. 21B illustrates a Daily Graph screen 632 for showing a daily graph of sensor readings obtained over a single day or 24 hour time period. For example, the daily graph 632 illustrates the readings obtained on Wednesday, February 22. The horizontal axis of graph 632 represents time throughout the day, while the vertical axis represents sensor reading values. A target zone 632d may also be provided on graph 632 to represent the target zone for readings. Graph 632 may also include a time change icon 632a to inform the user of a time change. Also shown, are event indicators 632b which indicate various events with symbols or icons on the graph 632. For example, the needle icon represents a logged insulin event indicating that an insulin dose was taken, and the apple icon represents a logged food event indicating that food was eaten. More details may be stored or logged for the given event, and in one embodiment, the event indicators 632b may be selected by the user to provide additional details regarding the event.

In certain embodiments, event indicators may only be applied to glucose values after a glucose reading has been taken, either via the glucose sensor or a test strip reading. Event details may be input logged or added as notes associated with glucose values or glucose events; such as high or low glucose levels. In certain embodiments, event details may be imported from another source (e.g., electronic diary or log) and stored in a memory device.

In the embodiment shown, trigger elements 632c (e.g., left and right arrows) are also provided to enable the user to navigate forwards and backwards to another day or 24-hour time period. For example, the user could navigate to the next day after Wednesday using the right arrow, or go to the previous day by selecting the left arrow.

Figure 21C:
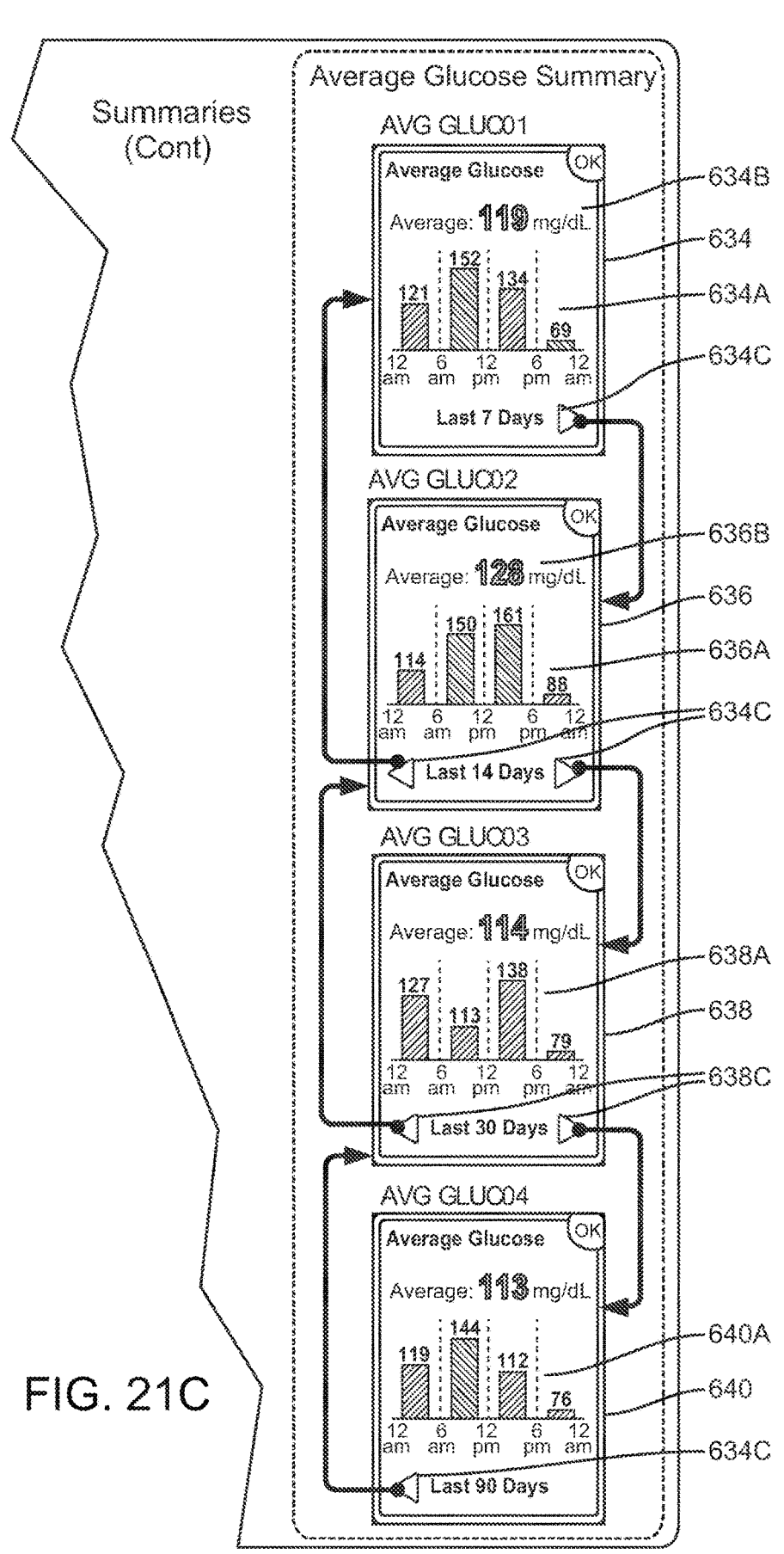
FIG. 21C illustrates an exemplary Average Glucose Summary interface for providing a graph of sensor readings obtained over a time period that is summarized with respect to a predetermined time period, according to one embodiment.

FIG. 21C illustrates an exemplary Average Glucose Summary interface for providing a graph of sensor readings obtained over a time period that is summarized with respect to a predetermined time period such as single day or 24 hour time period as shown. For example, Average Glucose (GLUC) 01 screen provides a bar graph 634a for sensor readings taken over the last 7 days. The bar graph 634a includes bars for various increments of time throughout a single day. Each bar represents the average glucose reading that was obtained at that increment of time of day for the last 7 days. For example, the average of all the sensor readings obtained between 12 am and 6 am over the last 7 days, is 121 mg/dL. For 6 am to 12, the average glucose reading was 152 mg/dL, etc.

Screen 634 also includes an average glucose value 634b for the time period of data. For example, the average glucose reading for all readings obtained over the last 7 days was 119 mg/dL. Screen 634 also includes a trigger element 634c (e.g., an arrow icon) for changing the different time period of obtained data. For example, if the user selects the right arrow icon 634c, the user is taken to AVG GLUC02 screen 636, which similarly displays a bar graph 636a and average glucose value 636b, but for a different time period, such as the last 14 days as shown. Similarly, screen 636 also includes trigger elements 634c for again increasing the time period. In this way, the user can change to AVG GLUC03 screen 638, which similarly displays a bar graph 638a and average glucose value 638b, but for a different time period, such as the last 30 days as shown. Similarly, the user can change to AVG GLUC04 screen 640, which similarly displays a bar graph 640a and average glucose value 640b, but for a different time period, such as the last 90 days as shown. Trigger elements 634c enable the user to navigate forwards and backwards between screens 634,636,638,640 to change the time periods as desired. From any of the screens, user confirmation (e.g., by selecting the "ok" button) will take the user back to the options menu interface 622,624.

FIG. 21D illustrates an exemplary screen for showing the percentage of time the sensor readings were within a target zone. Time In Target screen 642 displays a representation 642a of the percentage of time within a target zone, above a target zone, and below a target zone, for sensor readings obtained for a period of time (e.g., 7 days in the embodiment shown). Trigger element 642c is provided to enable the user to change the time period—e.g., similarly as described in FIG. 21C. Representation 642a also includes bar graphs for the associated percentages.

Summaries Menu—Masked Mode Interface

FIG. 21E illustrates an exemplary screen 644 for showing a graph 644a of the number of events associated with sensor readings obtained over a time period, wherein the events are summarized with respect to a predetermined time period, such as single day or 24 hour time period as shown. For example, screen 644 indicates a graph 644a for sensor readings obtained over the last 7 days, wherein 1 event occurred between 12 am and 6 am, 0 events occurred between 6 am and 12 pm, 3 events between 12 pm and 6 am, etc. In the embodiment shown, the event corresponds to a low glucose reading—e.g., with respect to a target zone. Other events may also be implemented—e.g., high glucose readings, insulin dosages, food intake events, etc. Trigger element 644c is provided to enable the user to change the time period.

FIG. 21F illustrates an exemplary screen 648 for indicating information associated with the use of the sensor over a time period. For example, screen 648 indicates the average scans per day, and the number of days with sensor data, for sensor readings obtained over the last 7 days. Similarly, trigger element 648c is provided to enable the user to change the time period.

FIG. 21G illustrates an example interface for providing a summaries menu on the analyte monitoring device, when the device is in masked mode. History Menu Masked screen 620 is shown provides a menu of summary options that the user can select. Option 620a takes the user to a Logbook screen for viewing logged data. Option 620b provides a screen showing summarizing information related to the use of the reader device. Since the device is in masked mode and does not permit the user from viewing sensor readings, summary screens related to obtained readings are also not available.

Logbook Interface

An exemplary embodiment of a graphical user interface which may be utilized in connection with a Reader as described herein and which facilitates a Logbook procedure 3600 for displaying, adding and/or editing logbook entries is provided. This graphical user interface is now described in greater detail with reference to FIG. 22.

Figure 22A:
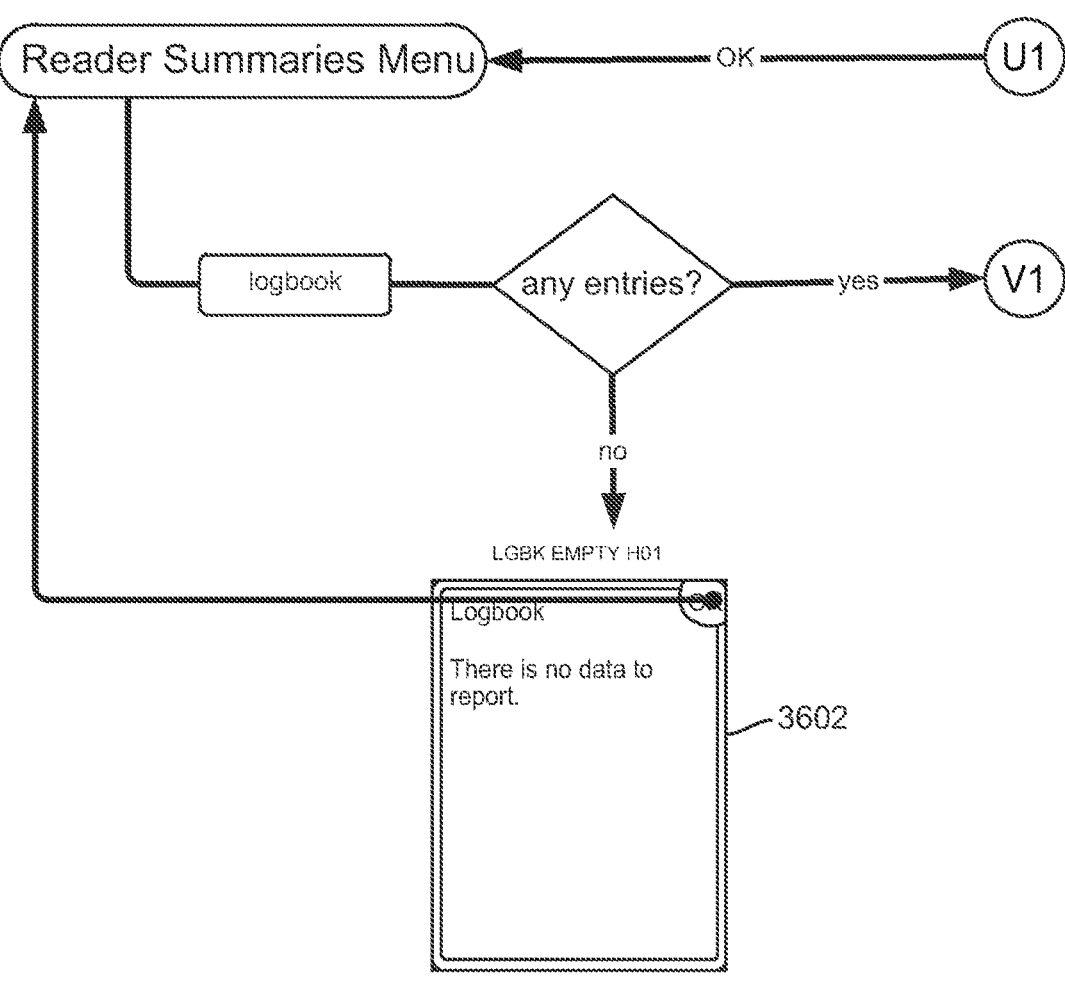
FIGS. 22A-22F illustrate a Logbook Interface for displaying, adding and/or editing logbook entries on a Reader, according to embodiments of the present disclosure.
Figure 22B:
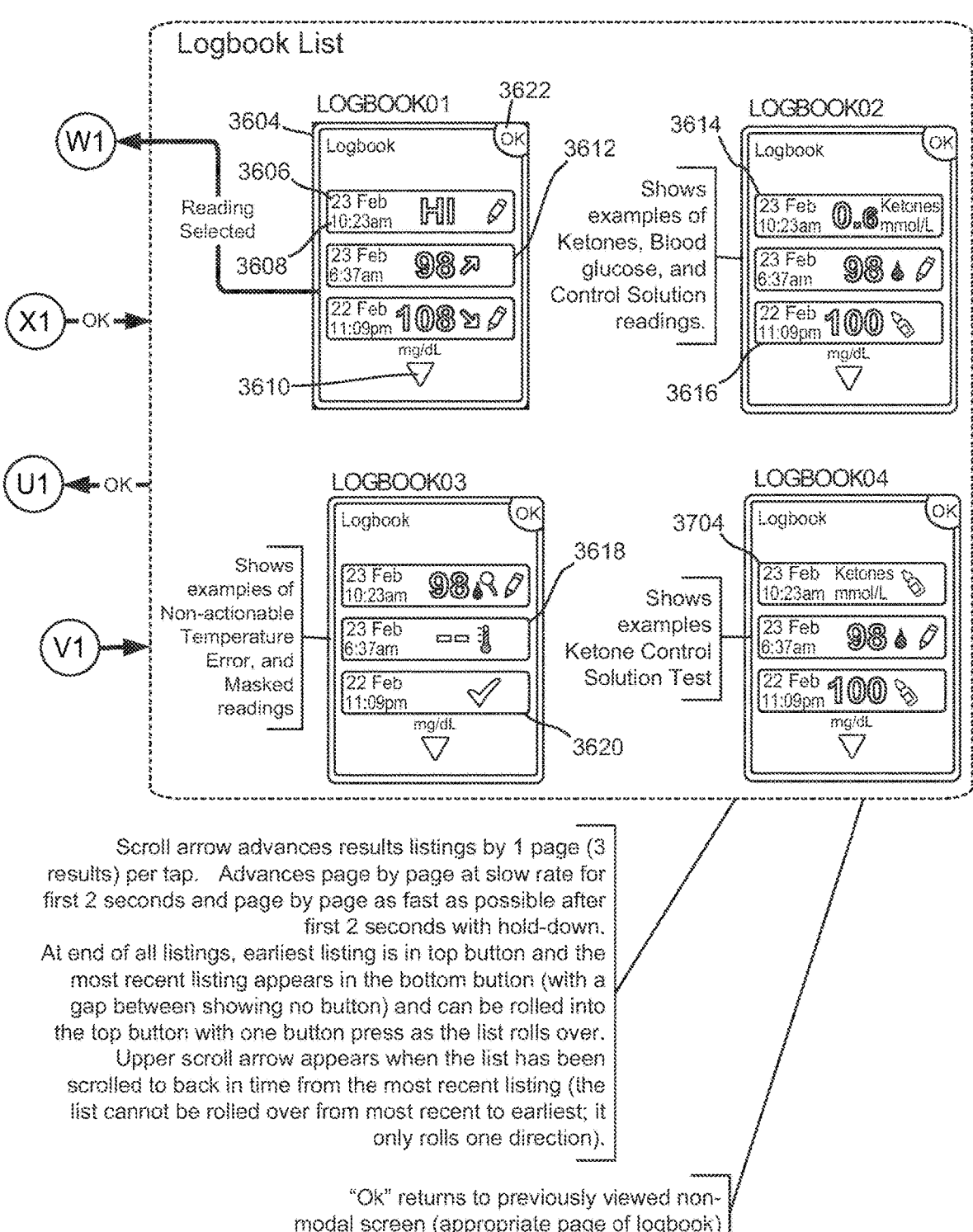

The Logbook Interface 3600, shown in FIG. 22A, may be accessed from the Consecutive Scans Interface (see FIG. 9), the Insulin Calculator Interface (see FIG. 17), and the Reader Summaries Interface (see FIG. 21). From the Reader Summaries Menu screen (see FIG. 21), pressing the Logbook touchscreen button advances the graphical user interface into the Logbook Interface 3600 (see FIG. 22). If there are no entries in the logbook, the Logbook Empty screen 3602 is displayed, indicating that there is no data to report in the logbook (see FIG. 22A). If there are one or more entries in the logbook, then the Logbook List screen 3604 is displayed via reference path (V1) (see FIG. 22B). FIG. 22B shows various examples of Logbook List screens and the type of logbook entries that may be displayed. Each logbook entry displays the date 3606 and time 3608 associated with its corresponding logbook entry. Three logbook entries may be displayed per screen. The Logbook List screen includes a down arrow 3610, and in some embodiments an up arrow (not shown) that may be pressed to scroll down or up, respectively, through the logbook entries in the Logbook List screens. The Logbook List screen may be scrolled page by page by pressing the up arrow (not shown) touchscreen button or the down arrow 3610 touchscreen button to scroll through the Logbook List screens as desired. For example, the Logbook List screens may be scrolled page by page by tapping the up arrow (not shown) or the down arrow 3610. In some embodiments, the pages scroll at a slow rate for the first 2 seconds and at a faster rate after 2 seconds when the up or down arrow is pressed and held.

Referring to FIG. 22B, various examples of Logbook List screens and the type of logbook entries that may be displayed are shown. For example, the Logbook List screen may display a logged glucose level 3612. The logged glucose level 3612 may be displayed as a number corresponding to the user's glucose level in mg/dL. The glucose level may have an upward trend arrow or a downward trend arrow associated with the glucose level, indicating a rising trend in glucose readings or a decreasing trend in glucose readings, respectively. In some cases, if the logged glucose reading was above a maximum threshold level, "HI" may be displayed instead of a numerical glucose level, indicating that the glucose level exceeded a maximum threshold level. Similarly, if the logged glucose reading was below a minimum threshold level, "LO" may be displayed instead of a numerical glucose level, indicating that the glucose level was below a minimum threshold level. In some instances, the glucose reading may be associated with a Note icon (e.g., a picture of a pencil), indicating that a note was entered with the logged glucose level.

In some instances, the Logbook List screen may display a logged ketone level 3614. The logged ketone level 3614 may be displayed as a number corresponding to the user's ketone level in mmol/L. In some instances, the Logbook List screen may display a logged glucose control solution test level 3616. The logged glucose control solution test level 3616 may be displayed as a number corresponding to the glucose control solution level in mg/dL. The glucose control solution test level 3616 may be associated with a corresponding control solution icon (e.g., a picture of a bottle of control solution). In some instances, the Logbook List screen may display a logged ketone control solution test level 3704. The logged ketone control solution test level 3704 may be displayed as a number corresponding to the ketone control solution level in mmol/L. The ketone control solution test level 3704 may be associated with a corresponding control solution icon (e.g., a picture of a bottle of control solution). In some instances, the Logbook List screen may display a logged temperature error 3618. The temperature error may be a low temperature error associated with a low temperature error icon (e.g., a picture of a blue thermometer), or a high temperature error associated with a high temperature error icon (e.g., a picture of a red thermometer). In some instances, the Logbook List screen may display a logged masked reading 3620. The logged masked reading may be associated with a masked reading icon (e.g., a checkmark icon). The Logbook List screen 3604 includes an "OK" touchscreen button 3622, which, when pressed, returns the graphical user interface to the previous screen displayed before entering the Logbook Interface 3600 (e.g., the Consecutive Scans Interface (see FIG. 9), the Insulin Calculator Interface (see FIG. 17), or the Reader Summaries Interface (see FIG. 21)). For example, pressing "OK" touchscreen button 3622 may cause the graphical user interface to return to the Reader Summaries Interface (see FIG. 21) via reference path (U1) (see FIG. 22A).

Figure 22C:
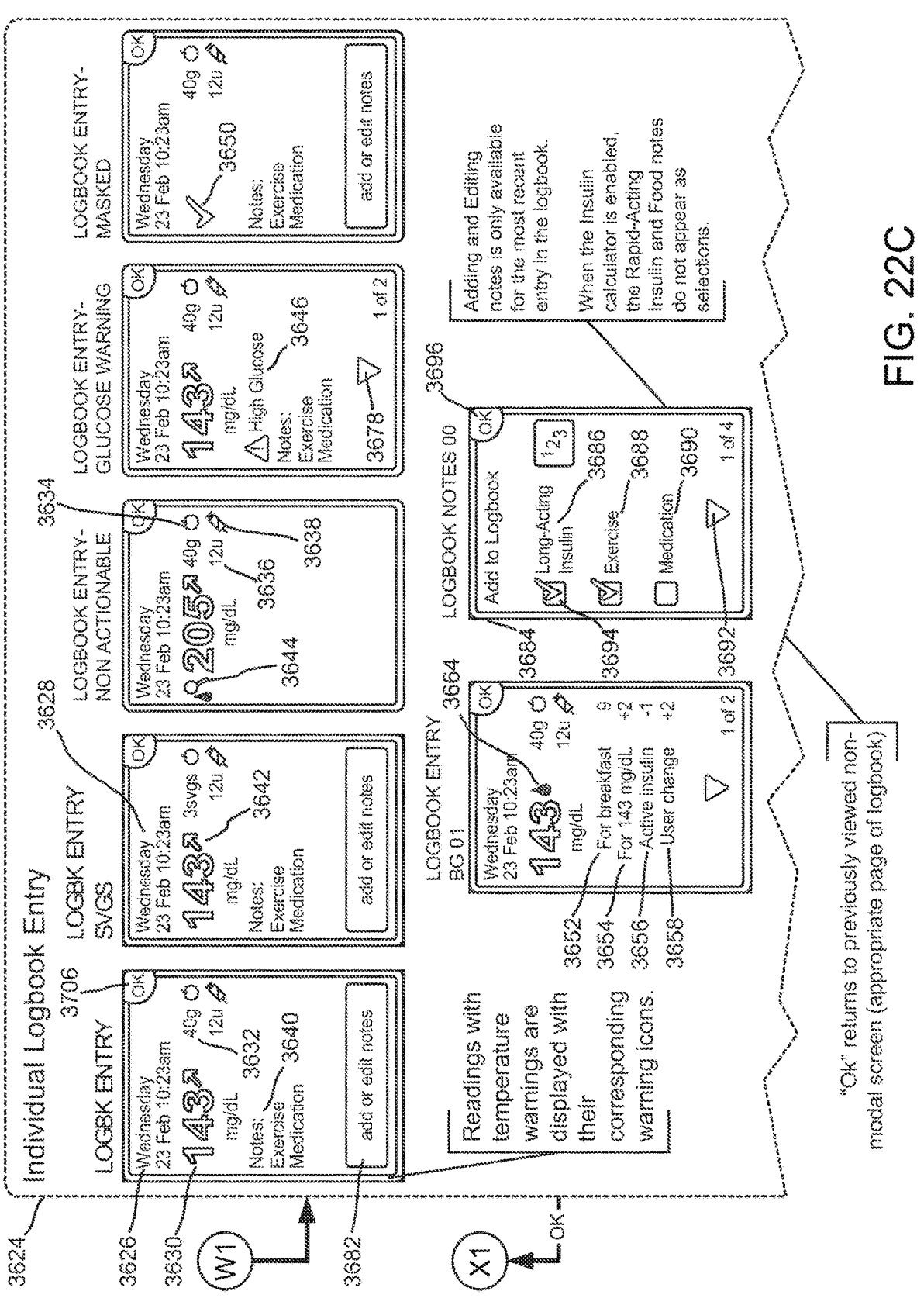
Figure 22D:
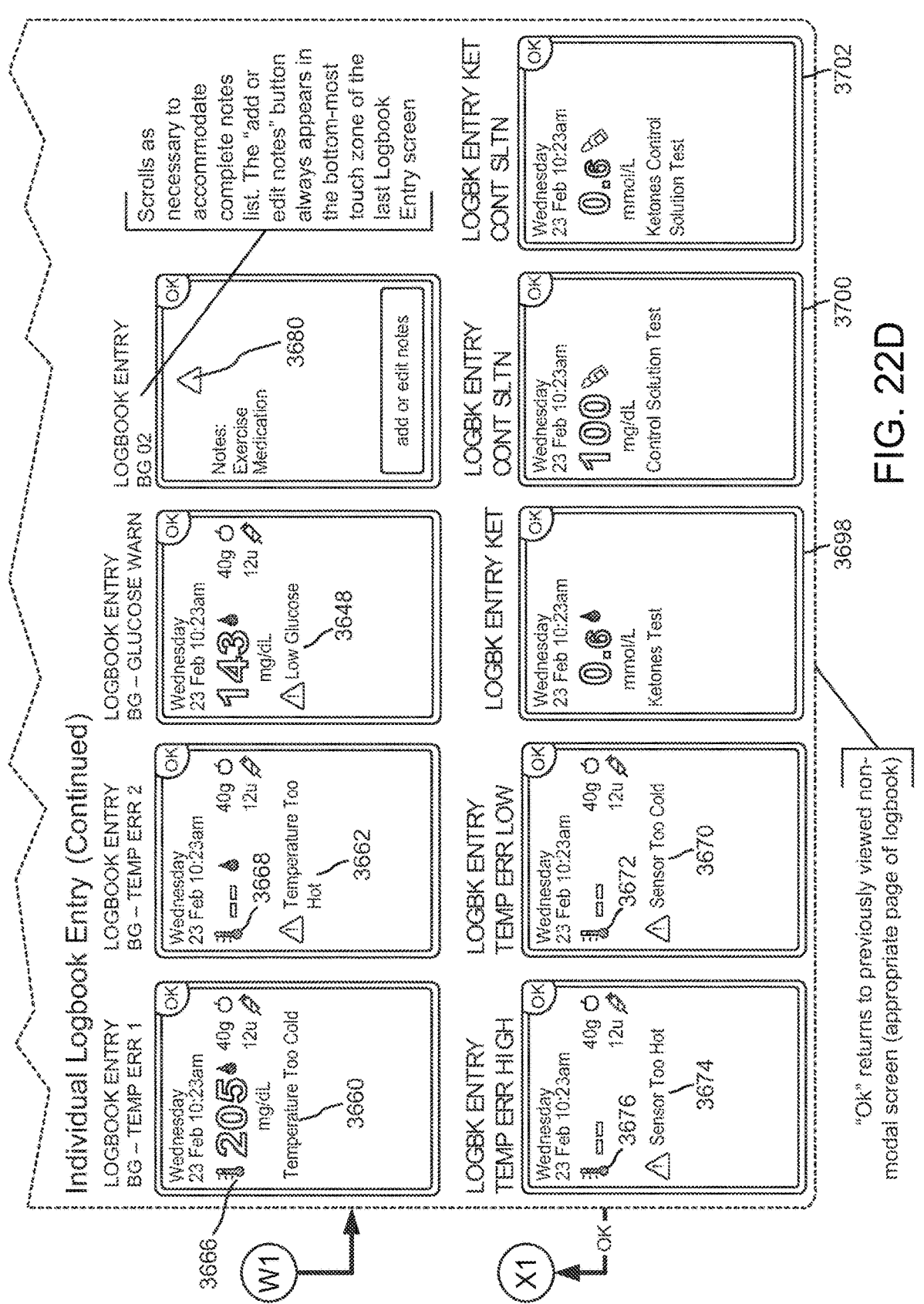

Each logbook entry on the Logbook List screen 3604 is a touchscreen button. Pressing a logbook entry on the Logbook List screen 3604 advances the graphical user interface to the Individual Logbook Entry screen 3624 associated with the selected logbook entry via reference path (W1) (see FIGS. 22C and 22D). Various examples of Individual Logbook Entry screens 3624 are shown in FIGS. 22C and 22D.

If a logged glucose level is selected from the Logbook List screen 3604, the glucose level individual logbook entry screen 3626 is displayed. The glucose level individual logbook entry screen 3626 includes one or more of the following information: the date and time 3628 of the logged glucose level; the glucose reading 3630 in mg/dL; the amount of carbs 3632 (if any); an meal icon 3634 indicating whether the logged glucose reading was pre-meal or post-meal (e.g., a whole apple icon for pre-meal readings or a eaten apple icon for post-meal readings); a suggested insulin dose 3636 (if any) and/or a suggested insulin dose icon 3638 (e.g., a syringe icon); notes 3640 that were associated with the logged glucose reading (if any); a glucose level trend arrow 3642 (e.g., an upward or a downward trend arrow), as appropriate; an non-actionable icon 3644 indicating that the glucose reading is non-actionable; a high glucose level warning 3646 (as text and/or a warning icon); a low glucose level warning 3648 (as text and/or a warning icon); an masked icon 3650 indicating that the glucose reading is masked (e.g., a checkmark icon); suggested insulin dose details (e.g., amount of carbs 3652, suggested insulin dose 3654, IOB 3656, user adjustments to the suggested insulin dose 3658); a low temperature error warning 3660 (e.g., as text and/or a low temperature warning icon 3666, such as a blue thermometer icon); a high temperature error warning 3662 (e.g., as text and/or a high temperature warning icon 3668, such as a red thermometer icon); an icon indicating that the glucose reading was obtained via test strip or via sensor (e.g., a drop of blood icon 3664 for readings obtained via test strip); a sensor low temperature error warning 3670 (e.g., as text and/or a sensor low temperature warning icon 3672, such as a blue thermometer); and a sensor high temperature error warning 3674 (e.g., as text and/or a sensor high temperature warning icon 3676, such as a blue thermometer icon).

If notes are associated with the logged glucose reading and the notes will not all fit on one screen, the Individual Logbook Entry screen 3626 may include a down arrow 3678 (see FIG. 22C), and in some embodiments an up arrow 3680 (see FIG. 22D) that may be pressed to scroll down or up, respectively, through the notes. The Individual Logbook Entry screen 3626 may include an "Add or edit notes" touchscreen button 3682, which, when pressed, causes graphical user interface to display the Add to Logbook screen 3684. The Add to Logbook screen 3684 includes a list of several different user selectable notes that may be entered into the Logbook. The list of user selectable notes may include one or more of the following: long-acting insulin 3686, exercise 3688, medication 3690, and the like. In certain embodiments, 3 user-selectable notes are displayed on the touchscreen at once. If there are more than 3 user-selectable notes, the list of notes may be scrolled as necessary to view the list using scroll touchscreen buttons, such as down arrow (e.g., down triangle) touchscreen button 3692 and up arrow (e.g., up triangle) touchscreen button (not shown). One or more user-selectable notes may be selected by touching the touchscreen checkbox adjacent the note desired to be selected. Touching a touchscreen checkbox will toggle the checkbox from a checked to unchecked state indicating whether the associated not is selected or not selected, respectively. For instance, the long-acting insulin note may be selected by touching the touchscreen checkbox 3694, which then displays a check mark in the touchscreen checkbox to indicate that the rapid-acting insulin note has been selected. The other user-selectable notes may be selected or unselected (e.g., checked or unchecked) as desired in an analogous manner. The selection of notes may be saved by pressing the "OK" touchscreen button 3696, which saves the selection of user-selectable notes and returns the graphical user interface to the previous individual logbook entry screen 3626.

If a logged ketone level is selected from the Logbook List screen 3604, the ketone level individual logbook entry screen 3698 is displayed, which displays the logged ketone reading in mmol/L. If a logged glucose control solution test is selected from the Logbook List screen 3604, the glucose control solution test level individual logbook entry screen 3700 is displayed, which displays the logged glucose control solution test reading in mg/dL. If a logged ketone control solution test is selected from the Logbook List screen 3604, the ketone control solution test level individual logbook entry screen 3702 is displayed, which displays the logged ketone control solution test reading in mmol/L.

Figure 22E:
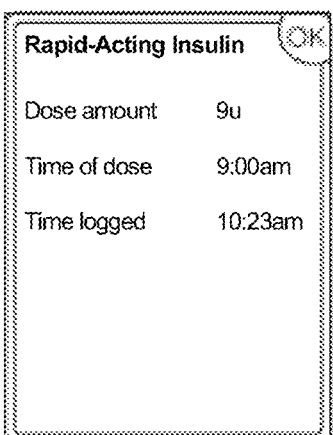
Figure 22F:
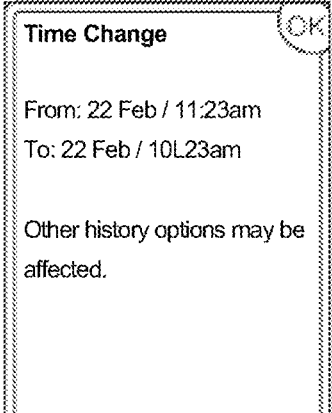

Additional Individual Logbook Entry screens include an unlogged dose of rapid-acting insulin, FIG. 22E, and a time change, FIG. 22F. The logbook entry of an unlogged dose of rapid acting insulin may include the dose amount information, time of dose information and time logged information. The logbook entry of a time change entry may include the before and after time change information. Time change logs may additionally include a warning that other historical options may be affected by the time change. Further, in certain embodiments, the user may be prompted to with a query regarding whether the user forgot to log any insulin dose since a set time (based on the duration of the insulin action, for example). If the user responds in the affirmative, the user is prompted further to enter the unlogged insulin dose information so that previously unlogged dose is logged in the logbook.

The Individual Logbook Entry screen 3626 includes an "OK" touchscreen button 3706, which, when pressed, returns the graphical user interface to the Logbook List screen 3604 via reference path (X1).

Strip/Hardware Errors Interface

An exemplary embodiment of a graphical user interface which may be utilized in connection with a Reader as described herein and which facilitates a procedure for displaying strip/hardware errors 3710 is provided. This graphical user interface is now described in greater detail with reference to FIG. 23.

Figure 23A:
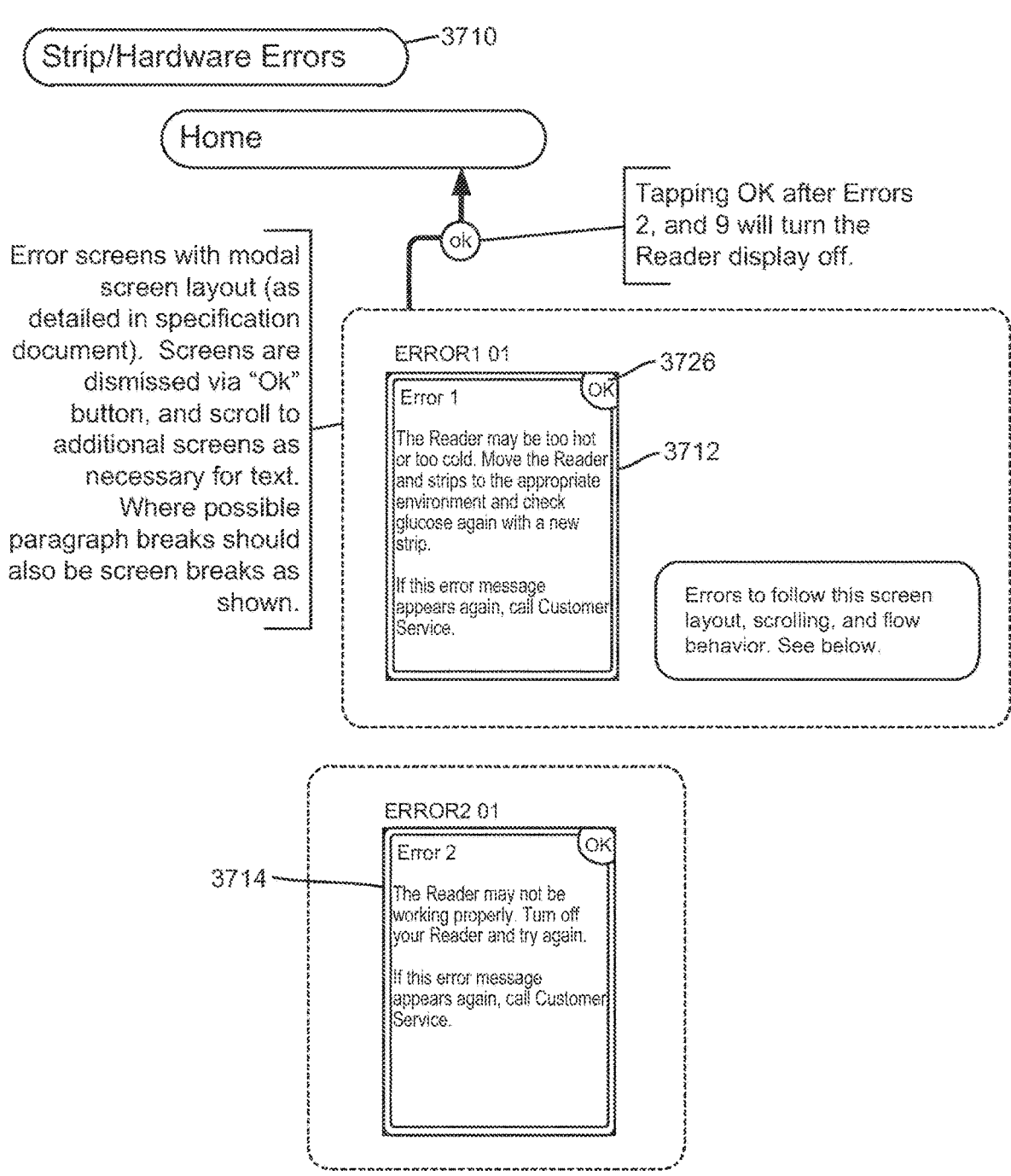
FIGS. 23A-23C illustrate a Strip/Hardware Errors Interface for displaying error messages on a Reader and steps for recovering date and time following time loss, according to embodiments of the present disclosure.
Figure 23B:
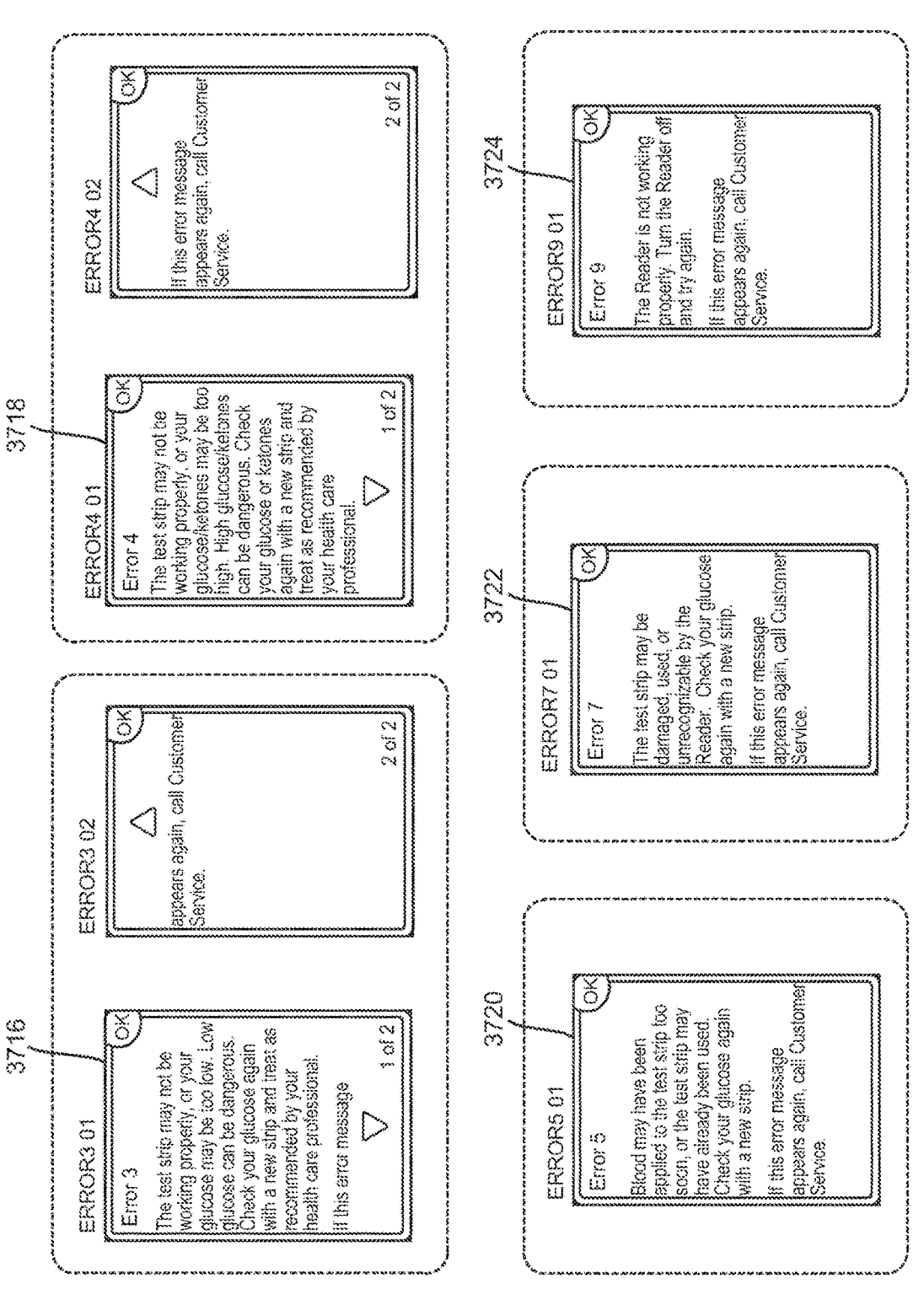

The Strip/Hardware Errors Interface 3710, shown in FIGS. 23A and 23B, may display strip and/or hardware errors as necessary as any relevant errors occur. A variety of different error messages may be displayed. For example, an "Error 1" screen 3712 may be displayed if the Reader detects a temperature error. The "Error 1" screen may display a message indicating that the Reader may be too hot or too cold, and that the user should move the Reader and strips to the appropriate environment and check glucose again with a new strip. "Error 1" screen may also display a message indicating that if this message appears again, the user should call Customer Service.

In certain embodiments, the Strip/Hardware Errors Interface 3710 may display an "Error 2" screen 3714 if the Reader may not be functioning properly. The "Error 2" screen 3714 may display a message indicating that the Reader may not be functioning properly and that the user should turn off the Reader and try again. The "Error 2" screen 3714 may also display a message indicating that if this message appears again, the user should call Customer Service.

In certain embodiments, the Strip/Hardware Errors Interface 3710 may display an "Error 3" screen 3716 if the test strip may not be working properly or if the user's glucose may be too low. The "Error 3" screen 3716 may display a message indicating that the test strip may not be working properly or the user's glucose may be too low. The "Error 3" screen 3716 may also display a message indicating that low glucose can be dangerous and that the user should check their glucose again with a new strip and treat as recommended by the user's health care professional. The "Error 3" screen 3716 may also display a message indicating that if this message appears again, the user should call Customer Service.

In certain embodiments, the Strip/Hardware Errors Interface 3710 may display an "Error 4" screen 3718 if the test strip may not be working properly or if the user's glucose/ketones may be too high. The "Error 4" screen 3718 may display a message indicating that the test strip may not be working properly or the user's glucose/ketones may be too high. The "Error 4" screen 3718 may also display a message indicating that high glucose/ketones can be dangerous and that the user should check their glucose or ketones again with a new strip and treat as recommended by the user's health care professional. The "Error 4" screen 3718 may also display a message indicating that if this message appears again, the user should call Customer Service.

In certain embodiments, the Strip/Hardware Errors Interface 3710 may display an "Error 5" screen 3720 if blood may have been applied to the test strip too soon or the test strip may have already been used. The "Error 5" screen 3720 may display a message indicating that blood may have been applied to the test strip too soon or the test strip may have already been used. The "Error 5" screen 3720 may also display a message indicating that the user should check their glucose again with a new strip. The "Error 5" screen 3720 may also display a message indicating that if this message appears again, the user should call Customer Service.

In certain embodiments, the Strip/Hardware Errors Interface 3710 may display an "Error 7" screen 3722 if the test strip may be damaged, used, or unrecognizable be the Reader. The "Error 7" screen 3722 may display a message indicating that the test strip may be damaged, used, or unrecognizable be the Reader. The "Error 7" screen 3722 may also display a message indicating that the user should check their glucose again with a new strip. The "Error 7" screen 3722 may also display a message indicating that if this message appears again, the user should call Customer Service.

In certain embodiments, the Strip/Hardware Errors Interface 3710 may display an "Error 9" screen 3724 if the Reader is not working properly. The "Error 9" screen 3724 may display a message indicating that the Reader is not working properly. The "Error 9" screen 3724 may also display a message indicating that the user should turn off the Reader and try again. The "Error 9" screen 3724 may also display a message indicating that if this message appears again, the user should call Customer Service.

The error screens include an "OK" touchscreen button 3726, which, when pressed, returns the graphical user interface to the Home Screen. In certain embodiments, pressing the "OK" touchscreen button 3726 from either the "Error 2" screen 3714 or the "Error 9" screen 3724 will cause the Reader display to turn off. The Reader may be activated by inserting a test strip or by pressing the hardware power button.

System Time Loss

Figure 23C:
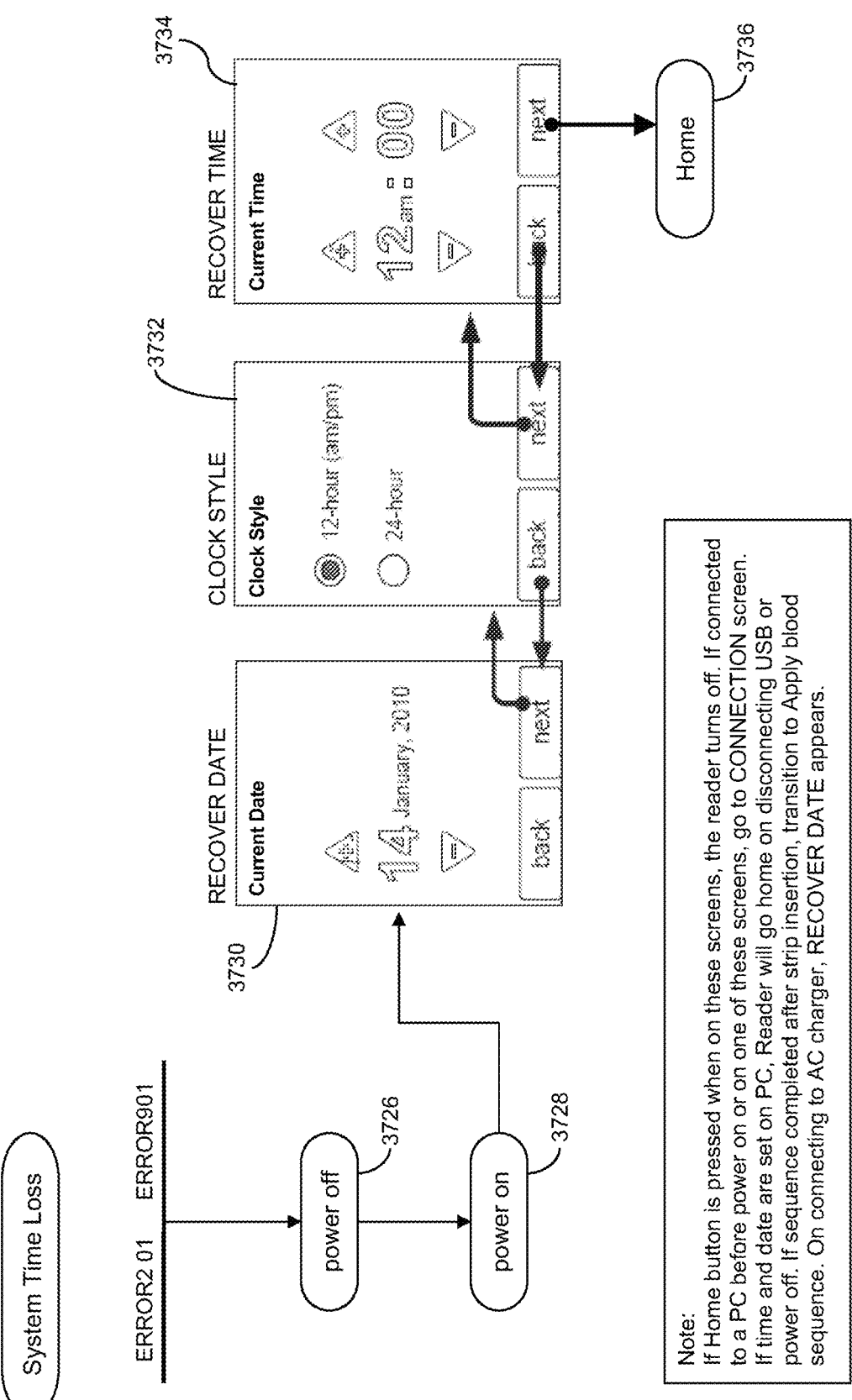

Upon restart of the device after a system time loss, a time recovery display screen may be displayed. FIG. 23C illustrates steps to recover the date and time following a system time loss. After a device power off, shown at block 3726, due to one or more errors, the user presses the home button or inserts a test strip to power on the device 3728. Upon power on, the device navigates to a time recovery flow of display screens, beginning with recover date 3730, clock style set 3732 and recover time 3734. The steps to recover date and time following a system time loss are similar to those described herein below with respect to first setup of the device. After the current date and time are entered into the device, pressing the "next" button on the final recover screen will navigate the device back to the home screen, as shown at block 3736.

Setup

An exemplary embodiment of a graphical user interface which may be utilized in connection with a reader as described herein and which facilitates a Setup procedure 2000 is provided. This graphical user interface is now described in greater detail with reference to FIGS. 24-27 and 29-33.

First Start Interface

A graphical user interface which facilitates a Setup procedure 2000 of the reader may include a First Start Interface 2001. First Start Interface 2001 begins with the display of an introduction screen 2002, e.g., for approximately 3 seconds. This introduction screen 2002 may include text and/or graphics designed to identify the manufacturer of the reader and/or the graphical user interface, e.g., the introduction screen 2002 may include the FreeStyle® butterfly trademark depicted in FIG. 24.

Language Selection

Following display of the introduction screen 2002, one or more Language Selection Screens 2003 are provided. In one embodiment, there is no default selection and the "OK" touch-screen button 2004 appears only after a language selection has been made, e.g., by touching the empty circle 2006 next to the language to be selected. The language selection options may be displayed in alphabetical order. If the list of language selection options includes more than 4 languages, the list may be scrolled as necessary to view the list using scroll touch-screen buttons 2005. The language list may be minimized by region and the order of language selection may be modified at a later time.

Date Selection

Figure 24:
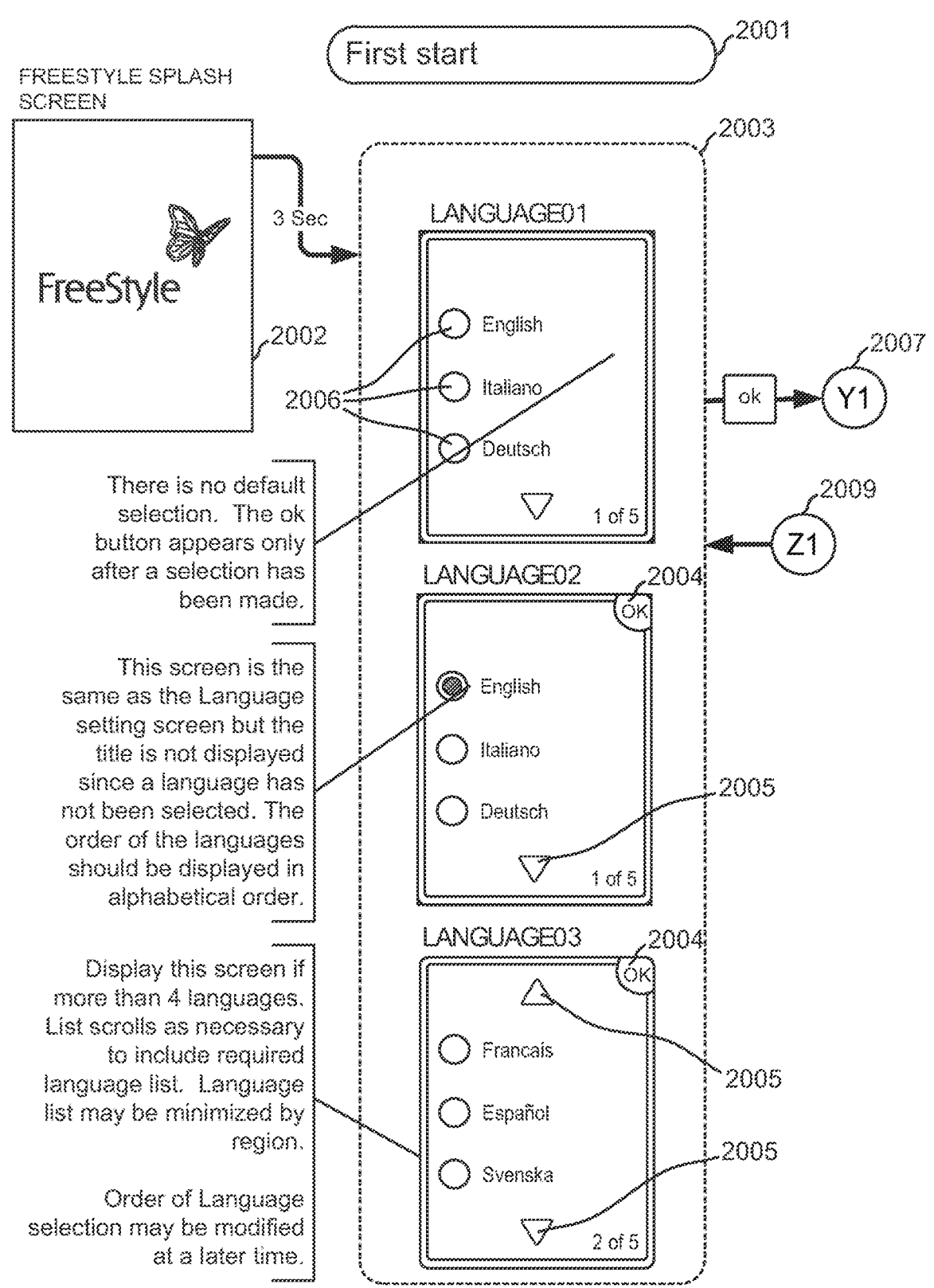
FIG. 24 illustrates methods for first starting an analyte monitoring device, according to one embodiment.
Figure 24:
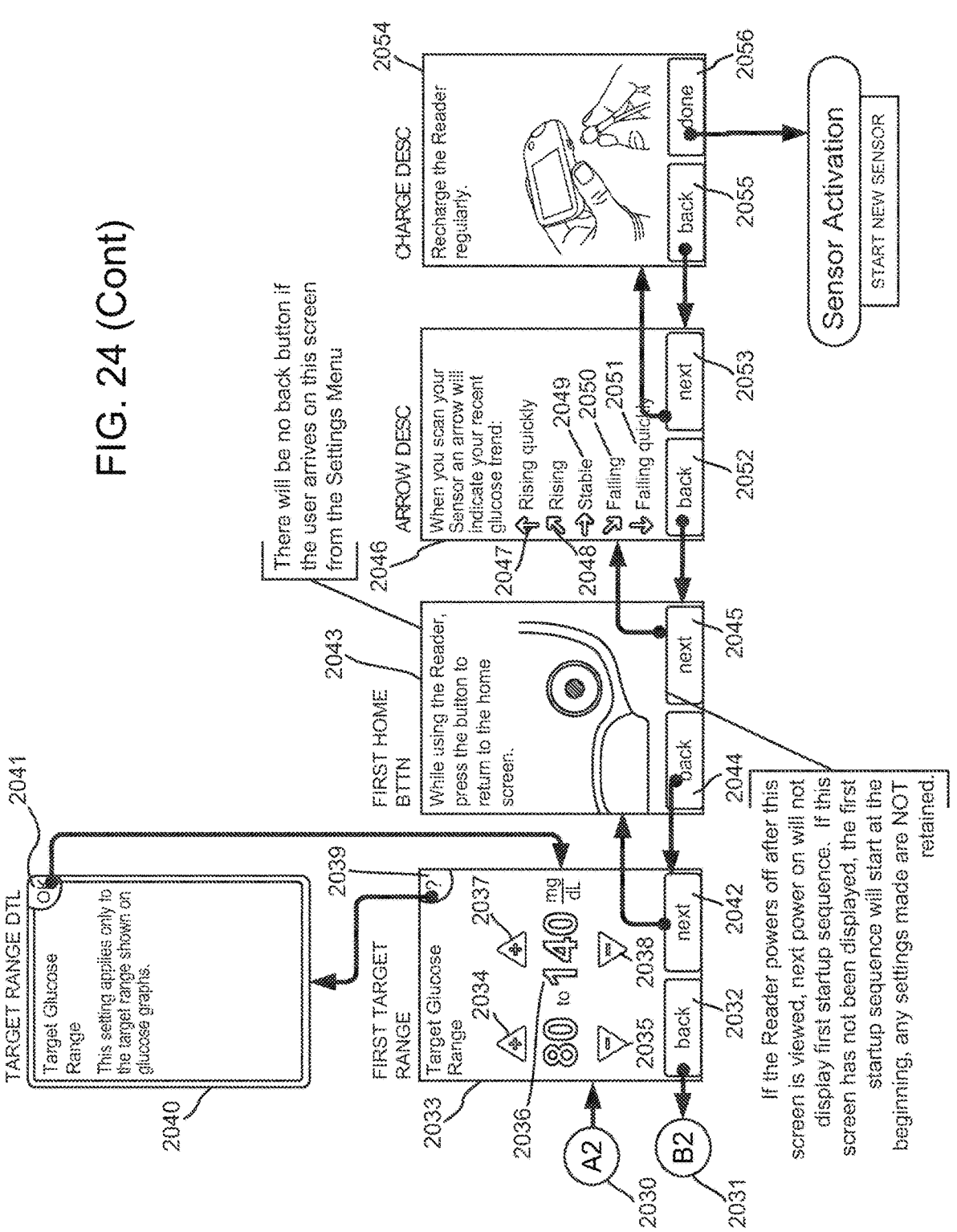

Once the language selection has been made by pressing an empty circle 2006 next to a language to be selected followed by the "OK" touch-screen button 2004, a First Date Selection Screen 2008 is displayed. This is depicted in FIG. 24 by reference path (Y1) 2007. At this stage, a user may return to the one or more Language Selection Screens via reference path (Z1) 2009 by pressing touch-screen "back" button 2010 if desired. First Date Selection Screen 2008 provides a prompt 2011 to enter the current date along with a sample date 2012 which can be adjusted to the current date by the user. First Date Selection Screen 2008 also includes touch-screen up-arrow 2013 and touchscreen down-arrow 2014 by which the sample date 2012 may be adjusted by the user. For example, the sample date 2012 may be adjusted by 1 day increments by tapping the up arrow 2013 or the down arrow 2014. In one embodiment, the date increases or decreases as appropriate at a slow-rate for the first 2 seconds and at a faster rate after 2 seconds when the up or down arrow is pressed and held. The date format is set for SKU by region (U.S. format depicted in FIG. 24), which applies to all screens showing date.

Clock Style Selection

The user may move to the next screen in the graphical user interface Setup procedure 2000 by pressing touchscreen "next" button 2015, which causes First Clock Style Selection Screen 2016 to be displayed. At this stage, a user may return to the First Date Selection Screen 2008 by pressing touch-screen "back" button 2018 if desired. First Clock Style Selection Screen 2016 provides a prompt 2017 to select a clock style, e.g., 12-hour (am/pm) or 24-hour by touching the empty circle 2019 next to the clock style to be selected. Note that FIG. 24 depicts a selection of 12-hour (am/pm) as the clock style.

Time Selection

The user may move to the next screen in the graphical user interface Setup procedure 2000 by pressing touchscreen "next" button 2020, which causes First Time Selection Screen 2021 to be displayed. At this stage, a user may return to the First Clock Style Selection Screen 2016 by pressing touch-screen "back" button 2022 if desired. First Time Selection Screen 2021 provides a prompt 2023 to enter the current time. As depicted in FIG. 24, First Time Selection Screen 2021 includes a first touchscreen up-arrow 2024 and a first touchscreen down-arrow 2025 for adjusting the hour increments of time 2026. First Time Selection Screen 2021 also includes a second touchscreen up-arrow 2027 and a second touchscreen down-arrow 2028 for adjusting the minute increments of time 2026. The initial time format (12 or 24 hour) is displayed as set for the appropriate region. Using the relevant up and down-arrows Time adjusts by 1 minute or 1 hour increments with arrow click. When pressing and holding the up or down-arrows, the appropriate time increments scroll at slow rate for the first 2 seconds and at faster rate after 2 seconds.

Target Glucose Range Selection

Once the current time has been entered on First Time Selection Screen 2021, the user can move to the next screen in the Setup procedure 2000 by pressing touchscreen "next" button 2029, which causes First Target Range Selection Screen 2033 to be displayed. This is depicted in FIG. 24 by reference path (A2) 2030. At this stage, the user may return to the First Time Selection Screen 2021 via reference path (B2) 2031 by pressing touchscreen "back" button 2032 if desired. First Target Range Selection Screen 2033 provides a first touchscreen up-arrow 2034 and a first touchscreen down-arrow 2035 for adjusting the low end (e.g., 80 mg/dL) of target glucose range 2036. First Target Range Selection Screen 2033 also provides a second touchscreen up-arrow 2037 and a second touchscreen down-arrow 2038 for adjusting the high end (e.g., 140 mg/dL) of target glucose range 2036. First Target Range Selection Screen 2033 also provides a touchscreen button "?" 2039, which, when pressed, provides a Target Range Details (DTL) screen 2040, which may display additional information related to the target glucose range 2036. Target Range Details (DTL) screen 2040 includes a touchscreen "OK" button 2041, which, when pressed, returns the user to the First Target Range Selection Screen 2033.

First Home Button

Once the target glucose range has been entered on First Target Range Selection Screen 2033, the user can move to the next screen in the Setup procedure 2000 by pressing touchscreen "next" button 2042, which causes First Home Button (BTTN) Screen 2043 to be displayed. The First Home Button (BTTN) Screen 2043 includes a prompt describing the function of the home button of the reader. For example, the prompt may be a text prompt which states "While using the Reader, press the button to return to the home screen" or the equivalent. This text may be provided with a graphical depiction of the location of the home button on the reader as shown in FIG. 24. At this stage, the user may return to the First Target Range Selection Screen 2033 by pressing touchscreen "back" button 2044 if desired. No "back" button will be displayed if the user arrives at the First Home Button Screen 2043 from the Settings Menu (discussed in greater detail below) If the reader powers off after this screen is viewed, the next power on event will not result in display of the First Start Interface startup sequence described above. If this screen has not been displayed, the First Start Interface startup sequence will start at the beginning, and any settings made are NOT retained.

Arrow Description Screen

Pressing the touchscreen "next" button 2045 displayed on the First Home Button Screen 2043 results in the display of Arrow Description Screen 2046, which includes a description of various trending arrows utilized by the graphical user interface to convey glucose trend information. For example, the Arrow Description Screen 2046 may display a text prompt which states "When you scan your Sensor an arrow will indicate your recent glucose trend" or the equivalent. This text prompt may be followed by various arrows and associated descriptions of the trending information conveyed thereby. For example, a first arrow 2047 pointing straight up may indicate that the user's glucose level is "Rising quickly", a second arrow 2048 pointing up and to the right at an approximately 45 degree angle may indicate that the user's glucose level is "Rising" or the equivalent, a third arrow 2049 pointing straight to the right may indicate that the user's glucose level is "Stable" or the equivalent, a fourth arrow 2050 pointing down and to the right at an approximately 45 degree angle may indicate that the user's glucose level is "Falling" or the equivalent, and a fifth arrow 2051 may indicate that the user's glucose level is "Falling quickly" or the equivalent. At this stage, the user may return to the First Home Button Screen 2043 by pressing touchscreen "back" button 2052 if desired.

Charge Description Screen

Pressing the touchscreen "next" button 2053 displayed on Arrow Description Screen 2046 results in the display of Charge Description Screen 2054. Charge Description Screen 2054 provides a text prompt reminding the user to recharge the reader on a regular basis. For example, Charge Description Screen 2054 may display the text prompt "Recharge the Reader regularly" or the equivalent. Charge Description Screen 2054 may also display a graphic demonstrating to the user how to connect the reader to a power source for recharging purposes. At this stage, the user may return to the Arrow Description Screen 2046 by pressing touchscreen "back" button 2055 if desired. Charge Description Screen 2054 also includes a touchscreen "done" button 2056, which, when pressed, completes the First Start Interface 2001. At this point, a sensor activation procedure may be implemented.

Settings Interface

A graphical user interface which facilitates a Setup procedure 2000 may include a Settings Interface 2057 which includes a Settings Menu 2058 which may be displayed on the reader. Settings Menu 2058 includes a first settings screen 2059, a second settings screen 2060, and a third settings screen 2061. First settings screen 2059 includes the following menu items: "Sounds", "Target Range", and "Control Solution Test." Each of these menu items is represented by a corresponding touchscreen button (touchscreen buttons 2062, 2063 and 2064 respectively). Second settings screen 2060 includes the following menu items: "Time & Date", "Display Brightness", and "Language". Each of these menu items is represented by a corresponding touchscreen button (touchscreen buttons 2065, 2066 and 2067 respectively). Finally, third settings screen 261 includes the following menu items: "System Status", "Calculator Settings", "Reader Basics", and "Professional Options". Each of these menu items is represented by a corresponding touchscreen button (touchscreen buttons 2068, 2069, 2070 and 2071 respectively). Touchscreen scroll buttons 2072, 2073, 2074 and 2075 may be used as appropriate to scroll between the first, second and third settings screens.

Sounds

Figure 25:
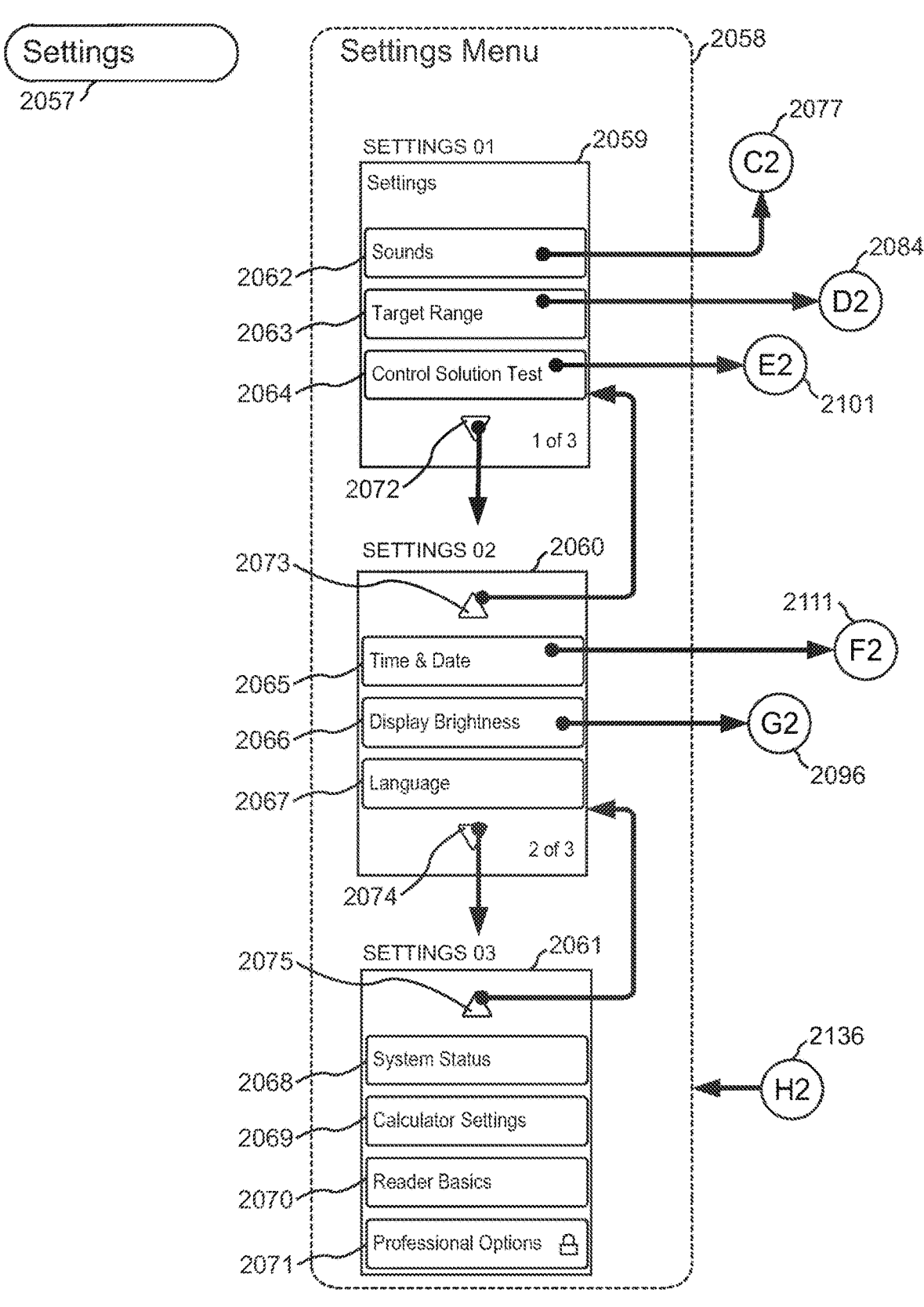
FIG. 25 illustrates a method of entering settings on an analyte monitoring device, according to one embodiment.
Figure 25:
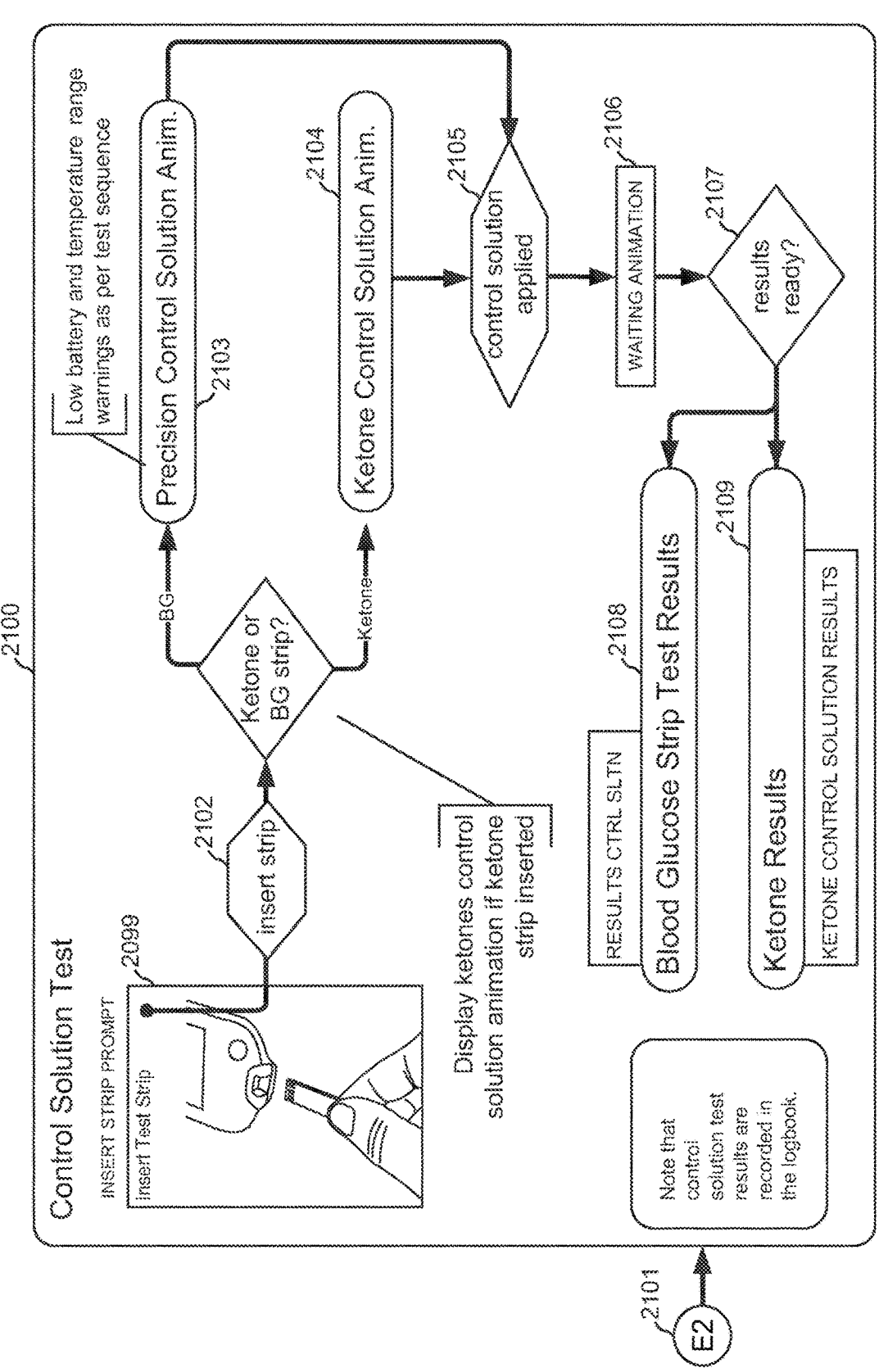
Figure 25:
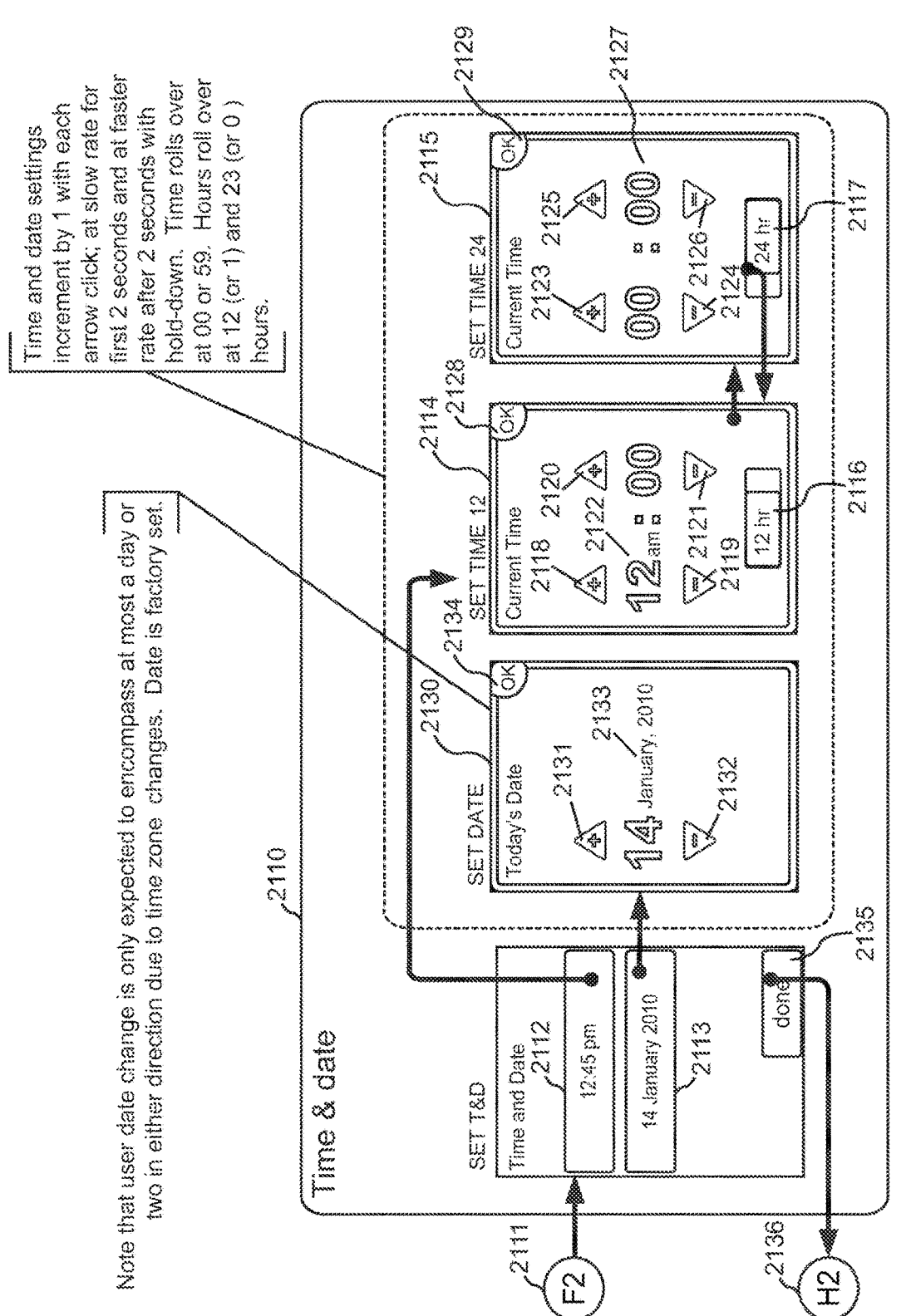

Pressing touchscreen button 2062 ("Sounds") results in the display of sound settings screen 2076. This is depicted in FIG. 25 by reference path (C2) 2077. Sound settings screen 2076 includes touchscreen toggle settings for "Volume" 2078, "Notification Tone" 2079, "Notification Vibrate" 2080, and "Button Tone" 2081. Sounds and vibration can be toggled on or off with these settings. Button sounds include, e.g., key presses and interactive notifications (e.g., result ready). The first two options impact screens that broadcast Notification, Confirmation and Reminder signals. Default button sound is Off. Default notification sound is On while vibration is Off. For hold-down scrolling, a sound is made for the initial touch only. Once the desired sound settings selections have been made using the touchscreen toggle settings, the settings can be accepted by touching touchscreen "OK" button 2082.

Target Range

Pressing touchscreen button 2063 ("Target Range") results in the display of Target Range settings screen 2083. This is depicted in FIG. 25 by reference path (D2) 2084. Target Range settings screen 2083 provides a first touchscreen up-arrow 2085 and a first touchscreen down-arrow 2086 for adjusting the low end (e.g., 70 mg/dL) of target glucose range 2089. Target Range settings screen 2083 also provides a second touchscreen up-arrow 2087 and a second touchscreen down-arrow 2088 for adjusting the high end (e.g., 130 mg/dL) of target glucose range 2089. At this stage, the user may return to first settings screen 2059 via reference path (D2) 202084 by pressing touchscreen "back" button 2093 if desired. The current settings can be selected by pressing touchscreen "done" button 2094. Target Range settings screen 2083 also provides a touchscreen button "?" 2090, which, when pressed, provides a Target Range Details (DTL) screen 2091, which may display additional information related to the target glucose range 2089. Target Range Details (DTL) screen 2091 includes a touchscreen "OK" button 2092, which, when pressed, returns the user to the Target Range settings screen 2083.

Display Brightness

Pressing touchscreen button 2066 ("Display Brightness") results in the display of Display Brightness settings screen 2095. This is depicted in FIG. 25 by reference path (G2) 2096. Display Brightness settings screen 2095 provides settings for "High", "Medium", and "Low" display brightness, which can be selected by touching one of empty circles 2097. Note that FIG. 25 shows the "High" brightness setting selected. Once the desired display brightness has been selected by pressing one of the empty circles 2097, the setting can be accepted by touching touchscreen "OK" button 2098.

Control Solution Test

Pressing touchscreen button 2064 ("Control Solution Test") results in the display of an "Insert Test Strip" (or the equivalent) prompt 2099 and initiates a Control Solution Test protocol as shown in flow-diagram 2100. This is depicted in FIG. 25 by reference path (E2) 2101. Generally, a test strip is inserted into the reader (Step 2102). Depending on whether the test strip is a blood glucose (BG) or ketone test strip, a corresponding Precision Control Solution animation (Step 2103) or a Ketone Control Solution animation (Step 2104) is displayed. See, e.g., FIG. 35 for respective Precision Control Solution animation and Ketone Control Solution animation. Once the appropriate control solution is applied (Step 2105), a waiting animation is displayed (Step 2106) while the results are processed. See, e.g., FIG. 34, described earlier in the Blood Glucose Strip Test and Ketone Strip Test section earlier. Once the results are ready (Step 2107), the blood glucose control results (Step 2108) or the ketone results (Step 2109) are provided. These results may be displayed or stored, e.g., in a log-book application of the reader.

FIG. 35 illustrates an example animation interface 2430 to instruct the user to apply control solution, according to one embodiment. Screens 2432, 2434, and 2436 display an image of a control solution dropper and an analyte monitoring device with test strip inserted into the strip port. The dropper and test strip move closer as the sequence of screens 2432, 2434, and 2436 progress to animate the application of the dropper on the test strip. Animation interface 2430 may be displayed, for example, when the analyte monitoring device is ready to receive the control solution.

FIG. 35 also illustrates an example animation interface 2438 to instruct the user to apply a ketone control solution, according to one embodiment. Similar to interface 2430, screens 2440, 2442, and 2444 display an image of a control solution dropper and an analyte monitoring device with test strip inserted into the strip port. The dropper and test strip move closer as the sequence of screens 2440, 2442, and 2444 progress to animate the application of the dropper on the test strip. Animation interface 2438, however, includes an indication that a Ketone test is being performed—e.g., displaying the words, "Ketone Test".

Time & Date

Pressing touchscreen button 2065 ("Time & Date") results in the display of Time & Date settings screen 2110. This is depicted in FIG. 25 by reference path (F2) 2111. Time & Date settings screen 2110 provides a touchscreen time button 2112 and a touchscreen date button 2113.

Pressing touchscreen time button 2112 results in the display of a Set Time 12 2114 or a Set Time 24 2115 screen. The Set Time 12 2114 screen includes a first touchscreen up-arrow 2118 and a first touchscreen down-arrow 2119 for adjusting the hour increments of time 2122. Set Time 12 screen 2114 also includes a second touchscreen up-arrow 2120 and a second touchscreen down-arrow 2121 for adjusting the minute increments of time 2122. The Set Time 24 screen 2115 includes a first touchscreen up-arrow 2123 and a first touchscreen down-arrow 2124 for adjusting the hour increments of time 2127. Set Time 24 screen 2115 also includes a second touchscreen up-arrow 2125 and a second touchscreen down-arrow 2126 for adjusting the minute increments of time 2127. The user can toggle between the Set Time 12 2114 and the Set Time 24 2115 screen by use of touchscreen toggle buttons 2115 and 2116 as appropriate. In addition, the Set Time 12 2114 and the Set Time 24 2115 screens include touchscreen "OK" buttons 2128 and 2129 respectively for accepting the entered time.

Pressing touchscreen date button 2113 results in the display of Set Date screen 2130. Set Date screen 2130 includes a touchscreen up-arrow button 2131 and a touchscreen down-arrow button 2132 for adjusting the day of the factory set date 2133. Set Date screen 2130 also includes touchscreen "OK" button 2134 for accepting the entered time.

Time & Date settings screen 2110 also includes touchscreen "done" button 2135, which, when pressed, returns the user to the Settings Menu 2058 via reference path (H2) 2136.

Language Settings

Figure 26:
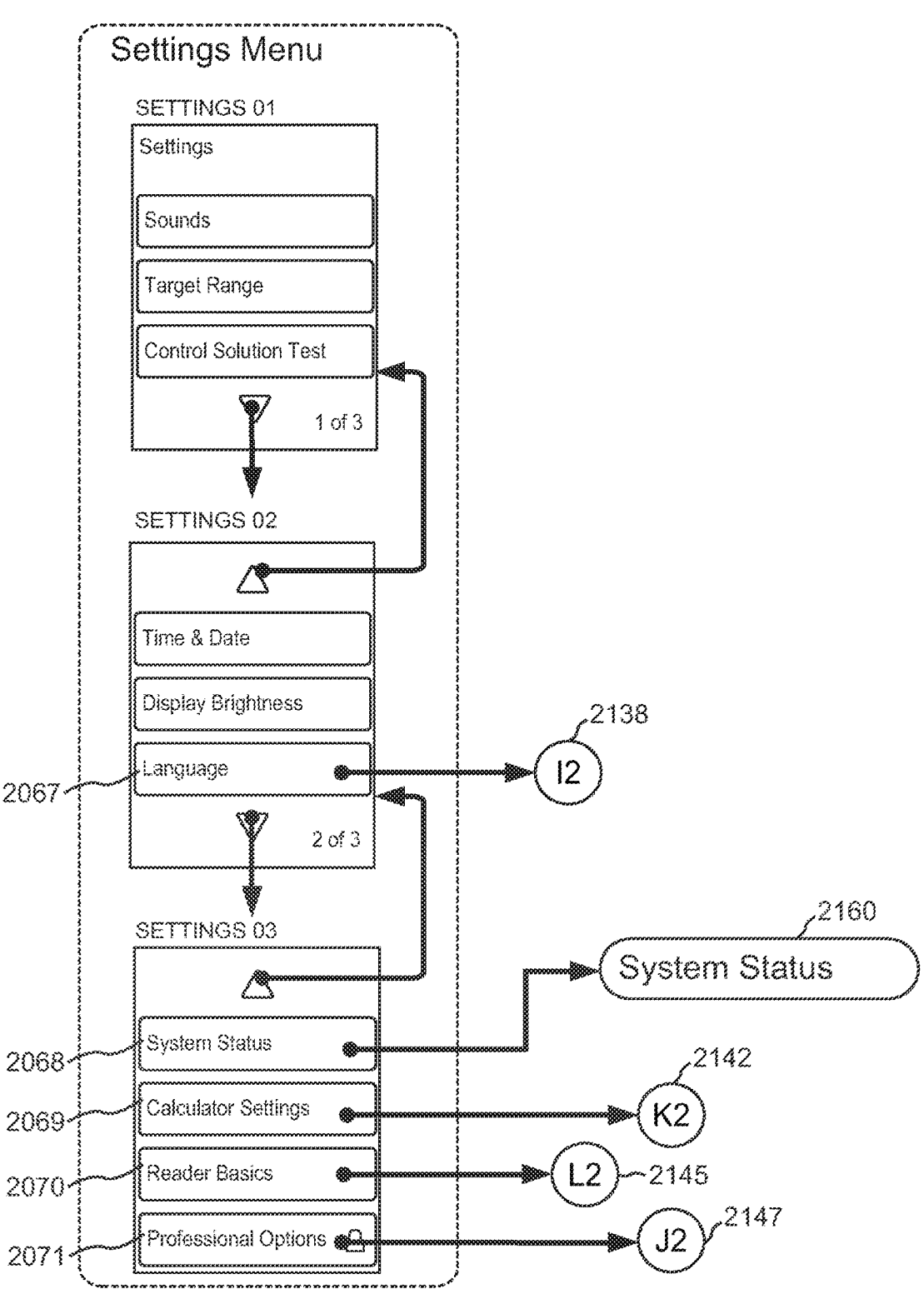
FIG. 26 illustrates methods of entering settings on an analyte monitoring device, according to one embodiment.
Figure 26:
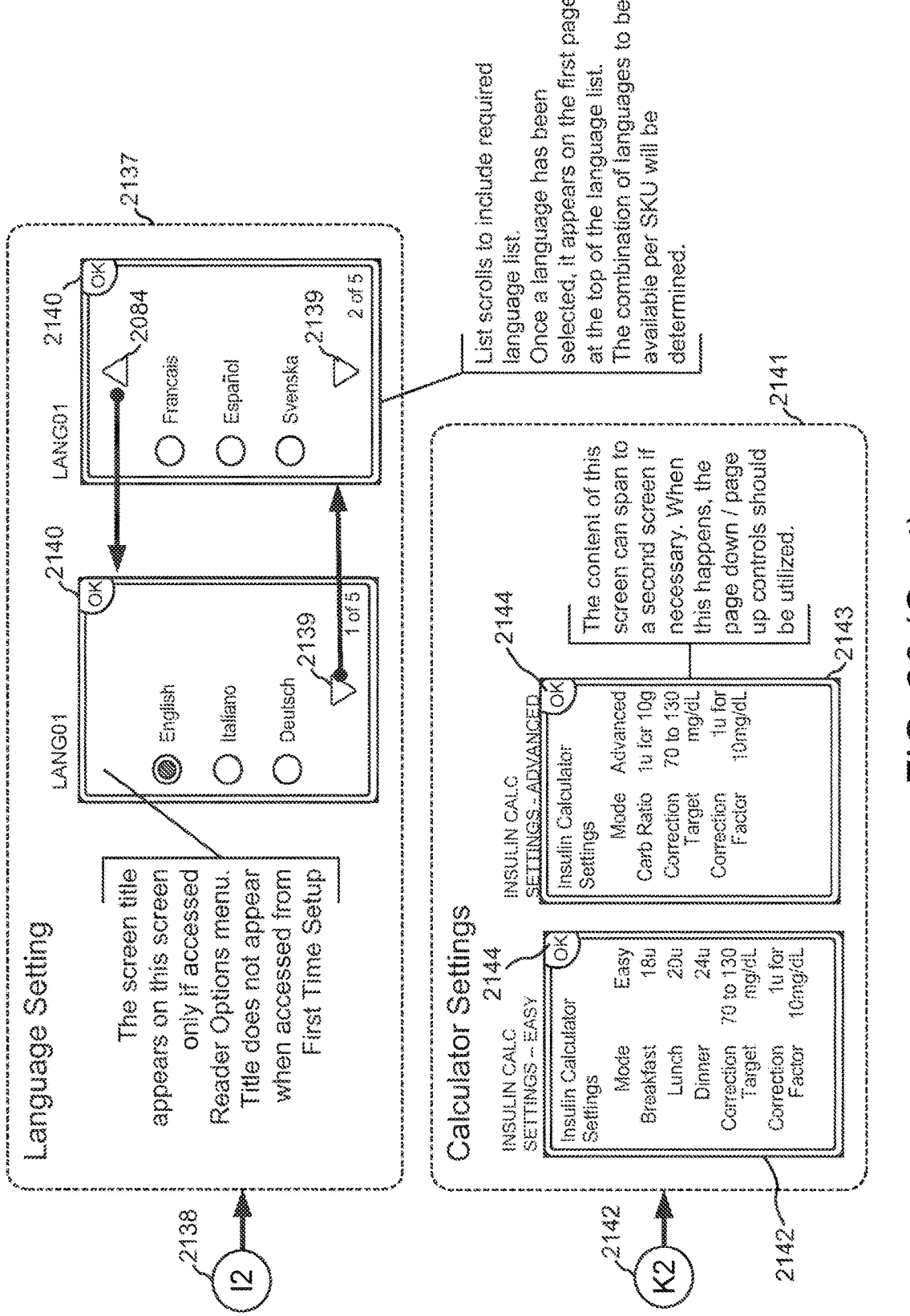
Figure 26:
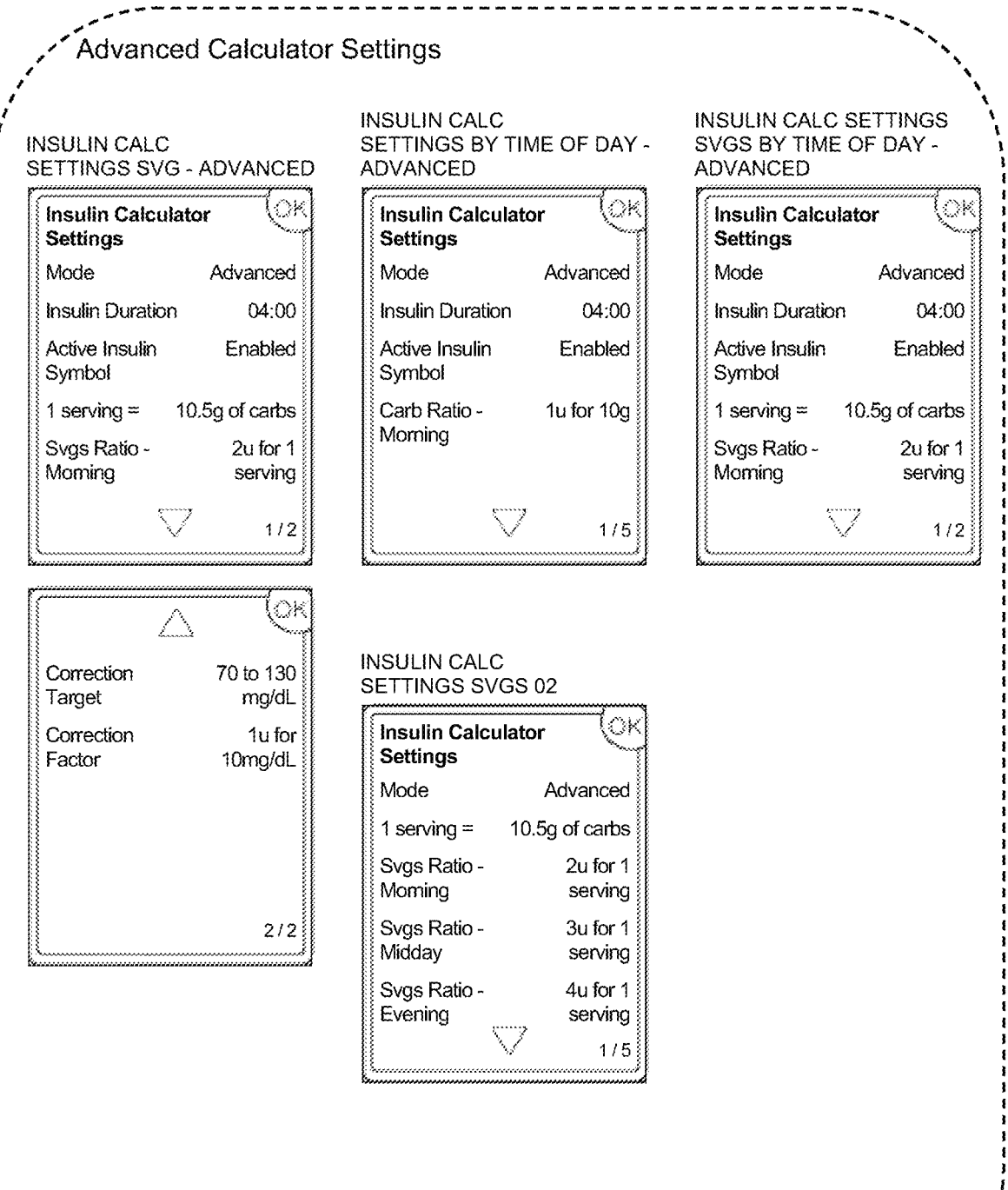
Figure 26:
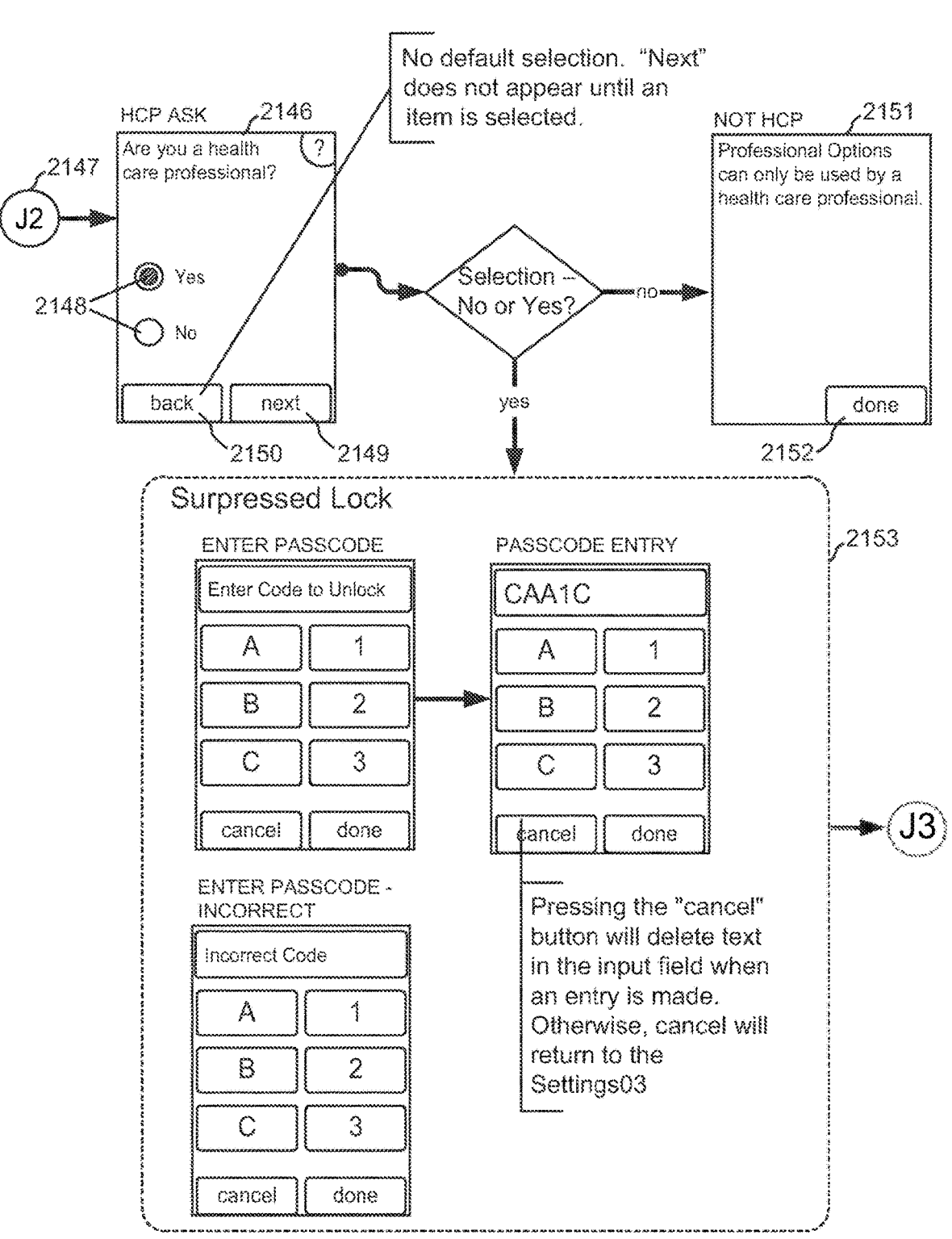
Figure 26:
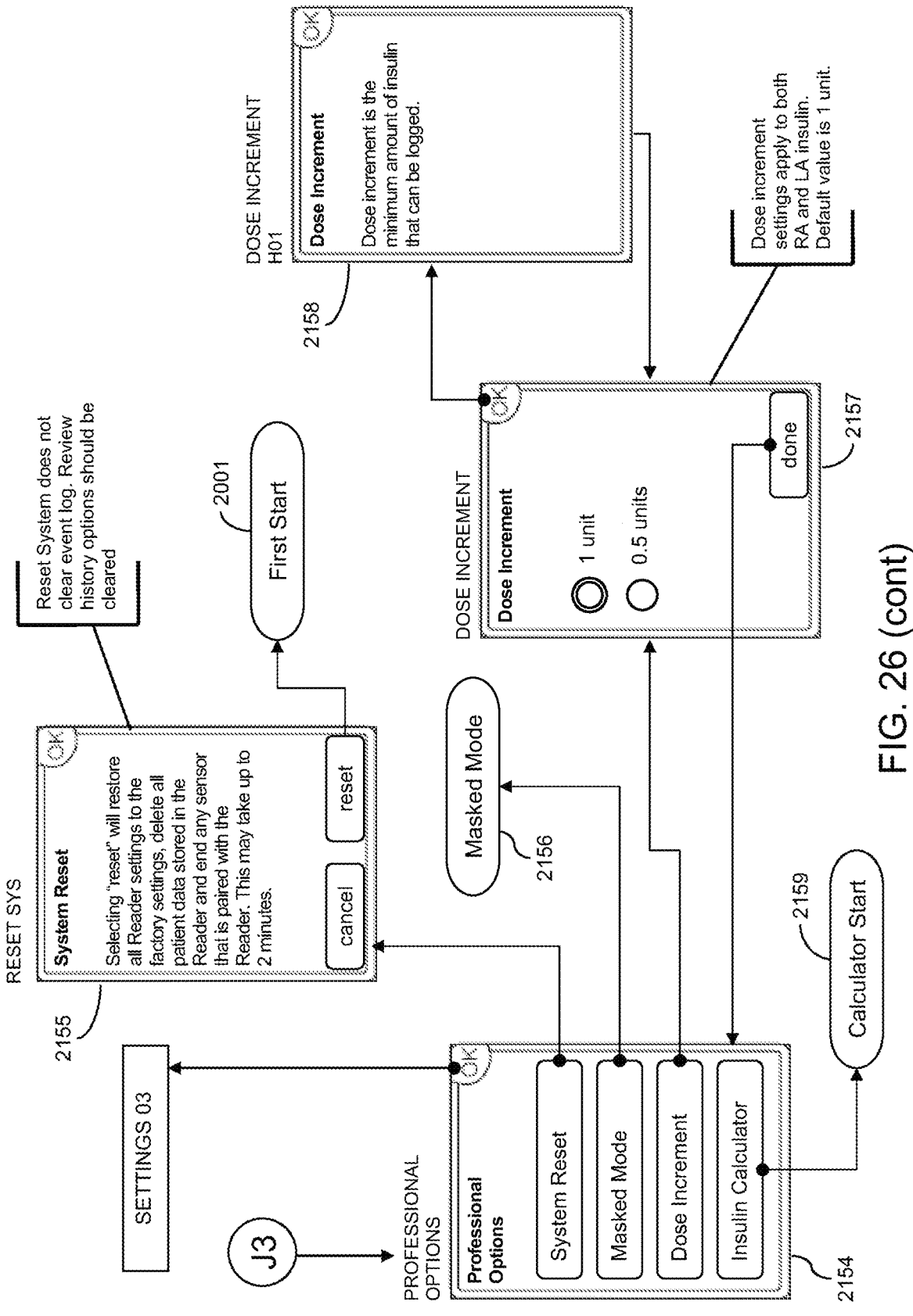

Pressing touchscreen button 2067 ("Language") results in the display of one or more Language Setting screens 2137. This is depicted in FIG. 26 by reference path (12) 2138. The one or more Language Setting screens 2137 include language options which can be selected by pressing the empty circle next to the corresponding language choice. Note that FIG. 26 shows the English language option selected. The user may scroll between the language setting screens using the displayed up or down-arrows 2139 as appropriate. The Language Setting screens 2137 also include touchscreen "OK" button 2140 for accepting the selected language.

Calculator Settings

Pressing touchscreen button 2069 ("Calculator Settings") results in the display of Calculator Setting screens 2141. This is depicted in FIG. 26 by reference path (K2) 2142. The Calculator Setting screens 2141 include, e.g., an Insulin Calculator Settings-Easy Mode screen 2142 and an Insulin Calculator Settings-Advanced Mode screen 2143. Insulin Calculator Settings-Easy Mode screen 2142 includes, e.g., insulin unit measurements of 18 u associated with breakfast, 20 u associated with lunch, 24 u associated with dinner, a correction target of 70 to 130 mg/dL and a correction factor of 10 mg/dL. Insulin Calculator Settings-Advanced Mode screen 2143 includes, e.g., a carbohydrate (Carb) ratio of 1 u for 10 g, a correction target of 70 to 130 mg/dL, and a correction factor of 1 u for 10 mg/dL. The Calculator Setting screens 2141 also include touchscreen "OK" button 2144 for accepting the indicated calculator settings.

Pressing touchscreen button 2070 ("Reader Basics") results in the display of the First Start Interface First Home Button screen 2043 discussed previously herein. This is depicted in FIG. 26 by reference path (L2) 2145.

Professional Options

As shown in FIG. 26, pressing touchscreen button 2071 ("Professional Options") results in the display of an HCP Ask screen 2146. This is depicted in FIG. 26 by reference path (J2) 2147. The HCP Ask screen 2146 displays a prompt asking whether the user is a health care professional. This question can be answered by touching the empty circle 2148 next to either the "Yes" or "No" option. Note that FIG. 26 shows the "Yes" option has been selected. No default selection is provided and touchscreen "next" button 2149 is not displayed until an option is selected. HCP Ask screen 2146 also includes a touchscreen "back" button 2150, which, when pressed, returns the user to the Settings Menu 2058 via reference path (J2) 2147. As indicated in FIG. 26, if the "No" option is selected a Not HCP screen 2151 is displayed which indicates, e.g., that "Professional Options can only be used by a health care professional." The Not HCP screen 2151 also includes a touchscreen "done" button 2152 which, e.g., returns the user to the Settings Menu 2058 via reference path (J2) 2147. If the "Yes" option is selected, a passcode entry screen 2153 is displayed which prompts the user to enter a passcode. Entry of an incorrect passcode will result in, e.g., an "Incorrect Code" prompt. Entry of the correct passcode allows the user access to the Professional Options screen 2154. Professional Options screen 2154 includes touchscreen button options; a System Reset 2155 option, a Masked Mode 2156 option, a Dose Increment 2157 option, and an Insulin Calculator 2159 option. Pressing the touchscreen button for the System Reset option results in the display of a Reset System (SYS) screen 2155. Selecting the "reset" option from this screen restores all reader settings to the factory defaults and deletes all patient data stored in the reader. The user is then returned to the First Start Interface 2001.

Pressing the touchscreen button for the Masked Mode option initiates a Masked Mode interface 2156 which is discussed elsewhere herein.

Pressing the touchscreen button for the Dose Increment option initiates a Dose Increment interface 2157. The Dose Increment interface 2157 allows the HCP to change the dose increment setting. The dose increment setting applies to both rapid-acting and long-acting insulin dosages. In one embodiment, the default value is 0.5 unit. However, the any other suitable increment value such as 0.1 unit, 0.2 unit, or some other suitable increment, for example, can be used. The dose increment is the minimum amount of insulin that can be logged, which may be displayed on the device as shown at 2158. Pressing the "done" button returns to the Professional Options screen 2154.

Pressing the touchscreen button for the Insulin Calculator option initiates an Insulin Calculator Start interface 2159 which is discussed in greater detail below.

Professional Options screen 2154 also includes a touchscreen "OK" button 2159, which, when pressed, returns the user to the Settings Menu 2058 via reference path (J2) 2147.

System Status

Pressing touchscreen button 2068 ("System Status") initiates a System Status Interface 2160. This aspect of the graphical user interface is discussed in greater detail below.

System Status Interface

A graphical user interface which facilitates a Setup procedure 2000 may include a System Status Interface 2160 which includes a System Status menu 2161, which may be displayed on the reader. System Status menu 2161 includes the following items: "System Info", "Self-Test", "Touchscreen Test", and "Error Log", which can be selected by touching corresponding touchscreen buttons 2162, 2163, 2164, and 2165 respectively. System Status menu 2161 includes a touchscreen "OK" button 2169, which, when pressed, returns the user to the Settings Interface 2057.

Figure 27:
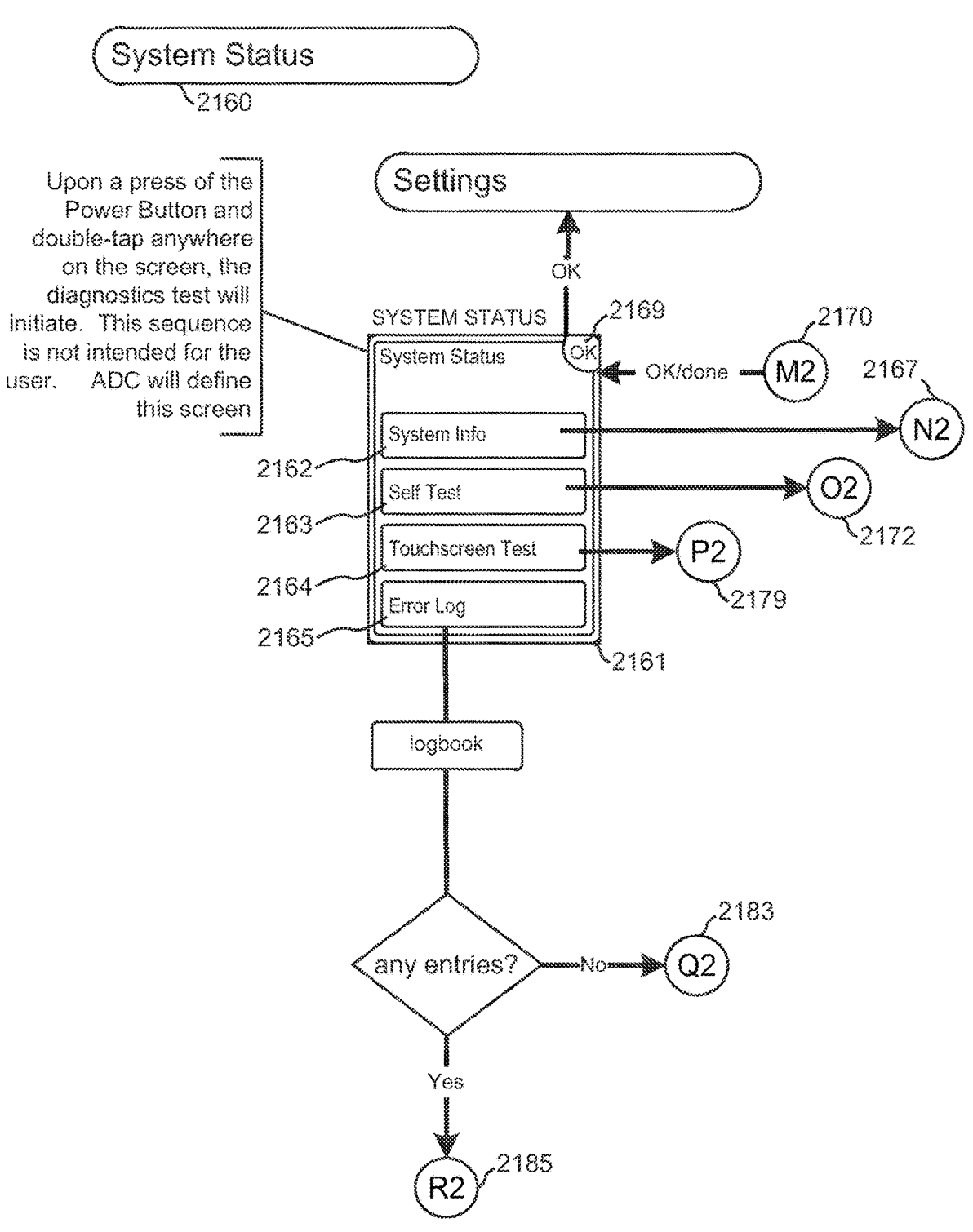
FIG. 27 illustrates methods of checking the system status of an analyte monitoring device, according to one embodiment.
Figure 27:
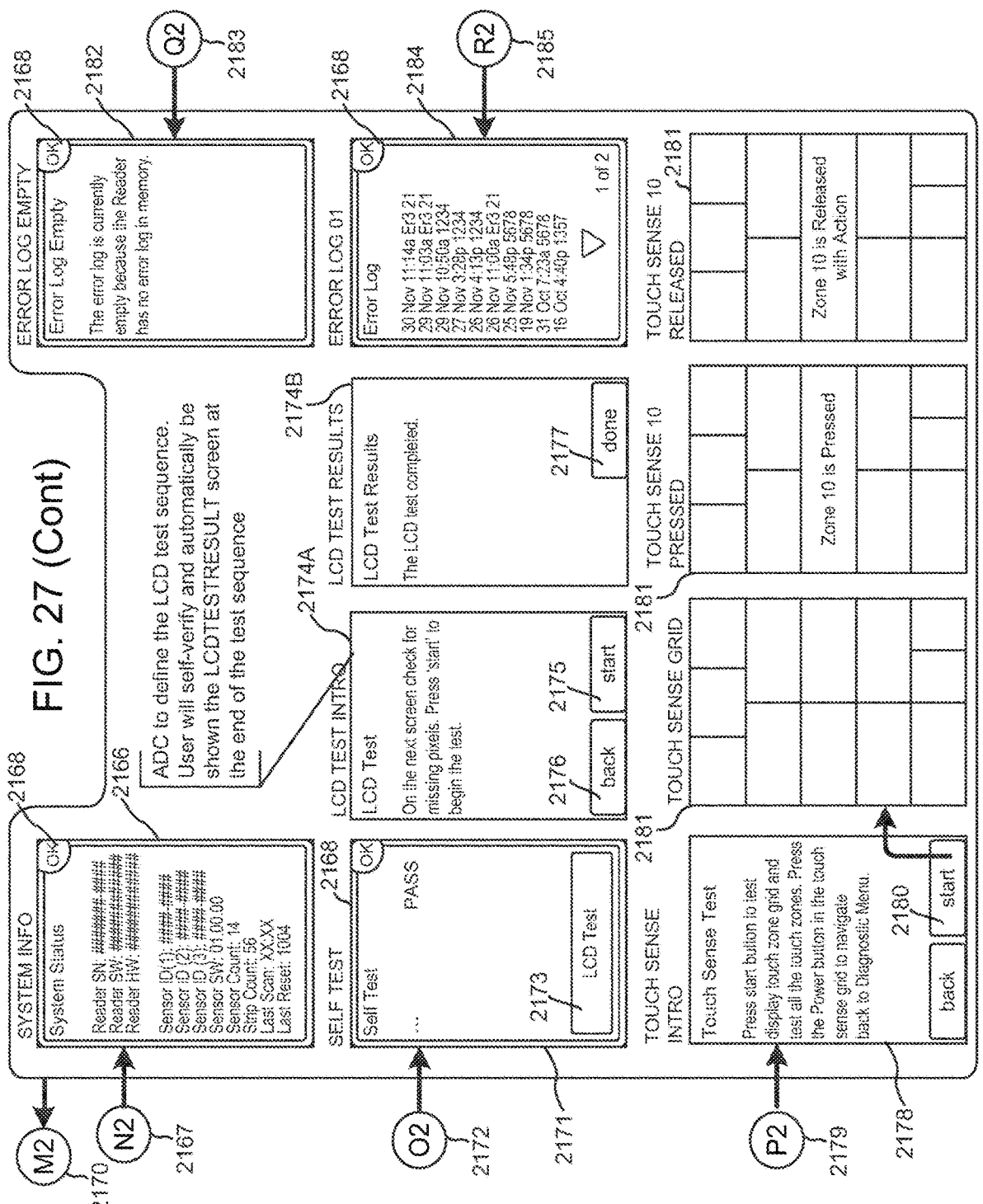

Pressing the touchscreen button 2162 for System Info results in display of System Info screen 2166, which may display information such as reader serial no., reader software no., reader hardware no., sensor ID, sensor software no., sensor count, strip count, date of last scan, last reset, and the like. This is depicted in FIG. 27 by reference path (N2) 2167. System Info screen 2166 includes a touchscreen "OK" button 2168, which, when pressed, returns the user to the System Status menu 2161 via reference path (M2) 2170.

Pressing the touchscreen button 2163 for Self-Test results in display of Self-Test screen 2171 and initiation of a self-diagnostics protocol. This is depicted in FIG. 27 by reference path (O2) 2172. The self-diagnostics protocol can also be initiated by a press of the power button and a double-tap anywhere on the screen. Self-Test screen 2171 includes a touchscreen "LCD Test" button 2173. Pressing touchscreen "LCD Test" button 2173 results in display of an LCD Test Intro screen 2174A. LCD Test Intro screen 2174A includes, e.g., a prompt indicating "On the next screen check for missing pixels. Press 'start' to begin the test." LCD Test Intro screen 2174A also includes a touchscreen "start" button 2175 and a touchscreen "back" button 2176. When pressed, the touchscreen "back" button 2176 returns the user to Self-Test screen 2171. Pressing the touchscreen "start" button 2175 initiates an LCD test and results in the display of an LCD Test Results screen 2174B. The LCD Test Results screen 2174B may include a prompt indicating that the LCD test has been completed. The LCD Test Results screen 2174B may also include a touchscreen "done" button 2177, which, when pressed returns the user to Self-Test screen 2171 or the System Status menu 2161 via reference path (M2) 2170. Self-Test screen 2171 also includes a touchscreen "OK" button 2168, which, when pressed, returns the user to the System Status menu 2161 via reference path (M2) 2170.

Pressing the touchscreen button for Sound Test results in display of a Sound Test screen. Sound Test screen may display a prompt indicating, e.g., "If you do not hear a series of tones and vibrations, contact Customer Service." Sound Test screen may include a "next" button which, when pressed, may navigate to the next settings test. Sound Test screen may include a "back" button which, when pressed, returns the user to the System Status menu 1261.

Pressing the touchscreen button 2164 for Touchscreen Test results in display of Touch Sense Test screen 2178. This is depicted in FIG. 27 by reference path (P2) 2179. Touch Sense Test screen 2178 may display a prompt indicating, e.g., "Press start button to test display touch zone grid and test all the touch zones. Press the Power button in the touch sense grid to navigate back to the Diagnostic Menu." Touch Sense Test screen 2178 includes a touchscreen "start" button 2180, which, when pressed, results in display of a touch sense grid 2181 for testing the responsiveness of the various zones of the touch sense grid 2181. Touch Sense Test screen 2178 also includes a touchscreen "back" button which, when pressed, returns the user to the System Status menu 2161 via reference path (M2) 2170.

Pressing the touchscreen button 2165 for Error Log results in display of an Error Log Empty screen 2182 or an Error Log screen 2184. This is depicted in FIG. 27 by reference paths (Q2) 2183 and (R2) 2185 respectively depending on whether any error entries are present in the logbook. Error Log screen 2184 may include one or more down or up-arrows to scroll between pages of the error log if necessary.

Masked Mode Interface

An exemplary embodiment of a graphical user interface which may be utilized in connection with a reader as described herein and which functions to enable the operation of the analyte monitoring device in a masked mode.

Figure 28:
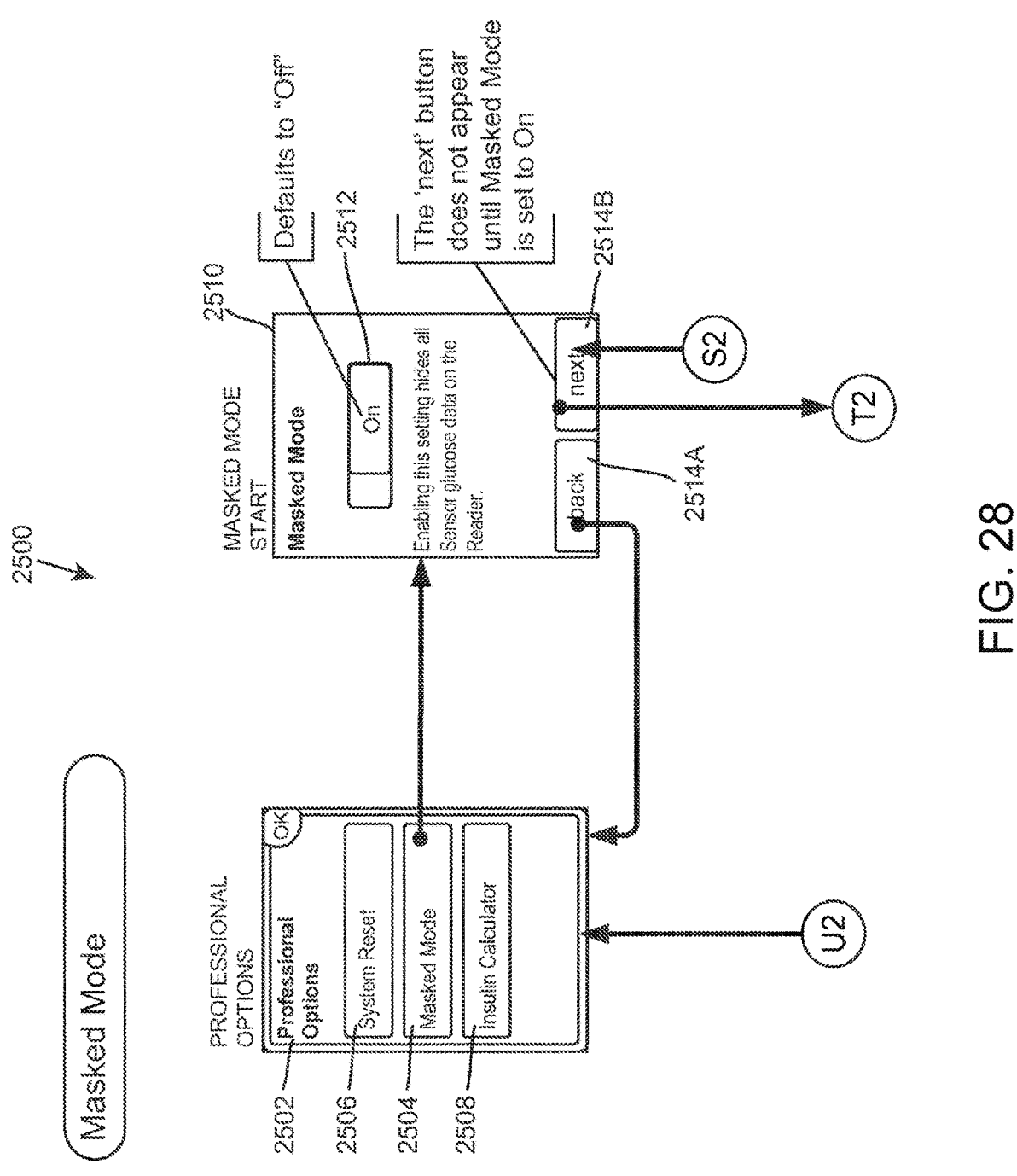
FIG. 28 illustrates a method of setting a masked mode for an analyte monitoring device, according to one embodiment.
Figure 28:
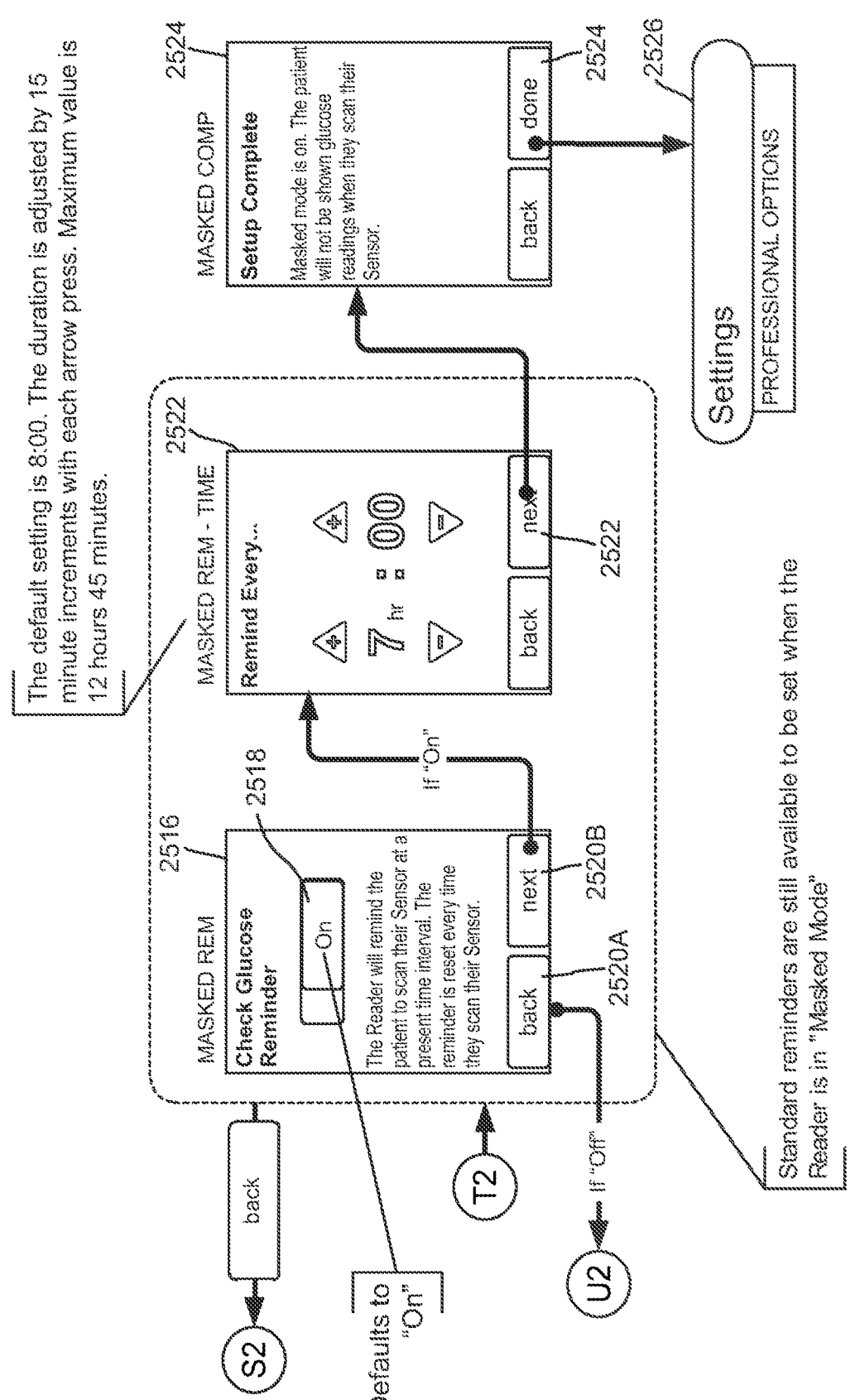

FIG. 28 illustrates a Professional Options screen 2502 that displays a menu of options for customizing the operation of the device. For example, the menu of options may be geared more for a physician or other health care professional to set up or otherwise configure the device for the patient. In one embodiment, the Professional Options screen 2502 may require a code or password to access, which the physician has but the patient does not. In another embodiment, the Professional Options screen 2502 may not restrict access and the patient may also change the configuration.

Professional Options screen 2502 includes a Masked Mode option 2504 for navigating to a Masked Mode interface 2510 that enables activation or deactivation of the Masked Mode. Examples of other options include an Insulin Calculator option 2508 for navigating to an interface for activating or deactivating the insulin calculator. A System Reset Option 2502 is also included to reset the option to a default setting.

Masked Mode interface 2510 includes an activation icon, symbol, trigger element, etc., that may be selected to activate the Masked Mode. Masked Mode interface 2510 may also provide additional information about the Masked Mode to inform the user of its use. Masked Mode interface 2510 also includes trigger element 2514*a* for navigating back to the Professional Options screen 2502. Trigger element 2514*b* takes the user to a screen for setting a reminder to take a sensor reading, as shown by reference path T2.

Upon selection of trigger element 2514*b*, Masked Rem screen 2516 is displayed to enable setting the device to provide reminders to the user to perform a reading. For example, element 2518 may be selected to activate or deactivate the reminder feature on the device. Additional information may also be provided to inform the user of the reminder option. If the reminder is "off" and the user selects trigger element 2520*a* takes the user back to the Professional Options screen 2502. If the reminder is "on" and the user selects trigger element 2520*b*, then a Masked REM-Time screen 2522 is displayed to enable the user to set times for initiating a reminder. Once the time is set, the user can select trigger element 2522*b* to trigger the Masked Complete (Comp) screen 2524 which indicates that the Masked Mode is activated. In some embodiments, the Masked Mode reminder is set for a predetermined time period, e.g., a number of hours, e.g., 8 hours, 12 hours, 24 hours, etc. In some embodiments, if the user runs a manual scan prior to the upcoming reminder, the reminder timer period automatically resets. In certain embodiments, the device includes a reminder delay option, such that upon activation of the reminder in Masked Mode, the user has the option of delaying the reminder for a preset length of time. Upon user confirmation of the trigger element 2524, the device navigates back to the Professional Options screen 2502.

Calculator Start Interface

A graphical user interface which facilitates a Setup procedure 2000 may include a Calculator Start Interface 2186 as mentioned previously herein. Calculator Start Interface 2186 may be initiated by pressing the touchscreen button for the Insulin Calculator 2157 option located on the Professional Options screen 2154. Pressing the touchscreen button for the Insulin Calculator 2157 option results in a calculator On/Off status determination. If the calculator is On, reference path (X2) 2187 is initiated, which results in display of a Calculation Edit screen 2188. Calculation Edit screen 2188 includes a touchscreen "Turn Off Calculator" button 2189. Pressing the "Turn Off Calculator" button 2189 results in display of a Calculation Off screen 2190, which provides a prompt indicating that the insulin calculator is turned off. In this case, the calculator button will no longer be available when checking glucose levels. The Calculation Off screen 2190 includes a touchscreen "done" button, which, when pressed, initiates reference path (V2) 2192, which returns the user to the Professional Options screen 2154.

Calculation Edit screen 2188 also includes a touchscreen "Change Calculator Settings" button 2193. Pressing the touchscreen "Change Calculator Settings" button 2193 results in initiation of reference path (B3) 2194 discussed in greater detail below. Calculation Edit screen 2188 also includes a touchscreen "back" button 2195, which, when pressed, initiates reference path (W2) 2196 which returns the user to the Professional Options screen 2154.

Figure 29:
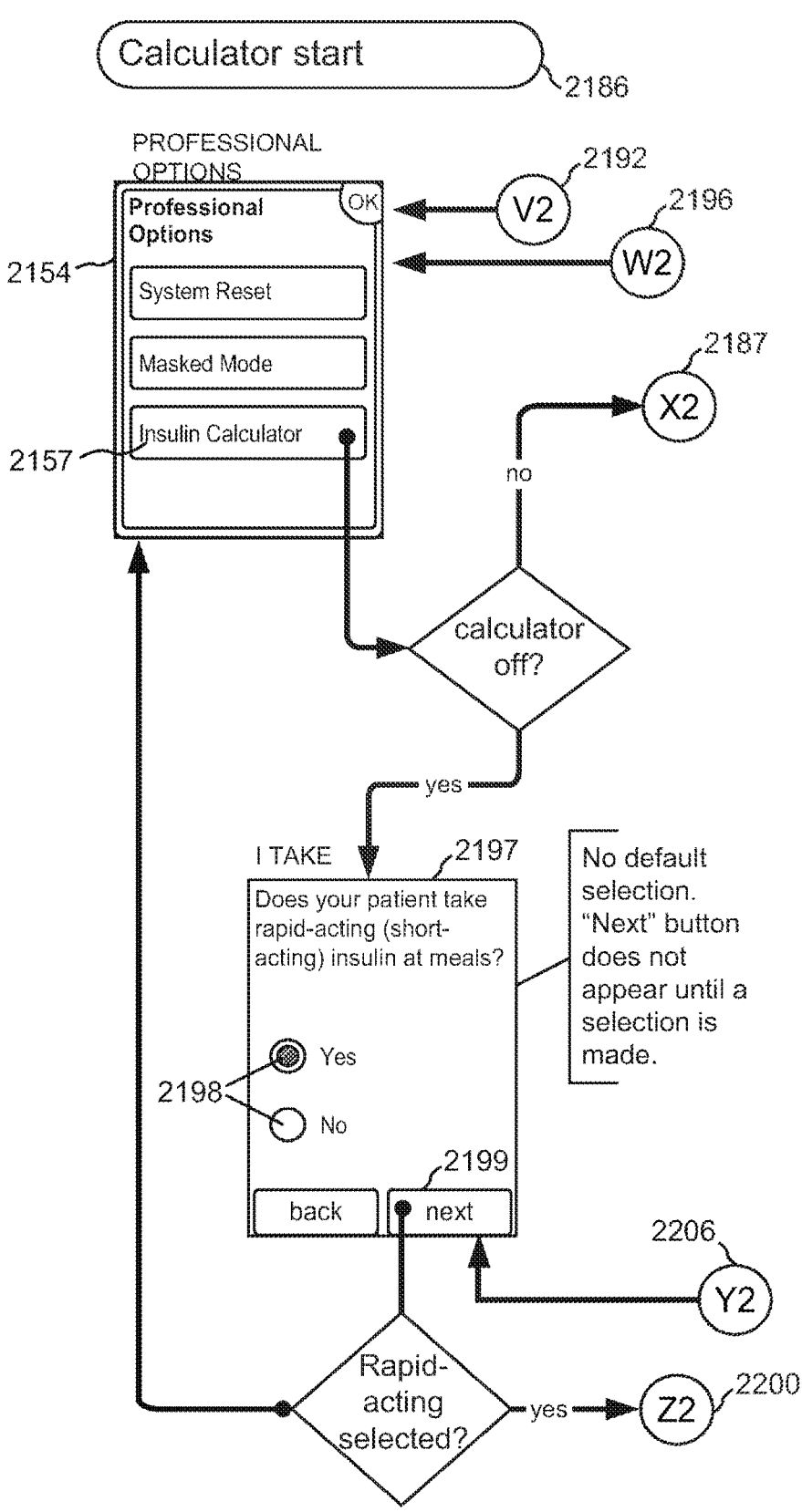
FIG. 29 illustrates a method of activating a calculator feature on an analyte monitoring device, according to one embodiment.
Figure 29:
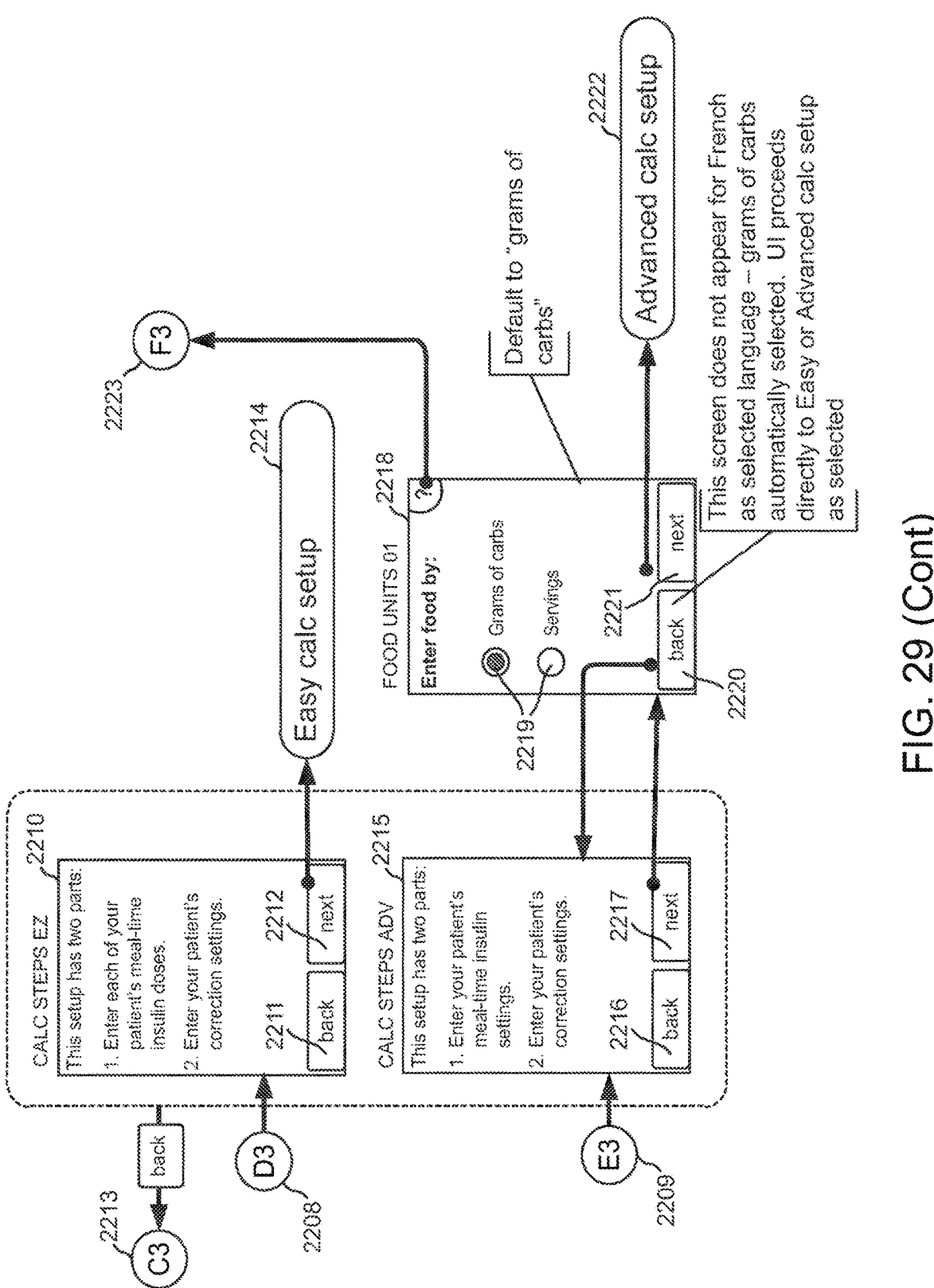

As discussed above, pressing the touchscreen button for the Insulin Calculator 2157 option results in a calculator On/Off status determination. If the calculator is Off, a I Take screen 2197 is displayed. The I Take screen 2197 includes a prompt, "Does your patient take rapid-acting (short acting) insulin at meals?" The I Take screen 2197 also includes empty circles 2198 which may be pressed so as to indicate a Yes or No answer to the above prompt. Note that FIG. 29 shows the Yes option selected. The I Take screen 2197 also includes a touchscreen "next" button 2199, which initiates a reference path (Z2) 2200 (discussed in greater detail below) in the event the Yes option was selected.

Reference path (B3) 2194 and reference path (Z2) 2200 result in display of Calculation Type 01 screen 2201 or a Calculation Type 02 screen 2202 depending on whether an "Easy" or "Advanced" Setup Option is selected respectively using touchscreen toggle element 2203. The "Easy" Setup Option is utilized for patients who start with a fixed dose of rapid-acting insulin at meals while the "Advanced" Setup Option is utilized for patients who count carbs (in grams or servings) to adjust their rapid-acting insulin dose at meals. Calculation Type 01 screen 2201 and Calculation Type 02 screen 2202 each include a touchscreen "back" button 2204 and a touchscreen "next" button 2205. Pressing "back" button 2204 returns the user to I Take 2197 via reference path (Y2) 2206 if I Take 2197 was the previously viewed screen. Pressing "back" button 2204 returns the user to Calculation Edit 2188 via reference path (A3) 2207 if Calculation Edit 2188 was the previously viewed screen. Touching touchscreen "next" button 2205 initiates reference path D3 2208 or E3 2209 depending on whether the Easy or Advanced Setup option is selected respectively.

Reference path D3 2208 results in display of a Calculation Steps EZ screen 2210, including the following prompts: "This setup has two parts: 1) Enter each of your patient's meal-time insulin doses; and 2) Enter your patient's correction settings." Calculation Steps EZ screen 2210 includes a touchscreen "back" button 2211 and a touchscreen "next" button 2212. Pressing touchscreen "back" button 2211 returns the user to Calculation Type 01 screen 2201 and Calculation Type 02 screen 2202 via reference path (C3) 2213. Pressing touchscreen "next" button 2212 results in initiation of an Easy Calculation Setup interface 2214 described in greater detail below.

Reference path E3 2209 results in display of a Calculation Steps Advanced screen 2215, including the following prompts: "This setup has two parts: 1) Enter your patient's meal-time insulin settings; and 2) Enter your patient's correction settings." Calculation Steps Advanced screen 2215 includes a touchscreen "back" button 2216 and a touchscreen "next" button 2217. Pressing touchscreen "back" button 2216 returns the user to Calculation Type 01 screen 2201 and Calculation Type 02 screen 2202 via reference path (C3) 2213. Pressing touchscreen "next" button 2217 results in display of a Food Units 01 screen 2218. Food Units 01 screen 2218 includes a prompt "Enter food by:" and includes two options "Grams of carbs" and "Servings" which can be selected by pressing one of corresponding empty circles 2219. Note that FIG. 29 shows the "Grams of carbs" option selected. Food Units 01 screen 2218 includes a touchscreen "back" button 2220 and a touchscreen "next" button 2221. Pressing touchscreen "back" button 2220 returns the user to Calculation Steps Advanced screen 2215. Pressing touchscreen "next" button 2221 results in initiation of an Advanced Calculation Setup interface 2222, discussed in greater detail below. Food Units 01 screen 2218 also includes a touchscreen "?" button, which, when pressed, initiates reference path (F3) 2223, which provides additional information regarding the selection of "Grams of carbs" or "Servings" as shown in FIG. 29 with reference to screens H01 2224, H02 2225 and H03 2226.

Easy Calculation Setup Interface

Figure 30:
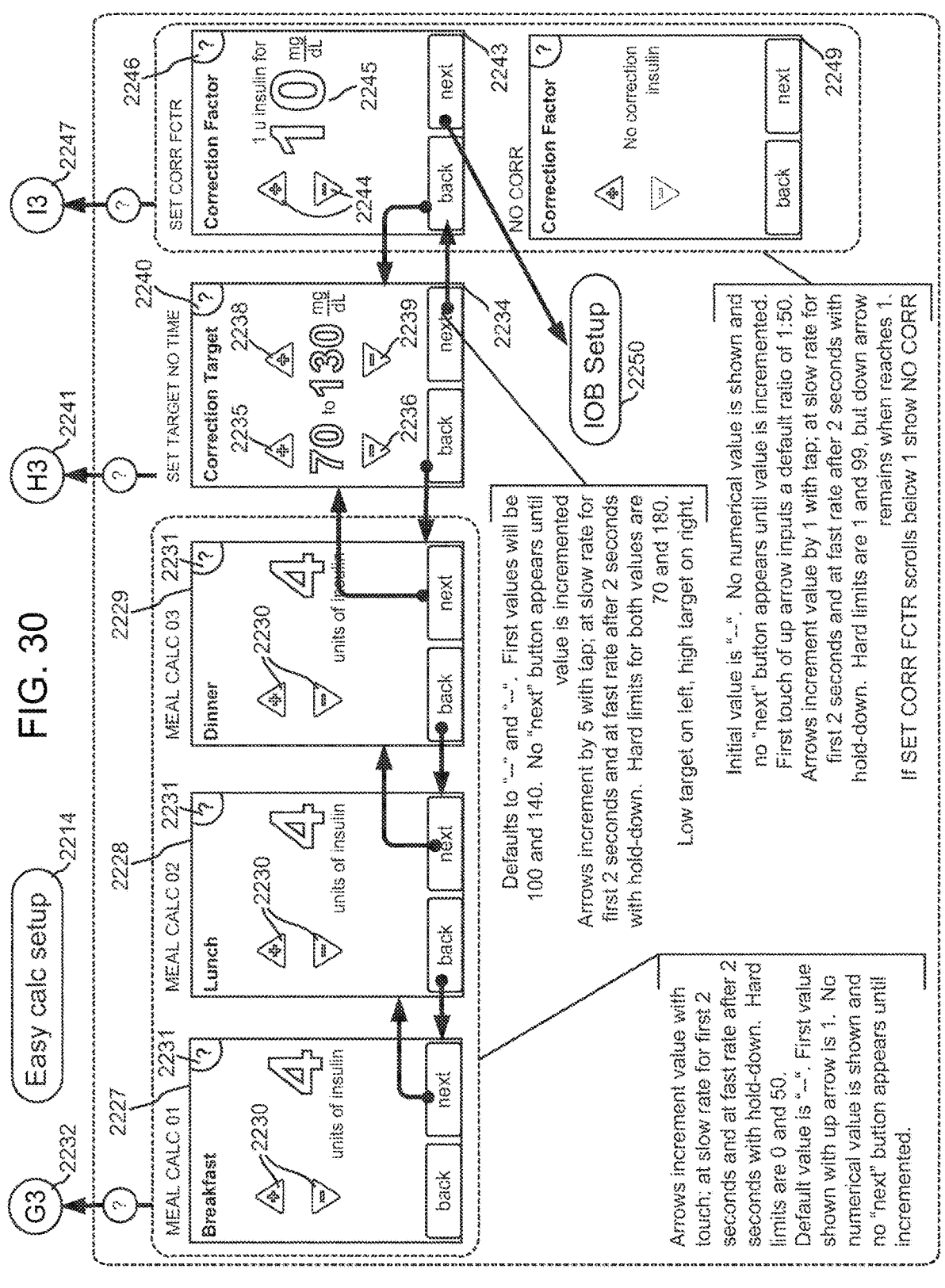
FIG. 30 illustrates a method of setting up a calculator on an analyte monitoring device, according to one embodiment.

Easy Calculation Setup interface 2214 is described with reference to FIG. 30. Three Meal Calculation screens are provided, one each for Breakfast 2227, Lunch 2228, and Dinner 2229. Each of these screens includes up and down-arrows 2230 for adjusting the displayed units of insulin associated with each meal. Each of these screens also includes touchscreen "back" and "next" buttons for navigating between screens of the Easy Calculation Setup interface 2214. Finally, each of these screens includes a touchscreen "?" button 2231, which, when pressed, initiates reference path G3 2232. Reference path G3 2232 results in display of a screen 2233 including the prompt: "Enter the units of rapid-acting insulin you recommended to cover this meal." Pressing the touchscreen "next" button from the Dinner 2229 screen results in display of a Correction Target screen 2234.

Correction Target screen 2234 includes first up and down-arrows (2235 and 2236) for adjusting a low target, e.g., 70 mg/dL, of the target glucose range 2237; and second up and down-arrows (2238 and 2239) for adjusting a high target, e.g., 130 mg/dL of the target glucose range 2237. Correction Target screen 2234 includes a touchscreen "?" button 2240, which, when pressed, initiates a reference path (H3) 2241. Reference path H3 2241 results in display of a screen 2242 including the prompt: "Target is the desired glucose value if extra rapid-acting insulin is needed to correct high glucose reading." Pressing the touchscreen "next" button from the Correction Target screen 2234 results in display of a Correction Factor screen 2243. Correction Factor screen 2243 includes up and down-arrows 2244 for adjusting the insulin correction factor 2245. If the set Correction Factor scrolls below 1, a No Correction screen 2249 is displayed with the prompt "No correction insulin". Correction Factor screen 2243 includes a touchscreen "?" button 2246, which, when pressed, initiates a reference path (I3) 2247. Reference path I3 2247 results in display of a screen 2248 including the prompt: "The Reader uses this value to determine how many units of rapid-acting insulin is needed to lower high glucose to a target value or range." Pressing the touchscreen "next" button from the Correction Factor screen 2243 screen results in initiation of an Insulin On Board (IOB) Setup interface 2250, which is described in greater detail below.

Advanced Calculation Setup Interface

Figure 31:
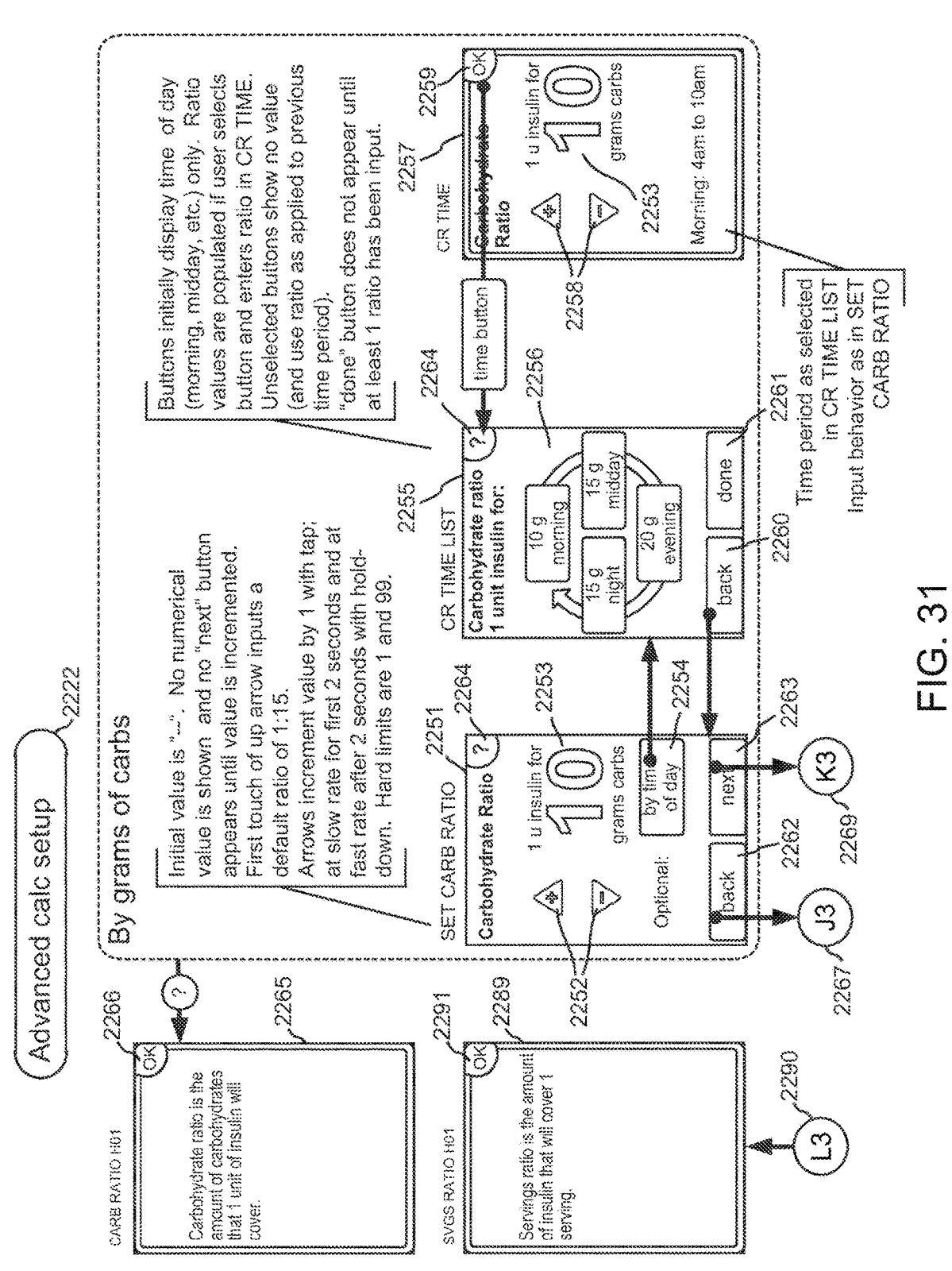
FIG. 31 illustrates a method of setting up a calculator on an analyte monitoring device, according to one embodiment.
Figure 31:
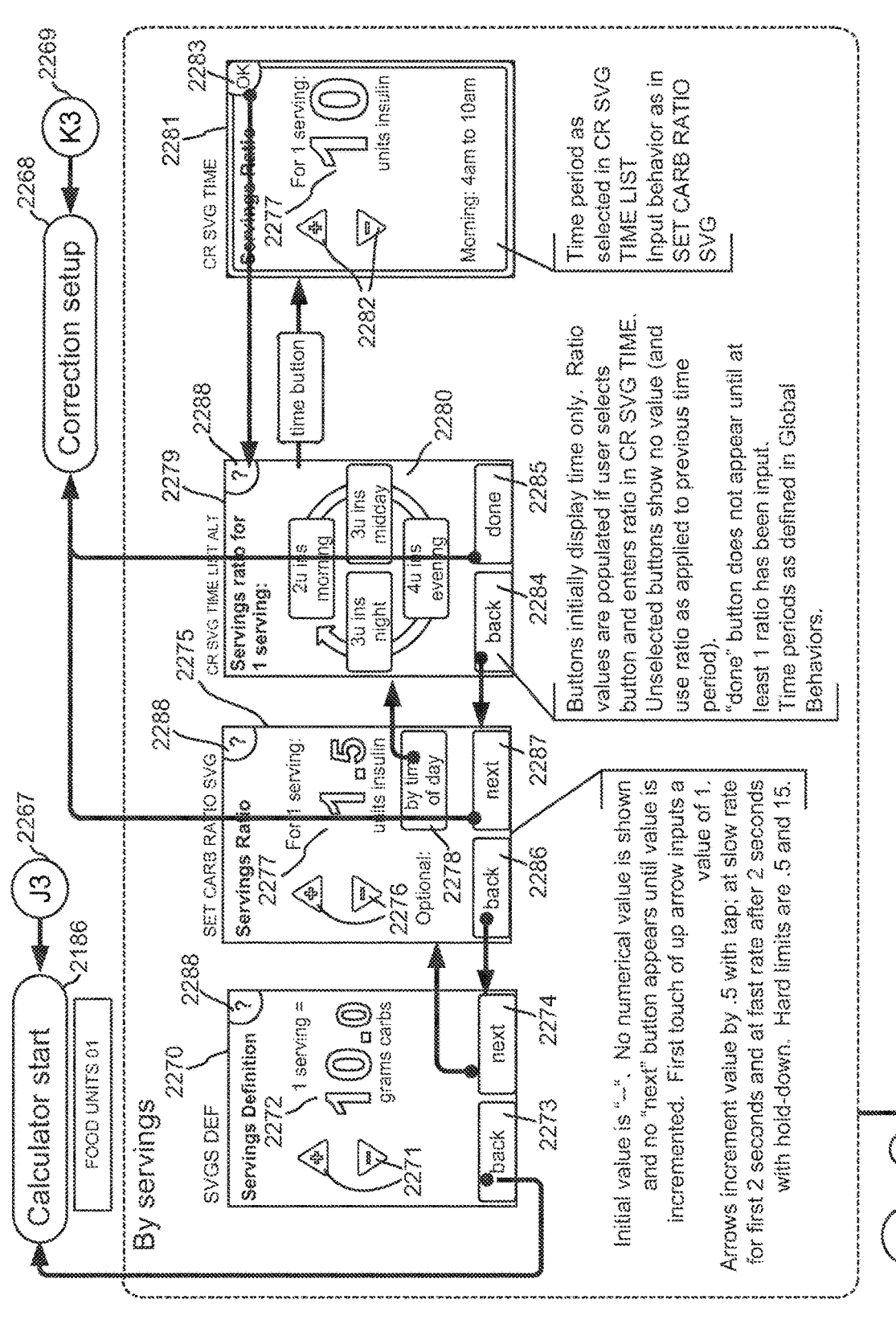

Advanced Calculation Setup interface 2222 is described with reference to FIG. 31. Initiation of Advanced Calculation Setup interface 2222 with "By grams of carbs" selected on screen 2218 results in display of a Set Carb Ratio screen 2251. Set Carb Ratio screen 2251 includes touchscreen up and down-arrows 2252 for adjusting correction factor 2253. Set Carb Ratio screen 2251 also includes a touchscreen "by time of day" button 2254.

Pressing the touchscreen "by time of day" button 2254 results in display of a CR Time List screen 2255. CR Time List screen 2255 includes touchscreen buttons 2256 which may be used to select a time period, e.g., morning, midday, evening, or night for the correction factor 2253. Pressing one of touchscreen buttons 2256 results in display of a CR Time screen 2257, which includes touchscreen up and down-arrows 2258 for adjusting correction factor 2253 by time of day. CR Time screen 2257 includes a touchscreen "OK" button 2259, which, when pressed, results in selection of the displayed correction factor 2253 by time of day and returns the user to the CR Time List screen 2255. Time List screen 2255 includes a touchscreen "back" button 2260 for returning to the Set Carb Ratio screen 2251 and a touchscreen "done" button 2261 for indicating completion of the correction factor 2253 by time of day setup and, in some embodiments, for initiating the Correction Setup interface 2268, discussed in greater detail below.

Set Carb Ratio screen 2251 and CR Time List screen 2255 each include a touchscreen "?" button 2264, which, when pressed, results in display of a Carb Ratio information screen 2265. Carb Ratio information screen 2265 displays a prompt indicating "Carbohydrate ratio is the amount of carbohydrates that 1 unit of insulin will cover." Pressing the touchscreen "OK" button 2266 from Carb Ratio information screen 2265 returns the user to the Set Carb Ratio screen 2251 or the CR Time List screen 2255 as appropriate.

Set Carb Ratio screen 2251 includes a touchscreen "back" button 2262 and a touchscreen "done" button 2263. Pressing touchscreen "back" button 2262 returns the user to the Calculation Start interface 2186 as described previously herein via reference path (J3) 2267. Pressing touchscreen "done" button 2263 initiates a Correction Setup interface 2268 via reference path (K3) 2269.

Initiation of Advanced Calculation Setup interface 2222 with "By servings" selected on screen 2218 results in display of a Servings Definition screen 2270. Servings Definition screen 2270 includes touchscreen up and down-arrows 2271 for adjusting servings definition 2272 (e.g., 1 serving=10.0 grams carbs). Servings Definition screen 2270 also includes a touchscreen "back" button 2273 and a touchscreen "next" button 2274. Pressing touchscreen "back" button 2273 returns the user to the Calculation Start interface 2186 as described previously herein. Pressing touchscreen "next" button 2274 results in display of a Set Carb Ratio Servings screen 2275. Set Carb Ratio Servings screen 2275 includes touchscreen up and down-arrows 2276 for adjusting servings ratio 2277 (e.g., For 1 serving:1.5 units insulin). Set Carb Ratio Servings screen 2275 also includes a touchscreen "by time of day" button 2278.

Pressing the touchscreen "by time of day" button 2278 results in display of a CR Servings Time List screen 2279. CR Servings Time List screen 2279 includes touchscreen buttons 2280 which may be used to select a time period, e.g., morning, midday, evening, or night for the servings ratio 2277. Pressing one of touchscreen buttons 2280 results in display of a CR Servings Time screen 2281, which includes touchscreen up and down-arrows 2282 for adjusting servings ratio 2277 by time of day. CR Servings Time screen 2281 includes a touchscreen "OK" button 2283, which, when pressed, results in selection of the displayed servings ratio 2277 by time of day and returns the user to the CR Servings Time List screen 2279. CR Servings Time List screen 2279 includes a touchscreen "back" button 2284 for returning to the Set Carb Ratio Servings screen 2275 and a touchscreen "done" button 2285 for initiating the Correction Setup interface 2268, discussed in greater detail below.

Set Carb Ratio Servings screen 2275 includes a touchscreen "back" button 2286 and a touchscreen "next" button 2287. Pressing touchscreen "back" button 2286 returns the user to the Servings Definition screen 2270. Pressing touchscreen "next" button 2287 results in initiation of the Correction Setup interface 2268, discussed in greater detail below.

Servings Definition screen 2270, Set Carb Ratio Servings screen 2275, and CR Servings Time List screen 2279 each include a touchscreen "?" button 2288, which, when pressed, results in display of a Servings Ratio information screen 2289 via reference path (L3) 2290. Servings Ratio information screen 2289 displays a prompt indicating "Servings ratio is the amount of insulin that will cover 1 serving" or the equivalent. Pressing the touchscreen "OK" button 2291 from Servings Ratio information screen 2289 returns the user to the Servings Definition screen 2270, Set Carb Ratio Servings screen 2275, or CR Servings Time List screen 2279 as appropriate.

Correction Setup Interface

Figure 32:
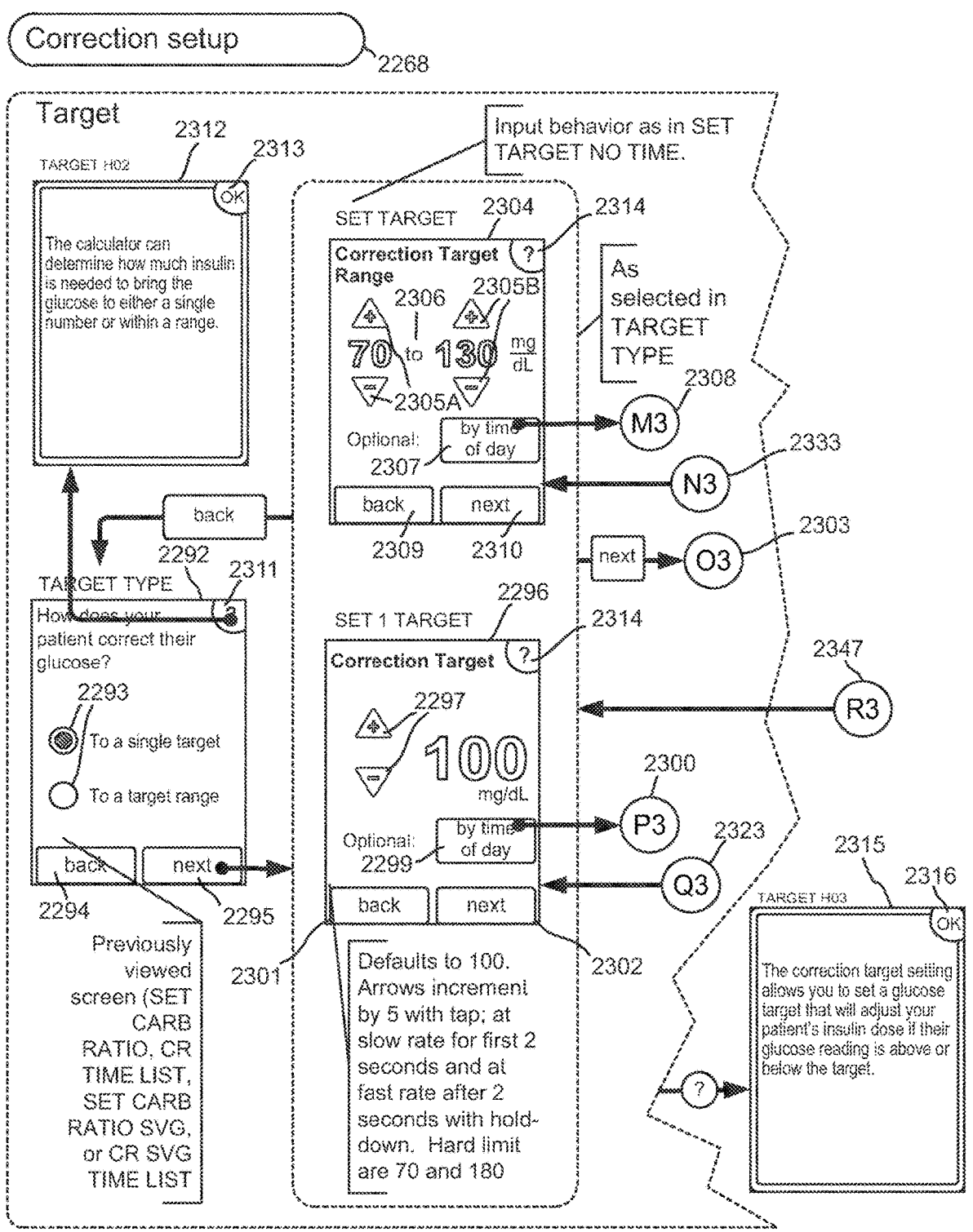
FIG. 32 illustrates a method for a correction setup, according to one embodiment.
Figure 32:
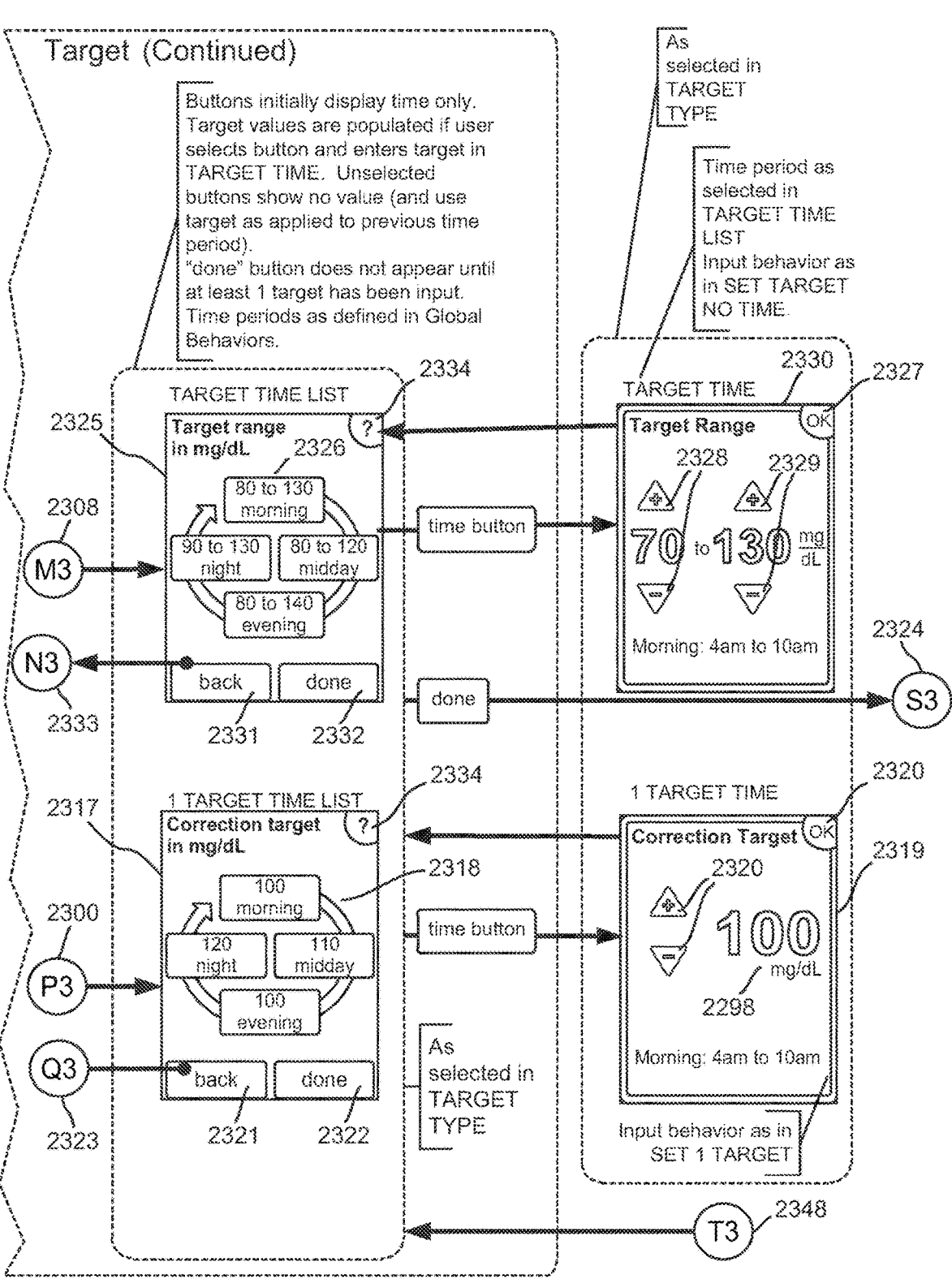
Figure 32:
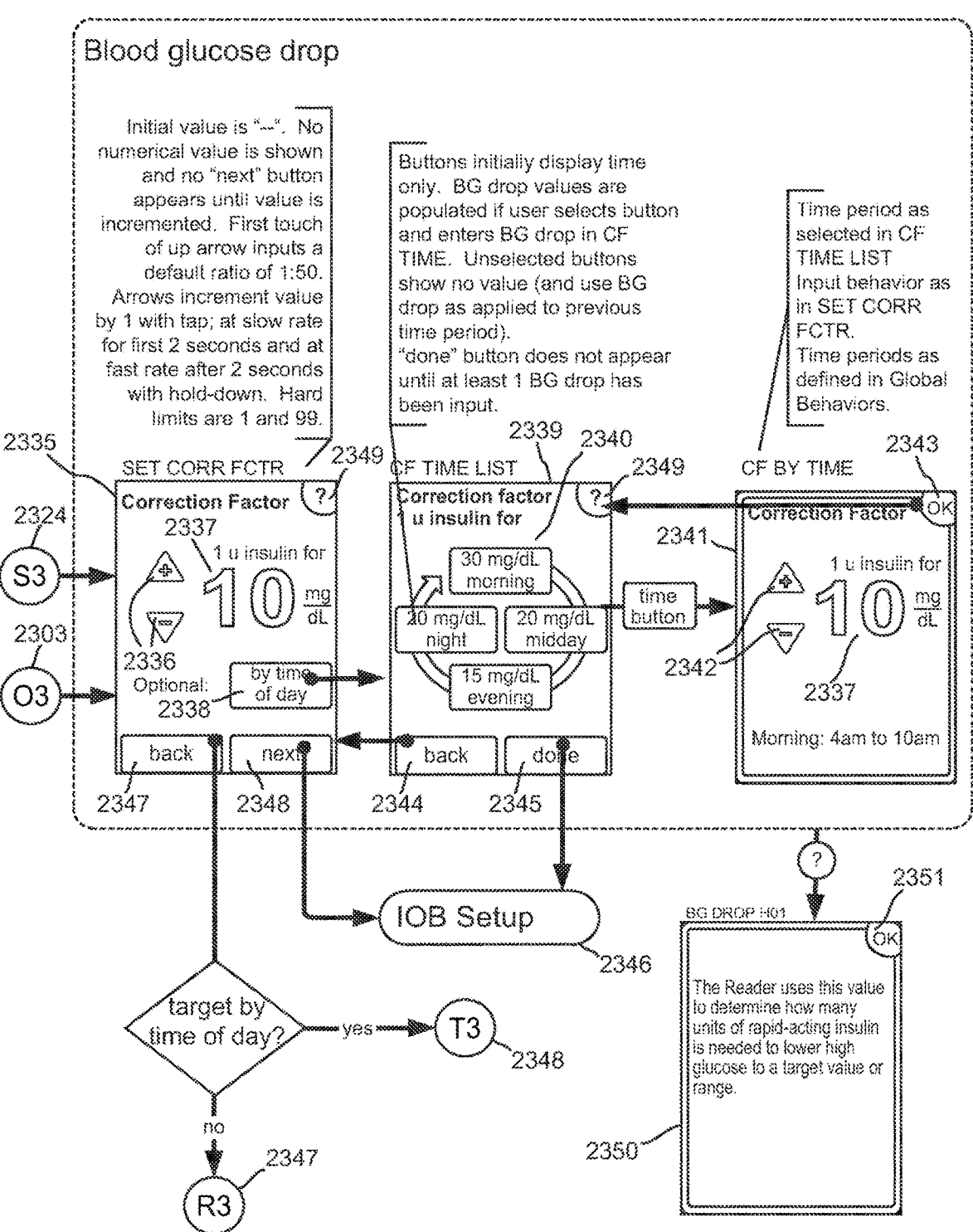

Correction Setup interface 2268 is described with reference to FIG. 32. Initiation of Correction Setup interface 2268 results in display of Target Type screen 2292. Target Type screen 2292 includes a prompt "How does your patient correct their glucose" or the equivalent. Target Type screen

2292 includes the following two options or their equivalent: 1) To a single target; and 2) To a target range, one of which may be selected by pressing one of the corresponding empty circles 2293 associated with the options. Note that FIG. 32 shows the "To a single target" options selected. Target Type screen 2292 also includes a touchscreen "back" button 2294 and a touchscreen "next" button 2295. Pressing touchscreen "back" button 2294 returns the user to the previously viewed screen (Set Carb Ratio screen 2251, CR Time List screen 2255, Set Carb Ratio Servings screen 2275, or CR Servings Time List screen 2279.

When the "To a single target" option is selected on screen 2292, pressing the touchscreen "next" button 2295 results in display of a Correction Target screen 2296. Correction Target screen 2296 includes touchscreen up and down-arrows 2297 for adjusting correction target 2298 (e.g., 100 mg/dL). Correction Target screen 2296 also includes a touchscreen "by time of day" button 2299. Pressing the touchscreen "by time of day" button 2299 results in initiation of reference pathway (P3) 2300, discussed in greater detail below. Correction Target screen 2296 also includes touchscreen "back" button 2301 and touchscreen "next" button 2302. Pressing touchscreen "back" button 2301 returns the user to Target Type screen 2292. Pressing touchscreen "next" button 2302 results in initiation of reference path (O3) 2303, discussed in greater detail below.

When the "To a target range" option is selected on screen 2292, pressing the touchscreen "next" button 2295 results in display of a Correction Target Range screen 2304. Correction Target Range screen 2304 includes first touchscreen up and down-arrows 2305A for adjusting the low end (e.g., 70 mg/dL) of correction target range 2306. Correction Target Range screen 2304 also includes second touchscreen up and down-arrows 2305B for adjusting the high end (e.g., 130 mg/dL) of correction target range 2306. Correction Target Range screen 2304 also includes a touchscreen "by time of day" button 2307. Pressing the touchscreen "by time of day" button 2307 results in initiation of reference pathway (M3) 2308, discussed in greater detail below. Correction Target Range screen 2304 also includes touchscreen "back" button 2309 and touchscreen "next" button 2310. Pressing touchscreen "back" button 2309 returns the user to Target Type screen 2292. Pressing touchscreen "next" button 2310 results in initiation of reference path (O3) 2303, discussed in greater detail below. Target Type screen 2292, includes a touchscreen "?" button 2311, which, when pressed, displays a target information screen 2312, including a prompt indicating that "The calculator can determine how much insulin is needed to bring the glucose to either a single number or within a range" or the equivalent. Pressing the touchscreen "OK" button 2313 returns the user to the Target Type screen 2292.

Each of Correction Target screen 2296, and Correction Target Range screen 2304 includes a touchscreen "?" button 2314, which, when pressed, displays a target information screen 2315, including a prompt indicating that "The correction target setting allows you to set a glucose target that will adjust your patient's insulin dose if their glucose readings is above or below the target" or the equivalent. Pressing the touchscreen "OK" button 2316 returns the user to the Correction Target screen 2296 or the Correction Target Range screen 2304 as appropriate.

As discussed above, pressing the touchscreen "by time of day" button 2299 on screen 2296 results in initiation of reference pathway (P3) 2300. Initiation of reference pathway (P3) 2300 results in display of Target Time List screen 2317, which includes touchscreen buttons 2318 for selecting a time of day (e.g., morning, midday, evening or night) for correction target 2298. Pressing one of touchscreen buttons 2318 results in display of a Target Time screen 2319. Target Time screen 2319 includes touchscreen up and down-arrows 2320 for adjusting correction target 2298 for the selected time of day. Target Time screen 2319 also includes touchscreen "OK" button 2320 for accepting the adjusted correction target 2298 for the selected time of day and returning the user to Target Time List screen 2317. Target Time List screen 2317 includes a touchscreen "back" button 2321 and a touchscreen "done" button 2322. Pressing touchscreen "back" button 2321 initiates reference pathway (Q3) 2323, which returns the user to the Correction Target screen 2296. Pressing touchscreen "done" button 2322 initiates reference path (S3) 2324, discussed in greater detail below.

As discussed above, pressing the touchscreen "by time of day" button 2307 on screen 2304 results in initiation of reference pathway (M3) 2308. Initiation of reference pathway (M3) 2308 results in display of Target Range Time List screen 2325, which includes touchscreen buttons 2326 for selecting a time of day (e.g., morning, midday, evening or night) for correction target range 2306. Pressing one of touchscreen buttons 2326 results in display of a Target Range Time screen 2327. Target Range Time screen 2327 includes first touchscreen up and down-arrows 2328 for adjusting the low end of correction target range 2306 for the selected time of day. Target Range Time screen 2327 includes second touchscreen up and down-arrows 2329 for adjusting the high end of correction target range 2306 for the selected time of day. Target Range Time screen 2327 also includes touchscreen "OK" button 2330 for accepting the adjusted correction target range 2306 for the selected time of day and returning the user to Target Range Time List screen 2325. Target Range Time List screen 2325 includes a touchscreen "back" button 2331 and a touchscreen "done" button 2332. Pressing touchscreen "back" button 2331 initiates reference pathway (N3) 2333, which returns the user to the Correction Target Range screen 2304. Pressing touchscreen "done" button 2332 initiates reference path (S3) 2324, discussed in greater detail below.

Each of Target Time List screen 2317 and Target Range Time List screen 2325 includes a touchscreen "OK" button 2334, which, when pressed, results in display of target information screen 2315, including a prompt indicating that "The correction target setting allows you to set a glucose target that will adjust your patient's insulin dose if their glucose readings is above or below the target" or the equivalent. Pressing the touchscreen "OK" button 2316 returns the user to the Target Time List screen 2317 or the Target Range Time List screen 2325 as appropriate.

As discussed above, pressing touchscreen "next" button 2302 or 2310 initiates reference path (O3) 2303. Similarly, pressing "done" button 2322 or 2332 initiates reference path (S3) 2324. Reference paths (O3) 2303 and (S3) 2324 both result in display of a Set Correction Factor screen 2335. Set Correction Factor screen 2335 includes touchscreen up and down-arrows 2336 for adjusting insulin correction factor 2337 (e.g., 1 u insulin for 10 mg/dL). Set Correction Factor screen 2335 also includes a touchscreen "By time of day" button 2338, which, when pressed, results in display of a Correction Factor Time List screen 2339. Correction Factor Time List screen 2339 includes touchscreen buttons 2340 for selecting a time of day (e.g., morning, midday, evening or night) for correction factor 2337.

Pressing one of touchscreen buttons 2340 results in display of a Correction Factor by Time screen 2341. Correction Factor by Time screen 2341 includes touchscreen up and down-arrows 2342 for adjusting correction factor 2337 for the selected time of day. Correction Factor by Time screen 2341 also includes a touchscreen "OK" button 2343 for accepting the adjusted correction factor 2337 for the selected time of day and returning the user to Correction Factor Time List screen 2339.

Correction Factor Time List screen 2339 includes a touchscreen "back" button 2344 and a touchscreen "done" button 2345. Pressing touchscreen "back" button 2344 returns the user to the Set Correction Factor screen 2335. Pressing touchscreen "done" button 2345 initiates an Insulin On Board (IOB) interface 2346, discussed in greater detail below.

Set Correction Factor screen 2335 includes a touchscreen "back" button 2347 and a touchscreen "next" button 2348. Pressing touchscreen "back" button 2347 initiates reference path (T3) 2348 or (R3) 2347, respectively, depending on whether the optional "target by time of day" format has been selected or not. Pressing touchscreen "next" button 2348 initiates the Insulin On Board (IOB) interface 2346. Reference path (R3) 2347 returns the user to the Correction Target Range screen 2304 or the Correction Target screen 2296 as appropriate. Reference path (T3) 2348 returns the user to the Target Range Time List screen 2325 or the Target Time List screen 2317 as appropriate.

Each of Set Correction Factor screen 2335 and Correction Factor Time List screen 2339 includes a touchscreen "?" button 2349, which, when pressed, results in display of informational screen 2350. Informational screen 2350 displays a prompt indicating "The Reader uses this value to determine how many units of rapid-acting insulin is needed to lower high glucose to a target value or range" or the equivalent. Informational screen 2350 also includes a touchscreen "OK" button 2351 for returning the user to Set Correction Factor screen 2335 or Correction Factor Time List screen 2339 as appropriate.

Insulin on Board (IOB) Setup Interface

Figure 33:
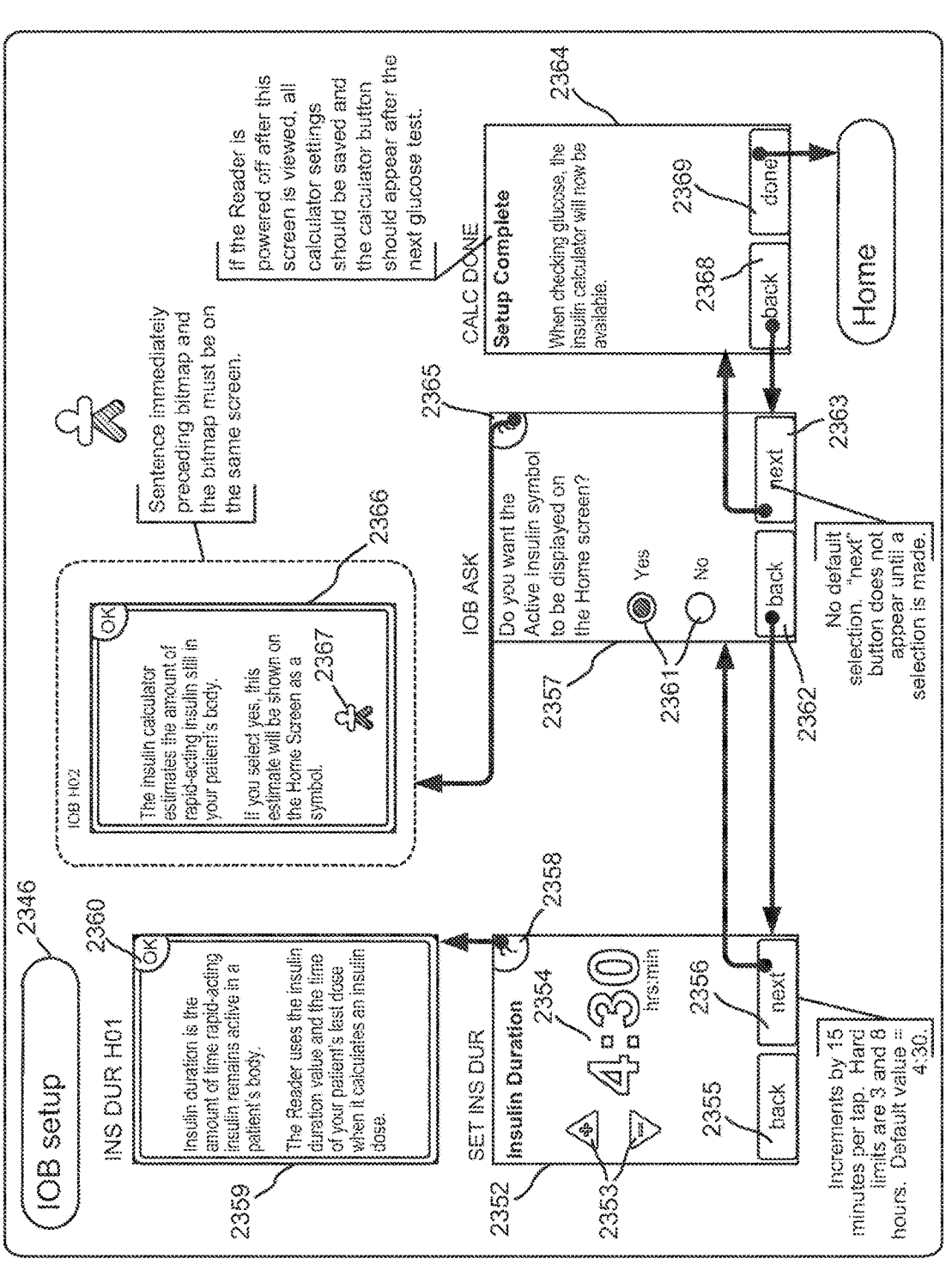
FIG. 33 illustrates a method for an insulin on board setup and a method for saving settings, according to one embodiment.
Figure 33:
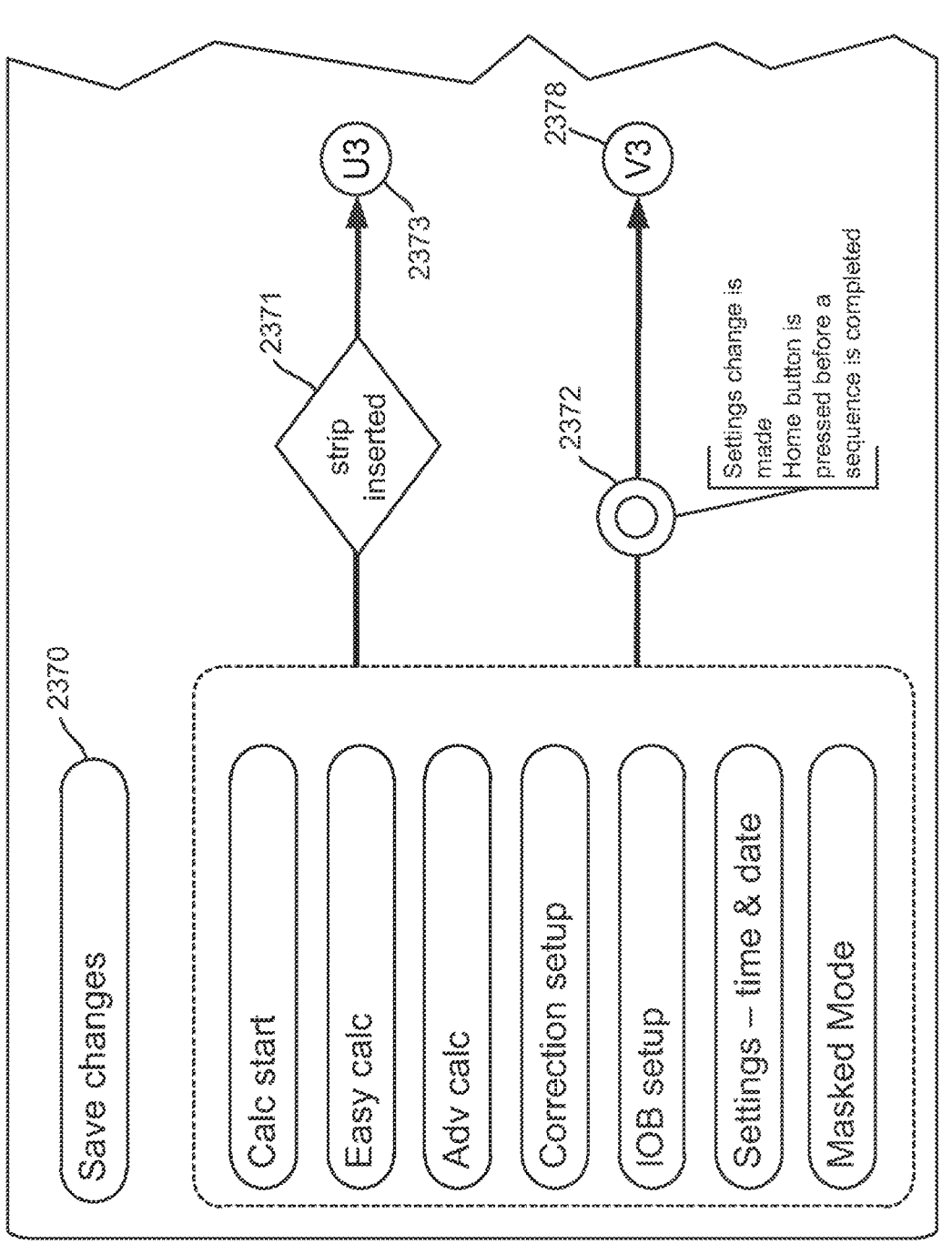
Figure 33:
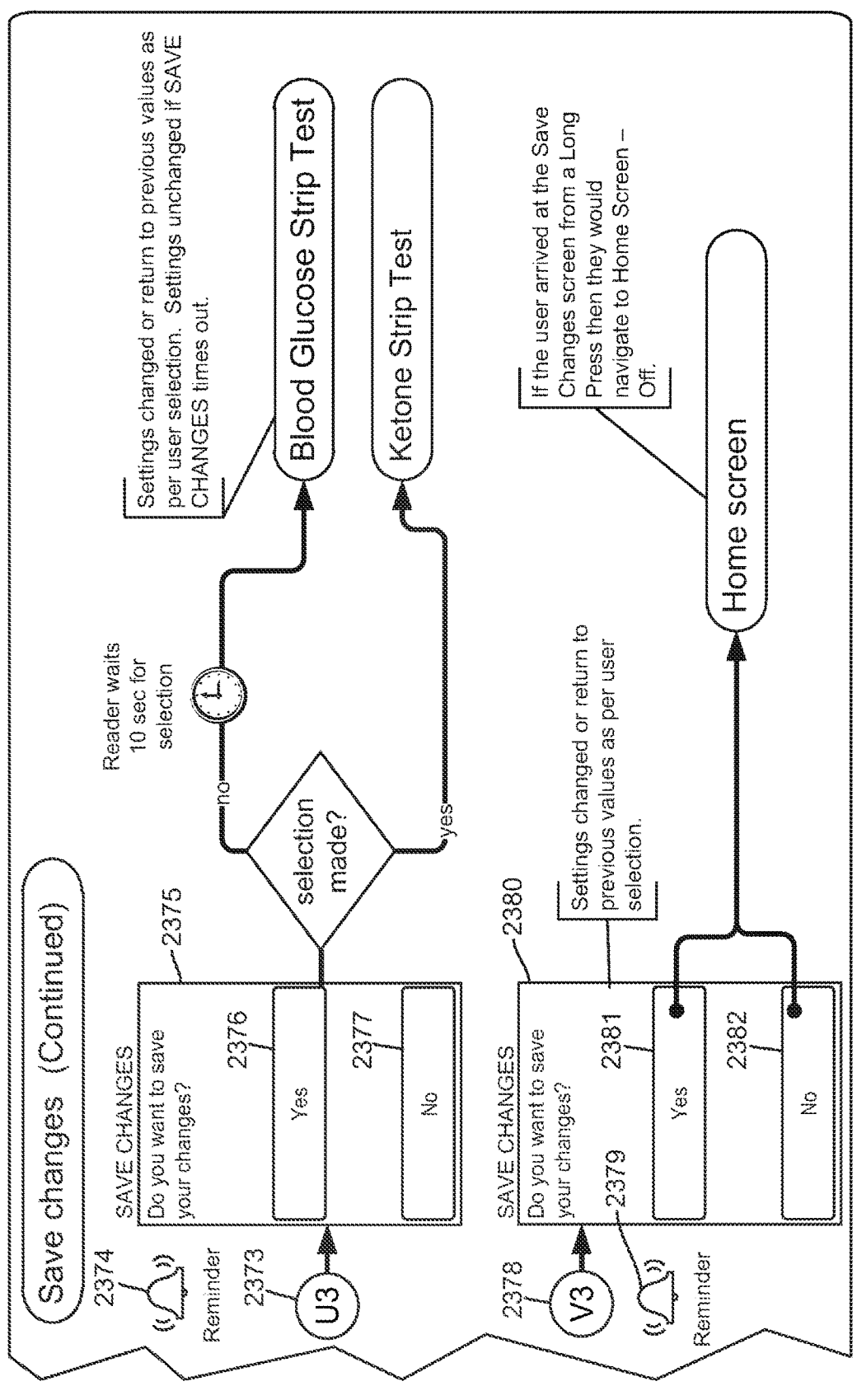

The Insulin On Board (IOB) Setup interface 2346 is described with reference to FIG. 33. Initiation of the IOB Setup interface 2346 results in display of Set Insulin Duration screen 2352. Set Insulin Duration screen 2352 includes touchscreen up and down-buttons 2353 for adjusting insulin duration (e.g., 4 hrs: 30 min). Set Insulin Duration screen 2352 also includes touchscreen "back" button 2355 and touchscreen "next" button 2356. Pressing touchscreen "back" button 2355 returns the user to the previously viewed screen, e.g. Set Correction Factor screen 2335 or Correction Factor Time List screen 2339. Pressing touchscreen "next" button 2356 results in display of IOB Ask screen 2357. Set Insulin Duration screen 2352 also includes touchscreen "?" button 2358, which, when pressed, results in display of insulin duration description screen 2359. Insulin duration description screen 2359 displays a prompt indicating "Insulin duration is the amount of time rapid-acting insulin remains active in a patient's body" or equivalent. "The Reader uses the insulin duration value and the time of your patient's last dose when it calculates an insulin dose" or equivalent" or equivalent. Insulin duration description screen 2359 includes a touchscreen "OK" button which, when pressed, returns the user to Set Insulin Duration screen 2352.

IOB Ask screen 2357 displays a prompt indicating "Do you want the Active Insulin symbol to be displayed on the Home screen?" or equivalent. IOB Ask screen 2357 includes a Yes and a No option, one of which may be selected by pressing one of the corresponding empty circles 2361 associated with the option. Note that FIG. 33 shows the Yes option selected. IOB Ask screen 2357 includes a touchscreen "back" button 2362 and a touchscreen "next" button 2363. Pressing touchscreen "back" button 2362 returns the user to Set Insulin Duration screen 2352. Pressing touchscreen "next" button 2363 results in display of a Calculation Done screen 2364. IOB Ask screen 2357 also includes a touchscreen "?" button 2365, which, when pressed, results in display of an insulin calculator description screen 2366. Insulin calculator description screen 2366 displays a prompt indicating that "The insulin calculator estimates the amount of rapid-acting insulin still in your patients body" or equivalent and "If you select yes, this estimate will be shown on the Home screen as a symbol" or equivalent. Note the symbol 2367 depicted in FIG. 33. The insulin calculator description screen 2366 includes a touchscreen "OK" button, which, when pressed, returns the user to the IOB Ask screen 2357.

Calculation Done screen 2364 includes a prompt indicating that setup is complete and may include a prompt indicating "When checking glucose, the insulin calculator will now be available" or equivalent. Calculation Done screen 2364 also includes a touchscreen "back" button 2368 and a touchscreen "done" button 2369. Pressing touchscreen "back" button 2368 returns the user to IOB Ask screen 2357. Pressing touchscreen "done" button 2369 returns the user to the reader Home Screen as described herein.

Save Changes Interface

A Save Changes interface 2370 operates to remind the user to save changes in the event a strip is inserted 2371 into the reader or the Home button is pressed 2372 before a sequence is completed. In the event a strip is inserted 2371 into the reader, reference path (U3) 2373 is initiated. Reference path (U3) 2373 results in display of a reminder prompt 2374 to the user. A Save Changes screen 2375 is displayed which includes a prompt indicating "Do you want to save your changes?" or equivalent. Save Changes screen 2375 includes a touchscreen "Yes" button 2376 and a touchscreen "No" button 2377. If the "No" button 2377 is pressed or a selection is not made in 10 seconds the settings return to their previous values. If the "Yes" button 2376 is pressed, the new settings are saved. In either case, either a Blood Glucose Strip Test interface or a Ketone Strip Test interface is initiated as appropriate based on the identity of the inserted test strip.

Reference path (V3) 2378 results in display of a reminder prompt 2379 to the user. A Save Changes screen 2380 is displayed which includes a prompt indicating "Do you want to save your changes?" or equivalent. Save Changes screen 2380 includes a touchscreen "Yes" button 2381 and a touchscreen "No" button 2382. If the "No" button 2382 is pressed, the settings return to their previous values. If the "Yes" button 2381 is pressed, the new settings are saved. In either case, the user is returned to the Home screen as described herein.

Additional Information Regarding Data Management Software

Additional information for the Auto Assist Software is provided in the following paragraphs and figures. It should be appreciated that the example interface flows are exemplary and should not be interpreted as limiting.

Example Interface Flows

Application Startup

Figure 36:
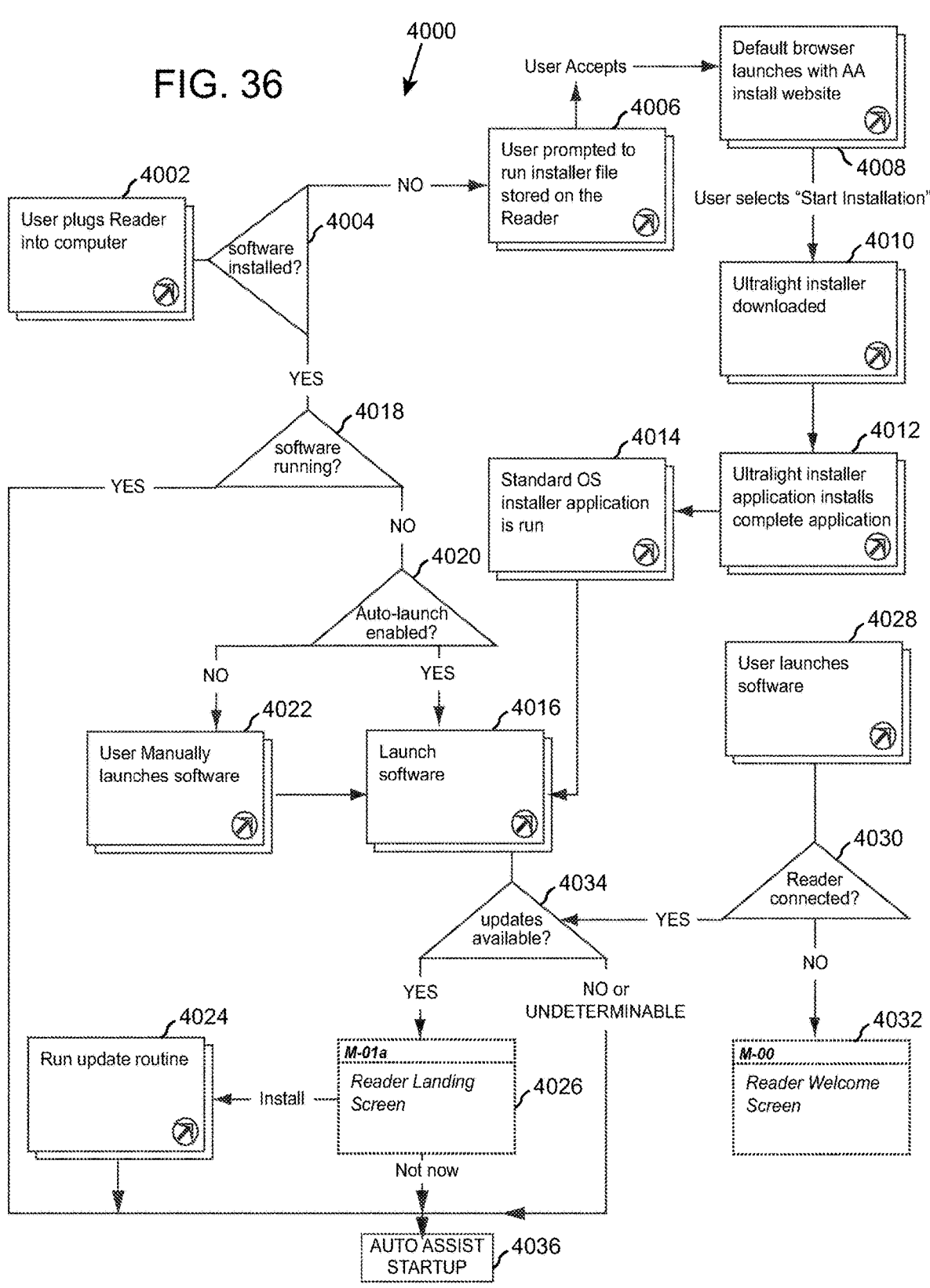
FIG. 36 illustrates a method when starting up Remote Device (RD) software on a remote data processing device, according to one embodiment.

FIG. 36 illustrates a method 4000 when starting up the RD software, according to one embodiment. At block 4002, the Reader is coupled to a remote processing device, such as the user's computer. At block 4004 it is determined whether the software is installed on the remote processing device. If not, then the user is prompted to run an installer file stored on the reader, as shown at block 4006. If the user accepts, a default browser is launched with the data management software (RD software) install website, as shown at block 4008. The user may elect to start the installation of the RD software and an installer application is downloaded to the remote device to install the complete installer application, as shown by blocks 1010 and 1012. The standard operation system (OS) installer application is run and the RD software is launched, as shown at block 4012 and 4014.

Referring back to block 4004, if the RD software is already installed on the remote device, then it is determined if the RD software is currently running. If so, then the user is taken to the Reader Landing screen at block 4026.

If the RD software is not currently running, then it is determined if an auto-launch is enabled to automatically launch the RD software if the analyte monitoring device is coupled to the remote device, as shown at block 4020. If the auto-launch is enabled, then the RD software is launched on the remote device. If the auto-launch is not enabled, then the user may manually launch the software when desired, as shown at block 4022.

When the RD software is launched, the software may automatically perform or ask to determine if updates to the software are available, as represented by block 4034. The RD software may, for example, access a server via the internet to determine what updates are currently available, and then compare the version of the software and any previous updates to see if any additional updates are missing. If new updates are not available, then the RD software application continues with the Data Management Startup process to enable the user to use the RD software, as represented at block 4036.

If new updates are available, then the Reader Landing screen is displayed, as shown at block 4026. If the user elects not to run the update routines at this time, the RD software application continues with the Data Management Startup process to enable the user to use the RD software, as represented at block 4036. If the user elects to install the updates, then the update routines are run, as shown at block 4024, before continuing on with the Data Management Startup process at block 4036

If instead of starting at block 4002, the user launches RD software already installed on a remote device, as shown at block 4028, then it is determined if the analyte monitoring device is coupled to the remote device, as shown at block 4030. If the reader device is not connected, then a Reader Welcome screen is displayed to assist the user as the RD software is running, as shown at block 4032. If the reader is coupled to the remote device, then it is determined if any updates are available as shown and discussed for block 4034.

Figure 37:
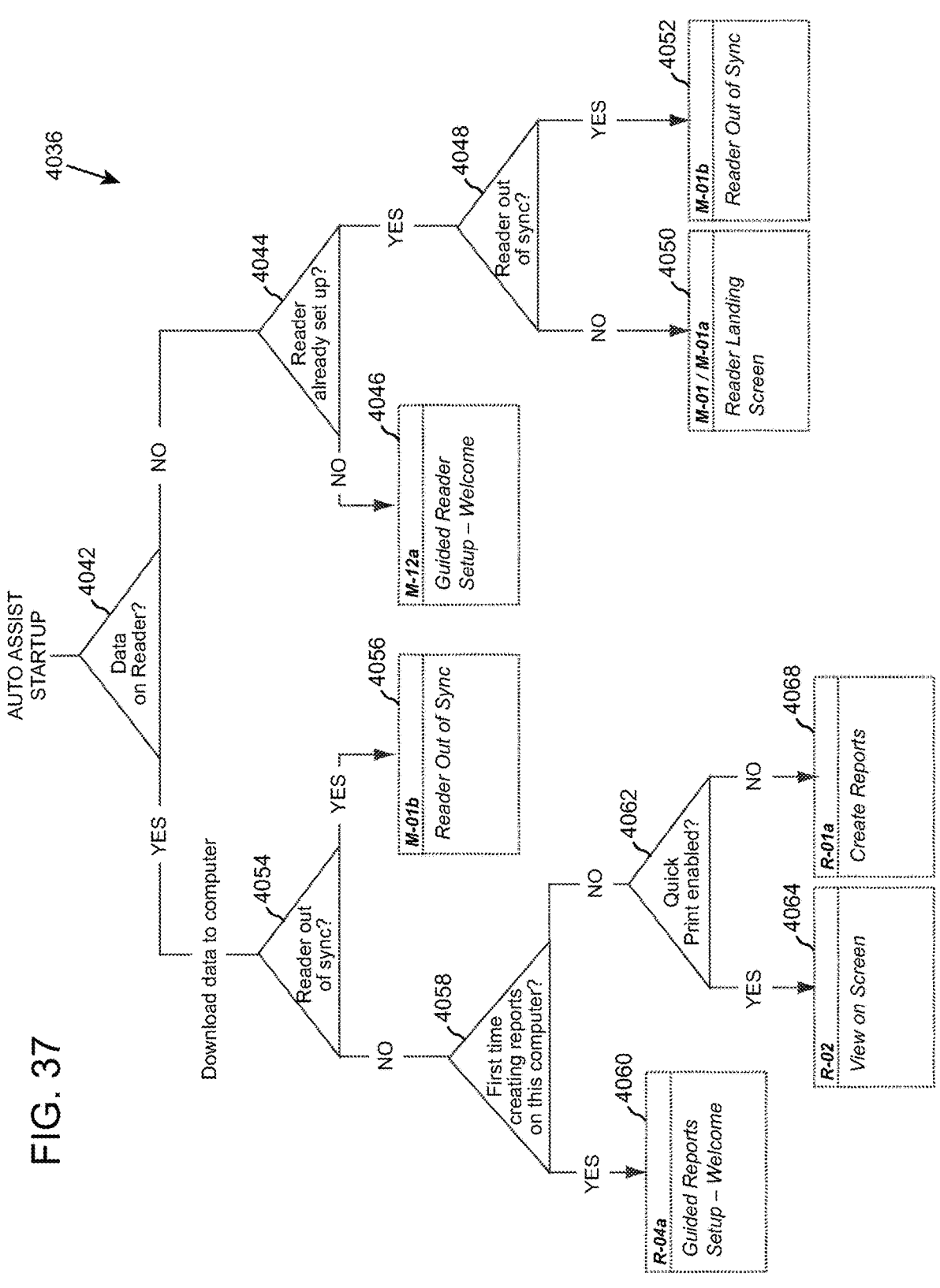
FIG. 37 illustrates a flowchart for the data management software startup process, according to one embodiment.

FIG. 37 illustrates a flowchart for the Data Management Startup process 4036, according to one embodiment. As the RD software starts up, it is determined if there is date (e.g., sensor readings) on the reader device, as shown at block 4042. If there is no data on the reader device, then it is determined if the reader device has already been set up, as shown at block 4044. If not, then the user is taken to a Guided Reader Setup-Welcome screen for guiding the user through the reader setup process, as shown at block 4046. If the reader device has been setup before, then it is determined if the reader device and remote device are out of sync (e.g., the time on the Reader device and the remote device are different) If the reader device is out of sync, then a Reader Out of Sync screen is provided, as shown at block 4052, to inform the user and to enable synchronization. If the reader device is not out of sync, then the Reader Landing Screen is displayed, as shown at block 4050.

Referring back to block 4042, if sensor reading data is on the reader device, then the data may be downloaded to the remote device, either automatically or upon user confirmation, as shown by block 4054. At block 4054, it is determined if the reader device and remote device are out of sync. If so, then the Reader Out of Sync screen is displayed. If no out of sync, then it is determined if it is the first time creating reports on the remote device, as shown at block 4058., If so, then a Guided Reports Setup—Welcome screen is displayed, as shown at block 4060, to assist the user with setting up reports. If it is not the first time creating reports on the remote device, then it is determined if a quick print feature is enabled to allow quick display and/or printing of predetermined or pre-customized reports. If the quick printing feature is not enabled, then the user is taken to a Generate Reports screen to enable the user to generate reports, as shown at block 4068.

Figure 38:
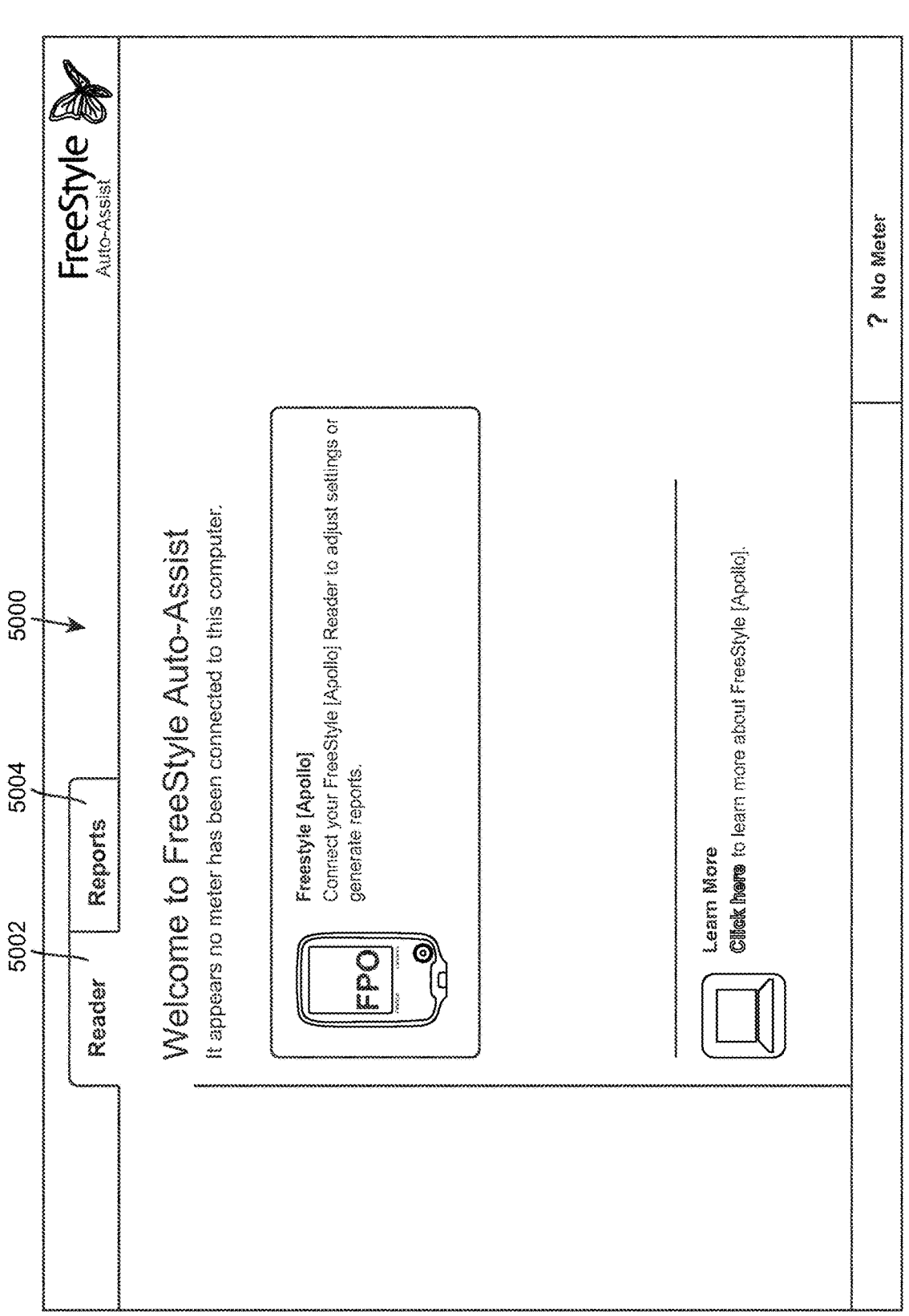
FIG. 38 illustrates an example Welcome screen, according to one embodiment.

FIG. 38 illustrates an example Welcome screen, according to one embodiment. The Welcome screen 5000, may be shown after the user launches the software prior to connecting the Reader device, for example, to inform the user that the system does not currently recognize a connected Reader and prompts them to connect one. Screen 5000 includes a Reader tab 5002 and a Reports tab 5004 that corresponds to a Reader Mode and a Reports mode, respectively, of the RD software. The tabs 5002,5004 are maintained on other screens for the RD software. In one embodiment, the Reader mode and Reports mode are not accessible to the user if a Reader is not connected to the remote device.

Reader Mode

Figure 39:
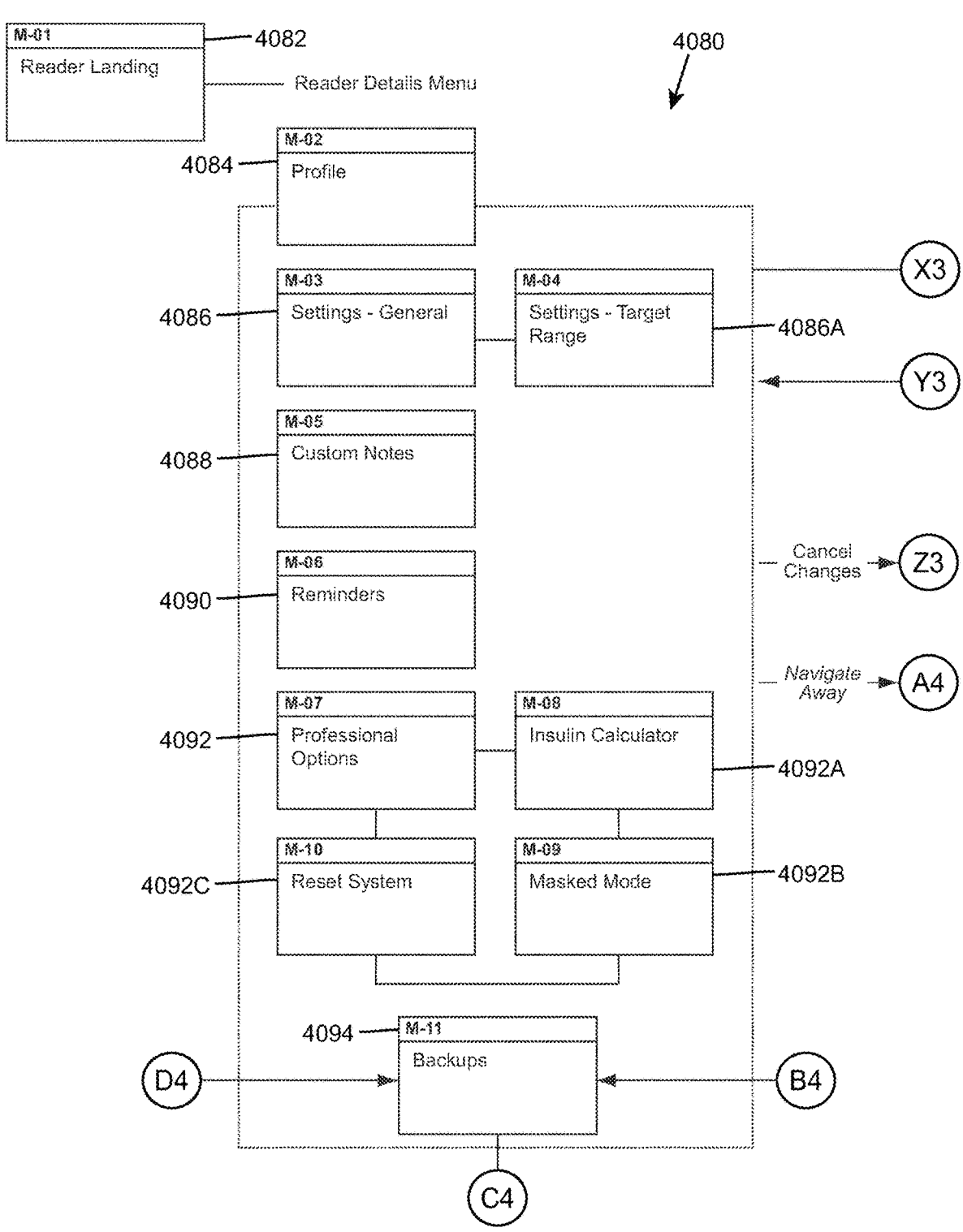
FIG. 39 illustrates a flowchart for a method of navigating through the Reader mode for accessing setting and functions that are used to setup and control the Reader device, according to one embodiment.
Figure 39:
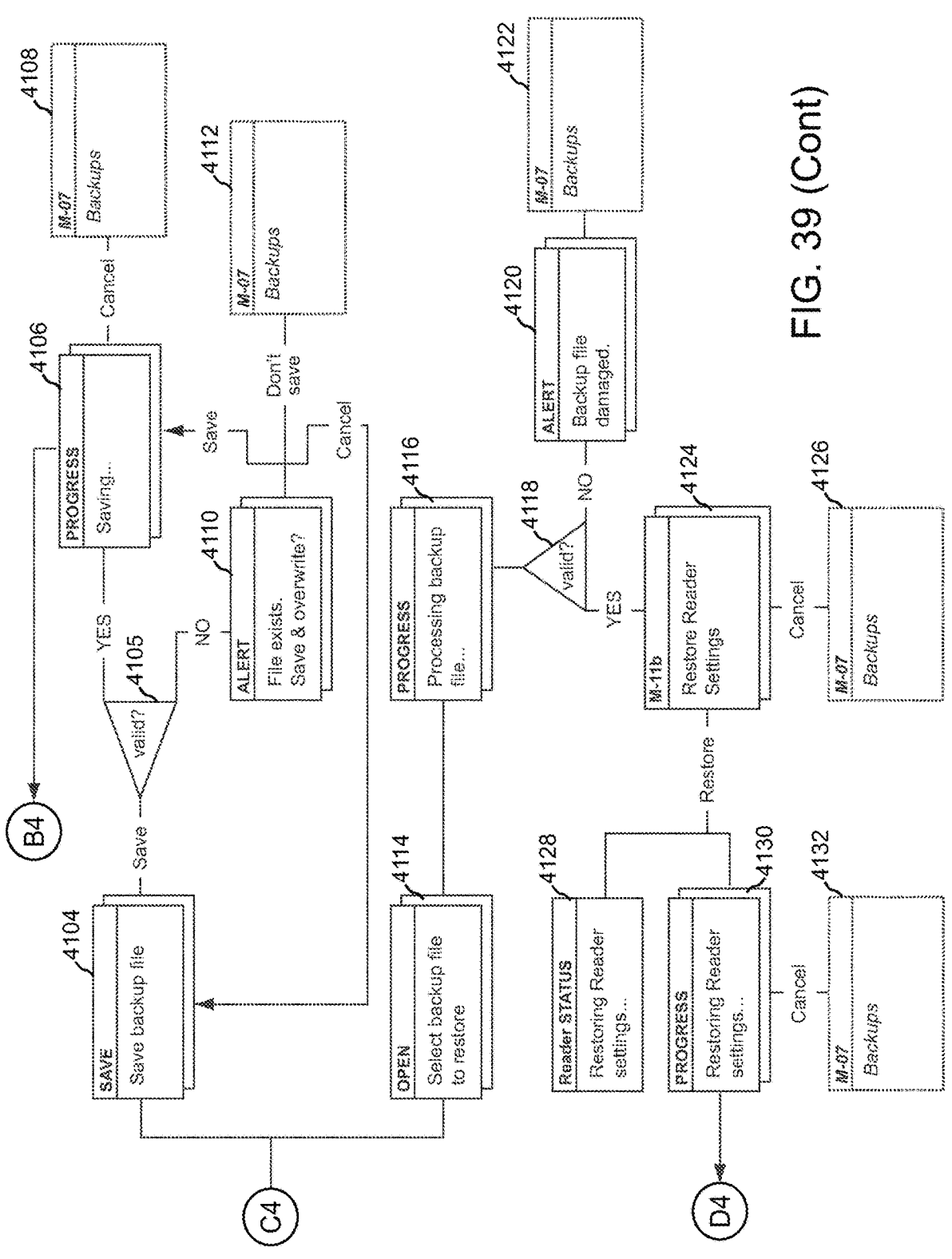
Figure 39:
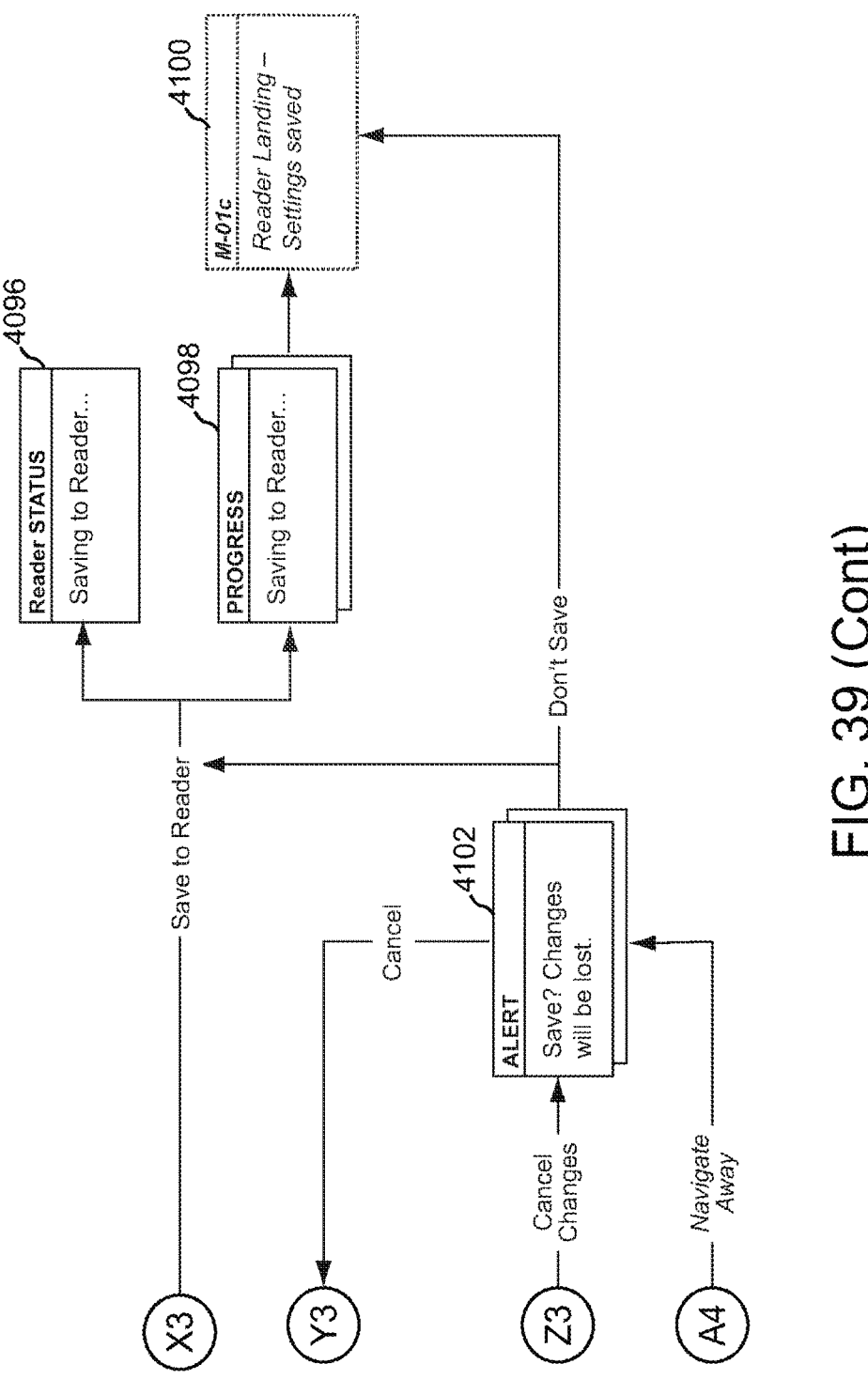

FIG. 39 illustrates a flowchart for a method 4080 of navigating through the Reader mode for accessing setting and functions that are used to setup and control the Reader device. Reader setting are directly read form or saved back to the Reader device via functions primarily originating from the Reader mode and collection of screens.

Figure 40:
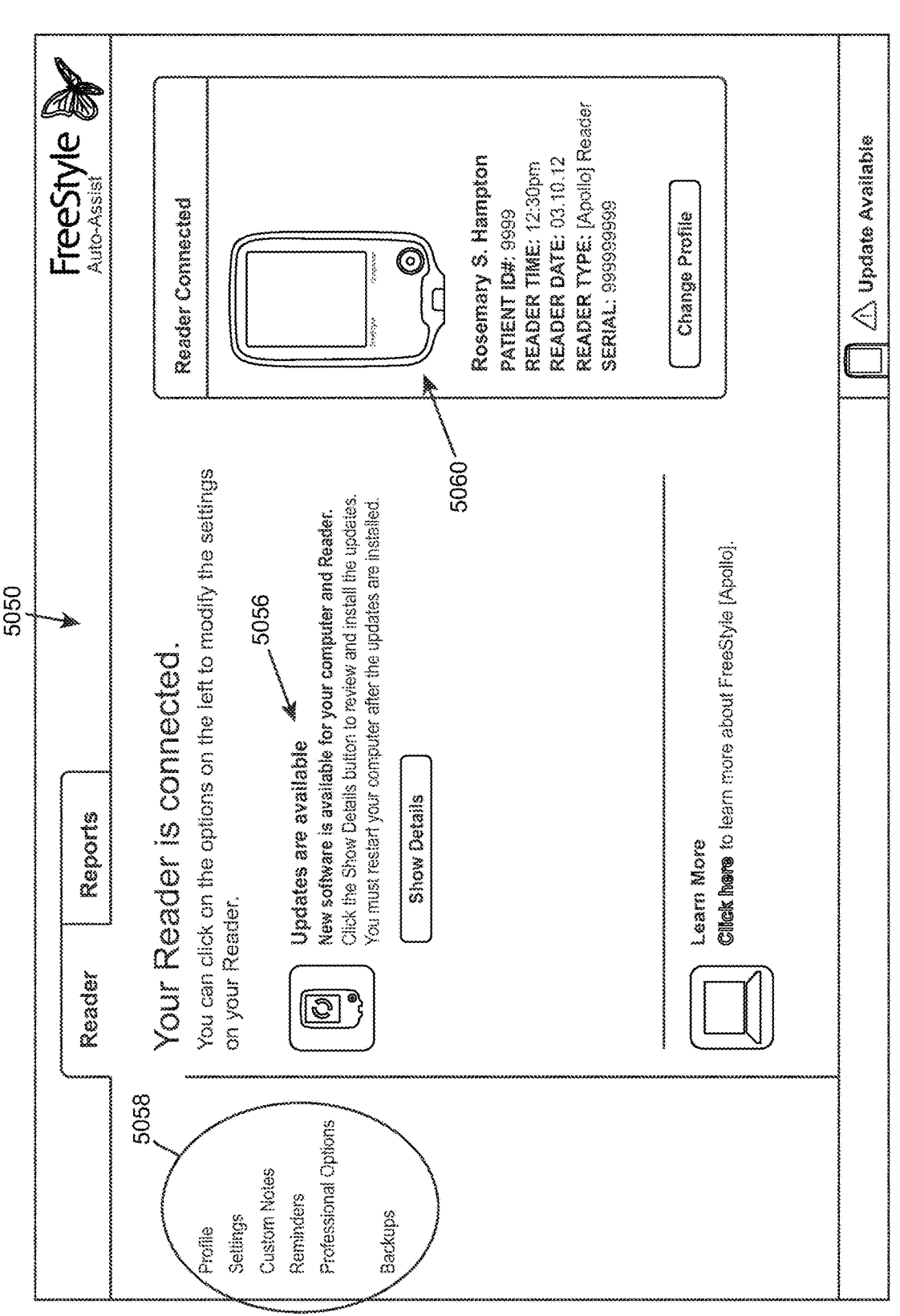
FIG. 40 illustrates an example Reader Landing screen, according to one embodiment.

Block 4082 represents a Reader Landing screen, wherein details regarding the Reader may be accessed. FIG. 40 illustrates an example screen displayed when the Reader device is connected, according to one embodiment. Screen 5050 includes the update notification 5056, as well as, a quick synopsis of the profile of the Reader that is connected. The screen 5050 also includes a menu 5058 of trigger elements for initiating other Reader Mode screens, such as a Profile screen, Settings screen, Custom Notes screen, Reminders screen, Professional Options screen, and a Backups screen, which are all discussed further later.

Figure 41:
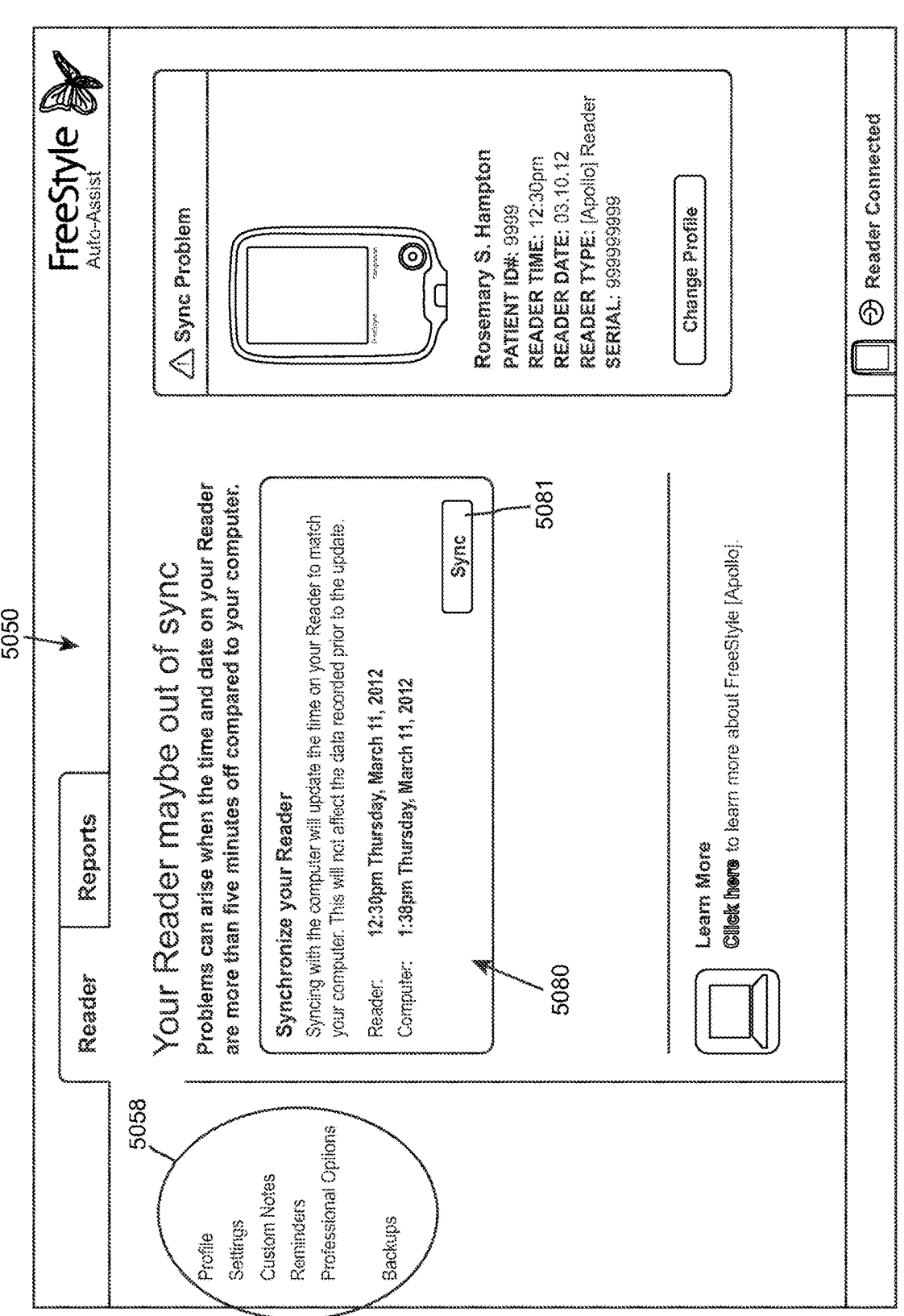
FIG. 41 illustrates a screen indicating that the Reader is out of sync, according to one embodiment.

FIG. 41 illustrates an example screen that is displayed to indicate that the Reader device is out of sync, according to one embodiment. Screen 5050 displays an Out of Sync content notification 5080 that informs the user that the Reader device may be out of sync, and may further provide additional details about the sync (e.g., the time on both the Reader and the remote device) and enable the user to sync the Reader device. For example, trigger element 5081 is provided to enable the user to elect to sync the Reader device.

As shown in FIG. 39, from the Reader Landing screen at block 4082, the user may select from a menu 5058 of trigger elements for initiating other Reader Mode screens, such as a Profile screen at block 4084, Settings screen at block 4086, Custom Notes screen at block 4088, Reminders screen at block 4090, Professional Options screen at block 4092, and a Backups screen at block 4094, are accessible from the Reader Landing screen.

Figure 42:
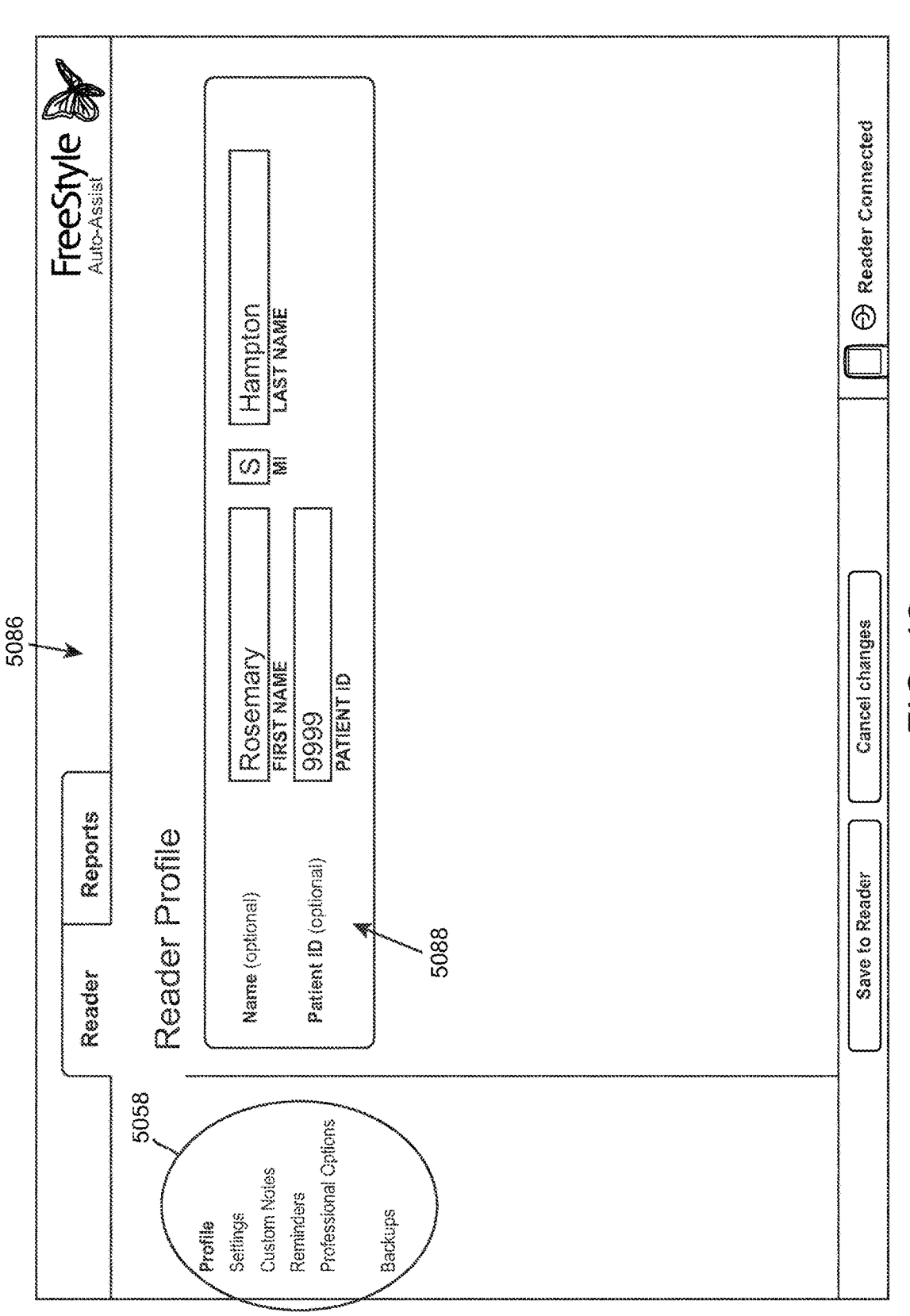
FIG. 42 illustrates a Profile screen, according to one embodiment.

At block 4084, the user is taken to a Profile screen. FIG. 42 illustrates a Profile screen 5086, according to one embodiment. As shown, Profile screen 5086 provides a section 5058 in which the user can set a name and patient ID, for example, to be associated with the Reader device. As shown, the menu 5058 of trigger elements for initiating various screens is maintained in the Profile screen 5086.

Referring back to FIG. 39, at block 4084, the user is taken to a Settings screen. The Settings screen provides screens for enabling the user to adjust general settings—e.g., as time, date, clock, style, language, sound and vibration options, sync settings—as well as target zone settings (e.g., glucose target zone settings.

At block 4084, the user is taken to a Custom Notes screen where the user can view, edit, and/or delete notes from the Reader device. These notes can be default notes or customized notes by the user.

At block 4086, the user is taken to a Reminders screen where the user can view, edit, and/or delete reminders from the Reader device. The reminders may be provided to remind the user to check glucose readings, take insulin, etc.

At block 4088, the user is taken to a Professional Options screen where the user can access restricted features that should only be accessed by trained health care professionals (HCP). A password or code only given to the HCP's may be required to access the settings. Example features that may be restricted are the activation and setting of an insulin calculation feature, a masked mode operation of the device, the resetting of the system and/or settings on the device, etc.

Insulin Calculator Setup Interface:

An exemplary embodiment of a graphical user interface which may be utilized in connection with Health Management Software for a Reader as described herein and which facilitates a procedure for inputting the insulin calculator settings via the Health Management Software is provided. This graphical user interface is now described in greater detail with reference to FIGS. 43-46.

In some cases, the Health Management Software for the Reader may include programming for two or more types of medication dosage calculators. During setup of the Health Management Software, the Health Management Software may prompt the user and/or the health care professional to select a type of medication dosage calculator (e.g., insulin bolus calculator). The initial selection of the type of medication dosage calculator may be changed as desired by the user or the health care professional. In certain embodiments, the two or more types of medication dosage calculators include two types of bolus calculators. For instance, the two types of bolus calculators can include an easy bolus calculator and an advanced bolus calculator.

By "easy calculator", "easy bolus calculator", "simple bolus calculator", "easy insulin calculator" or "simple insulin calculator" is meant a bolus calculator that includes basic features for determining a recommended medication dosage amount, such as a recommended insulin dosage amount. For example, an easy bolus calculator may include algorithms configured to determine a recommended medication dosage amount based on a fixed medication dosage amount. In these instances, the easy bolus calculator may be appropriate for a user that administers a fixed medication dosage amount (e.g., a fixed insulin dosage amount) for each meal. In some embodiments, the easy bolus calculator only takes into account the fixed medication dosage amount when recommending the medication dosage amount to the user, and thus functions as a reminder and/or log for the fixed medication dosage amount.

The insulin calculator setup procedure begins on the Insulin Calculator Interface Setup screen 3800, where the user can select an Insulin Calculator On/Off toggle button 3802 to turn the insulin calculator on or off. When the Insulin Calculator On/Off toggle button is selected into the "On" position, the insulin calculator is activated and may be set up as described below. The desired type of insulin calculator (e.g., easy or advanced calculator) can be selected by selecting the insulin calculator selection box 3804, which allows the selection of "Easy" to activate the easy insulin calculator, and "Advanced" to activate the advanced insulin calculator.

Figure 43:
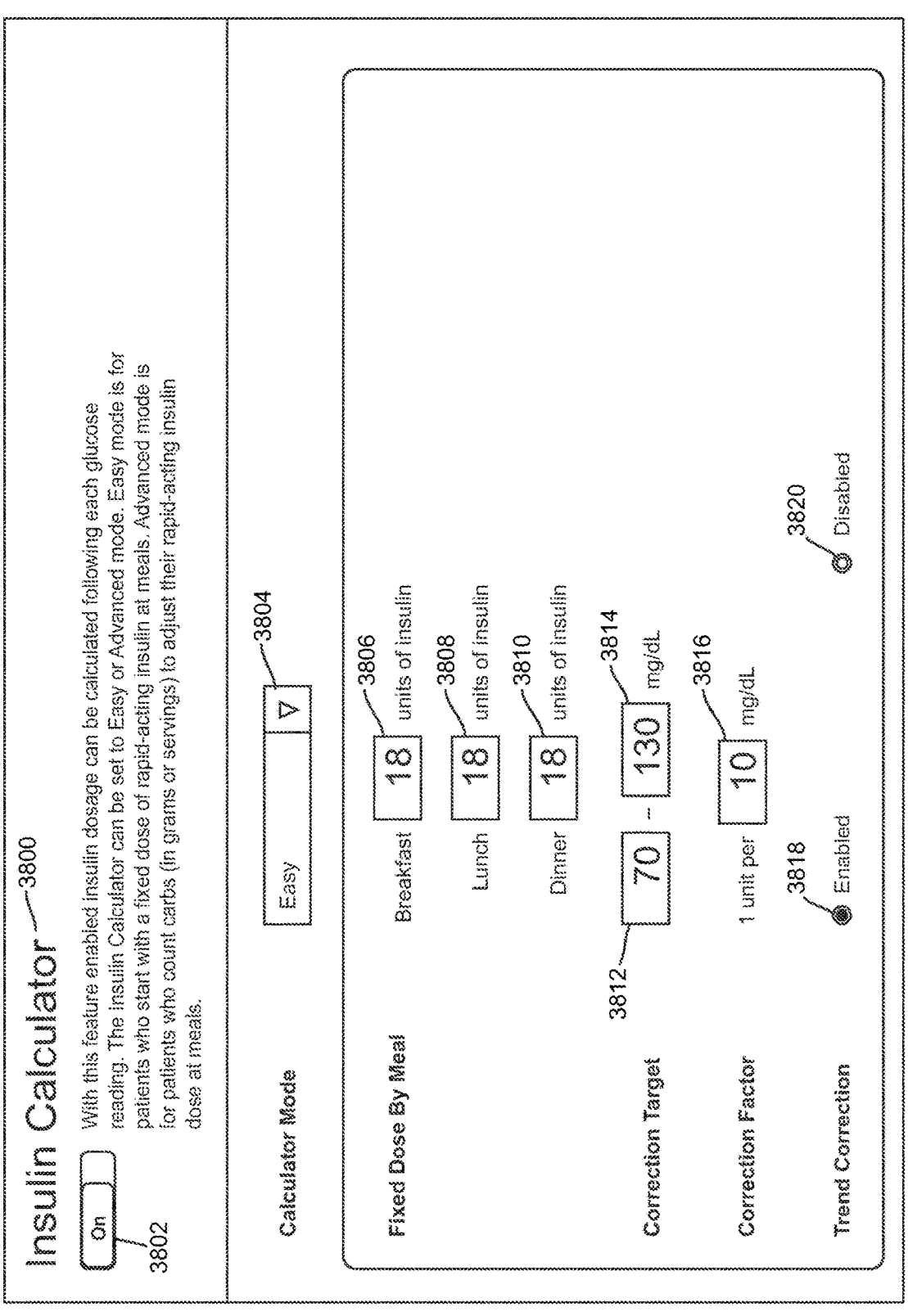
FIG. 43 illustrates an Insulin Calculator Setup Interface for health management software configured for an easy insulin calculator, according to embodiments of the present disclosure.

If the user selects the "Easy" selection in the insulin calculator selection box 3804, the Insulin Calculator Setup Interface screen 3800 displays the set up options for the easy bolus calculator. Set up for the easy bolus calculator is shown in FIG. 43.

In certain embodiments, the easy bolus calculator may determine a recommended medication dosage amount (e.g., a recommended rapid-acting insulin dosage amount) based on information, such as, but not limited to, a fixed medication dosage amount, a target blood glucose range (e.g., correction target), and an insulin sensitivity (e.g., correction factor). In some instances, the easy bolus calculator may also include information, such as the patient's insulin on board, in the determination of a recommended medication dosage amount. For example, a fixed medication dosage amount may be entered by meal (e.g., breakfast, lunch and dinner).

The Insulin Calculator Setup Interface screen 3800 includes amount entry boxes for each meal. A fixed medication dosage amount may be entered into the breakfast amount entry box 3806, the lunch amount entry box 3808 and the dinner amount entry box 3810 as units of insulin. In some embodiments, the correction target range may be entered. The Insulin Calculator Setup Interface screen 3800 includes correction target range amount entry boxes for the minimum target range value 3812 and the maximum target range value 3814. In some embodiments, the Insulin Calculator Setup Interface screen 3800 includes a correction factor amount entry box 3816 in which the insulin sensitivity (e.g., correction factor) may be entered as 1 unit per X mg/dL, where X is the amount entered for the correction factor. In some embodiments, the Insulin Calculator Setup Interface screen 3800 includes radio buttons for enabling or disabling insulin calculator trend correction by selecting either the trend correction enabled radio button 3818 or the trend correction disabled radio button 3820, respectively.

Figure 44:
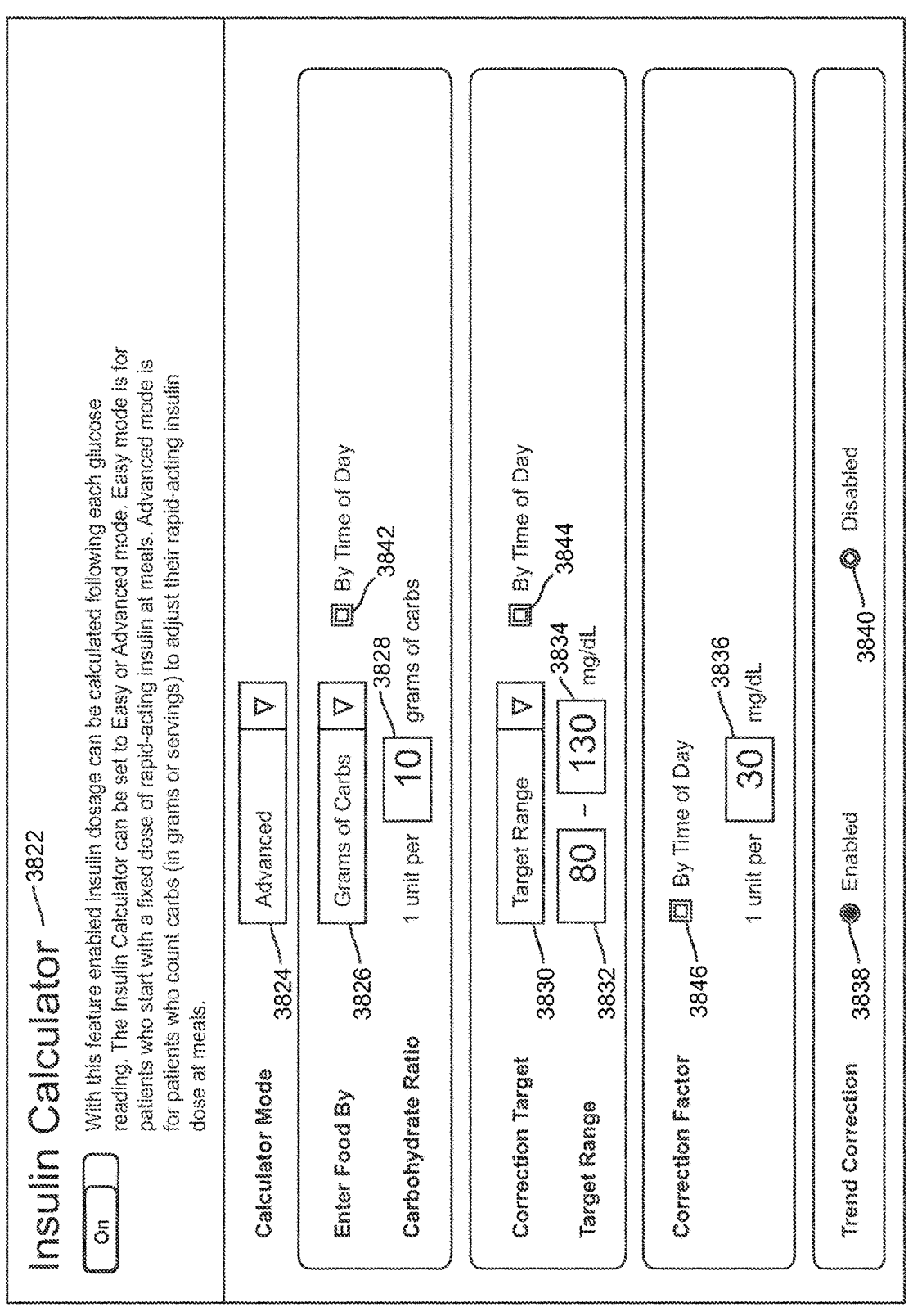
FIG. 44 illustrates an Insulin Calculator Setup Interface for health management software configured for an advanced insulin calculator set to count carbs by grams of carbs, according to embodiments of the present disclosure.

If the user selects the "Advanced" selection in the insulin calculator selection box 3824, the Insulin Calculator Setup Interface screen 3822 displays the set up options for the advanced bolus calculator. Set up for the advanced bolus calculator is shown in FIG. 44, which shows advanced bolus calculator settings available when the insulin calculator is set to count carbs by grams of carbs.

By "advanced calculator", "advanced bolus calculator" or "advanced insulin calculator" is meant a bolus calculator that includes additional information, such as, but not limited to, the amount of carbohydrates consumed, the carbohydrate ratio, a target blood glucose range (e.g., correction target), and an insulin sensitivity (e.g., correction factor), in determining a recommended medication dosage amount (e.g., a recommended insulin dosage amount). For example, rather than using a fixed medication dosage amount for each meal as in the easy calculator, the advanced bolus calculator may use dose determination information entered by the user, such as the amount of carbohydrates consumed, to determine a recommended medication dosage amount. The advanced bolus calculator may also include additional dose determination information into the determination of the recommended medication dosage amount, such as but not limited to, a patient's the current blood glucose level, an amount of exercise, a target analyte concentration (e.g., a target blood glucose range), an insulin sensitivity (e.g., correction factor), a duration of insulin action, a carbohydrate ratio, and insulin on board information, such as an administered medication dose time information, an administered dose frequency information over a predetermined time period, and an administered medication dose amount.

The Insulin Calculator Setup Interface screen 3822 includes an "Enter Food By" selection box 3826, which, when selected, allows the user to set the insulin calculator to enter food by grams of carbs or by servings. If "Grams of Carbs" is selected in the "Enter Food By" selection box 3826, then Insulin Calculator Setup Interface screen 3822 displays the set up options for the advanced bolus calculator by grams of carbs.

In some embodiments, the carbohydrate ratio may be entered. The Insulin Calculator Setup Interface screen 3822 includes a carbohydrate ratio amount entry box 3828 for entering the amount of the user's carbohydrate ratio as 1 unit per X grams of carbs, where X is the amount entered. In some embodiments, the correction target range may be entered. The Insulin Calculator Setup Interface screen 3822 includes correction target range amount entry boxes for the minimum target range value 3832 and the maximum target range value 3834. In some instances, the correction target may be entered as a single target value rather than a target range by selecting "Single Target" (not shown) from the correction target selection box 3830. In some embodiments, the Insulin Calculator Setup Interface screen 3822 includes a correction factor amount entry box 3836 in which the insulin sensitivity (e.g., correction factor) may be entered as 1 unit per X mg/dL, where X is the amount entered for the correction factor. In some embodiments, the Insulin Calculator Setup Interface screen 3822 includes radio buttons for enabling or disabling insulin calculator trend correction by selecting either the trend correction enabled radio button 3838 or the trend correction disabled radio button 3840, respectively.

In certain instances, the carbohydrate ratio, the target range, and/or the correction factor may be entered by time of day, as shown in FIG. 45. To enable the carbohydrate ratio time of day settings, the carbohydrate ratio "By Time of Day" checkbox 3842 may be selected. To enable the target range time of day settings, the target range "By Time of Day" checkbox 3844 may be selected. To enable the correction factor time of day settings, the correction factor "By Time of Day" checkbox 3846 may be selected.

If the carbohydrate ratio "By Time of Day" checkbox 3842 is selected, Insulin Calculator Setup Interface screen 3848 displays the time of day settings for the carbohydrate ratio (see FIG. 45A). The carbohydrate ratio may be set to the same or different values at 4 different times of day, such as morning (e.g., 4 am-10 am), midday (e.g., 10 am-4 pm), evening (e.g., 4 pm-10 pm), and night (e.g., 10 pm-4 am). The morning carbohydrate ratio may be entered in the morning carbohydrate ratio amount entry box 3850, the midday carbohydrate ratio may be entered in the midday carbohydrate ratio amount entry box 3852, the evening carbohydrate ratio may be entered in the evening carbohydrate ratio amount entry box 3854, and the night carbohydrate ratio may be entered in the night carbohydrate ratio amount entry box 3856.

Figure 45B:
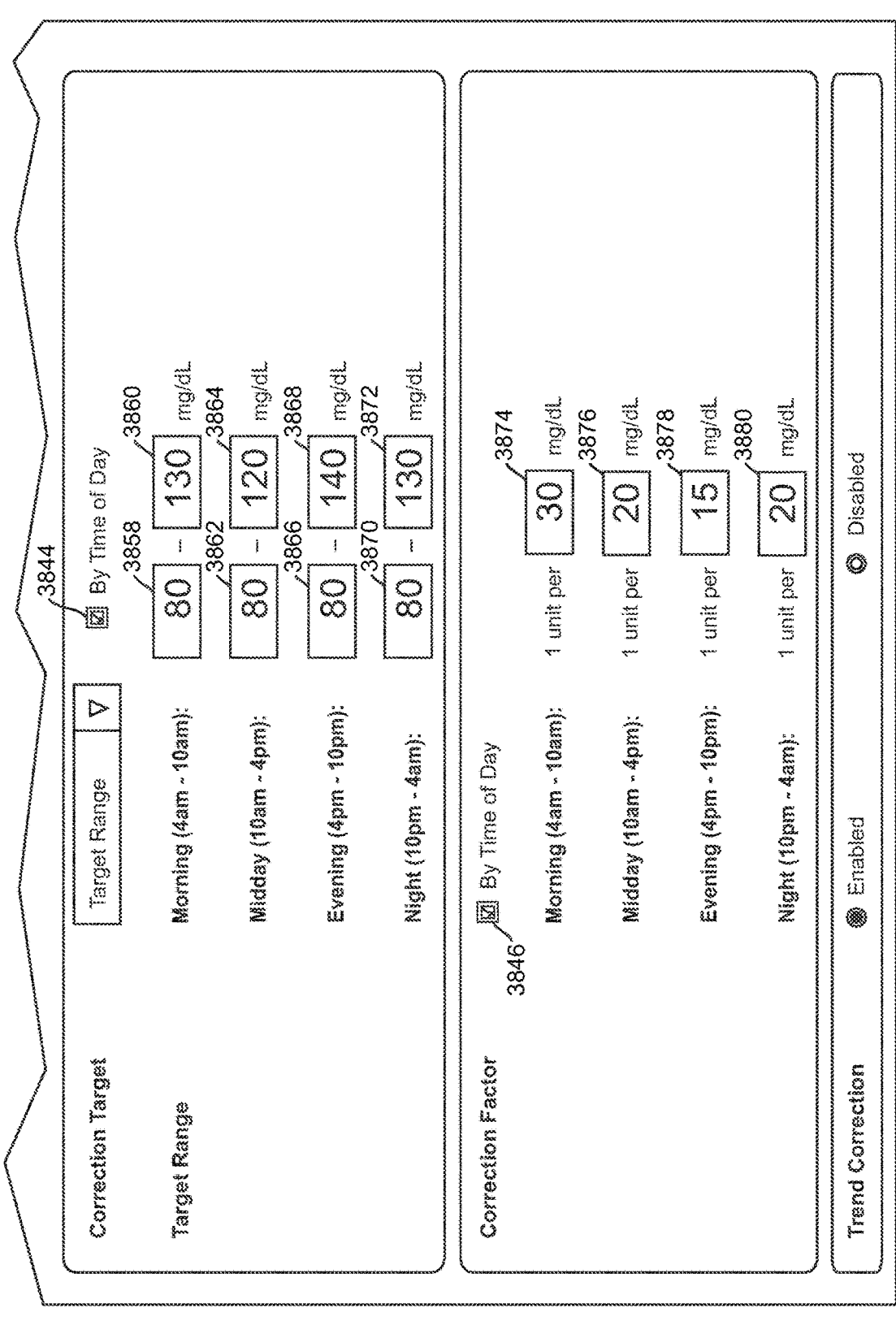

If the correction target range "By Time of Day" checkbox 3844 is selected, Insulin Calculator Setup Interface screen 3848 displays the time of day settings for the target range (see FIG. 45B). The target range may be set to the same or different values at 4 different times of day, such as morning (e.g., 4 am-10 am), midday (e.g., 10 am-4 pm), evening (e.g., 4 pm-10 pm), and night (e.g., 10 pm-4 am). The morning target range may be entered in the minimum value morning target range amount entry box 3858 and the maximum value morning target range amount entry box 3860, the midday target range may be entered in the minimum value midday target range amount entry box 3862 and the maximum value midday target range amount entry box 3864, the evening target range may be entered in the minimum value evening target range amount entry box 3866 and the maximum value evening target range amount entry box 3868, and the night target range may be entered in the minimum value night target range amount entry box 3870 and the maximum value night target range amount entry box 3872.

If the correction factor "By Time of Day" checkbox 3846 is selected, Insulin Calculator Setup Interface screen 3848 displays the time of day settings for the correction factor (see FIG. 45B). The correction factor may be set to the same or different values at 4 different times of day, such as morning (e.g., 4 am-10 am), midday (e.g., 10 am-4 pm), evening (e.g., 4 pm-10 pm), and night (e.g., 10 pm-4 am). The morning correction factor may be entered in the morning correction factor amount entry box 3874, the midday correction factor may be entered in the midday correction factor amount entry box 3876, the evening correction factor may be entered in the evening correction factor amount entry box 3878, and the night correction factor may be entered in the night correction factor amount entry box 3880.

Figure 46A:
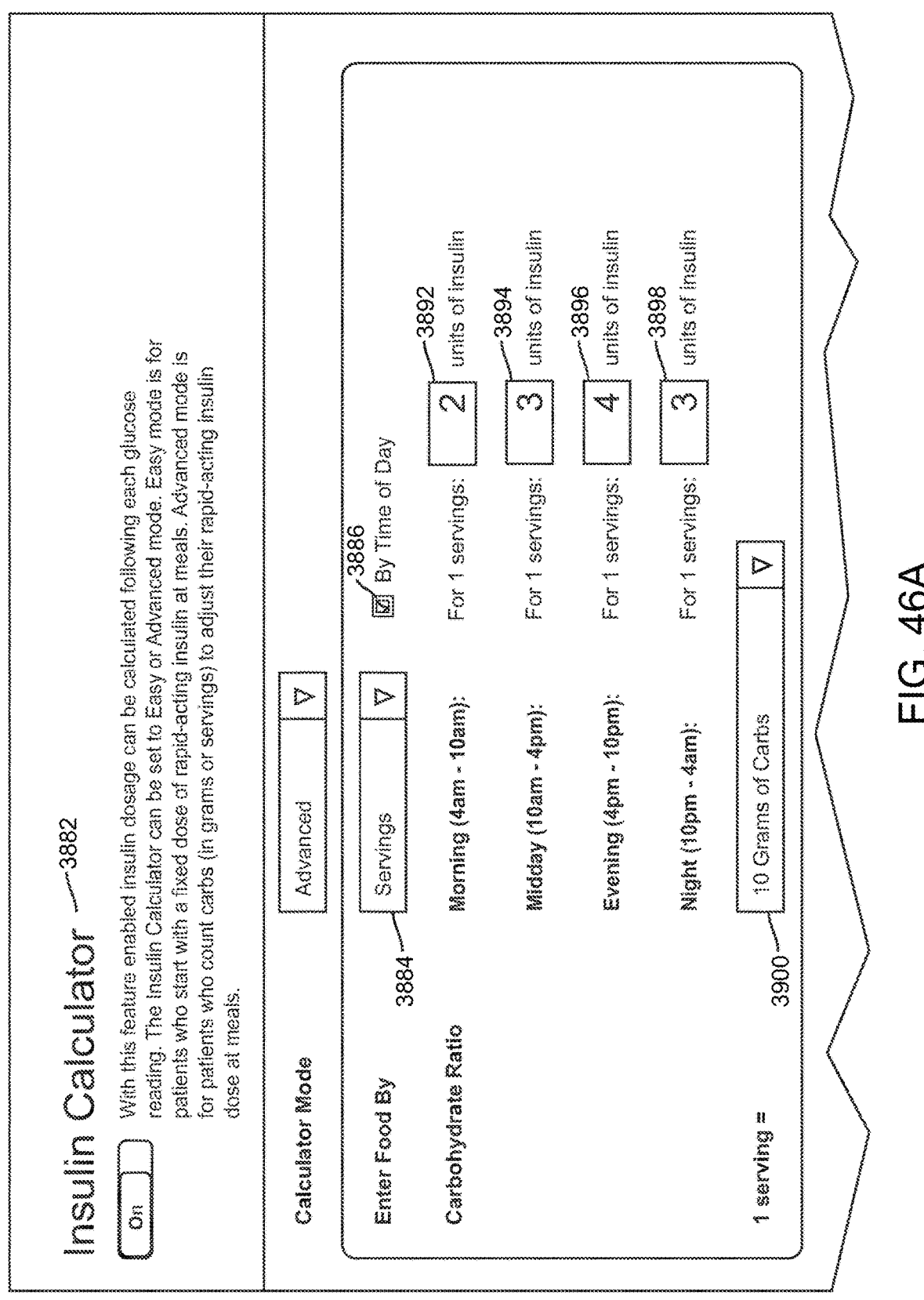
FIGS. 46A and 46B illustrate an Insulin Calculator Setup Interface for health management software configured for an advanced insulin calculator set to count carbs by servings of carbs and by time of day, according to embodiments of the present disclosure.

The Insulin Calculator Setup Interface screen 3882 includes an "Enter Food By" selection box 3884, which, when selected, allows the user to set the insulin calculator to enter food by grams of carbs or by servings (see FIG. 46A). If "Servings" is selected in the "Enter Food By" selection box 3884, then Insulin Calculator Setup Interface screen 3882 displays the set up options for the advanced bolus calculator by servings of carbs.

FIGS. 43-46 show the Insulin Calculator Setup Interface screen 3882 when the carbohydrate ratio, the target range, and the correction factor are selected to be entered by time of day by selecting the carbohydrate ratio "By Time of Day" checkbox 3886, the target range "By Time of Day" checkbox 3888, and the correction factor "By Time of Day" checkbox 3890.

Insulin Calculator Setup Interface screen 3882 displays the time of day settings for the carbohydrate ratio (see FIG. 46A). The carbohydrate ratio may be set to the same or different values at 4 different times of day, such as morning (e.g., 4 am-10 am), midday (e.g., 10 am-4 pm), evening (e.g., 4 pm-10 pm), and night (e.g., 10 pm-4 am). The morning carbohydrate ratio may be entered in the morning carbohydrate ratio amount entry box 3892, the midday carbohydrate ratio may be entered in the midday carbohydrate ratio amount entry box 3894, the evening carbohydrate ratio may be entered in the evening carbohydrate ratio amount entry box 3896, and the night carbohydrate ratio may be entered in the night carbohydrate ratio amount entry box 3898. The number of grams of carbs per 1 serving may be selected from the servings selection box 3900.

Figure 46B:
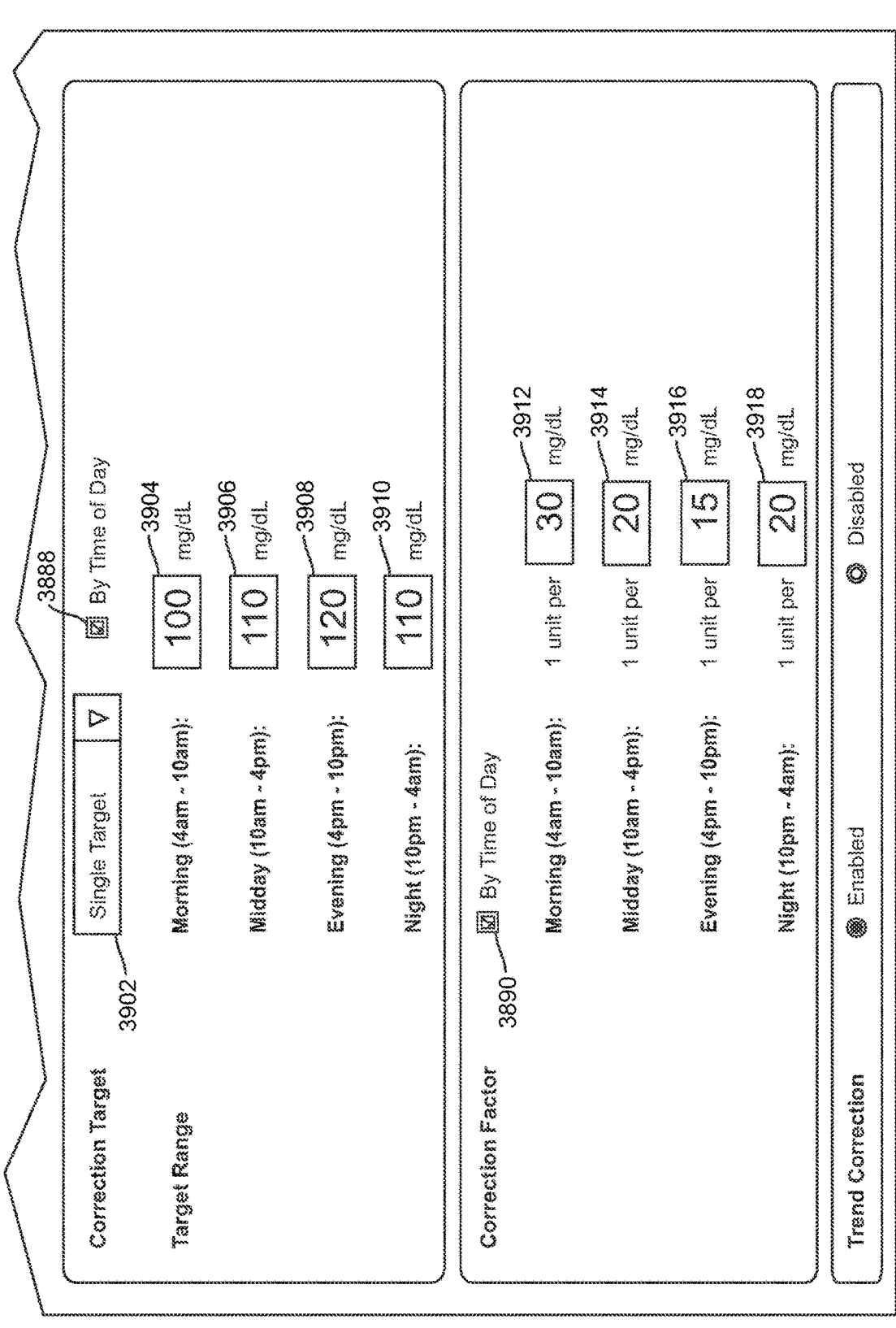

Insulin Calculator Setup Interface screen 3882 displays the time of day settings for the target range (see FIG. 46B). The target range may be set to the same or different values at 4 different times of day, such as morning (e.g., 4 am-10 am), midday (e.g., 10 am-4 pm), evening (e.g., 4 pm-10 pm), and night (e.g., 10 pm-4 am). As shown in FIG. 46B, the target range is selected to be entered as a "Single Target" rather than a target range, as shown in the correction target selection box 3902. The morning target value may be entered the morning target value amount entry box 3904, the midday target value may be entered in the midday target value amount entry box 3906, the evening target value may be entered in the evening target value amount entry box 3908, and the night target value may be entered in the night target value amount entry box 3910.

Insulin Calculator Setup Interface screen 3882 displays the time of day settings for the correction factor (see FIG. 46B). The correction factor may be set to the same or different values at 4 different times of day, such as morning (e.g., 4 am-10 am), midday (e.g., 10 am-4 pm), evening (e.g., 4 pm-10 pm), and night (e.g., 10 pm-4 am). The morning correction factor may be entered in the morning correction factor amount entry box 3912, the midday correction factor may be entered in the midday correction factor amount entry box 3914, the evening correction factor may be entered in the evening correction factor amount entry box 3916, and the night correction factor may be entered in the night correction factor amount entry box 3918.

Masked Mode Setup Interface:

The Professional Options screen also enables the Masked Mode setup to be viewed and set on the remote device. The setup screen provided functions similar to the Masked Mode setup discussed earlier, except that the setup takes place via the RD software application.

Figure 47:
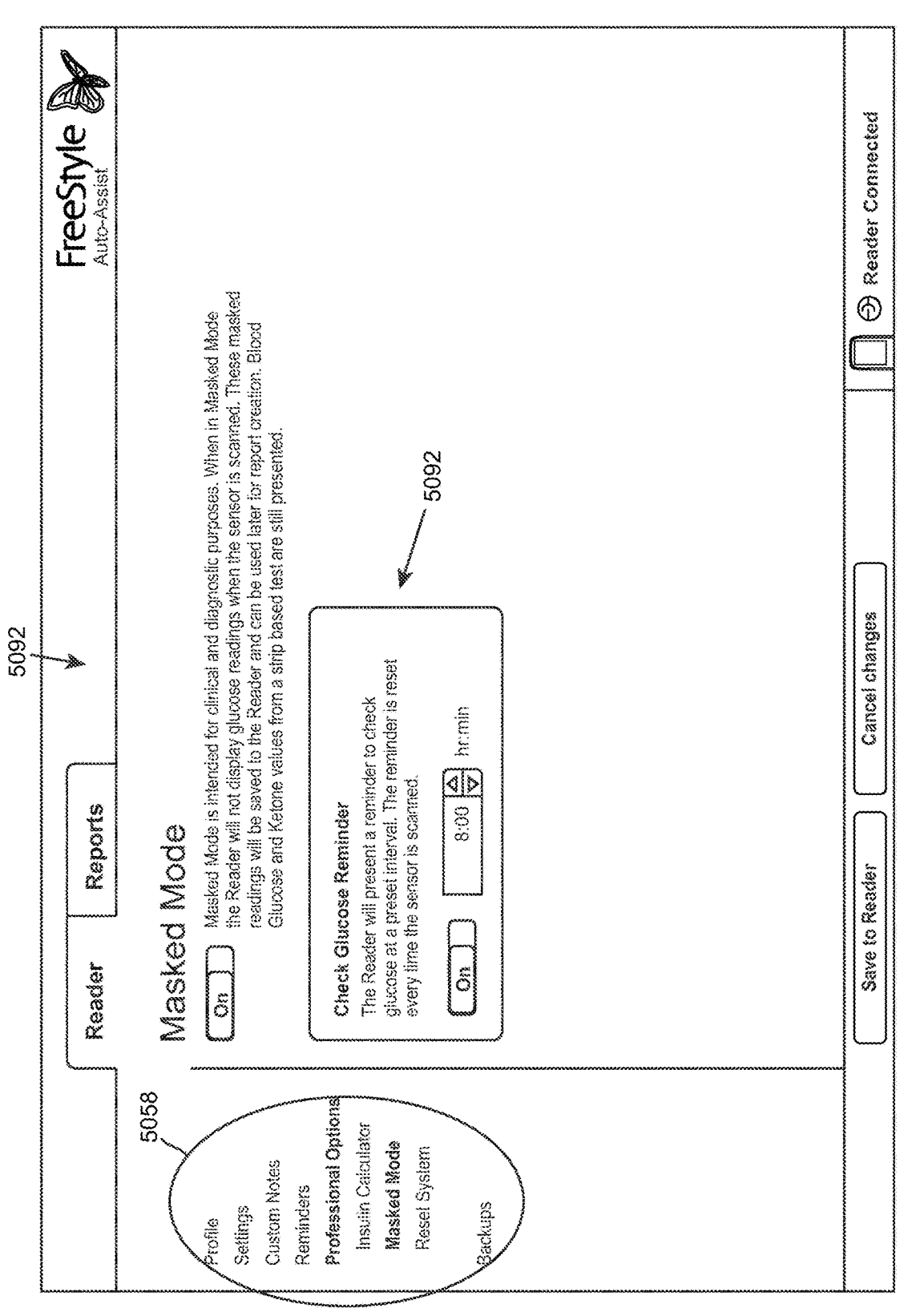
FIG. 47 illustrates a Masked Mode setup screen, according to one embodiment.

FIG. 47 illustrates a Masked Mode setup screen 5090, according to one embodiment. As shown, Masked Mode setup screen 5090 provides a section 5092 in which the user can activate the Masked Mode and set reminders to check glucose at preset intervals. For example, the reminder is reset every time the sensor is scanned. As shown, the menu 5058 of trigger elements for initiating various screens is maintained in the Profile screen 5086.

Reset System:

The Professional Options screen also enables the user reset settings of the Reader device. The Reset System interface may permit reset of all settings at once, and/or permit the user to selectively reset specific setting on the device.

Referring back to FIG. 39, at block 4094, the user is taken to a Backups screen where the user can save a backup file of a current Reader setting. In one embodiment, the backup files do not save glucose results or other Reader logbook entries.

Thus, from the menu 5058 of trigger elements for initiating various Reader Mode screens, which remains on the various Reader Mode screens to enable quick reference and access to those screens, the user is able to navigate to the desired Reader Mode screen. Once the settings are viewed, edited, or deleted, the user can save the setting to the reader, as shown by reference path X3. At block 4096, a Reader Status screen is displayed to indicate to the user that a save is in progress. In block 4098, a Progress screen is shown to indicate a save to the reader, and after the save the user is taken to a Reader Landing-Settings saved screen to indicate that the save was successful, as shown by block 4100.

If changes to any settings in menu 5058 are cancelled, as shown by reference path Y3, or the user navigates away, as shown by reference path A4, then the user is taken to a warming Alert screen to alert the user that changes will be lost, as shown at 4102 via reference path Z3. If changes are cancelled, then the user is navigated back to the Reader Landing screen 4082. If the user elects to save the changes, then to blocks 4096 and 4098 as previous described. If the user elects to not save the settings, then the user is taken to the Reader Landing-Setting saved screen 4100.

From the Backups screen, the user can save a backup file, as shown at block 4104. Progress screen 4106 is displayed while the save is in progress. If the save should be cancelled before complete, then the user is taken back to the Backups screen 4108.

If the save is determined to be not valid, as shown at block 4105, then the user is taken to an Alert screen 4110 to indicate to the user that a save is not valid. For example, if the filename already exists, then the user can elect to either save it and overwrite the previous file, and will be taken to the Progress screen 4106. If the user elects not to save it, then the user is then back to the Backups screen 4112.

From the Backups screen at block 4094, the user can select a backup file to restore, as shown by block 4114 and reference path C4. Once the backup file is selected the user is taken to a Progress screen 4116 that indicates that the backup file is being processed. If the processing of the backup file is determined to not be valid or encounters an error, then the Alert screen 4120 is displayed to indicate that there was an error with the backup file (e.g., that the file is damaged). The user is then taken back to the Backups screen, as shown by block 4122. If the processing of the backup file is valid, then the Restore Reader Setting is displayed to indicate that the Reader settings are being restored to the settings on the backup file. If the restore should be cancelled, then the user is taken back to the Backups screen, as shown by block 4126. If the restore is not cancelled, then the user is taken to either a Reader Status screen 4128, or to a Progress screen 4130 and Backups screen 4132, similarly as described above.

Out of Sync Flow

Figure 48:
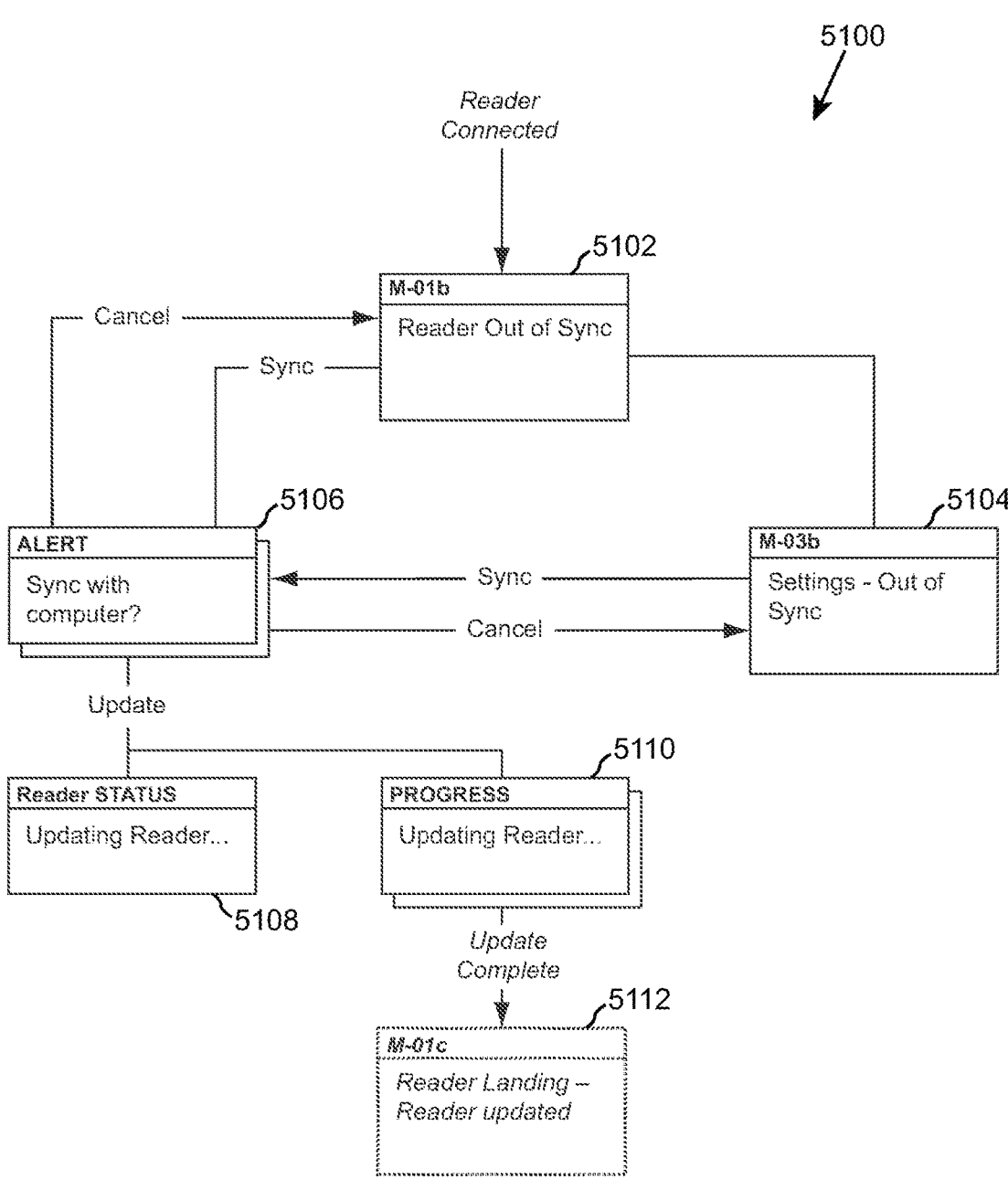
FIG. 48 illustrates a method for syncing a Reader device with a remote device, according to one embodiment.

FIG. 48 illustrates a method 5100 for a flow for syncing the Reader device when the Reader is coupled to the remote device and determined to be out of sync with the remote device. For example, when out of sync, the time on the Reader is different than the time on the remote device.

If the Reader is coupled to the remote device and determined to be out of sync with the remote device, then the Reader Out of Sync screen at 5102 is initiated, as shown by block 5102. An Alert screen is displayed to alert the user of the sync and ask if the user wishes to synch the Reader with the remote device. The user is also taken to the Alert screen at 5106 from the General Reader Settings screen when it is determined that the two devices are out of sync, as shown by block 5104.

If the user elects to sync the two devices, then a Reader Status screen at 5108 and Progress screen at 5110 are displayed while the update is in progress. When the update is complete, the user is taken back to the Reader Landing-Reader updated screen, as shown at block 5112.

Guided Reader Setup Flow

When a new Reader that has never been used is connected to the remote device, the user is guided through the initial setup of that Reader in a step-by-step fashion. Along the way, basic Reader configuration settings such as name, patient ID, date, time, and language are collected for the purpose of initializing the Reader. In one embodiment, the patient name and ID are optional settings while the date, time, and language options must be set to complete the setup process.

Figure 49:
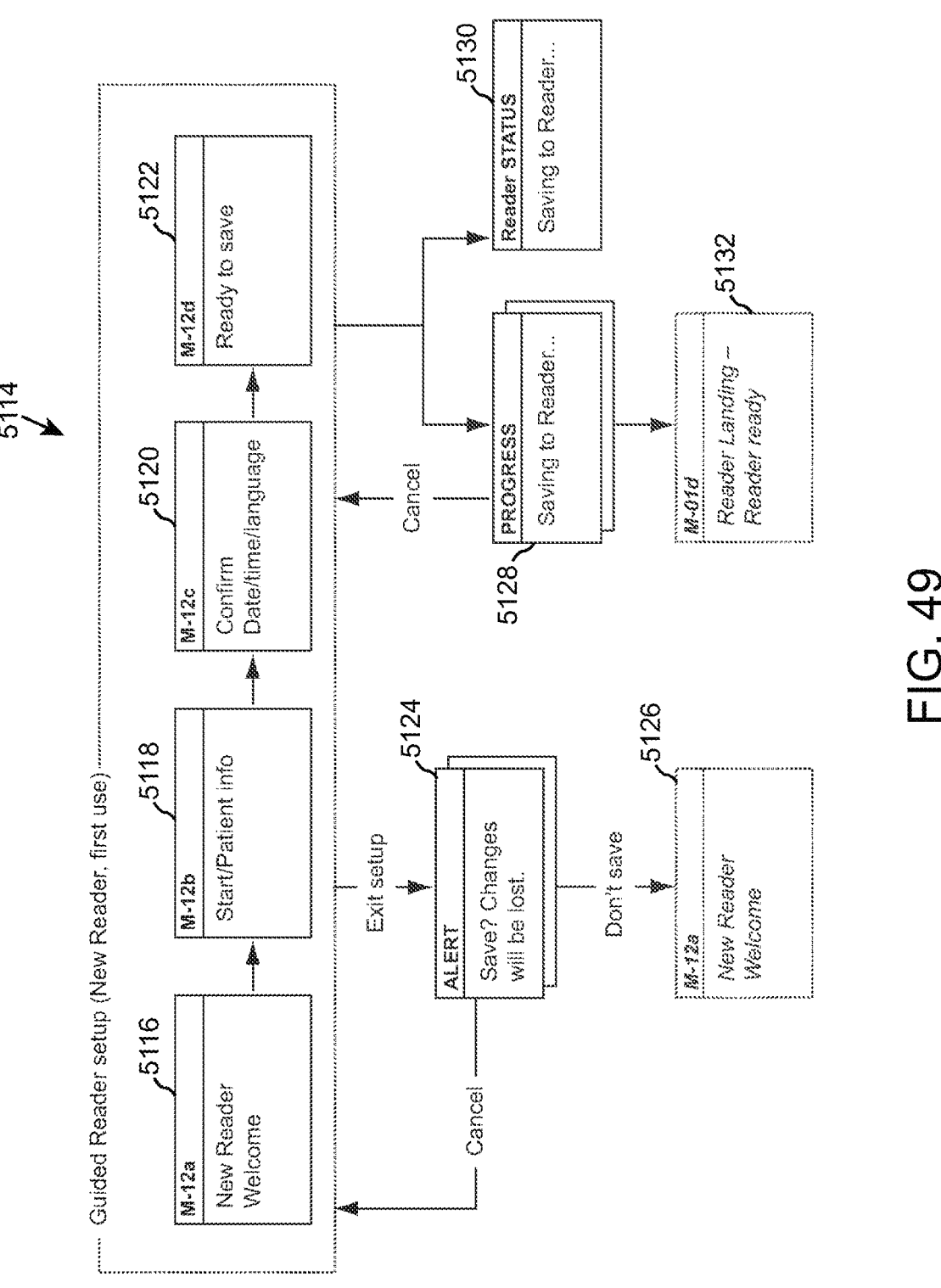
FIG. 49 illustrates a method for a Guided Reader Setup interface, according to one embodiment.

FIG. 49 illustrates a method 5100 for a flow for the Guided Reader Setup interface, according to one embodiment. When a new Reader that has never been used is connected to the remote device, the New Reader Welcome screen is displayed to start the guided setup process, as shown at block 5116. The Start/Patient info screen is initiated to receive patient info, as shown at block 5118. The Confirm Date/Time/Language screen is initiated to receive the appropriate entries from the user, as shown at block 5118. Once entered, the Ready to Save screen is initiated to indicate to the user that the entries are to be saved. As the save is in progress, the Reader Status screen at 5130 or the Progress screen at 5128 is displayed. From the Progress screen at block 5128, the Reader Landing-Reader ready screen at block 5132 is displayed when the save is complete.

If the setup process is interrupted or exited from any of blocks 5118,5120,5122, then the Alert screen at block 5124 is displayed to alert the user that any changes will be lost if not saved. After the Alert screen is displayed at block 5124, the user is taken to the New Reader Welcome screen so that the initial setup can be completed, as shown by blocks 5116,5126.

Figure 50:
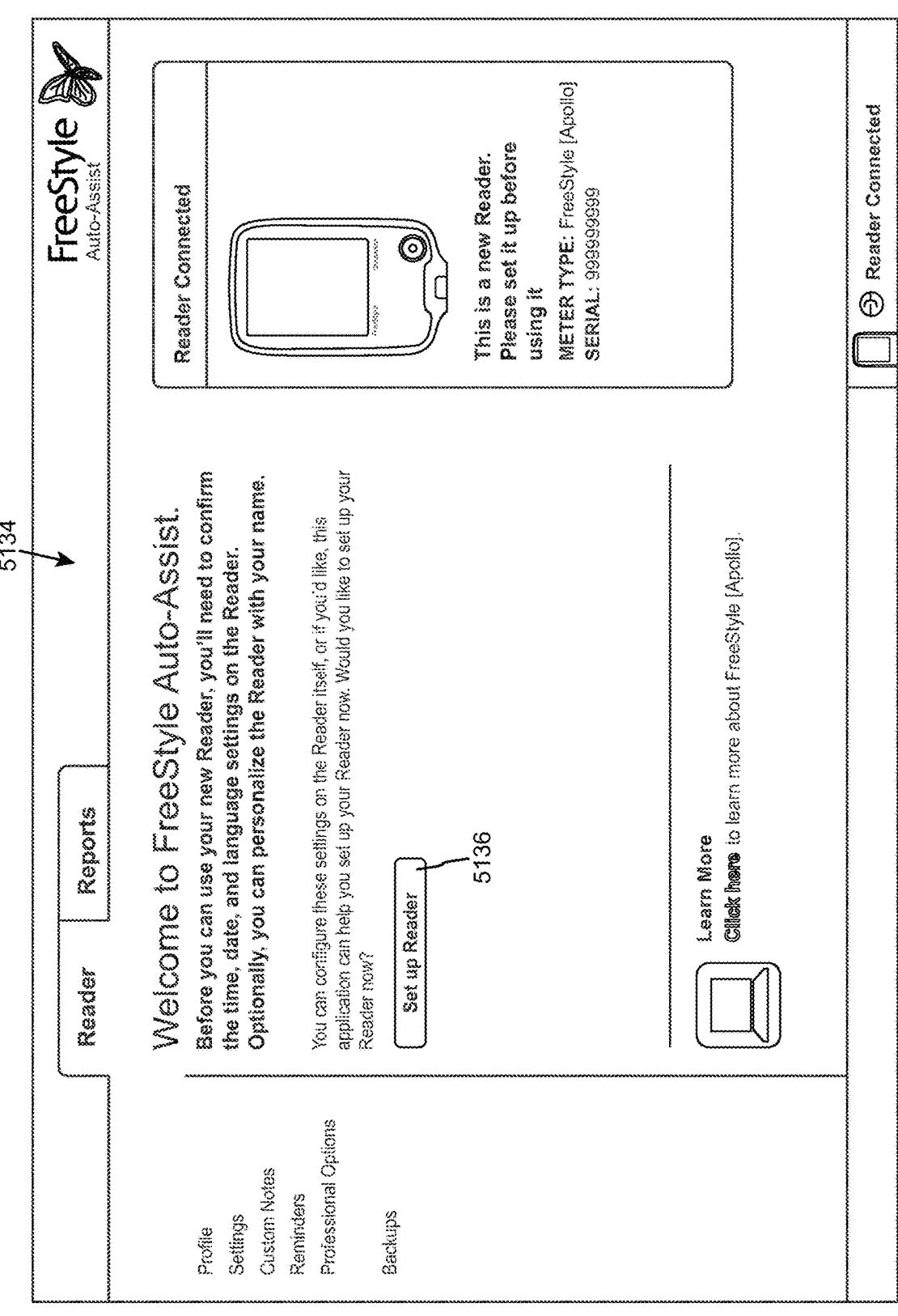
FIG. 50 illustrates a single screen of a Guided Reader setup interface, according to one embodiment.

FIG. 50 illustrates a single screen of the Guided Reader setup interface, according to one embodiment. The initial screen of the Guided Reader setup interface includes information regarding the guided setup and provides a trigger element 5136 that enables the user to begin the guided setup.

Reader Mode

Reports Mode Flow

Figure 51:
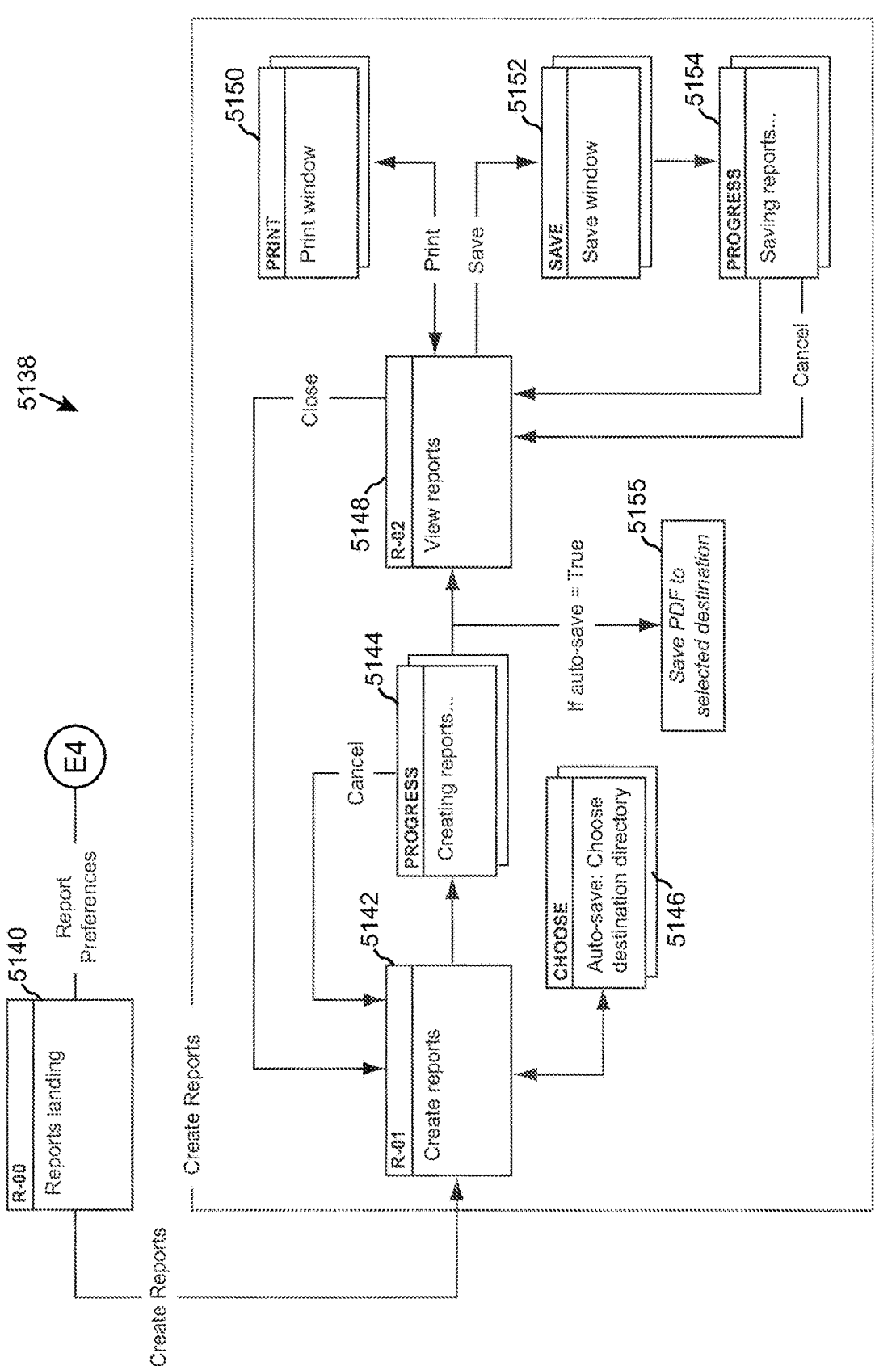
FIG. 51 illustrates a flowchart for navigating through the Reports mode of the RD software, according to one embodiment.
Figure 51:
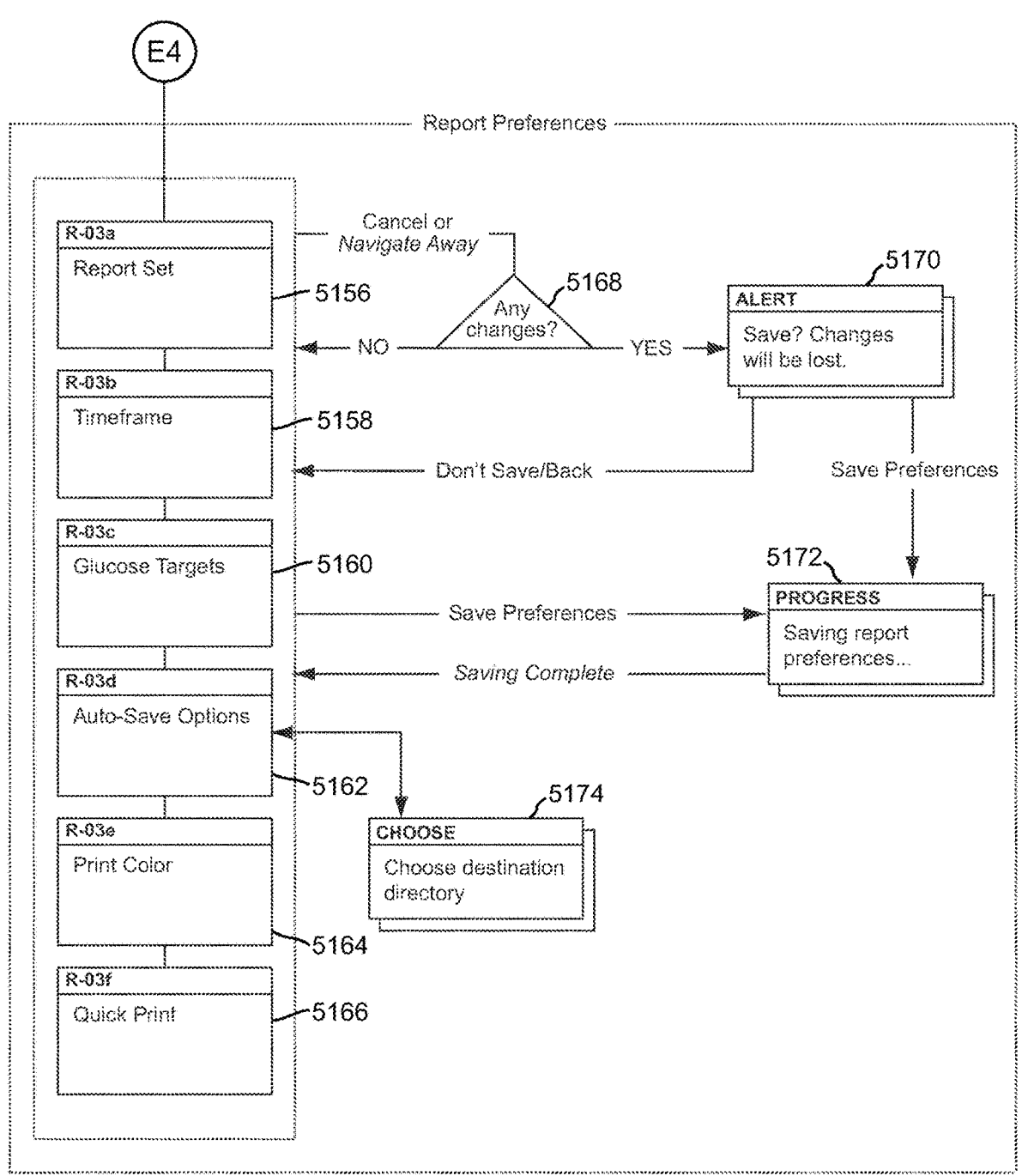

FIG. 51 illustrates a flowchart for a method 4080 of navigating through the Reports mode of the RD software, according to one embodiment. The reports mode of the application provides access to settings and functions for creating, viewing, saving, and printing reports. In the examples shown, the Reports mode is provided as a tab on the interface screens for the RD software, along with the tab for the Reader mode.

At block 5140, the Reports Landing screen is displayed on the remote device when the Reports tab is selected. The user is provided with the option to generate reports or to view or edit Report Preferences—e.g., the user may select, for example, between corresponding trigger elements on the Landing Screen to navigate to the Generate Reports interface or the Report Preferences interface.

From the Generate Reports screen at block 5142, the user can select the parameter of the particular Report to be generated. The Choose screen at block 5146 enables the user to set the destination of the directory for auto-saving. When a report is generated, the Progress screen at block 5144 is displayed while the report is being generated. When complete, the View reports screen at block 5148 displays the generated report, or provides a menu to select from various reports generated. The Reports can be saved via a Save window screen at block 5152 and the progress screen at block 5154 will be displayed when the save is in progress. After the save is complete, the user is taken back to the View Reports screen at block 5148.

If the View Reports screen at block 5148 is closed, then the user is taken back to the Generate Reports screen at block 5142. The user may also print one or more Reports from the View Reports screen 5148 via Print screen at block 5150.

From the Reports Landing screen at block 5140, the user may elect to navigate to the Report Set screen at block 5156. The Set Reports screen at block 5156 enable the user to pre-select reports to be generated each time the user generates reports with the data management software. Example reports may include, a Snapshot, Calendar, Average Day, Logbook, Daily Statistics, Mealtime Averages, and Reader Settings, as will be discussed further later. The various reports are selectable and will be set as the default preferences for the creation of reports from the Reader. The Calendar may default to a predetermined time period, such as 3 months for example. If the user selects the Mealtime Averages report they are presented with an overly that allows them to set the default pre and post meal target ranges.

From the Reports Landing screen at block 5140, the user may also elect to navigate to: Timeframe screen at block 5158 to enable the user to establish default timeframes used when reports are generated; Glucose Targets screen at block 5160 to enable the user to establish the default setting for the glucose target range and hypoglycemia threshold to be applied to generated reports; Auto-Save Options screen at block 5162 to enable the user to activate and set the auto save feature, as well as, choose the file name format, and save location (as shown at block 5174) that will used during report creation; Print Color screen at block 5164 that enables the user to choose default print color options; and Quick Print screen at block 5166 which allows the user to enable or disable the quick print feature, which causes the software to immediately generate reports once a Reader with data is connect to the computer.

Settings or changes made to the screens 5156, 5158, 5160, 5162, 5164, and 5166 can be saved, at which point the Progress screen at block 5172 is displayed during the save. If the user cancels or navigates away from any of screens 5156, 5158, 5160, 5162, 5164, and 5166, it is determined if any changes were made, as shown at block 5168. If not, the user is able to navigate away to the desired screen. If changes were made, then an Alert screen is displayed to alert the user that changes may be lost and to provide the user with the option to save, as represented by the Progress screen at block 5172.

Figure 52:
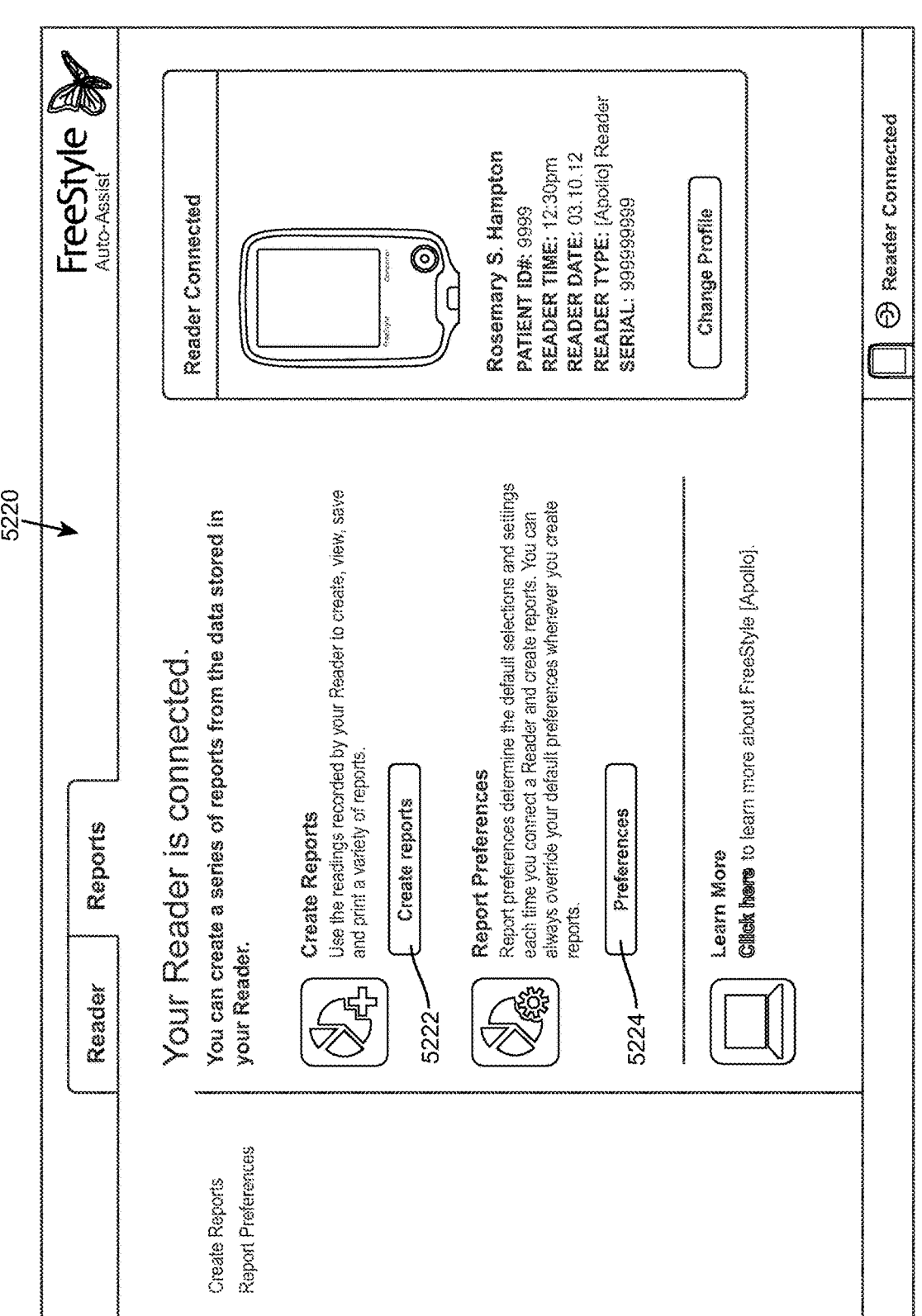
FIG. 52 illustrates an example Reports landing screen, according to one embodiment.

FIG. 52 illustrates an example Reports landing screen that is displayed when the user first connects a Reader with stored data, according to one embodiment. As shown, Reports landing screen 5220 includes trigger elements 5222 and 5224 to initiate the Generate Reports interface and Report Preferences interface, respectively.

Figure 53:
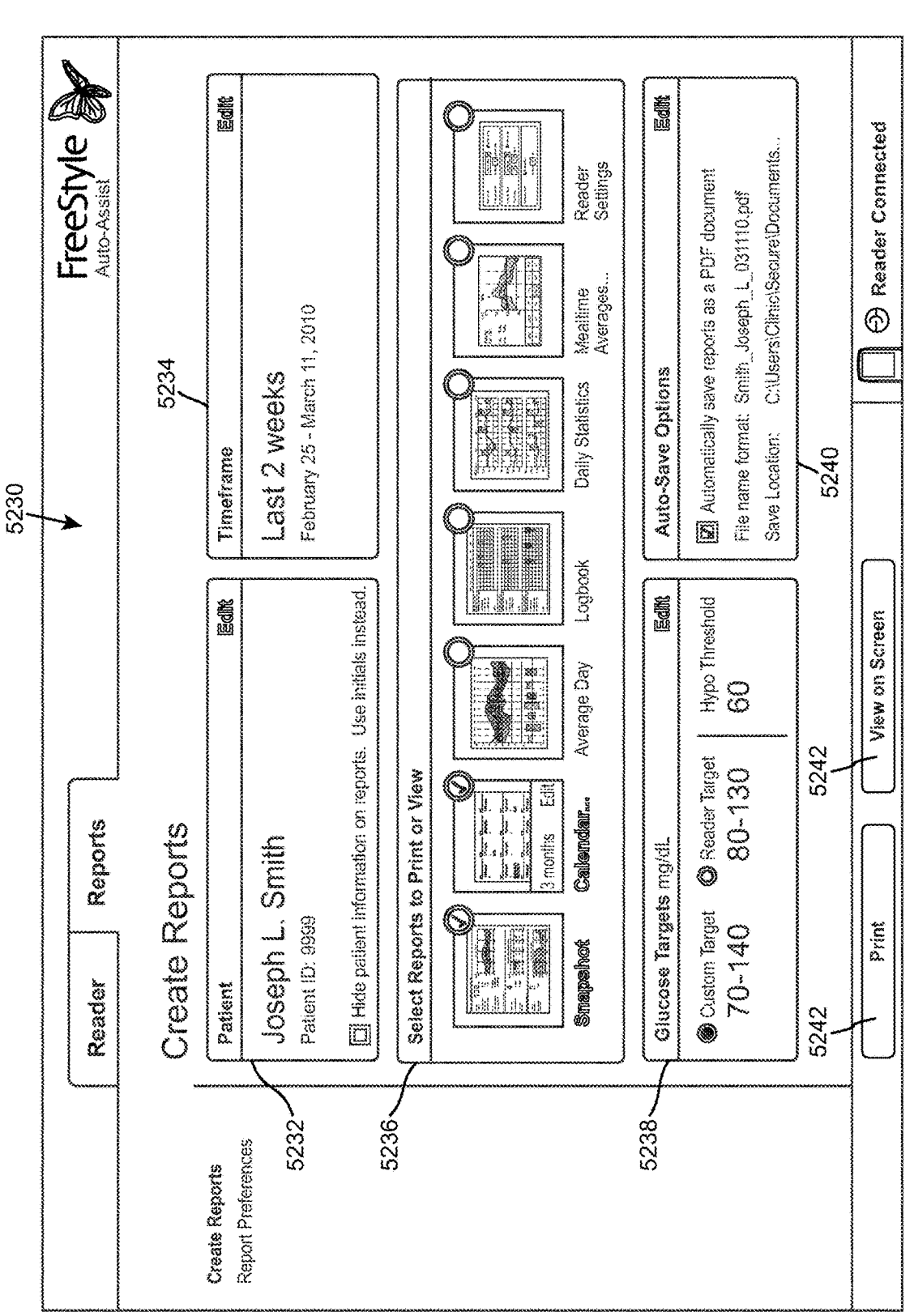
FIG. 53 illustrates an example Generate Reports screen, according to one embodiment.

FIG. 53 illustrates an example Generate Reports screen, according to one embodiment. Generates Reports screen 5230 is shown providing information regarding the current settings for creation of reports, as well as providing the user with navigation options (e.g., trigger elements) to make changes to the current settings—e.g., patient information 5232, timeframe 5234, reports 5236 selected to print or view, glucose targets 5238, and auto-save options 5240. Screen 5230 also provides trigger elements 5240,5242 to print the reports or view them, respectively.

Figure 54:
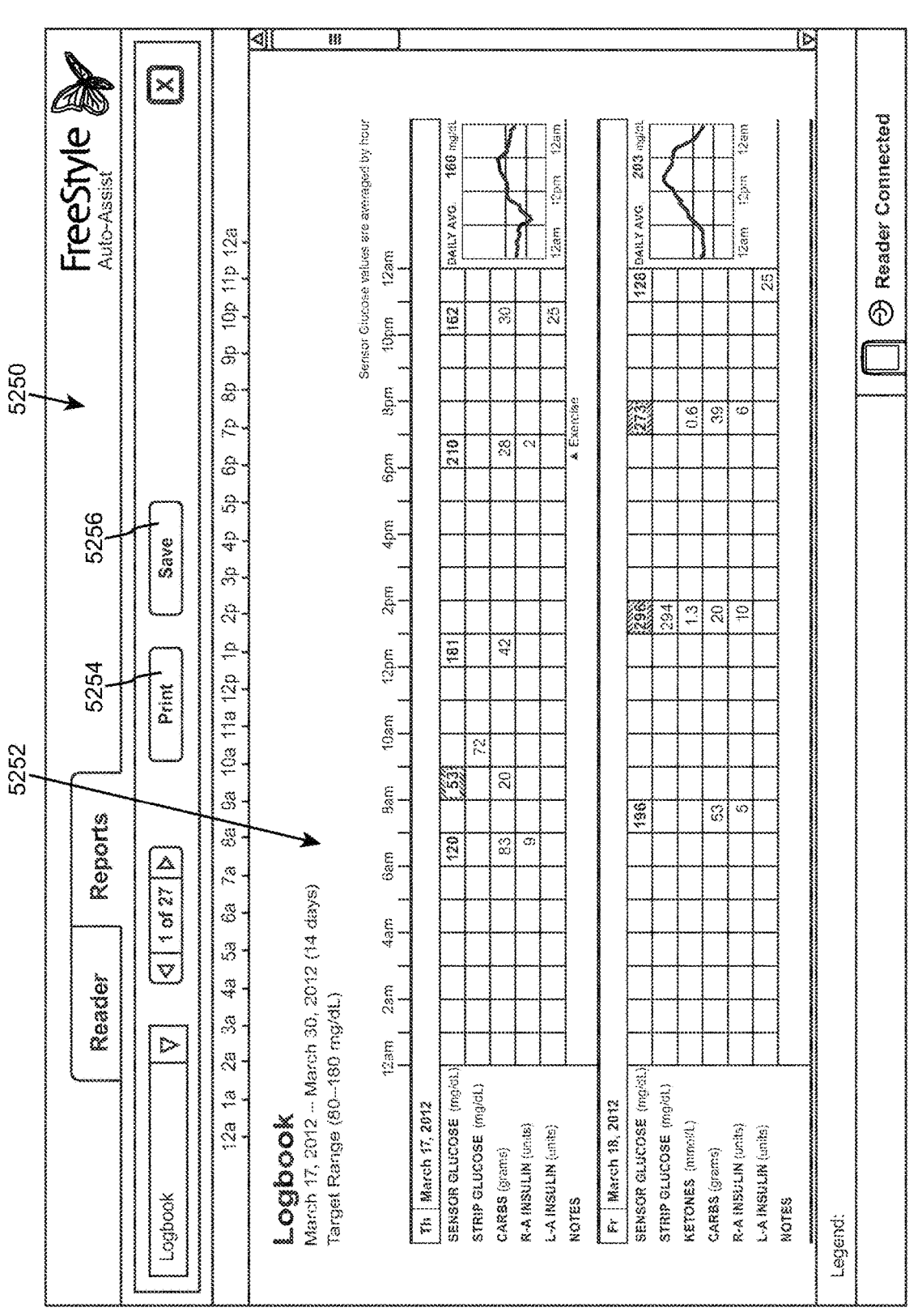
FIG. 54 illustrates an example Logbook Report screen when viewed from the Reports Mode, according to one embodiment.

FIG. 54 illustrates an example Logbook Report screen when viewed from the Reports Mode, according to one embodiment. As show, Logbook Report screen includes a table 5252 of the data in the Logbook Report as well as trigger elements 5254,5256 for printing and saving the report, respectively.

Guided Reports Setup Interface

The first time a user accesses the printing features of the application, they are guided through the reports setup and creation process in a step-by-step fashion by a Guided Reports Setup interface. Along the way, the RD software collects default reports preferences such as patient information, timeframe, report set, glucose targets, and auto-save options, as well as prepares the first set of reports for viewing, saving, and printing.

Figure 55:
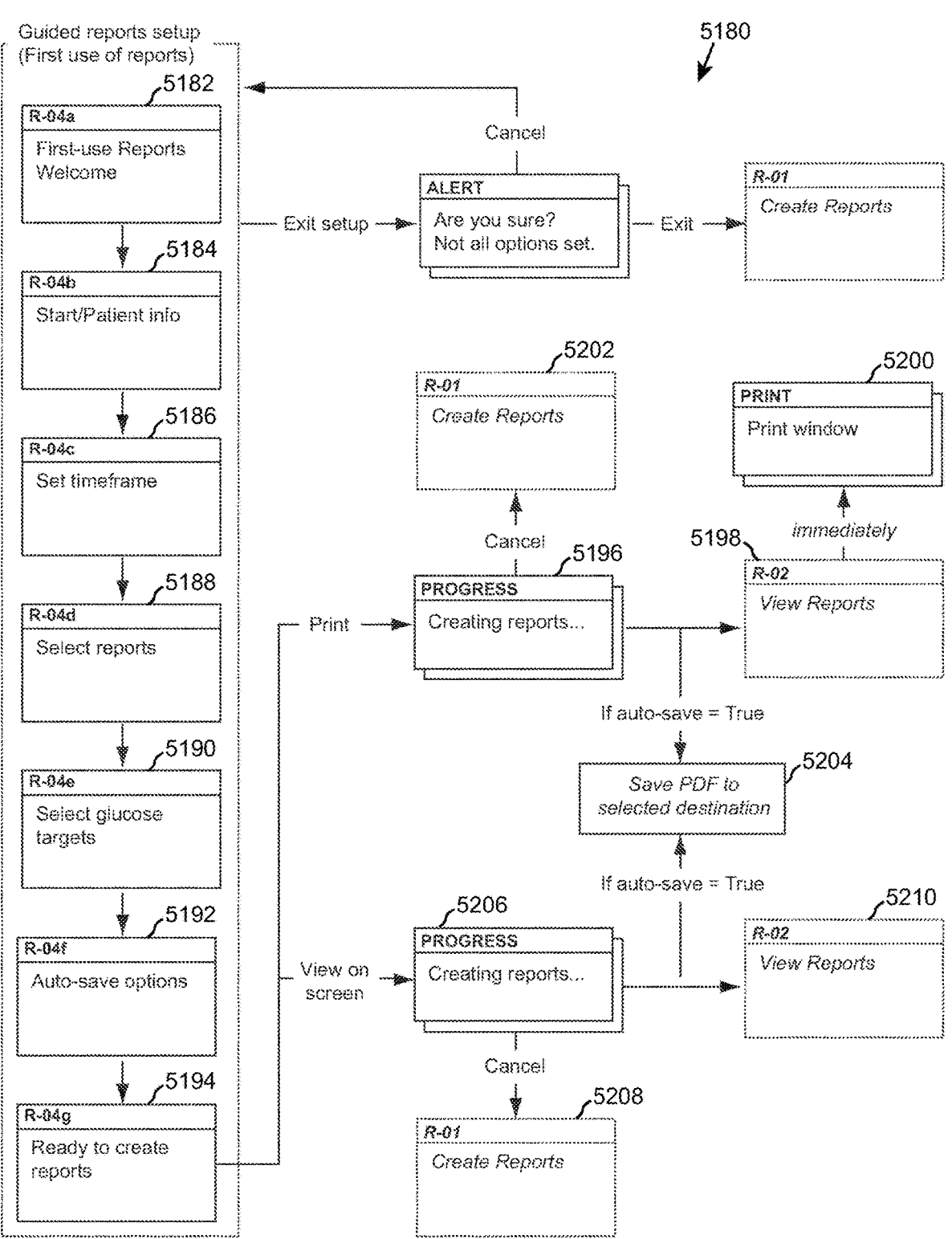
FIG. 55 illustrates a flowchart for a Guided Reports Setup interface, according to one embodiment.

FIG. 55 illustrates a flowchart for a Guided Reports Setup interface, according to one embodiment. The first time a user accesses the printing features of the application, user is taken to the First-Use Reports Welcome screen to begin the guided setup. The Start/Patient info screen is initiated to receive patient info, as shown at block 5182. Then the user is navigated through the following screens: Timeframe screen at block 5186 to enable the user to establish default timeframes used when reports are generated; Set Reports screen at block 5188 enable the user to pre-select reports to be generated each time the user generates reports with the data management software; Glucose Targets screen at block 5190 to enable the user to establish the default setting for the glucose target range and hypoglycemia threshold to be applied to generated reports; Auto-Save Options screen at block 5192 to enable the user to activate and set the auto save feature, as well as, choose the file name format, and save location that will used during report creation; and Ready to Generate Reports screen at block 5194 which allows the user to generate the selected reports and either view them or print them.

When printing the selected reports, the Progress screen at block 5196 is displayed while the report is being generated. When complete, the View reports screen at block 5198 displays the generated report, or provides a menu to select from various reports generated. The Reports are then immediately printed via a Print window screen at block 5200. If auto save is set, once the reports are generated at block 5196, the selected reports are automatically saved to the selected destination, as shown at block 5204. If the creation at block 5196 is interrupted or cancelled, then the user is taken back to the Generate Reports screen at block 5202.

When electing to view the selected reports form block 5194, the Progress screen at block 5206 is displayed while the report is being generated. When complete, the View reports screen at block 5210 displays the generated report, or provides a menu to select from various reports generated. If auto save is set, once the reports are generated at block 5206, the selected reports are automatically saved to the selected destination, as shown at block 5204. If the creation at block 5206 is interrupted or cancelled, then the user is taken back to the Generate Reports screen at block 5208.

Export Reader Flow

The RD software provides a function for users to export data from a Reader coupled to the computer as a tab-delimited file or other spreadsheet-compatible format, for example. The Export function may be accessed, for example, via the "File" menu of the application.

Figure 56:
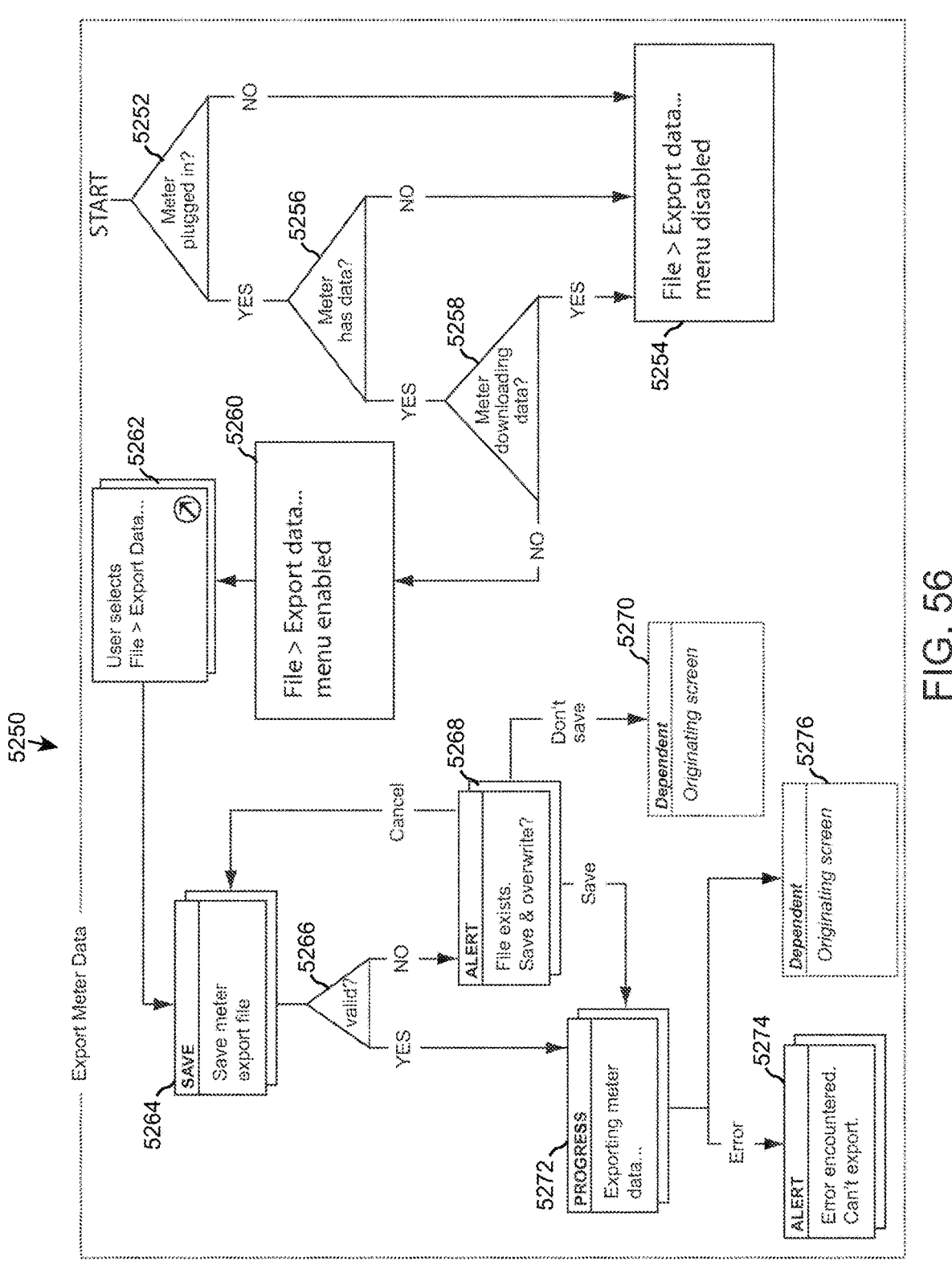
FIG. 56 illustrates a method for exporting Reader data, according to one embodiment.

FIG. 56 illustrates a method for exporting Reader data, according to one embodiment. At block 5252 of Export Meter Data interface 5250, it is determined if the Reader device is coupled to the remote device. If not coupled, then the Export data feature is disabled (e.g., in the File menu) as shown at block 4254. If the Reader device is coupled to the remote device, then it is determined if the Reader device has sensor data stored, as shown at block 5256. If the Reader has no data stored, then the Export data feature is disabled at block 4254. If the Reader does have data, then it is determined if the Reader is downloading data. If so, then the Export data feature is disabled at block 4254. If the Reader is not downloading data, then the Export data feature is enabled (e.g., in the File menu).

Once enabled, the user can select to export data from the Reader, as represented by block 5262. Once selected, the meter export file is saved as shown at block 5264. If the save is determined to be valid, then the Progress screen 5272 is shown to indicate that the process of exporting data is in progress. If no error occurs, the user is taken back to the originating screen as shown at block 5276. If an error occurs, an Alert screen is provided to notify the user of the failed export, as shown at block 5274.

If at block 5266, it is determined that the saving of the meter export file was not valid, then an Alert screen is provided to notify that the save was not valid (e.g., the file already exists), as shown at block 5268. The user is provided with the option to overwrite the existing file, which navigates the user to the Progress screen at block 5272. The user is also provided the option to not save the invalid file, in which case the user is taken back to the originating screen, as shown at block 5270.

Reports

In some embodiments, the RD software provides a user interface to manage and/or control features related to reports. For example, the RD software provides a reports mode for creating, editing, viewing, printing, and for performing any other functions associated with report generation and management.

Different types of reports may be generated. For example, FIGS. 45-53 illustrate various types of reports, according to certain embodiments. It should be appreciated that the reports illustrated are exemplary and should not be interpreted as limiting. Further details regarding various reports that may be implemented with the software is described in U.S. patent application Ser. No. 11/146,897, filed on Jun. 6, 2005, and U.S. Provisional Application Nos. 61/451,488, filed Mar. 10, 2011; and 60/577,064, filed Jun. 4, 2004, the entireties of which are incorporated herein by reference.

As stated above, reports may be generated and communicated to a remote device—e.g., for display on the remote device and/or printing on the remote device. The remote device may be, for example, a desktop computer, laptop, cell phone, etc. For example, the remote device may be a personal computer accessed by the user, enabling the user to view and/or printout the reports. In other instances, the remote device may be a computer accessed by another party, such as a physician or health care professional. The user may, for example, bring the device to their physician so that the physician could transfer the data to his or her computer for display and/or printing of the reports.

The analyte monitoring device may communicate the reports to the remote device using any variety of wired (e.g., USB, FireWire, SPI, SDIO, RS-232 port, etc.) or wireless technologies (e.g., radio frequency (RF) communication, Zigbee® communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM), etc).

In some instances, the analyte monitoring device may include software that is loaded onto the remote device—e.g., the first time connecting to the remote device. In other instances, the software may be loaded to the remote device via the internet or storage device (e.g., CD-ROM, FLASH memory drive, etc.).

In some instances, the reports may be communicated to a remote device and thereafter communicated to another remote device. For example, the user may download the data to his own computer and thereafter transmit the data to the physician for further analysis. Upon receipt, the physician could view and download reports to assess the activities and events of the user.

Example Reports

In the following paragraphs, example reports are provided and described. The various reports may include general identification information for the associated patient (e.g., name of the patient, identification number, etc.) and/or associated device (e.g., name of the device; model of the device, etc.).

Snapshot:

In some aspects of the present disclosure, a Snapshot report is provided. The Snapshot report captures the overall condition of the patient's health management (e.g., diabetes management). For instance, the report may highlight the key metrics for the user's activities over a specific time period. In some embodiments, the Snapshot report provides significant pieces of information related to one or more of the following: utilization, glucose levels, events, and notes.

Figure 57:
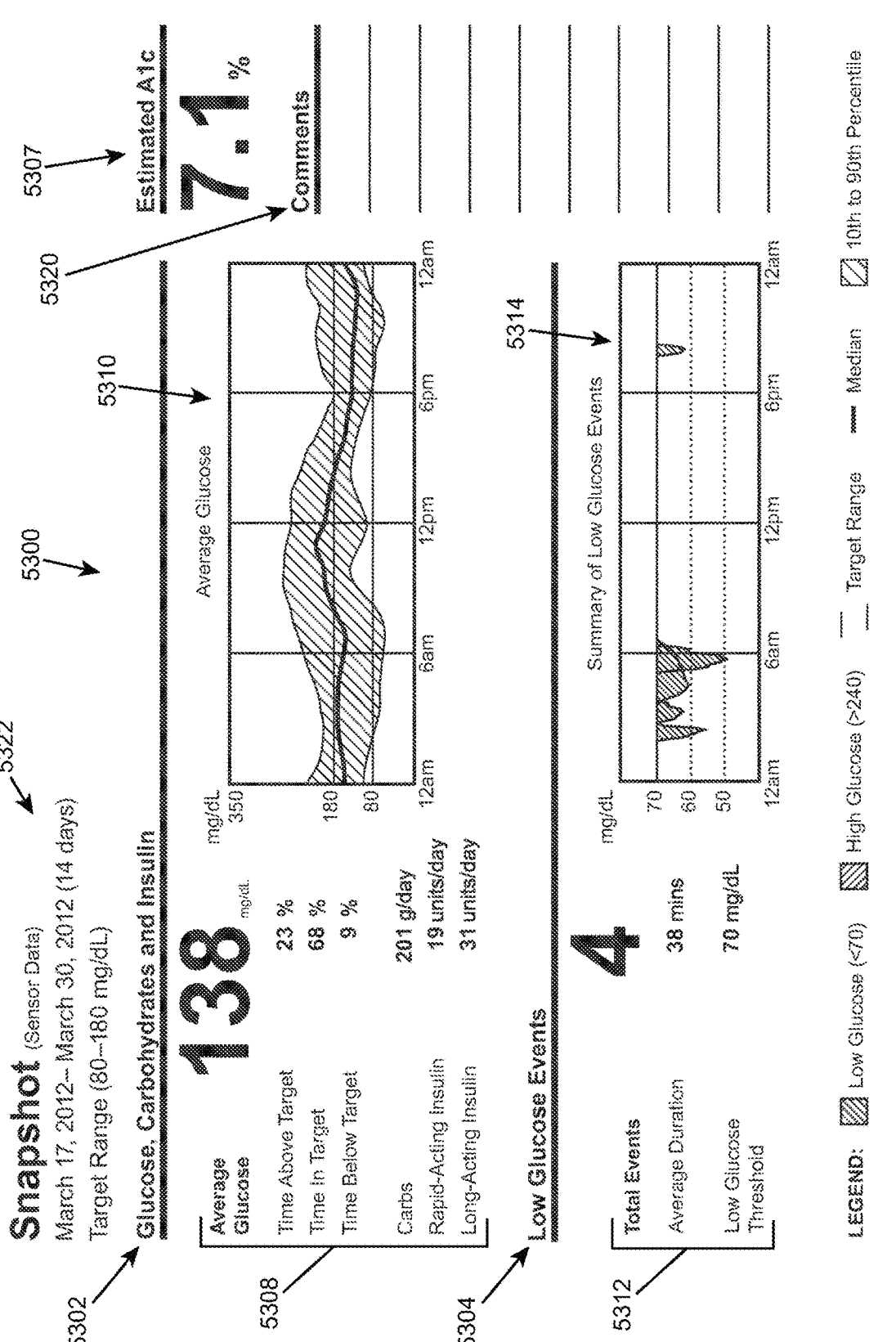
FIG. 57 illustrates an exemplary Snapshot report for a specific time frame, according to certain embodiments.
Figure 57:
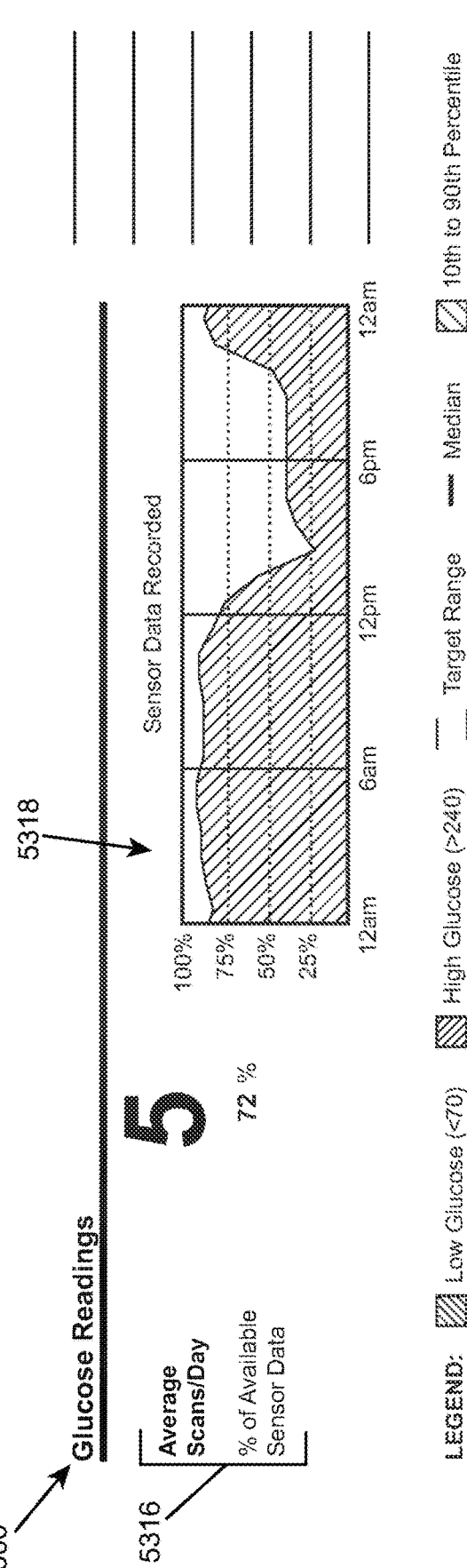

FIG. 57 illustrates an exemplary Snapshot report for a specific time frame (e.g., a two week period as shown), according to certain embodiments. The Snapshot report 5300 includes key metrics associated with the user's history over the two week period of time. For example, Snapshot report includes: section 5302 displaying metrics 5308 regarding the user's glucose, insulin, and carbohydrate intake are provided for the given two-week time period; section 5304 displaying metrics 5312 regarding low glucose events for the two-week time period; section 5306 displaying metrics 5316 regarding glucose readings for the two-week time period; and section 5307 displaying the estimated A1c percentage for the two week period.

In the embodiment shown, metrics 5308 includes average glucose value; time above, in, and below the target zone, average carb intake per day; average rapid-acting insulin intake per day; and average long-acting insulin intake per day. Section 5302 also includes a graph 5310 of glucose values for the two week period that have been averaged with respect to specific times throughout the day. Graph 5310 also indicates the range of glucose readings for the specific time throughout the day.

Metrics 5312 includes the total number of low glucose events, the average duration of a low glucose event, and the low glucose threshold. Section 5304 also includes a graph 5314 of a summary of low glucose events for the two week period that have been averaged with respect to specific times throughout the day.

Metrics 5316 includes the average number of scans per day and the percentage of available sensor data. Section 5306 also includes a graph 5318 of the percentage high glucose readings of sensor data recorded for the two week period, categorized with respect to specific times throughout the day.

Snapshot Screen 5300 also includes a Comments section 5320 that indicates any comments that the user has logged. In some embodiments, the comments section provides software generated comments generated from analysis of the sensor data. Snapshot Screen 5300 also includes a section for identifying the Report, the time period applicable to the reports, and the target range.

Calendar:

In some aspects of the present disclosure, a Calendar report is provided. The Calendar report provides an overview of the patient's involvement and highlights points of concern (e.g., hypoglycemic events).

Figure 58:
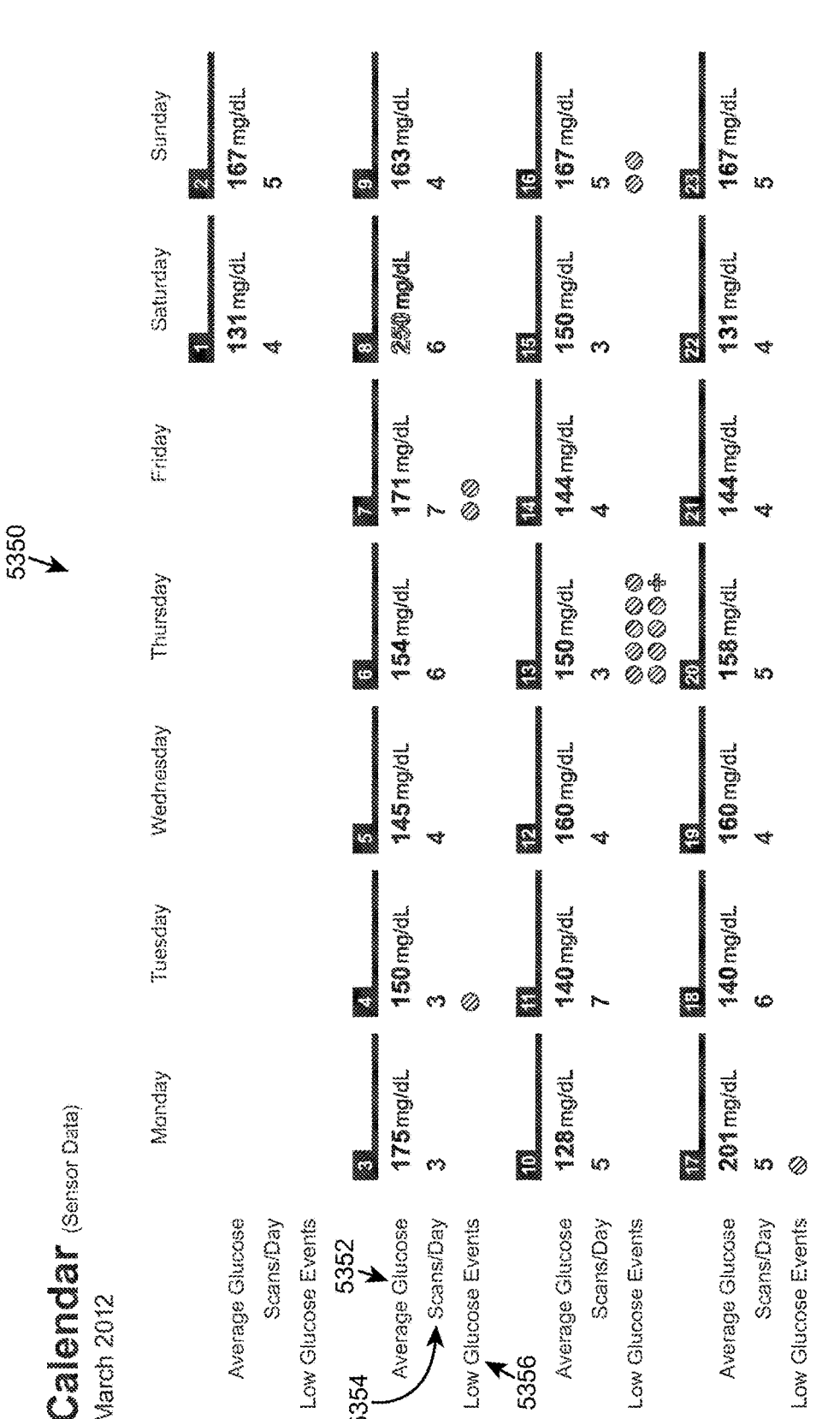
FIG. 58 illustrates a Calendar report, according to certain embodiments.
Figure 58:
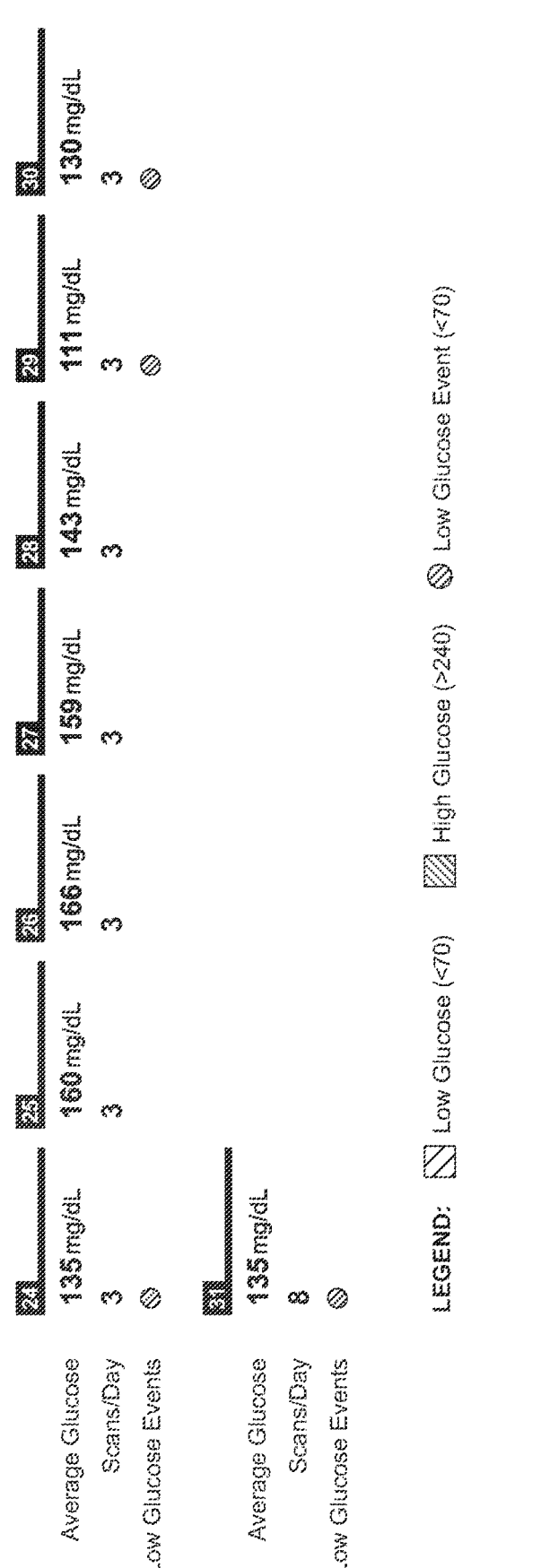

For example, FIG. 58 illustrates a Calendar report that highlights the key metrics for the user's activities in calendar format, according to certain embodiments. The events of each day of the selected month are detailed in calendar-format. The Calendar report is provided for a one-month period, e.g., March, with the following events indicated: average glucose readings for the given day 5352; number of scans per the given day 5354; and the occurrence of low glucose events for the given day. For example, on March 7, the average glucose reading was 171 mg/dL; there were 7 scans; and 2 low glucose events.

Daily Patterns:

In some aspects of the present disclosure, a Daily Patterns report is provided. A Daily Patterns report communicates the trend in glucose levels for the given time period, with respect to times throughout the day.

Figure 59:
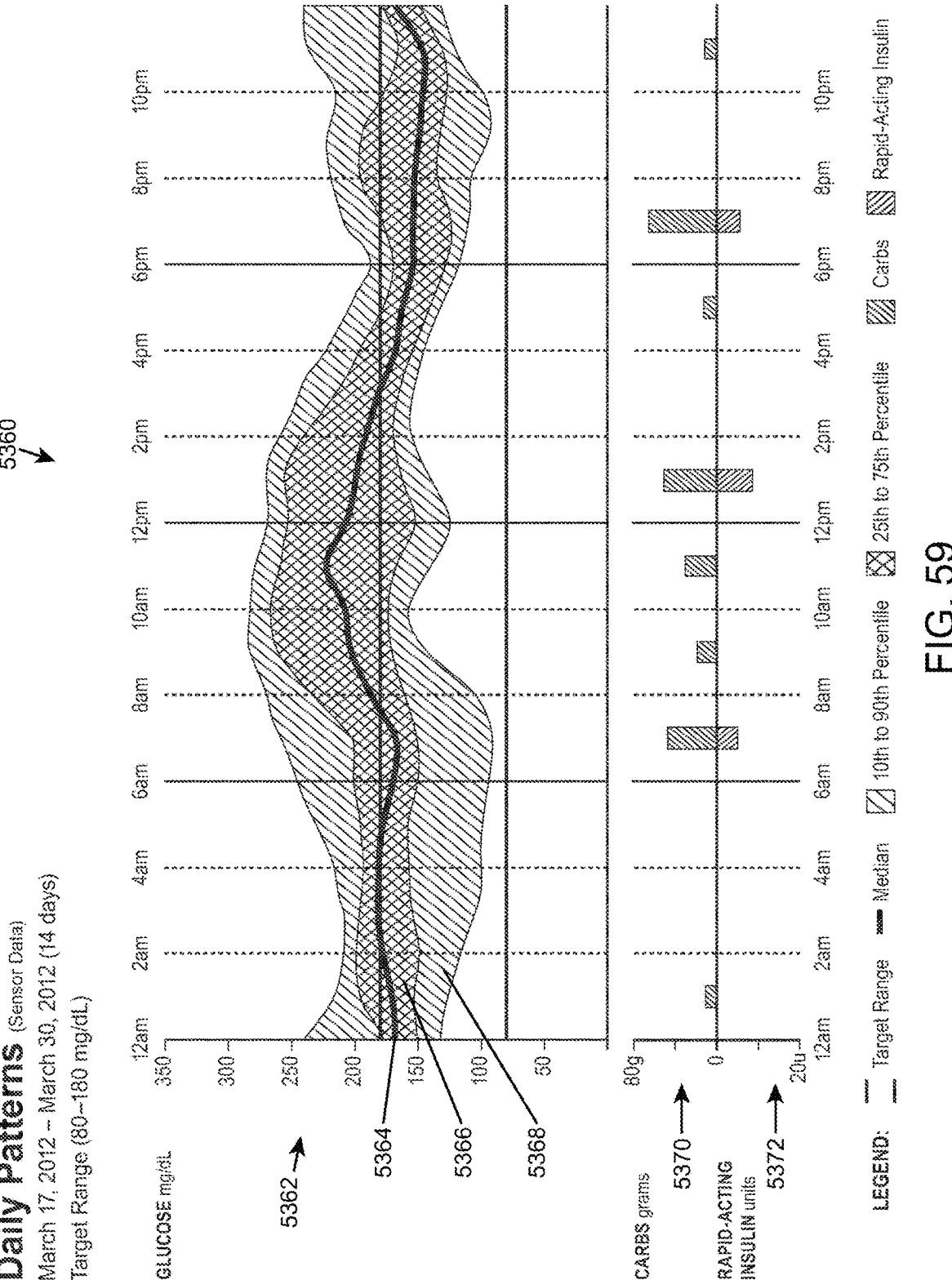
FIG. 59 illustrates a Daily Patterns report, according to one embodiment.

FIG. 59 illustrates a Daily Patterns report, according to one embodiment. Daily Patterns Report 5360 includes a graph 5362 displaying the median glucose values 5364 with respect to time periods throughout a day; the range of glucose values associated with the 25th to 75th percentile of readings 5366; and the range of glucose values associated with the 10th to 90th percentile of readings 68.

Below graph 5362, and aligned with respect to the time periods, is a graph of carbs taken and logged 5370, as represented above the horizontal axis, and of rapid-acting insulin taken and logged 5372, as represented below the horizontal axis.

Daily Patterns Report 5360 also includes sections 5374, 5376, and 5378 next to graph 5362 and aligned with respect to time periods throughout the day. Section 5374 indicates the daily average glucose value for each time period throughout the day. Section 5376 indicates the daily average carb intake per time period, as well as the number of related notes taken. Section 5378 indicates the daily averages for intake of rapid-acting insulin and long-acting insulin for each time period throughout the day, as well as the number of related notes.

Mealtime Patterns:

In some aspects of the present disclosure, a Mealtime Patterns report is provided. A Mealtime Patterns report communicates the rise and fall in glucose levels relative to meals.

FIG. 60 illustrates a Meal Patterns report, according to one embodiment. The report includes data for a given time period 5414 (e.g., two weeks) and includes plots of the glucose values before and after specific meals of the day.

The report includes plots 5402, 5404, and 5406 for three different meal events—e.g., meals occurring at different time periods 5416a, 5416b, 5416c of the day (e.g., Morning, Midday, and Evening, respectively). The number of notes logged for food intake and insulin intake are also provided at sections 5418a, 5418b, and 5418c. Furthermore, the average carbs taken and logged 5420a, 5420b, and 5420c for the respective time period is also shown. The average insulin taken and logged 5422a, 5422b, and 5422c for the respective time period is also shown.

The meal time reference points 5412a, 5412b, and 5412c indicate the time at which the meal was taken. One hour incremental time periods before and after the reference points are provided. Median glucose plots 5408a, 5408b, and 5408c are displayed for the respective periods. The $10^{th}$ to $90^{th}$ Percentile range 5410a, 5410b, and 5410c are also provided on plots 5402, 5404, and 5406, respectively. The average glucose values 5426a, 5426b, and 5426c for the respective incremental time periods are also provided below and aligned with the respective plots.

Daily Statistics:

In some aspects of the present disclosure, a Daily Statistics report is provided. The Daily Statistics report highlights glucose readings for days within the given time period (e.g., 2 weeks). The data may be used to assist in the identification of causes of hypoglycemic events and other abnormalities, for example.

Figure 61:
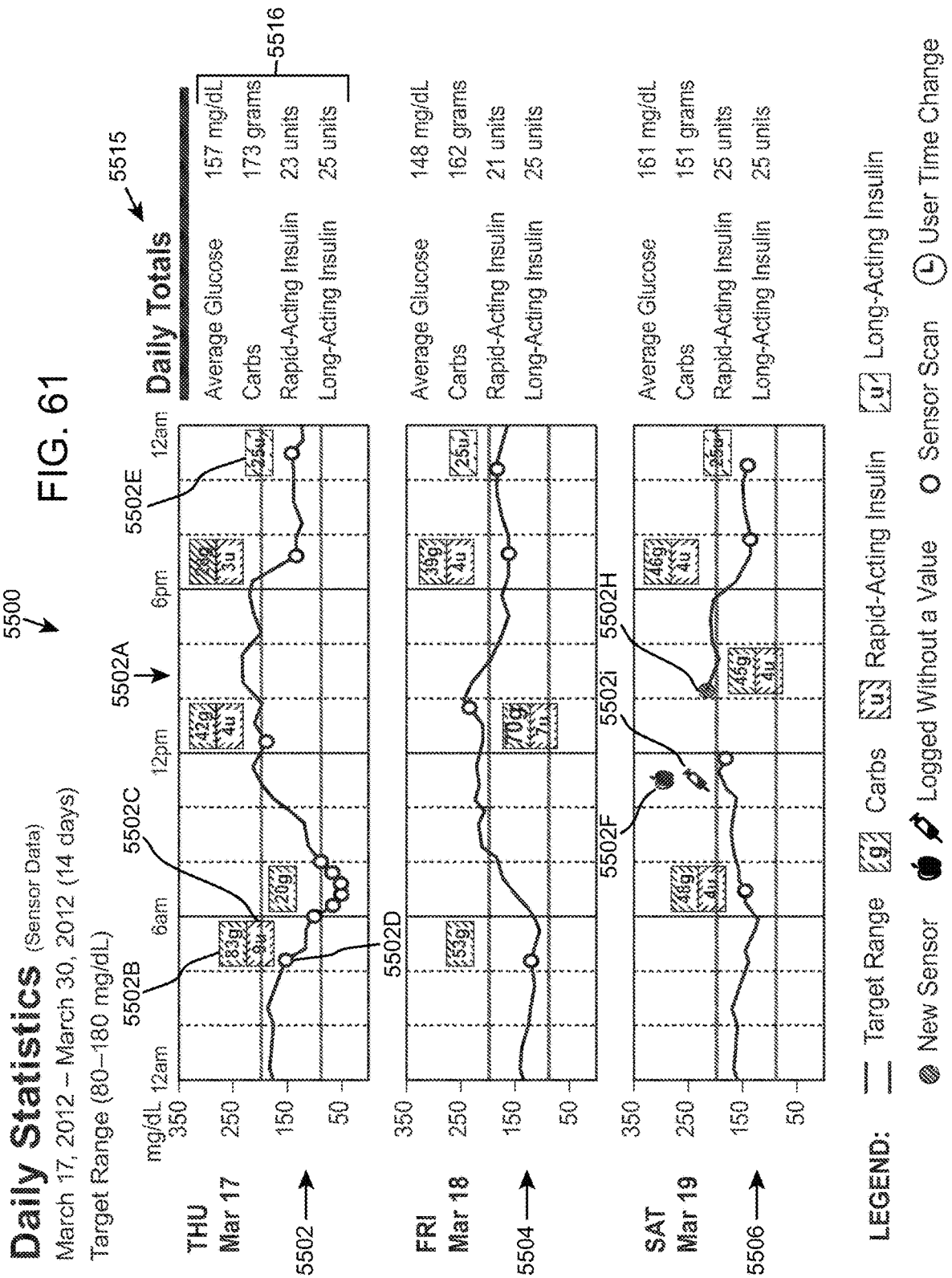
FIG. 61 illustrates the first page of a Daily Statistics report for a given time period, according to one embodiment.
Figure 61:
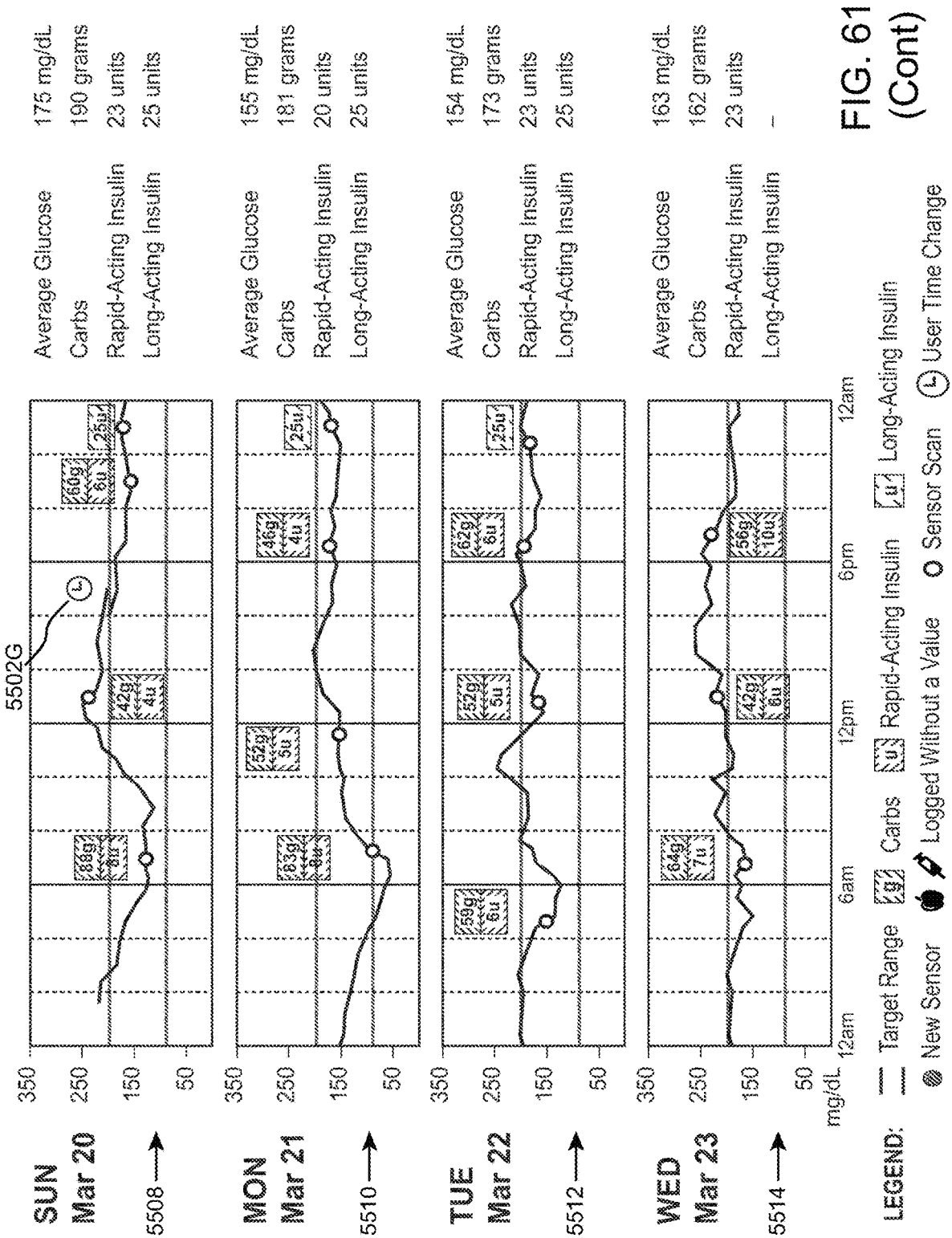

FIG. 61 illustrates the first page of a Daily Statistics report 5500 for a given time period (e.g., two week period). The first page includes the daily statistics for the first seven days of the given two-week time period. Plots 5502, 5504, 5506, 5508, 5510, 5512, and 5514 of glucose values for each of the seven days are displayed.

The day is broken up into incremental time periods (e.g., two hour periods as shown) and event information may be indicated on the chart. For example, a carb intake event 5502b is indicated at the corresponding incremental time period in which it occurred.

Rapid and long acting insulin intake events 5502c and 5502e, respectively, are indicated at the corresponding incremental time period in which it occurred.

Events associated with food intake and insulin logged without a value 5502f and 5502i, respectively, are indicated at the corresponding incremental time period in which it occurred.

User Time change event 5502g is indicated at the corresponding incremental time period in which it occurred. For example, if the user changes the time on the Reader device, this event would be indicated at the appropriate time and day.

Sensor scan event 5502h is indicated at the corresponding incremental time period in which it occurred. In this way, any discontinuities in glucose readings are also displayed, as represented as breaks in the glucose plot.

Furthermore, Daily Totals section 5516 displays daily totals of additional glucose related data. For example, section 5516 provides daily totals for the first day—March $17^{th}$. Section 5516 includes the average glucose for the day, the total number of carbs for the day, the amount of rap-acting insulin taken for the day, and the amount of long-acting insulin taken from the day.

Logbook:

In some aspects of the present disclosure, a Logbook report is provided. A Logbook report provides a detailed look at obtained sensor readings and, in some cases, other relevant data—e.g., insulin dosages, meal events, notes, strip glucose measurements, and ketone events—categorized by time period (e.g., by day).

Figure 62:
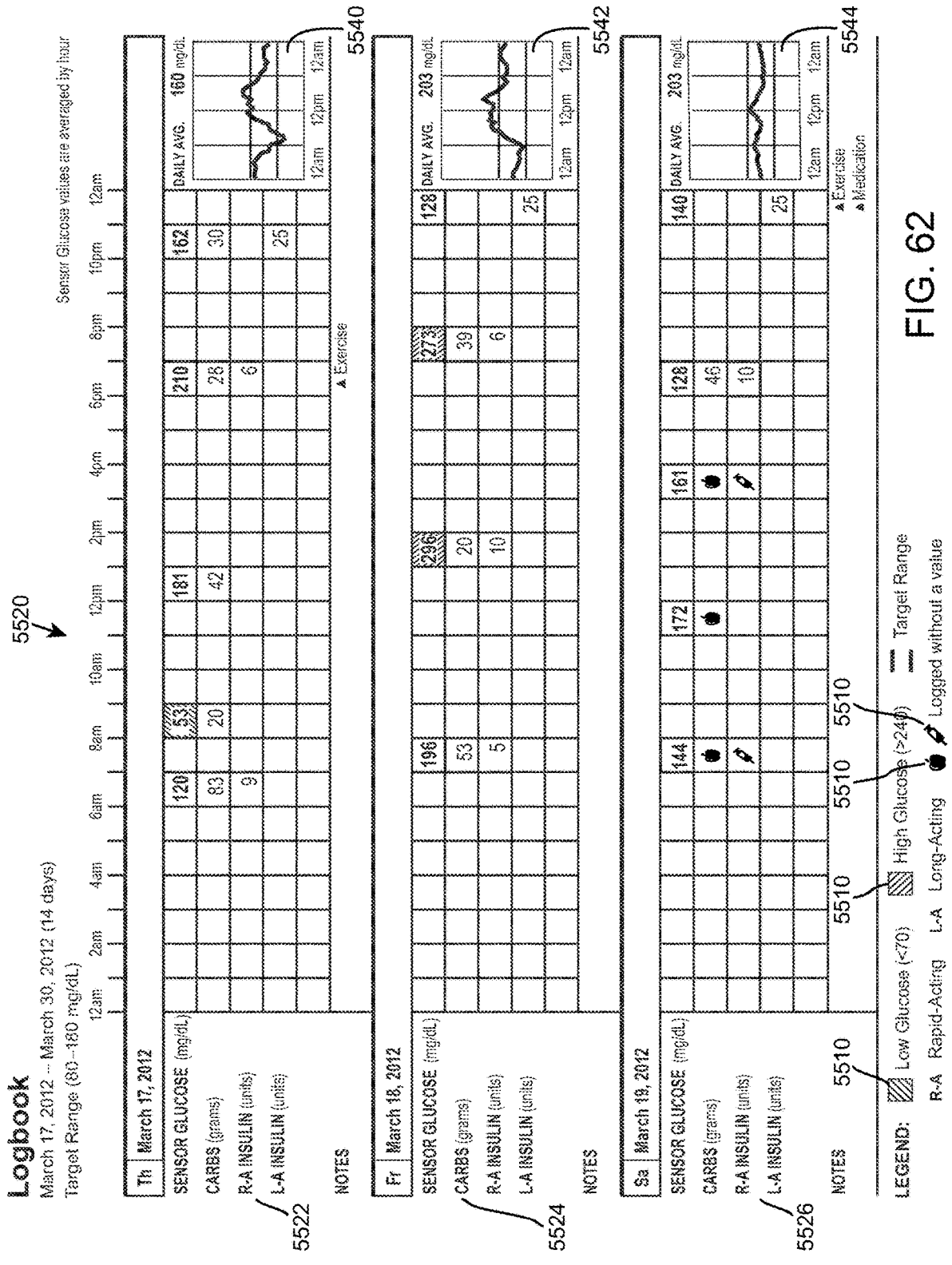
FIG. 62 illustrates an exemplary Logbook report, according to one embodiment.

FIG. 62 illustrates an exemplary Logbook report, according to one embodiment. The exemplary Logbook report 5520 illustrates the first page of the Logbook report 5520 and shows glucose related data in tables 5522, 5524, and 5526 for first 3 days of the two week time period. Glucose readings, carb intake, insulin data (e.g., intake for rapid and long acting insulin) are provided for time periods (e.g., hourly time periods as shown) throughout the day. Various events are also represented in the table (e.g., via shading, symbols, icons, etc.), such as a low glucose readings 5428, high glucose readings 5530, food intake 5532 and insulin intake 5534 that was logged without a value. Notes are also indicated in the table—e.g., notes indicating exercise or other relevant events.

Graphs 5540, 5542, and 5544 of the glucose values throughout the associated day are also provided for each day shown. The daily average is also indicated for each day.

Figure 63:
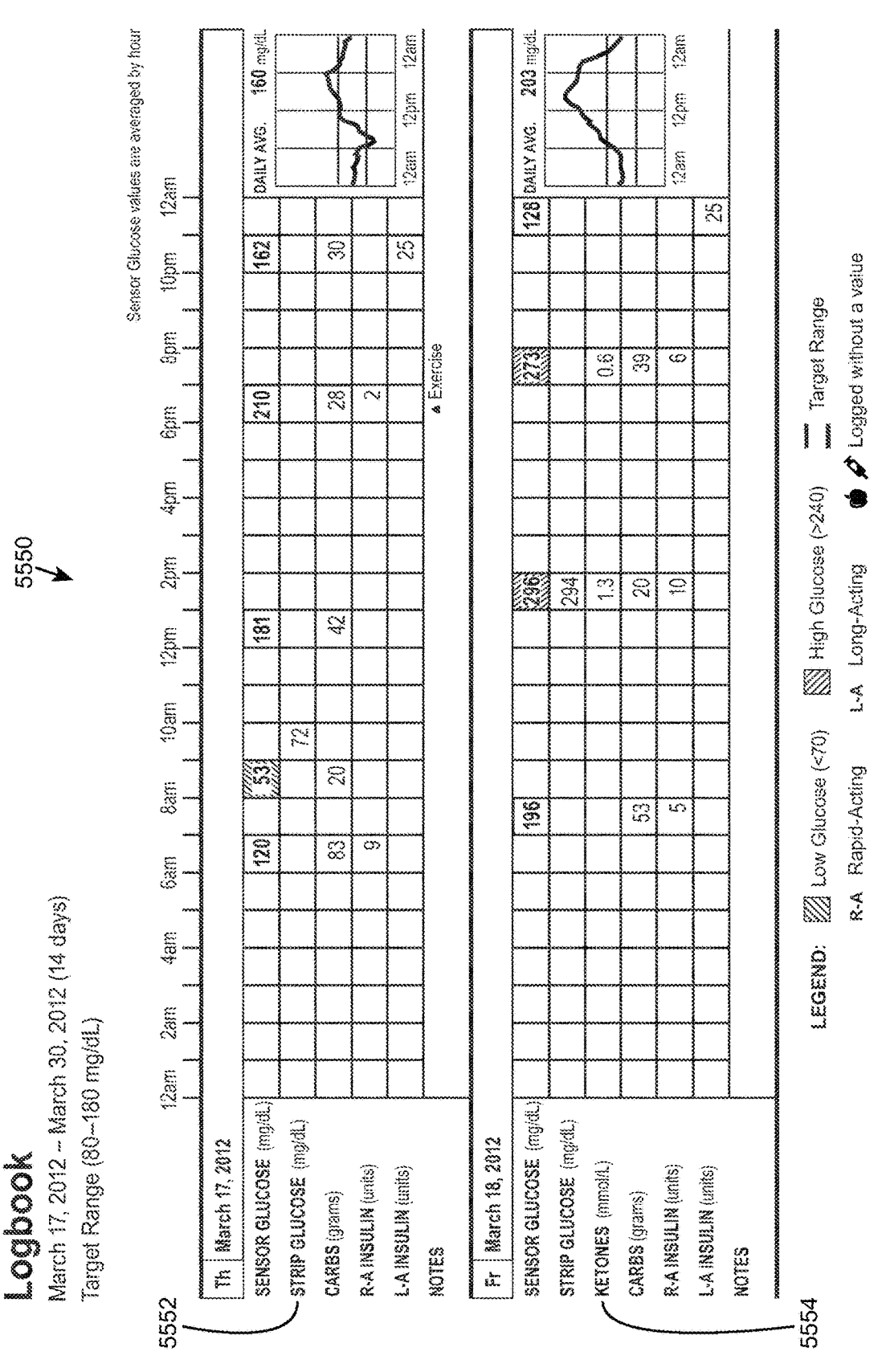
FIG. 63 illustrates an exemplary Logbook report, according to one embodiment.
Figure 63:
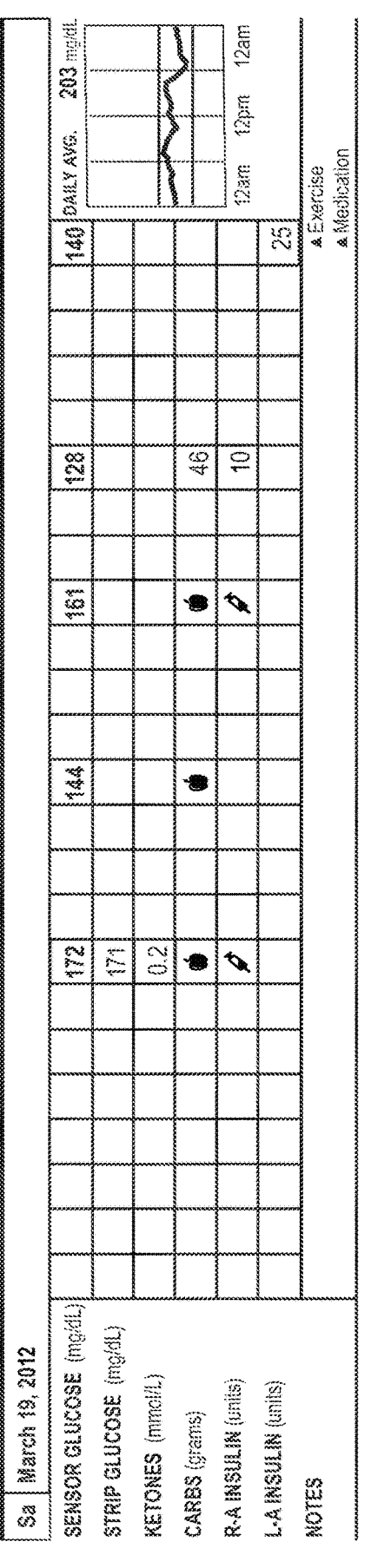

FIG. 63 illustrates another exemplary Logbook report, according to one embodiment. The exemplary Logbook report 5550 is similar to the Logbook report 5520 in FIG. 62, and similar features will not be repeated for FIG. 63 for the sake of clarity and brevity. Logbook report 5550 includes strip glucose measurements 5552 and ketone measurements 5554 in the associated tables at the associated time and day.

Reader Settings:

In some aspects of the present disclosure, a Reader Settings Report is provided. A Reader Settings Report provides a summary of settings that are currently set for the Reader device.

FIG. 64 illustrates an example Reader Settings Report, according to one embodiment. Reader Settings Report 5600 includes a Profile section 5602, which displays profile settings, such as the patients name and ID. Reader Settings Report 5600 includes a Settings section 5604, which displays general settings on the Reader, such as date, time, clock style, notification sound, button tone, vibration, and target glucose range. Reader Settings Report 5600 also includes a Notes section 5606, which displays Notes settings, such as which categories of notes are available. Example categories of notes may relate to rapid acting insulin, long acting insulin, food, exercise, medication, control solution, stress, etc. Reader Settings Report 5600 also includes a Reminders section 5608, which displays Reminder settings, such as alarms to check glucose and to take insulin dosages. Reader Settings Report 5600 also includes a Changes section 5610, which displays any changes to the Reader settings within a given time period (e.g., the last 30 days as shown).

If insulin calculation or masked mode operation are available on the Reader device, the Reader Setting Report may also include summary sections for these settings as well. For example, FIG. 65 illustrates a Reader Settings Report 5620 including an Insulin Calculator section 5622, which displays Insulin Calculator settings—e.g., whether rapid or long acting insulin calculator is on, a calculator mode (e.g., advanced or easy as discussed earlier), carbohydrate ration, correction target, and correction factors. Reader Settings Report 5620 also includes a Masked Mode section 5624, which displays Masked Mode settings, such as whether the Masked Mode is activated, whether the check glucose reminder is activated, and the frequency or time settings for the reminder, etc.

Data Management Software

In certain embodiments, the data management software may include a data management software version. Information for the data management software is provided in the following described embodiments and associated figures. It should be appreciated that the example interfaces and flows are exemplary and should not be interpreted as limiting.

Home Screens

Figure 66:
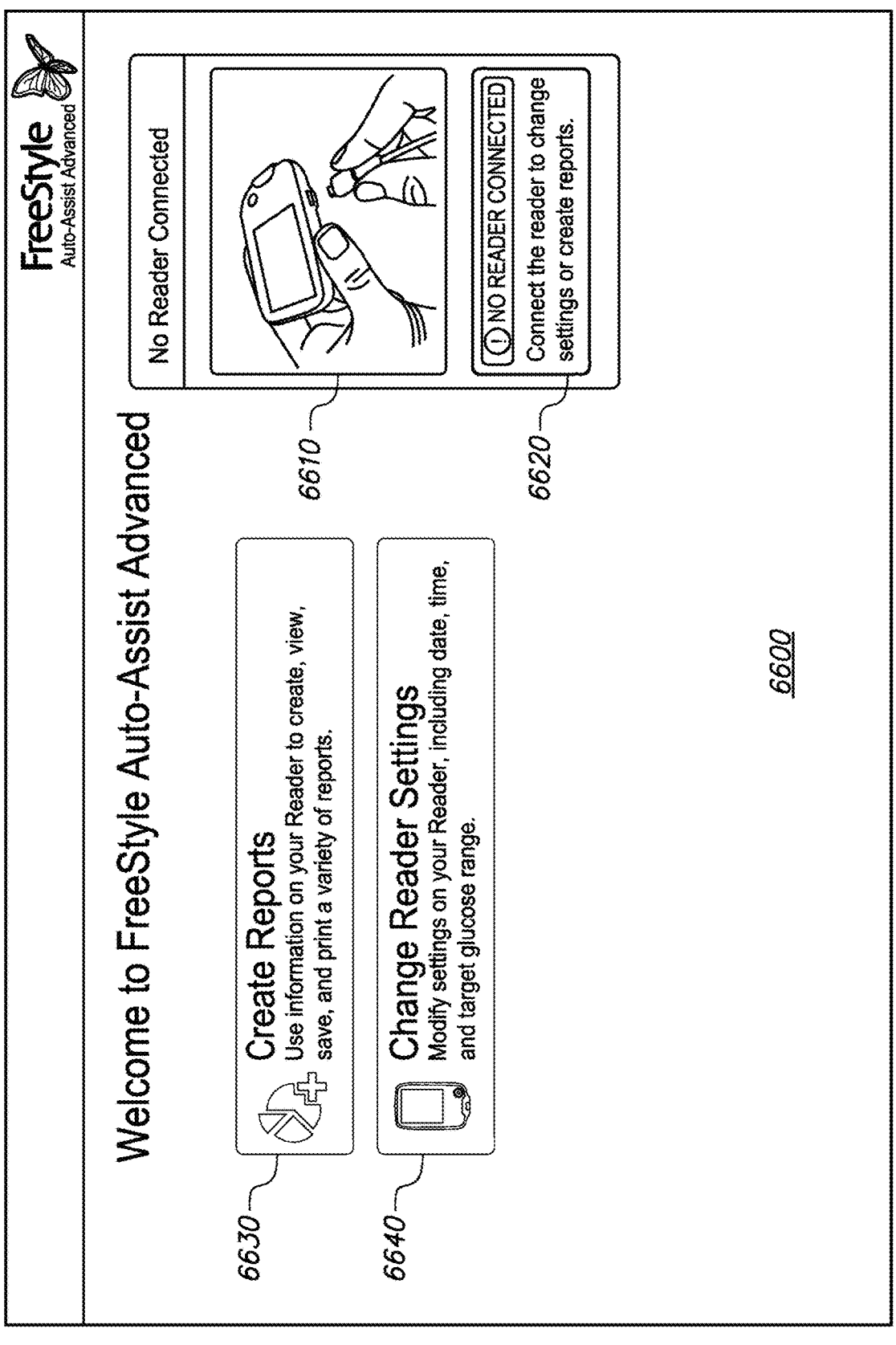
FIG. 66 illustrates a home screen for the data management software when the Reader device is not connected to the PC on which the data management software resides in accordance with some embodiments of the present disclosure.

FIG. 66 illustrates a home screen for the data management software when the Reader device is not connected to the PC on which the data management software resides. In certain embodiments, the home screen of FIG. 66, i.e., a 'no Reader connected' screen 6600, is displayed prior to a Reader device being connected, and the software will return to the home screen upon disconnection of the Reader device. As shown in the figure, the 'no Reader connected' screen includes an image 6610 representative of the state of the Reader device, that is, no Reader connected. As can be seen, the image 6610 depicts a Reader device and a connection cable, wherein the Reader device is not connected to the connection cable. The 'no Reader connected' screen 6600 also includes a text notification of the status of the Reader, as seen by notification 6620. The home screen further includes two main menu icons: Generate Reports 6630 and Change Reader Settings 6640. In the 'no Reader connected' home screen 6600, both the Generate Reports 6630 and Change Reader Settings 6640 menu are disabled, represented by the menus being shown in as a dimmed output.

Figure 67A:
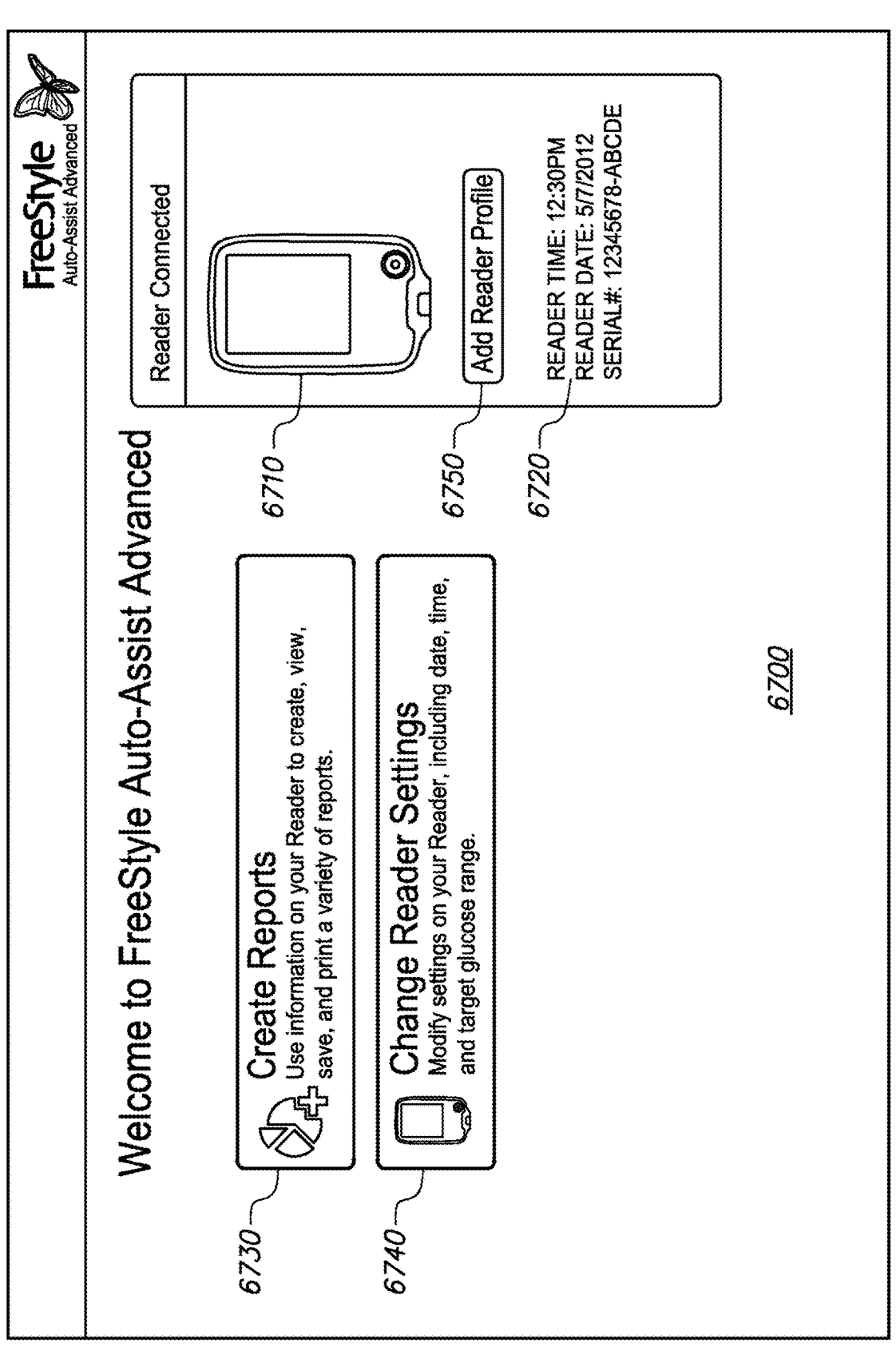
FIGS. 67A and 67B illustrate a home screen for the data management software when an unconfigured Reader device is connected to the PC on which the data management software resides in accordance with some embodiments of the present disclosure.

FIG. 67A illustrates a home screen for the data management software when an unconfigured Reader device is connected to the PC on which the data management software resides. In certain embodiments, the home screen of FIG. 67A, i.e., an 'unconfigured Reader connected' screen 6700, is displayed when a Reader that has not yet been configured for a user, is connected. As shown in the figure, the 'unconfigured Reader connected' screen includes an image 6710 representative of the connected Reader device. In certain embodiments, the data management software may be compatible with a plurality of different Reader device models, and the image 6710 may automatically display an image of the particular model currently connected. The 'unconfigured Reader connected' screen 6700 also includes text information 6720 associated with the connected Reader. On the 'unconfigured Reader connected' screen, the text information includes a serial number of the Reader and the date and time information as stored on the Reader for current date and time.

Figure 67B:
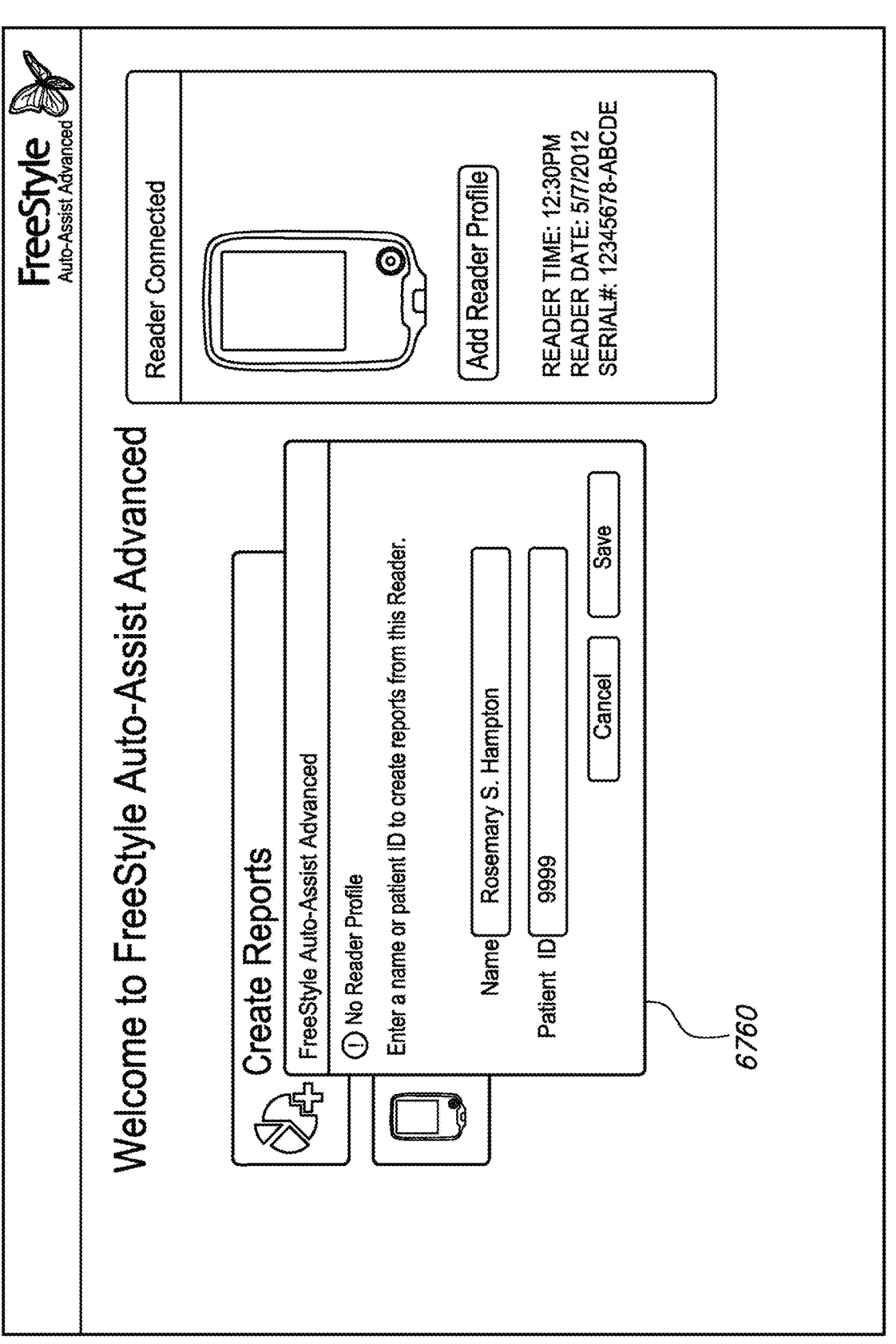

The text information, in certain embodiments, includes a menu 6750, to add a reader profile associated with the Reader device. When selected, the add a reader profile menu 6750 launches a pop-up screen 6760 to enter a name and/or patient ID of the user of the Reader, as illustrated in FIG. 67B. The pop-up screen allows the user of the Reader to associate their information, including name and patient ID. After entry of the name and patient ID, the 'save' button is selected to save the information and associate it with the connected Reader. Once reader profile information is associated with a Reader, the next time it is connected to the software, the user information will load with the Reader device.

Returning to FIG. 67A, the home screen further includes two main menu icons: Generate Reports 6730 and Change Reader Settings 6740. In the 'unconfigured Reader connected' home screen 6700, both the Generate Reports 6730 and Change Reader Settings 6740 menu are shown in full brightness, indicating the Generate Reports 6730 and Change Reader Settings 6740 menus are active. In certain embodiments, prior to entry and association of a name and patient ID, selection of either the Generate Reports 6730 or Change Reader Settings 6740 menu will activate the pop-up screen to enter the name and patient ID, thus not allowing the running of reports or changing of settings until after the Reader is configured with user information.

Figure 68:
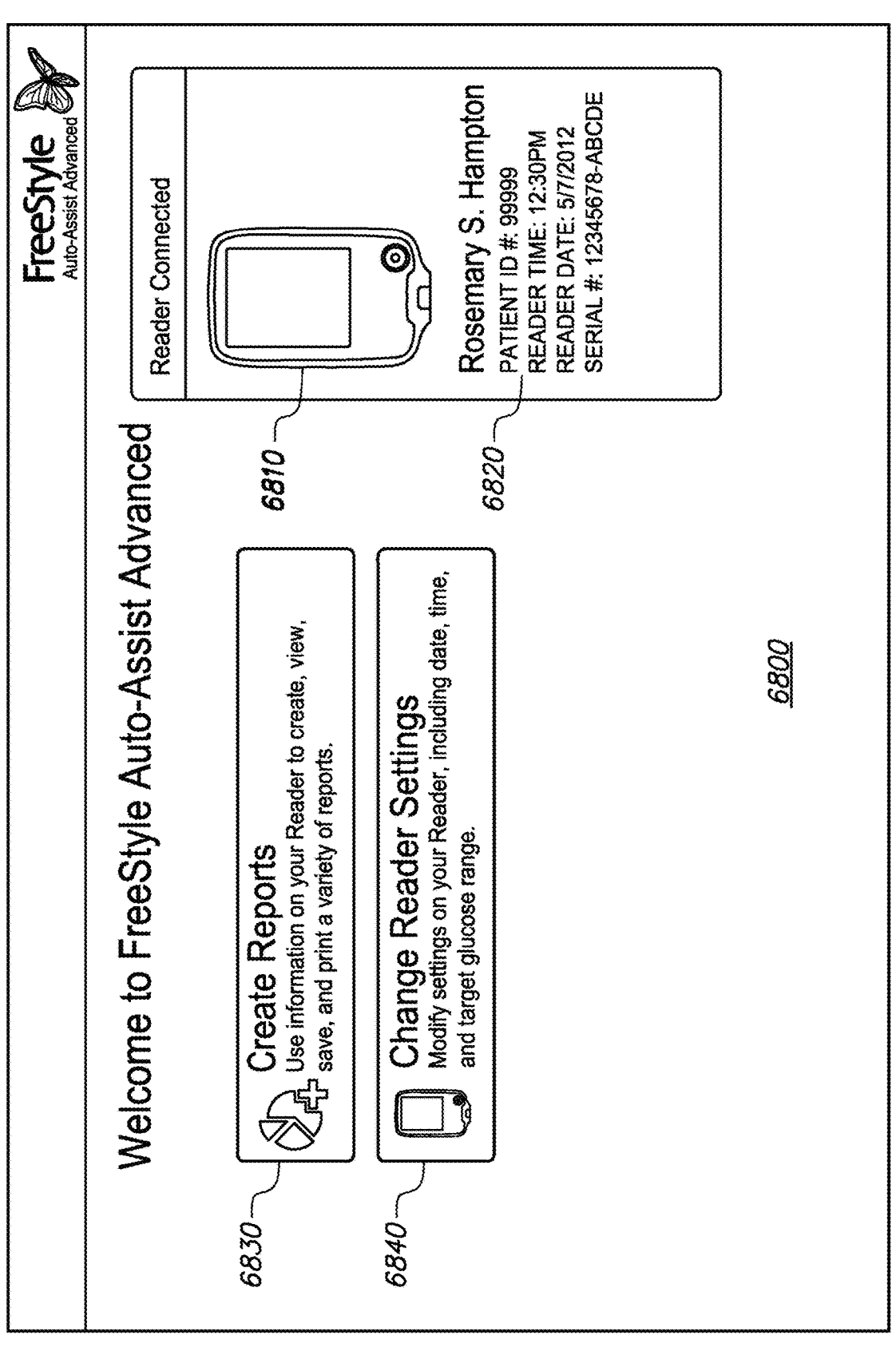
FIG. 68 illustrates a home screen for the data management software when the Reader device is connected to the PC on which the data management software resides in accordance with some embodiments of the present disclosure.

FIG. 68 illustrates a home screen for the data management software when the Reader device is connected to the PC on which the data management software resides. In certain embodiments, the home screen of FIG. 68, i.e., a 'Reader connected' screen 6800, is displayed when a Reader is successfully connected. As shown in the figure, the 'Reader connected' screen includes an image 6810 representative of the state of the Reader device, that is, Reader successfully connected. In certain embodiments, the data management software may be compatible with a plurality of different Reader device models, and the image 6810 representative of the state of the Reader device may automatically display an image of the particular model currently connected. The 'Reader connected' screen 6800 also includes text information 6820 for the connected Reader. In certain embodiments, the information included may be the name of the user of the Reader, a patient ID number of the user, a serial number of the Reader, and the date and time information as stored on the Reader for current date and time. The home screen further includes two main menu icons: Generate Reports 6830 and Change Reader Settings 6840. In the 'Reader connected' home screen 6800, the Generate Reports and Change Reader Settings 6840 menu are both enabled, represented by the menus being shown in full brightness.

Figure 69A:
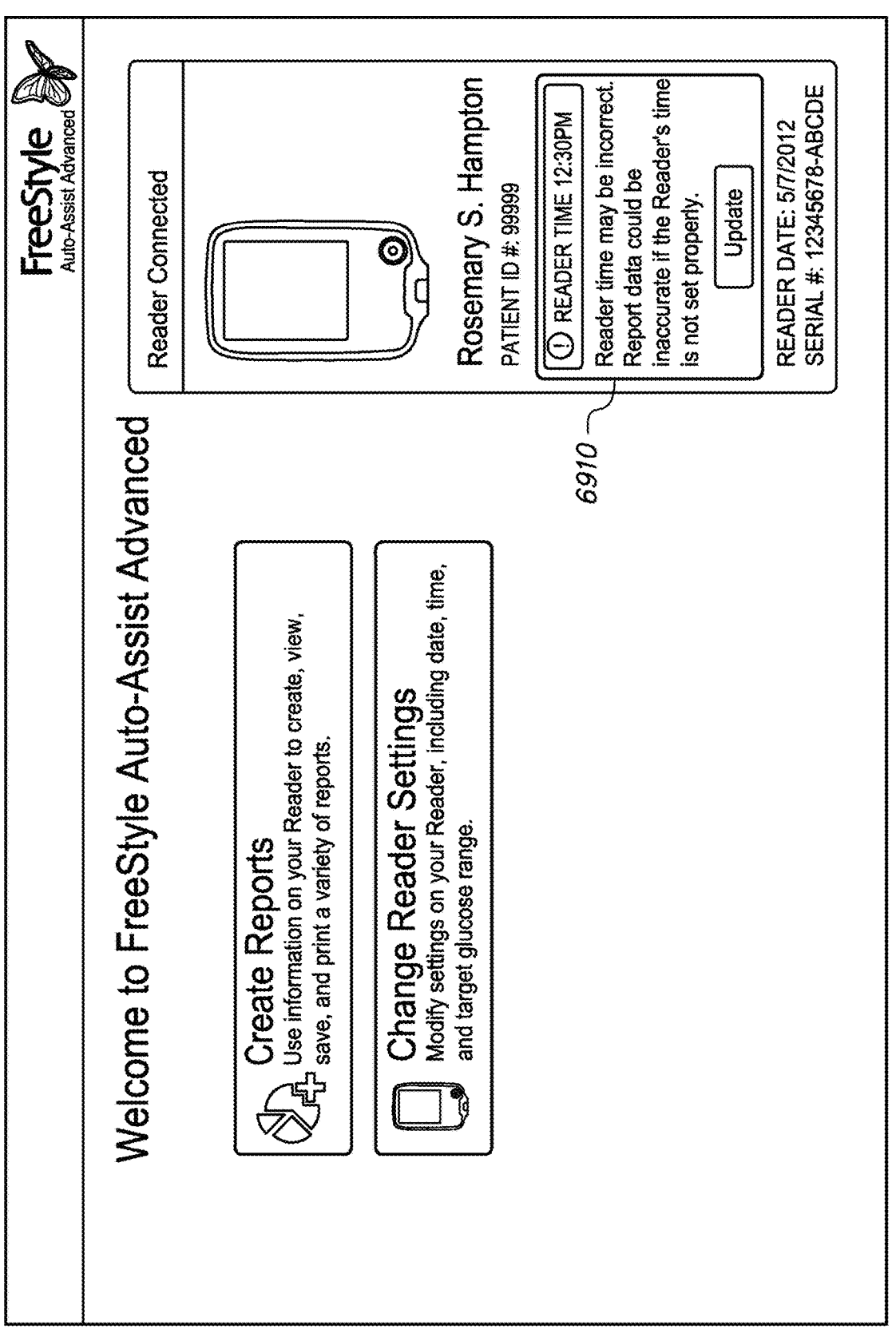
FIGS. 69A and 69B illustrate a home screen for the data management software when the time and date of connected Reader device isn't synchronized with the time of the computer on which the software is loaded in accordance with some embodiments of the present disclosure.
Figure 69B:
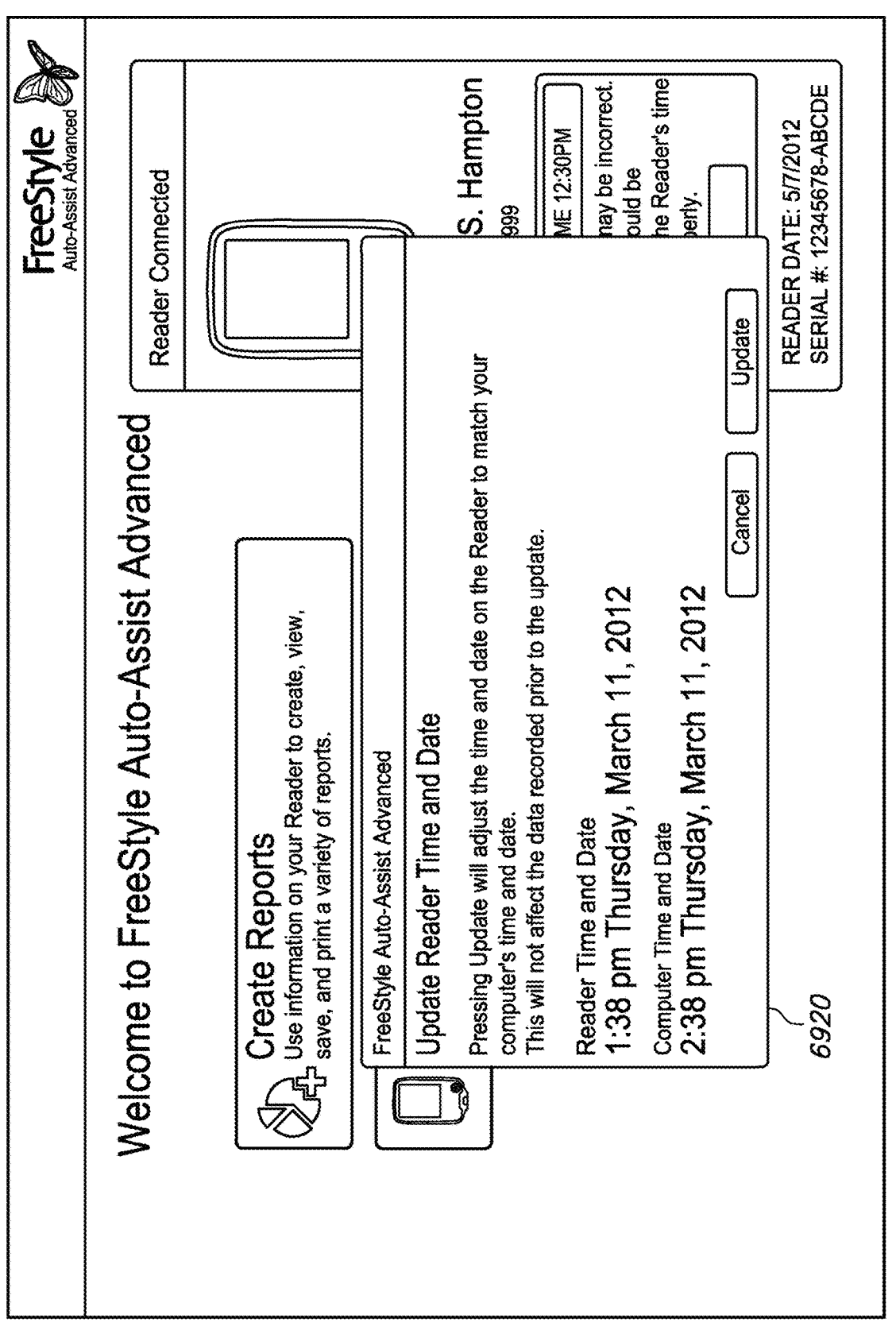

FIG. 69A illustrates a home screen for the data management software when the time and date of connected Reader device isn't synchronized with the time of the computer on which the software is loaded. In certain embodiments, when the time stored on the Reader device is off from the time of the computer by more than a predetermined length of time—e.g., five minutes or more—an alert 6910 may be displayed in place of the time information for the connected Reader. The alert 6910 includes an 'update' button which, when pressed, launches an update time and date pop-up window 6920, as shown in FIG. 69B. In certain embodiments, the update time and date pop-up window 6920 is an automatic update, whereby the Reader device will be synchronized with the time of the computer or synchronizes with a time obtained via the internet. In other embodiments, the update time and date pop-up window is a manual update, such that the user manually adjusts the time shown on the pop-up window via entry of numbers corresponding to the hour and minute of the time, or by selecting arrows to increase or decrease the shown time. In certain embodiments, when an update of the time is required, the Generate Reports and/or Change Reader Settings menus are unavailable to the user. In other embodiments, the Generate Reports and Change Reader Settings menus are available despite the unsynchronized clock.

Figure 70A:
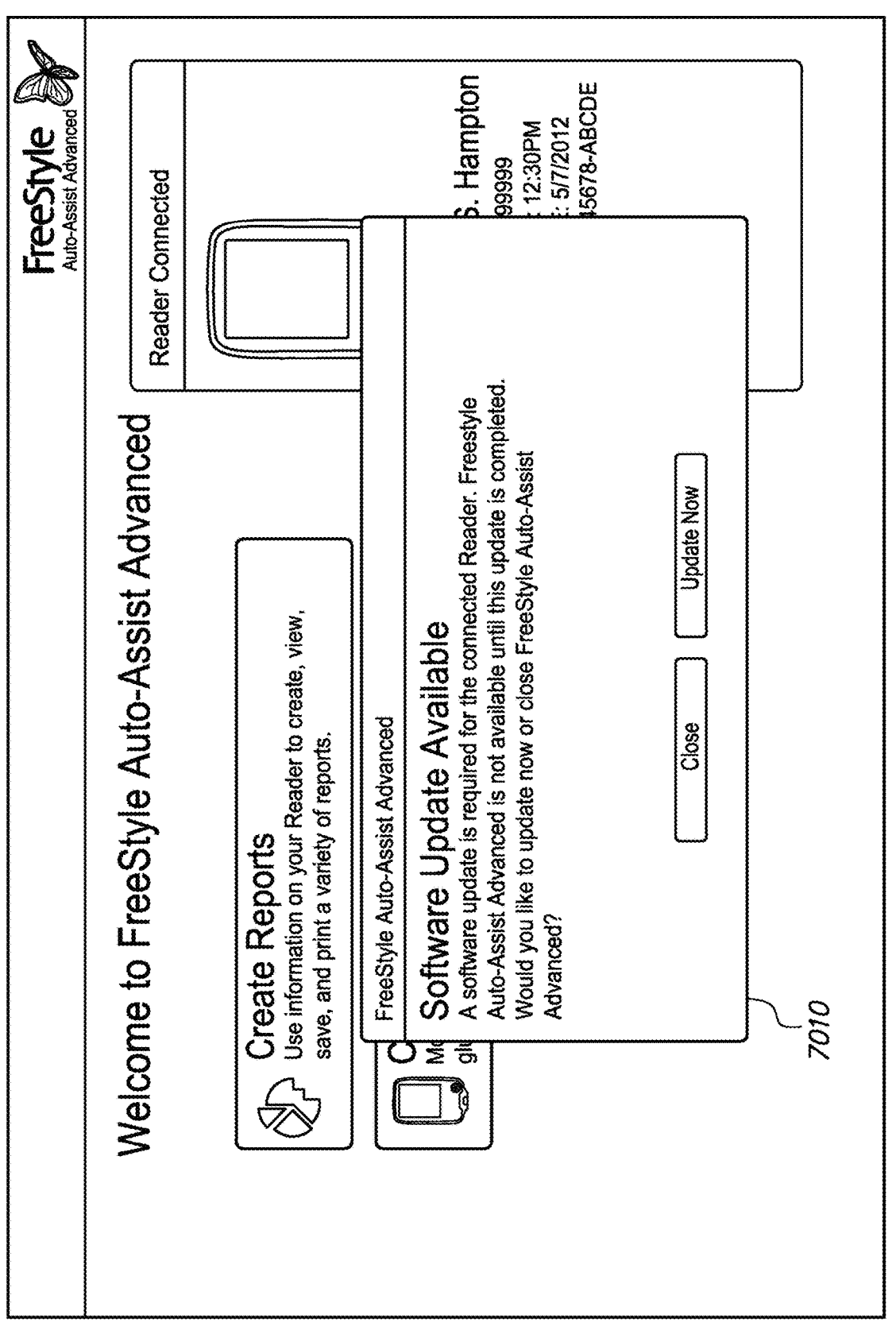
Figure 70B:
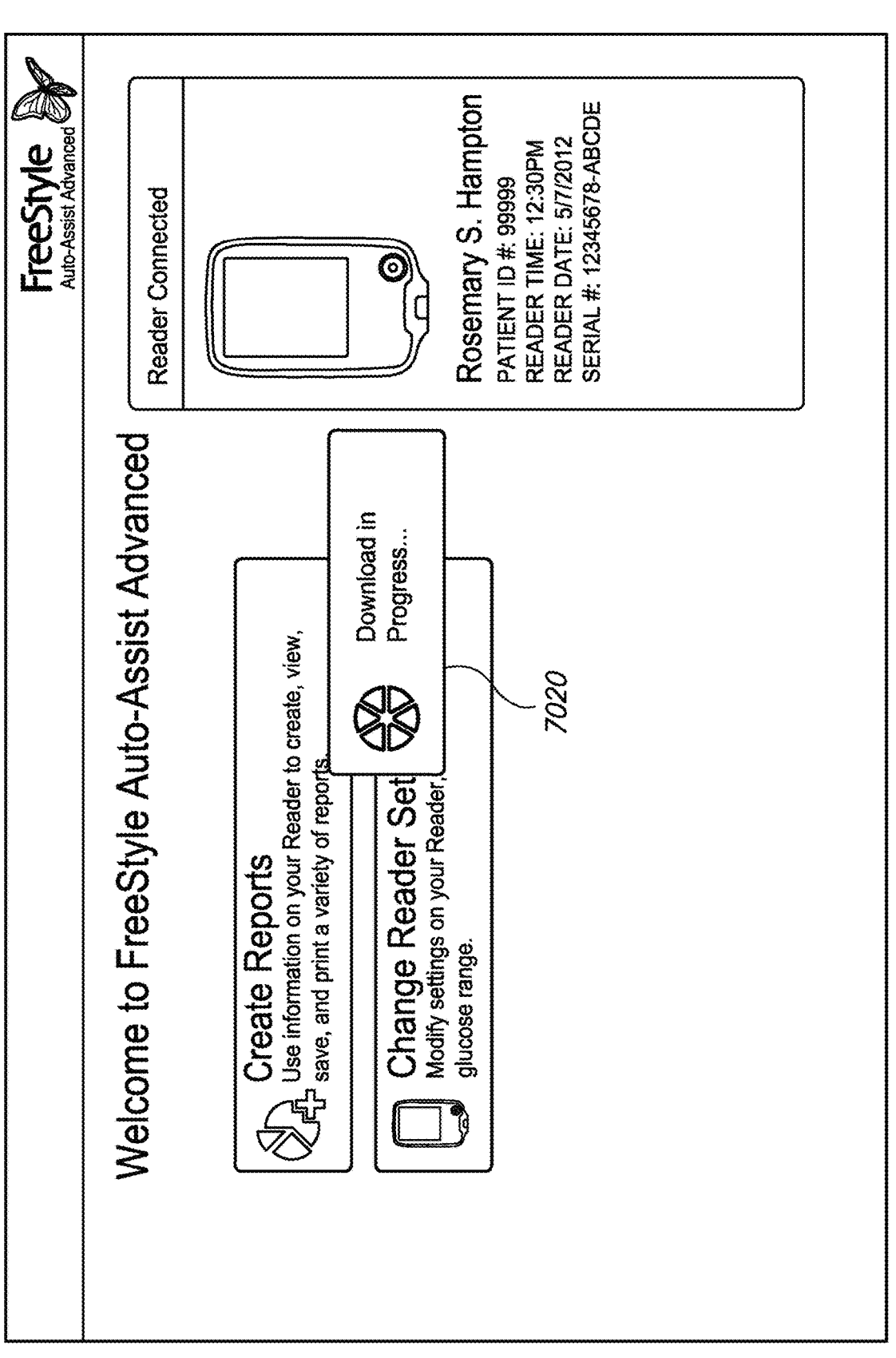

FIGS. 70A-70D illustrate a home screen for the data management software when an update to the software is available. In certain embodiments there may be two types of software updates, wherein a first type of update requires immediate attention, and a second type of update which can be applied at application shutdown. FIG. 70A shows a pop-up window 7010 associated with an update that requires immediate attention. As can be seen in the figure, window 7010 includes a text notification to the user that an update is required, and the software is unavailable until the update is applied. The window 7010 also includes two options for the user to choose: 'close' and 'update now'. If 'close' is chosen, the software may shut down. If 'update now' is chosen, a download of the update is initiated. While the download is in progress, as illustrated in FIG. 70B, a notification 7020 is shown on the screen indicating the download is in progress which prevents any user interaction with the software while the download is in progress. Upon completion of the download of the update, an updater may automatically launch and guide the user through installation of the update. In certain embodiments, updates requiring immediate action may include updates to the software or firmware of the Reader device itself.

Figure 70C:
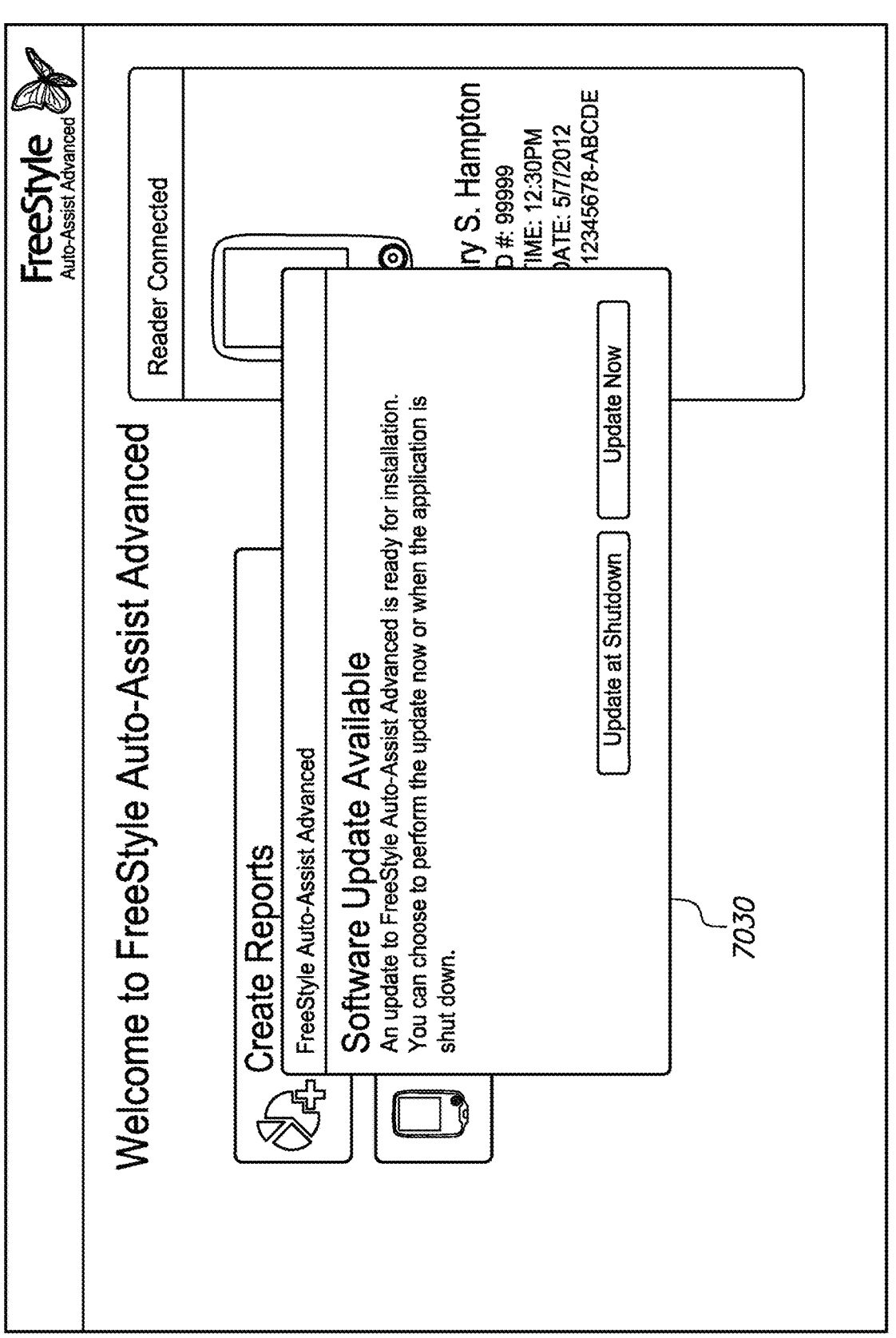

FIG. 70C shows a pop-up window 7030 associated with an update that can be applied immediately or at application shutdown. As can be seen in the figure, window 7030 includes a text notification to the user than an update is available and may be applied immediately or at application shutdown. The window 7030 also includes two options for the user to choose 'update at shutdown' or 'update now'. If 'update now' is chosen, a download of the update is initiated as described above, and a download in progress notification is shown. If 'update at shutdown' is chosen, the update is downloaded in the background of the software, and a passive notification 7040, as illustrated in FIG. 70D, may be displayed at the bottom of the home screen informing the user when the download has been completed. This passive notification 7040 would not preclude normal use of the software, and would display a reminder to the user that an update has been downloaded and will be applied upon shutdown of the software. In certain embodiments, disconnection of the Reader device may trigger a software shutdown and the update installation. In certain embodiments, updates that may be delayed until application shutdown may include updates to the data management software.

Generate Reports

Figure 71:
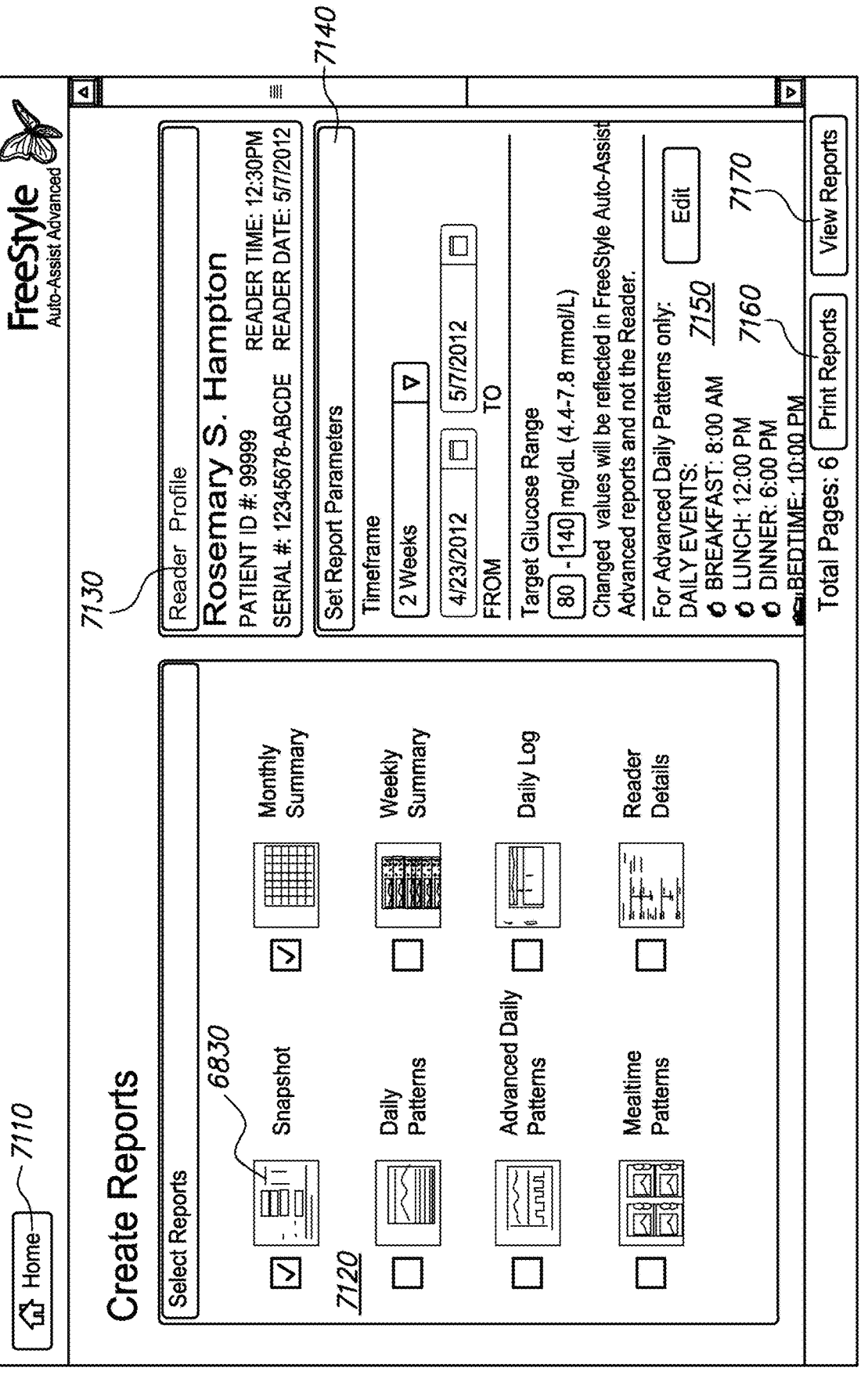
FIG. 71 illustrates a generate reports screen for the data management software in certain embodiments.

FIG. 71 illustrates a generate reports screen for the data management software in certain embodiments. The generate reports screen 7100 may be accessed after selection of the 'Generate Reports' menu on the home screen as described above. The generate reports screen 7100 may include a 'Home' button to navigate the software back to the home screen. In certain embodiments, the generate reports screen 7100 may include multiple frames. Such frames include a select reports section 7120, a reader profile section 7130, and a set report parameters section 7140.

In certain embodiments, the reader profile section 7130 may include patient and Reader information, such as patient name, patient ID, Reader serial number and Reader current time and date information.

The set report parameters section 7140 may include settings associated with reports to be run, such as the timeframe for the reports to be run, which can be set as a number of days or weeks, or by selecting a particular date range. The report parameters section may additionally include an option to set the target glucose range for certain reports, as described below. The set report parameters section 7140 may also include report specific settings, such as settings applicable only to the advanced daily patterns report 7150 as shown in the exemplary embodiment of FIG. 71.

In certain embodiments, the select reports section 7120 includes a plurality of report types. The report types may be represented as icons, text, or combinations of both. The plurality of report types may include a snapshot report, a daily patterns report, an advanced daily patterns report, a mealtime patterns report, a monthly summary report, a weekly summary report, a daily log report and a Reader details report. In certain embodiments, multiple reports may be selected by selecting a selection box next to each report in the reports section. In certain embodiments, the selection of certain reports automatically triggers the selection of other reports (for example, selection of the advanced daily patterns report automatically triggers the selection of the daily patterns report. In this manner, multiple reports may be selected simultaneously, such that a single command can instruct the software to run multiple reports at once. Reports are then available for the user to view on screen or print, by use of the 'View Reports' 7170 and 'Print Reports' 7160 buttons. In one embodiment, reports are printed in a preset order—e.g. snapshot, daily patterns, advanced daily patterns, mealtime patterns, monthly summary, weekly summary, daily log, and reader details.

Figure 72:
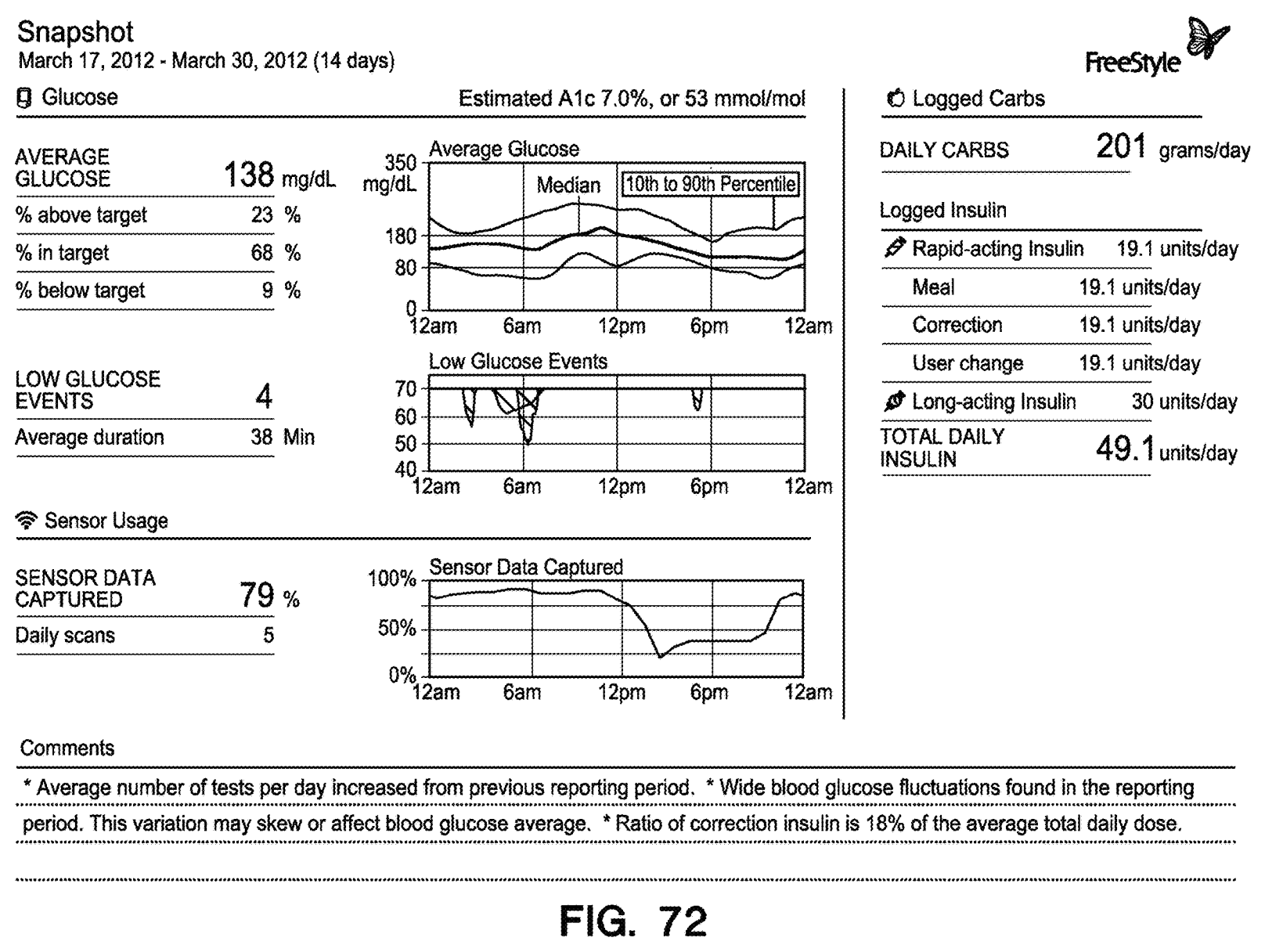

FIG. 72 illustrates an exemplary snapshot report. As can be seen in the figure, the snapshot report may include the time period—e.g. 14 days—to which the report applies, an indication of average glucose level, including indications of the percentage of time the glucose level was above the target glucose level, a percentage of time the glucose level was within the target, and a percentage of time the glucose level was below the target, and a number of low (or high) glucose events during the time period, including an indication of the average duration of such events. The report may further include a percentage of the available sensor data that was captured by the Reader and a count of the number of daily scans that were taken during the time period. Further, the report may include carbohydrate and insulin information, such as the average daily intake of carbs per day and the amount of units of insulin (rapid acting and long acting) taken per day. The snapshot report may also include comments associated with the snapshot results, such as comments related to increase or decrease in number of daily glucose tests from the current time period compared to the past time period, possible sources of error in the snapshot data, or comparisons of the current time period results to the past time period.

Figure 73A:
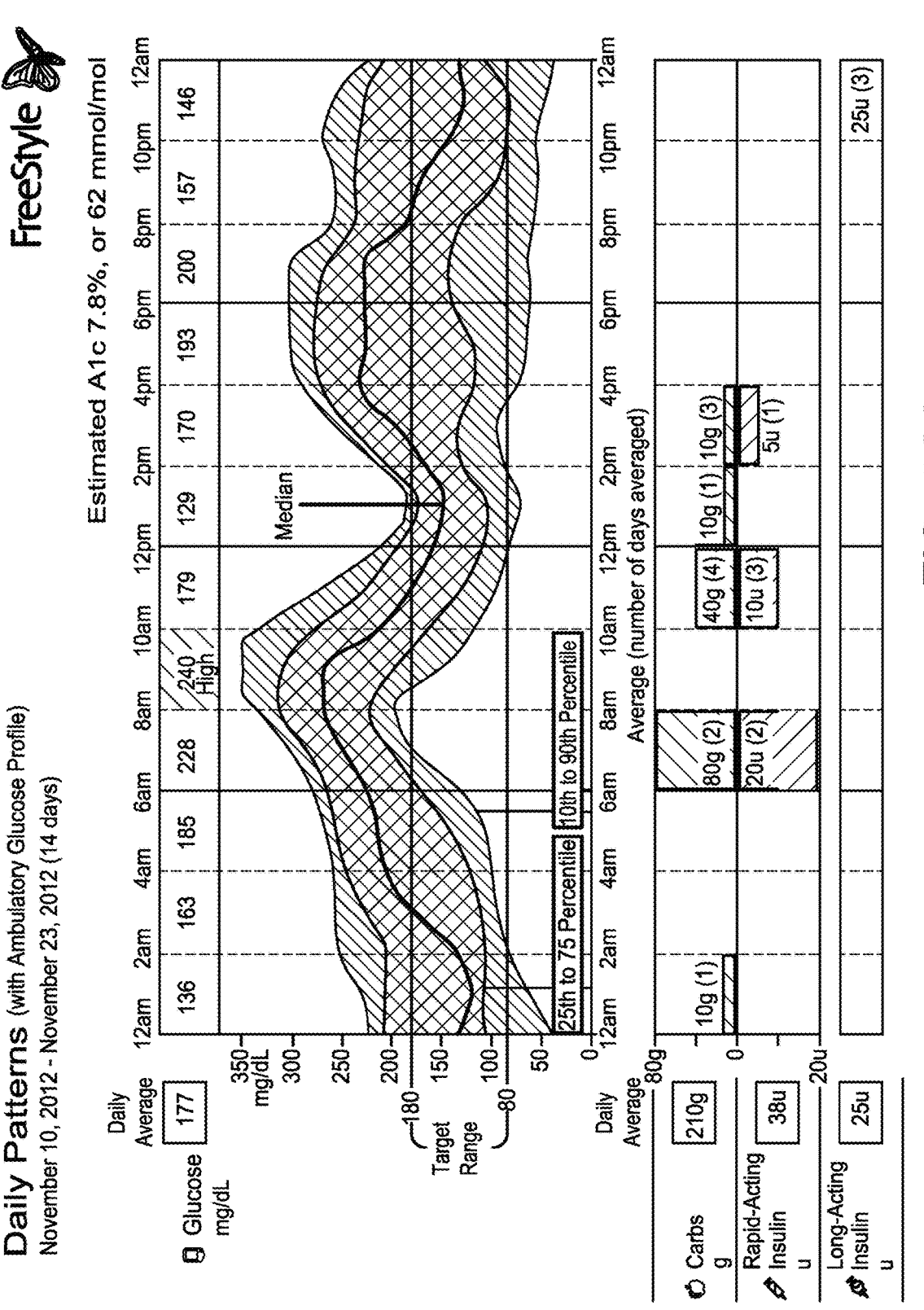
FIGS. 73A and 73B illustrate exemplary daily patterns reports in accordance with some embodiments of the present disclosure.
Figure 73B:
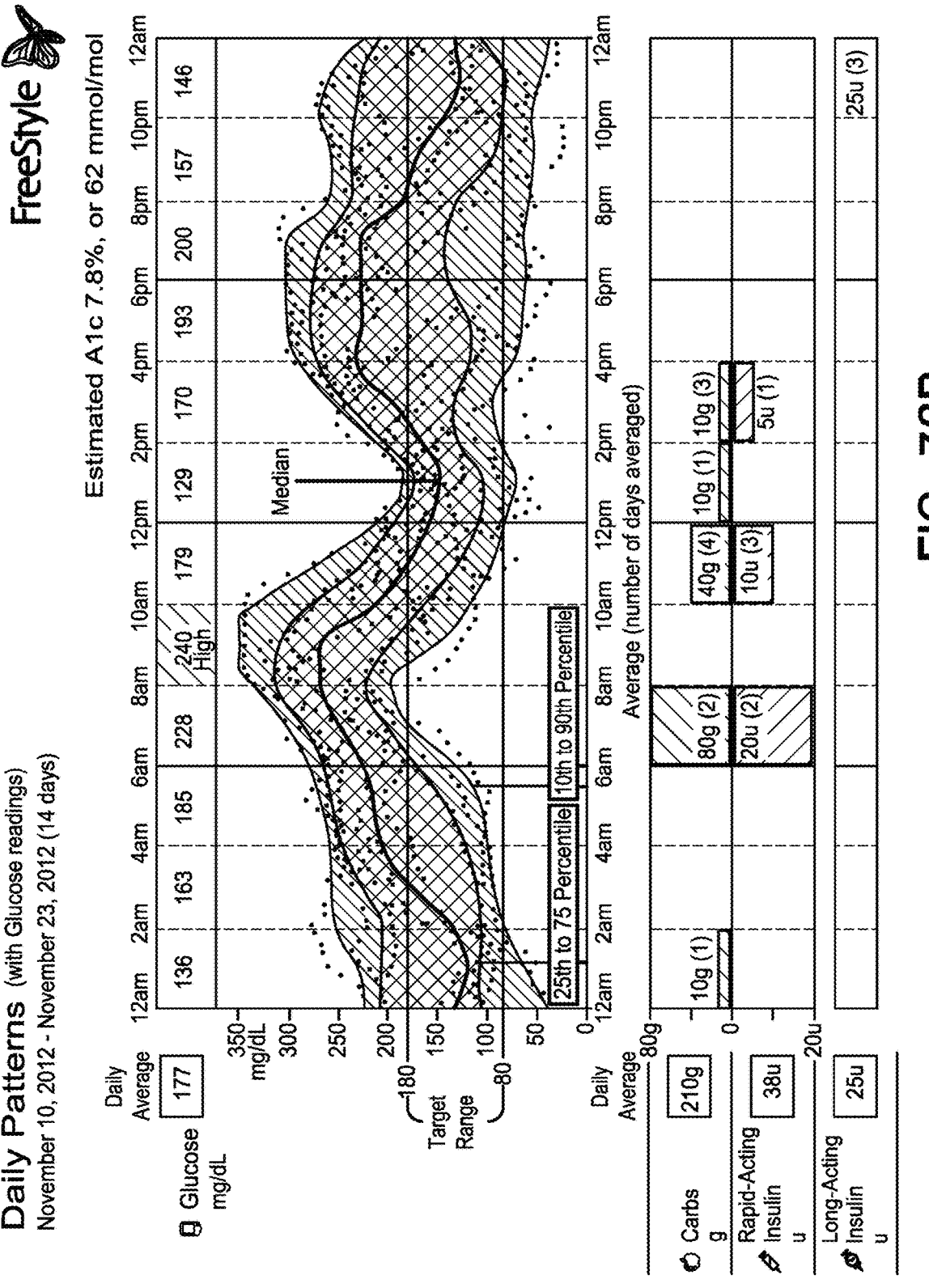

FIGS. 73A and 73B illustrate exemplary daily patterns reports. FIG. 73A illustrates a daily pattern report including a user's ambulatory glucose profile and FIG. 73B illustrates a daily pattern report including indications of glucose measurement values. As can be seen in the figures, the daily pattern report shows a 1 day, i.e., 24 hour, time period graphical representation of glucose measurement values organized by time of day for a period of days—e.g., 14 days. The glucose measurement values may be displayed as individual points, or may be averaged into a gradient pattern representative of density of measurement values within particular ranges. The graph may include a representation of the target glucose range for the user, as well as a median over time, represented by an average line, and lines representing the 10 percentile, 25 percentile, 75 percentile and 90 percentiles. In certain embodiments, the daily pattern report may include numerical averages for shorter periods throughout the day, such as for every two hours, as is shown in FIGS. 73A and 73B. In some embodiments, the time of day period with the highest average glucose level may be highlighted for the user's attention. In certain embodiments, bins with average glucose above a predetermined threshold (e.g., 240 mg/dL for example, or below a pre-determined threshold (e.g., 70 mg.dL, for example) are highlighted. In other embodiments, what is outside the target range or a fixed level outside or beyond the target range is highlighted. The daily pattern report may also have an indication of the daily average glucose level. In addition to measured glucose levels, the daily pattern report may include other average daily information, such as carbohydrates, rapid-acting insulin, and long-acting insulin. As shown in the figures, daily information can be displayed as numerical daily averages, and also as average ingestion amounts by time of day.

Figure 74A:
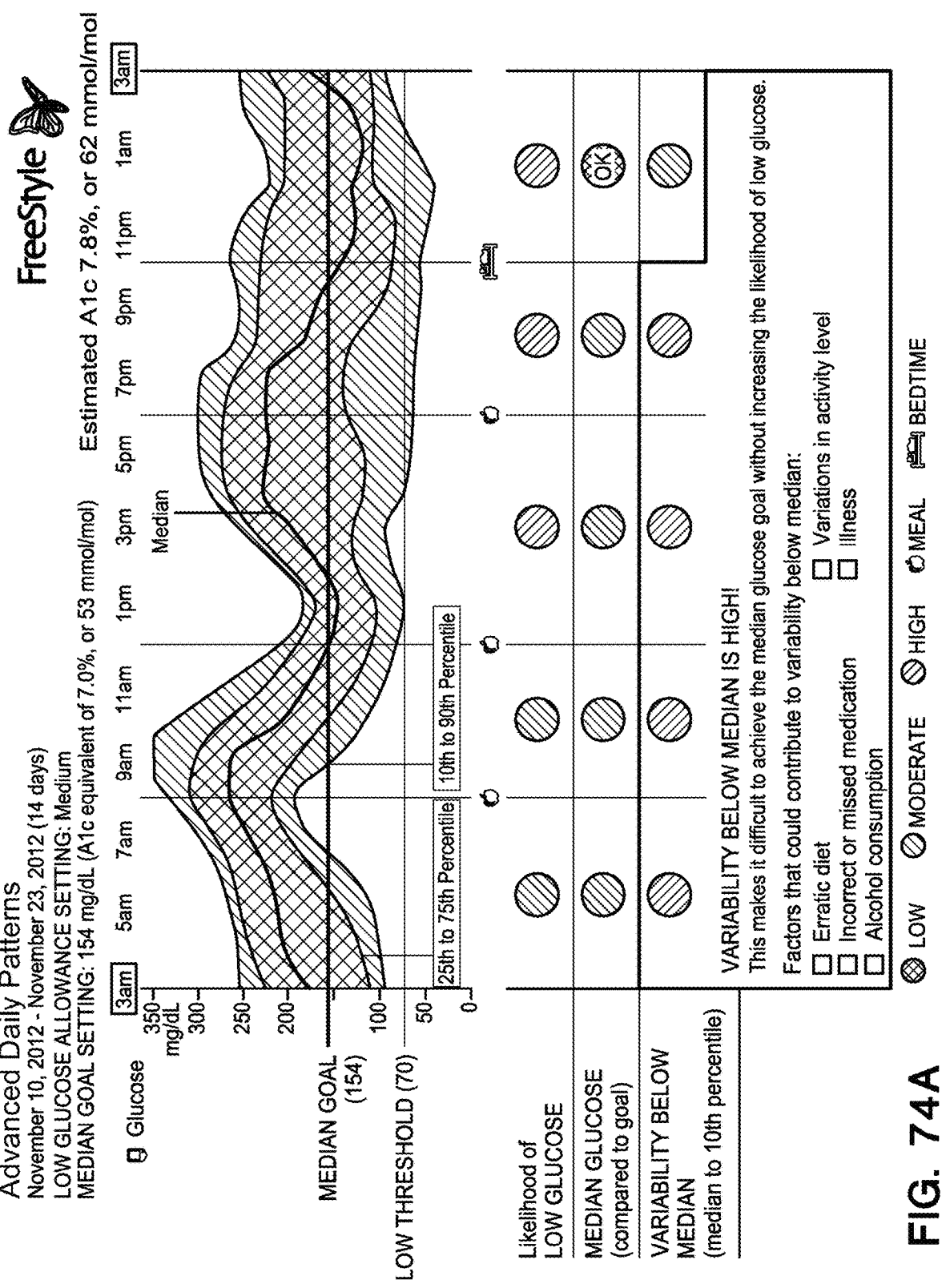
FIGS. 74A and 74B illustrate exemplary advanced daily pattern reports in accordance with some embodiments of the present disclosure.
Figure 74B:
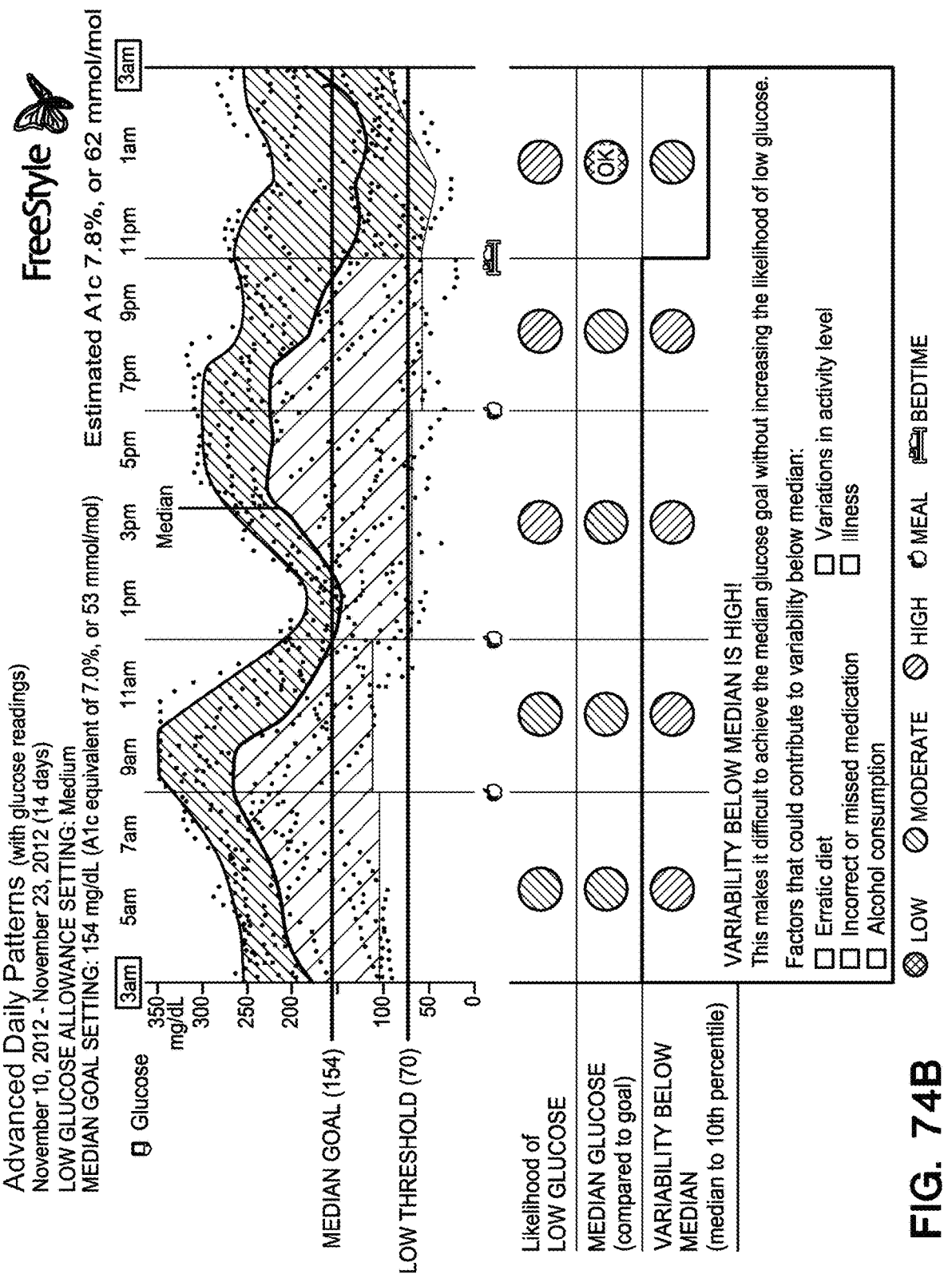

FIGS. 74A and 74B illustrate exemplary advanced daily pattern reports. Similar to the daily pattern report, the advanced daily pattern report may include a graphical representation of glucose measurement values and the average distribution of glucose measurement values over a period of time. The graph may additionally include a median goal glucose level line and a low threshold glucose level line. In certain embodiments, the low threshold glucose level line is representative of a level of glucose low enough to risk health problems for the user, such as is described above herein. The advanced daily pattern report may further include an indication system for notifying the user of variability and warnings with respect to the averaged measured glucose levels. As shown in the figures, the advanced daily patterns report may include indications of the likelihood of low glucose, comparison between the median glucose level and the glucose level goal, and indications of the variability of measured glucose levels below the median. An analysis of the glucose measurement values and variability factors may result in a notification to the user of a likely situation with respect to their level of glucose control. In the example of FIGS. 74A and 74B, the user's glucose variability below the median is high. In certain aspects, the notification to the user may include warnings and possible factors contributing to the determined issue or problem.

FIG. 75 illustrates an exemplary mealtime pattern report. As can be seen in the figure, the mealtime pattern report may include graphical and numerical representations of glucose level information with respect to particular times of the day that may be associated with meals, i.e., morning (breakfast), midday (lunch), evening (dinner), and nighttime (bedtime). As illustrated in the figures, a time indication is displayed in terms of hours before and after the corresponding meal. Further, the representations may include numerical indications of the average current glucose level at the time of the meals' ingestion and peak glucose levels. In certain embodiments, a target glucose level line is shown on the graphs, as well as a low limit glucose level line. In certain other embodiments, the two lines shown on the graph represent the target range. In addition to the graphs, a representation of the average amount of carbohydrates ingested and insulin taken may also be displayed.

FIG. 76 illustrates an exemplary monthly summary report. As can be seen in the figure, the monthly summary report includes a calendar display of the current month, as well as numerical indications of average glucose level, number of scans per day, and indications of low glucose events. In the example shown in the figures, the 5$^{th}$ day of the month had a low average glucose level of 64 mg/dL, had 3 scans in the day, and had a plurality of low glucose event notifications. In certain embodiments, the days with average glucose above a predetermined threshold (e.g., 240 mg/dL) or below a predetermined threshold (e.g., 70 mg/dL) are highlighted. In other embodiments, outside of the target range or a fixed level beyond the target range are highlighted.

Figure 77:
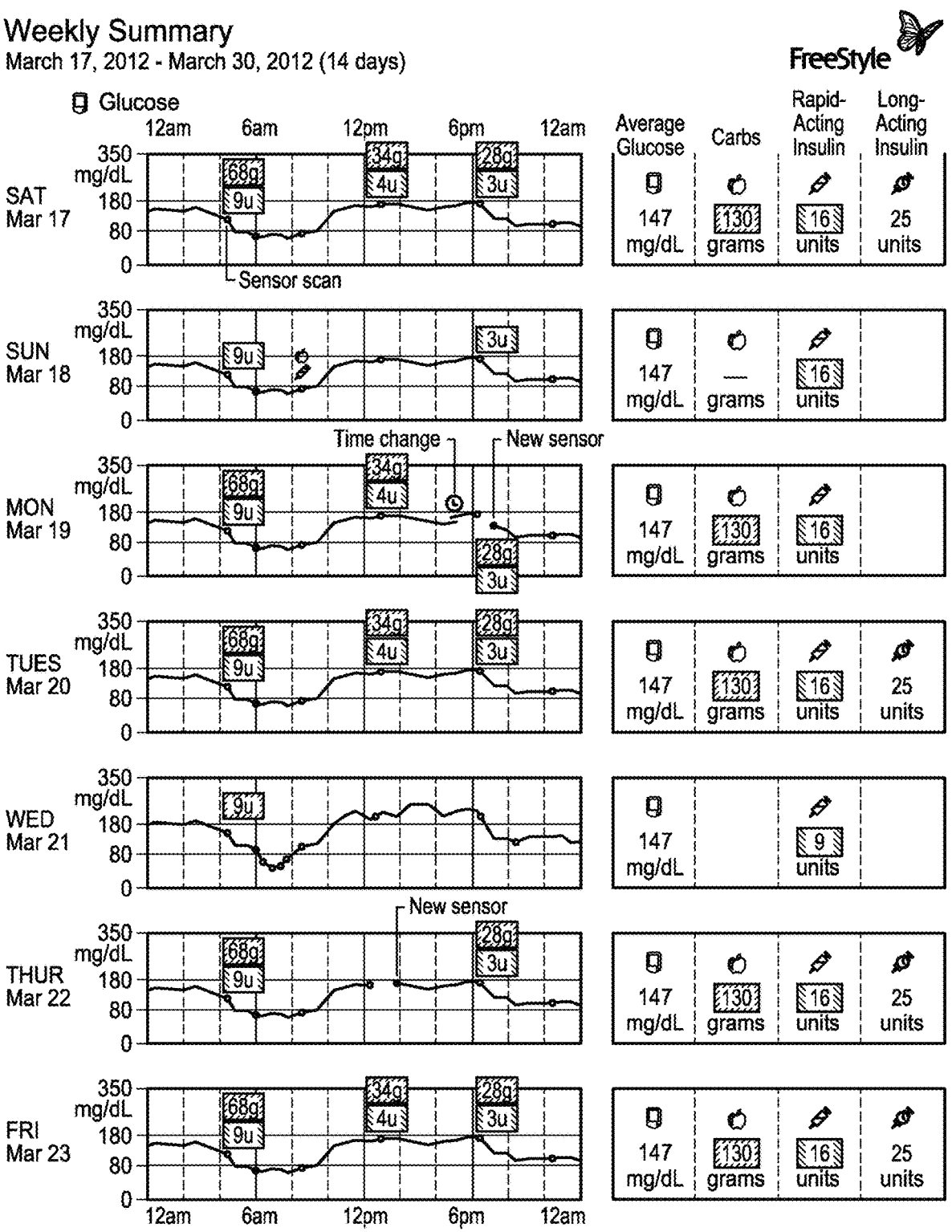
FIG. 77 illustrates an exemplary weekly summary report in accordance with some embodiments of the present disclosure.

FIG. 77 illustrates an exemplary weekly summary report. As can be seen in the figure, the weekly summary report includes a representation of the 7 days of the week. For each day of the week, a graphical representation of the 15 minute historical glucose data during the day is displayed. Each graphical representation may also include an indication of when a sensor scan was taken, and in certain embodiments, the specific data associated with the scan, including glucose level, carbohydrates, and current insulin on board. As also shown in the figure, a target glucose range may be shown in a differentiated color to highlight good glucose control. In some embodiments the graphical representations include icons representative of glucose related events, including injection of rapid-acting insulin, ingestion of carbohydrates, time changes, and insertion or activation of a new sensor.

Still referring to FIG. 77, each daily information line may include numerical and iconic representations of information, including average glucose, carbohydrate intake, rapid-acting insulin, and long-acting insulin.

Figure 78:
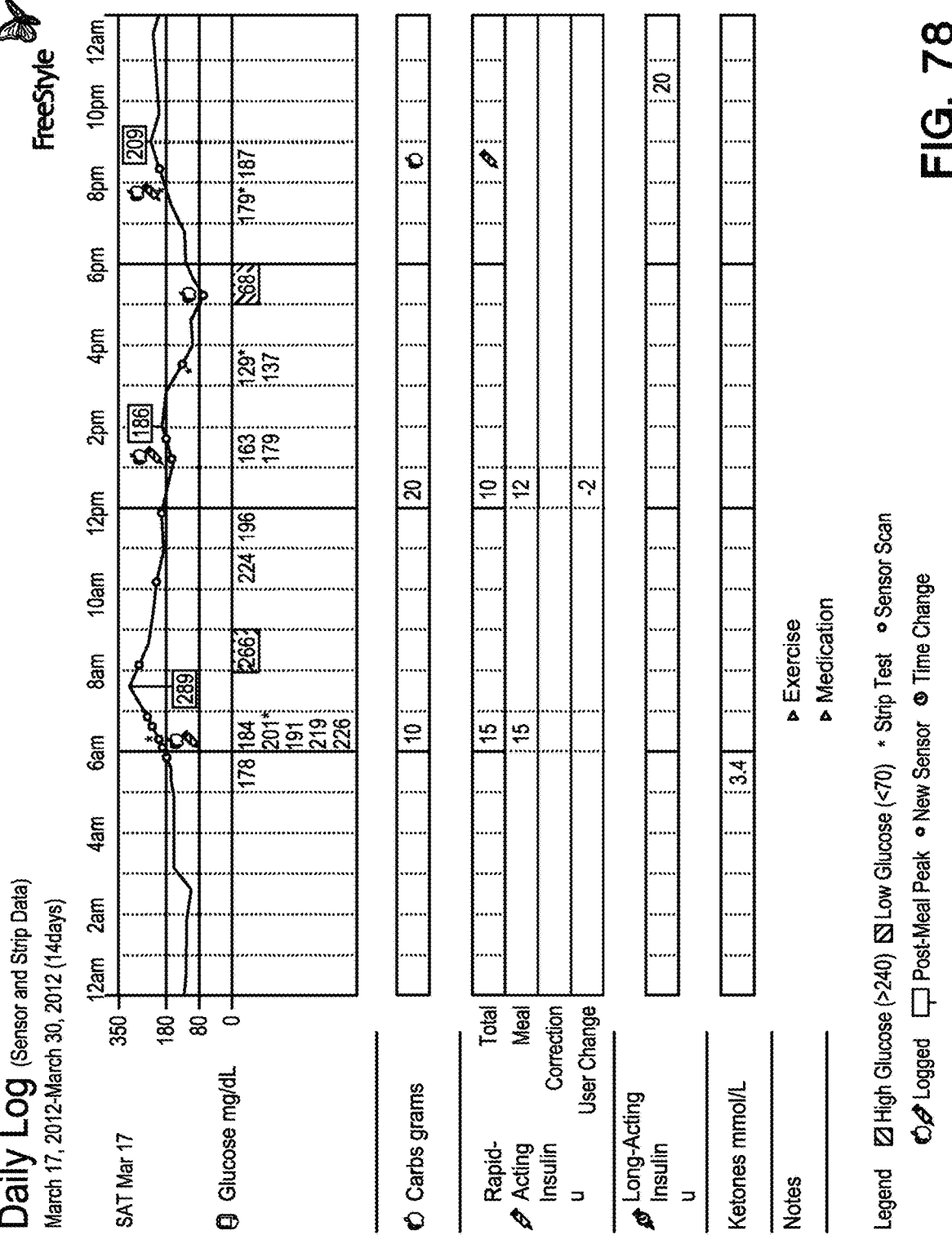
FIG. 78 illustrates an exemplary daily log report in accordance with some embodiments of the present disclosure.

FIG. 78 illustrates an exemplary daily log report. In certain embodiments, the daily log report may comprise a combination of graphical, numerical, and text information related to the user's glucose management. Referring to the figure, the daily log may include a graphical representation of the glucose level over time for the selected day, including specific indications of when sensor data was received and icons representative of carbohydrate intake and insulin injection. Also shown in the exemplary embodiment of a daily log report are numerical indications of specific glucose measurements taken during a time period, amount of carbohydrate intake for a period, amount of rapid-acting and long-acting insulin for a period, measured ketone levels for a time period, and any notes associated with the time period, such as an indication of medication ingested or exercise performed. In certain embodiments, low or high or dangerous glucose level measurements may be highlighted for particular attention by the user. In certain embodiments, the daily log report is configured to present to the user all the real-time value including sensor reading or blood glucose test strip measurements overlayed over the historical data, and providing real time results.

FIGS. 79A and 79B illustrate an exemplary reader details report. In certain embodiments, the reader details report may include user information, configurable settings, change logs, and notes. For example, as shown in the figures, the reader details report may include user profile information including patient name and ID, settings, including date and time, clock style, and sound/vibration settings, available notes, currently set reminders and alarms, insulin calculator settings and masked mode settings. In certain embodiments, settings changes for a past period of time, such as 30 days, may be displayed in a footnote style, such that settings changes are indicated to the user for review.

Referring again to FIG. 79A, also shown is Reader time change information where the user can configure the Reader to modify the time setting of the reader, and upon saving the time change in the Reader, such change is shown as presented in FIG. 79A with the date and time of the Reader time change, as well as what the time change was (e.g., "The time was set ahead 2 hours"). A corresponding icon is also provided under Settings shown in FIG. 79A corresponding to "Reader Date & Time".

FIG. 80 illustrates an exemplary frame of the generate reports menu for setting report parameters. As can be seen in the figure, the set report parameters frame 7140 includes an option to set a timeframe associated with the reports to be executed. The timeframe may be chosen as a length of time, i.e., 2 weeks as shown in the figure, or by choosing a date range. In certain embodiments, the length of time timeframe will apply to the length of time preceding the current date. The set report parameters frame 7140 also includes an option for setting the target glucose range to display on the executed reports, including the snapshot report, the daily patterns report, the mealtime patterns report, the weekly summary report, and the daily log report.

Figure 81A:
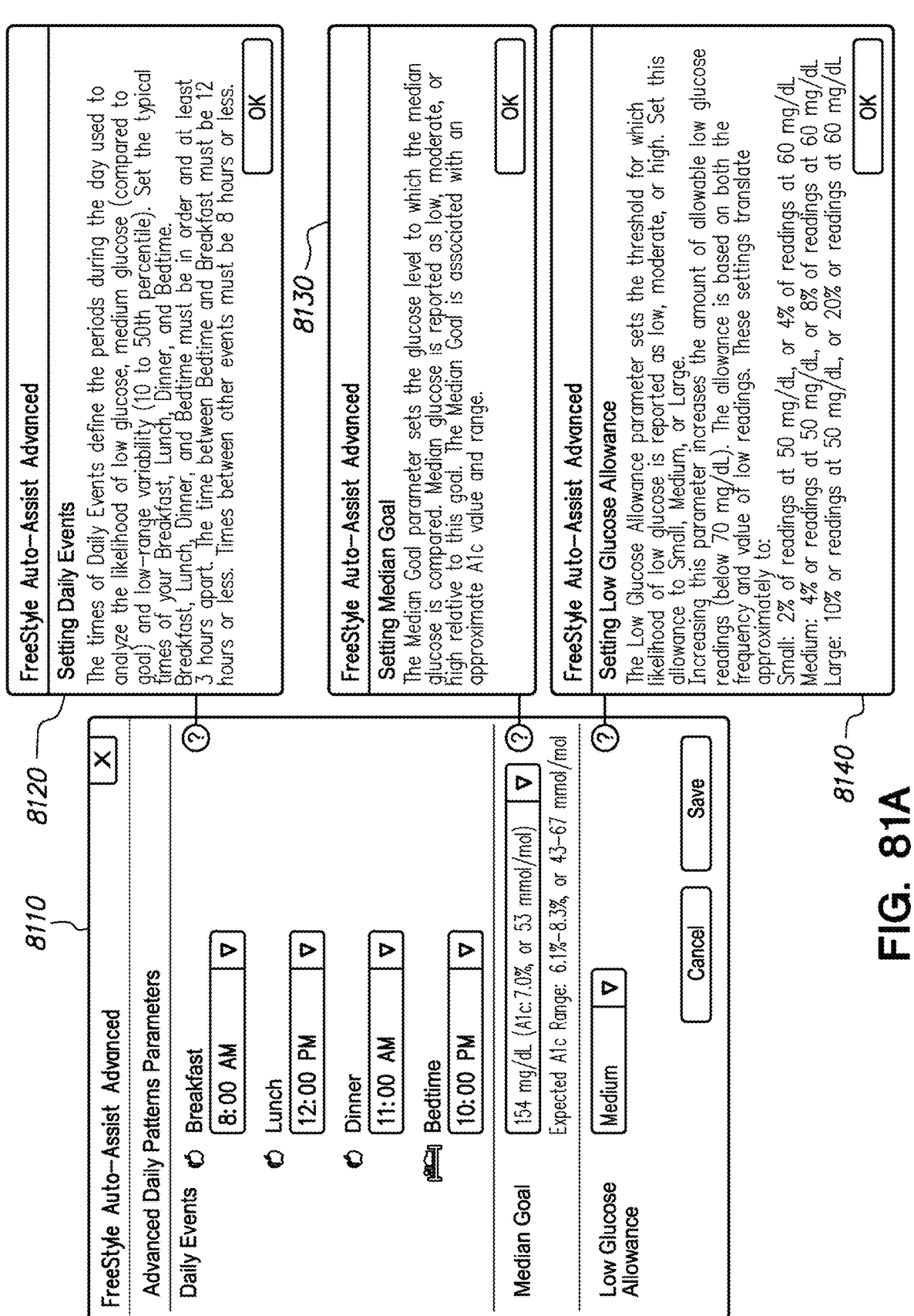

Also shown in FIG. 80 are settings associated with a specific report, i.e., the advanced daily patterns report 7150. In certain embodiments, the settings for the advanced daily patterns report cannot be changed from the main set report parameters frame, but instead requires selection of an 'edit' button to enter a screen for editing the advanced daily patterns report settings. When the 'edit' button is selected, the data management software may launch a sub-menu to edit the advanced daily patterns report settings, such as shown in FIG. 81A. As shown in the figure, the advanced daily patterns settings screen 8110 includes options to change settings for times associated with daily events or meals, such as breakfast time, lunch time, dinner time and bedtime. The screen 8110 also includes options to change the median goal glucose level and a low glucose allowance parameter.

Referring still to FIG. 81A, in certain embodiments, each section of the settings screen 8110 may include a help or details button, represented by a '?' indication as shown. The daily events settings help menu 8120 may include an explanation of the purpose of the daily events, the definition of the daily events for the purposes of calculation and suggestions, and the rules associated with the daily events. For example, the time between bedtime and breakfast must be 12 hours or less. The setting median goal help menu 8130 may include an explanation of what a median goal is, and what it is utilized for in the advanced daily patterns report. The low glucose allowance help menu 8140 includes an explanation of the available settings. For example, the menu 8140 includes an explanation to the user that increasing the low glucose allowance parameter increases the amount of allowable low glucose readings (below a preset parameter, such as 70 mg/dL). In certain embodiments, a small low glucose allowance parameter translates to approximately 2% of readings at 50 mg/dL, or 4% of readings at 60 mg/dL, a medium low glucose allowance parameter translates to approximately 4% of readings at 50 mg/dL, or 8% of readings at 6 mg/dL, and a large low glucose allowance parameter translates to approximately 10% of readings at 50 mg/dL, or 20% of readings at 60 mg/dL.

Figure 81B:
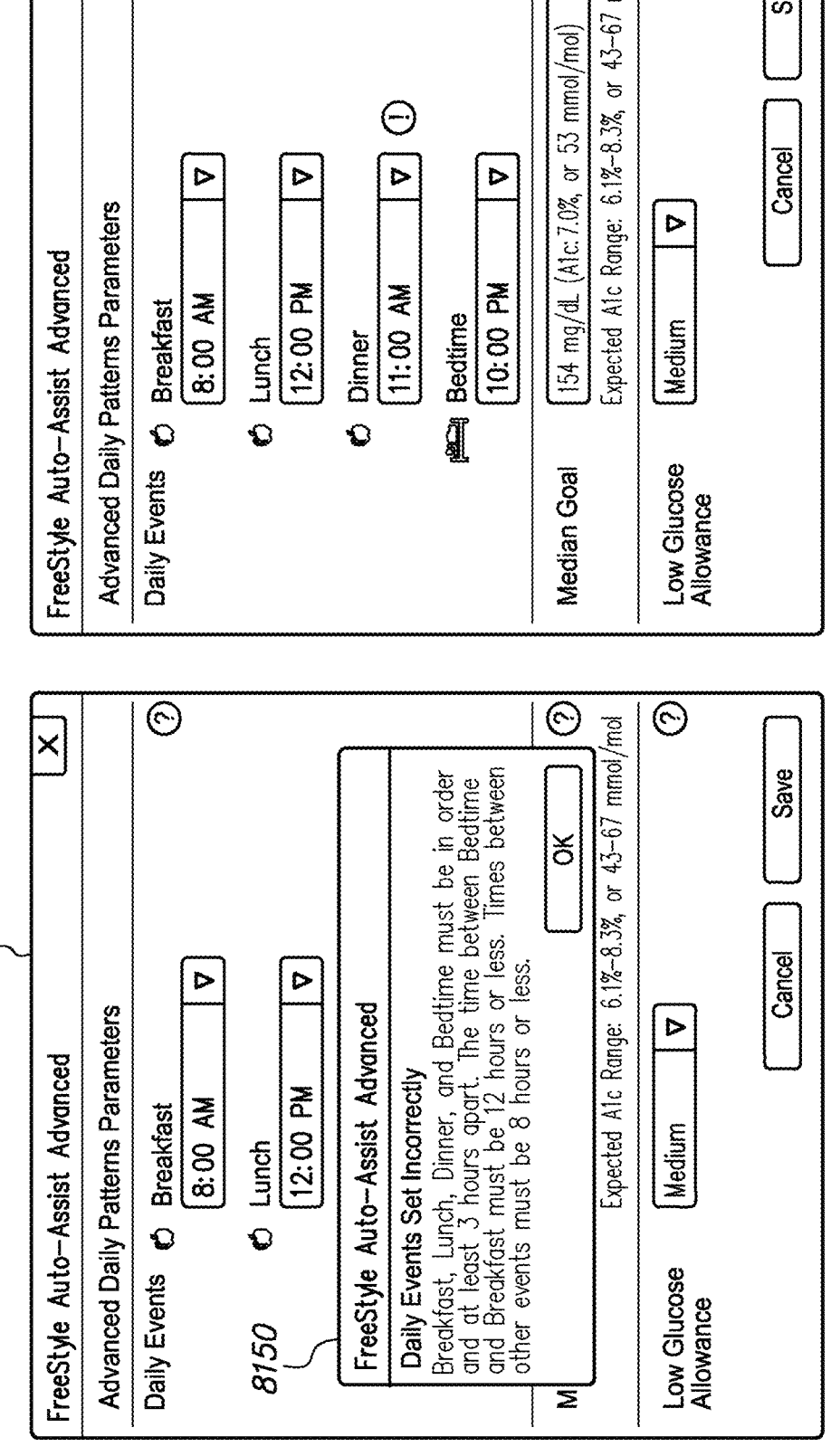

Still referring to FIG. 81A, the advanced daily patterns parameters menu also includes a 'save' and a 'cancel' button. When the 'save' button is selected, any changes made to the settings are kept, and when the 'cancel' button is selected, any changes made to the settings are discarded. In certain embodiments, when 'cancel' is chosen, a notification may pop-up on the screen requesting confirmation from the user to discard changes. In certain embodiments, when any settings or parameters are configured with invalid values, the data management software will not allow the user to save the changes made to the parameters and settings. In certain embodiments, when such situation occurs, the software will display a notification 8150 informing the user that the settings are invalid, as illustrated in FIG. 81B. The notification 8150 may include an explanation of which settings are invalid, and the corresponding requirements associated with the settings, and allow the user an opportunity to correct the settings. In some embodiments, an icon, such as a '!' symbol, are displayed next to the particular setting that is out of range or is invalid. Once all invalid settings are corrected, the configurations may be saved by the user clicking the 'save' button.

Reader Settings

Figure 82:
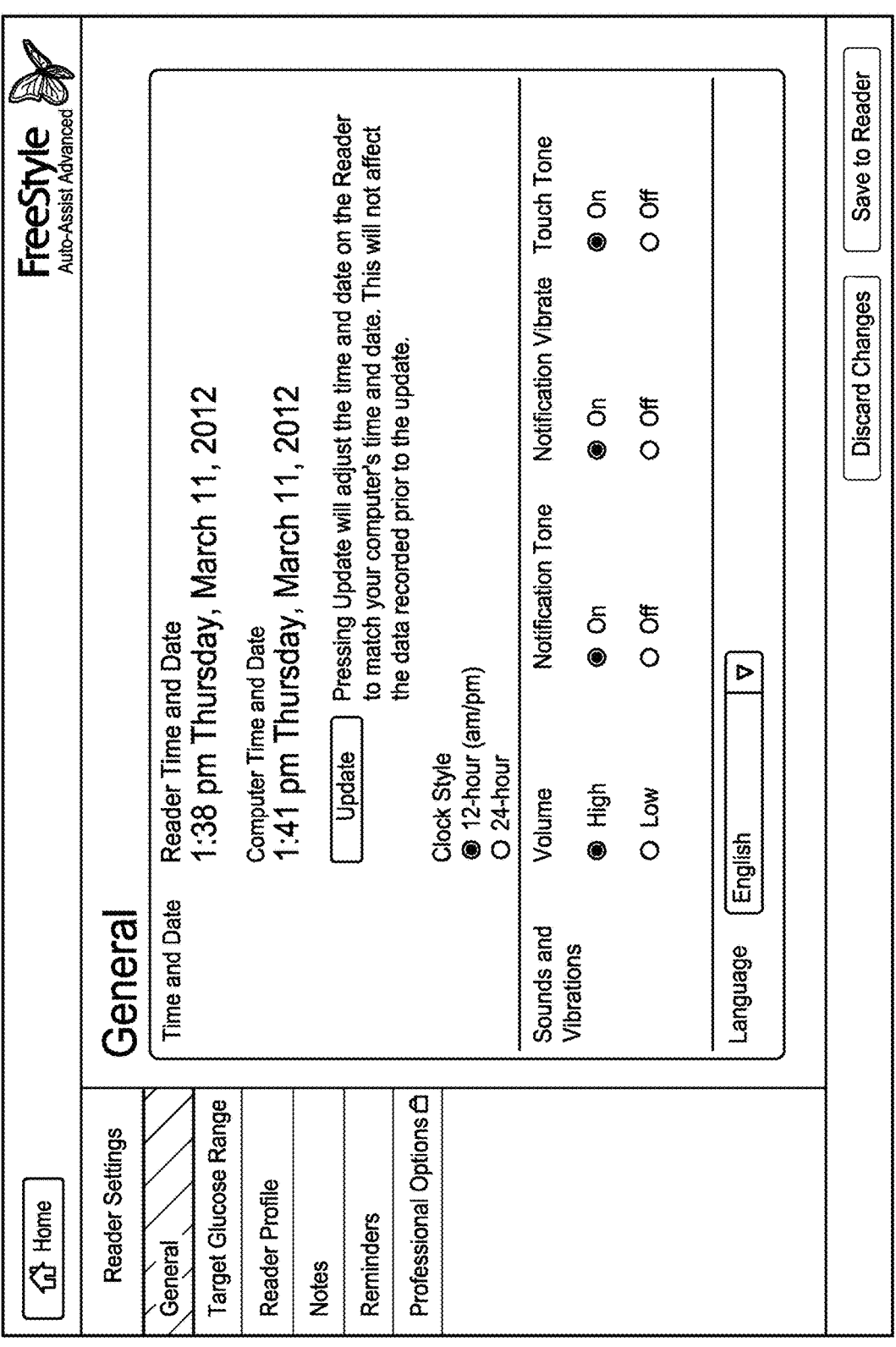

FIGS. 82-86 illustrate exemplary screens for adjusting settings of the Reader device in certain embodiments. FIG. 82 is an example of a general settings screen. General settings include settings including time and date, clock style, sound and vibration settings, and language settings. In certain embodiments the time and date may be automatically updated based on the current time and date settings of the computer to which the Reader is connected, or via the internet. As shown, an 'update' button is made available, whereby the Reader time and date is updated to match the computer time and date. In certain embodiments, updating the time and date does not affect data recorded on the Reader prior to the time and date change. Another available setting, in certain embodiments, includes a clock style setting. The Reader device may be configured to display the time in 12-hour (am/pm) format or in 24-hour format. Further, sound and vibration settings may also be adjustable. Such settings include volume level (high/low) and whether to include tones/vibrations for items such as notifications and touches.

Figure 83A:
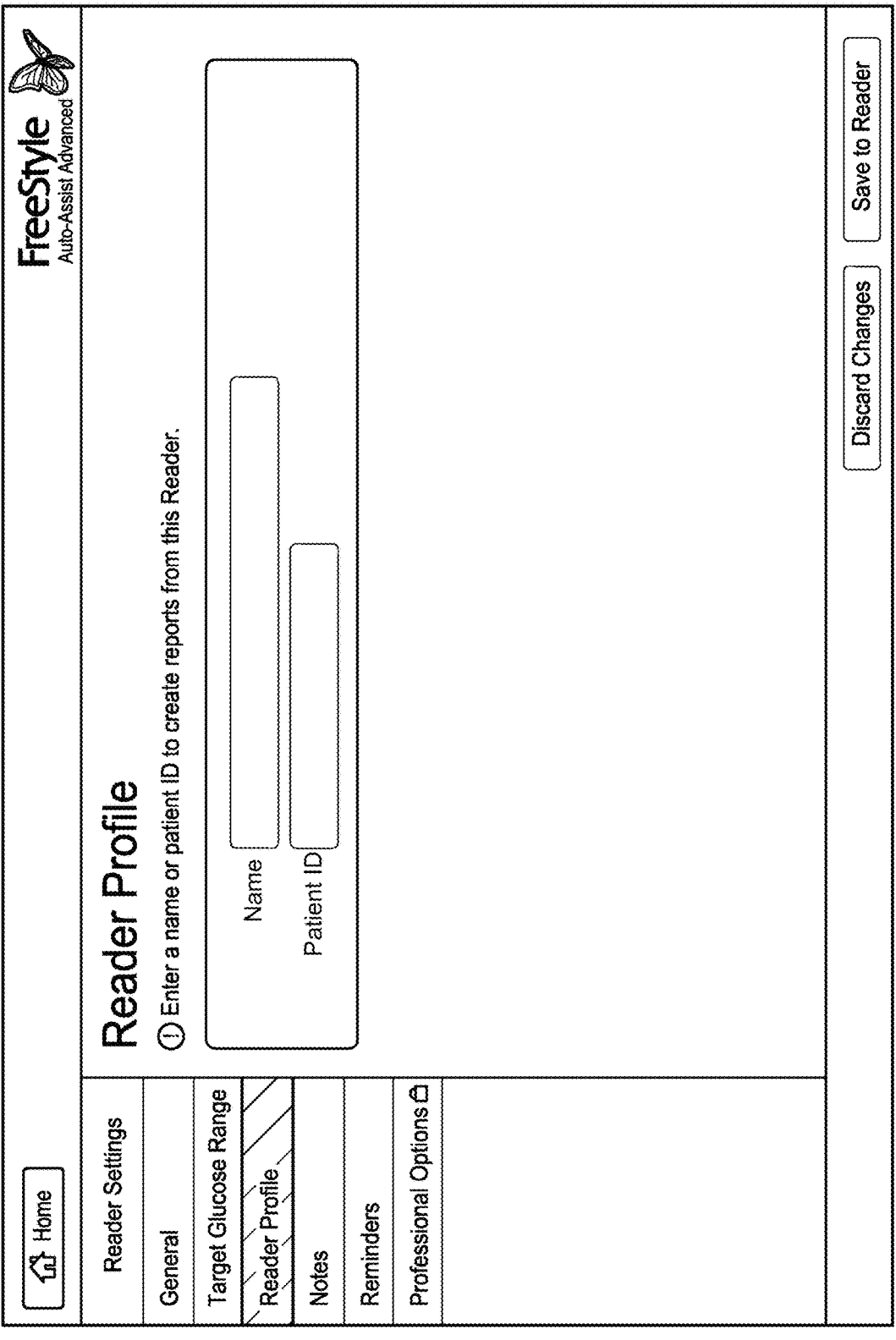
Figure 83B:
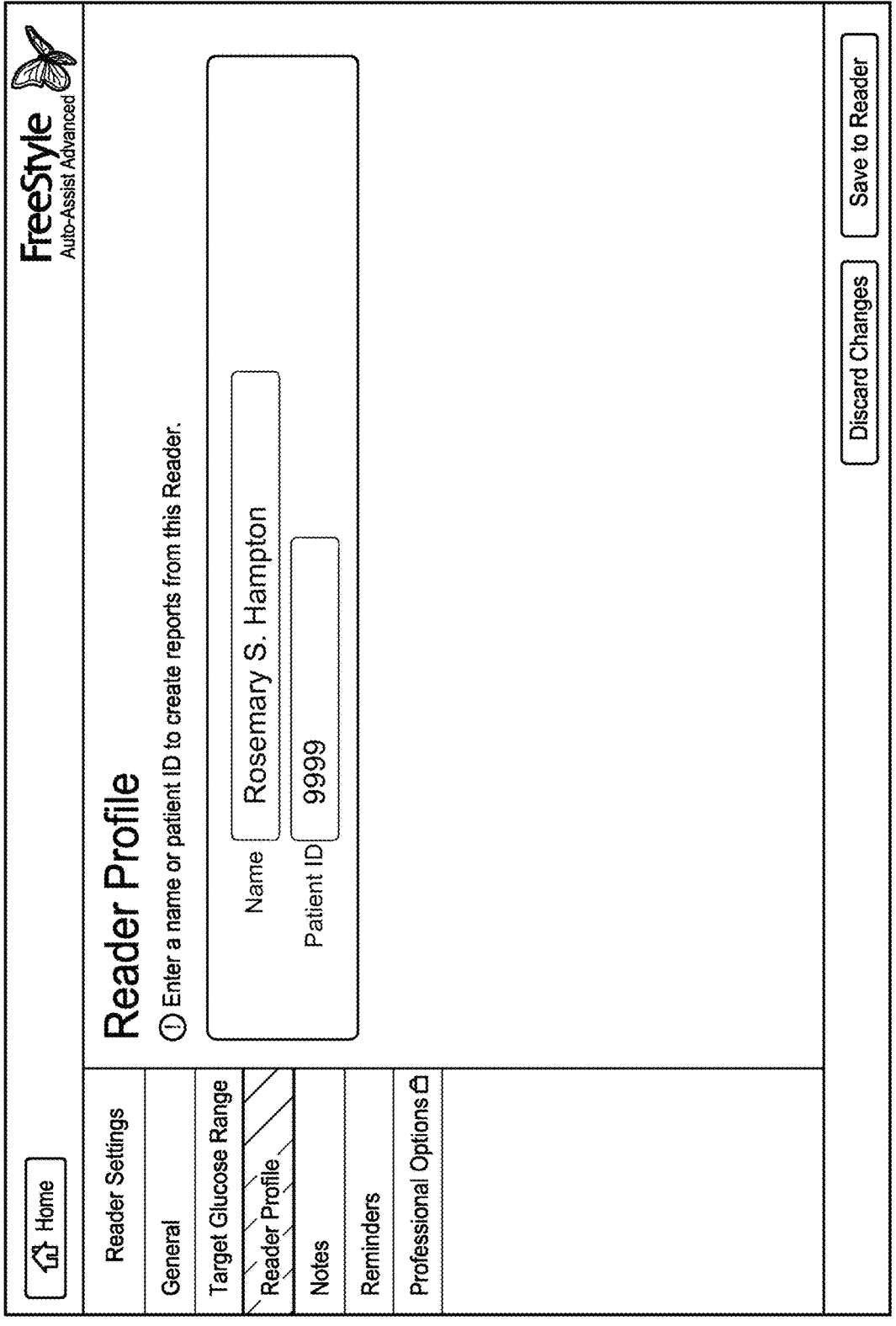
Figure 83C:
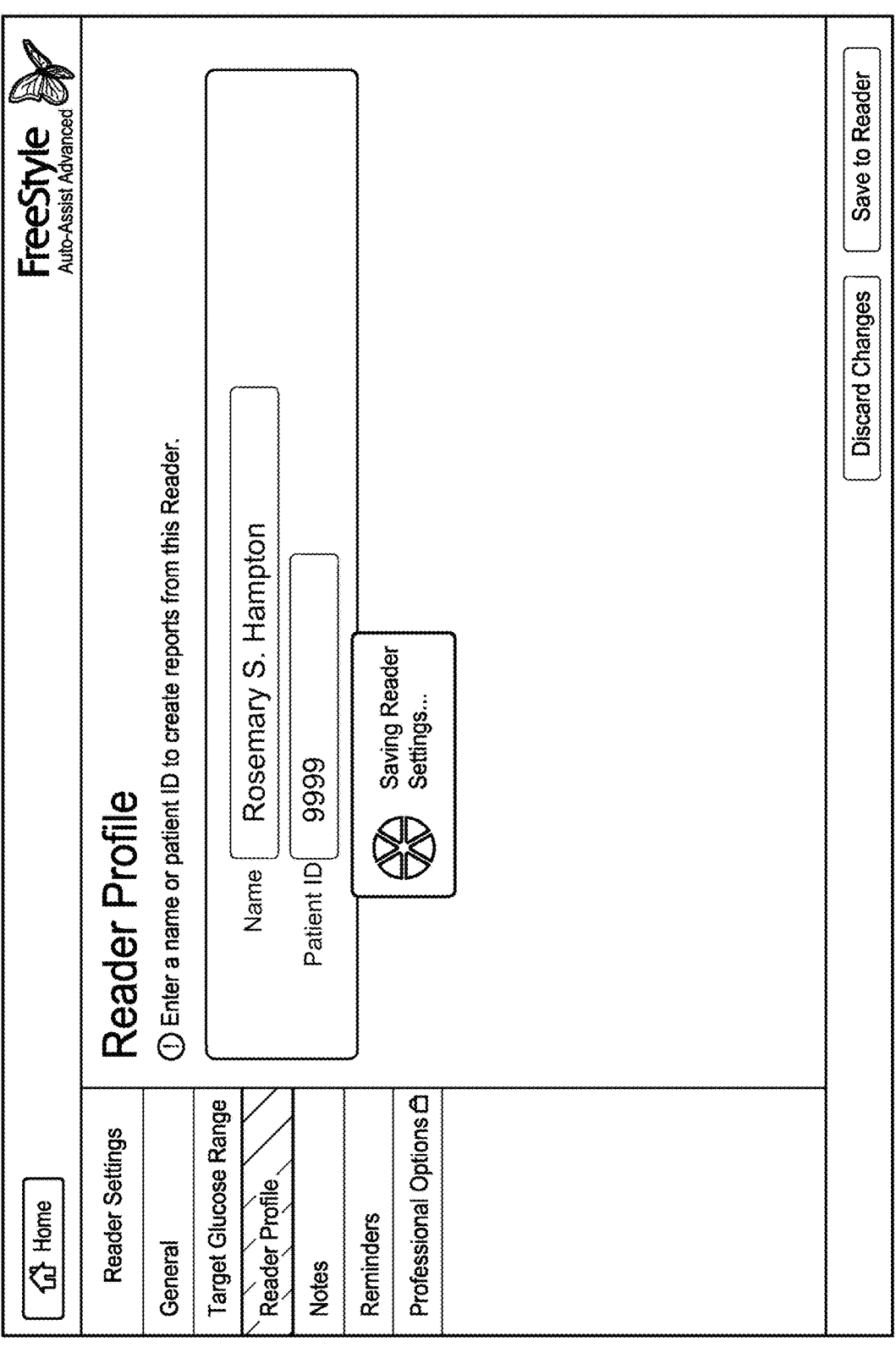
Figure 83D:
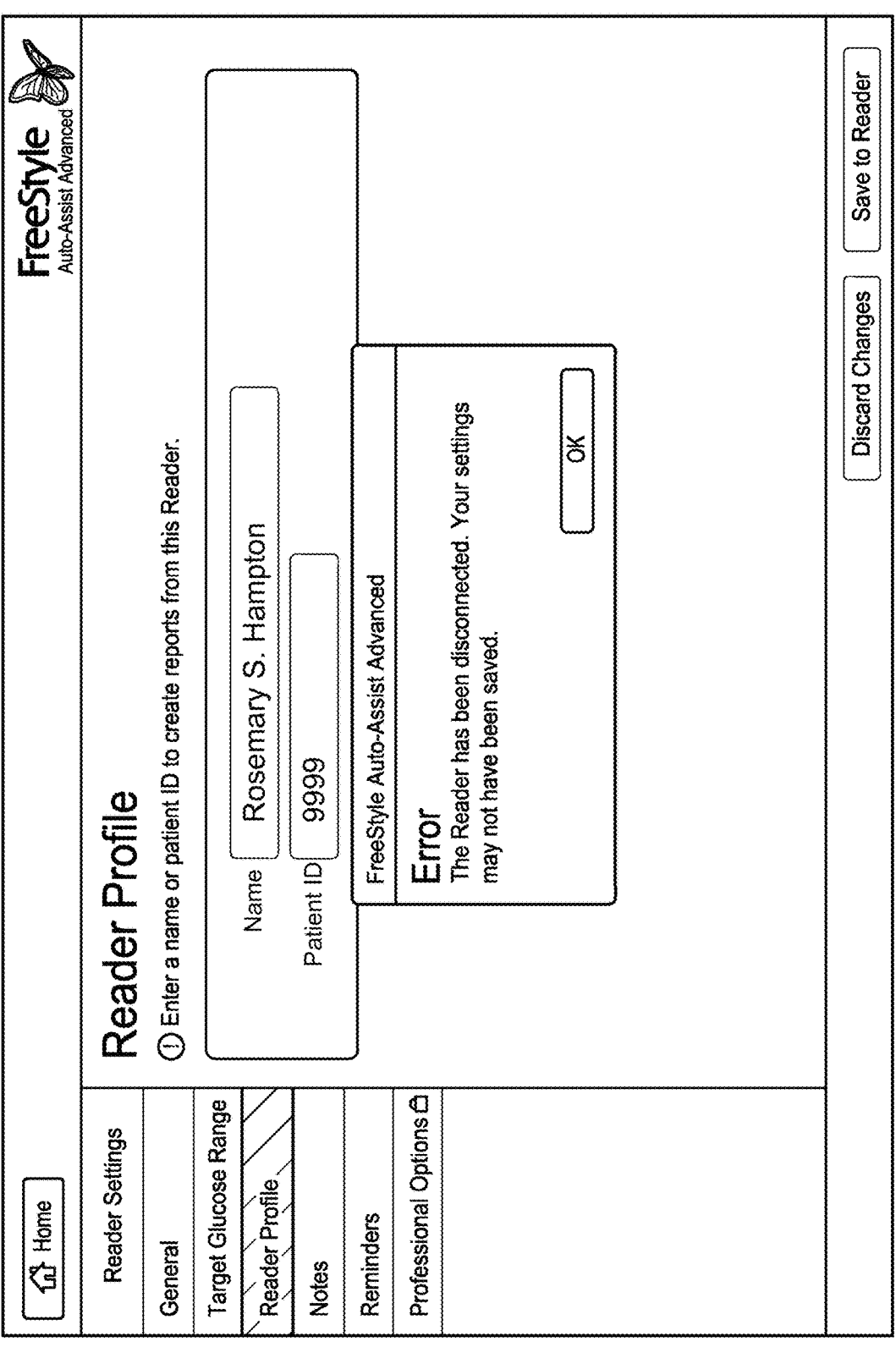
Figure 83E:
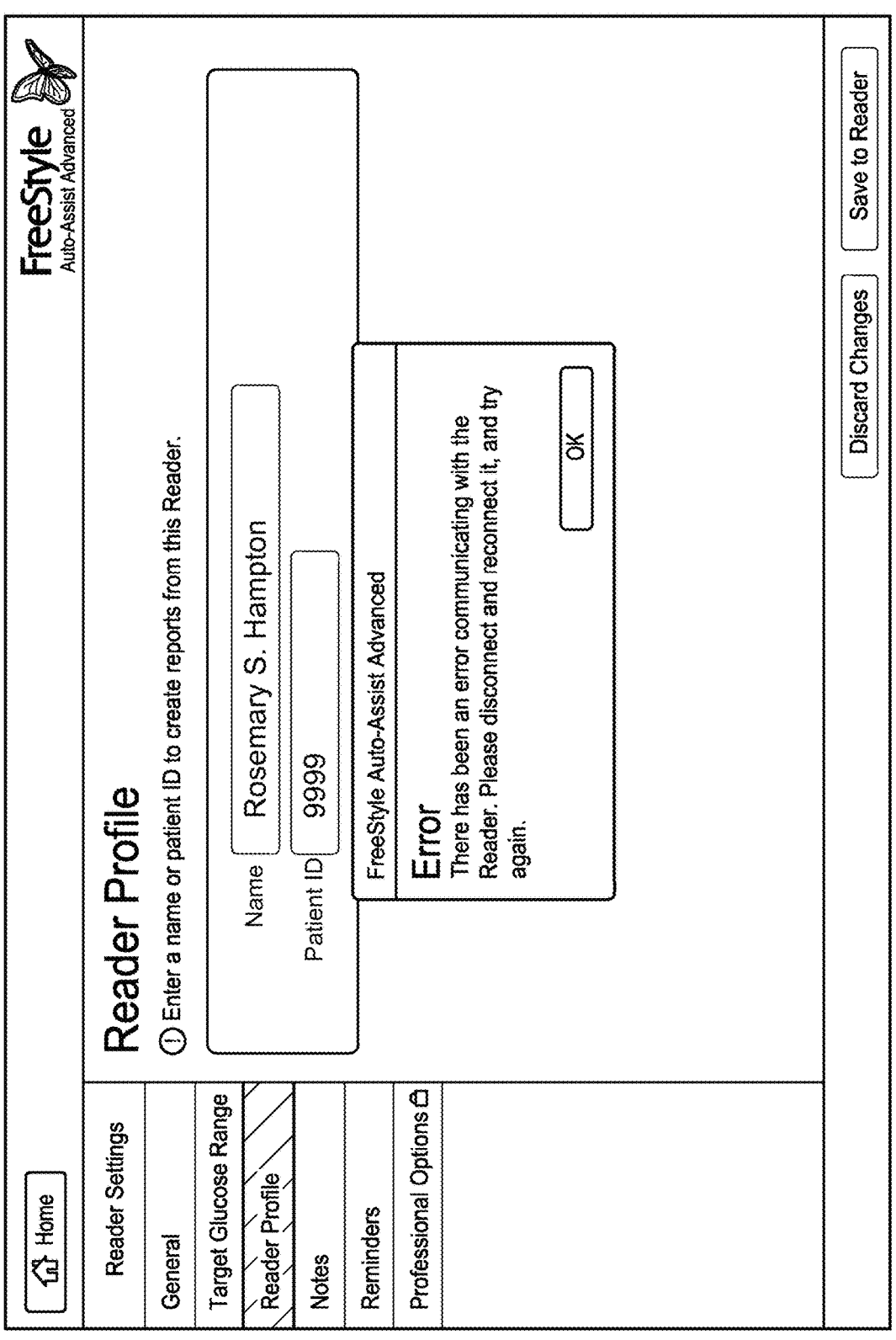

FIG. 83A is an exemplary reader profile settings screen, wherein a reader profile has not yet been stored on the Reader device. As previously described above, a reader profile may include information including a patient name and patient ID. The settings screen when a reader profile is not yet stored includes fillable fields for reader profile information including name and patient ID. Once completed, as illustrated in FIG. 83B, the settings screen includes available buttons to 'discard changes' or 'save to reader'. Selection of 'discard changes' will cancel the entered reader profile information, while 'save to reader' will save the changes to the Reader and thus next time the Reader is connected to the data management software, the reader profile information will be available. Once 'save to reader' is chosen, a 'saving reader settings' notification is displayed to inform the user that the settings are being saved, and to preclude the user from making any additional modifications while the save is in progress, as shown in FIG. 83C. In certain embodiments, the notification may be an animated notification. In certain embodiments, as illustrated in FIG. 83D, when the Reader is disconnected from the data management software prior to the saving of any settings modifications, the software may launch a pop-up notification to inform the user of the error. In certain embodiments, as illustrated in FIG. 83E, when there is an error between the Reader and the data management software prior to the saving of any settings modifications, the software may launch a pop-up notification to inform the user of the error. In certain embodiments, upon confirmation of the error notification, the data management software may revert back to the home screen. In other embodiments, reconnection of the Reader to the data management software may automatically confirm the error notification, and return back to the settings screen to allow the user to reattempt a 'save to reader' option.

Figure 84:
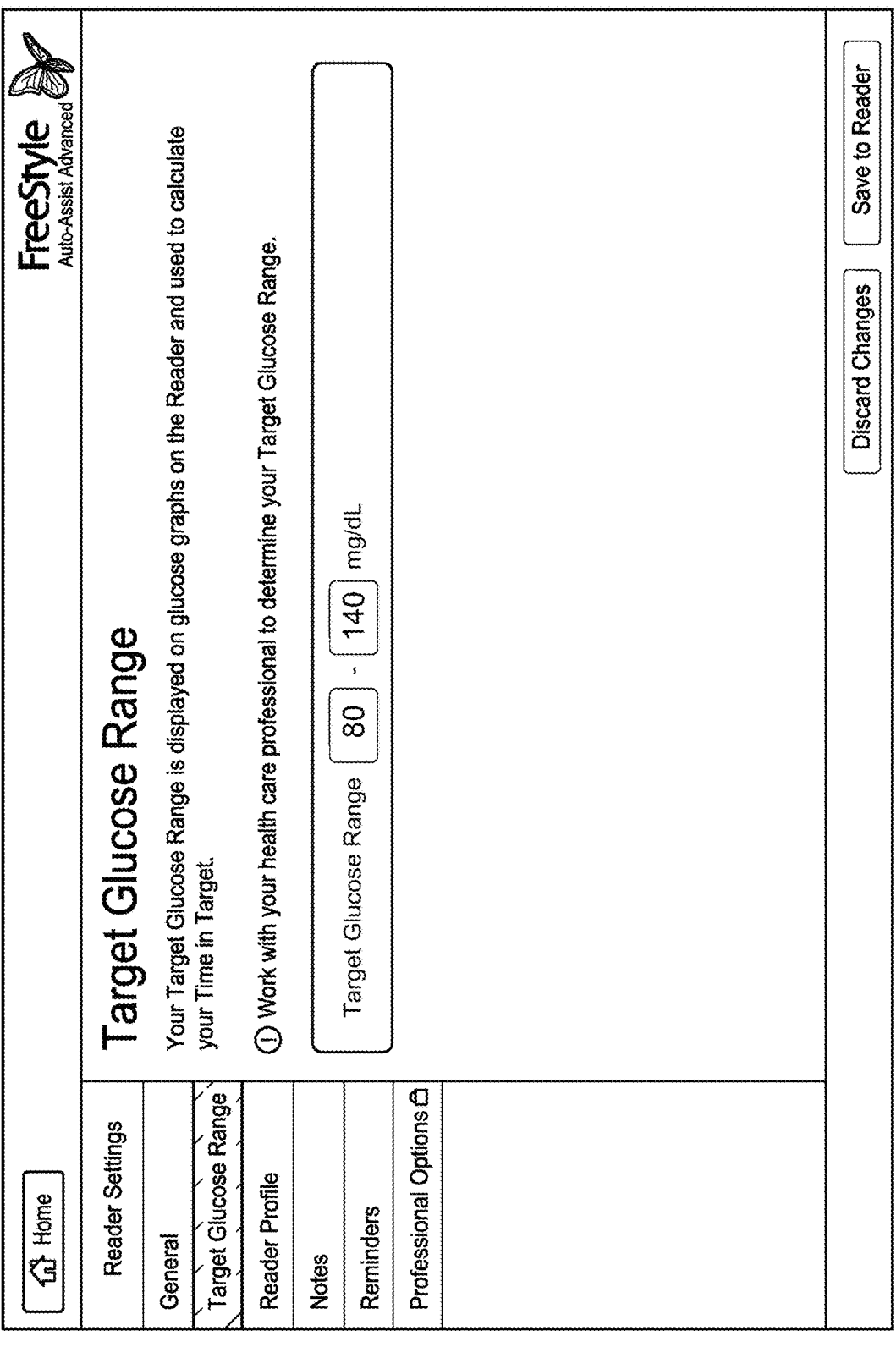

FIG. 84 illustrates a target glucose range settings screen. The target glucose settings screen allows the user to choose the target glucose range associated with glucose graphs and the Reader's calculator for managing glucose levels. The Reader will also utilize the target glucose range to determine percentage or amount of time within target. In certain embodiments, the target glucose settings screen will include a warning to the user to consult with a health care professional prior to determining and entering a target glucose range. In certain embodiments, when a modification is made to the target glucose range, the software enables the 'discard changes' and 'save to reader' options. As described above, upon selection of the 'save to reader' option, a 'saving reader settings' notification is displayed to inform the user that the settings are being saved, and to preclude the user from making any additional modifications while the save is in progress.

Figure 85B:
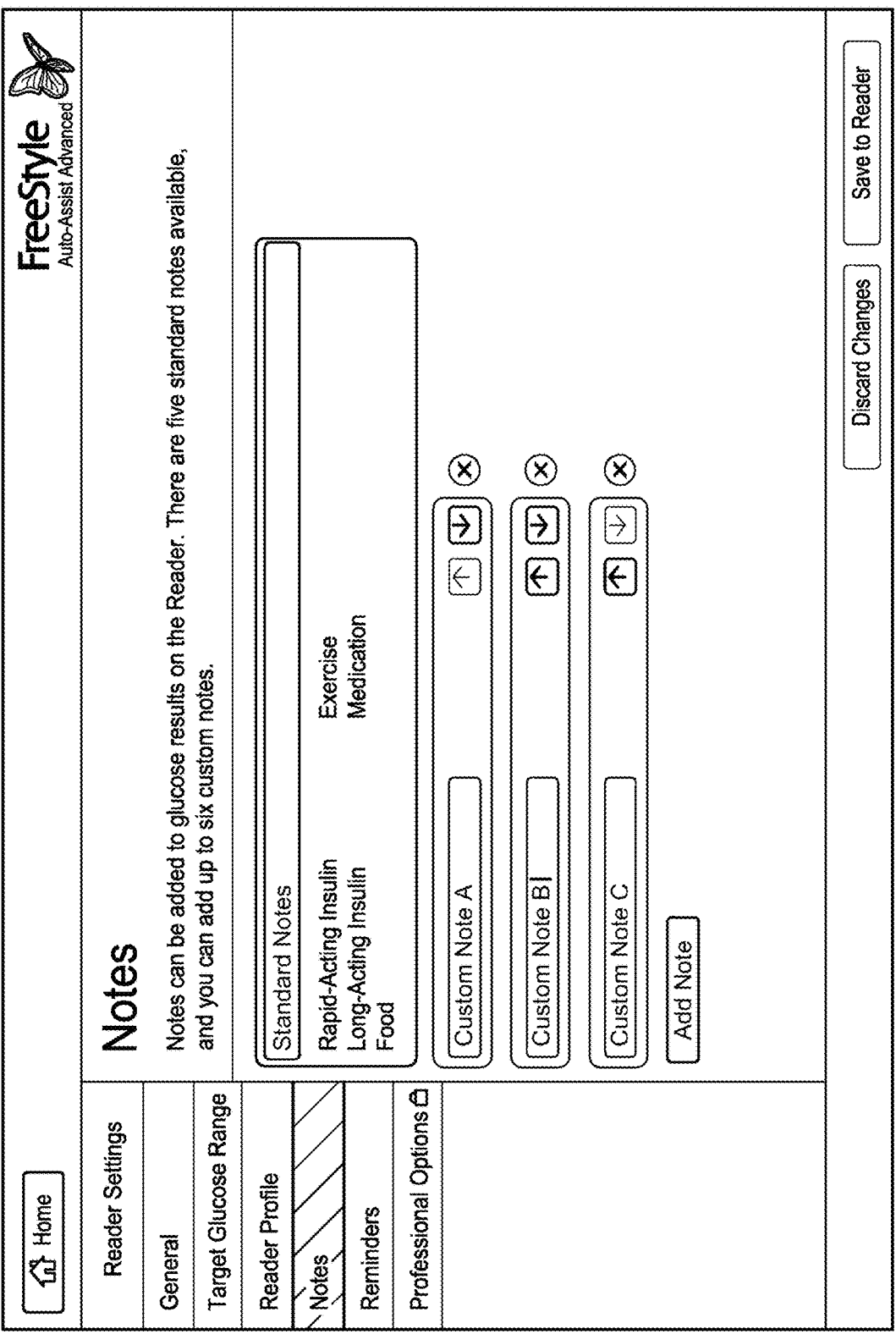

FIGS. 85A and 85B illustrate a notes screen, wherein custom notes can be configured by the user. FIG. 85A illustrates a screen when no custom notes have yet been configured. As can be seen in the figure, in certain embodiments, some standard notes may be pre-stored on the Reader device, including rapid-acting insulin, long-acting insulin, food, exercise, and medication notes. To add a custom note, an 'add note' button is made available to the user. Selecting the 'add note' button will make available a line item for a custom note, such as shown on the screen of FIG. 85B. FIG. 85B illustrates a notes screen with custom notes ready for configuration. In certain embodiments, any custom notes already saved on the Reader device will be shown in the software. In certain embodiments, all custom notes are always available for editing, including changing the name of the note and the priority of the note (position in the list from top to bottom). Additionally, an 'x' option is provided to delete a custom note. Upon modification to any custom note, the software enables the 'discard changes' and 'save to reader' options. As described above, upon selection of the 'save to reader' option, a 'saving reader settings' notification is displayed to inform the user that the settings are being saved, and to preclude the user from making any additional modifications while the save is in progress. Changes to the notes are not applied to the Reader until the 'save to reader' option is selected.

Figure 86:
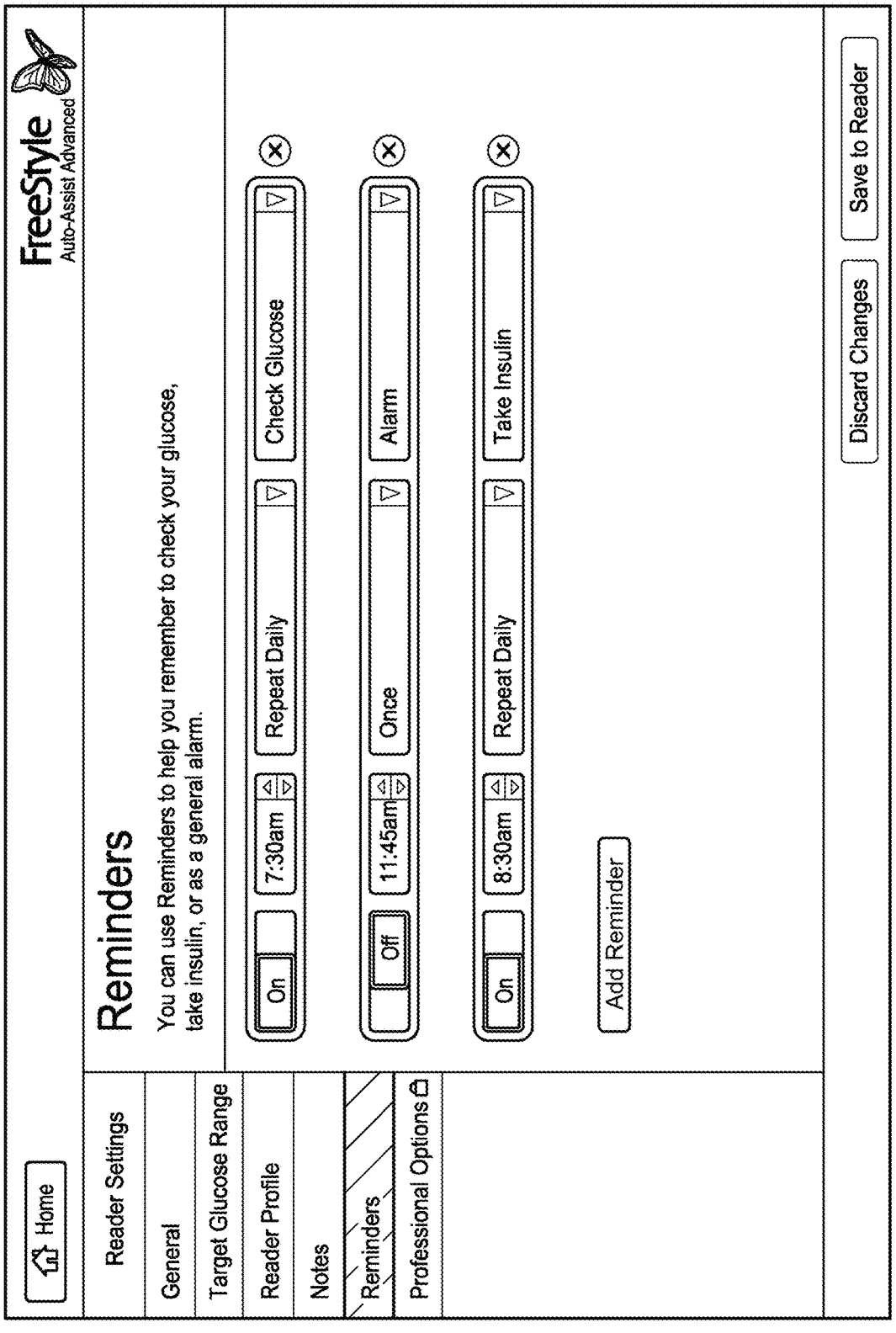

FIG. 86 illustrates a reminders screen. As can be seen in the figure, all configured reminders are displayed and available for editing by the user. Each reminder includes an option to turn on and off the reminder, the ability to change the time of execution of the reminder, an option related to the occurrence of the reminder (repeating daily, weekly, etc. or once only), and a selection of the type of alarm, such as a check glucose alarm, a take insulin alarm, or a general alarm. Additionally, an 'x' option is provided to delete a reminder. New reminders can be added by selecting the 'add reminder' button, whereby a new reminder line will appear and be ready for configuration. Upon modification to any reminder, the software enables the 'discard changes' and 'save to reader' options. As described above, upon selection of the 'save to reader' option, a 'saving reader settings' notification is displayed to inform the user that the settings are being saved, and to preclude the user from making any additional modifications while the save is in progress. Changes to the reminders are not applied to the Reader until the 'save to reader' option is selected.

Figure 87A:
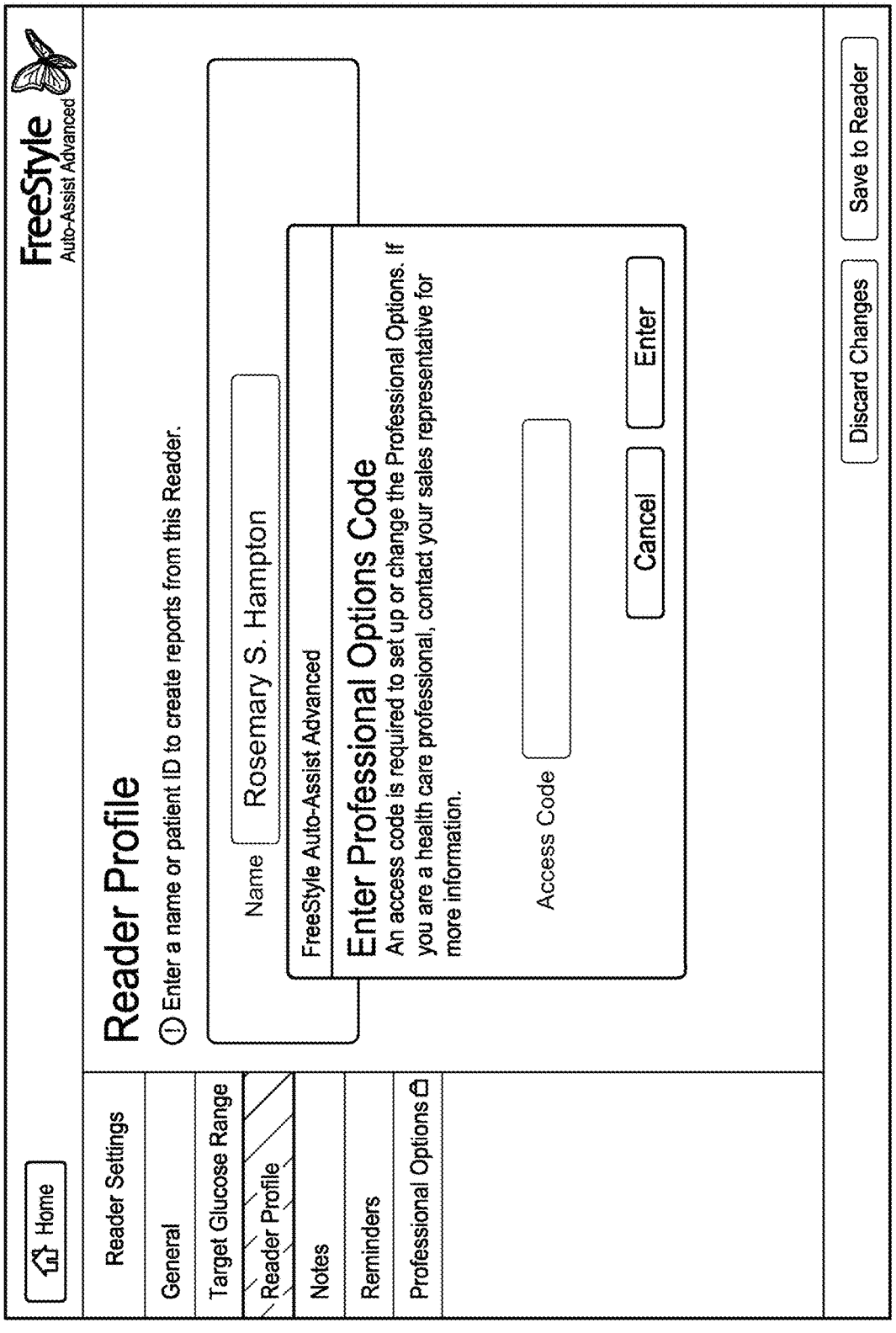

FIGS. 87A-87E illustrate screens associated with professional options of the Reader device. As described above, professional options are options made available only to a healthcare provider or other professional associated with the Reader device, and are not made readily available to the user. As shown in FIG. 87A, the professional options menu choice includes a 'locked' icon, in certain embodiments represented by an icon of a padlock. Upon selection of the professional options menu, a pop-up menu is initiated requesting an access code in order to gain access to the professional options menu. Upon entry of a valid access code, the software navigates to the masked mode options screen. In certain embodiments, upon entry of a valid access code, the professional options menu is made available without the need to reenter an access code. In such embodiments, the professional options menu choice is then displayed without the locked icon, or with an alternate unlocked icon.

Figure 87B:
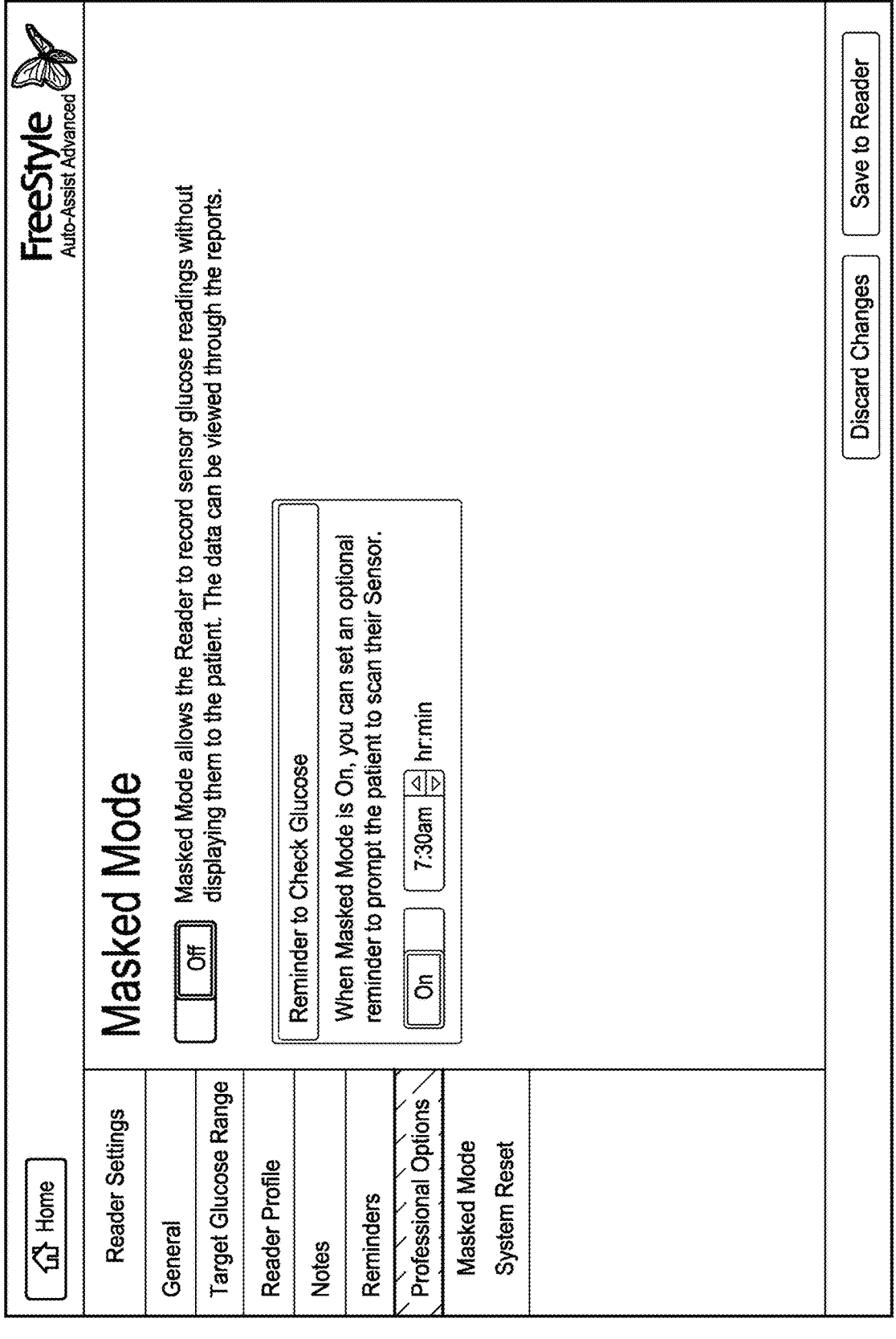
Figure 87C:
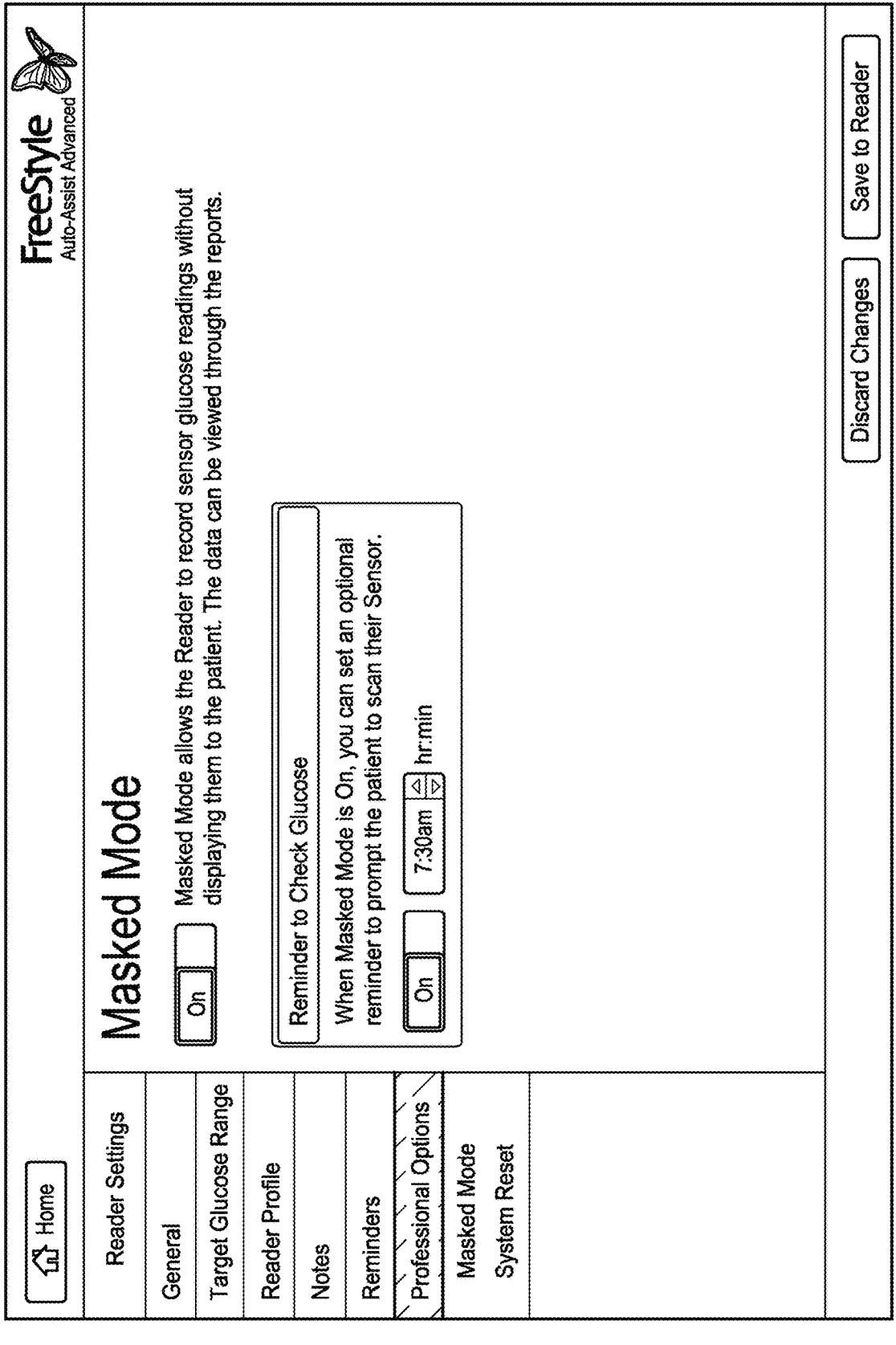

FIG. 87B illustrates a masked mode options screen, which is part of the professional options as described above. The masked mode settings screen, in certain embodiments, includes two components: enabling the masked mode feature and adjustment of the check glucose reminder. In certain embodiments, the check glucose reminder settings are unavailable while the masked mode setting is off. Once the masked mode is enabled, the reminder to check glucose settings are made available, which includes an option to turn on/off the reminder and set the time for the reminders, as shown in FIG. 87C.

Figure 87E:
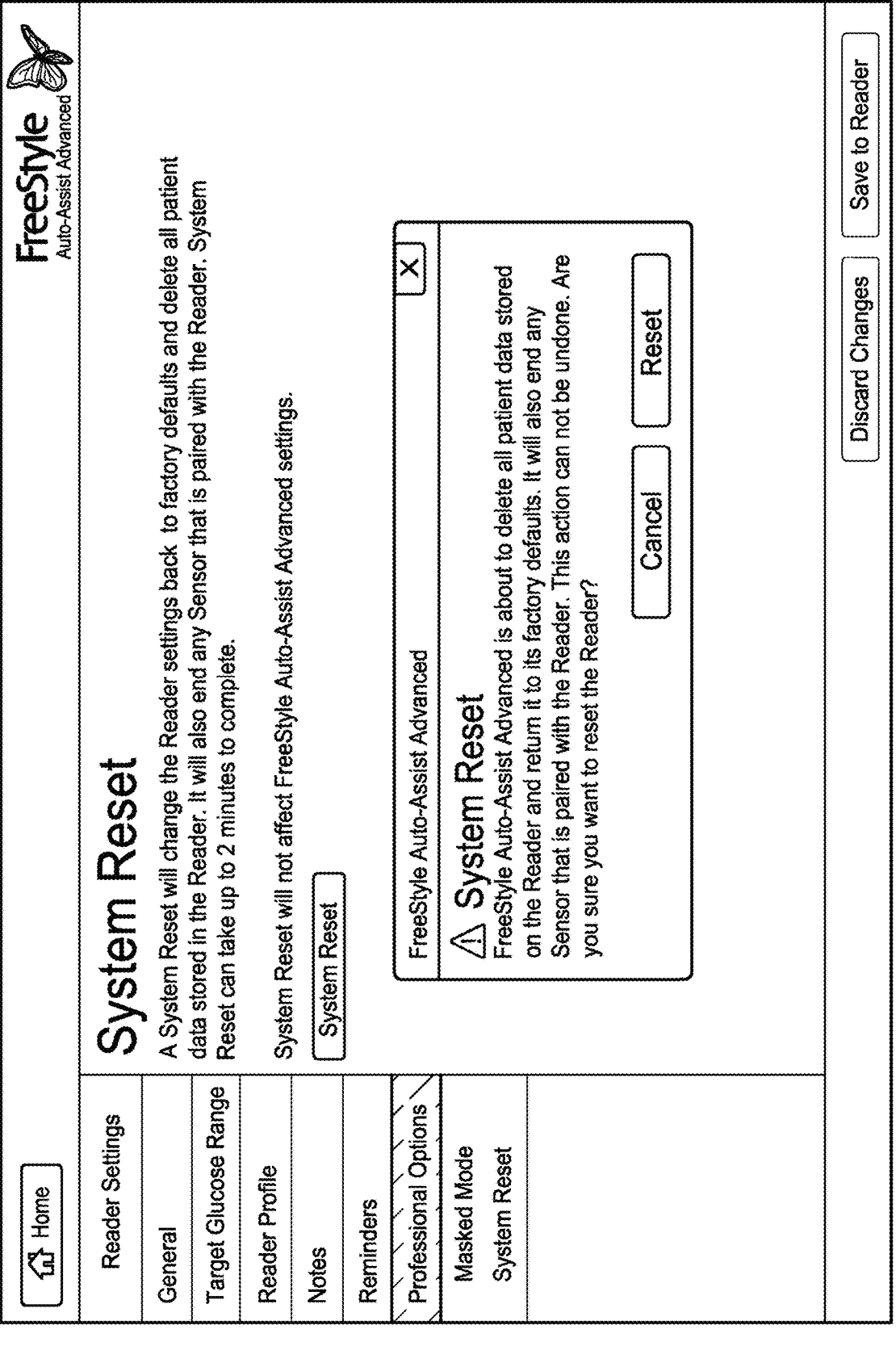

The professional options additionally include a system reset screen, as shown in FIG. 87D, whereby the Reader can be reset to factory defaults. Activation of the system reset will restore all Reader settings to factory defaults, delete all patient data stored in the Reader, and end any sensor paired with the Reader. In certain embodiments, a system reset may take up to 2 minutes or more to complete. Selection of the system reset button, in certain embodiments, will activate a confirmation notification as shown in FIG. 87E, which will require confirmation prior to proceeding with the reset. The notification may include a warning to the user that all patient data will be deleted, the settings will be reset to factory defaults, and the paired sensor, if applicable, will be ended. The notification also includes an option to cancel the system reset before it is initiated.

Figures 88, 89:
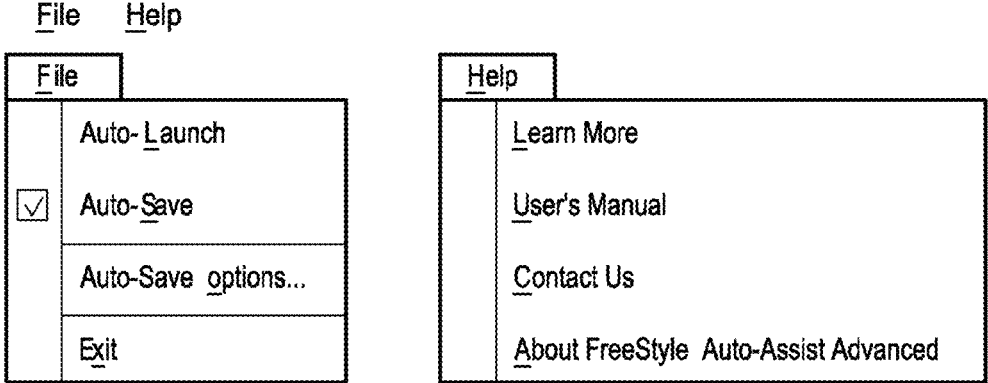

FIG. 88 illustrates options available in main systems menus of the data management software. Such menus include a 'File' menu and a 'Help' menu. The 'File' menu may include options such as auto-launch, auto-save, auto-save options, and exit. Selection of the auto-launch option will cause the data management software to launch automatically upon detection by the computer of a connected Reader device. Selection of the auto-save option will cause the software to automatically save a copy, such as a PDF copy, of any reports run in the data management software. Auto-save includes settings configurable by the user, including an option to enable auto-save, a file name format option, and a file save location option, as shown in FIG. 89.

EXAMPLE EMBODIMENTS

In some aspects of the present disclosure, methods of operating an analyte monitoring device are provided that include receiving an indication for powering on an analyte monitoring device; powering on the analyte monitoring device; providing power to an RF reader element within the analyte monitoring device; activating a scan state for scanning an analyte sensor; receiving an indication of a predetermined event; and powering off the RF reader and maintaining power to the analyte monitoring device.

In one embodiment, the scan state comprises displaying a prompt to scan the analyte sensor on a display of the analyte monitoring device.

In one embodiment, the predetermined event is a lapse of a predetermined period of time without performing a scan. In some instances, the predetermined event is a deactivation of the scan state. In some instances, the predetermined event is a user-initiated change from a scan prompt screen to a home screen. In some instances, the predetermined event is an occurrence of a scan error or failed scan.

In one embodiment, the methods comprise: receiving an indication to perform a sensor scan; repowering the RF reader; and reactivating the scan state for scanning the analyte sensor.

In one embodiment, the methods comprise: detecting the analyte sensor; and scanning the analyte sensor to perform an analyte reading.

In one embodiment, the analyte is glucose or a ketone body.

In some aspects of the present disclosure, analyte monitoring devices are provided. The analyte monitoring devices include a processor; and memory operably coupled to the processor, wherein the memory includes instructions stored therein for operating an analyte monitoring device, the instructions comprising instructions for performing the previously described methods.

In some aspects of the present disclosure, methods of operating an analyte monitoring device are provided that include performing a first scan of an analyte sensor; displaying a reading resulting from the first scan; preventing performance of a second scan for a predetermined period of time; and enabling performance of a second scan after lapse of the predetermined period of time.

In one embodiment, the methods include powering the analyte monitoring device off after the reading is displayed; and powering on the analyte monitoring device before the lapse of the predetermined period of time.

In one embodiment, the methods include receiving an indication of an attempt of a second scan before the lapse of the predetermined period of time; and indicating that the second scan cannot be performed. In some instances, the methods include indicating an estimated time remaining before performance of a second scan is enabled.

In one embodiment, the methods include exiting a screen displaying the reading; and indicating that any results displayed before the lapse of the predetermined period of time is for the first scan.

In one embodiment, the methods include performing the second scan of the analyte sensor after the lapse of the predetermined period of time.

In one embodiment, the predetermined period of time is between 1 and 5 minutes.

In one embodiment, the analyte is glucose or a ketone body.

In some aspects of the present disclosure, analyte monitoring devices are provided. The analyte monitoring devices include a processor; and memory operably coupled to the processor, wherein the memory includes instructions stored therein for operating an analyte monitoring device, the instructions comprising instructions for performing the previously described methods.

In some aspects of the present disclosure, methods of operating an analyte monitoring device are provided that include performing a first scan of an analyte sensor; displaying a screen for calculating a suggested insulin dose based on a result of the first scan; exiting the screen for calculating a suggested dose before logging the suggested dose calculation; enabling logging of the suggested dose calculation for a predetermined period of time; and preventing logging of the suggested dose calculation for the first scan after a lapse of the predetermined period of time.

In one embodiment, the methods include powering the device off and then back on after displaying the screen for calculating the suggest dose and before the lapse of the predetermined period of time; wherein the exiting of the screen results from powering the analyte monitoring device off. In some instances, the screen for calculating the suggested dose is displayed when the device is powered back on, and wherein the screen for calculating the suggested dose enables the user to log the suggested dose calculation.

In one embodiment, the methods include receiving an indication to log the suggested dose calculation; and associating the suggested dose calculation with the first scan and with a time the first scan was performed; wherein a countdown for an estimated amount of insulin remaining in-body starts at a time of the logging of the suggested dose calculation.

In one embodiment, the methods include powering the device off after displaying the screen for calculating the suggest dose and before lapse of the predetermined period of time, wherein the exiting of the screen results from powering the analyte monitoring device off; and powering the device back on after the lapse of the predetermined period of time.

In one embodiment, the methods include displaying a prompt to scan the analyte sensor for a second scan when the device is powered back on.

In one embodiment, the analyte is glucose or a ketone body.

In some aspects of the present disclosure, analyte monitoring devices are provided. The analyte monitoring devices include a processor; and memory operably coupled to the processor, wherein the memory includes instructions stored therein for operating an analyte monitoring device, the instructions comprising instructions for performing the previously described methods.

In some aspects of the present disclosure, methods are provided that include performing consecutive scans of an analyte sensor; displaying, on a display of the analyte monitoring device, a resulting reading for each of the consecutive scans; displaying a graph on the display of the analyte monitoring device, the graph displaying resulting readings for a first predetermined period of time and tracking subsequent resulting readings during a second predetermined period of time following the first predetermined period of time; and after the subsequent resulting readings are tracked for the entire second predetermined period of time, shifting the subsequent resulting readings into the first predetermined period of time and continuing to track subsequent resulting readings during the second period of time; and repeatedly shifting the subsequent resulting readings after tracking occurs for the entire second period of time.

In one embodiment, the graph is displayed on the display after resulting readings are obtained for the first predetermined period of time.

In one embodiment, before resulting readings are obtained for the first predetermined period of time, the graph is displayed without any resulting readings; and the resulting readings for the first predetermined period of time are displayed on the graph after the resulting readings are obtained for the first predetermined period of time. In some instances, the first predetermined period of time is a multiple of the second predetermined period of time. In some instances, the first predetermined period of time is 8 hours and the second predetermined period of time is 1 hour.

In one embodiment, the analyte is glucose or a ketone body.

In some aspects of the present disclosure, analyte monitoring devices are provided. The analyte monitoring devices include a processor; and memory operably coupled to the processor, wherein the memory includes instructions stored therein, the instructions comprising instructions for performing the previously described methods.

In some aspects of the present disclosure, methods of displaying analyte sensor readings on an analyte monitoring device are provided that include obtaining sensor readings from an analyte sensor; and displaying on a display on the analyte monitoring device, a graph of sensor readings obtained over a prior 24-hour period.

In one embodiment, the methods include displaying a trigger element for shifting the graph forward or backward by 24 hours; receiving an indication that the trigger element was initiated by a user; and shifting the graph forward or backward by 24 hours.

In some aspects of the present disclosure, analyte monitoring devices are provided. The analyte monitoring devices include a processor; and memory operably coupled to the processor, wherein the memory includes instructions stored therein for displaying analyte sensor readings on an analyte monitoring device, the instructions comprising instructions for performing the previously described methods.

In some aspects of the present disclosure, methods of displaying analyte sensor readings on an analyte monitoring device are provided that include obtaining sensor readings from an analyte sensor; and displaying on a display on the analyte monitoring device, a summary of average sensor readings for a prior predetermined period of time, wherein the average sensor readings include an average sensor reading for a plurality of divisions within a day.

In one embodiment, the prior predetermined period of time is a 7 day period, and the average sensor readings include an average sensor reading for four divisions within a day.

In one embodiment, the methods include displaying a total average of each average sensor reading for the plurality of divisions within a day.

In one embodiment, the methods include displaying a trigger element for shifting the graph forward or backward by the predetermined period of time; receiving an indication that the trigger element was triggered by a user; and shifting the graph forward or backward by the predetermined period of time.

In some aspects of the present disclosure, analyte monitoring devices are provided. The analyte monitoring devices include a processor; and memory operably coupled to the processor, wherein the memory includes instructions stored therein for displaying analyte sensor readings on an analyte monitoring device, the instructions comprising instructions for performing the previously described methods.

In some aspects of the present disclosure, analyte monitoring devices are provided. The analyte monitoring devices include a processor; and memory operably coupled to the processor, wherein the memory includes instructions stored therein for displaying analyte sensor readings on an analyte monitoring device, the instructions including instructions for instructions for obtaining sensor readings from an analyte sensor; and instructions for displaying on a display on the analyte monitoring device, a summary of average sensor readings for a prior predetermined period of time, wherein the average sensor readings include an average sensor reading for a plurality of divisions within a day.

In one embodiment, the prior predetermined period of time is a 7 day period, and the average sensor readings include an average sensor reading for four divisions within a day.

In one embodiment, the instructions include instructions for displaying a total average of each average sensor reading for the plurality of divisions within a day.

In one embodiment, the instructions include instructions for displaying a trigger element for shifting the graph forward or backward by the predetermined period of time; instructions for receiving an indication that the trigger element was triggered by a user; and instructions for shifting the graph forward or backward by the predetermined period of time.

In some aspects of the present disclosure, methods of displaying analyte sensor readings on an analyte monitoring device are provided that include obtaining sensor readings from an analyte sensor; and displaying on a display on the analyte monitoring device, a summary of average events associated with the sensor readings obtained for a prior predetermined period of time, wherein the average events include an average event for a plurality of divisions within a day; wherein the summary is displayed upon user-selection.

In one embodiment, the prior predetermined period of time is a 7 day period, and the average event include an average event for four divisions within a day.

In one embodiment, the methods include displaying a total average of each average event for the plurality of divisions within a day.

In one embodiment, the methods include displaying a trigger element for shifting the summary forward or backward by the predetermined period of time; receiving an indication that the trigger element was triggered by a user; and shifting the summary forward or backward by the predetermined period of time.

In one embodiment, the event is a low glucose reading.

In some aspects of the present disclosure, analyte monitoring devices are provided. The analyte monitoring devices include a processor; and memory operably coupled to the processor, wherein the memory includes instructions stored therein for displaying analyte sensor readings on an analyte monitoring device, the instructions comprising instructions for performing the previously described methods.

In some aspects of the present disclosure, analyte monitoring devices are provided. The analyte monitoring devices include a processor; and memory operably coupled to the processor, wherein the memory includes instructions stored therein for displaying analyte sensor readings on an analyte monitoring device, the instructions including instructions for obtaining sensor readings from an analyte sensor; and instructions for displaying on a display on the analyte monitoring device, a summary of average events associated with the sensor readings obtained for a prior predetermined period of time, wherein the average events include an average event for a plurality of divisions within a day; wherein the summary is displayed upon user-selection.

In one embodiment, the prior predetermined period of time is a 7 day period, and the average event include an average event for four divisions within a day.

In one embodiment, the analyte monitoring devices include instructions for displaying a total average of each average event for the plurality of divisions within a day.

In one embodiment, the analyte monitoring devices include instructions for displaying a trigger element for shifting the summary forward or backward by the predetermined period of time; instructions for receiving an indication that the trigger element was triggered by a user; and instructions for shifting the summary forward or backward by the predetermined period of time.

In one embodiment, the event is a low glucose reading.

In some aspects of the present disclosure, methods of displaying analyte sensor readings on an analyte monitoring device are provided that include obtaining sensor readings from an analyte sensor; and displaying on a display on the analyte monitoring device, a summary of sensor readings obtained for a prior predetermined period of time, wherein the summary of sensor readings include one or more numbers or percentages of sensor readings with respect to a target range; wherein the summary is displayed upon user-selection.

In one embodiment, a number or percentage of sensor readings above, below, and within a target range are included in the summary.

In some aspects of the present disclosure, analyte monitoring devices are provided. The analyte monitoring devices include a processor; and memory operably coupled to the processor, wherein the memory includes instructions stored therein for operating an analyte monitoring device, the instructions comprising instructions for performing the previously described methods.

In some aspects of the present disclosure, methods are provided that include obtaining sensor readings from an analyte sensor; and displaying on a display on the analyte monitoring device, a summary of data associated with use of the sensor for a prior predetermined period of time, wherein the use of the sensor includes an average number of scans per day; wherein the summary is displayed upon user-selection.

In one embodiment, the use of the sensor includes a number of days having sensor data within the prior predetermined period of time.

In some aspects of the present disclosure, analyte monitoring devices are provided. The analyte monitoring devices include a processor; and memory operably coupled to the processor, wherein the memory includes instructions stored therein for displaying analyte sensor readings on an analyte monitoring device, the instructions comprising instructions for obtaining sensor readings from an analyte sensor; and instructions for displaying on a display on the analyte monitoring device, a summary of data associated with use of the sensor for a prior predetermined period of time, wherein the use of the sensor includes an average number of scans per day; wherein the summary is displayed upon user-selection.

In one embodiment, the use of the sensor includes a number of days having sensor data within the prior predetermined period of time.

In some aspects of the present disclosure, methods are provided that include obtaining sensor readings from an analyte sensor; and displaying on a display on the analyte monitoring device, a graph of daily patterns for a prior predetermined period of time, wherein the graph of daily patterns includes an average sensor reading for a plurality of divisions within a day; wherein the graph is displayed upon user-selection.

In one embodiment, the prior predetermined period of time is a 7 day period, and the graph of daily patterns includes an average sensor reading for four divisions within a day.

In one embodiment, the chart of daily patterns indicates a range of average sensor readings for the plurality of divisions within a day.

In one embodiment, the methods include displaying a trigger element for shifting the graph forward or backward by the predetermined period of time; instructions for receiving an indication that the trigger element was triggered by a user; and shifting the graph forward or backward by the predetermined period of time.

In one embodiment, the analyte is glucose or a ketone body.

In some aspects of the present disclosure, analyte monitoring devices are provided. The analyte monitoring devices include a processor; and memory operably coupled to the processor, wherein the memory includes instructions stored therein for displaying analyte sensor readings on an analyte monitoring device, the instructions including instructions for obtaining sensor readings from an analyte sensor; and instructions for displaying on a display on the analyte monitoring device, a graph of daily patterns for a prior predetermined period of time, wherein the graph of daily patterns includes an average sensor reading for a plurality of divisions within a day; wherein the graph is displayed upon user-selection.

In one embodiment, the prior predetermined period of time is a 7 day period, and the graph of daily patterns includes an average sensor reading for four divisions within a day.

In one embodiment, the chart of daily patterns indicates a range of average sensor readings for the plurality of divisions within a day.

In one embodiment, the instructions include instructions for displaying a trigger element for shifting the graph forward or backward by the predetermined period of time; instructions for receiving an indication that the trigger element was triggered by a user; and instructions for shifting the graph forward or backward by the predetermined period of time.

In one embodiment, the analyte is glucose or a ketone body.

In some aspect of the present disclosure, methods of operating an analyte monitoring device are provided that include receiving an indication to operate in a masked mode; performing scans of an analyte sensor; and storing sensor readings obtained from the scans without displaying the sensor readings on a display of the analyte monitoring device.

In one embodiment, the methods include receiving an indication to operate in a non-masked mode; performing scans of an analyte sensor; and displaying sensor readings on a display of the analyte monitoring device.

In one embodiment, the methods include transmitting the stored sensor readings to a remote device.

In one embodiment, the methods include the analyte is glucose or a ketone body.

In some aspects of the present disclosure, analyte monitoring devices are provided. The analyte monitoring devices include a processor; and memory operably coupled to the processor, wherein the memory includes instructions stored therein for operating an analyte monitoring device, the instructions comprising instructions for performing the previously described methods.

In some aspect of the present disclosure, methods of operating an analyte sensor are provided that include communicating between an analyte sensor and a first analyte monitoring device; establishing a pairing with the first analyte monitoring device to enable the first analyte monitoring device to perform analyte readings with the analyte sensor; receiving an identification code for the first analyte monitoring device from the first analyte monitoring device; and storing the device identification code in memory to indicate the established pairing with the first analyte monitoring device.

In one embodiment, the methods include receiving a request for the device identification form a second analyte monitoring device; and transmitting the device identification code for the first analyte monitoring device to the second analyte monitoring device.

In some aspects of the present disclosure, analyte monitoring devices are provided. The analyte monitoring devices include a processor; and memory operably coupled to the processor, wherein the memory includes instructions stored therein for operating an analyte monitoring device, the instructions comprising instructions for performing the previously described methods.

In some aspects of the present disclosure, methods for operating an analyte monitoring device are provided that include communicating between a first analyte monitoring device and a first sensor; determining, with a processor of the first analyte monitoring device, that the first sensor is not paired with any analyte monitoring device; determining, with the processor, that the first analyte monitoring device is not paired with any analyte sensor; and pairing the first analyte monitoring device with the first sensor to enable the first analyte monitoring device to perform analyte readings with the first sensor; and transmitting an identification code for the first analyte monitoring device to the first sensor to indicate the pairing.

In some aspects of the present disclosure, analyte monitoring devices are provided. The analyte monitoring devices include a processor; and memory operably coupled to the processor, wherein the memory includes instructions stored therein for operating an analyte monitoring device, the instructions comprising instructions for performing the previously described methods.

In some aspects of the present disclosure, methods of operating an analyte monitoring device are provided that include communicating between a first analyte monitoring device and a first sensor; determining, with a processor of the first analyte monitoring device, that the first sensor is paired with a second analyte monitoring device; and preventing, with the processor, the first analyte monitoring device from performing analyte readings with the first sensor; wherein the determining that the first sensor is paired comprises receiving, with the processor, an indication that the first sensor contains an identification (ID) code for the second analyte monitoring device that is paired to the first sensor.

In one embodiment, the methods include visually indicating on a display on the first analyte monitoring device that the first sensor cannot be used.

In one embodiment, the methods include communicating between the first analyte monitoring device and a second sensor; determining, with the processor, that the second sensor is not paired with any analyte monitoring device; determining, with the processor, that the first analyte monitoring device is not paired with any analyte sensor; pairing the first analyte monitoring device with the second sensor to enable the first analyte monitoring device to perform analyte readings with the second sensor; and transmitting an identification code for the first analyte monitoring device to the second sensor for storage on the second sensor, the identification code indicating a pairing of the first analyte monitoring device with the second sensor.

In one embodiment, the methods include communicating between the first analyte monitoring device and a third sensor; determining, with the processor, that the third sensor is not paired with any analyte monitoring device; and preventing, with the processor, the first analyte monitoring from performing analyte readings with the second sensor.

Certain embodiments include a reader device for receiving analyte data from an analyte sensing device, the reader device comprising a housing, a display mounted on the housing, a processor mounted in the housing, and memory storing instructions which, when executed by the processor, causes the processor to navigate from a current user interface screen on the display to a home screen in response to an input from a user, wherein navigating from the current user interface screen to the home screen including checking whether the analyte sensing device is expired and, if the analyte sensing device is expired, displaying a sensor expired notification, calculate a time remaining until the analyte sensing device expires, display the home screen, wherein the home screen includes an indication of the remaining time until the analyte sensing device expires, receive analyte information from the analyte sensing device, and display the received analyte information on the display.

In some embodiments, the sensor expired notification requires confirmation prior to navigating to the home screen.

In some embodiments, the indication of the time remaining before expiration of the analyte sensing device includes an indication of no active sensor, and the time remaining is displayed as a number of days when the time remaining is greater than 1 day, as a number of hours when the time remaining is greater than 1 hour and less than 1 day, and as a number of minutes when the time remaining is less than 1 hour.

In some embodiments, the home screen includes an indication of an estimated insulin-on-board amount.

In some embodiments, the indication of the estimated insulin-on-board amount includes a person-shaped icon, wherein the estimated insulin-on-board amount is represented by a fill percentage of the person-shaped icon.

In some embodiments, the displayed analyte information includes a numerical current analyte level, a graphical representation of past analyte levels, and an arrow representing a trend of the numerical current analyte level.

Certain embodiments include instructions causing the processor to determine whether a current analyte level is above a high analyte level threshold, below a low analyte level threshold, above a high projected analyte level threshold or below a low projected analyte level threshold.

In some embodiments, the high analyte level threshold is 240 mg/dL, the low analyte level threshold is 70 mg/dL, the high projected analyte level threshold is 240 mg/dL within the next 15 minutes, and the low projected analyte level threshold is 70 mg/dL within the next 15 minutes.

In some embodiments, the graphical representation of past analyte levels includes 8 hours of past analyte data.

Certain embodiments include instructions causing the processor to not allow consecutive analyte level scans within a predetermined period of time.

Certain embodiments include instructions causing the processor to not allow more than one analyte level scan within a predetermined period of time.

In some embodiments, the predetermined period of time is 3 minutes.

Certain embodiments include a method of operating a reader device of an analyte monitoring system, comprising scanning for a new sensor with the reader device, wherein scanning includes waiting a predetermined length of time before timing out the scanning for the new sensor, checking whether the new sensor has previously been paired with a different reader device, not allowing a pairing of the reader device with the new sensor if the sensor has already been paired with the different reader device, waiting a predetermined length of time for a paired sensor to warm up, displaying a home screen after waiting the predetermined length of time, wherein the home screen includes an indication of the remaining time until the paired sensor expires, starting a glucose scan using the paired sensor and displaying results of the glucose scan, a display including a simultaneous display of a numerical current glucose level, a graphical representation of historical glucose levels for a past predetermined time period, and an arrow representation of a current glucose trend.

Certain embodiments include displaying a sensor expiring soon notification when the new sensor expires within a predetermined length of upcoming time.

In some embodiments, the predetermined length of upcoming time includes 3 days.

In some embodiments, the sensor expiring soon notification is displayed after first scan of the day for the last 3 days before sensor expiration and after every scan for the last 8 hours before sensor expiration.

In some embodiments, a time remaining notification is contextual and units of display vary based on how much time remaining before sensor expiration.

In some embodiments, when the time remaining before sensor expiration is more than 3 days, the time remaining is displayed in units of days, when the time remaining before sensor expiration is between 1 hour and 1 day, the time remaining is displayed in units of hours, and when the time remaining before sensor expiration is less than 1 hour, the time remaining is displayed in units of minutes.

In some embodiments, when the time remaining before sensor expiration reaches zero, the reader device automatically navigates back to the home screen.

Certain embodiments include displaying a high or low glucose value indication.

In some embodiments, the high glucose value indication is 240 mg/dL and the low glucose value indication is 70 mg/dL.

Certain embodiments include selecting the high or low glucose value indication and navigating to a high or low glucose notification screen, wherein the high or low glucose notification screen includes an option to set a reminder for a next glucose scan.

Certain embodiments include displaying a high or low projected glucose value indication.

In some embodiments, the high projected glucose value indication is 240 mg/dL within the next 15 minutes and the low projected glucose value indication is 70 mg/dL within the next 15 minutes.

Certain embodiments include selecting the high or low projected glucose value indication and navigating to a high or low projected glucose notification screen, wherein the high or low projected glucose notification screen includes an option to set a reminder for a next glucose scan.

In some embodiments, the graphical representation of historical glucose levels includes the prior 8 full clock hours and minutes of the current clock hour.

Certain embodiments include a method of operating a reader device in a masked mode, the method comprising, entering a masked mode, wherein the masked mode precludes display of sensor data on a display of the reader device.

In some embodiments, the masked mode can only be activated or deactivated by a health care professional.

In some embodiments, notifications of completed sensor scans are displayed without results on the display of the reader device.

Certain embodiments include setting reminders to scan for current sensor data after a predetermined time interval.

In some embodiments, a next reminder is reset upon a manual scan.

Certain embodiments include a glucose monitoring system comprising a glucose sensor, a reader device paired with the glucose sensor and a reader software executable on a personal computer, the reader software configured to analyze data saved on the reader device and configure settings associated with the reader device, wherein the reader software automatically launches upon connection of the reader device to the personal computer, wherein the reader software is configured to automatically update the reader device firmware or the reader software upon detection of an available update and wherein the reader software includes a plurality of reports related to glucose data saved on the reader device executable by the reader software.

Certain embodiments include a glucose monitoring system comprising a glucose sensor, a reader device paired with the glucose sensor and including firmware and a reader software executable on a personal computer, the reader software configured to analyze data saved on the reader device and configure settings associated with the reader device, wherein the reader software automatically launches upon connection of the reader device to the personal computer, wherein the reader software is configured to automatically update the reader device firmware or the reader software upon detection of an available update and wherein the reader software includes a plurality of reports related to glucose data saved on the reader device executable by the reader software.

In some embodiments, the reader device must be configured prior to use, wherein configuring the reader device includes associating a user profile with the reader device.

In some embodiments, the reader device software requires a user to configure the reader device prior to use, wherein configuring the reader device includes associating a user profile with the reader device.

In some embodiments, the user profile includes a patient name and a patient ID.

In some embodiments, reader software options are unavailable until the reader device is associated with the user profile.

In some embodiments, the reader software automatically discovers the user profile associated with the reader device when the reader device is connected to the personal computer.

In some embodiments, the reader software checks a time and date information stored on the reader device upon connection of the reader device to the personal computer, and wherein the time and date information are checked versus current time and date information stored on the personal computer.

In some embodiments, the time and date information of the reader device are synchronized automatically or manually with the current time and date information stored on the personal computer.

In some embodiments, the time and date information of the reader device are synchronized with the current time and date information stored on the personal computer.

In some embodiments, the reader software is unavailable to the user when a software or firmware update is in progress.

In some embodiments, the reader software executes one or more of the plurality of reports simultaneously.

In some embodiments, the results of the executed plurality of reports are saved in a PDF format.

In some embodiments, the plurality of reports includes a snapshot report, a daily patterns report, a mealtime patterns report, a monthly summary report, a weekly summary report, and a daily log report.

In some embodiments, the one or more of the plurality of reports includes graphical information and numerical information.

In some embodiments, the reader software includes customizable notes for events associated with the glucose data.

In some embodiments, the reader software includes customizable reminders configurable for execution on the reader device.

In some embodiments, the reader software includes authorized access only options.

In some embodiments, the authorized access only options require an access code for access.

In some embodiments, the authorized access only options include an option to disable or enable a masked mode, wherein the masked mode configures the reader device to not display the glucose data on a display of the reader device.

In some aspects of the present disclosure, analyte monitoring devices are provided. The analyte monitoring devices include a processor; and memory operably coupled to the processor, wherein the memory includes instructions stored therein for operating an analyte monitoring device, the instructions comprising instructions for performing the previously described methods.

It should be understood that techniques introduced herein can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium" ", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc. The term "logic", as used herein, can include, for example, special purpose hardwired circuitry, software and/or firmware in conjunction with programmable circuitry, or a combination thereof.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A glucose monitoring system, comprising:
(1) an on body electronics unit configured to be worn on a user's skin, the on body electronics unit comprising:
an on body electronics unit housing;
a glucose sensor, at least a portion of which is configured to be positioned in the user's body and detect a glucose level in a bodily fluid of the user; and
on body electronics disposed within the on body electronics unit housing and coupled with the glucose sensor, the on body electronics comprising processing circuitry, a battery, and an antenna, wherein the on body electronics are configured to transmit data indicative of the glucose level to a reader device in response to a request from the reader device; and
(2) the reader device comprising:
a display;
a wireless communication module configured to receive the data indicative of the glucose level;
one or more processors;
memory coupled with the one or more processors, the memory storing a glucose monitoring software program that, when executed by the one or more processors, causes the one or more processors to:
determine if a glucose sensor warmup time is active and, if so, output to the display the glucose sensor warmup time, wherein the glucose sensor warmup time indicates a time when the glucose sensor is ready,
output to the display a glucose sensor expiration time in a time unit based on a comparison of the glucose sensor expiration time and a predetermined threshold, output to the display a graphical user interface comprising a plurality of bar portions, wherein each bar portion of the plurality of bar portions represents a corresponding percentage of time a plurality of glucose level readings in a predetermined time period were within a corresponding glucose range, and output to the display a logbook interface comprising a plurality of user-selectable options, wherein the plurality of user-selectable options includes an insulin option, a food option, and a custom note option.

2. The glucose monitoring system of claim 1, wherein the glucose sensor warmup time is displayed on a home screen graphical user interface.

3. The glucose monitoring system of claim 1, wherein the glucose sensor warmup time is displayed alone in a separate graphical user interface.

4. The glucose monitoring system of claim 1, wherein the glucose sensor warmup time is displayed as a countdown of minutes until the glucose sensor is ready.

5. The glucose monitoring system of claim 1, wherein determining if the glucose sensor warmup time is active comprises determining an amount of time after the on body electronics unit was activated.

6. The glucose monitoring system of claim 1, wherein the time unit is a first time unit if the glucose sensor expiration time is above the predetermined threshold.

7. The glucose monitoring system of claim 6, wherein the time unit is a second time unit if the glucose sensor expiration time is not above the predetermined threshold.

8. The glucose monitoring system of claim 7, wherein the first time unit is a unit of days, and the second time unit is a unit of hours.

9. The glucose monitoring system of claim 7, wherein the glucose sensor expiration time is rounded up according to the first time unit or the second time unit.

10. The glucose monitoring system of claim 1, wherein the predetermined threshold is twenty-four hours.

11. The glucose monitoring system of claim 1, wherein the glucose sensor expiration time is displayed on a home screen graphical user interface.

12. The glucose monitoring system of claim 1, wherein the glucose sensor expiration time is displayed alone in a separate graphical user interface.

13. The glucose monitoring system of claim 1, wherein the predetermined time period is user configurable.

14. The glucose monitoring system of claim 1, wherein the graphical user interface further comprises a graphical element provided to enable a user to change the predetermined time period.

15. The glucose monitoring system of claim 14, wherein the graphical element is configured to set the predetermined time period to seven days.

16. The glucose monitoring system of claim 14, wherein the graphical element is configured to set the predetermined time period to fourteen days.

17. The glucose monitoring system of claim 1, wherein selection of the insulin option causes display of an insulin logbook interface configured to receive a number of units of insulin.

18. The glucose monitoring system of claim 17, wherein the insulin logbook interface is further configured to receive a type of insulin.

19. The glucose monitoring system of claim 1, wherein selection of the food option causes display of a food logbook interface configured to receive a number of grams of carbohydrates.

20. The glucose monitoring system of claim 1, wherein the glucose monitoring software program, when executed by the one or more processors, further causes the one or more processors to:

output to the display a logbook list interface comprising one or more entries, wherein each entry of the one or more entries includes a date, a time, an associated glucose level, and an associated user-selectable option.

21. The glucose monitoring system of claim 1, wherein the on body electronics are further configured to transmit the data indicative of the glucose level to the reader device according to a Bluetooth communication protocol.

22. The glucose monitoring system of claim 1, further comprising a sensor insertion device, wherein the on body electronics unit is pre-loaded in an interior of the sensor insertion device.

23. The glucose monitoring system of claim 22, wherein the interior of the sensor insertion device comprises a sterile environment.

24. The glucose monitoring system of claim 1, wherein the glucose sensor has a predetermined monitoring time period of about ten days or more.

25. The glucose monitoring system of claim 1, wherein the glucose sensor has a predetermined monitoring time period of about fourteen days or more.

26. The glucose monitoring system of claim 1, wherein the reader device is a smartphone.

27. The glucose monitoring system of claim 1, wherein the glucose sensor is a transcutaneous glucose sensor.

* * * * *